United States Patent
Chari et al.

(10) Patent No.: US 10,238,751 B2
(45) Date of Patent: Mar. 26, 2019

(54) CYTOTOXIC BENZODIAZEPINE DERIVATIVES

(71) Applicant: ImmunoGen, Inc., Waltham, MA (US)

(72) Inventors: Ravi V. J. Chari, Newton, MA (US); Michael Louis Miller, Framingham, MA (US); Manami Shizuka, Belmont, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 15/581,749

(22) Filed: Apr. 28, 2017

(65) Prior Publication Data

US 2017/0340748 A1 Nov. 30, 2017

Related U.S. Application Data

(62) Division of application No. 14/843,520, filed on Sep. 2, 2015, now Pat. No. 9,669,102.

(60) Provisional application No. 62/164,305, filed on May 20, 2015, provisional application No. 62/149,370, filed on Apr. 17, 2015, provisional application No. 62/087,040, filed on Dec. 3, 2014, provisional application No. 62/045,248, filed on Sep. 3, 2014.

(51) Int. Cl.

| | | |
|---|---|---|
| *C07D 487/04* | (2006.01) | |
| *A61K 47/64* | (2017.01) | |
| *C07K 16/28* | (2006.01) | |
| *C07D 519/00* | (2006.01) | |
| *C07K 5/093* | (2006.01) | |
| *C07K 5/113* | (2006.01) | |
| *C07K 5/02* | (2006.01) | |
| *A61K 39/00* | (2006.01) | |

(52) U.S. Cl.
CPC .......... *A61K 47/64* (2017.08); *C07D 487/04* (2013.01); *C07D 519/00* (2013.01); *C07K 5/0202* (2013.01); *C07K 5/0819* (2013.01); *C07K 5/1021* (2013.01); *C07K 16/28* (2013.01); *C07K 16/2863* (2013.01); *C07K 16/2866* (2013.01); *A61K 2039/505* (2013.01); *C07K 2317/24* (2013.01); *C07K 2317/92* (2013.01)

(58) Field of Classification Search
CPC .................................................. C07D 487/04
See application file for complete search history.

(56) References Cited

U.S. PATENT DOCUMENTS

| | | |
|---|---|---|
| 8,426,402 B2 | 4/2013 | Li et al. |
| 8,765,740 B2 | 7/2014 | Li et al. |
| 8,802,667 B2 | 8/2014 | Li et al. |
| 8,809,320 B2 | 8/2014 | Li et al. |
| 8,889,669 B2 | 11/2014 | Li et al. |
| 9,169,272 B2 | 10/2015 | Li et al. |
| 9,669,102 B2 | 6/2017 | Chari et al. |
| 2012/0238731 A1 | 9/2012 | Fishkin et al. |
| 2015/0030616 A1 | 1/2015 | Li et al. |
| 2015/0315193 A1 | 11/2015 | Li et al. |

FOREIGN PATENT DOCUMENTS

| | | |
|---|---|---|
| WO | WO 2010/091150 A1 | 8/2010 |
| WO | WO 2012/112687 A1 | 8/2012 |

*Primary Examiner* — Bruck Kifle

(74) *Attorney, Agent, or Firm* — McCarter & English, LLP; Yu Lu; Xin Zhang

(57) ABSTRACT

The invention relates to novel benzodiazepine derivatives with antiproliferative activity and more specifically to novel benzodiazepine compounds of formula (I)-(VI). The invention also provides conjugates of the benzodiazepine compounds linked to a cell-binding agent. The invention further provides compositions and methods useful for inhibiting abnormal cell growth or treating a proliferative disorder in a mammal using the compounds or conjugates of the invention.

20 Claims, 32 Drawing Sheets

Specification includes a Sequence Listing.

FIG. 4A
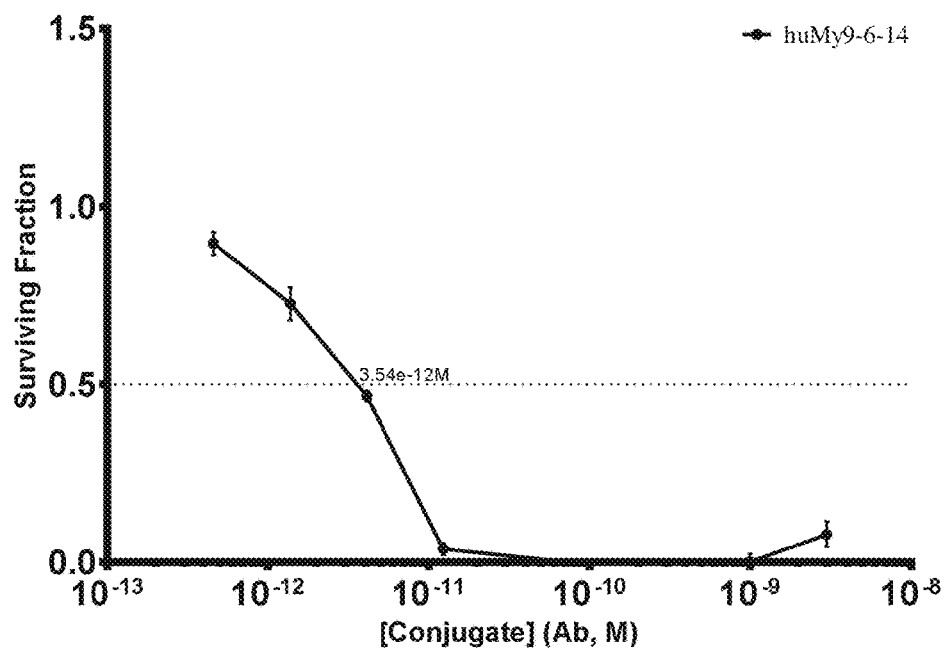
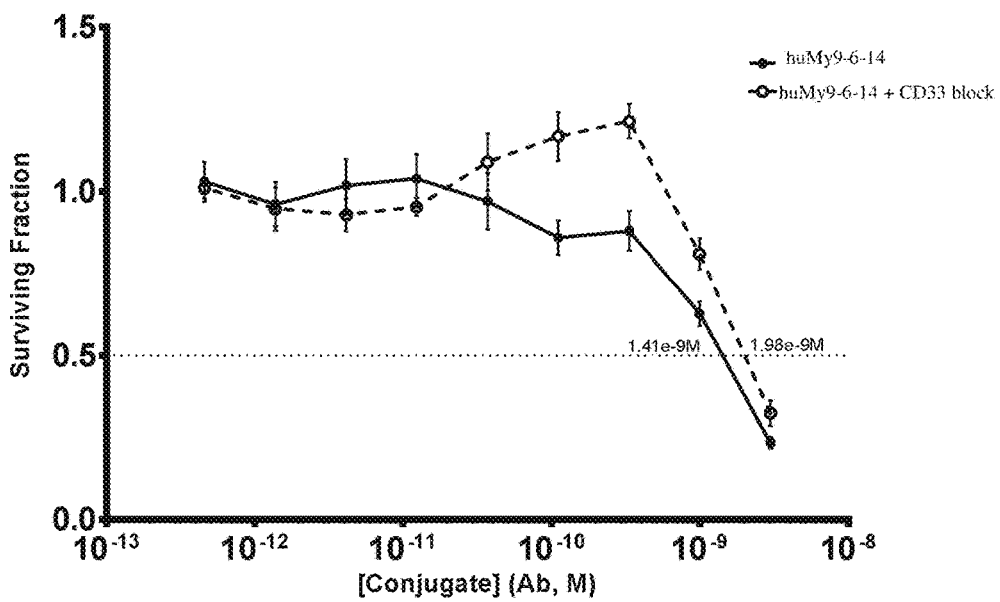

FIG. 4B
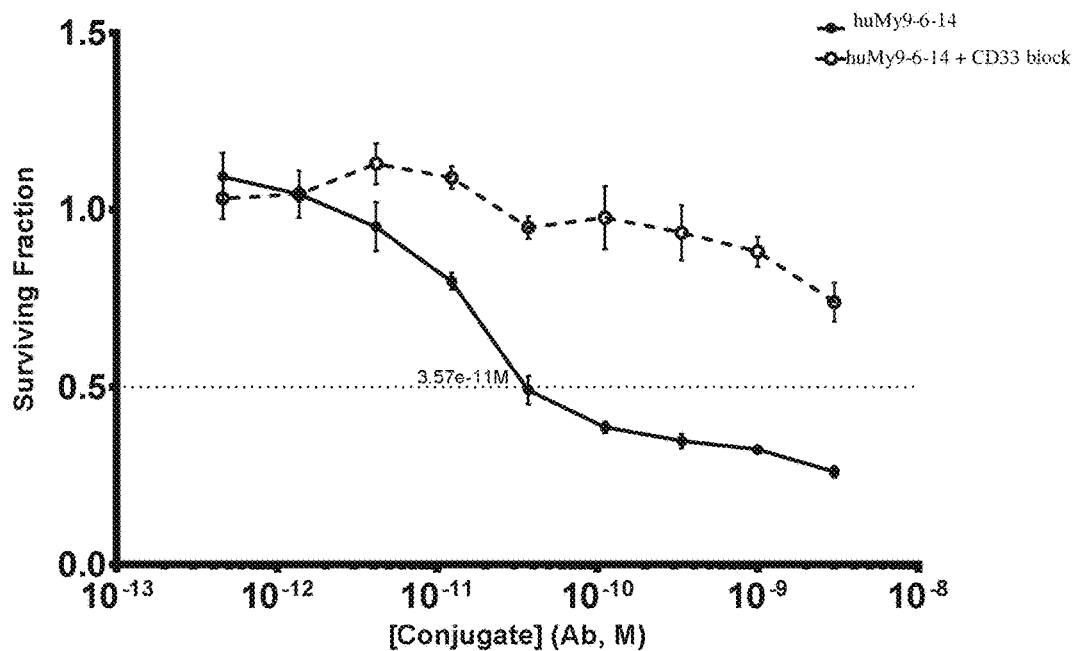
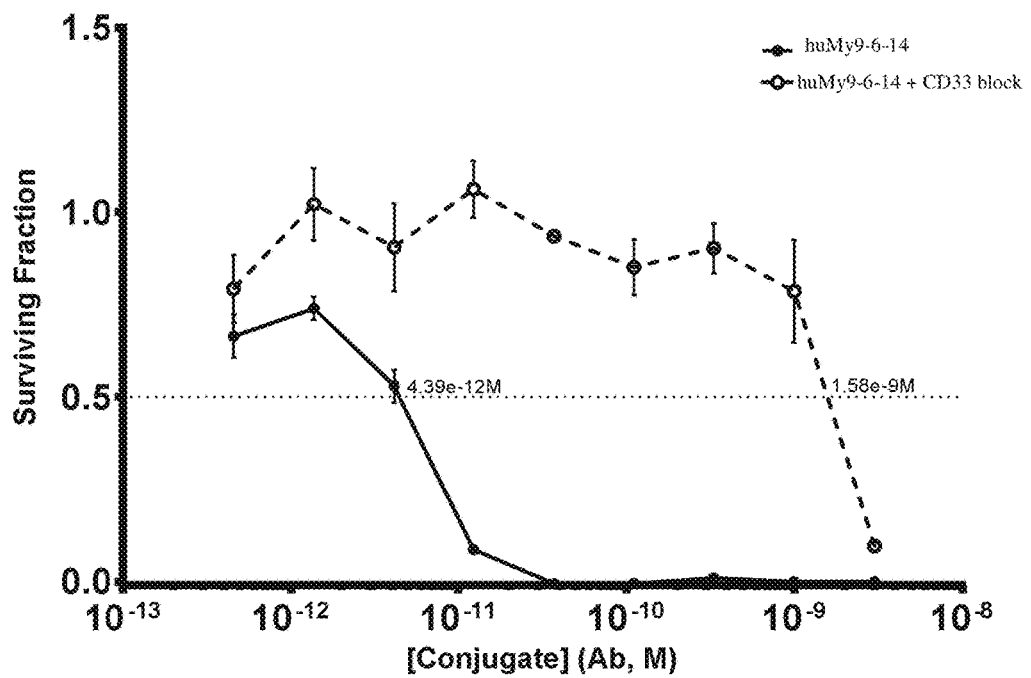

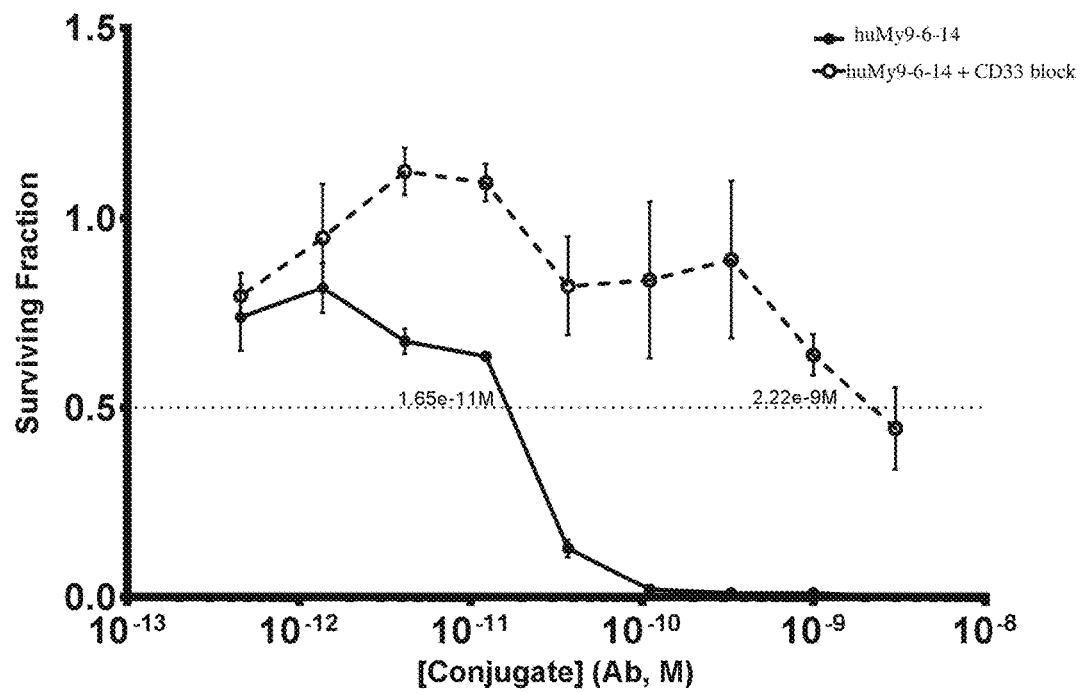

Anti-Tumor Activity (Median Tumor Volume, mm$^3$) of huMOV19-80 and huMOV19-90 in SCID Mice Bearing NCI-H2110 Xenografts

| Treatment Group | | Dose (ug/kg) | T/C (Day 23) | Regressions | | Result |
|---|---|---|---|---|---|---|
| | | | | PR | CR | |
| A | Control | - | - | - | - | - |
| B | huMOV19-80 | 5 | 47% | 0/6 | 0/6 | Inactive |
| C | huMOV19-80 | 25 | 5% | 5/6 | 1/6 | Highly Active |
| D | huMOV19-90 | 5 | 0% | 6/6 | 6/6 | Highly Active |
| E | huMOV19-90 | 25 | 0% | 6/6 | 6/6 | Highly Active |

FIG. 7A
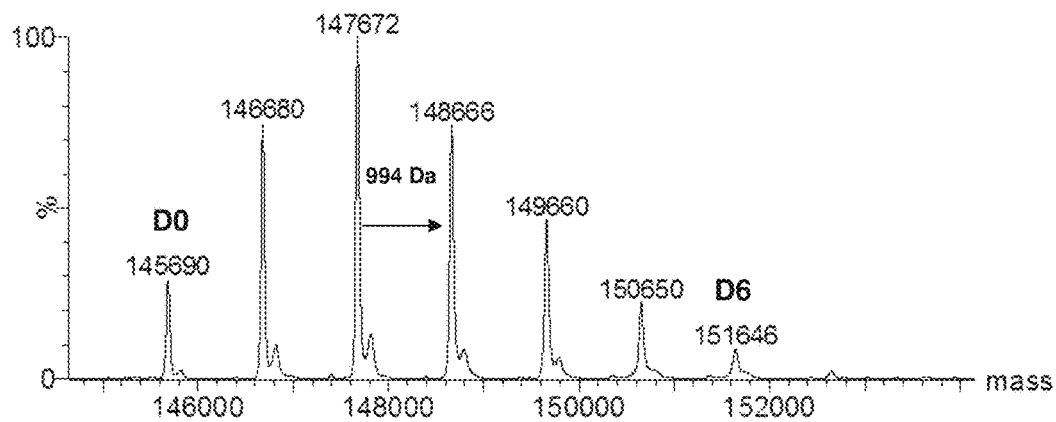
MS for deglycosylated huMov19-14 Conjugate
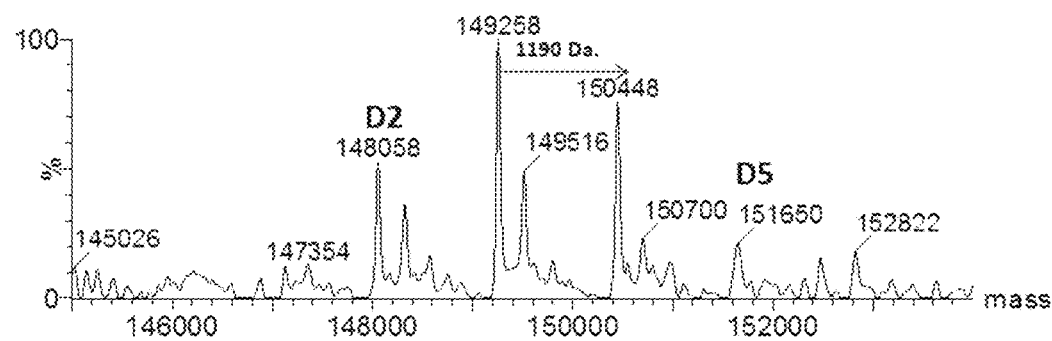
MS for deglycosylated huMov19-sulfo-SPDB-98 Conjugate
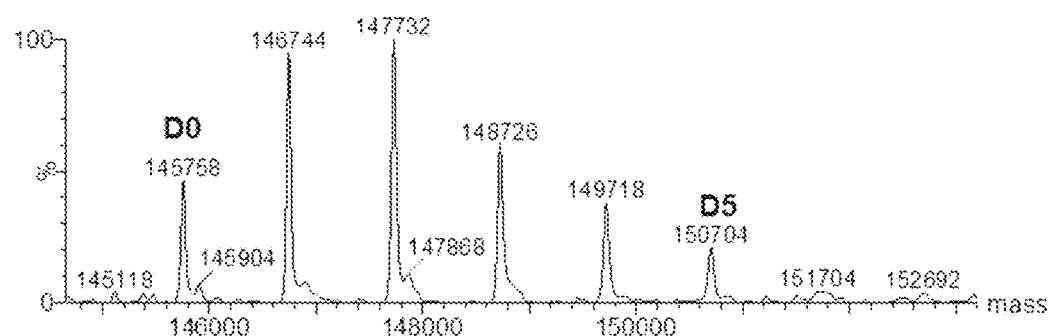
MS for deglycosylated huMov19-35 Conjugate FIG. 7B
MS for deglycosylated huMov19-63 Conjugate
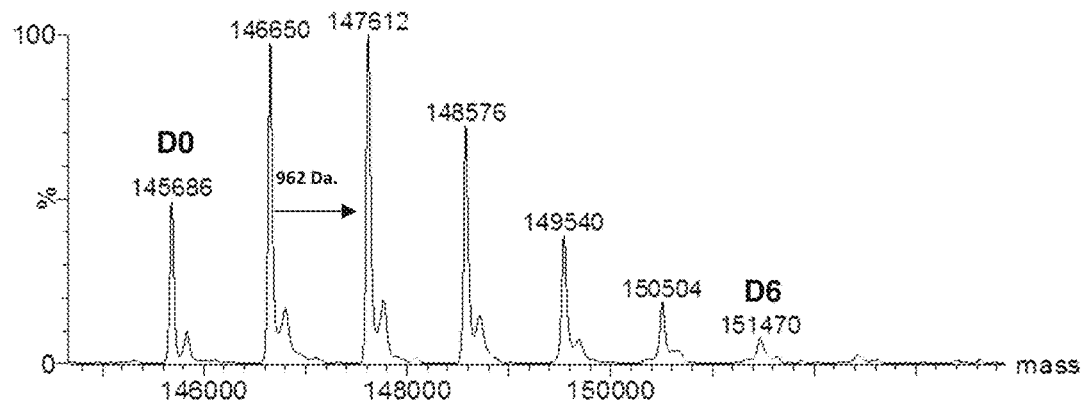
MS for deglycosylated huMov19-80 Conjugate
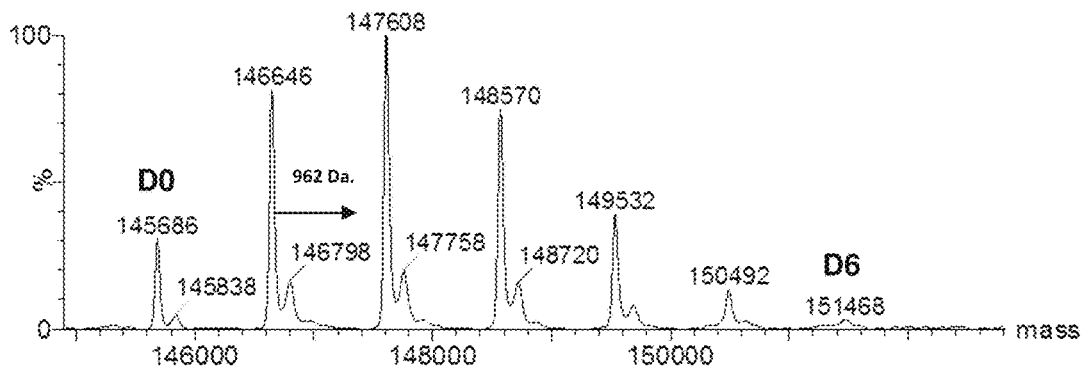
MS for deglycosylated huMOV19-90 Conjugate
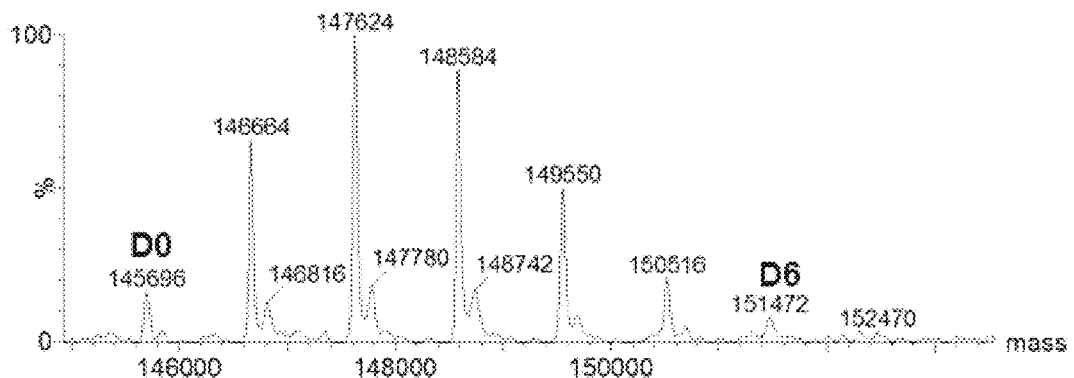

FIG. 7C
MS for deglycosylated huMov19-49 Conjugate
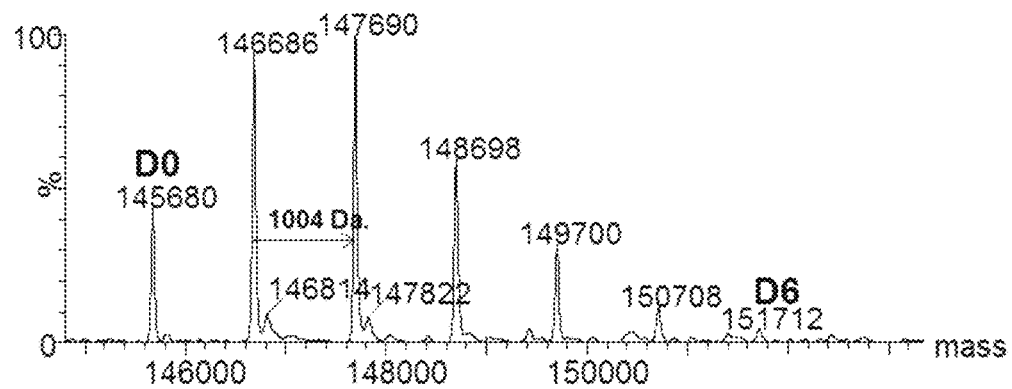
MS for deglycosylated huMov19-sulfo-SPDB-99 Conjugate
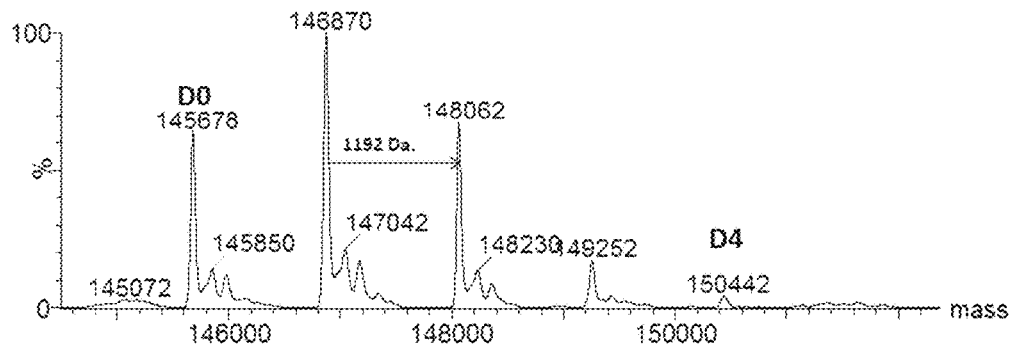
MS for deglycosylated huMov19-70 Conjugate
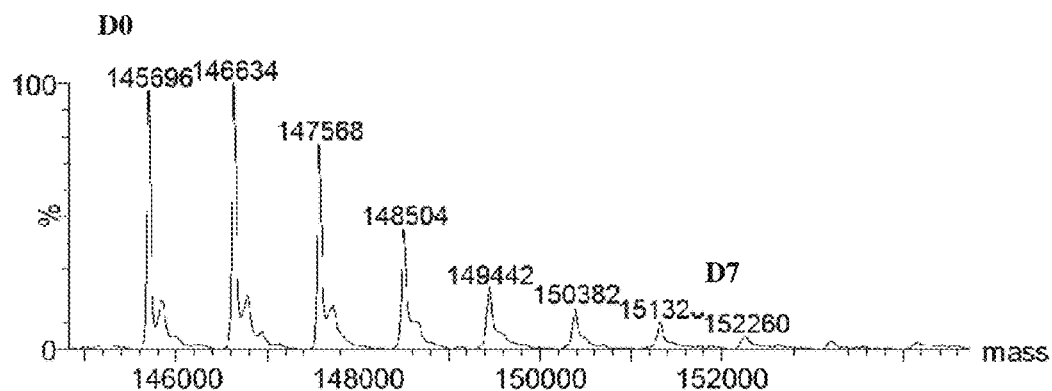

Anti-Tumor Activity (Median Tumor Volume, mm$^3$) of huMov19-90 in SCID Mice Bearing NCI-H2110 Xenografts

| | Treatment Group | Compound Dose (μg/kg) | T/C (Day 28) | Regressions | | Result |
|---|---|---|---|---|---|---|
| | | | | PR | CR | |
| A | Control | - | - | - | - | - |
| B | huMov19-90 | 1 | 107% | 0/6 | 0/6 | Inactive |
| C | huMov19-90 | 3 | 14% | 1/6 | 0/6 | Active |
| D | huMov19-90 | 5 | 1% | 6/6 | 3/6 | Highly Active |

MS for deglycosylated huMov19-sulfo-SPDB-107 Conjugate

Anti-Tumor Activity (Median Tumor Volume, mm$^3$) of huML66-90 conjugate in SCID Mice Bearing NCI-H1703 Xenografts

| Agent | Compound 90 dose (µg/kg) | Ab dose (mg/kg) | T/C (%) | CR | Results |
|---|---|---|---|---|---|
| huML66-90 conjugate | 5 | 0.3 | 46 | 0/6 | inactive |
| | 20 | 1.1 | 4 | 3/6 | highly active |
| | 50 | 2.8 | 0 | 6/6 | highly active |

Pharmacokinetics of huMov19-90 in CD-1 mice

FIG. 21A Ishikawa cells
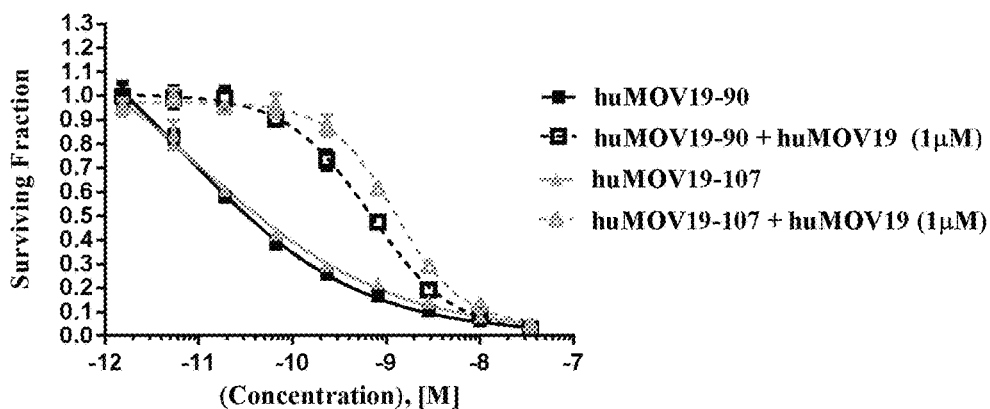
FIG. 21B KB cells
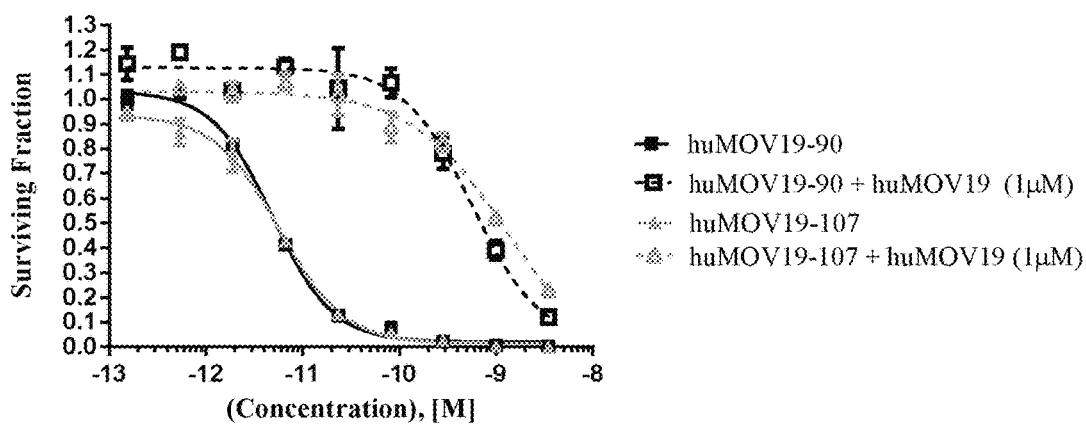
FIG. 21C NCI-H2110 cells
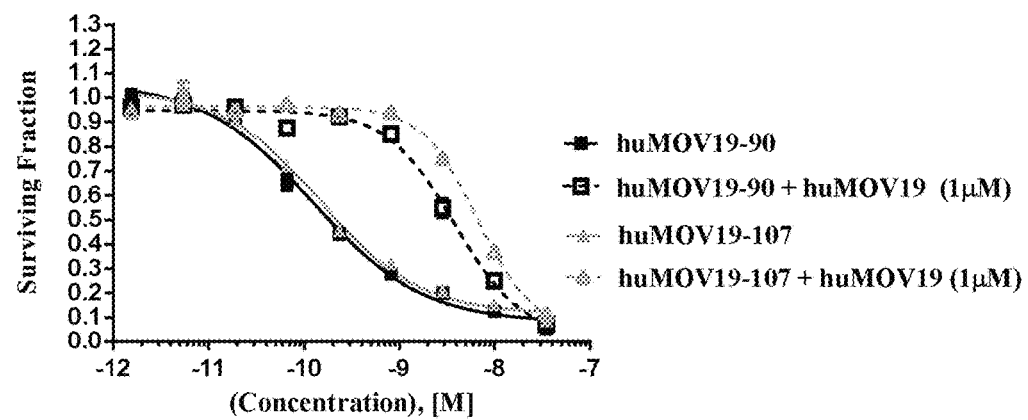

| Treatment Group | | Dose (µg/kg) | T/C (Day 24) | Regressions | | Result |
|---|---|---|---|---|---|---|
| | | | | PR | CR | |
| A | Vehicle Control | — | — | — | — | — |
| B | huMov19-90 | 1 | 117% | 0/6 | 0/6 | Inactive |
| C | huMov19-90 | 3 | 13% | 1/6 | 0/6 | Active |
| D | huMov19-90 | 5 | 2% | 6/6 | 4/6 | Highly Active |

| Treatment Group | | Dose (μg/kg) | T/C (Day 33) | Regressions | | Result |
|---|---|---|---|---|---|---|
| | | | | PR | CR | |
| A | Vehicle Control | - | - | - | - | - |
| B | huMov19-90 | 10 | 15% | 1/6 | 0/6 | Active |
| C | huMov19-90 | 30 | 9% | 6/6 | 6/6 | Highly Active |
| D | chKTI-90 | 30 | 34% | 0/6 | 0/6 | Active |

| Treatment Group | | Dose (µg/kg) | T/C (Day 32) | Regressions | | Result |
| --- | --- | --- | --- | --- | --- | --- |
| | | | | PR | CR | |
| A | Vehicle Control | - | - | - | - | - |
| E | huMov19-90 | 10 | 27% | 6/6 | 6/6 | Active |
| F | huMov19-90 | 30 | 15% | 6/6 | 6/6 | Active |
| G | chKTI-90 | 30 | 24% | 4/6 | 0/6 | Active |

| Treatment Group | | Dose (μg/kg) | T/C (Day 28) | Regressions | | Result |
|---|---|---|---|---|---|---|
| | | | | PR | CR | |
| A | Vehicle Control | - | - | - | - | - |
| B | huMov19-107 | 1 | 102% | 0/6 | 0/6 | Inactive |
| C | huMov19-107 | 3 | 60% | 1/6 | 1/6 | Inactive |
| D | huMov19-107 | 10 | 0% | 6/6 | 6/6 | Highly Active |
| E | chKTI-107 | 10 | 89% | 0/6 | 0/6 | Inactive |

CYTOTOXIC BENZODIAZEPINE DERIVATIVES

REFERENCE TO RELATED APPLICATIONS

This application is a divisional application of U.S. patent application Ser. No. 14/843,520, filed Sep. 2, 2015, which claims the benefit of the filing date under 35 U.S.C. § 119(e), of U.S. Provisional Application No. 62/045,248, filed on Sep. 3, 2014, U.S. Provisional Application No. 62/087,040, filed on Dec. 3, 2014, U.S. Provisional Application No. 62/149,370, filed on Apr. 17, 2015, and U.S. Provisional Application No. 62/164,305, filed on May 20, 2015, the entire contents of each of which, including all drawings, formulae, specifications, and claims, are incorporated herein by reference.

FIELD OF THE INVENTION

The present invention relates to novel cytotoxic compounds, and cytotoxic conjugates comprising these cytotoxic compounds and cell-binding agents. More specifically, this invention relates to novel benzodiazepine compounds, derivatives thereof, intermediates thereof, conjugates thereof, and pharmaceutically acceptable salts thereof, which are useful as medicaments, in particular as antiproliferative agents.

BACKGROUND OF THE INVENTION

Benzodiazepine derivatives are useful compounds for treating various disorders, and include medicaments such as, antiepileptics (imidazo[2,1-b][1,3,5]benzothiadiazepines, U.S. Pat. Nos. 4,444,688; 4,062,852), antibacterials (pyrimido[1,2-c][1,3,5]benzothiadiazepines, GB 1476684), diuretics and hypotensives (pyrrolo(1,2-b)[1,2,5]benzothiadiazepine 5,5 dioxide, U.S. Pat. No. 3,506,646), hypolipidemics (WO 03091232), anti-depressants (U.S. Pat. No. 3,453,266); osteoporosis (JP 2138272).

It has been shown in animal tumor models that benzodiazepine derivatives, such as pyrrolobenzodiazepines (PBDs), act as anti-tumor agents (N-2-imidazolyl alkyl substituted 1,2,5-benzothiadiazepine-1,1-dioxide, U.S. Pat. No. 6,156,746), benzopyrido or dipyrido thiadiazepine (WO 2004/069843), pyrrolo[1,2-b][1,2,5]benzothiadiazepines and pyrrolo[1,2-b][1,2,5]benzodiazepine derivatives (WO2007/015280), tomaymycin derivatives (e.g., pyrrolo[1,4]benzodiazepines), such as those described in WO 00/12508, WO2005/085260, WO2007/085930, and EP 2019104. Benzodiazepines are also known to affect cell growth and differentiation (Kamal A., et al., Bioorg Med Chem. 2008 Aug. 15; 16(16):7804-10 (and references cited therein); Kumar R, Mini Rev Med Chem. 2003 June; 3(4):323-39 (and references cited therein); Bednarski J J, et al., 2004; Sutter A. P, et al., 2002; Blatt N B, et al., 2002), Kamal A. et al., Current Med. Chem., 2002; 2; 215-254, Wang J-J., J. Med. Chem., 2206; 49:1442-1449, Alley M. C. et al., Cancer Res. 2004; 64:6700-6706, Pepper C. J., Cancer Res 2004; 74:6750-6755, Thurston D. E. and Bose D. S., Chem Rev 1994; 94:433-465; and Tozuka, Z., et al., Journal of Antibiotics, (1983) 36; 1699-1708. General structure of PBDs is described in US Publication Number 20070072846. The PBDs differ in the number, type and position of substituents, in both their aromatic A rings and pyrrolo C rings, and in the degree of saturation of the C ring. Their ability to form an adduct in the minor groove and crosslink DNA enables them to interfere with DNA processing, hence their potential for use as antiproliferative agents.

The first pyrrolobenzodiazepine to enter the clinic, SJG-136 (NSC 694501) is a potent cytotoxic agent that causes DNA inter-strand crosslinks (S. G Gregson et al., 2001, *J. Med. Chem.*, 44: 737-748; M. C. Alley et al., 2004, *Cancer Res.*, 64: 6700-6706; J. A. Hartley et al., 2004, *Cancer Res.*, 64: 6693-6699; C. Martin et al., 2005, *Biochemistry.*, 44: 4135-4147; S. Arnould et al., 2006, *Mol. Cancer Ther.*, 5: 1602-1509). Results from a Phase I clinical evaluation of SJG-136 revealed that this drug was toxic at extremely low doses (maximum tolerated dose of 45 $\mu g/m^2$, and several adverse effects were noted, including vascular leak syndrome, peripheral edema, liver toxicity and fatigue. DNA damage was noted at all doses in circulating lymphocytes (D. Hochhauser et al., 2009, *Clin. Cancer Res.*, 15: 2140-2147). Thus, there exists a need for improved benzodiazepine derivatives that are less toxic and still therapeutically active for treating a variety of proliferative disease states, such as cancer.

SUMMARY OF THE INVENTION

The novel benzodiazepine compounds described herein and the conjugates thereof have surprisingly high potency againt various tumor cells.

One object of the invention is to provide a cytotoxic compound represented by any one of the following formulas:

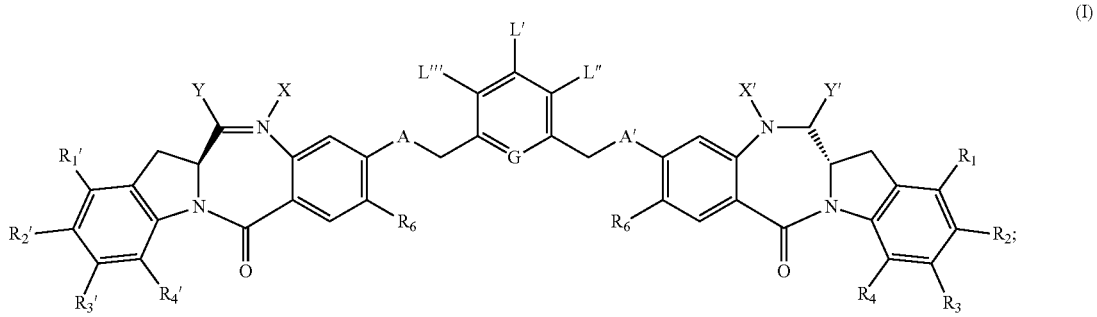

(I)

-continued
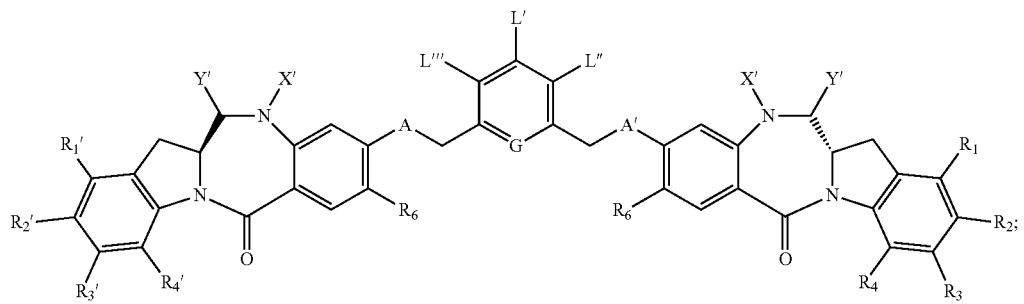
(II)
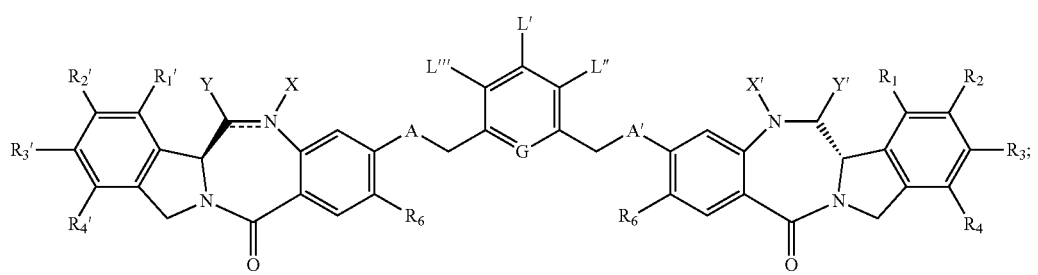
(III)
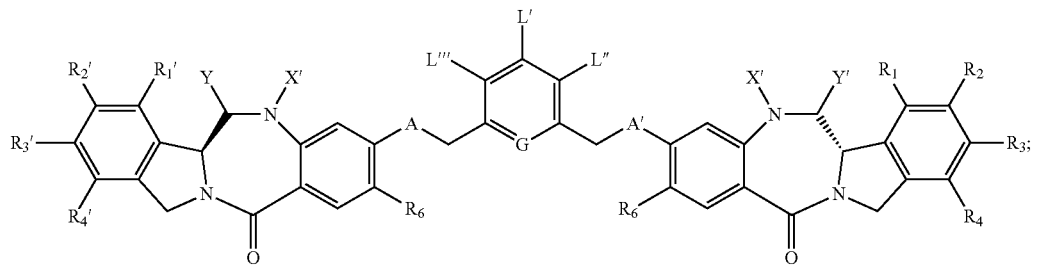
(IV)
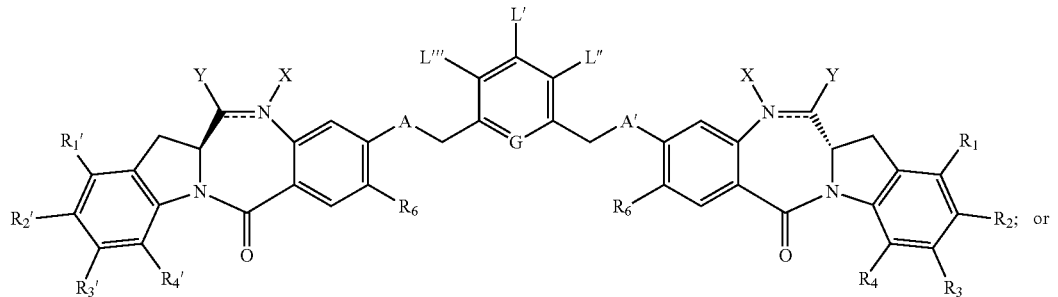
(V)
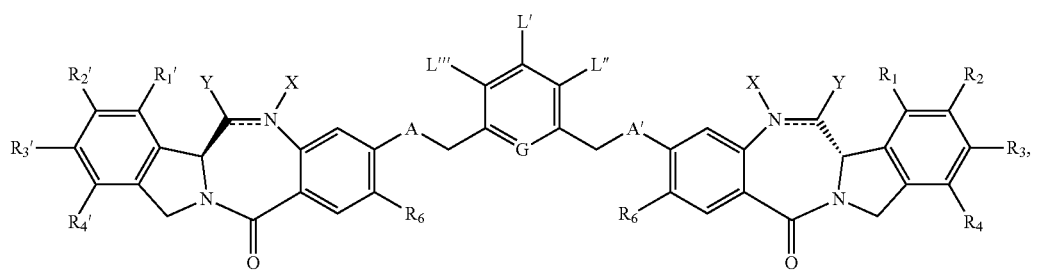
(VI)

or a pharmaceutically acceptable salt thereof, wherein:
one of L', L", and L'" is represented by the following formula:

$$-Z_1-P-Z_2-R_x-J \quad (A)$$

and the other two are the same or different, and are independently selected from —H, an optionally substituted linear, branched or cyclic alkyl, alkenyl or alkynyl having from 1 to 10 carbon atoms, a polyethylene glycol unit —$(CH_2CH_2O)_n$—$R^c$, halogen, guanidinium [—NH(C=NH)NH_2], —OR, —NR'R", —NO_2, —NR'COR", —SR, —SOR', —SO_2R', —SO_3H, —OSO_3H, —SO_2NR'R", cyano, an azido, —COR', —OCOR', and —OCONR'R";

one of the $Z_1$ and $Z_2$ is —C(=O)—, and the other is —$NR_5$—;

P is an amino acid residue or a peptide containing between 2 to 20 amino acid residues;

$R_x$ is an optionally substituted linear, branched or cyclic alkyl, alkenyl or alkynyl having from 1 to 10 carbon atoms;

J is a moiety comprising a reactive group that is capable of covalently linking the cytotoxic compound to a cell-binding agent;

the double line = between N and C represents a single bond or a double bond, provided that when it is a double bond X is absent and Y is —H, or a linear or branched alkyl having 1 to 4 carbon atoms, and when it is a single bond, X is —H or an amine protecting moiety;

Y is a leaving group selected from —OR, —OCOR', —OCOOR', —OCONR'R", —NR'R", —NR'COR", —NR'NR'R", an optionally substituted 5- or 6-membered nitrogen-containing heterocycle (e.g., piperidine, tetrahydropyrrole, pyrazole, morpholine, etc. attached through the nitrogen atom), a guanidinum represented by —NR'(C=NH)NR'R", an amino acid residue, or a peptide represented by —NRCOP', —SR, —SOR', halogen, cyano, azido, —OSO_3H, sulfite (—SO_3H or —SO_2H), metabisulfite ($H_2S_2O_5$), mono-, di-, tri-, and tetra-thiophosphate ($PO_3SH_3$, $PO_2S_2H_2$, $POS_3H_2$, $PS_4H_2$), thio phosphate ester $(R^iO)_2PS(OR^i)$, $R^iS$—, $R^iSO$, $R^iSO_2$, $R^iSO_3$, thiosulfate ($HS_2O_3$), dithionite ($HS_2O_4$), phosphorodithioate ($P(=S)(OR^{k'})(S)(OH)$), hydroxamic acid ($R^{k'}C(=O)NOH$), and formaldehyde sulfoxylate ($HOCH_2SO_2^-$) or a mixture thereof, wherein $R^i$ is a linear or branched alkyl having 1 to 10 carbon atoms and is substituted with at least one substituent selected from —$N(R^j)_2$, —$CO_2H$, —$SO_3H$, and —$PO_3H$; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;

P' is an amino acid residue or a polypeptide containing between 2 to 20 amino acid residues, R, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —$NR_2$, —COR, an optionally substituted linear, branched or cyclic alkyl, alkenyl or alkynyl having from 1 to 10 carbon atoms, a polyethylene glycol unit —$(CH_2CH_2O)_n$—$R^c$, and an optionally substituted 3- to 18-membered heterocyclic ring having 1 to 6 heteroatoms independently selected from O, S, N and P;

$R^c$ is —H or an optionally substituted linear or branched alkyl having 1 to 4 carbon atoms;

n is an integer from 1 to 24;

X' is selected from —H, an amine-protecting group, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;

Y' is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, and sulfur, an optionally substituted 3- to 18-membered heterocyclic ring having 1 to 6 heteroatoms;

$R_1$, $R_2$, $R_3$, $R_4$, $R_1'$, $R_2'$, $R_3'$ and $R_4'$ are each independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, halogen, guanidinium [—NH(C=NH)NH_2], —OR, —NR'R", —NO_2, —NCO, —NR'COR", —SR, —SOR', —SO_2R', —SO_3—H, —OSO_3H, —SO_2NR'R", cyano, an azido, —COR', —OCOR', and —OCONR'R";

$R_6$ is —H, —R, —OR, —SR, —NR'R", —NO_2, or halogen;

G is —CH— or —N—;

A and A' are the same or different, and are independently selected from —O—, oxo (—C(=O)—), —CRR'O—, —CRR'—, —S—, —CRR'S—, —$NR_5$ and —CRR'N($R_5$)—; and $R_5$ for each occurrence is independently —H or an optionally substituted linear or branched alkyl having 1 to 10 carbon atoms.

In one embodiment, for compounds of structural formulas (I)-(VI), G is —CH—.

A second object of the invention is to provide conjugates of cell binding agents with the novel benzodiazepine compounds or derivatives thereof of the present invention. These conjugates are useful as therapeutic agents, which are delivered specifically to target cells and are cytotoxic.

Specifically, a conjugate of the invention may comprise: a cytotoxic compound and a cell-binding agent (CBA), wherein the cytotoxic compound is covalently linked to the CBA, and wherein said cytotoxic compound is represented by any one of the following formulas:

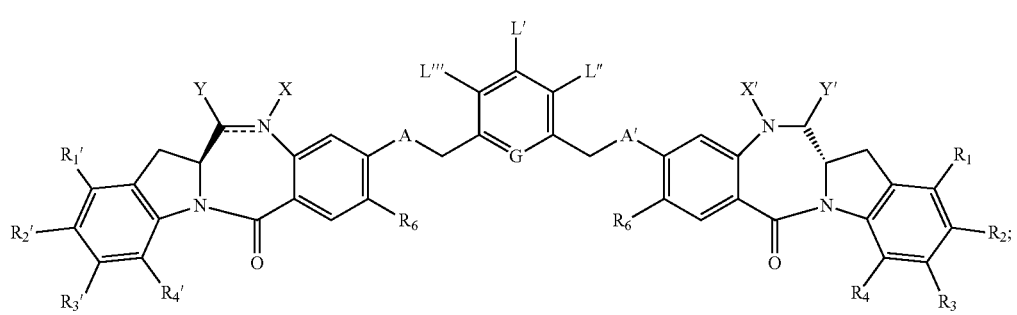
(I')
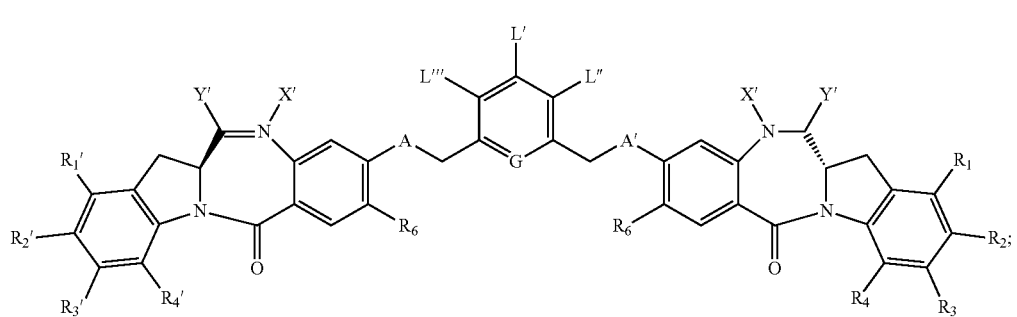
(II')
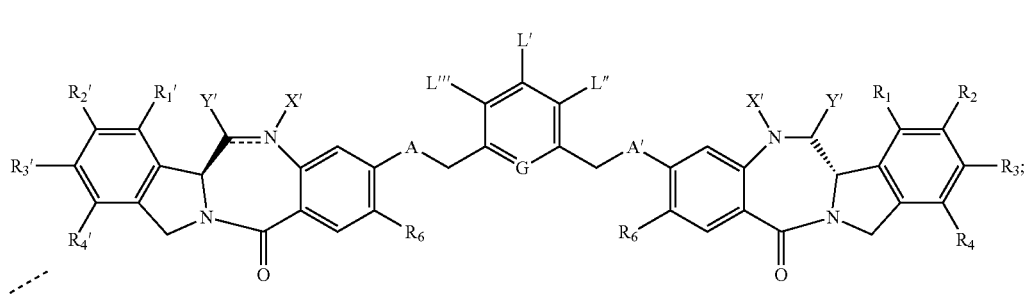
(III')
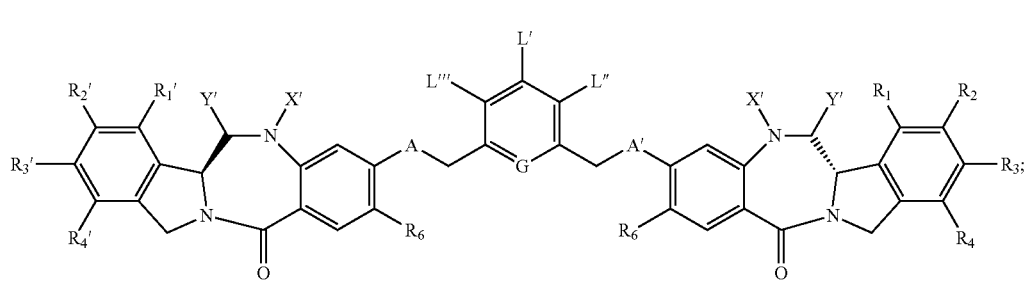
(IV')
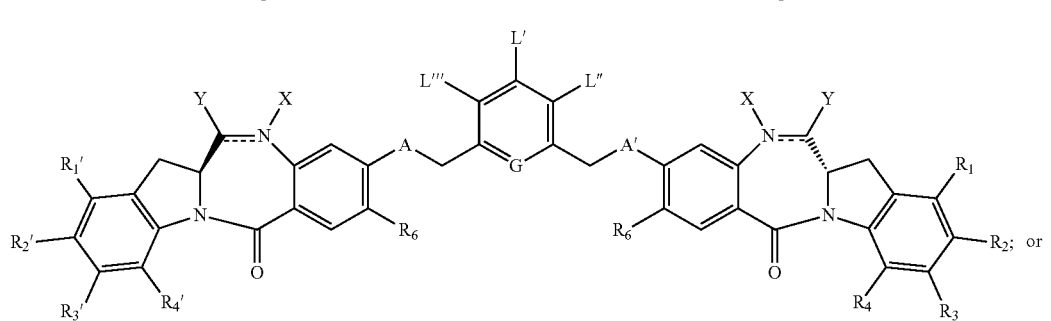
(V'); or

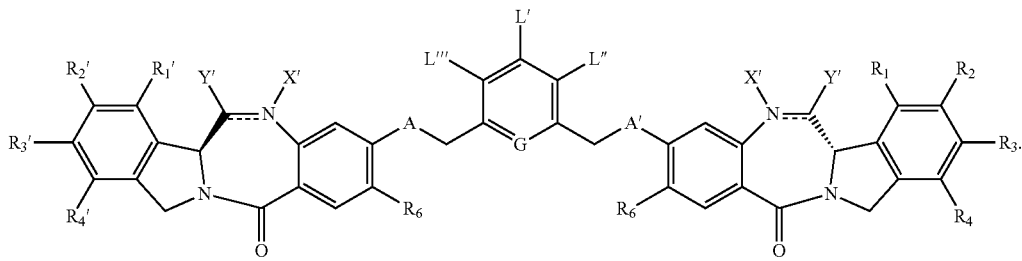

(VI')

or a pharmaceutically acceptable salt thereof, wherein:
one of L', L", and L'" is represented by the following formula:

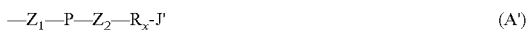

$-Z_1-P-Z_2-R_x-J'$        (A')

and the other two are the same or different, and are independently selected from —H, an optionally substituted linear, branched or cyclic alkyl, alkenyl or alkynyl having from 1 to 10 carbon atoms, a polyethylene glycol unit —$(CH_2CH_2O)_n$—$R^c$, halogen, guanidinium [—NH(C=NH)$NH_2$], —OR, —NR'R", —$NO_2$, —NR'COR", —SR, a sulfoxide represented by —SOR', a sulfone represented by —$SO_2R'$, a sulfonate —$SO_3M$, a sulfate —$OSO_3M$, a sulfonamide represented by —$SO_2NR'R"$, cyano, an azido, —COR', —OCOR', and —OCONR'R";

J' is a moiety comprising a linking group that is covalently linked to the cell-binding agent; and the remaining of the variables are as described above for formulas (I)-(VI).

In one embodiment, for conjugates of structural formulas (I')-(VI'), G is —CH—.

In another embodiment, for conjugates of structural formulas (I')-(VI'), the cell-binding agent is an anti-folate receptor antibody or an antibody fragment thereof. More specifically, the anti-folate receptor antibody is huMOV19 antibody.

In yet another embodiment, for conjugates of structural formulas (I')-(VI'), the cell-binding agent is an anti-EGFR antibody or an antibody fragment thereof. In one embodiment, the anti-EGFR antibody is a non-antagonist antibody, including, for example, the antibodies described in WO2012058592, herein incorporated by reference. In another embodiment, the anti-EGFR antibody is a non-functional antibody, for example, humanized ML66. More specifically, the anti-EGFR antibody is huML66.

The present invention also includes a composition (e.g., a pharmaceutical composition) comprising novel benzodiazepine compounds, derivatives thereof, or conjugates thereof, (and/or solvates, hydrates and/or salts thereof) and a carrier (a pharmaceutically acceptable carrier). The present invention additionally includes a composition (e.g., a pharmaceutical composition) comprising novel benzodiazepine compounds, derivatives thereof, or conjugates thereof (and/or solvates, hydrates and/or salts thereof), and a carrier (a pharmaceutically acceptable carrier), further comprising a second therapeutic agent. The present compositions are useful for inhibiting abnormal cell growth or treating a proliferative disorder in a mammal (e.g., human). The present compositions are useful for treating conditions such as cancer, rheumatoid arthritis, multiple sclerosis, graft versus host disease (GVHD), transplant rejection, lupus, myositis, infection, immune deficiency such as AIDS, and inflammatory diseases in a mammal (e.g., human).

The present invention includes a method of inhibiting abnormal cell growth or treating a proliferative disorder in a mammal (e.g., human) comprising administering to said mammal a therapeutically effective amount of novel benzodiazepine compounds, derivatives thereof, or conjugates thereof, (and/or solvates and salts thereof) or a composition thereof, alone or in combination with a second therapeutic agent.

The present invention includes a method of synthesizing and using novel benzodiazepine compounds, derivatives thereof, and conjugates thereof for in vitro, in situ, and in vivo diagnosis or treatment of mammalian cells, organisms, or associated pathological conditions.

The compounds of this invention, derivatives thereof, or conjugates thereof, and compositions comprising them, are useful for treating or lessening the severity of disorders, such as, characterized by abnormal growth of cells (e.g., cancer). Other applications for compounds and conjugates of this invention include, but are not limited to, treating conditions such as cancer, rheumatoid arthritis, multiple sclerosis, graft versus host disease (GVHD), transplant rejection, lupus, myositis, infection, immune deficiency such as AIDS and inflammatory diseases in a mammal (e.g., human).

BRIEF DESCRIPTION OF THE FIGURES

FIGS. 4A, 4B and 4C show in vitro cytotoxicity of huMy9-6-14 conjugate against various cell lines.

FIG. 7A-7D show mass spectrometry profiles of representative conjugates of the present invention.

FIGS. 21A, 21B and 21C show in vitro cytotoxicity and specificity of huMOV19-90 and huMOV19-107 conjugates.

DETAILED DESCRIPTION OF THE INVENTION

Figure 1:
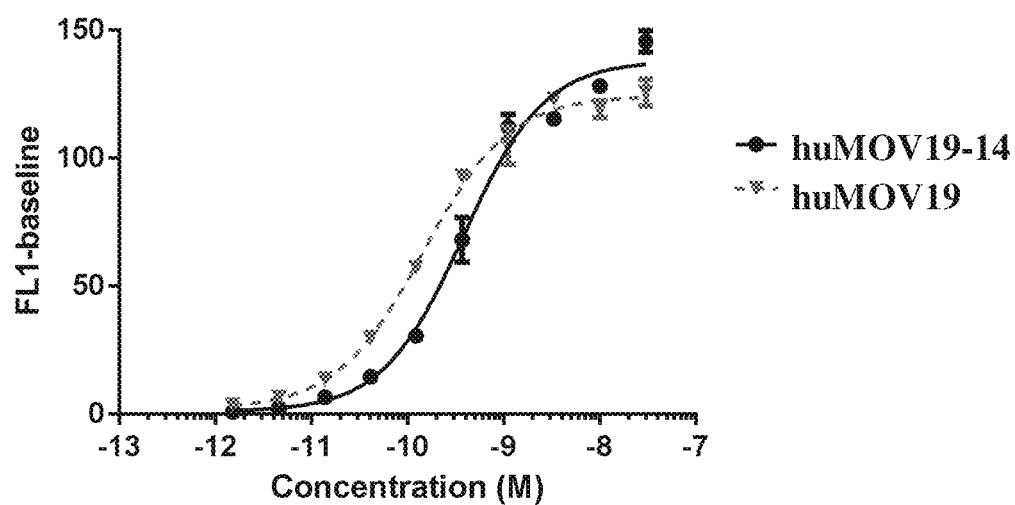
FIG. 1 shows binding affinity of huMOV19-14 conjugate as compared to unconjugated antibody huMOV19 on T47D cells.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention (e.g., compounds, compound-linker molecules, conjugates, compositions, methods of making and using) and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Definitions

As used herein, the term "cell-binding agent" or "CBA" refers to a compound that can bind a cell (e.g., on a cell-surface ligand) or bind a ligand associated with or proximate to the cell, preferably in a specific manner. In certain embodiments, binding to the cell or a ligand on or near the cell is specific. The CBA may include peptides and non-peptides.

"Linear or branched alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —CH$_2$CH(CH$_3$)$_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms. More preferably, the alkyl has one to four carbon atoms.

"Linear or branched alkenyl" refers to linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like. Preferably, the alkenyl has two to ten carbon atoms. More preferably, the alkyl has two to four carbon atoms.

"Linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The term "carbocycle," "carbocyclyl" and "carbocyclic ring" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6], or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo [3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "cyclic alkyl" and "cycloalkyl" can be used interchangeably. They refer to a monovalent saturated carbocyclic ring radical. Preferably, the cyclic alkyl is 3 to 7 membered monocyclic ring radical. More preferably, the cyclic alkyl is cyclohexyl.

The term "cyclic alkenyl" refers to a carbocyclic ring radical having at least one double bond in the ring structure.

The term "cyclic alkynyl" refers to a carbocyclic ring radical having at least one triple bond in the ring structure.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar." Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

The terms "heterocycle," "heterocyclyl," and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen, phosphorus, and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclcyl include the oxidized forms such as NO, SO, and $SO_2$.

The term "halo" or "halogen" refers to F, Cl, Br or I.

The alkyl, alkenyl, alkynyl, cyclic alkyl, cyclic alkenyl, cyclic alkynyl, carbocyclyl, aryl, heterocyclyl and heteroaryl described above can be optionally substituted with one more (e.g., 2, 3, 4, 5, 6 or more) substituents.

If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR' R", wherein R' and R" together with the nitrogen atom to which they are attached, may form a heterocyclic ring. The heterocyclic ring formed from R' and R" together with the nitrogen atom to which they are attached may be partially or fully saturated. In one embodiment, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocyclyl, halogen, guanidinium [—NH(C=NH)NH$_2$], —OR$^{100}$, NR$^{101}$R$^{102}$, —NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—CH$_2$CH$_2$O)$_n$R$^{101}$ wherein M is H or a cation (such as Na$^+$ or K$^+$); R$^{101}$, R$^{102}$ and R$^{103}$ are each independently selected from H, linear, branched or cyclic alkyl, alkenyl or alkynyl having from 1 to 10 carbon atoms, a polyethylene glycol unit (—CH$_2$CH$_2$O)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$, aryl, heteroaryl, heterocyclyl, —SR$^{101}$, —SOR$^{101}$, —SO$_2$R$^{101}$ and —SO$_3$M.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound described herein or a derivative thereof that is linked to a cell binding agent.

The term "linkable to a cell binding agent" as used herein refers to the compounds described herein or derivates thereof comprising at least one linking group or a precursor thereof suitable to bond these compounds or derivatives thereof to a cell binding agent.

The term "precursor" of a given group refers to any group which may lead to that group by any deprotection, a chemical modification, or a coupling reaction.

The term "linked to a cell binding agent" refers to a conjugate molecule comprising at least one of the compounds described herein (e.g., compounds of formula (I)-(IV) and (VIII)-(XI) and drug-linker compounds describe herein), or derivative thereof bound to a cell binding agent via a suitable linking group or a precursor thereof.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "prodrug" is also meant to include a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs."

One preferred form of prodrug of the invention includes compounds (with or without any linker groups) and conjugates of the invention comprising an adduct formed between an imine bond of the compounds/conjugates and an imine reactive reagent. Another preferred form of prodrug of the invention includes compounds such as those of formula (I)-(IV), wherein when the double line == between N and C represents a single bond, X is H or an amine protecting group, and the compound becomes a prodrug. A prodrug of the invention may contain one or both forms of prodrugs described herein (e.g., containing an adduct formed between an imine bond of the compounds/conjugates and an imine reactive reagent, and/or containing a Y leaving group when X is —H).

The term "imine reactive reagent" refers to a reagent that is capable of reacting with an imine group. Examples of imine reactive reagent includes, but is not limited to, sulfites ($H_2SO_3$, $H_2SO_2$ or a salt of $HSO_3^-$, $SO_3^{2-}$ or $HSO_2^-$ formed with a cation), metabisulfite ($H_2S_2O_5$ or a salt of $S_2O_5^{2-}$ formed with a cation), mono, di, tri, and tetra-thiophosphates ($PO_3SH_3$, $PO_2S_2H_3$, $POS_3H_3$, $PS_4H_3$ or a salt of $PO_3S^{3-}$, $PO_2S_2^{3-}$, $POS_3^{3-}$ or $PS_4^{3-}$ formed with a cation), thio phosphate esters (($R^iO)_2PS(OR^i$), $R^iSH$, $R^iSOH$, $R^iSO_2H$, $R^iSO_3H$), various amines (hydroxyl amine (e.g., $NH_2OH$), hydrazine (e.g., $NH_2NH_2$), $NH_2O$—$R^i$, $R^{i\prime}NH$—$R^i$, $NH_2$—$R^i$), $NH_2$—CO—$NH_2$, $NH_2$—C(═S)—$NH_2$, thiosulfate ($H_2S_2O_3$ or a salt of $S_2O_3^{2-}$ formed with a cation), dithionite ($H_2S_2O_4$ or a salt of $S_2O_4^{2-}$ formed with a cation), phosphorodithioate (P(═S)($OR^k$)(SH)(OH) or a salt thereof formed with a cation), hydroxamic acid ($R^kC$(═O)NHOH or a salt formed with a cation), hydrazide ($R^kCONHNH_2$), formaldehyde sulfoxylate ($HOCH_2SO_2H$ or a salt of $HOCH_2SO_2^-$ formed with a cation, such as $HOCH_2SO_2^-$ $Na^+$), glycated nucleotide (such as GDP-mannose), fludarabine or a mixture thereof, wherein $R^i$ and $R^{i\prime}$ are each independently a linear or branched alkyl having 1 to 10 carbon atoms and are substituted with at least one substituent selected from —$N(R^j)_2$, —$CO_2H$, —$SO_3H$, and —$PO_3H$; $R^i$ and $R^{i\prime}$ can be further optionally substituted with a substituent for an alkyl described herein; $R^j$ is a linear or branched alkyl having 1 to 6 carbon atoms; and $R^k$ is a linear, branched or cyclic alkyl, alkenyl or alkynyl having 1 to 10 carbon atoms, aryl, heterocyclyl or heteroaryl (preferably, $R^k$ is a linear or branched alkyl having 1 to 4 carbon atoms; more preferably, $R^k$ is methyl, ethyl or propyl). Preferably, the cation is a monovalent cation, such as Na$^+$ or K$^+$. Preferably, the imine reactive reagent is selected from sulfites, hydroxyl amine, urea and hydrazine. More preferably, the imine reactive reagent is NaHSO$_3$ or KHSO$_3$.

As used herein and unless otherwise indicated, the terms "biohydrolyzable amide," "biohydrolyzable ester," "biohydrolyzable carbamate," "biohydrolyzable carbonate," "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines. Particularly favored prodrugs and prodrug salts are those that increase the bioavailability of the compounds of this invention when such compounds are administered to a mammal.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound which further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells, and/or benign or pre-cancerous cells.

A "therapeutic agent" encompasses both a biological agent such as an antibody, a peptide, a protein, an enzyme or a chemotherapeutic agent.

A "chemotherapeutic agent" is a chemical compound useful in the treatment of cancer.

A "metabolite" is a product produced through metabolism in the body of a specified compound, a derivative thereof, or a conjugate thereof, or salt thereof. Metabolites of a compound, a derivative thereof, or a conjugate thereof, may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound. Such groups are well known in the art (see for example P. Wuts and T. Greene, 2007, Protective Groups in Organic Synthesis, Chapter 7, J. Wiley & Sons, NJ) and exemplified by carbamates such as methyl and ethyl carbamate, FMOC, substituted ethyl carbamates, carbamates cleaved by 1,6-β-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, Protective Groups in Organic Synthesis, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "bifunctional crosslinking agent," "bifunctional linker" or "crosslinking agents" refers to modifying agents that possess two reactive groups; one of which is capable of reacting with a cell binding agent while the other one reacts with the cytotoxic compound to link the two moieties together. Such bifunctional crosslinkers are well known in the art (see, for example, Isalm and Dent in *Bioconjugation* chapter 5, p 218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc. P.O. Box 117, Rockland, Ill. 61105, USA) and include, but not limited to, bis-maleimidopolyethyleneglycol (BMPEO), BM(PEO)$_2$, BM(PEO)$_3$, N-(β-maleimidopropyloxy)succinimide ester (BMPS), γ-maleimidobutyric acid N-succinimidyl ester (GMBS), ε-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido)hexanoate (SMPH), succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

A "linker," "linker moiety," or "linking group" as defined herein refers to a moiety that connects two groups, such as a cell binding agent and a cytotoxic compound, together. Typically, the linker is substantially inert under conditions for which the two groups it is connecting are linked. A bifunctional crosslinking agent may comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a linker moiety and a second reactive group, which can then react with a cytotoxic compound. The linking moiety may contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference, each of which is expressly incorporated herein by reference.

In one embodiment, the linking group with a reactive group attached at one end, such as a reactive ester, is selected from the following:

—O(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X",

—O(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X",

—O(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —O(CR$_{20}$R$_{21}$)$_m$(piperazino)$_{t'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —O(CR$_{20}$R$_{21}$)$_m$(pyrrolo)$_{t'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —O(CR$_{20}$R$_{21}$)$_m$A"$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(alkynyl)$_{n'}$(CR$_{22}$R$_{23}$)(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(piperazino)$_{t'}$(CR$_{22}$R$_{23}$)(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(pyrrolo)$_{t'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$A"$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p''}$(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p''}$(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p''}$(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$—(CO)$_t$X", —NR$_{33}$(C=O)$_{p''}$(CR$_{20}$R$_{21}$)$_m$(piperazino)$_{t'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p''}$(CR$_{20}$R$_{21}$)$_m$(pyrrolo)$_{t'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$$^-$(CO)$_t$X", —NR$_{33}$(C=O)$_{p''}$(CR$_{20}$R$_{21}$)$_m$A"$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(alkynyl)$_{n'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(piperazino)$_{t'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$A"$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n'}$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n'}$(alkynyl)$_{n'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$-(CO)$_t$X", —(CR$_{20}$R$_{21}$)$_m$(CR$_{29}$=N—NR$_{30}$)$_{n'}$A"$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", wherein:

m, n, p, q, m', n', t' are integer from 1 to 10, or are optionally 0;

t, m", n", and p" are 0 or 1;

X" is selected from OR$_{36}$, SR$_{37}$, NR$_{38}$R$_{39}$, wherein R$_{36}$, R$_{37}$, R$_{38}$, R$_{39}$ are H, or linear, branched or cyclic alkyl, alkenyl or alkynyl having from 1 to 20 carbon atoms and, or, a polyethylene glycol unit —(OCH$_2$CH$_2$)$_n$, R$_{37}$, optionally, is a thiol protecting group when t=1, COX" forms a reactive ester selected from N-hydroxysuccinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide bond formation;

Y" is absent or is selected from O, S, S—S or NR$_{32}$, wherein R$_{32}$ has the same definition as given above for R; or when Y" is not S—S and t=0, X" is selected from a maleimido group, a haloacetyl group or SR$_{37}$, wherein R$_{37}$ has the same definition as above;

A" is an amino acid residue or a polypeptide containing between 2 to 20 amino acid residues;

R$_{20}$, R$_{21}$, R$_{22}$, R$_{23}$, R$_{24}$, R$_{25}$, R$_{26}$, and R$_{27}$ are the same or different, and are —H or a linear or branched alkyl having from 1 to 5 carbon atoms;

R$_{29}$ and R$_{30}$ are the same or different, and are —H or alkyl from 1 to 5 carbon atoms;

R$_{33}$ is —H or linear, branched or cyclic alkyl, alkenyl or alkynyl having from 1 to 12 carbon atoms, a polyethylene glycol unit R—(OCH$_2$CH$_2$)$_n$—, or R$_{33}$ is —COR$_{34}$, —CSR$_{34}$, —SOR$_{34}$, or —SO$_2$R$_{34}$, wherein R$_{34}$ is H or linear, branched or cyclic alkyl, alkenyl or alkynyl having from 1 to 20 carbon atoms or, a polyethylene glycol unit —(OCH$_2$CH$_2$)$_n$; and one of R$_{40}$ and R$_{41}$ is optionally a negatively or positively charged functional group and the other is H or alkyl, alkenyl, alkynyl having 1 to 4 carbon atoms.

Any of the above linking groups may be present in any of the compounds, drug-linker compounds, or conjugates of the invention, including replacing the linking groups of any of the formulas described herein.

The term "amino acid" refers to naturally occurring amino acids or non-naturally occurring amino acid. In one embodiment, the amino acid is represented by NH$_2$—C(R$^{aa'}$R$^{aa}$)—C(=O)OH, wherein R$^{aa}$ and R$^{aa'}$ are each independently H, an optionally substituted linear, branched or cyclic alkyl, alkenyl or alkynyl having 1 to 10 carbon atoms, aryl, heteroaryl or heterocyclyl, or R$^{aa}$ and the N-terminal nitrogen atom can together form a heterocyclic ring (e.g., as in proline). The term "amino acid residue" refers to the corresponding residue when one hydrogen atom is removed from the amine and/or carboxy end of the amino acid, such as —NH—C(R$^{aa'}$R$^{aa}$)—C(=O)O—.

The term "cation" refers to an ion with positive charge. The cation can be monovalent (e.g., Na$^+$, K$^+$, etc.), bi-valent (e.g., Ca$^{2+}$, Mg$^{2+}$, etc.) or multi-valent (e.g., Al$^{3+}$ etc.). Preferably, the cation is monovalent.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

Cytotoxic Compounds

In a first embodiment, the present invention is directed to cytotoxic compounds described herein (e.g., compounds of structural formula (I), (II), (III), (IV), (V) or (VI), or a pharmaceutically acceptable salt thereof). In certain embodiments, the cytotoxic compound is represented by structural formula (I) or a pharmaceutically acceptable salt thereof.

In certain embodiments, for structural formulas (I), (II), (III), (IV), (V) and (VI), one of L', L" and L'" is represented by formula (A), and the others are each independently —H, an linear or branched alkyl having from 1 to 6 carbon atoms, halogen, —OH, (C$_1$-C$_6$)alkoxy, or —NO$_2$. Specifically, one of L', L" and L'" is represented by formula (A), and the others are —H.

In a 1$^{st}$ specific embodiment, for structural formulas (I), (II), (III), (IV), (V) and (VI), L' is represented by formula (A) and L" and L'" are both —H; and the remaining variables are as described above in the first embodiment.

In a 2$^{nd}$ specific embodiment, for structural formulas (I), (II), (III), (IV), (V) and (VI), R$_x$ is a linear, branched or cyclic alkyl having 1 to 6 carbon atoms optionally substituted with halogen, —OH, (C$_1$-C$_3$)alkyl, (C$_1$-C$_3$)alkoxy, halo(C$_1$-C$_3$)alkyl, or a charged substituent or an ionizable group Q; and the remaining variables are as described above in the first embodiment or the 1$^{st}$ specific embodiment.

In certain embodiments, Q is i) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, or a pharmaceutically acceptable salt thereof; or, ii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene or an optionally substituted phenylene; $R_{14}$ to $R_{16}$ are each independently an optionally substituted alkyl; and $X^-$ is a pharmaceutically acceptable anion; and the remaining variables are as described above in the $2^{nd}$ specific embodiment. More specifically, Q is $-SO_3H$ or a pharmaceutically acceptable salt thereof.

In a $3^{rd}$ specific embodiment, for structural formulas (I), (II), (III), (IV), (V) and (VI), J is a moiety comprising a reactive group selected from the group consisting of $NHR^{c1}$, $-COOH$, and $-COE$, wherein $-COE$ represents a reactive ester and $R^{c1}$ is $-H$ or linear or branched alkyl having 1 to 4 carbon atoms optionally substituted with halogen, $-OH$ or $(C_1-C_3)$alkoxy; and the remaining variables are as described above in the first embodiment or the $1^{st}$ or $2^{nd}$ specific embodiment.

In certain embodiments, J is COE selected from N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5,6-tetrafluorophenyl) ester, and pentafluorophenyl ester; and the remaining variables are as described above in the $3^{rd}$ specific embodiment. More specifically, COE is a N-hydroxysuccinimide ester.

In a $4^{th}$ specific embodiment, for structural formulas (I), (II), (III), (IV), (V) and (VI), L' is represented by the following formula:

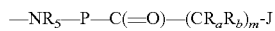  (B1);

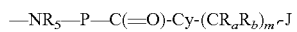  (B2);

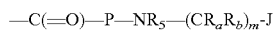  (C1);

or

  (C2), wherein:
J is $-COE$;
$R_a$ and $R_b$, for each occurrence, are each independently $-H$, $(C_1-C_3)$alkyl or a charged substituent or an ionizable group Q;
m is an integer from 1 to 6;
m' is 0 or an integer from 1 to 6;
Cy is a cyclic alkyl having 5 or 6 ring carbon atoms optionally substituted with halogen, $-OH$, $(C_1-C_3)$alkyl, $(C_1-C_3)$alkoxy, or halo$(C_1-C_3)$alkyl; and the remaining variables are as described above in the first embodiment or the $1^{st}$, $2^{nd}$ or $3^{rd}$ specific embodiment.

In certain embodiments, $R_a$ and $R_b$ are both H; Cy for formulas (B2) and (C2) is cyclohexane; and $R_5$ is H or Me; and the remaining variables are as described above in the $4^{th}$ specific embodiment. More specifically, m' in formulas (B2) and (C2) is 0 or 1.

In a $5^{th}$ specific embodiment, for structural formulas (I), (II), (III), (IV), (V) and (VI), L' is represented by the following formula:

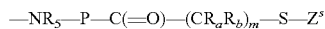  (B3);

or

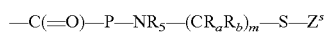  (C3), wherein:
$R_a$ and $R_b$, for each occurrence, are each independently $-H$, $(C_1-C_3)$alkyl or a charged substituent or an ionizable group Q;
m is an integer from 1 to 6;

$Z^s$ is $-H$, $-SR^d$, $-C(=O)R^{d1}$ or is selected from any one of the following formulas:

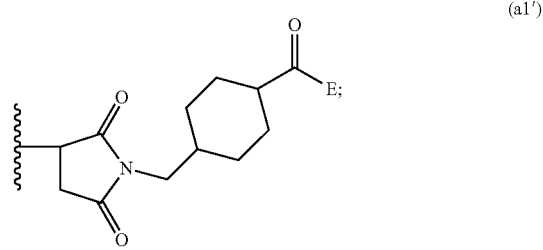  (a1')

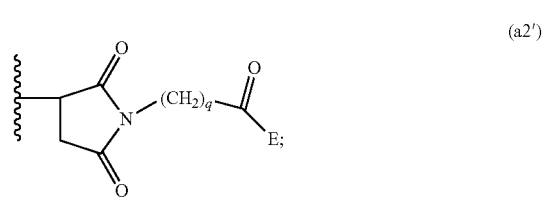  (a2')

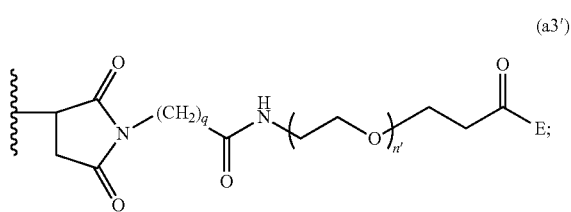  (a3')

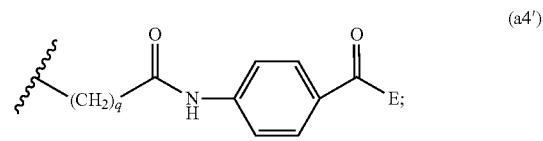  (a4')

  (a5')

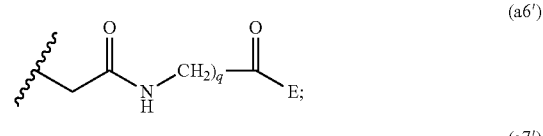  (a6')

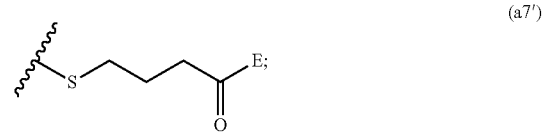  (a7')

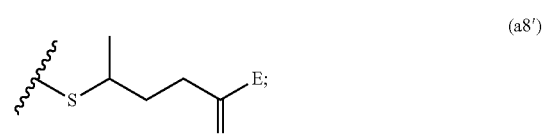  (a8')

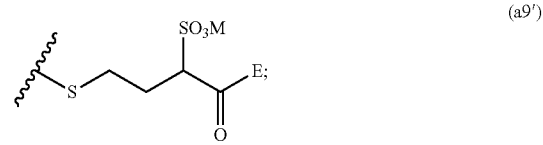  (a9')

-continued (a10′)
(a11′)
(a12′)
(a13′)
(a14′)

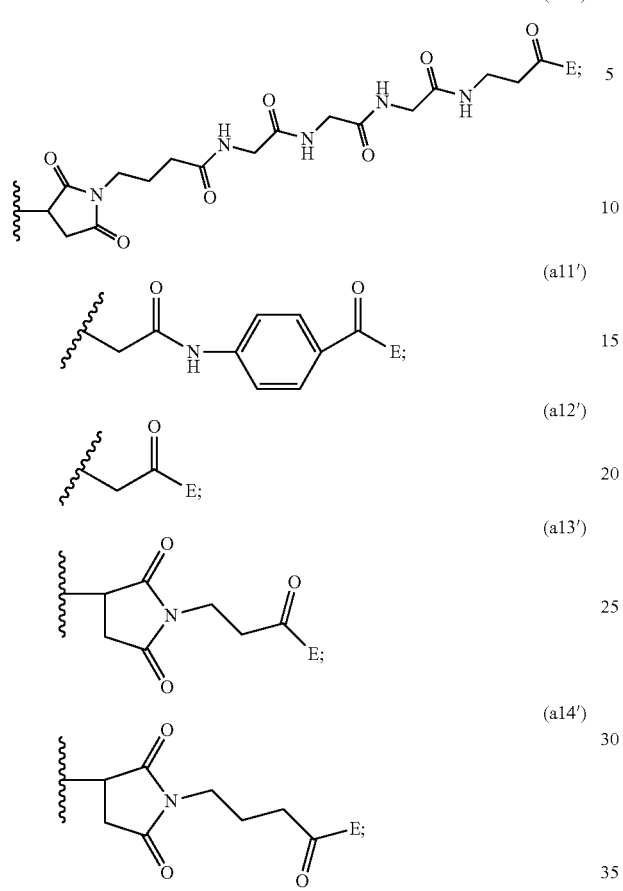

(a15′)

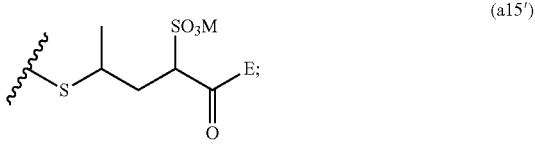

wherein:

q is an integer from 1 to 5;

n' is an integer from 2 to 6;

M is a cation (e.g., $H^+$, $Na^+$ or $K^+$);

$R^d$ is a linear or branched alkyl having 1 to 6 carbon atoms or selected from phenyl, nitrophenyl (e.g., 2 or 4-nitrophenyl), dinitrophenyl (e.g., 2,4-dinitrophenyl), carboxynitrophenyl (e.g., 3-carboxy-4-nitrophenyl), pyridyl or nitropyridyl (e.g., 4-nitropyridyl);

$R^{d1}$ is a linear or branched alkyl having 1 to 6 carbon atoms;

and the remaining variables are as described above in the first embodiment or the $1^{st}$, $2^{nd}$, $3^{rd}$ or $4^{th}$ specific embodiment.

In one embodiment, $Z^s$ is —H. In another embodiment, $Z^s$ is —SMe or —SPy (Py is a pyridyl).

In yet another embodiment, $Z^s$ is selected from any one of the following formulas:

(a1)

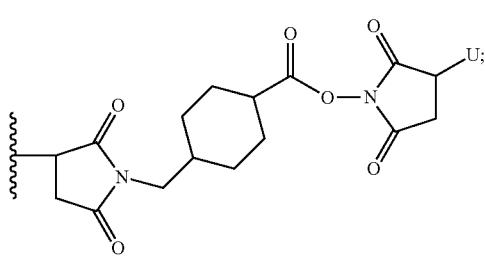

(a2)

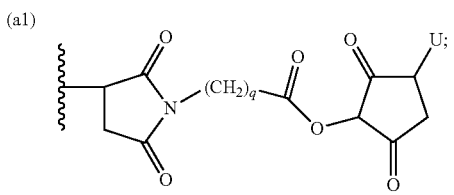

(a3)

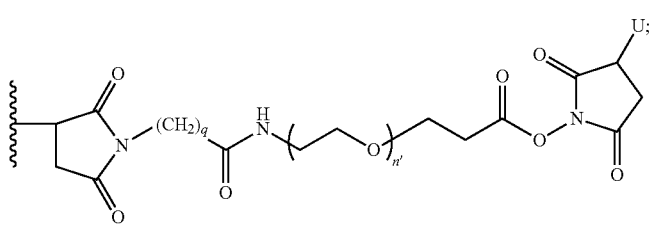

(a4)

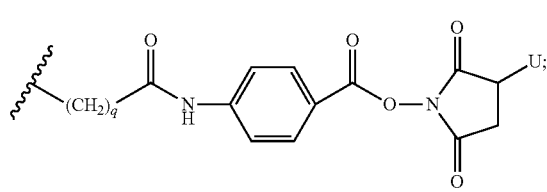

(a5)

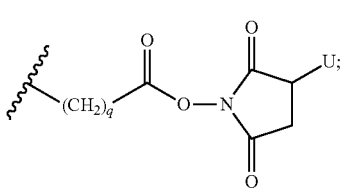

-continued
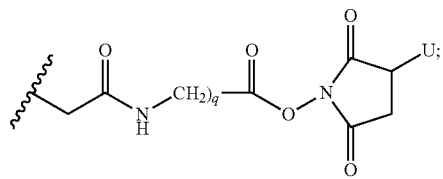 (a6)
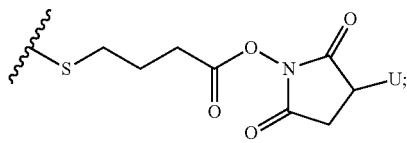 (a7)
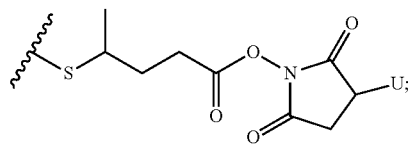 (a8)
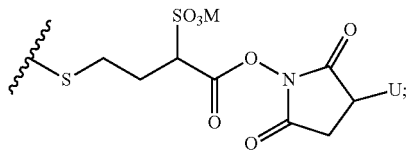 (a9)
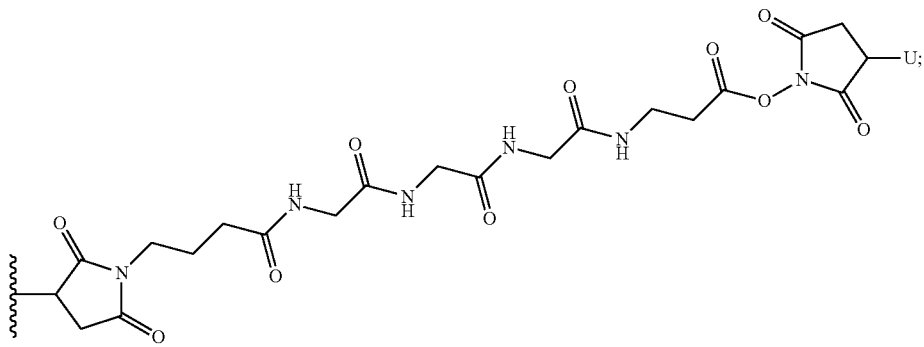 (a10)
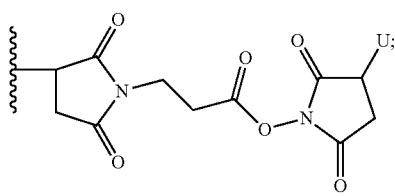 (a11)
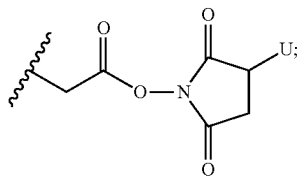 (a12)
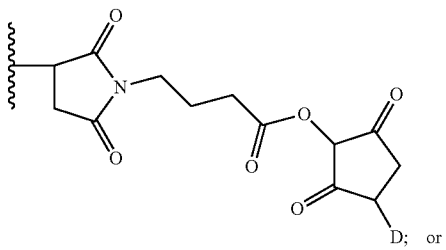 (a13) (a14)
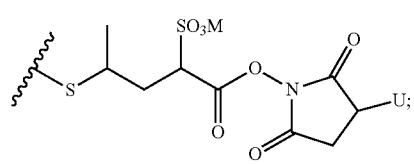 (a15)

wherein U is —H or —SO$_3$M; and the remaining variables are as described above for formulas (a1')-(a15').

In certain embodiments, the charged substituent or an ionizable group Q is i) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, or a pharmaceutically acceptable salt thereof; or, ii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene or an optionally substituted phenylene; R$_{14}$ to R$_{16}$ are each independently an optionally substituted alkyl; and X$^-$ is a pharmaceutically acceptable anion; and the remaining variables are as described above in the 5$^{th}$ specific embodiment. More specifically, Q is —SO$_3$H or a pharmaceutically acceptable salt thereof.

In certain embodiments, R$_a$ and R$_b$ are both —H and R$_5$ is H or Me; and the remaining variables are as described above in the 5$^{th}$ specific embodiment.

In certain embodiments, —(CR$_a$R$_b$)$_m$— is —(CH$_2$)$_{m''}$—C(Me$_2$)- and m'' is an integer from 1 to 5; the remaining variables are as described above in the 5$^{th}$ specific embodiment.

In a 6$^{th}$ specific embodiment, for structural formulas (I), (II), (III), (IV), (V) and (VI), P is a peptide containing 2 to 10 amino acid residues; and the remaining variables are as described above in the first embodiment or the 1$^{st}$, 2$^{nd}$, 3$^{rd}$, 4$^{th}$ or 5$^{th}$ specific embodiment.

In certain embodiments, P is a peptide containing 2 to 5 amino acid residues; and the remaining variables are as described above in the 6$^{th}$ specific embodiment.

In certain embodiments, P is selected from Gly-Gly-Gly, Ala-Val, Val-Ala, Val-Cit, Val-Lys, Phe-Lys, Lys-Lys, Ala-Lys, Phe-Cit, Leu-Cit, Lle-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu, β-Ala-Leu-Ala-Leu and Gly-Phe-Leu-Gly, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala; and the remaining variables are as described above in the 6$^{th}$ specific embodiment.

In certain embodiments, P is Gly-Gly-Gly, Ala-Val, Ala-Ala, Ala-D-Ala, D-Ala-Ala, and D-Ala-D-Ala; and the remaining variables are as described above in the 6$^{th}$ specific embodiment.

In a 7$^{th}$ specific embodiment, for structural formulas (I), (II), (III), (IV), (V) and (VI), the double line == between N and C represents a double bond; and the remaining variables are as described above in the first embodiment, or the 1$^{st}$, 2$^{nd}$, 3$^{rd}$, 4$^{th}$, 5$^{th}$ or 6$^{th}$ specific embodiment.

In a 8$^{th}$ specific embodiment, for structural formulas (I), (II), (III), (IV), (V) and (VI), the double line == between N and C represents a single bond, X is —H or an amine protecting group; and Y is selected from —H, —OR, —OCOR', —SR, —NR'R'', an optionally substituted 5- or 6-membered nitrogen-containing heterocycle, —SO$_3$H, —SO$_2$H and —OSO$_3$H; and the remaining variables are as described in the first embodiment or the 1$^{st}$, 2$^{nd}$, 3$^{rd}$, 4$^{th}$, 5$^{th}$, 6$^{th}$ or 7$^{th}$ specific embodiment.

In certain embodiments, Y is selected from —H, —SO$_3$M, —OH, —OMe, —OEt or —NHOH, wherein M is —H, Na$^+$ or K$^+$; and the remaining variables are as described above in the 8$^{th}$ specific embodiment. More specifically, Y is —H, —SO$_3$M or —OH.

In a 9$^{th}$ specific embodiment, for structural formulas (I), (II), (III), (IV), (V) and (VI), X' is selected from the group consisting of —H, —OH, an optionally substituted linear, branched or cyclic alkyl, alkenyl or alkynyl having from 1 to 10 carbon atoms, and phenyl; and the remaining variables are as described in the first embodiment or the 1$^{st}$, 2$^{nd}$, 3$^{rd}$, 4$^{th}$, 5$^{th}$, 6$^{th}$, 7$^{th}$ or 8$^{th}$ specific embodiment.

In certain embodiments, X' is —H, —OH, (C$_1$-C$_3$)alkyl, halo(C$_1$-C$_3$)alkyl, or phenyl; and the remaining variables are as described above in the 9$^{th}$ specific embodiment. More specifically, X' is —H, —OH or -Me. Even more specifically, X' is —H.

In a 10$^{th}$ specific embodiment, for structural formulas (I), (II), (III), (IV), (V) and (VI), Y' is —H, an oxo group, (C$_1$-C$_3$)alkyl or halo(C$_1$-C$_3$)alkyl; and the remaining variables are as described in the first embodiment or the 1$^{st}$, 2$^{nd}$, 3$^{rd}$, 4$^{th}$, 5$^{th}$, 6$^{th}$, 7$^{th}$ 8$^{th}$ or 9$^{th}$ specific embodiment. More specifically, Y' is —H or oxo. Even more specifically, Y' is —H.

In a 11$^{th}$ specific embodiment, for structural formulas (I), (II), (III), (IV), (V) and (VI), A and A' are the same or different, and are selected from —O—, —S—, —NR$_5$—, and oxo —(C=O)—; and the remaining variables are as described in the first embodiment or the 1$^{st,}$ 2$^{nd}$, 3$^{rd}$, 4$^{th}$, 5$^{th}$, 6$^{th}$, 7$^{th}$ 8$^{th}$, 9$^{th}$ or 10$^{th}$ specific embodiment. More specifically, A and A' are the same or different, and are selected from —O— and —S—. Even more specifically, A and A' are —O—.

In a 12$^{th}$ specific embodiment, for structural formulas (I), (II), (III), (IV), (V) and (VI), R$_6$ is —OMe; and the remaining variables are as described in the first embodiment or the 1$^{st}$, 2$^{nd}$, 3$^{rd}$, 4$^{th}$, 5$^{th}$, 6$^{th}$, 7$^{th}$, 9$^{th}$, 10$^{th}$ or 11$^{th}$ specific embodiment.

In a 13$^{th}$ specific embodiment, for structural formulas (I), (II), (III), (IV), (V) and (VI), R$_1$, R$_2$, R$_3$, R$_4$, R$_1$', R$_2$', R$_3$' and R$_4$' are independently —H, halogen, —NO$_2$, —OH, (C$_1$-C$_3$)alkyl, halo(C$_1$-C$_3$)alkyl or (C$_1$-C$_3$)alkoxy; and the remaining variables are as described in the first embodiment or the 1$^{st}$, 2$^{nd}$, 3$^{rd}$, 4$^{th}$, 5$^{th}$, 6$^{th}$ 7$^{th}$, 8$^{th}$, 9$^{th}$, 10$^{th}$, 11$^{th}$ or 12$^{th}$ specific embodiment. More specifically, R$_1$, R$_2$, R$_3$, R$_4$, R$_1$', R$_2$', R$_3$' and R$_4$' are all —H.

In a 14$^{th}$ specific embodiment, for structural formulas (I), (II), (III), (IV), (V) and (VI), R, R', R'' and R$_5$ are each independently —H or (C$_1$-C$_3$)alkyl; and the remaining variables are as described in the first embodiment or the 1$^{st}$, 2$^{nd}$ 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$ or 13$^{th}$ specific embodiment.

In a 15$^{th}$ specific embodiments, for structural formulas (I), (II), (III), (IV), (V) and (VI), the double line == between N and C represents a single bond or double bond, provided that when it is a double bond X is absent and Y is —H, and when it is a single bond, X is —H, Y is —OH or —SO$_3$M;

R$_1$, R$_2$, R$_3$, R$_4$, R$_1$', R$_2$', R$_3$' and R$_4$' are all —H;

R$_6$ is —OMe;

X' and Y' are both —H;

A and A' are —O—;

M is H, Na$^+$ or K$^+$; and the remaining variables are as described in the first embodiment or the 1$^{st}$, 2$^{nd}$, 3$^{rd}$, 4$^{th}$, 5$^{th}$ or 6$^{th}$ specific embodiment.

In a 16$^{th}$ specific embodiment, the cytotoxic compound of the present invention is selected from the following formulas:

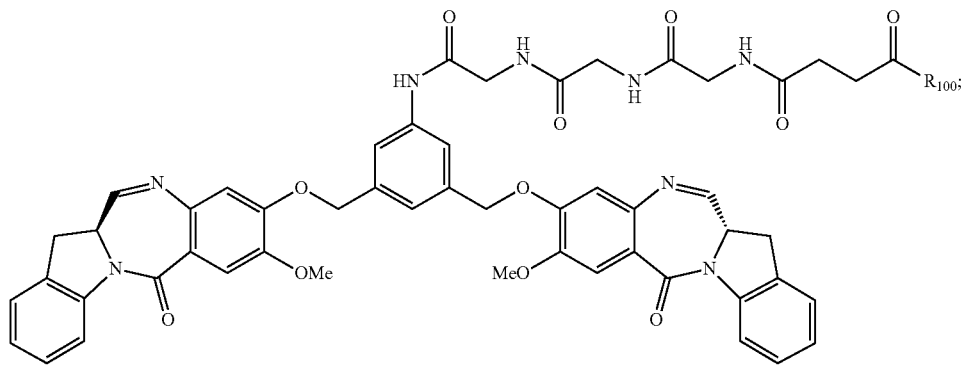
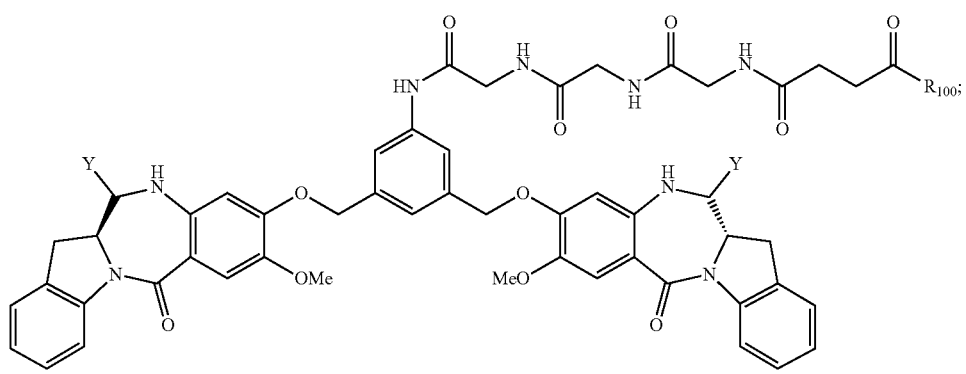
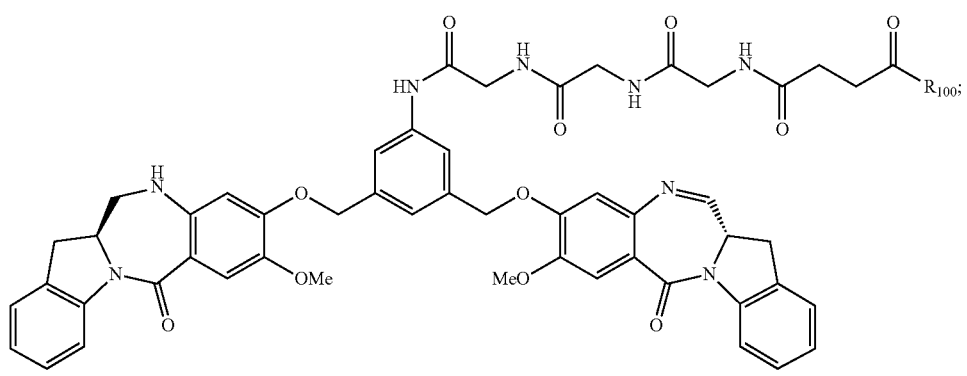
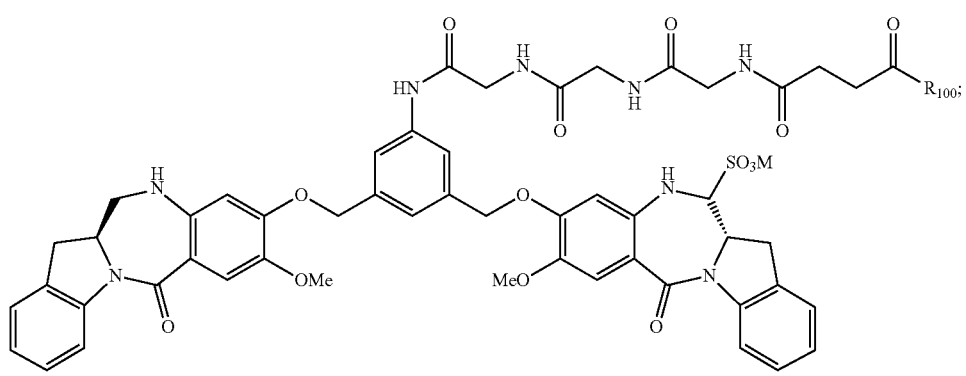

-continued
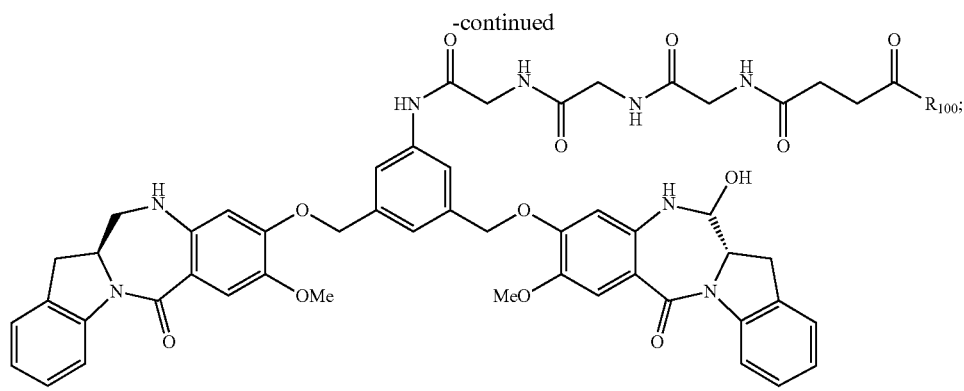
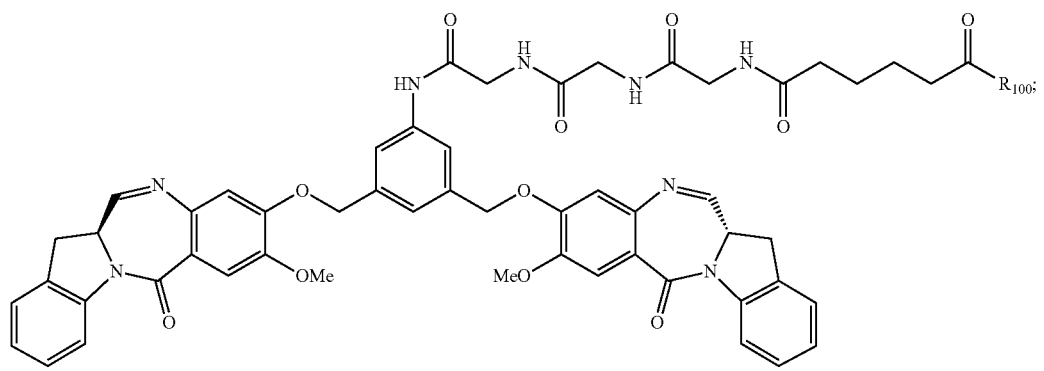
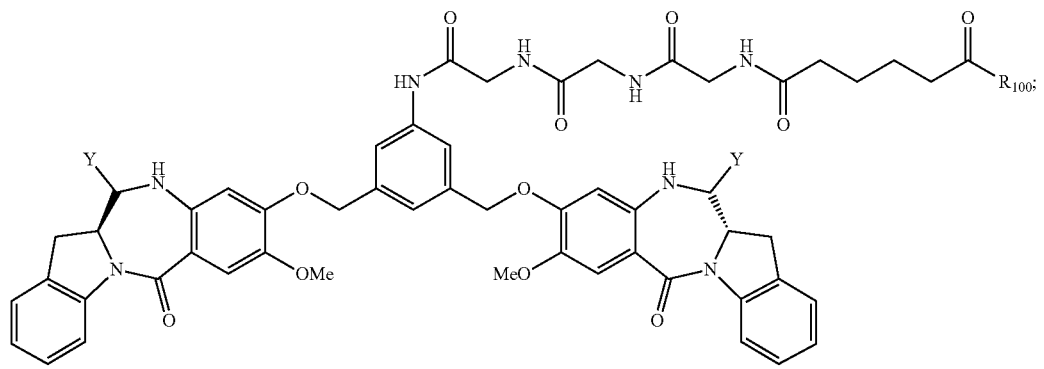
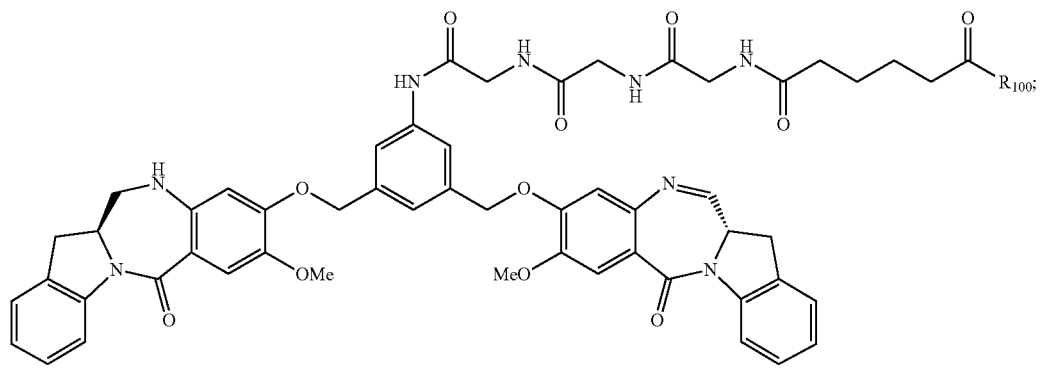

-continued
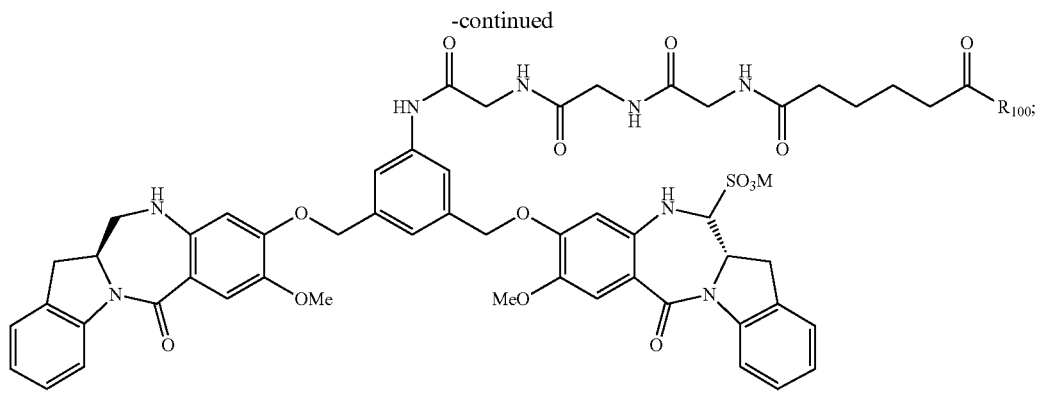
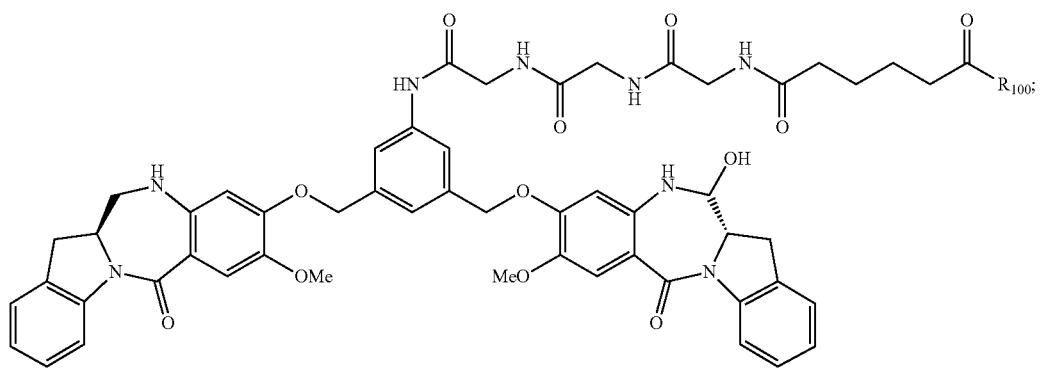
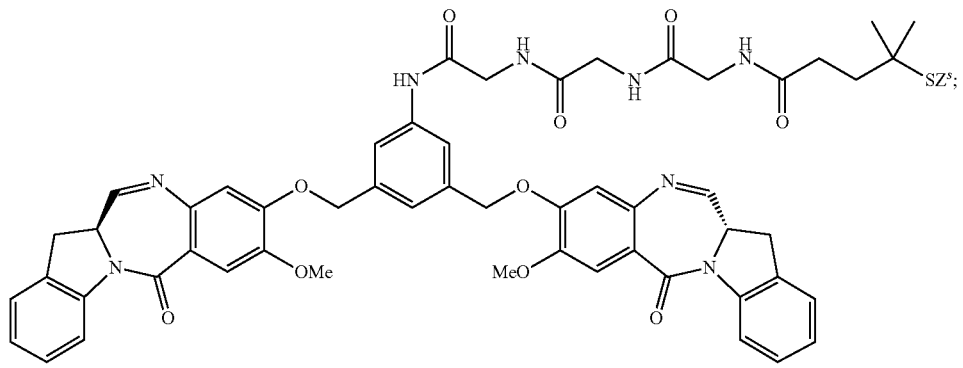
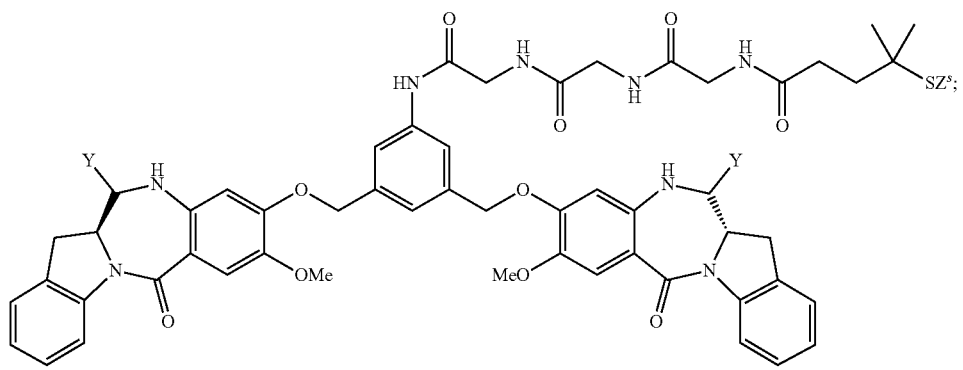

-continued
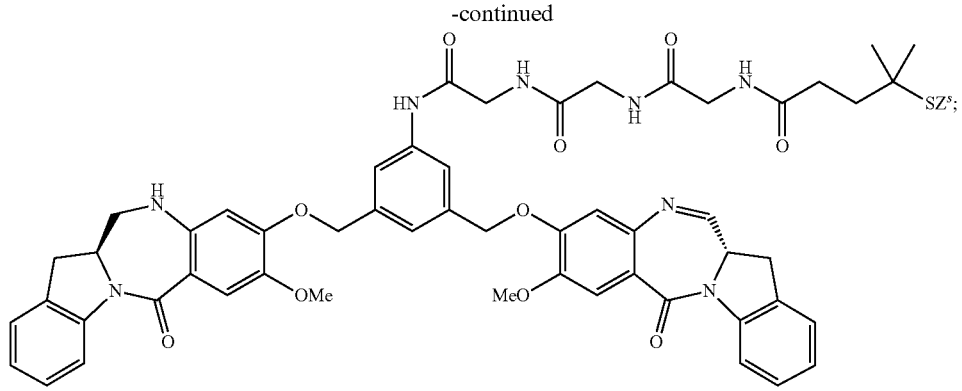
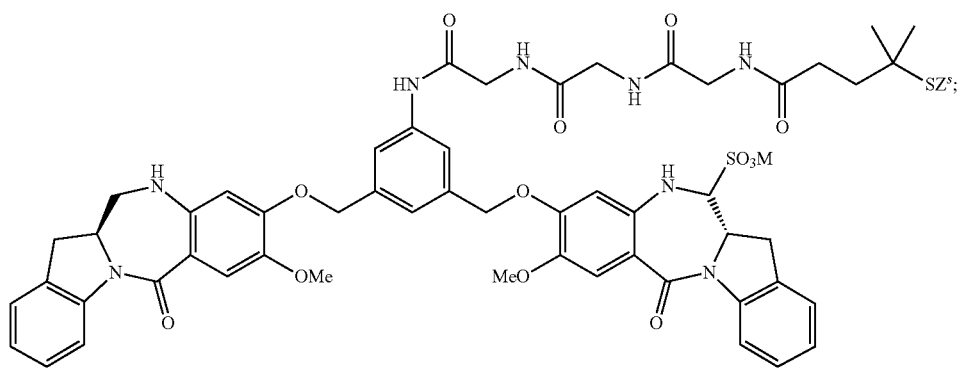
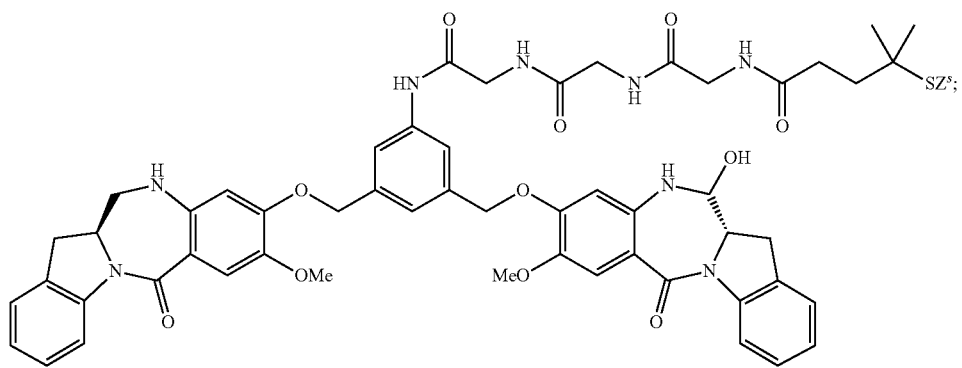
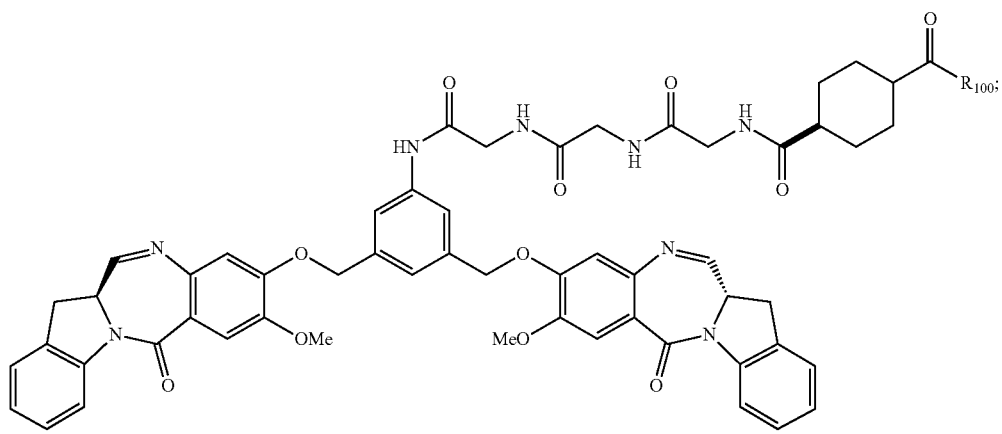

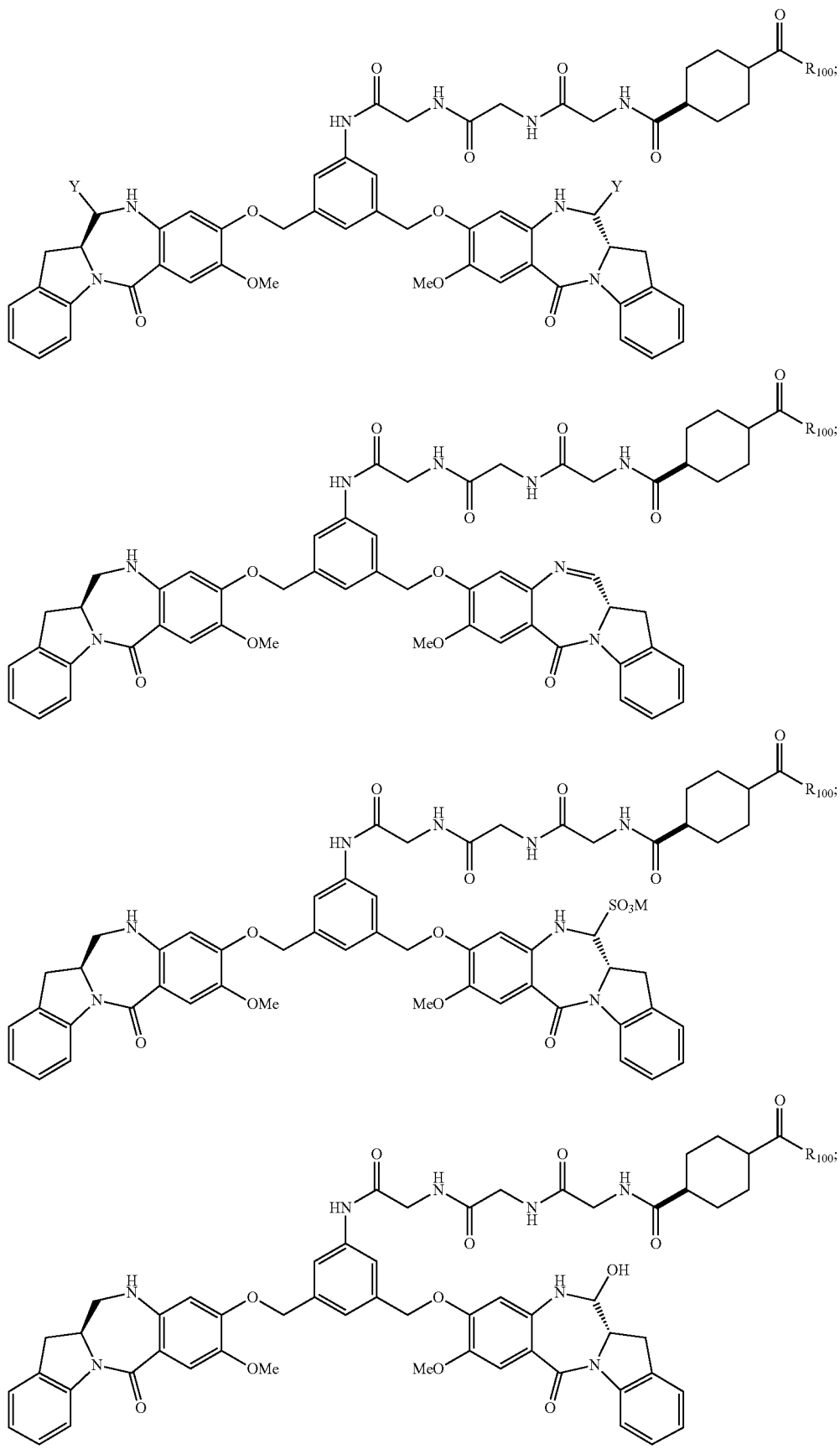

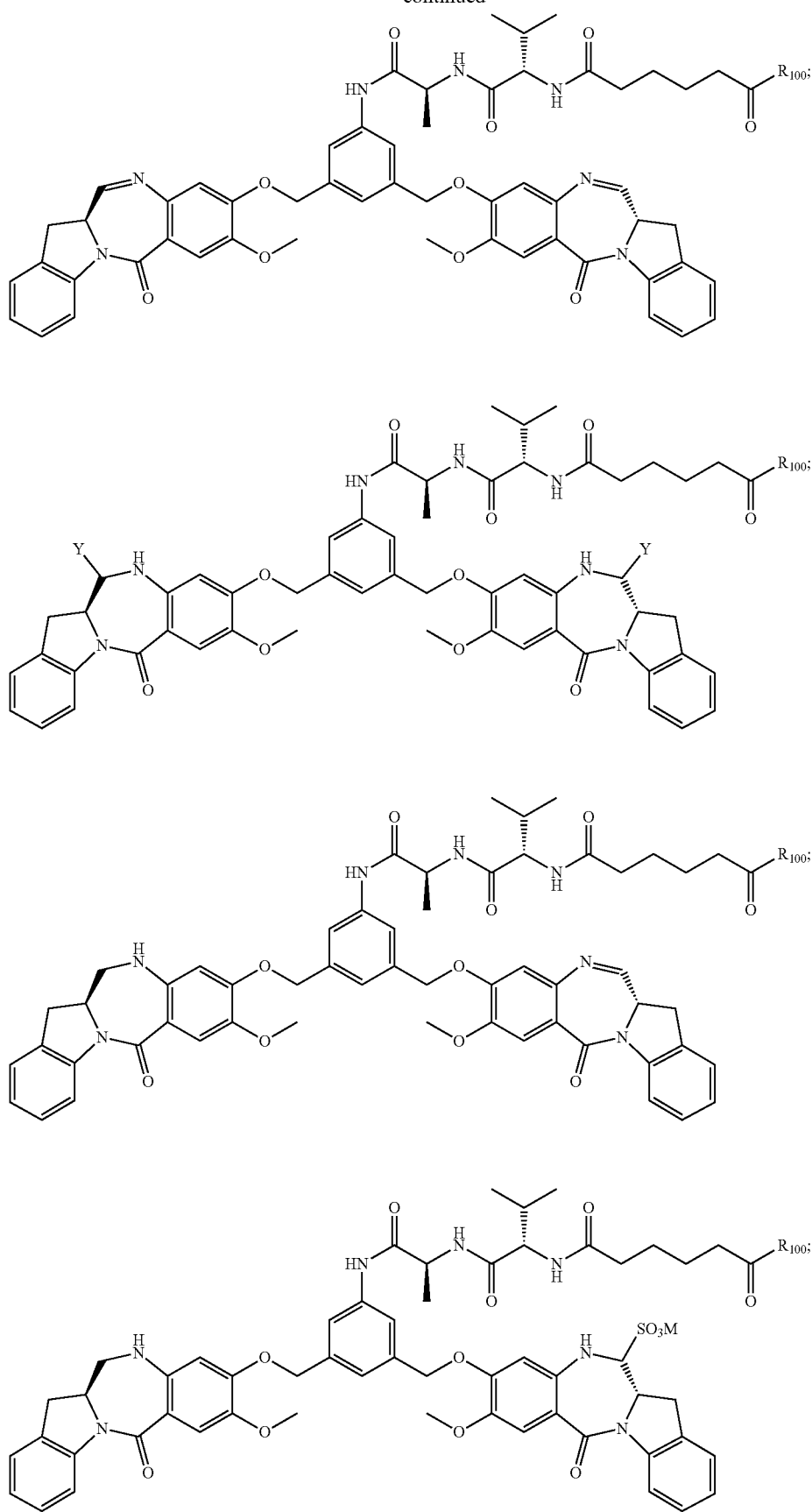

-continued
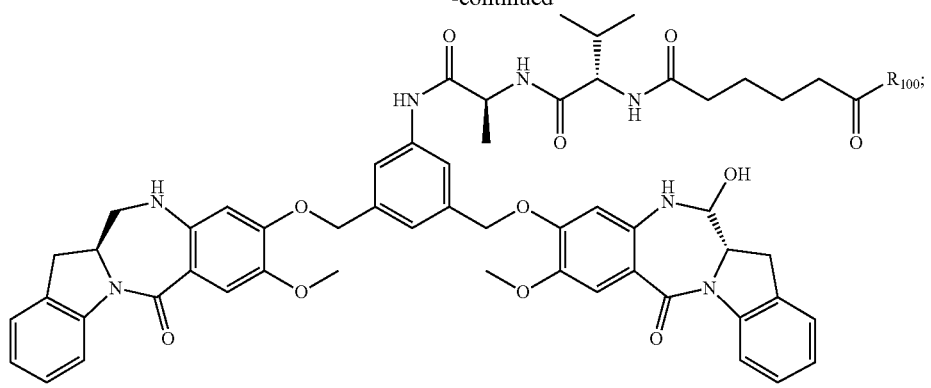
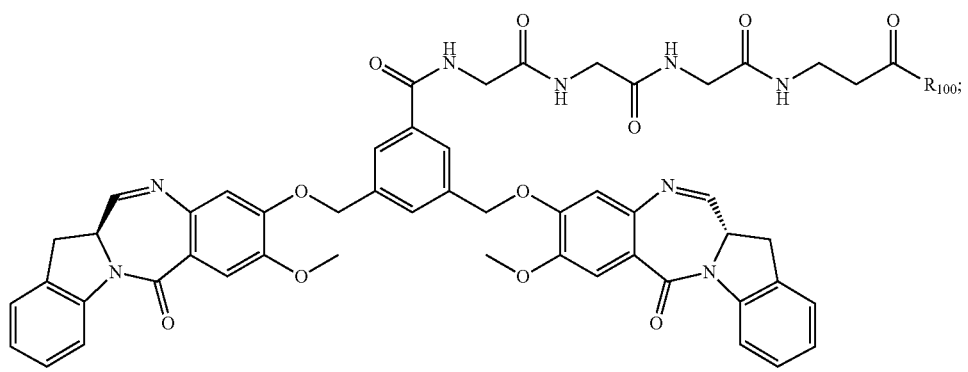
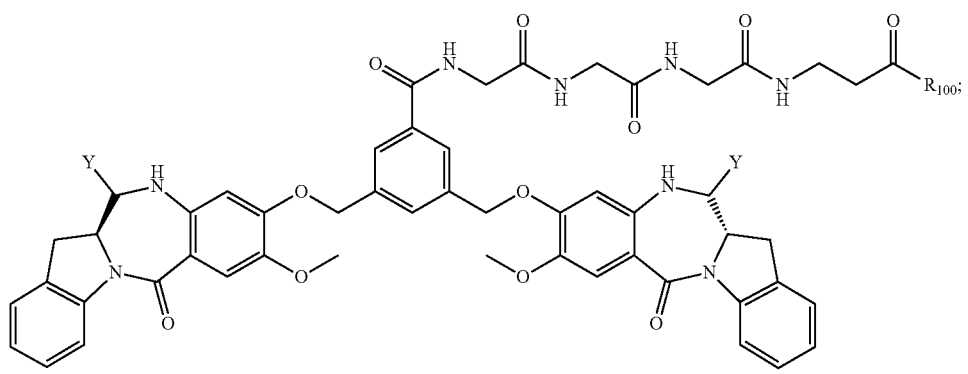
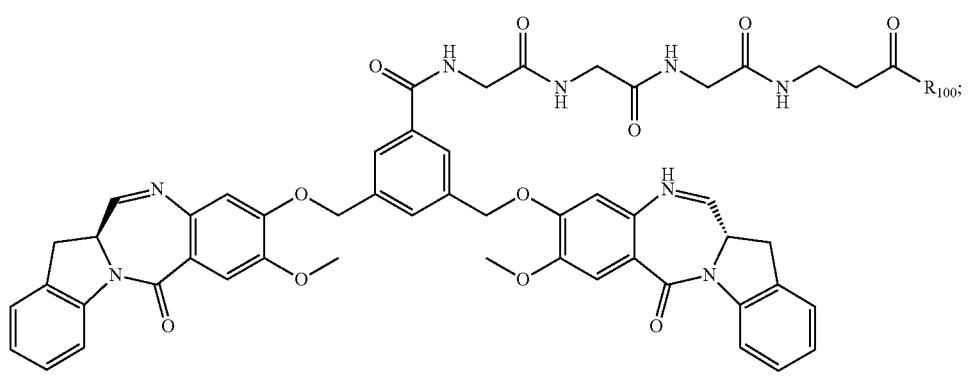

-continued
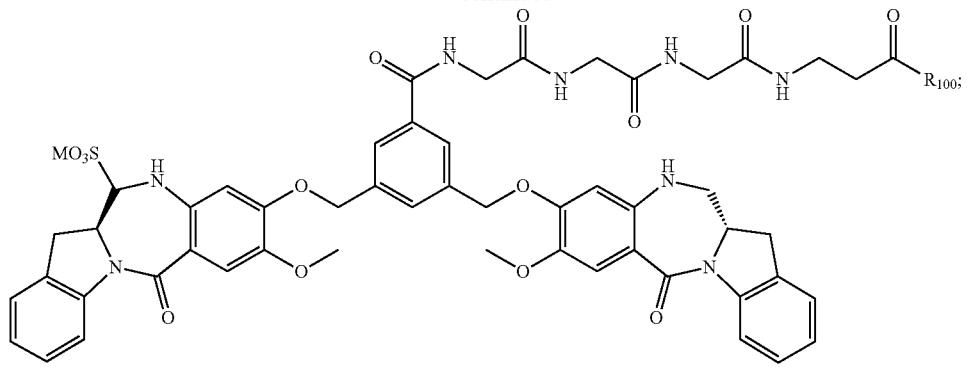
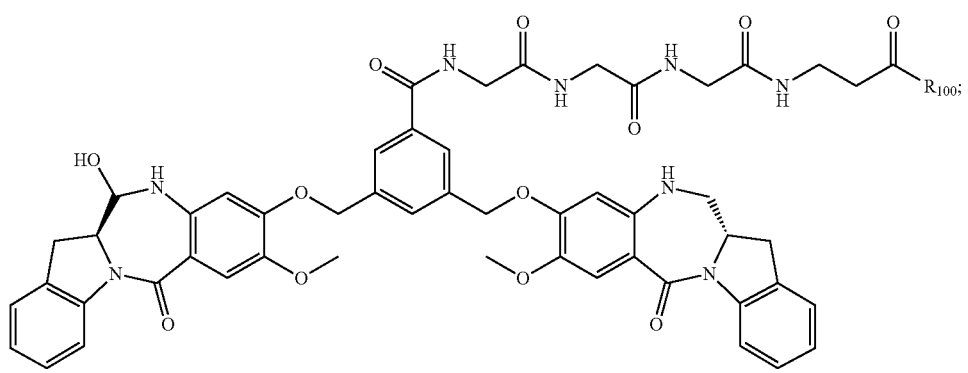
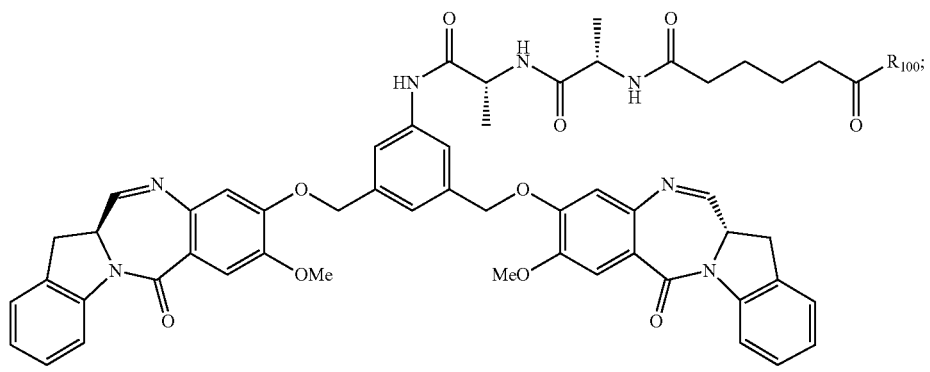
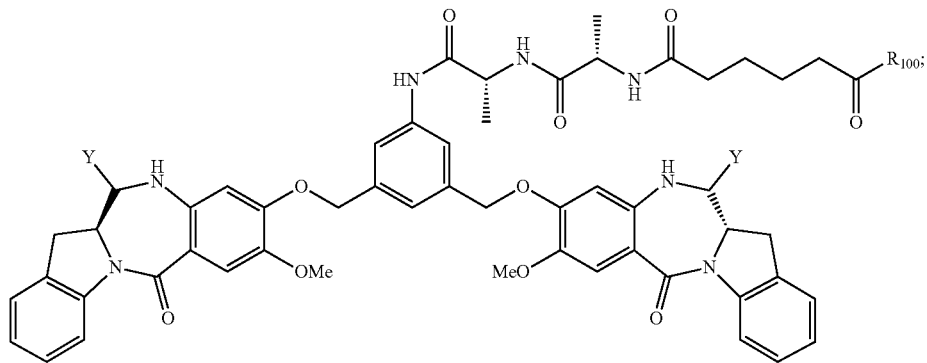

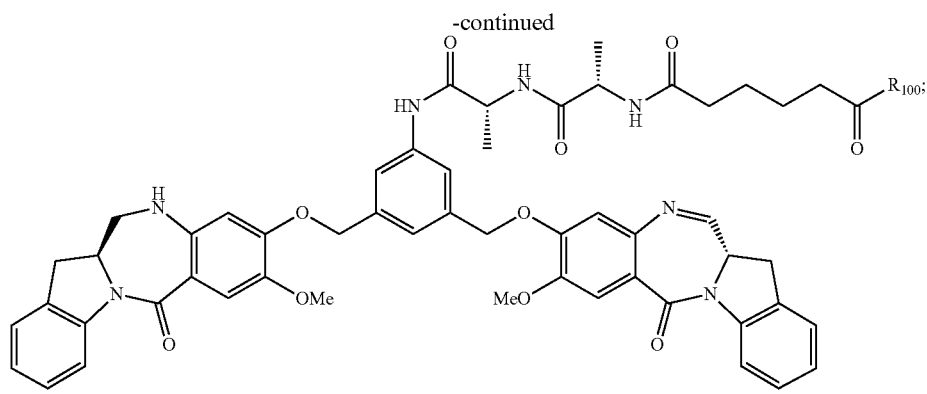
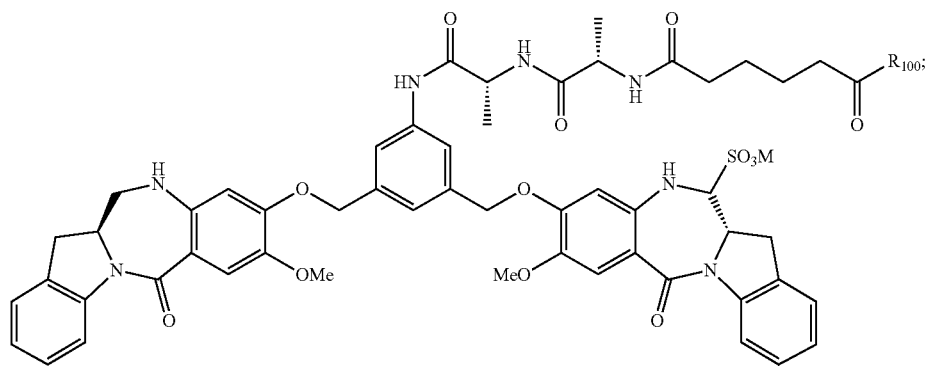
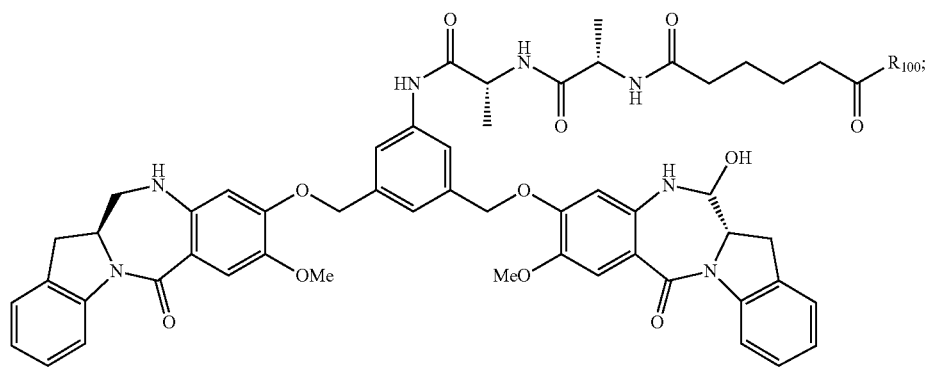
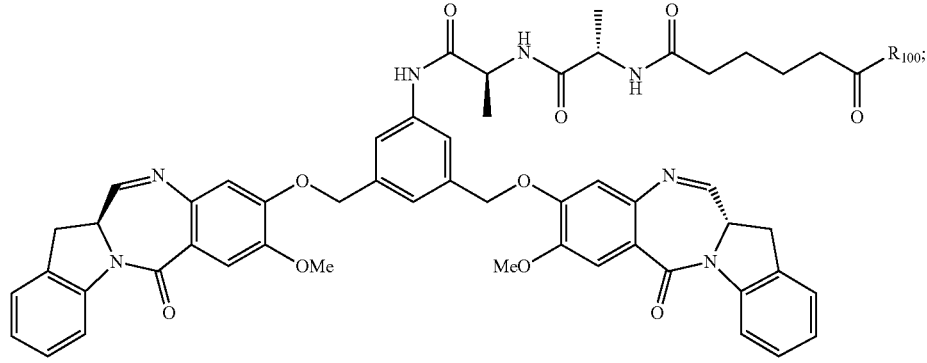

-continued
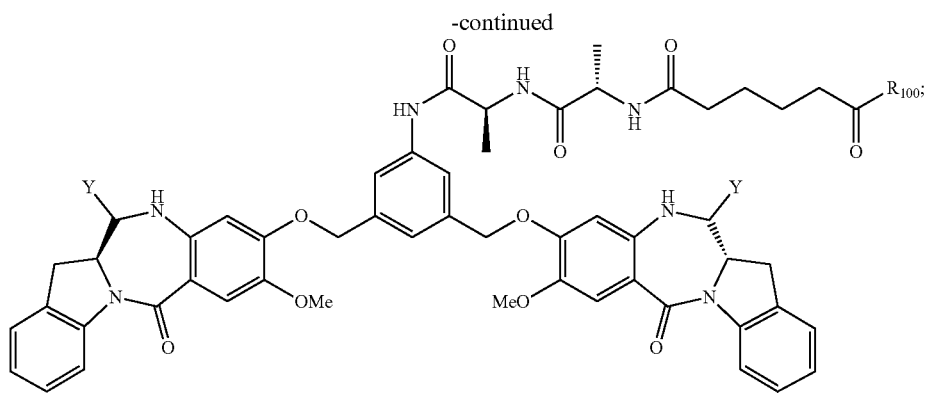
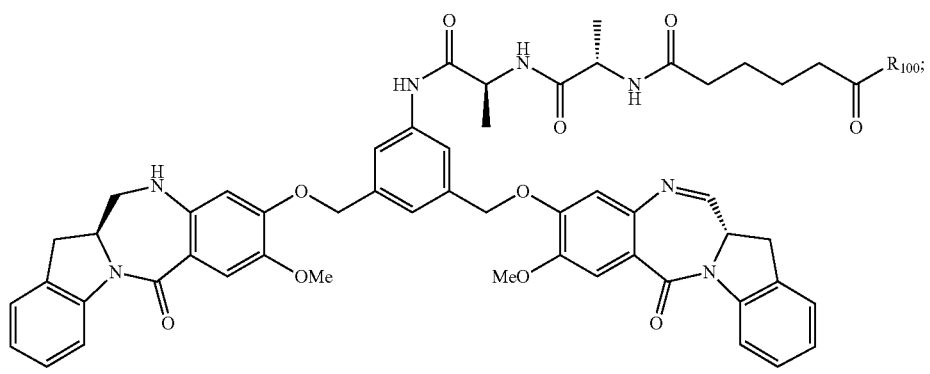
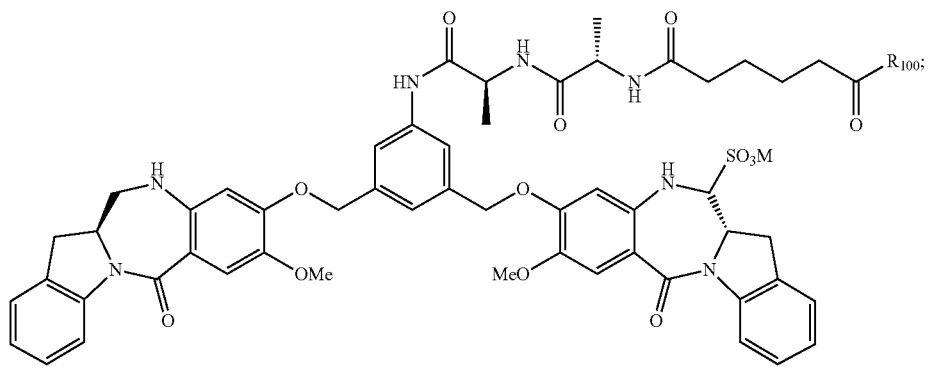
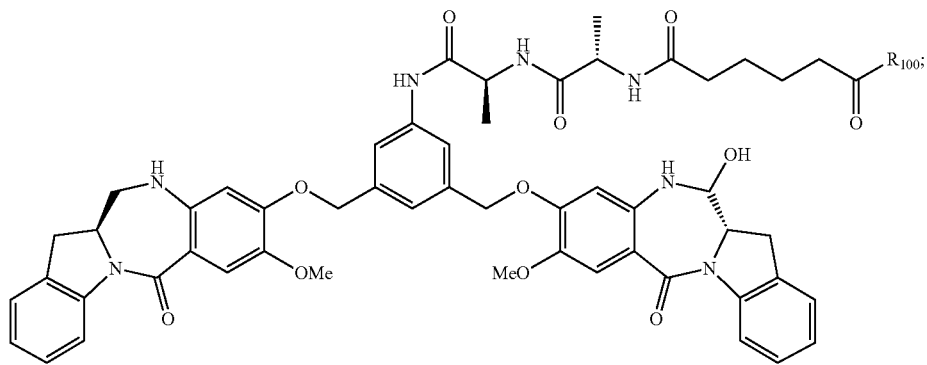

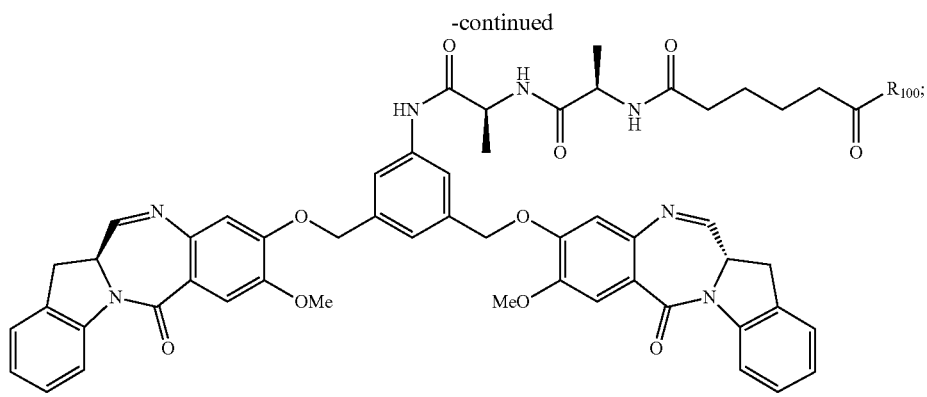
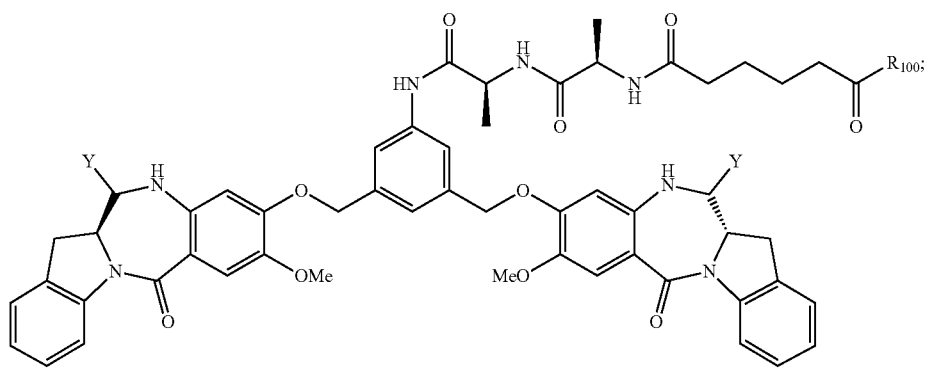
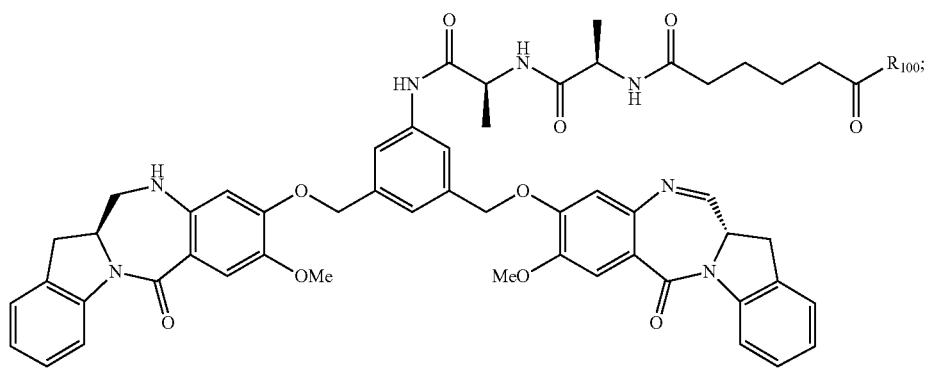
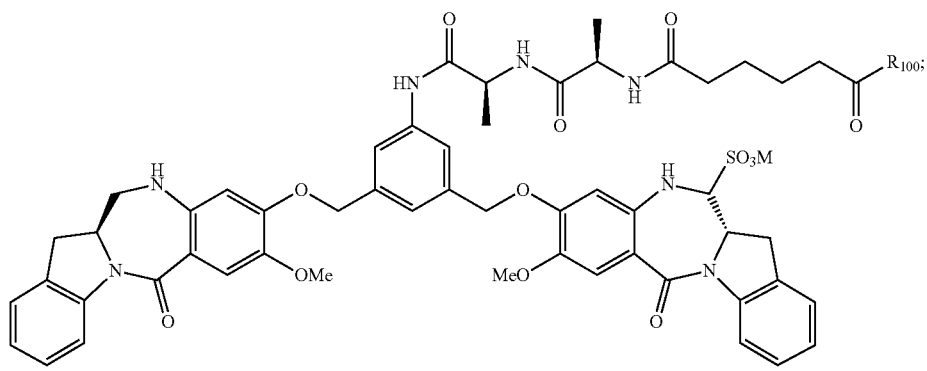

-continued
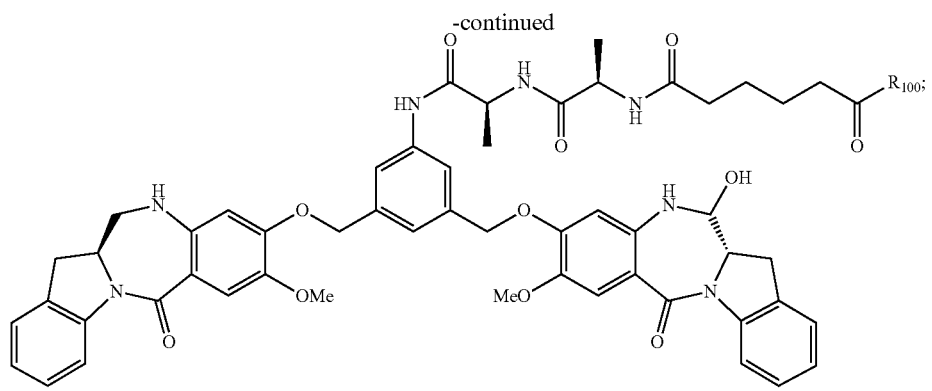
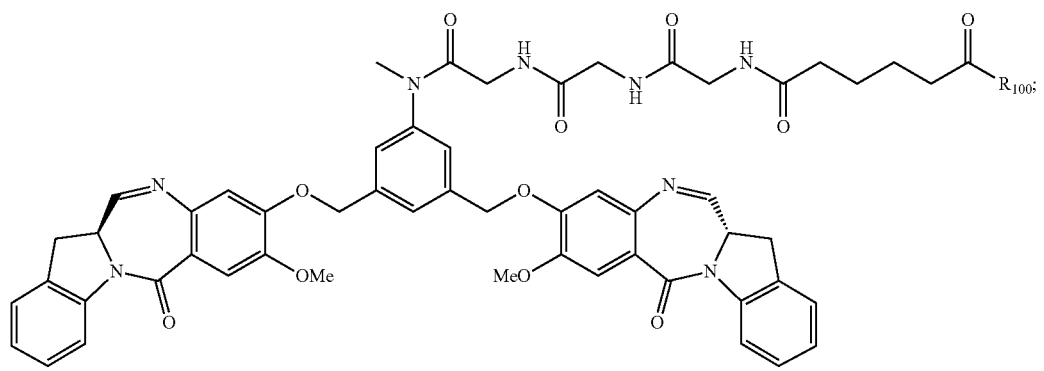
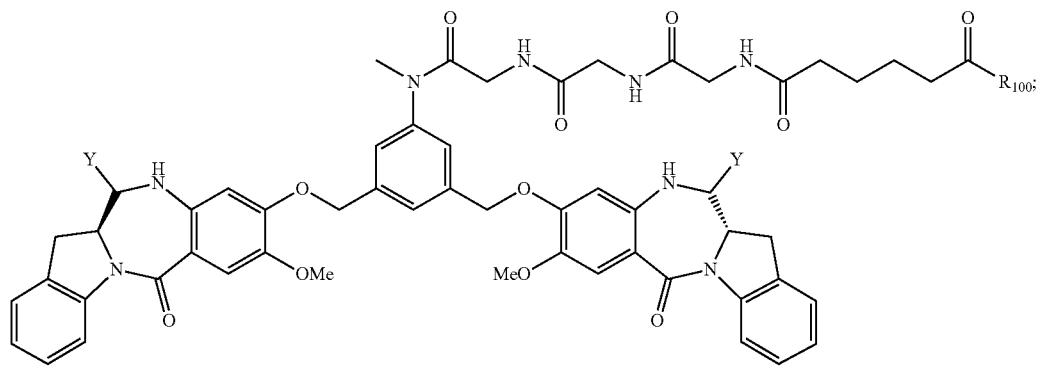
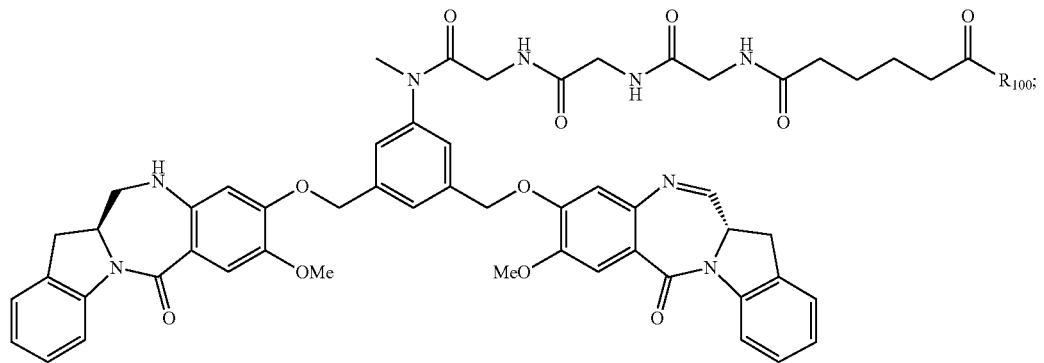

-continued
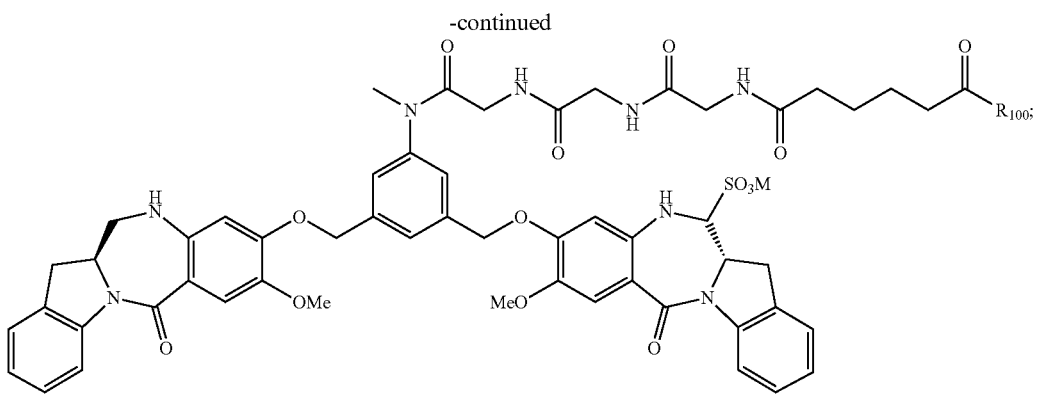
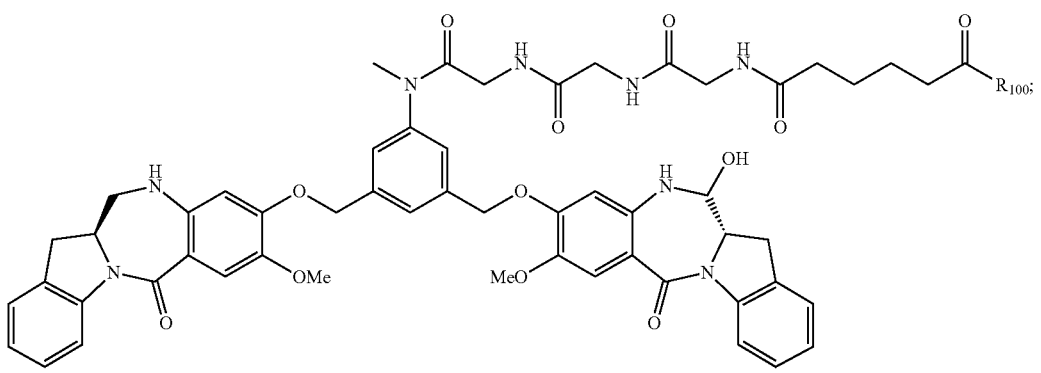
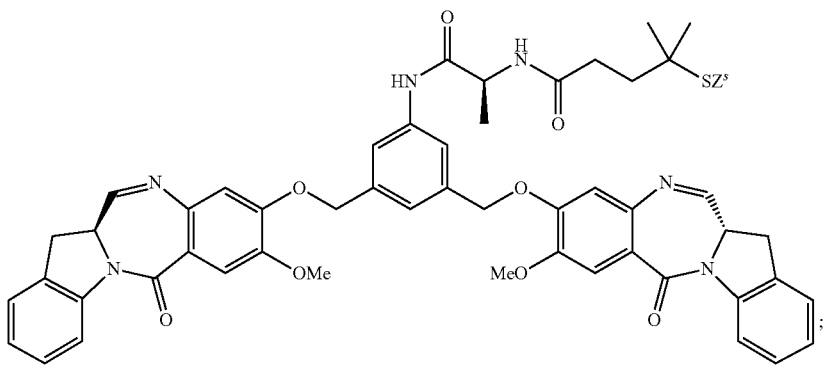
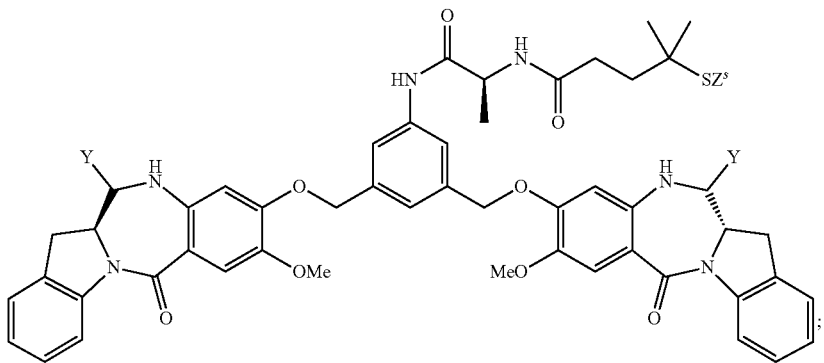

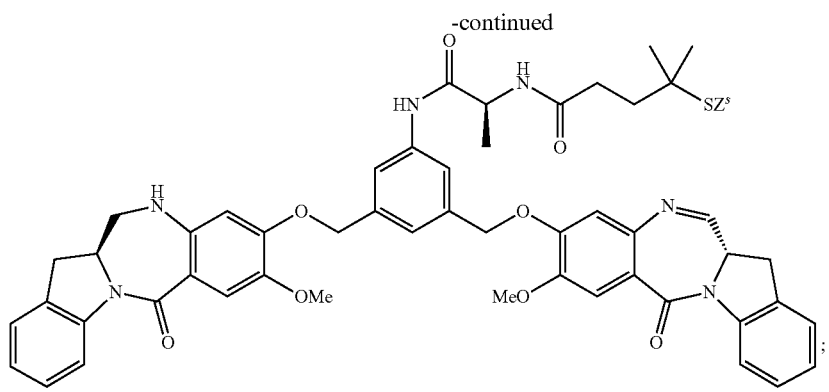
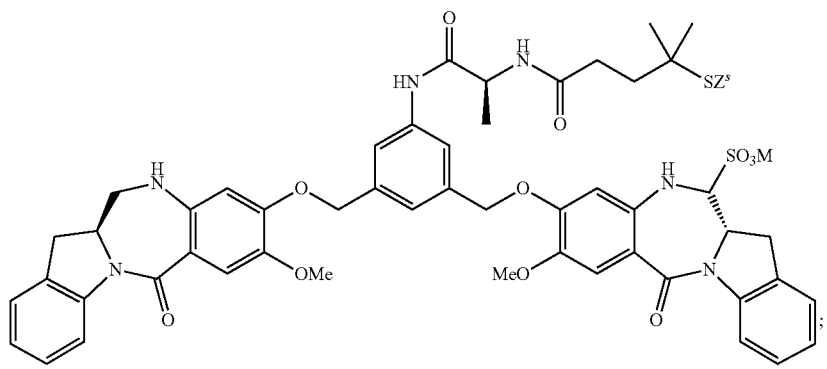
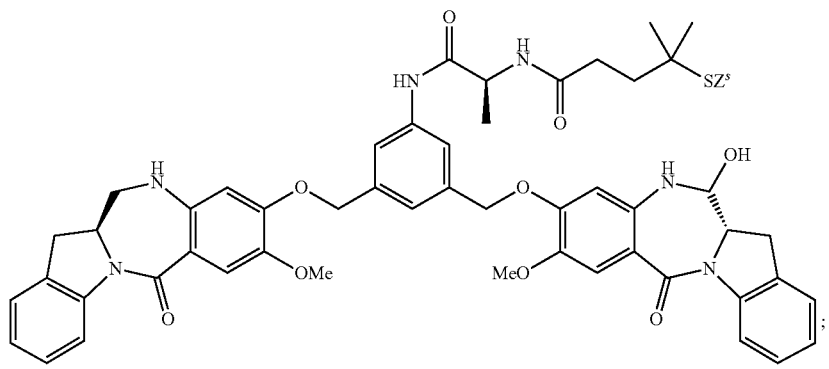
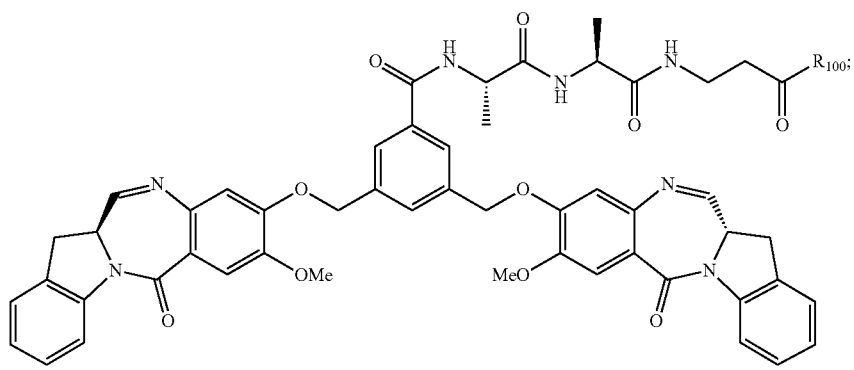

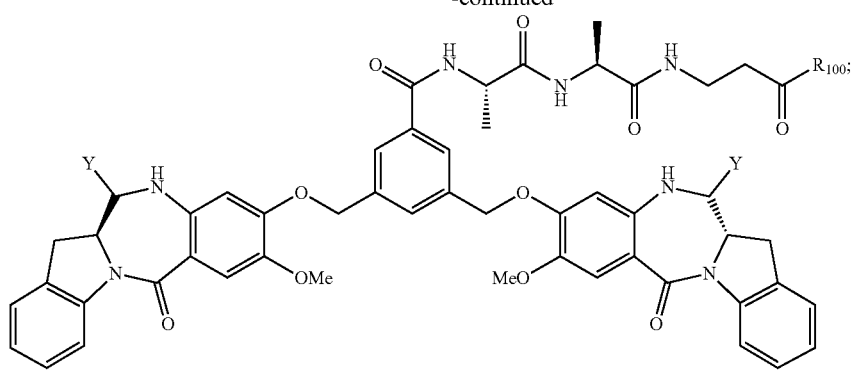
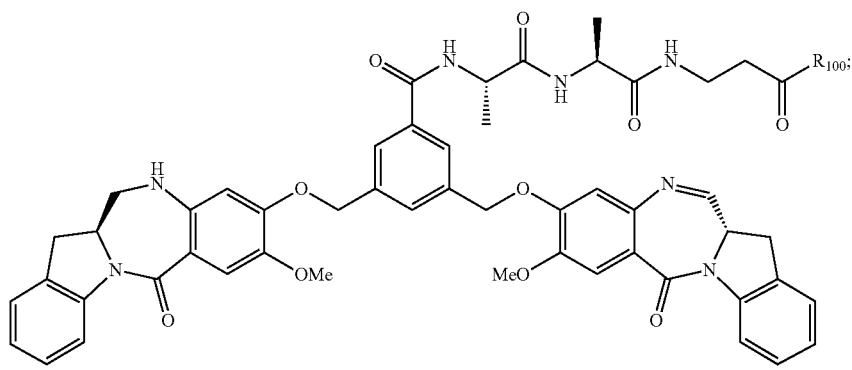
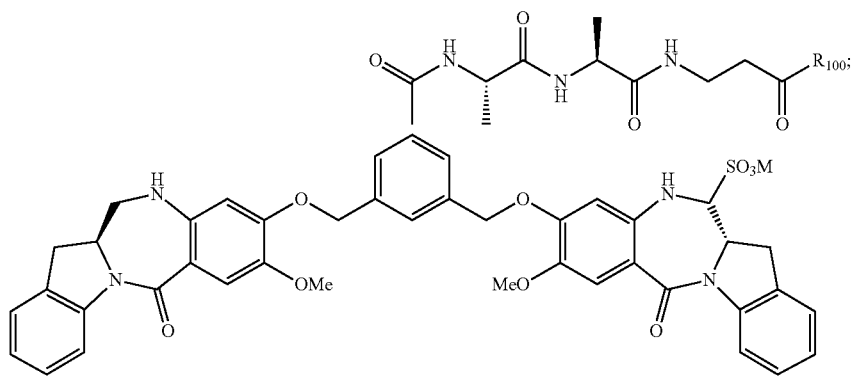
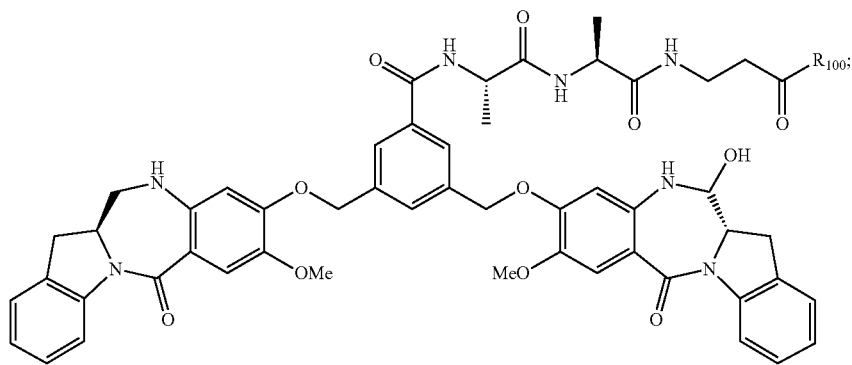

-continued
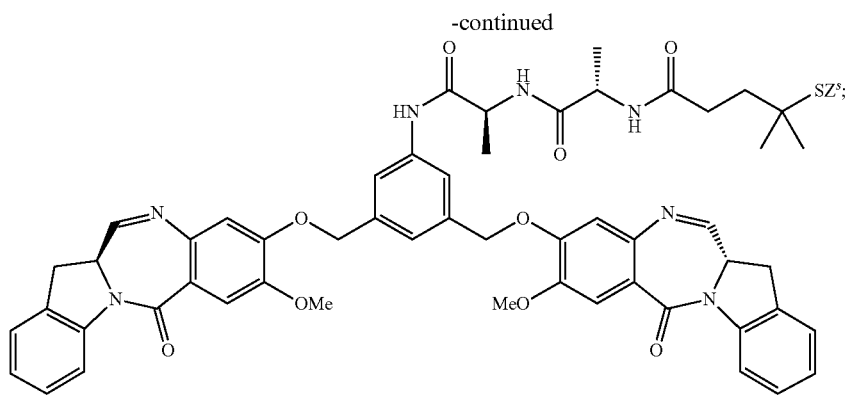
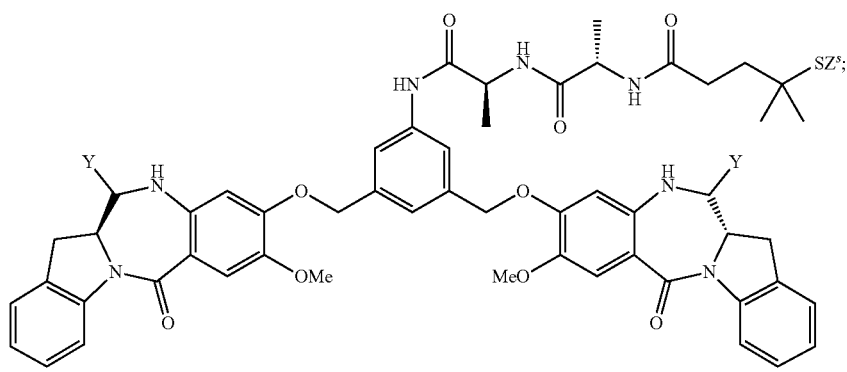
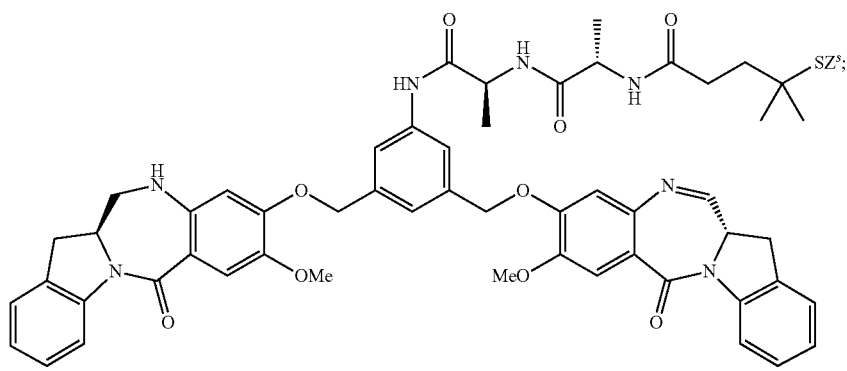
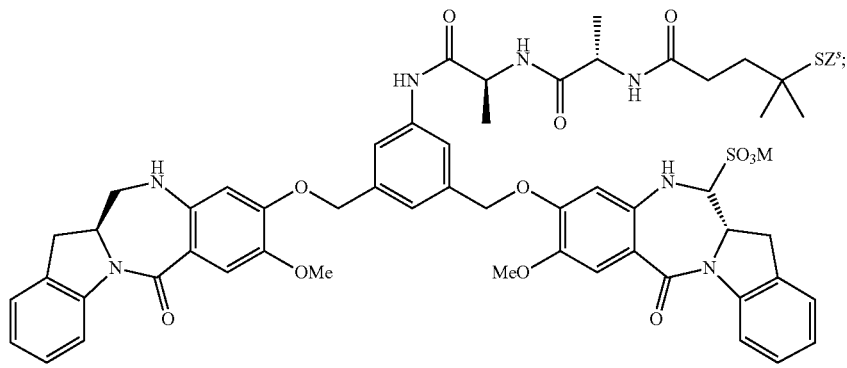

-continued
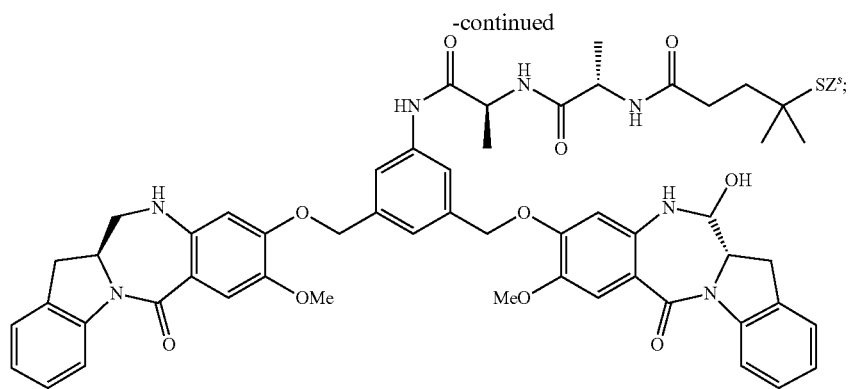
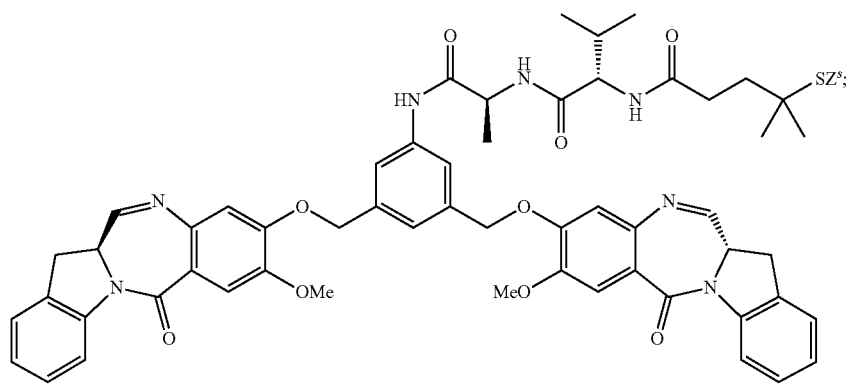
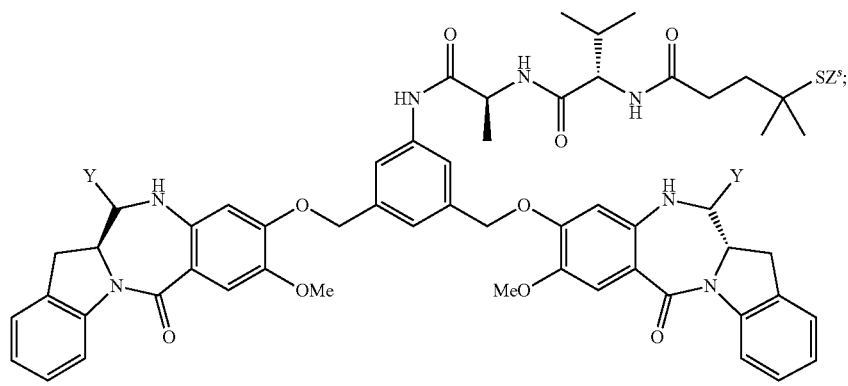
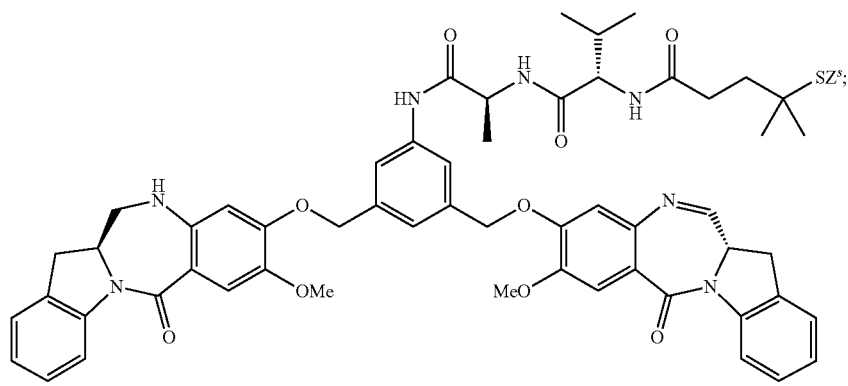

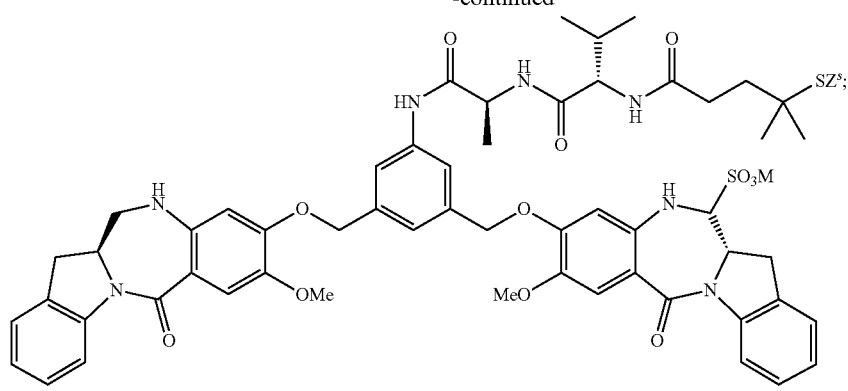
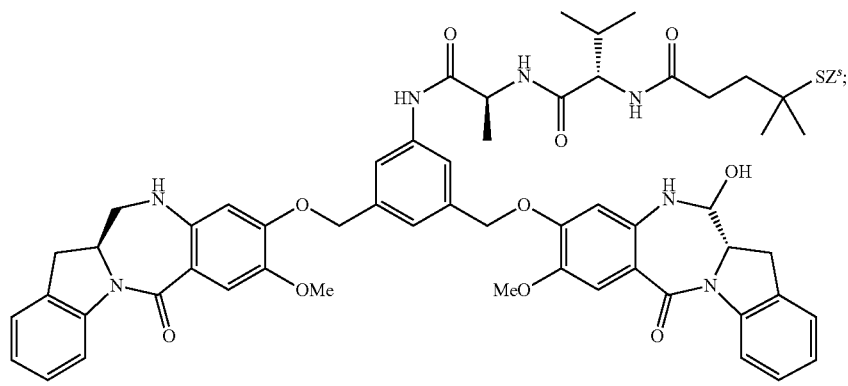
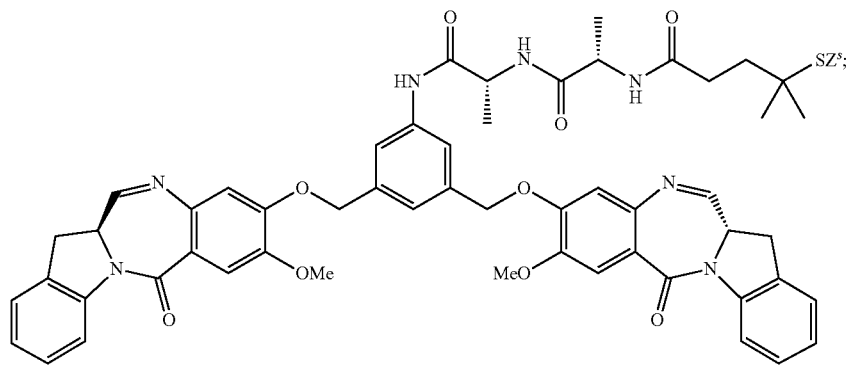
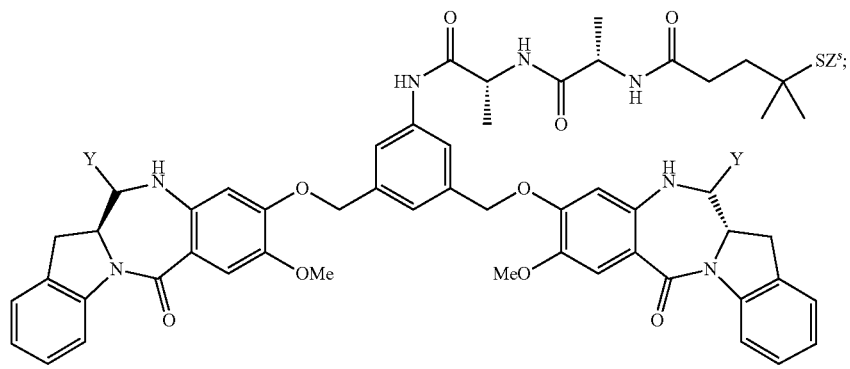

-continued

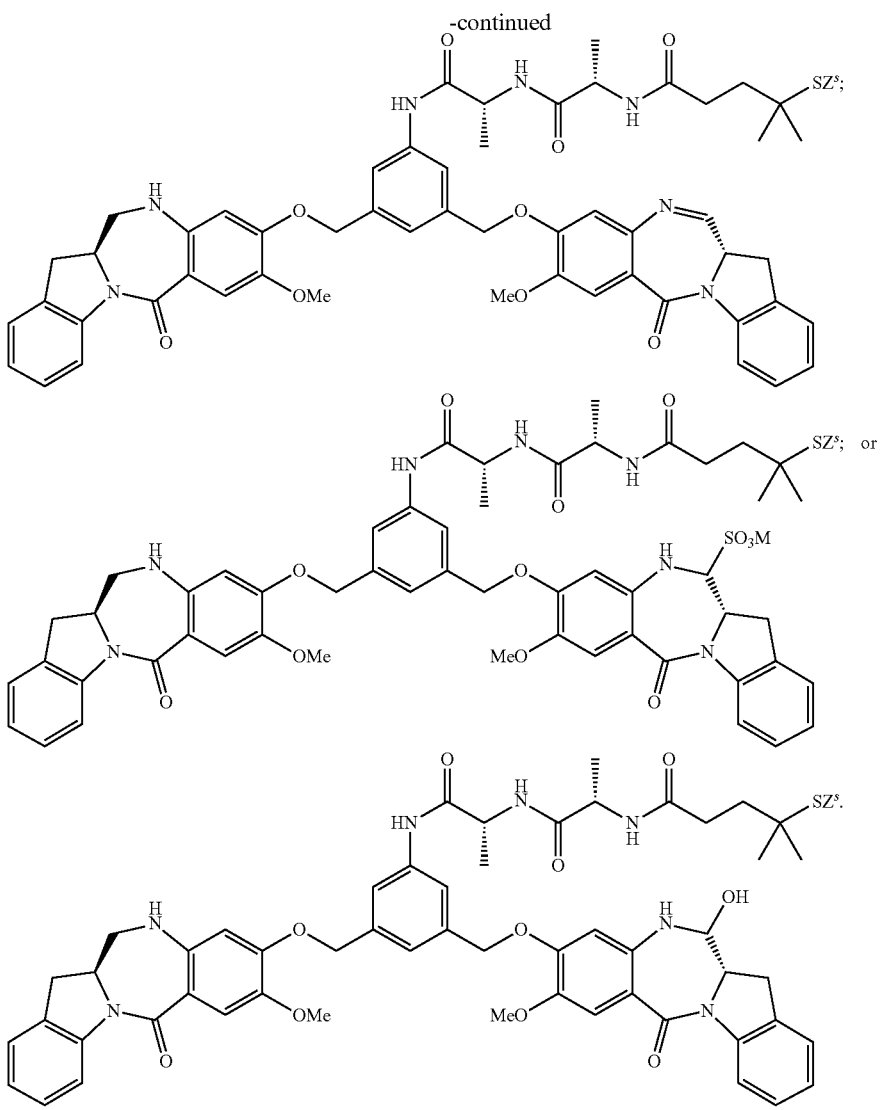

or a pharmaceutically acceptable salt thereof, wherein:

$R_{100}$ is —OH, —OMe or

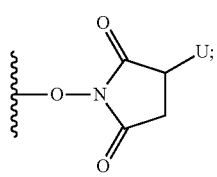

Y is —H, —OH or —$SO_3M$; and

M is a pharmaceutically acceptable cation (e.g., $H^+$, $Na^+$ or $K^+$);

$Z^s$ is —H, —$SR^d$, —C(=O)$R^{d1}$ or is selected from formulas (a1')-(a15') described above.

In a specific embodiment, $Z^s$ is selected from formulas (a1)-(a15) described above.

In a more specific embodiment, $Z^s$ is selected from formulas (a7), (a8), (a9) and (a15). In a even more specific embodiment, $Z^s$ is represented by formula (a9). Alternatively, $Z^s$ is represented by formula (a7).

In another specific embodiment, $Z^s$ is —H.

In another specific embodiment, Y is —$SO_3M$. Alternatively, Y is —OH.

Also included in the present invention is metabolites of any cytotoxic compounds or cell-binding agent-cytotoxic agent conjugates described herein.

Synthesis of Cytotoxic Compounds

The cytotoxic compounds of the present invention can be prepared according to methods described in U.S. Pat. No. 8,765,740 and U.S. Application Publication No. 2012/0238731.

Representative processes for preparing the cytotoxic dimer compounds of the present invention are shown in Examples 1-10.

Cell-Binding Agents

The effectiveness of the conjugates of the invention as therapeutic agents depends on the careful selection of an appropriate cell-binding agent. Cell-binding agents can be of any kind presently known, or that become known, including peptides and non-peptides. Generally, these can be antibodies (such as polyclonal antibodies and monoclonal antibodies, especially monoclonal antibodies), lymphokines, hormones, growth factors, vitamins (such as folate etc., which can bind to a cell surface receptor thereof, e.g., a folate receptor), nutrient-transport molecules (such as transferrin), or any other cell-binding molecule or substance.

Selection of the appropriate cell-binding agent is a matter of choice that partly depends upon the particular cell population that is to be targeted, but in many (but not all) cases, human monoclonal antibodies are a good choice if an appropriate one is available. For example, the monoclonal antibody MY9 is a murine $IgG_1$ antibody that binds specifically to the CD33 Antigen (J. D. Griffin et al., *Leukemia Res.,* 8:521 (1984)), and can be used if the target cells express CD33 as in the disease of acute myelogenous leukemia (AML).

In certain embodiments, the cell-binding agent is not a protein. For example, in certain embodiments, the cell binding agent may be a vitamin that binds to a vitamin receptor, such as a cell-surface receptor. In this regard, vitamin A binds to retinol-binding protein (RBP) to form a complex, which complex in turn binds the STRA6 receptor with high affinity and increases vitamin A in-take. In another example, folic acid/folate/vitamin $B_9$ binds the cell-surface folate receptor (FR), for example, FRα, with high affinity. Folic acid or antibodies that bind to FRα can be used to target the folate receptor expressed on ovarian and other tumors. In addition, vitamin D and its analog bind to vitamin D receptor.

In other embodiments, the cell-binding agent is a protein or a polypeptide, or a compound comprising a protein or polypeptide, including antibody, non-antibody protein, or polypeptide. Preferably, the protein or polypeptides comprise one or more Lys residues with side chain —$NH_2$ group. The Lys side chain —$NH_2$ groups can be covalently linked to the bifunctional crosslinkers, which in turn are linked to the dimer compounds of the invention, thus conjugating the cell-binding agents to the dimer compounds of the invention. Each protein-based cell-binding agents can contain multiple Lys side chain —$NH_2$ groups available for linking the compounds of the invention through the bifunctional crosslinkers.

In one embodiment, GM-CSF, a ligand/growth factor which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Epidermal growth factor can be used to target squamous cancers, such as lung and head and neck. Somatostatin can be used to target neuroblastomas and other tumor types. Estrogen (or estrogen analogues) can be used to target breast cancer. Androgen (or androgen analogues) can be used to target testes.

In certain embodiments, the cell-binding agent can be a lymphokine, a hormone, a growth factor, a colony stimulating factor, or a nutrient-transport molecule.

In certain embodiments, the cell-binding agent is an antibody mimetic, such as an ankyrin repeat protein, a Centyrin, or an adnectin/monobody.

In other embodiments, the cell-binding agent is an antibody, a single chain antibody, an antibody fragment that specifically binds to the target cell, a monoclonal antibody, a single chain monoclonal antibody, a monoclonal antibody fragment (or "antigen-binding portion") that specifically binds to a target cell, a chimeric antibody, a chimeric antibody fragment (or "antigen-binding portion") that specifically binds to the target cell, a domain antibody (e.g., sdAb), or a domain antibody fragment that specifically binds to the target cell.

In certain embodiments, the cell-binding agent is a humanized antibody, a humanized single chain antibody, or a humanized antibody fragment (or "antigen-binding portion"). In a specific embodiment, the humanized antibody is huMy9-6 or another related antibody, which is described in U.S. Pat. Nos. 7,342,110 and 7,557,189. In another specific embodiment, the humanized antibody is an anti-folate receptor antibody described in U.S. Provisional Application Nos. 61/307,797, 61/346,595, and 61/413,172 and U.S. application Ser. No. 13/033,723 (published as US 2012/0009181 A1). The teachings of all these applications are incorporated herein by reference in its entirety.

In certain embodiments, the cell-binding agent is a resurfaced antibody, a resurfaced single chain antibody, a resurfaced antibody fragment (or "antigen-binding portion"), or a bispecific antibody.

In certain embodiments, the cell-binding agent is a minibody, an avibody, a diabody, a tribody, a tetrabody, a nanobody, a probody, a domain antibody, or an unibody.

In other words, an exemplary cell binding agent may include an antibody, a single chain antibody, an antibody fragment that specifically binds to the target cell, a monoclonal antibody, a single chain monoclonal antibody, a monoclonal antibody fragment that specifically binds to a target cell, a chimeric antibody, a chimeric antibody fragment that specifically binds to the target cell, a bispecific antibody, a domain antibody, a domain antibody fragment that specifically binds to the target cell, an interferon (e.g., α, β, γ), a lymphokine (e.g., IL-2, IL-3, IL-4, and IL-6), a hormone (e.g., insulin, thyrotropin releasing hormone (TRH), melanocyte-stimulating hormone (MSH), and a steroid hormone (e.g., androgen and estrogen)), a vitamin (e.g., folate), a growth factor (e.g., EGF, TGF-alpha, FGF, VEGF), a colony stimulating factor, a nutrient-transport molecule (e.g., transferrin; see O'Keefe et al. (1985) *J. Biol. Chem.* 260:932-937, incorporated herein by reference), a Centyrin (a protein scaffold based on a consensus sequence of fibronectin type III (FN3) repeats; see U.S. Patent Publication 2010/0255056, 2010/0216708 and 2011/0274623 incorporated herein by reference), an Ankyrin Repeat Protein (e.g., a designed ankyrin repeat protein, known as DARPin; see U.S. Patent Publication Nos. 2004/0132028, 2009/0082274, 2011/0118146, and 2011/0224100, incorporated herein by reference, and also see C. Zahnd et al., *Cancer Res.* (2010) 70:1595-1605; Zahnd et al., *J. Biol. Chem.* (2006) 281(46):35167-35175; and Binz, H. K., Amstutz, P. & Pluckthun, A., *Nature Biotechnology* (2005) 23:1257-1268, incorporated herein by reference), an ankyrin-like repeats protein or synthetic peptide (see e.g., U.S. Patent Publication No. 2007/0238667; U.S. Pat. No. 7,101,675; WO 2007/147213; and WO 2007/062466, incorporated herein by reference), an Adnectin (a fibronectin domain scaffold protein; see US Patent Publication Nos. 2007/0082365; 2008/0139791, incorporated herein by reference), Avibody (including diabodies, triabodies, and tetrabodies; see U.S. Publication Nos. 2008/0152586 and 2012/0171115), dual receptor retargeting (DART) molecules (P. A. Moore et al., *Blood,* 2011; 117(17):4542-4551; Veri M C, et al., *Arthritis Rheum,* 2010 Mar. 30; 62(7):1933-43; Johnson S, et al. *J Mol Biol,* 2010 Apr. 9; 399(3):436-49), cell penetrating supercharged proteins (*Methods in Enzymol.* 502, 293-319 (2012), and other cell-binding molecules or substances.

In certain embodiments, the cell-binding agent may be a ligand that binds to a moiety on the target cell, such as a cell-surface receptor. For example, the ligand may be a growth factor or a fragment thereof that binds to a growth factor receptor; or may be a cytokine or a fragment thereof that binds to a cytokine receptor. In certain embodiments, the growth factor receptor or cytokine receptor is a cell-surface receptor.

In certain embodiments, wherein the cell-binding agent is an antibody or an antigen-binding portion thereof (including antibody derivatives), or certain antibody mimetics, the CBA may bind to a ligand on the target cell, such as a cell-surface ligand, including cell-surface receptors.

Specific exemplary antigens or ligands may include renin; a growth hormone (e.g., human growth hormone and bovine growth hormone); a growth hormone releasing factor; a parathyroid hormone; a thyroid stimulating hormone; a lipoprotein; alpha-1-antitrypsin; insulin A-chain; insulin B-chain; proinsulin; a follicle stimulating hormone; calcitonin; a luteinizing hormone; glucagon; a clotting factor (e.g., factor vmc, factor IX, tissue factor, and von Willebrands factor); an anti-clotting factor (e.g., Protein C); an atrial natriuretic factor; a lung surfactant; a plasminogen activator (e.g., a urokinase, a human urine or tissue-type plasminogen activator); bombesin; a thrombin; hemopoietic growth factor; tumor necrosis factor-alpha and -beta; an enkephalinase; RANTES (i.e., the regulated on activation normally T-cell expressed and secreted); human macrophage inflammatory protein-1-alpha; a serum albumin (human serum albumin); Muellerian-inhibiting substance; relaxin A-chain; relaxin B-chain; prorelaxin; a mouse gonadotropin-associated peptide; a microbial protein (beta-lactamase); DNase; IgE; a cytotoxic T-lymphocyte associated antigen (e.g., CTLA-4); inhibin; activin; a vascular endothelial growth factor; a receptor for hormones or growth factors; protein A or D; a rheumatoid factor; a neurotrophic factor (e.g., bone-derived neurotrophic factor, neurotrophin-3, -4, -5, or -6), a nerve growth factor (e.g., NGF-β); a platelet-derived growth factor; a fibroblast growth factor (e.g., aFGF and bFGF); fibroblast growth factor receptor 2; an epidermal growth factor; a transforming growth factor (e.g., TGF-alpha, TGF-β1, TGF-β2, TGF-β3, TGF-β4, and TGF-β5); insulin-like growth factor-I and -II; des(1-3)-IGF-I (brain IGF-I); an insulin-like growth factor binding protein; melanotransferrin; EpCAM; GD3; FLT3; PSMA; PSCA; MUC1; MUC16; STEAP; CEA; TENB2; an EphA receptor; an EphB receptor; a folate receptor; FOLR1; mesothelin; cripto; an alpha$_v$beta$_6$; integrins; VEGF; VEGFR; EGFR; transferrin receptor; IRTA1; IRTA2; IRTA3; IRTA4; IRTA5; CD proteins (e.g., CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD123, CD134, CD137, CD138, and CD152), one or more tumor-associated antigens or cell-surface receptors (see US Publication No. 2008/0171040 or US Publication No. 2008/0305044, incorporated in their entirety by reference); erythropoietin; an osteoinductive factor; an immunotoxin; a bone morphogenetic protein; an interferon (e.g., interferon-alpha, -beta, and -gamma); a colony stimulating factor (e.g., M-CSF, GM-CSF, and G-CSF); interleukins (e.g., IL-1 to IL-10); a superoxide dismutase; a T-cell receptor; a surface membrane protein; a decay accelerating factor; a viral antigen s (e.g., a portion of the HIV envelope); a transport protein, a homing receptor; an addressin; a regulatory protein; an integrin (e.g., CD11a, CD11b, CD11c, CD18, an ICAM, VLA-4, and VCAM); a tumor associated antigen (e.g., HER2, HER3 and HER4 receptor); endoglin; c-Met; c-kit; 1GF1R; PSGR; NGEP; PSMA; PSCA; TMEFF2; LGR5; B7H4; and fragments of any of the above-listed polypeptides.

As used herein, the term "antibody" includes immunoglobulin (Ig) molecules. In certain embodiments, the antibody is a full-length antibody that comprises four polypeptide chains, namely two heavy chains (HC) and two light chains (LC) inter-connected by disulfide bonds. Each heavy chain is comprised of a heavy chain variable region (HCVR or VH) and a heavy chain constant region (CH). The heavy chain constant region is comprised of three domains, CH1, CH2, and CH3. Each light chain is comprised of a light chain variable region (LCVR or VL) and a light chain constant region, which is comprised of one domain, CL. The VH and VL regions can be further subdivided into regions of hypervariability, termed complementarity determining regions (CDRs). Interspersed with such regions are the more conserved framework regions (FRs). Each VH and VL is composed of three CDRs and four FRs, arranged from amino-terminus to carboxy-terminus in the following order: FR1, CDR1, FR2, CDR2, FR3, CDR3, and FR4.

In certain embodiments, the antibody is IgG, IgA, IgE, IgD, or IgM. In certain embodiments, the antibody is IgG1, IgG2, IgG3, or IgG4; or IgA1 or IgA2.

In certain embodiments, the cell-binding agent is an "antigen-binding portion" of a monoclonal antibody, sharing sequences critical for antigen-binding with an antibody (such as huMy9-6 or its related antibodies described in U.S. Pat. Nos. 7,342,110 and 7,557,189, incorporated herein by reference).

As used herein, the term "antigen-binding portion" of an antibody (or sometimes interchaneably referred to as "antibody fragments"), include one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding portion" of an antibody include (without limitation): (i) a Fab fragment, a monovalent fragment consisting of the VL, VH, CL and CH1 domains (e.g., an antibody digested by papain yields three fragments: two antigen-binding Fab fragments, and one Fc fragment that does not bind antigen); (ii) a F(ab')$_2$ fragment, a bivalent fragment comprising two Fab fragments linked by a disulfide bridge at the hinge region (e.g., an antibody digested by pepsin yields two fragments: a bivalent antigen-binding F(ab')$_2$ fragment, and a pFc' fragment that does not bind antigen) and its related F(ab') monovalent unit; (iii) a Fd fragment consisting of the VH and CH1 domains (i.e., that portion of the heavy chain which is included in the Fab); (iv) a Fv fragment consisting of the VL and VH domains of a single arm of an antibody, and the related disulfide linked Fv; (v) a dAb (domain antibody) or sdAb (single domain antibody) fragment (Ward et al., Nature 341:544-546, 1989), which consists of a VH domain; and (vi) an isolated complementarity determining region (CDR). In certain embodiments, the antigen-binding portion is a sdAb (single domain antibody).

In certain embodiments, antigen-binding portion also include certain engineered or recombinant derivatives (or "derivative antibodies") that also include one or more fragments of an antibody that retain the ability to specifically bind to an antigen, in addition to elements or sequences that may not be found in naturally existing antibodies.

For example, although the two domains of the Fv fragment, VL and VH, are coded for by separate genes, they can be joined, using standard recombinant methods, by a synthetic linker that enables them to be made as a single protein chain in which the VL and VH regions pair to form monovalent molecules (known as single chain Fv (scFv); see, e.g., Bird et al. Science 242:423-426, 1988: and Huston et al., Proc. Natl. Acad. Sci. USA 85:5879-5883, 1988).

In all embodiments described herein, the N-terminus of an scFv may be a VH domain (i.e., N-VH-VL-C), or a VL domain (i.e., N-VL-VH-C).

Divalent (or bivalent) single-chain variable fragments (di-scFvs, bi-scFvs) can be engineered by linking two scFvs. This produces a single peptide chain with two VH and two VL regions, yielding a tandem scFvs (tascFv). More tandem repeats, such as tri-scFv, may be similarly produced by linking three or more scFv in a head-to-tail fashion.

In certain embodiments, scFvs may be linked through linker peptides that are too short (about five amino acids) for the two variable regions to fold together, forcing scFvs to dimerize, and form diabodies (see, e.g., Holliger et al., Proc. Natl. Acad. Sci. USA 90:6444-6448, 1993; Poljak et al., Structure 2:1121-1123, 1994). Diabodies may be bi-specific or monospecific. Diabodies have been shown to have dissociation constants up to 40-fold lower than corresponding scFvs, i.e., having a much higher affinity to the target.

Still shorter linkers (one or two amino acids) lead to the formation of trimers, or so-called triabodies or tribodies. Tetrabodies have also been produced similarly. They exhibit an even higher affinity to their targets than diabodies. Diabodies, triabodies, and tetrabodies are sometimes collectively called "AVIBODY™" cell binding agents (or "AVIBODY" in short). That is, AVIBODY having two, three, or four Target Binding Regions (TBRs) are commonly known as Dia-, Tria- and Tetrabodies. See, for example, U.S. Publication Nos. 2008/0152586 and 2012/0171115 for details, the entire teachings of which are incorporated herein by reference.

All of these formats can be composed from variable fragments with specificity for two or more different antigens, in which case they are types of bi- or multi-specific antibodies. For example, certain bispecific tandem di-scFvs, are known as bi-specific T-cell engagers (BiTEs).

In certain embodiments, each scFv in the tandem scFv or diabody/triabody/tetrabody may have the same or different binding specificity, and each may independently have an N-terminal VH or N-terminal VL.

Single chain Fv (scFv) can also be fused to an Fc moiety, such as the human IgG Fc moiety to obtain IgG-like properties, but nevertheless they are still encoded by a single gene. As transient production of such scFv-Fc proteins in mammalians can easily achieve milligram amounts, this derivative antibody format is particularly suitable for many research applications.

Fcabs are antibody fragments engineered from the Fc constant region of an antibody. Fcabs can be expressed as soluble proteins, or they can be engineered back into a full-length antibody, such as IgG, to create mAb2. A mAb2 is a full-length antibody with an Fcab in place of the normal Fc region. With these additional binding sites, mAb2 bispecific monoclonal antibodies can bind two different targets at the same time.

In certain embodiments, the engineered antibody derivatives have reduced size of the antigen-binding Ig-derived recombinant proteins ("miniaturized" full-size mAbs), produced by removing domains deemed non-essential for function. One of the best examples is SMIPs.

A Small modular immunopharmaceutical, or SMIP, is an artificial protein largely built from parts of antibodies (immunoglobulins), and is intended for use as a pharmaceutical drug. SMIPs have similar biological half-life as antibodies, but are smaller than antibodies and hence may have better tissue penetration properties. SMIPs are single-chain proteins that comprise one binding region, one hinge region as a connector, and one effector domain. The binding region comprises a modified single-chain variable fragment (scFv), and the rest of the protein can be constructed from the Fc (such as CH2, and CH3 as the effector domain) and the hinge region of an antibody, such as IgG1. Genetically modified cells produce SMIPs as antibody-like dimers that are about 30% smaller than real antibodies.

Another example of such engineered miniaturized antibody is "unibody," in which the hinge region has been removed from IgG4 molecules. IgG4 molecules are unstable and can exchange light-heavy chain heterodimers with one another. Deletion of the hinge region prevents heavy chain-heavy chain pairing entirely, leaving highly specific monovalent light/heavy heterodimers, while retaining the Fc region to ensure stability and half-life in vivo.

A single-domain antibody (sdAb, including but not limited to those called nanobody by Ablynx) is an antibody fragment consisting of a single monomeric variable antibody domain. Like a whole antibody, it is able to bind selectively to a specific antigen, but is much smaller due to its molecular weight of only 12-15 kDa. In certain embodiments, the single-domain antibody is engineered from heavy-chain antibodies (hcIgG). The first such sdAb was engineered based on an hcIgG found in camelids, called $V_HH$ fragments. In certain embodiments, the single-domain antibody is engineered from IgNAR ("immunoglobulin new antigen receptor," see below) using a $V_{NAR}$ fragment. Cartilaginous fishes (such as shark) have such heavy-chain IgNAR antibodies. In certain embodiments, the sdAb is engineered by splitting the dimeric variable domains from common immunoglobulin G (IgG), such as those from humans or mice, into monomers. In certain embodiments, a nanobody is derived from a heavy chain variable domain. In certain embodiments, a nanobody is derived from light chain variable domain. In certain embodiments, the sdAb is obtained by screening libraries of single domain heavy chain sequences (e.g., human single domain HCs) for binders to a target antigen.

The single variable new antigen receptor domain antibody fragments ($V_{NAR}$s, or $V_{NAR}$ domains) are derived from cartilaginous fish (e.g., shark) immunoglobulin new antigen receptor antibodies (IgNARs). Being one of the smallest known immunoglobulin-based protein scaffolds, such single domain proteins demonstrate favorable size and cryptic epitope recognition properties. Mature IgNAR antibodies consist of homodimers of one variable new antigen receptor ($V_{NAR}$) domain and five constant new antigen receptor ($C_{NAR}$) domains. This molecule is highly stable, and possesses efficient binding characteristics. Its inherent stability can likely be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulphide bridges, and patterns of intra-loop hydrogen bonds.

A minibody is an engineered antibody fragment comprising an scFv linked to a CH domain, such as the CH3γ1 (CH3 domain of IgG1) or CH4ε (CH4 domain of IgE). For example, an scFv specific for carcinoembryonic antigen (CEA) has been linked to the CH3γ1 to create a minibody, which has previously been demonstrated to possess excellent tumor targeting coupled with rapid clearance in vivo (Hu et al., *Cancer Res.* 56:3055-3061, 1996). The scFv may have a N-terminal VH or VL. The linkage may be a short peptide (e.g., two amino acid linker, such as ValGlu) that resultes in a non-covalent, hingeless minibody. Alternatively, the linkage may be an IgG1 hinge and a GlySer linker peptide that produces a covalent, hinge-minibody.

Natural antibodies are mono-specific, but bivalent, in that they express two identical antigen-binding domains. In contrast, in certain embodiments, certain engineered antibody derivatives are bi- or multi-specific molecules possess two or more different antigen-binding domains, each with different target specificity. Bispecific antibodies can be generated by fusing two antibody-producing cells, each with distinct specificity. These "quadromas" produced multiple molecular species, as the two distinct light chains and two distinct heavy chains were free to recombine in the quadromas in multiple configurations. Since then, bispecific Fabs, scFvs and full-size mAbs have been generated using a variety of technologies (see above).

The dual variable domain immunoglobulin (DVD-Ig) protein is a type of dual-specific IgG that simultaneously target two antigens/epitopes (DiGiammarino et al., *Methods Mol Biol.* 899:145-56, 2012). The molecule contains an Fc region and constant regions in a configuration similar to a conventional IgG. However, the DVD-Ig protein is unique in that each arm of the molecule contains two variable domains (VDs). The VDs within an arm are linked in tandem and can possess different binding specificities.

Trispecific antibody derivative molecules can also been generated by, for example, expressing bispecific antibodies with two distinct Fabs and an Fc. One example is a mouse IgG2a anti-Ep-CAM, rat IgG2b anti-CD3 quadroma, called BiUII, which is thought to permit the co-localization of tumor cells expressing Ep-CAM, T cells expressing CD3, and macrophages expressing FCγRI, thus potentiating the costimulatory and anti-tumor functions of the immune cells.

Probodies are fully recombinant, masked monoclonal antibodies that remain inert in healthy tissue, but are activated specifically in the disease microenvironment (e.g., through protease cleavage by a protease enriched or specific in a disease microenvironment). See Desnoyers et al., *Sci Transl Med* 5:207ra144, 2013. Similar masking techniques can be used for any of the antibodies or antigen-binding portions thereof described herein.

An intrabody is an antibody that has been modified for intracellular localization, for working within the cell to bind to an intracellular antigen. The intrabody may remain in the cytoplasm, or may have a nuclear localization signal, or may have a KDEL sequence for ER targeting. The intrabody may be a single-chain antibody (scFv), modified immunoglobulin VL domains with hyperstability, selected antibody resistant to the more reducing intracellular environment, or expressed as a fusion protein with maltose binding protein or other stable intracellular proteins. Such optimizations have improved the stability and structure of intrabodies, and may have general applicability to any of the antibodies or antigen-binding portions thereof described herein.

The antigen-binding portions or derivative antibodies of the invention may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody from which they are derived/engineered. Sequences within these regions may contain conservative amino acid substitutions, including substitutions within the CDR regions. In certain embodiments, there is no more than 1, 2, 3, 4, or 5 conservative substitutions. In an alternative, the antigen-binding portions or derivative antibodies have a light chain region and/or a heavy chain region that is at least about 90%, 95%, 99% or 100% identical to an antibody from which they are derived/engineered. These antigen-binding portions or derivative antibodies may have substantially the same binding specificity and/or affinity to the target antigen compared to the antibody. In certain embodiments, the $K_d$ and/or $k_{off}$ values of the antigen-binding portions or derivative antibodies are within 10-fold (either higher or lower), 5-fold (either higher or lower), 3-fold (either higher or lower), or 2-fold (either higher or lower) of an antibody described herein.

In certain embodiments, the antigen-binding portions or derivative antibodies may be derived/engineered from fully human antibodies, humanized antibodies, or chimeric antibodies, and may be produced according to any art-recognized methods.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies.

Cell-binding agent can also be peptides derived from phage display (see, for example, Wang et al., *Proc. Natl. Acad. Sci. USA* (2011) 108(17), 6909-6914) or peptide library techniques (see, for example, Dane et al., *Mol. Cancer. Ther.* (2009) 8(5):1312-1318).

In certain embodiments, the CBA of the invention also includes an antibody mimetic, such as a DARPin, an affibody, an affilin, an affitin, an anticalin, an avimer, a Fynomer, a Kunitz domain peptide, a monobody, or a nanofitin.

As used herein, the terms "DARPin" and "(designed) ankyrin repeat protein" are used interchangeably to refer to certain genetically engineered antibody mimetic proteins typically exhibiting preferential (sometimes specific) target binding. The target may be protein, carbohydrate, or other chemical entities, and the binding affinity can be quite high. The DARPins may be derived from natural ankyrin repeat-containing proteins, and preferably consist of at least three, usually four or five ankyrin repeat motifs (typically about 33 residues in each ankyrin repeat motif) of these proteins. In certain embodiments, a DARPin contains about four- or five-repeats, and may have a molecular mass of about 14 or 18 kDa, respectively. Libraries of DARPins with randomized potential target interaction residues with diversities of over $10^{12}$ variants can be generated at the DNA level, for use in selecting DARPins that bind desired targets (e.g., acting as receptor agonists or antagonists, inverse agonists, enzyme inhibitors, or simple target protein binders) with picomolar affinity and specificity, using a variety of technologies such as ribosome display or signal recognition particle (SRP) phage display. See, for example, U.S. Patent Publication Nos. 2004/0132028, 2009/0082274, 2011/0118146, and 2011/0224100, WO 02/20565 and WO 06/083275 for DAR- Pin preparation (the entire teachings of which are incorporated herein by reference), and also see C. Zahnd et al. (2010) *Cancer Res.*, 70:1595-1605; Zahnd et al. (2006) *J. Biol. Chem.*, 281(46):35167-35175; and Binz, H. K., Amstutz, P. & Pluckthun, A. (2005) *Nature Biotechnology*, 23:1257-1268 (all incorporated herein by reference). Also see U.S. Patent Publication No. 2007/0238667; U.S. Pat. No. 7,101,675; WO 2007/147213; and WO 2007/062466 (the entire teachings of which are incorporated herein by reference), for the related ankyrin-like repeats protein or synthetic peptide.

Affibody molecules are small proteins engineered to bind to a large number of target proteins or peptides with high affinity, thus imitating monoclonal antibodies. An Affibody consists of three alpha helices with 58 amino acids and has a molar mass of about 6 kDa. They have been shown to withstand high temperatures (90° C.) or acidic and alkaline conditions (pH 2.5 or pH 11), and binders with an affinity of down to sub-nanomolar range have been obtained from naïve library selections, and binders with picomolar affinity have been obtained following affinity maturation. In certain embodiments, affibodies are conjugated to weak electrophiles for binding to targets covalently.

Monobodies (also known as Adnectins), are genetically engineered antibody mimetic proteins capable of binding to antigens. In certain embodiments, monobodies consist of 94 amino acids and have a molecular mass of about 10 kDa. They are based on the structure of human fibronectin, more specifically on its tenth extracellular type III domain, which has a structure similar to antibody variable domains, with seven beta sheets forming a barrel and three exposed loops on each side corresponding to the three complementarity determining regions. Monobodies with specificity for different proteins can be tailored by modifying the loops BC (between the second and third beta sheets) and FG (between the sixth and seventh sheets).

A tribody is a self-assembly antibody mimetic designed based on the C-terminal coiled-coil region of mouse and human cartilage matrix protein (CMP), which self-assembles into a parallel trimeric complex. It is a highly stable trimeric targeting ligand created by fusing a specific target-binding moiety with the trimerization domain derived from CMP. The resulting fusion proteins can efficiently self-assemble into a well-defined parallel homotrimer with high stability. Surface plasmon resonance (SPR) analysis of the trimeric targeting ligands demonstrated significantly enhanced target-binding strength compared with the corresponding monomers. Cellular-binding studies confirmed that such tribodies have superior binding strength toward their respective receptors.

A Centyrin is another antibody mimetic that can be obtained using a library built upon the framework of a consensus FN3 domain sequence (Diem et al., *Protein Eng Des Sel.*, 2014). This library employs diversified positions within the C-strand, CD-loop, F-strand and FG-loop of the FN3 domain, and high-affinity Centyrin variants can be selected against specific targets.

In one embodiment, the cell-binding agent is an anti-folate receptor antibody. More specifically, the anti-folate receptor antibody is a humanized antibody or antigen binding fragment thereof that specifically binds a human folate receptor 1 (also known as folate receptor alpha (FR-α)). The terms "human folate receptor 1," "FOLR1," or "folate receptor alpha (FR-α)", as used herein, refers to any native human FOLR1, unless otherwise indicated. Thus, all of these terms can refer to either a protein or nucleic acid sequence as indicated herein. The term "FOLR1" encompasses "full-length," unprocessed FOLR1 as well as any form of FOLR1 that results from processing within the cell. The FOLR1 antibody comprises: (a) a heavy chain CDR1 comprising GYFMN (SEQ ID NO: 1); a heavy chain CDR2 comprising RIHPYDGDTFYNQXaa$_1$FXaa$_2$Xaa$_3$ (SEQ ID NO: 2); and a heavy chain CDR3 comprising YDGSRAMDY (SEQ ID NO: 3); and (b) a light chain CDR1 comprising KASQSVSFAGTSLMH (SEQ ID NO: 4); a light chain CDR2 comprising RASNLEA (SEQ ID NO: 5); and a light chain CDR3 comprising QQSREYPYT (SEQ ID NO: 6); wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIHPYDGDTFYNQKFQG (SEQ ID NO: 7).

In another embodiment, the anti-folate receptor antibody is a humanized antibody or antigen binding fragment thereof that specifically binds the human folate receptor 1 comprising the heavy chain having the amino acid sequence of

```
                                          (SEQ ID NO: 8)
QVQLVQSGAEVVKPGASVKISCKASGYTFTGYFMNWVKQSPGQSLEWIGR

IHPYDGDTFYNQKFQGKATLTVDKSSNTAHMELLSLTSEDFAVYYCTRYD

GSRAMDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK.
```

In another embodiment, the anti-folate antibody receptor is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof that specifically binds the human folate receptor 1 comprising the light chain having the amino acid sequence of

```
                                          (SEQ ID NO: 9)
DIVLTQSPLSLAVSLGQPAIISCKASQSVSFAGTSLMHWYHQKPGQQPRL

LIYRASNLEAGVPDRFSGSGSKTDFTLNISPVEAEDAATYYCQQSREYPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC;
or
                                          (SEQ ID NO: 10)
DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

In another embodiment the anti-folate receptor antibody is a humanized antibody or antigen binding fragment thereof that specifically binds the human folate receptor 1 comprising the heavy chain having the amino acid sequence of SEQ ID NO: 8, and the light chain having the amino acid sequence of SEQ ID NO: 9 or SEQ ID NO: 10. Preferably, the antibody comprises the heavy chain having the amino acid sequence of SEQ ID NO: 8 and the light chain having the amino acid sequence of SEQ ID NO: 10 (hu FOLR1).

In another embodiment, the anti-folate receptor antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof that specifically binds the human folate receptor 1, and comprising a heavy chain variable domain at least about 90%, 95%, 99% or 100% identical to QVQLVQSGAEV-VKPGASVKISCKASGYTFTGYFMN-WVKQSPGQSLEWIGRIHPYDGDTFYNQKFQGKATLT-VDKSSNTAHMELLSLTSEDFAVYYCTRYDGSRAMDY WGQGTTVTVSS (SEQ ID NO: 11), and a light chain variable domain at least about 90%, 95%, 99% or 100% identical to

```
                                  (SEQ ID NO: 12)
DIVLTQSPLSLAVSLGQPAIISCKASQSVSFAGTSLMHWYHQKPGQQPRL

LIYRASNLEAGVPDRFSGSGSKTDFTLNISPVEAEDAATYYCQQSREYPY

TFGGGTKLEIKR;
or
                                  (SEQ ID NO: 13)
DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKR.
```

In another embodiment, the anti-folated receptor antibody is huMov19 or M9346A (see, for example, U.S. Pat. Nos. 8,709,432, 8,557,966, and WO2011106528, all incorporated herein by reference).

In another embodiment, the cell-binding agent is an anti-EGFR antibody or an antibody fragment thereof. In one embodiment, the anti-EGFR antibody is a non-antagonist antibody, including, for example, the antibodies described in WO2012058592, herein incorporated by reference. In another embodiment, the anti-EGFR antibody is a non-functional antibody, for example, humanized ML66 or EGFR-8. More specifically, the anti-EGFR antibody is huML66.

In yet another embodiment, the anti-EGFR antibody comprising the heavy chain having the amino acid sequence of SEQ ID NO: 14, and the light chain having the amino acid sequence of SEQ ID NO: 15. As used herein, double underlined sequences represent the variable regions (i.e., heavy chain variable region or HCVR, and light chain variable region or LCVR) of the heavy or light chain sequences, while bold sequences represent the CDR regions (i.e., from N-terminal to C-terminal, CDR1, CDR2, and CDR3, respectively, of the heavy chain or light chain sequences).

| Antibody | Full-Length Heavy/Light Chain Amino Acid Sequence |
|---|---|
| huML66HC | <u>QVQLQESGPGLVKPSETLSLTCTVSGLSLASNSVSWIR QPPGKGLEWMGVIWNHGGTDYNPSIKSRLSISRDTSKS</u> |

| Antibody | Full-Length Heavy/Light Chain Amino Acid Sequence |
|---|---|
| | <u>QVFLKMNSLTAADTAMYFCVRKGGIYFDYWGQGVLVTV</u> SSASTKGPSVFPLAPSSKSTSGGTAALGCLVKDYFPEP VTVSWNSGALTSGVHTFPAVLQSSGLYSLSSVVTVPSS SLGTQTYICNVNHKPSNTKVDKKVEPKSCDKTHTCPPC PAPELLGGPSVFLFPPKPKDTLMISRTPEVTCVVVDVS HEDPEVKFNWYVDGVEVHNAKTKPREEQYNSTYRVVSV LTVLHQDWLNGKEYKCKVSNKALPAPIEKTISKAKGQP REPQVYTLPPSRDELTKNQVSLTCLVKGFYPSDIAVEW ESNGQPENNYKTTPPVLDSDGSFFLYSKLTVDKSRWQQ GNVFSCSVMHEALHNYTQKSLSLSPG<br>(SEQ ID NO: 14) |
| huML66LC | <u>DTVLTQSPSLAVSPGERATISCRASESVSTLMHWYQQK PGQQPKLLIYLASHRESGVPARFSGSGSGTDFTLTIDP MEAEDTATYYCQQSRNDPWTF</u>GQGTKLELKRTVAAPSV FIFPPSDEQLKSGTASVVCLLNNFYPREAKVQWKVDNA LQSGNSQESVTEQDSKDSTYSLSSTLTLSKADYEKHKV YACEVTHQGLSSPVTKSFNRGEC<br>(SEQ ID NO: 15) |

In yet another embodiment, the anti-EGFR antibody comprises the heavy chain CDR1-CDR3 of SEQ ID NO: 14, and/or the light chain CDR1-CDR3 of SEQ ID NO: 15, and preferrably specifically binds EGFR.

In yet another embodiment, the anti-EGFR antibody comprises a heavy chain variable region (HCVR) sequence at least about 90%, 95%, 97%, 99%, or 100% identical to SEQ ID NO: 14, and/or a light chain variable region (LCVR) sequence at least about 90%, 95%, 97%, 99%, or 100% identical to SEQ ID NO: 15, and preferrably specifically binds EGFR.

In another embodiment, the anti-EGFR antibody are antibodies described in U.S. Pat. No. 8,790,649 and WO 2012/058588, herein incorporated by reference. In one embodiment, the anti-EGFR antibody is huEGFR-7R antibody.

In one embodiment, the anti-EGFR antibody comprises an immunoglobulin heavy chain region having the amino acid sequence of QVQLVQSGAEVAKPGASVKLSCKASGYTFTSYWMQ-WVKQRPGQGLECIGTIYPGDGDTTYTQKFQGKATL-TADKSSSTAYMQLSSLRSEDSAVYYCARYDAPG-YAMDYWGQGTLVTVSSASTKGPSVFPLAPSSKST-SGGTAALGCLVKDYFPEPVTVSWNSGALTSGVHTFP-AVLQSSGLYSLSSVVTVPSSSLGTQTYICNVNH-KPSNTKVDKKVEPKSCDKTHTCPPCPAPELLGGPSV-FLFPPKPKDTLMISRTPEVTCVVVDVSHEDPEVKFN-WYVDGVEVHNAKTKPREEQYNSTYRVVSVLTVLHQ-DWLNGKEYKCKVSNKALPAPIEKTISKAKGQPREP QVYTLPPSRDELTKNQVSLTCLVKGFYPSDIAVEW-ESNGQPENNYKTTPPVLDSDGSFFLYSKLTVDKSR-WQQGNVFSCSVMHEALHNYTQKSLSLSPG (SEQ ID NO:16) and an immunoglobulin light chain region having the amino acid sequence of DIQMTQSPSSLSASVGDRVTITCRASQDINNYLAWYQ-HKPGKGPKLLIHYTSTLHPGIPSRFSGSGSGRDYSF-SISSLEPEDIATYYCLQYDNLLYTFGQGTKLEIKRT-VAAPSVFIFPPSDEQLKSGTASVVCLLNNFYPREAK-VQWKVDNALQSGNSQESVTEQDSKDSTYSLSSTLTL-SKADYEKHKVYACEVTHQGLSSPVTKSFNRGEC (SEQ ID NO:17), or an immunoglobulin light chain region having the amino acid sequence of DIQMTQSPSSLSASVGDRVTITCKASQQDINNYLAWY-QHKPGKGPKLLIHYTSTLHPGIPSRFSGSGSGRDYSF-SISSLEPEDIATYYCLQYDNLLYTFGQGTKLEIKRTV AAPSVFIFPPSDEQLKSGTASVVCLLNNFYPREAKVQ
WKVDNALQSGNSQESVTEQDSKDSTYSLSSTLTLSK
ADYEKHKVYACEVTHQGLSSPVTKSFNRGEC (SEQ
ID NO:18).

In another embodiment, the anti-EGFR antibody comprises an immunoglobulin heavy chain region having the amino acid sequence set forth in SEQ ID NO:16 and an immunoglobulin light chain region having the amino acid sequence set forth in SEQ ID NO:17.

In another embodiment, the anti-EGFR antibody comprises an immunoglobulin heavy chain region having the amino acid sequence set forth in SEQ ID NO:16 and an immunoglobulin light chain region having the amino acid sequence set forth in SEQ ID NO:18.

In yet another embodiment, the anti-EGFR antibody comprises the heavy chain CDR1-CDR3 of SEQ ID NO: 16, and/or the light chain CDR1-CDR3 of SEQ ID NO: 17 or 18, and preferably specifically binds EGFR.

In yet another embodiment, the anti-EGFR antibody comprises a heavy chain variable region (HCVR) sequence at least about 90%, 95%, 97%, 99%, or 100% identical to SEQ ID NO: 16, and/or a light chain variable region (LCVR) sequence at least about 90%, 95%, 97%, 99%, or 100% identical to SEQ ID NO: 17 or 18, and preferably specifically binds EGFR.

In another embodiment, the cell-binding agent is an anti-CD19 antibody, such as those described in U.S. Pat. No. 8,435,528 and WO2004/103272, herein incorporated by reference. In one embodiment, the anti-CD19 antibody comprises an immunoglobulin heavy chain region having the amino acid sequence of QVQLVQPGAEVVKPGAS-VKLSCKTSGYTFTSNWMHWVKQAPGQGLEWI GEI-DPSDSYTNYNQNFQGKAKLTVDKSTSTAYMEVSSL-RSDDTAVYYCARGSNPYYYAMDYWGQGTSVTVSSA-STKGPSVFPLAPSSKSTSGGTAALGCLVKDYFPEPVT-VSWNSGALTSGVHTFPAVLQSSGLYSLSSVVTVPSSS-LGTQTYICNVNHKPSNTKVDKKVEPKSCDKTHTC PP CPAPELLGGPSVFLFPPKPKDTLMISRTPEVTCVVVD-VSHEDPEVKFNWYVDGVEVHNAKTKPREEQYNST YRVVSVLTVLHQDWLNGKEYKCKVSNKALPAPIEK-TISKAKGQPREPQVYTLPPSRDELTKNQVSLTCLVKG-FYPSDIAVEWESNGQPENNYKTTPPVLDSDGSFFLY-SKLTVDKSRWQQGNVFSCSVMHEALHNHYTQKSLS-LSPGK (SEQ ID NO: 19) and an immunoglobulin light chain region having the amino acid sequence of (SEQ ID NO: 20)
EIVLTQSPAIMSASPGERVTMTCSASSGVNYMHWYQQKPGTSPRRWIYDT

SKLASGVPARFSGSGSGTDYSLTISSMEPEDAATYYCHQRGSYTFGGGTK

LEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSS

PVTKSFNRGEC.

In another embodiment, the anti-CD19 antibody is huB4 antibody.

In yet another embodiment, the anti-CD19 antibody comprises the heavy chain CDR1-CDR3 of SEQ ID NO: 19, and/or the light chain CDR1-CDR3 of SEQ ID NO: 20, and preferably specifically binds CD19.

In yet another embodiment, the anti-CD19 antibody comprises a heavy chain variable region (HCVR) sequence at least about 90%, 95%, 97%, 99%, or 100% identical to SEQ ID NO: 19, and/or a light chain variable region (LCVR) sequence at least about 90%, 95%, 97%, 99%, or 100% identical to SEQ ID NO: 20, and preferably specifically binds CD19.

In yet another embodiment, the cell-binding agent is an anti-Muc1 antibody, such as those described in U.S. Pat. No. 7,834,155, WO 2005/009369 and WO 2007/024222, herein incorporated by reference. In one embodiment, the anti-Muc1 antibody comprises an immunoglobulin heavy chain region having the amino acid sequence of QAQLVQSGAEVVKPGASVKMSCKASGYTFTSYNM-HWVKQTPGQGLEWIGYIYPGNGATNYNQKFQGKA TLTADTSSSTAYMQISSLTSEDSAVYFCARGDSVPFAY-WGQGTLVTVSAASTKGPSVFPLAPSSKSTSGGTAAL-GCLVKDYFPEPVTVSWNSGALTSGVHTFPAVLQSSG LYSLSSVVTVPSSSLGTQTYICNVNHKPSNTKVDK K VEPKSCDKTHTCPPCPAPELLGGPSVFLFPPKPKDTL MISRTPEVTCVVVDVSHEDPEVKFNWYVDGVEVH-NAKTKPREEQYNSTYRVVSVLTVLHQDWLNGKEYK CKVSNKALPAPIEKTISKAKGQPREPQVYTL PPSRD ELTKNQVSLTCLVKGFYPSDIAVEWESNGQPENNYK-TTPPVLDSDGSFFLYSKLTVDKSRWQQGNVFSCSVM-HEALHNHYTQKSLS LSPGK (SEQ ID NO:21) and an immunoglobulin light chain region having the amino acid sequence of (SEQ ID NO: 22)
EIVLTQSPATMSASPGERVTITCSAHSSVSFMHWFQQKPGTSPKLWIYST

SSLASGVPARFGGSGSGTSYSLTISSMEAEDAATYYCQQRSSFPLTFGAG

TKLELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC.

In another embodiment, the anti-Muc1 antibody is huDS6 antibody.

In yet another embodiment, the anti-Muc1 antibody comprises the heavy chain CDR1-CDR3 of SEQ ID NO: 21, and/or the light chain CDR1-CDR3 of SEQ ID NO: 22, and preferably specifically binds Muc1.

In yet another embodiment, the anti-Muc1 antibody comprises a heavy chain variable region (HCVR) sequence at least about 90%, 95%, 97%, 99%, or 100% identical to SEQ ID NO: 21, and/or a light chain variable region (LCVR) sequence at least about 90%, 95%, 97%, 99%, or 100% identical to SEQ ID NO: 22, and preferably specifically binds Muc1.

In another embodiment, the cell-binding agent is an anti-CD33 antibody or fragment thereof, such as the antibodies or fragments thereof described in U.S. Pat. Nos. 7,557,189, 7,342,110, 8,119,787 and 8,337,855 and WO2004/043344, herein incorporated by reference. In another embodiment, the anti-CD33 antibody is huMy9-6 antibody.

In one embodiment, the anti-CD33 antibody comprises an immunoglobulin heavy chain region having the amino acid sequence of QVQLQQPGAEVVKPGASVKMSCKASGYTFTSYYIH-WIKQTPGQGLEWVGVIYPGNDDISYNQKFQGKATL-TADKSSTTAYMQLSSLTSEDSAVYYCAREVRLRYFD-VWGQGTTVTVSSASTKGPSVFPLAPSSKSTSGGTA A LGCLVKDYFPEPVTVSWNSGALTSGVHTFPAVLQSS-GLYSLSSVVTVPSSSLGTQTYICNVNHKPSNTKVDK-KVEPKSCDKTHTCPPCPAPELLGGPSVFLFPPKPKDT LMISRTPEVTCVVVDVSHEDPEVKFNWYVDGVEVH-NAKTKPREEQYNSTYRVVSVLTVLHQDWLNGKEY KCKVSNKALPAPIEKTISKAKGQPREP QVYTL PP SR DELTKNQVSLTCLVKGFYPSDIAVEWESNGQPENNY KTTPPVLDSDGSFFLYSKLTVDKSRWQQGNVFS CSV MHEALHNHYTQKSLSLSPG (SEQ ID NO:23), and an immunoglobulin light chain region having the amino acid sequence of (SEQ ID NO: 24)
EIVLTQSPGSLAVSPGERVTMSC<u>KSSQSVFFSSSQKNYL</u>AWYQQIPGQSP RLLIY<u>WASTRES</u>GVPDRFTGSGSGTDFTLTISSVQPEDLAIYYC<u>HQYLSS</u>

<u>RT</u>FGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

In yet another embodiment, the anti-CD33 antibody comprises the heavy chain CDR1-CDR3 of SEQ ID NO: 23, and/or the light chain CDR1-CDR3 of SEQ ID NO: 24, and preferrably specifically binds CD33.

In yet another embodiment, the anti-CD33 antibody comprises a heavy chain variable region (HCVR) sequence at least about 90%, 95%, 97%, 99%, or 100% identical to SEQ ID NO: 23, and/or a light chain variable region (LCVR) sequence at least about 90%, 95%, 97%, 99%, or 100% identical to SEQ ID NO: 24, and preferrably specifically binds CD33.

In another embodiment, the cell-binding agent is an anti-CD37 antibody or an antibody fragment thereof, such as those described in U.S. Pat. No. 8,765,917 and WO 2011/112978, herein incorporated by reference. In one embodiment, the anti-CD37 antibody is huCD37-3 antibody.

In one embodiment, the anti-CD37 antibody comprises an immunoglobulin light chain region having the amino acid sequence of DIQMTQSPSSLSVSVGERVTITCRASENIRSNLAWYQ-QKPGKSPKLLVNVATNLADGVPSRFSGSGSGTDYSL KINSLQPEDFGTYYCQHYWGTTWTFGQGTKLEI KRT VAAPSVFIFPPSDEQLKSGTASVVCLLNNFYPREAKV QWKVDNALQSGNSQESVTEQDSKDSTYSLSSTLTL-SKADYEKHKVYACEVTHQGLSSPVTKSFNRGEC (SEQ ID NO:25) and an immunoglobulin heavy chain region having the amino acid sequence of QVQVQESGPGLVAPSQTLSITCTVSGFSLTTSGVSWV-RQPPGKGLEWLGVIWG DGSTNYHPSLKSRLSIKKDHSKSQVFLKLNSLTAAD-TATYYCAKGGYSLAHWG QGTLVTVSSASTKGPSVFPLAPSSKSTSGGTAALGCL-VKDYFPEPVTVSWNSGALTSGVHTFPAVLQSSGLY SLSSVVTVPSSSLGTQTYICNVNHKPSNTKVDKKVE-PKSCDKTHTCPPCPAPELLGGPSVFLFPPKPKDTLM ISRTPEVTCVVVDVSHEDPEVKFNWYVDGVEVHNA KTKPREEQYNSTYRVVSVLTVLHQDWLNGKEYKCK-VSNKALPAPIEKTISKAKGQPREP QVYTLPPSRDELT-KNQVSLTCLVKGFYPSDIAVEWESNGQPENNYKTTP-PVLDSDGSFFLYSKLTVDKSRWQQGNVFSCSVMHE-ALHNHYTQKSLSLSPG (SEQ ID NO:26), or an immunoglobulin heavy chain region having the amino acid sequence of (SEQ ID NO: 27)
QVQVQESGPGLVAPSQTLSITCTVSGFSLT<b>TSGVS</b>WVRQPPGKGLEWLGV <b>IWGDGSTN</b>YHSSLKSRLSIKKDHSKSQVFLKLNSLTAADTATYYCAK<b>GGY</b>

<b>SLAH</b>WG<u>QGTLVTVSS</u>ASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

In another embodiment, the anti-CD37 antibody comprises an immunoglobulin light chain region having the amino acid sequence set forth in SEQ ID NO:25 and an immunoglobulin heavy chain region having the amino acid sequence set forth in SEQ ID NO:26.

In yet another embodiment, the anti-CD37 antibody comprises an immunoglobulin light chain region having the amino acid sequence set forth in SEQ ID NO:25 and an immunoglobulin heavy chain region having the amino acid sequence set forth in SEQ ID NO:27.

In yet another embodiment, the anti-CD37 antibody comprises the heavy chain CDR1-CDR3 of SEQ ID NO: 26 or 27, and/or the light chain CDR1-CDR3 of SEQ ID NO: 25, and preferrably specifically binds CD37.

In yet another embodiment, the anti-CD37 antibody comprises a heavy chain variable region (HCVR) sequence at least about 90%, 95%, 97%, 99%, or 100% identical to SEQ ID NO: 26 or 27, and/or a light chain variable region (LCVR) sequence at least about 90%, 95%, 97%, 99%, or 100% identical to SEQ ID NO: 25, and preferrably specifically binds CD37.

In yet another embodiment, the anti-CD37 antibody comprises an immunoglobulin light chain region having the amino acid sequence of EIVLTQSPATMSASPGERVTMTCSATSSVTYMHWYQ-QQQKPGQSPKRWIYDTSNL PYGVPARFSGSGSGTSYSLTISSMEAEDAATYYCQQ-WSDNPPTFGQGTKLEIKRTVAAPSVFIFPPSDEQLKS-GTASVVCLLNNFYPREAKVQWKVDNALQSGNSQES-VTEQDSKDSTYSLSSTLTLSKADYEKHKVYACEVTH QGLSSPVTKSFNRGEC (SEQ ID NO:28) and an immunoglobulin heavy chain reion having the amino acid sequence of (SEQ ID NO: 29)
QVQLQESGPGLLKPSQSLSLTCTVSGYSIT<b>SGFAWH</b>WIRQHPGNKLEWMG <u>YILYSGSTV</u>YSPSLKSRISITRDTSKNHFFLQLNSVTAADTATYYCAR<u>GY</u>

<u>YGYGAWFAY</u>WGQGTLVTVSAASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG.

In yet another embodiment, the anti-CD37 antibody comprises the heavy chain CDR1-CDR3 of SEQ ID NO: 29, and/or the light chain CDR1-CDR3 of SEQ ID NO: 28, and preferrably specifically binds CD37.

In yet another embodiment, the anti-CD37 antibody comprises a heavy chain variable region (HCVR) sequence at least about 90%, 95%, 97%, 99%, or 100% identical to SEQ ID NO: 29, and/or a light chain variable region (LCVR) sequence at least about 90%, 95%, 97%, 99%, or 100% identical to SEQ ID NO: 28, and preferrably specifically binds CD37.

In yet another embodiment, the anti-CD37 antibody is huCD37-50 antibody.

Cell-Binding Agent-Drug Conjugates

The present invention also provides cell-binding agent-drug conjugates comprising a cell-binding agent linked to one or more cytotoxic compounds of the present invention via a variety of linkers, including, but not limited to, disulfide linkers, thioether linkers, amide bonded linkers, peptidase-labile linkers, acid-labile linkers, esterase-labile linkers.

In a second embodiment, the invention provides a conjugate comprising: a cytotoxic compound and a cell binding agent (CBA), wherein the cytotoxic compound is covalently covalently linked to the CBA, and wherein the cytotoxic compound is represented by structural formulas (I'), (II'), (III'), (IV'), (V') or (VI'), wherein the variables are as described above.

In certain embodiments, the cytotoxic compound is represented by structural formula (I') or a pharmaceutically acceptable salt thereof.

In certain embodiments, for structural formulas (I'), (II'), (III'), (IV'), (V') and (VI'), one of L', L'' and L''' is represented by formula (A'):

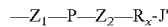    (A'), and the others are —H, an linear or branched alkyl having from 1 to 6 carbon atoms, halogen, —OH, ($C_1$-$C_6$)alkoxy, or —NO$_2$. Specifically, one of L', L'' and L''' is represented by formula (A'), and the others are —H.

In a 1$^{st}$ specific embodiment, for structural formulas (I'), (II'), (III'), (IV'), (V') and (VI'), L' is represented by formula (A') and L'' and L''' are both —H; and the remaining variables are as described above in the first embodiment.

In a 2$^{nd}$ specific embodiment, for structural formulas (I'), (II'), (III'), (IV'), (V') and (VI'), R$_x$ is a linear, branched or cyclic alkyl having 1 to 6 carbon atoms optionally substituted with halogen, —OH, ($C_1$-$C_3$)alkyl, ($C_1$-$C_3$)alkoxy, halo($C_1$-$C_3$)alkyl, or a charged substituent or an ionizable group Q; and the remaining variables are as described above in the first embodiment or the 1$^{st}$ specific embodiment.

In certain embodiments, Q is i) —SO$_3$H, —Z'—SO$_3$H, —OPO$_3$H$_2$, —Z'—OPO$_3$H$_2$, —PO$_3$H$_2$, —Z'—PO$_3$H$_2$, —CO$_2$H, —Z'—CO$_2$H, —NR$_{11}$R$_{12}$, or —Z'—NR$_{11}$R$_{12}$, or a pharmaceutically acceptable salt thereof; or, ii) —N$^+$R$_{14}$R$_{15}$R$_{16}$X$^-$ or —Z'—N$^+$R$_{14}$R$_{15}$R$_{16}$X$^-$; Z' is an optionally substituted alkylene, an optionally substituted cycloalkylene or an optionally substituted phenylene; R$_{14}$ to R$_{16}$ are each independently an optionally substituted alkyl; and X$^-$ is a pharmaceutically acceptable anion; and the remaining variables are as described above in the 2$^{nd}$ specific embodiment. More specifically, Q is —SO$_3$H or a pharmaceutically acceptable salt thereof.

In a 3$^{rd}$ specific embodiment, for structural formulas (I'), (II'), (III'), (IV'), (V') and (VI'), J' comprises a moiety that is covalently linked to the CBA, and is —NR$^{c1}$ or —C(=O)—, wherein R$^{c1}$ is —H or linear or branched alkyl having 1 to 4 carbon atoms optionally substituted with halogen, —OH or ($C_1$-$C_3$)alkoxy; and the remaining variables are as described above in the first embodiment or the 1$^{st}$ or 2$^{nd}$ specific embodiment.

In certain embodiments, J' is —C(=O)—; and the remaining variables are as described above in the 3$^{rd}$ specific embodiment.

In a 4$^{th}$ specific embodiment, for structural formulas (I'), (II'), (III'), (IV'), (V') and (VI'), L' is represented by the following formula:

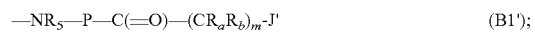    (B1');

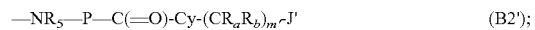    (B2');

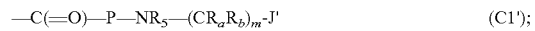    (C1');

or

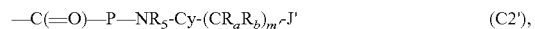    (C2'), wherein:

J' is —C(=O)—;

R$_a$ and R$_b$, for each occurrence, are each independently —H, ($C_1$-$C_3$)alkyl or a charged substituent or an ionizable group Q;

m is an integer from 1 to 6;

m' is 0 or an integer from 1 to 6; and

Cy is a cyclic alkyl having 5 or 6 ring carbon atoms optionally substituted with halogen, —OH, ($C_1$-$C_3$)alkyl, ($C_1$-$C_3$)alkoxy, or halo($C_1$-$C_3$)alkyl; and the remaining variables are as described above in the first embodiment or the 1$^{st}$, 2$^{nd}$ or 3$^{rd}$ specific embodiment.

In certain embodiments, R$_a$ and R$_b$ are both H; Cy for formulas (B2') and (C2') is cyclohexane; and R$_5$ is H or Me; and the remaining variables are as described above in the 4$^{th}$ specific embodiment. More specifically, m' in formulas (B2') and (C2') is 0 or 1.

In a 5$^{th}$ specific embodiment, for structural formulas (I'), (II'), (III'), (IV'), (V') and (VI'), L' is represented by the following formula:

    (B3');

or

    (C3'), wherein:

R$_a$ and R$_b$, for each occurrence, are each independently —H, ($C_1$-$C_3$)alkyl, or a charged substituent or an ionizable group Q;

m is an integer from 1 to 6;

$Z^{s1}$ is selected from any one of the following formulas:
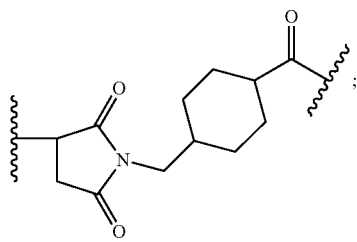
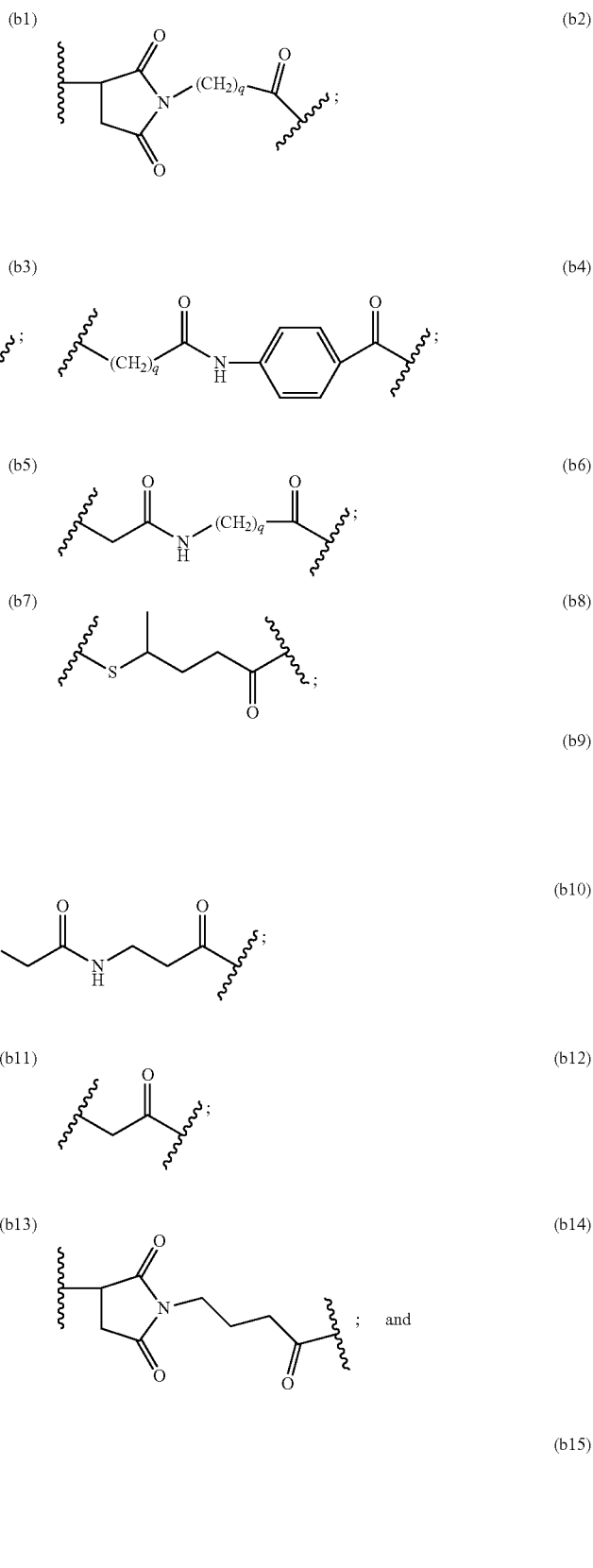

wherein:
q is an integer from 1 to 5;
n' is an integer from 2 to 6;
U is —H or $SO_3M$;
M is a pharmaceutically acceptable cation (e.g., $H^+$, $Na^+$ or $K^+$); and the remaining variables are as described above in the first embodiment or the $1^{st}$, $2^{nd}$, $3^{rd}$ or $4^{th}$ specific embodiment.

In certain embodiments, the charged substituent or an ionizable group Q is i) —$SO_3H$, —Z'—$SO_3H$, —$OPO_3H_2$, —Z'—$OPO_3H_2$, —$PO_3H_2$, —Z'—$PO_3H_2$, —$CO_2H$, —Z'—$CO_2H$, —$NR_{11}R_{12}$, or —Z'—$NR_{11}R_{12}$, or a pharmaceutically acceptable salt thereof; or, ii) —$N^+R_{14}R_{15}R_{16}X^-$ or —Z'—$N^+R_{14}R_{15}R_{16}X^-$; Z' is an optionally substituted alkylene, an optionally substituted cycloalkylene or an optionally substituted phenylene; $R_{14}$ to $R_{16}$ are each independently an optionally substituted alkyl; and $X^-$ is a pharmaceutically acceptable anion; and the remaining variables are as described above in the $5^{th}$ specific embodiment. More specifically, Q is —$SO_3H$ or a pharmaceutically acceptable salt thereof.

In certain embodiments, $R_a$ and $R_b$ are both —H and $R_5$ is H or Me; and the remaining variables are as described above in the $5^{th}$ specific embodiment.

In certain embodiments, —$(CR_aR_b)_m$— is —$(CH_2)_{m''}$—$C(Me_2)$- and m" is an integer from 1 to 5; the remaining variables are as described above in the $5^{th}$ specific embodiment.

In a $6^{th}$ specific embodiment, for structural formulas (I'), (II'), (III'), (IV'), (V') and (VI'), P is a peptide containing 2 to 10 amino acid residues; and the remaining variables are as described above in the first embodiment or the $1^{st}$, $2^{nd}$, $3^{rd}$, $4^{th}$ or $5^{th}$ specific embodiment.

In certain embodiments, P is a peptide containing 2 to 5 amino acid residues; and the remaining variables are as described above in the $6^{th}$ specific embodiment.

In certain embodiments, P is selected from Gly-Gly-Gly, Ala-Val, Val-Ala, Val-Cit, Val-Lys, Phe-Lys, Lys-Lys, Ala-Lys, Phe-Cit, Leu-Cit, Lle-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu, β-Ala-Leu-Ala-Leu and Gly-Phe-Leu-Gly, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Met-Ala; and the remaining variables are as described above in the $6^{th}$ specific embodiment.

In certain embodiments, P is Gly-Gly-Gly, Ala-Val, Ala-Ala, Ala-D-Ala, D-Ala-Ala, and D-Ala-D-Ala; and the remaining variables are as described above in the $6^{th}$ specific embodiment.

In a $7^{th}$ specific embodiment, for structural formulas (I'), (II'), (III'), (IV'), (V') and (VI), the double line ═ between N and C represents a double bond; and the remaining variables are as described above in the first embodiment, or the $1^{st}$, $2^{nd}$, $3^{rd}$, $4^{th}$, $5^{th}$ or $6^{th}$ specific embodiment.

In a $8^{th}$ specific embodiment, for structural formulas (I'), (II'), (III'), (IV'), (V') and (VI'), the double line ═ between N and C represents a single bond, X is —H or an amine protecting group; and Y is selected from —H, —OR, —OCOR', —SR, —NR'R", an optionally substituted 5- or 6-membered nitrogen-containing heterocycle, —$SO_3H$, —$SO_2H$ and —$OSO_3H$; ane the remaining variables are as described in the first embodiment or the $1^{st}$, $2^{nd}$, $3^{rd}$, $4^{th}$, $5^{th}$, $6^{th}$ or $7^{th}$ specific embodiment.

In certain embodiments, Y is selected from —H, —$SO_3M$, —OH, —OMe, —OEt or —NHOH, wherein M is —H, $Na^+$ or $K^+$; and the remaining variables are as described above in the $8^{th}$ specific embodiment. More specifically, Y is —H, —$SO_3M$ or —OH.

In a $9^{th}$ specific embodiment, for structural formulas (I'), (II'), (III'), (IV'), (V') and (VI'), X' is selected from the group consisting of —H, —OH, an optionally substituted linear, branched or cyclic alkyl, alkenyl or alkynyl having from 1 to 10 carbon atoms, and phenyl; and the remaining variables are as described in the first embodiment or the $1^{st}$, $2^{nd}$, $3^{rd}$, $4^{th}$, $5^{th}$, $6^{th}$, $7^{th}$ or $8^{th}$ specific embodiment.

In certain embodiments, X' is —H, —OH, $(C_1-C_3)$alkyl, halo$(C_1-C_3)$alkyl, or phenyl; and the remaining variables are as described above in the $9^{th}$ specific embodiment. More specifically, X' is —H, —OH or -Me. Even more specifically, X' is —H.

In a $10^{th}$ specific embodiment, for structural formulas (I'), (II'), (III'), (IV'), (V') and (VI'), Y' is —H, an oxo group, $(C_1-C_3)$alkyl or halo$(C_1-C_3)$alkyl; and the remaining variables are as described in the first embodiment or the $1^{st}$, $2^{nd}$, $3^{rd}$, $4^{th}$, $5^{th}$, $6^{th}$, $7^{th}$, $8^{th}$ or $9^{th}$ specific embodiment. More specifically, Y' is —H or oxo. Even more specifically, Y' is —H.

In a $11^{th}$ specific embodiment, for structural formulas (I'), (II'), (III'), (IV'), (V') and (VI'), A and A' are the same or different, and are selected from —O—, —S—, —$NR_5$—, and oxo —(C═O)—; and the remaining variables are as described in the first embodiment or the $1^{st}$, $2^{nd}$, $3^{rd}$, $4^{th}$, $5^{th}$, $6^{th}$, $7^{th}$, $8^{th}$, $9^{th}$ or $10^{th}$ specific embodiment. More specifically, A and A' are the same or different, and are selected from —O— and —S—. Even more specifically, A and A' are —O—.

In a $12^{th}$ specific embodiment, for structural formulas (I'), (II'), (III'), (IV'), (V') and (VI'), $R_6$ is —OMe; and the remaining variables are as described in the first embodiment or the $1^{st}$, $2^{nd}$, $3^{rd}$, $4^{th}$, $5^{th}$, $6^{th}$, $7^{th}$, $8^{th}$, $9^{th}$, $10^{th}$ or $11^{th}$ specific embodiment.

In a $13^{th}$ specific embodiment, for structural formulas (I'), (II'), (III'), (IV'), (V') and (VI'), $R_1$, $R_2$, $R_3$, $R_4$, $R_1'$, $R_2'$, $R_3'$ and $R_4'$ are independently —H, halogen, —$NO_2$, —OH, $(C_1-C_3)$alkyl, halo$(C_1-C_3)$alkyl or $(C_1-C_3)$alkoxy; and the remaining variables are as described in the first embodiment or the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$ or $12^{th}$ specific embodiment. More specifically, $R_1$, $R_2$, $R_3$, $R_4$, $R_1'$, $R_2'$, $R_3'$ and $R_4'$ are all —H.

In a $14^{th}$ specific embodiment, for structural formulas (I'), (II'), (III'), (IV'), (V') and (VI'), R, R', R" and $R_5$ are each independently —H or $(C_1-C_3)$alkyl; and the remaining variables are as described in the first embodiment or the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$ or $13^{th}$ specific embodiment.

In a $14^{th}$ specific embodiment, for structural formulas (I'), (II'), (III'), (IV'), (V') and (VI'), the double line ═ between N and C represents a single bond or double bond, provided that when it is a double bond X is absent and Y is —H, and when it is a single bond, X is —H, Y is —OH or —$SO_3M$;
$R_1$, $R_2$, $R_3$, $R_4$, $R_1'$, $R_2'$, $R_3'$ and $R_4'$ are all —H;
$R_6$ is —OMe;
X' and Y' are both —H;
A and A' are —O—;
M is H, $Na^+$ or $K^+$; and the remaining variables are as described in the first embodiment or the $1^{st}$, $2^{nd}$, $3^{rd}$, $4^{th}$, $5^{th}$ or $6^{th}$ specific embodiment.

In a $15^{th}$ specific embodiment, the conjugate of the present invention is represented by any one of the following structural formula:

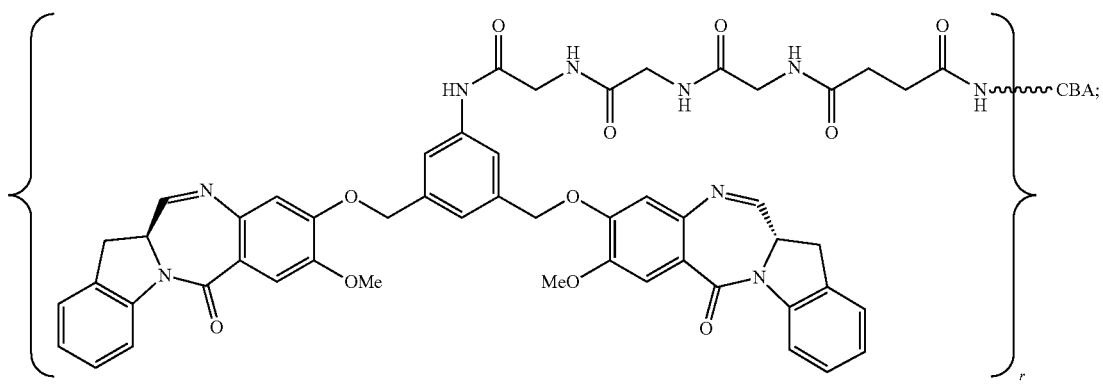
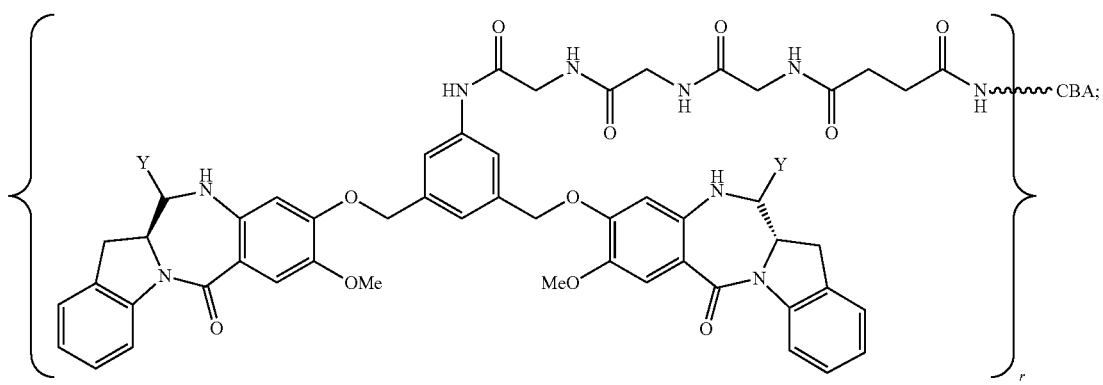
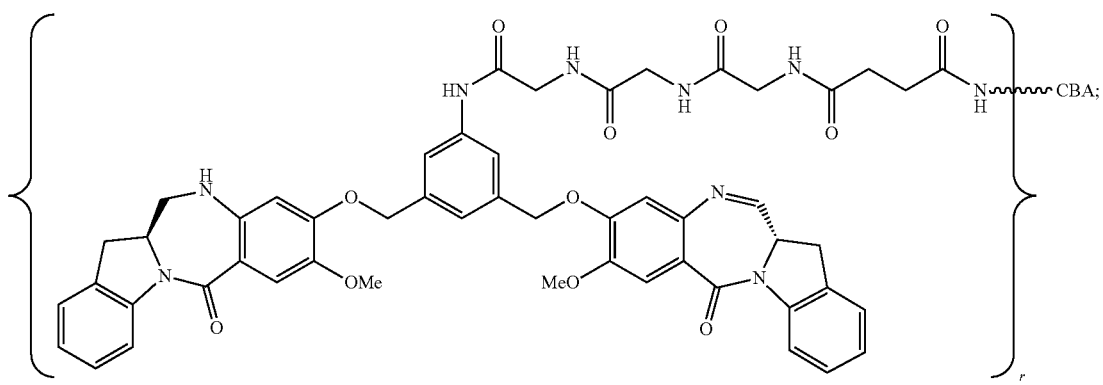
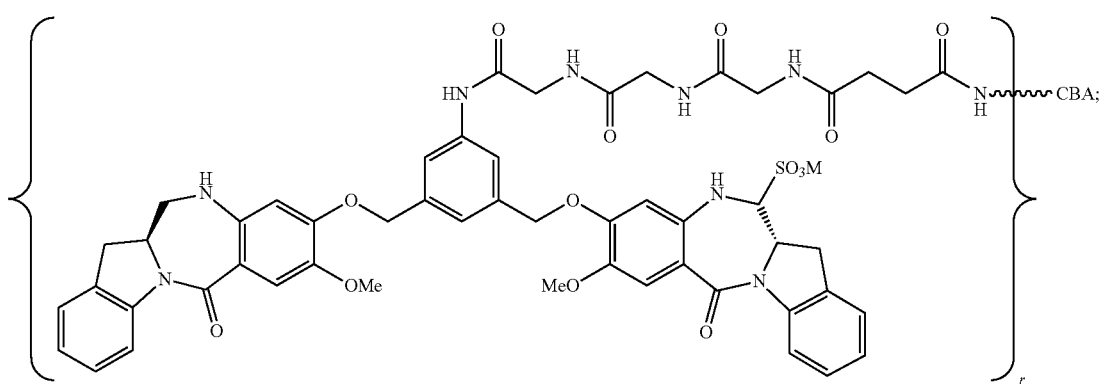

-continued
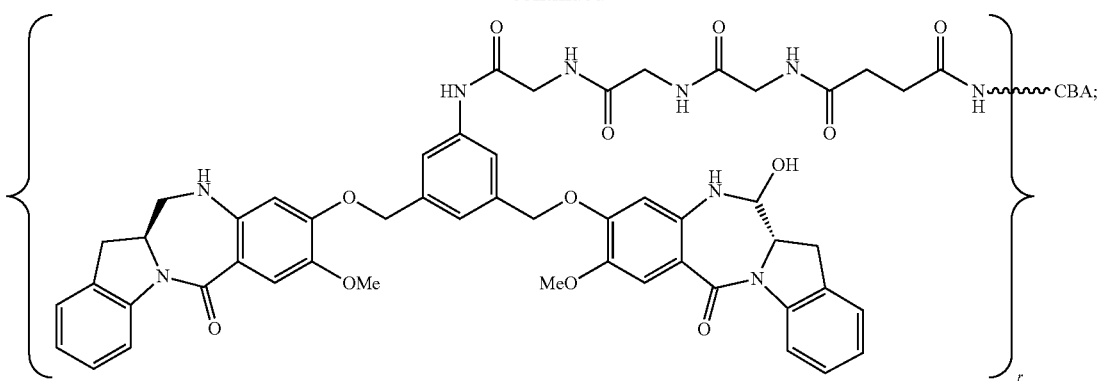
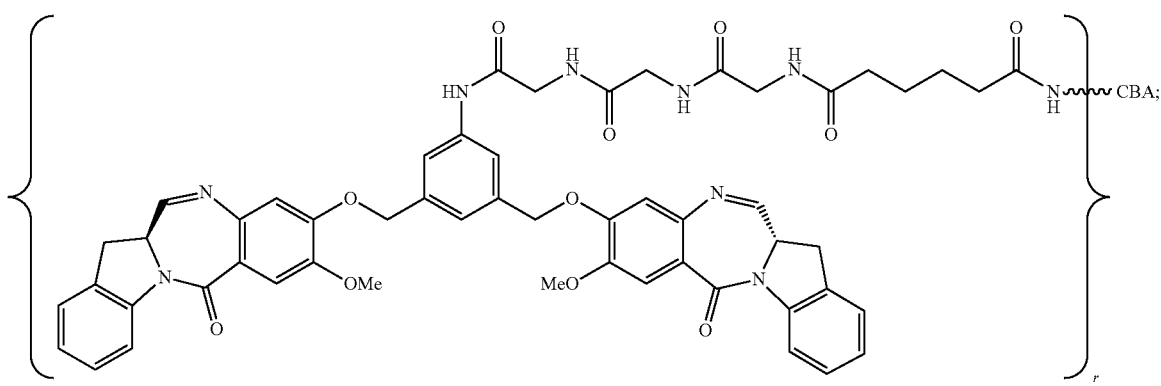
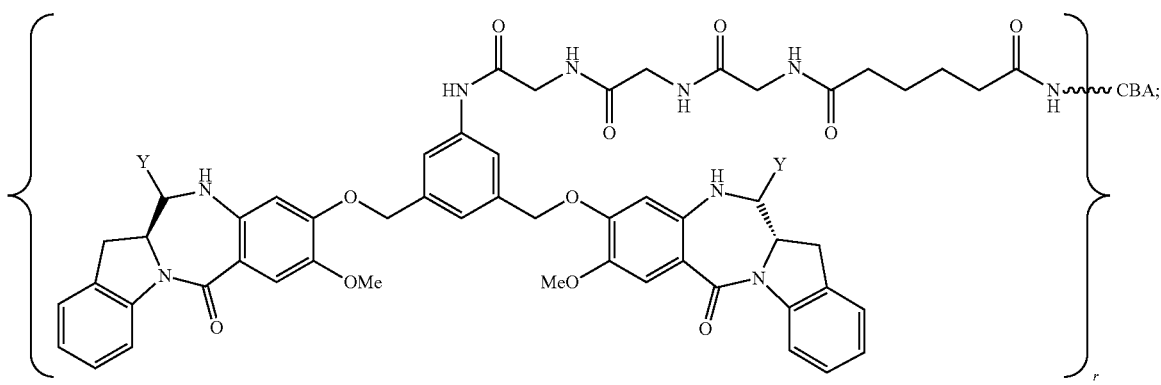
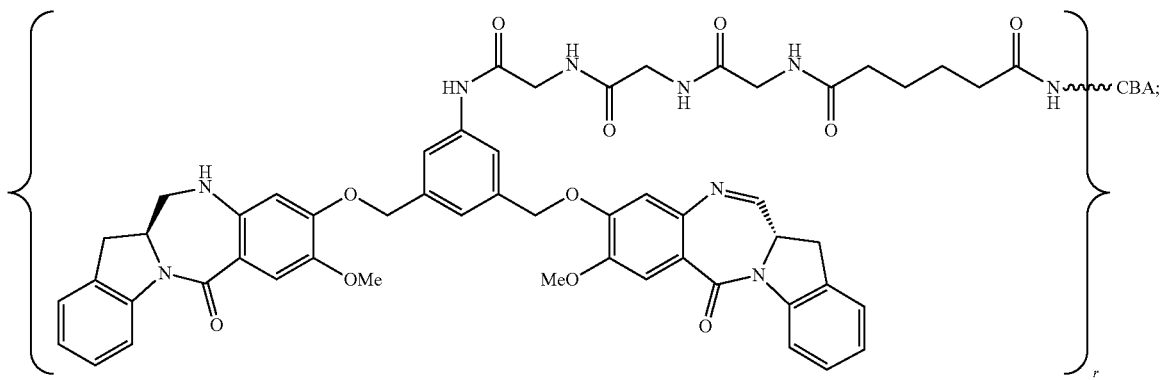

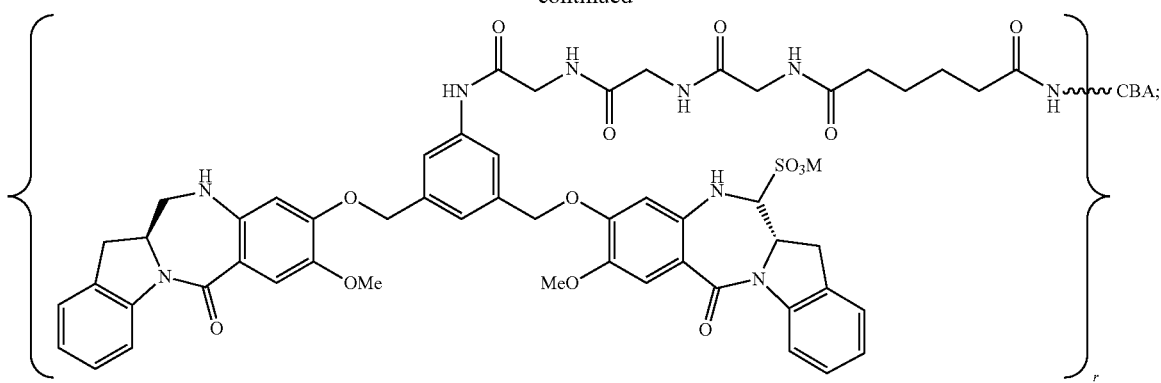
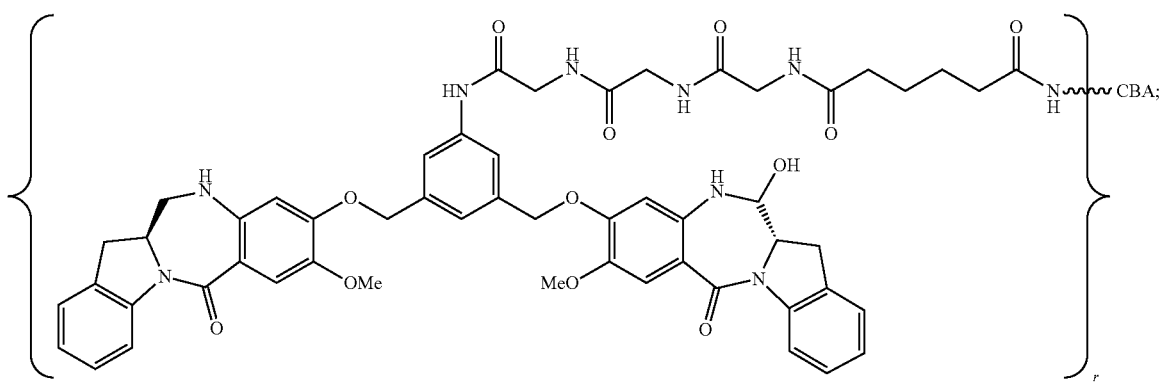
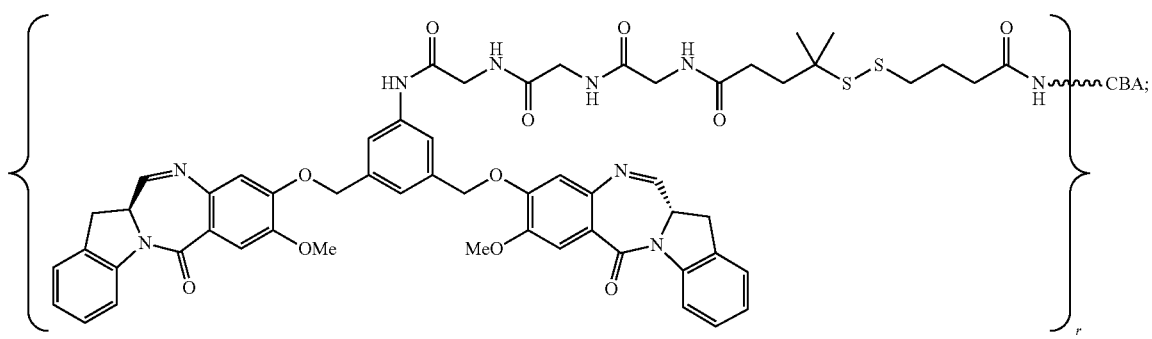
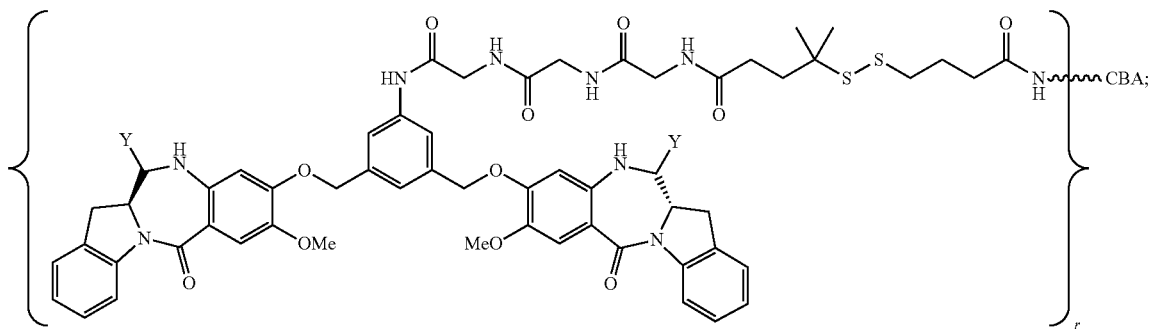

-continued
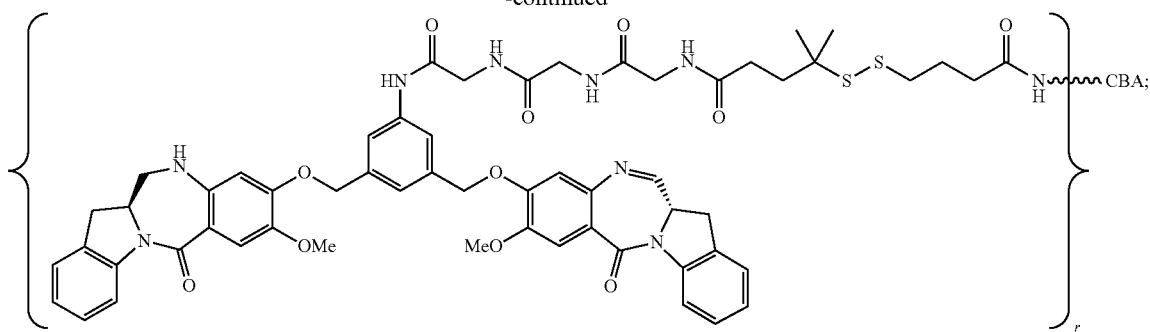
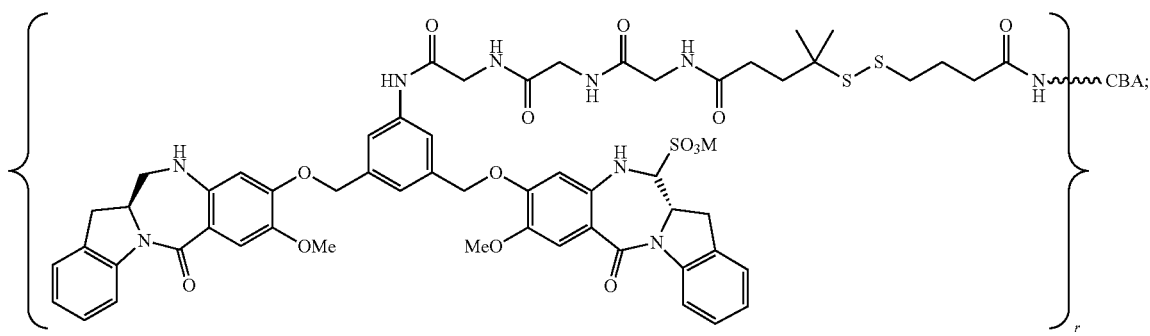
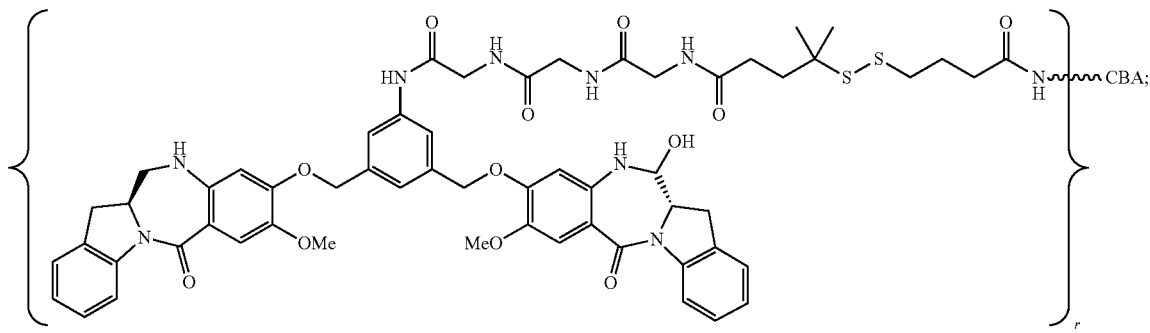
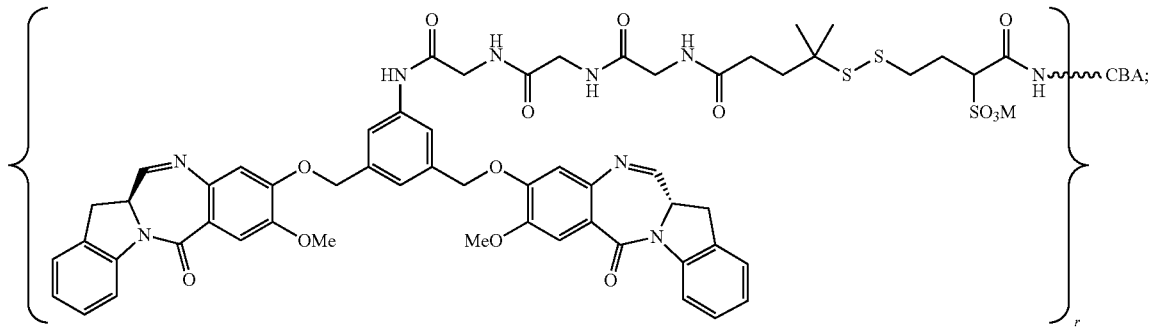
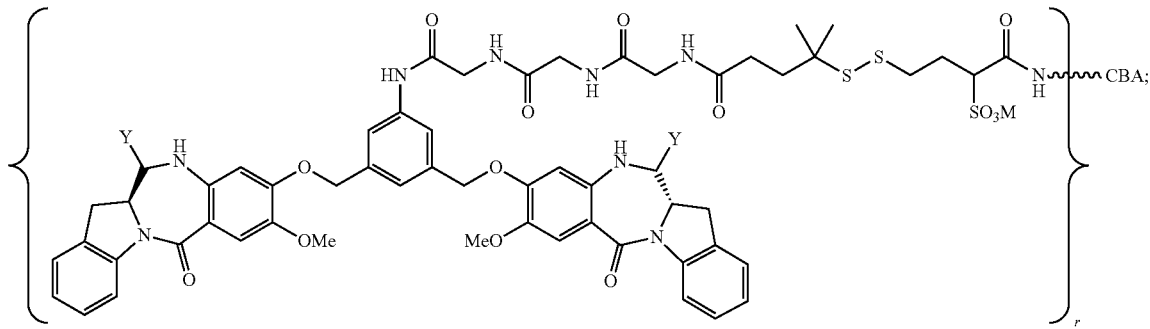

101  102
-continued
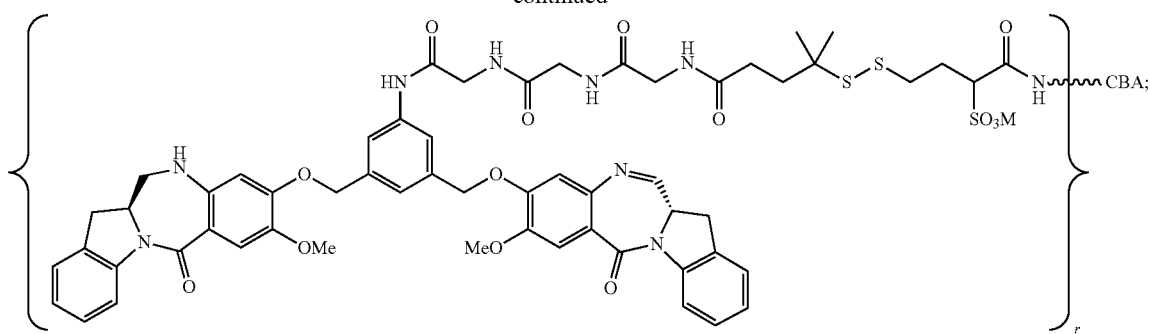
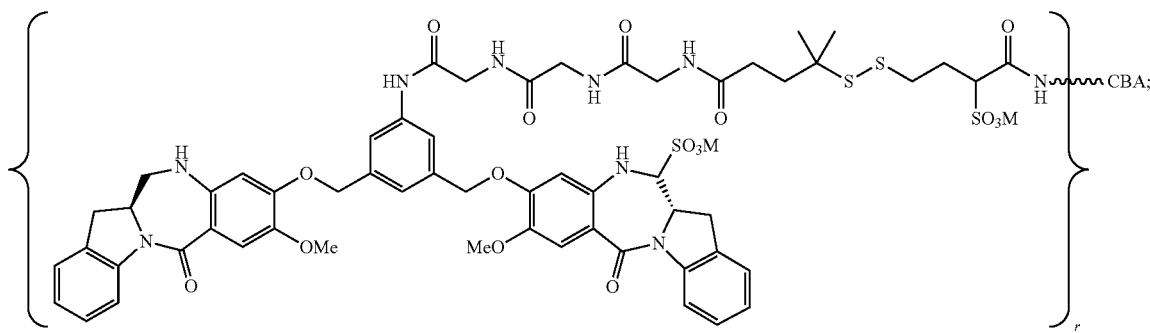
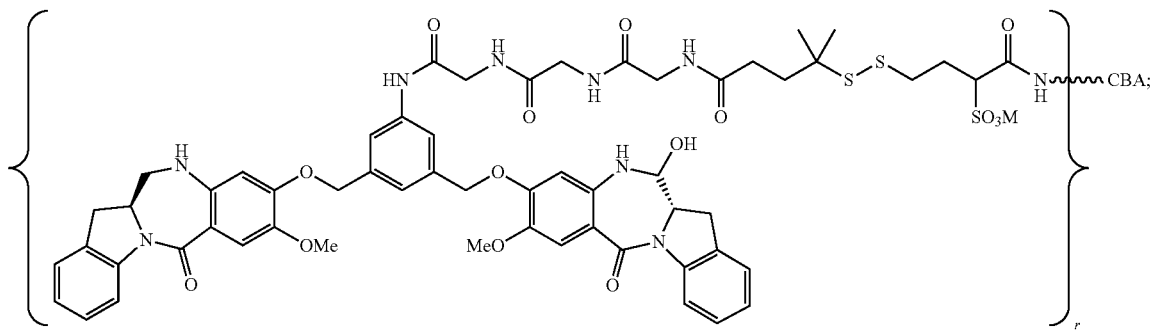
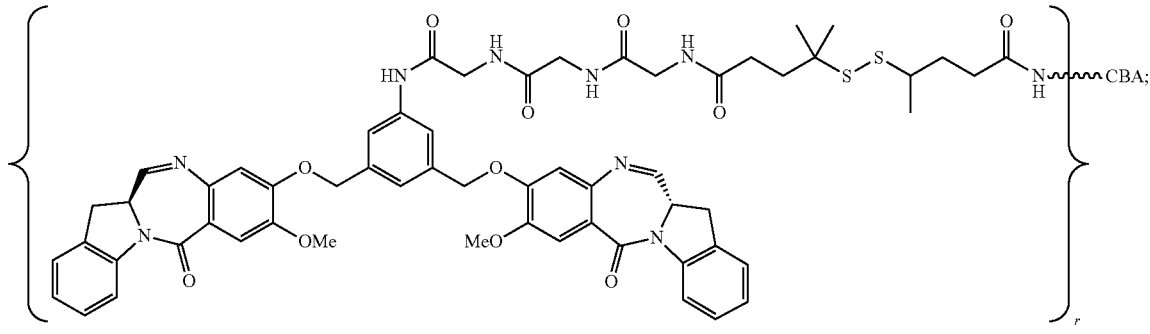
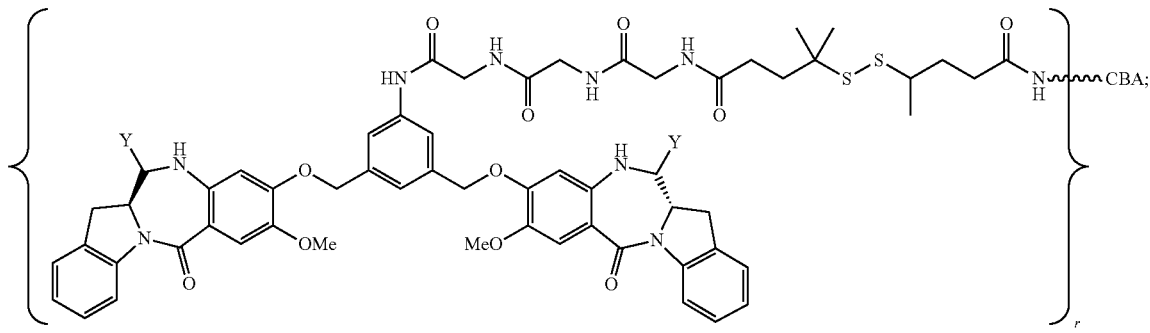

-continued
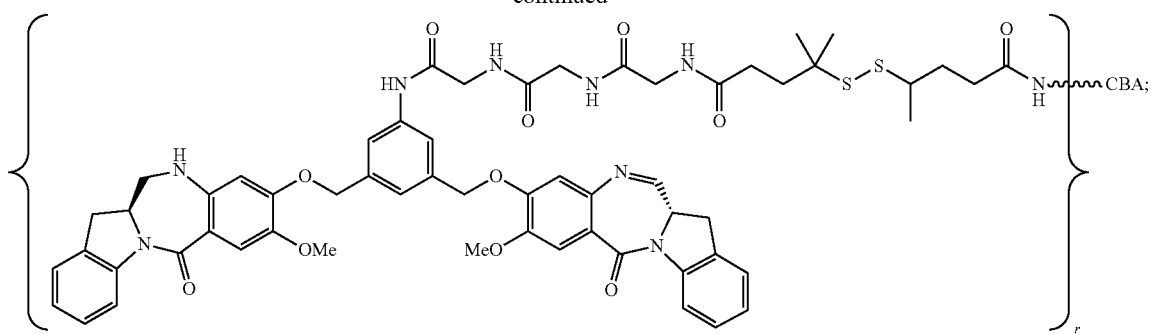
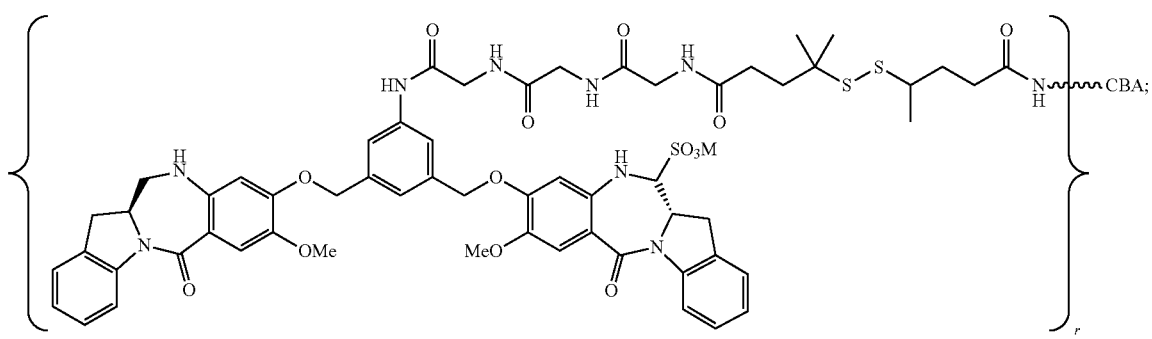
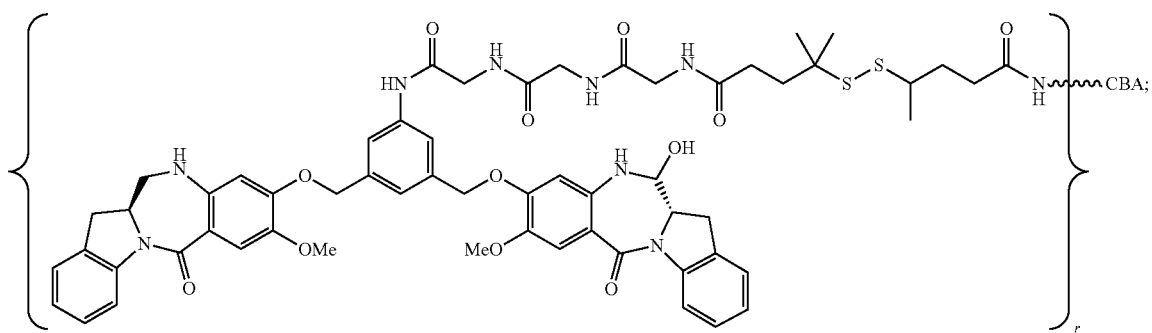
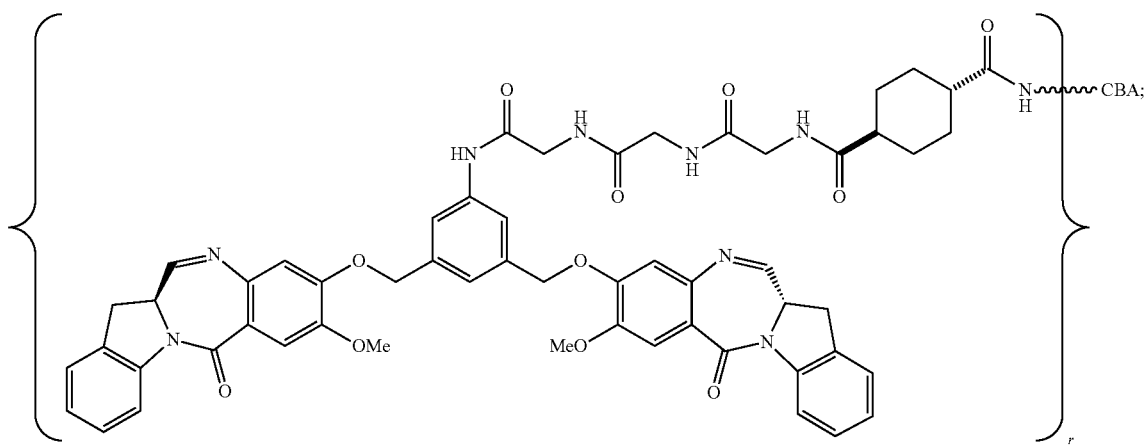

-continued
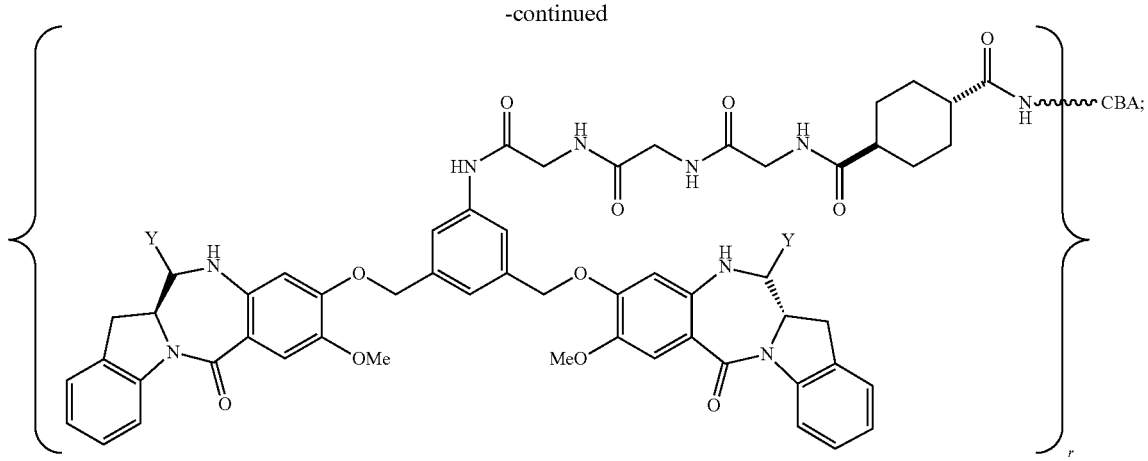
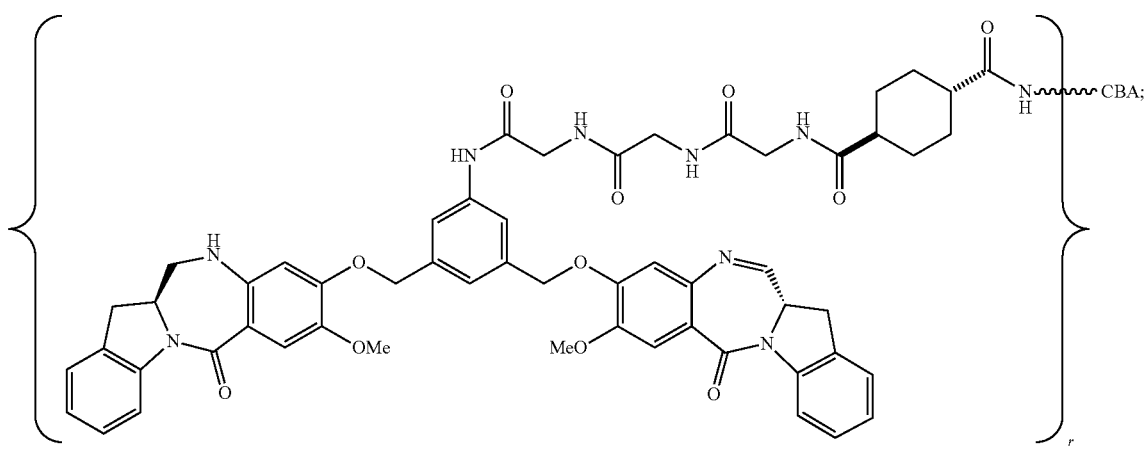
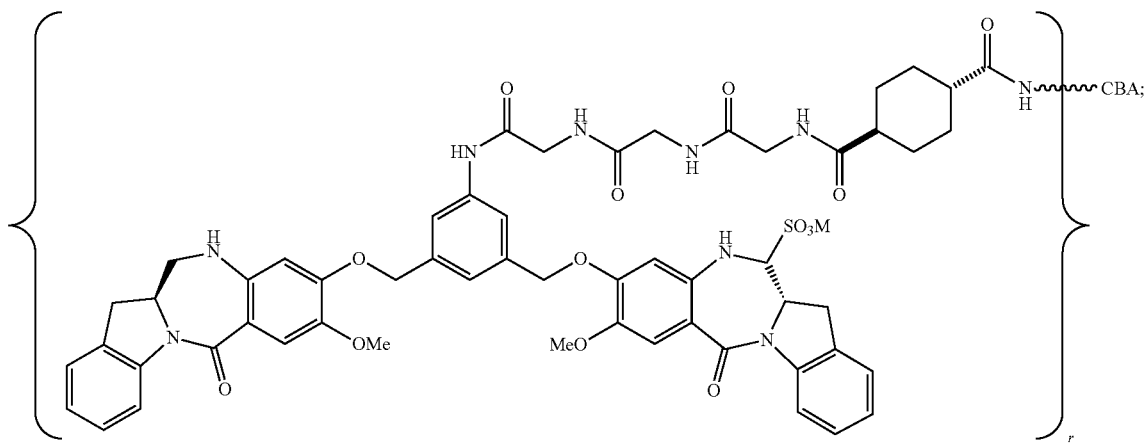

107 108
-continued
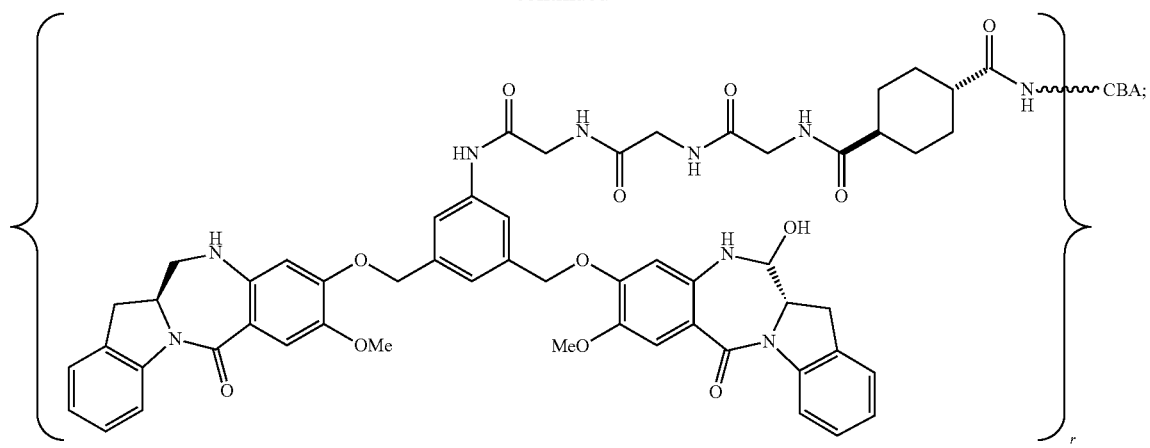
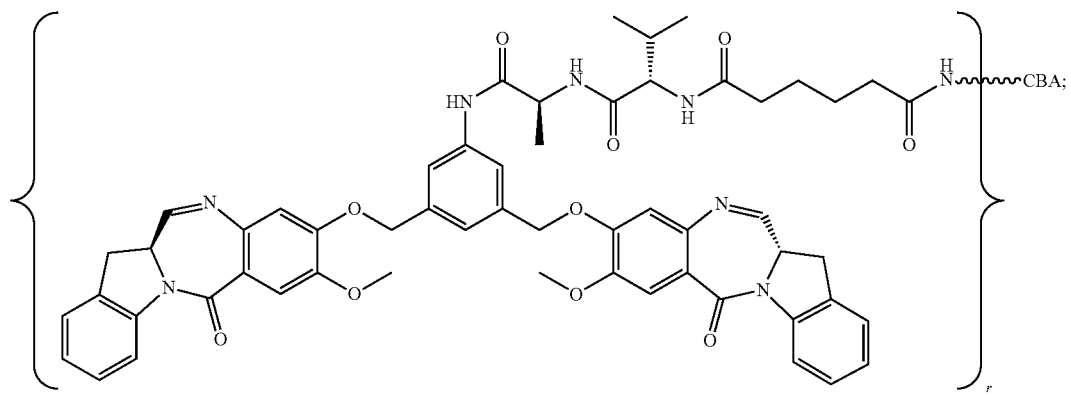
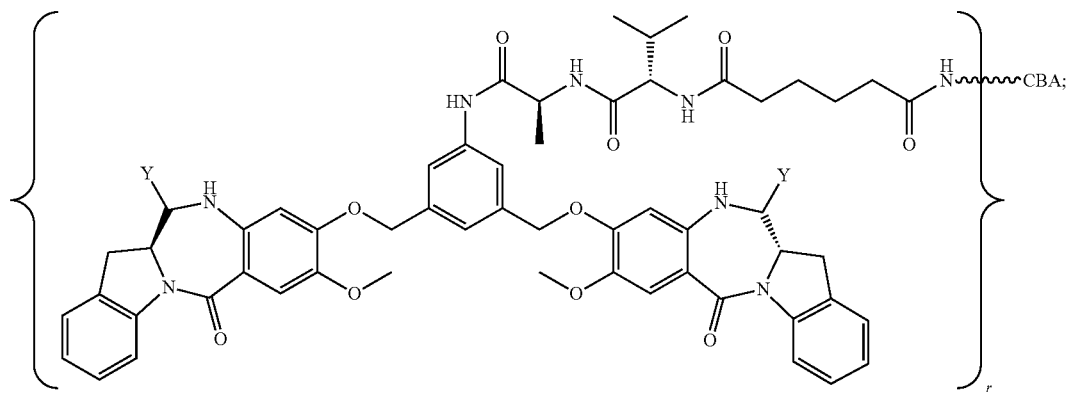
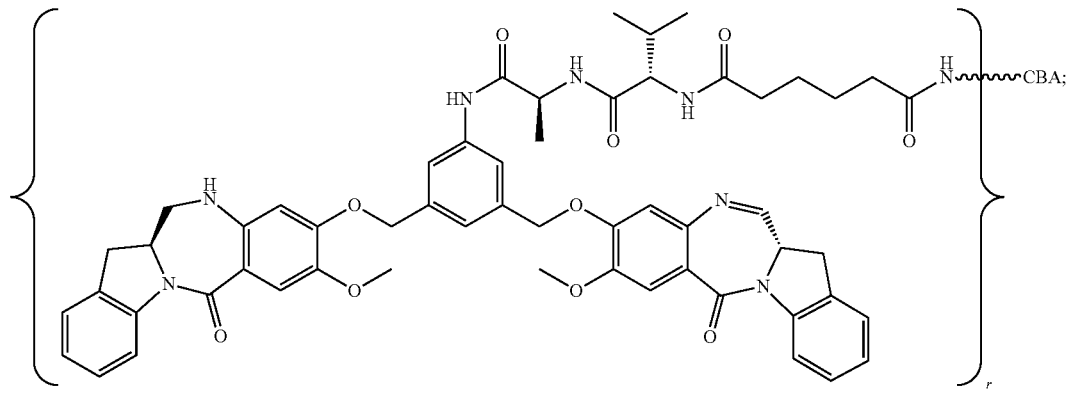

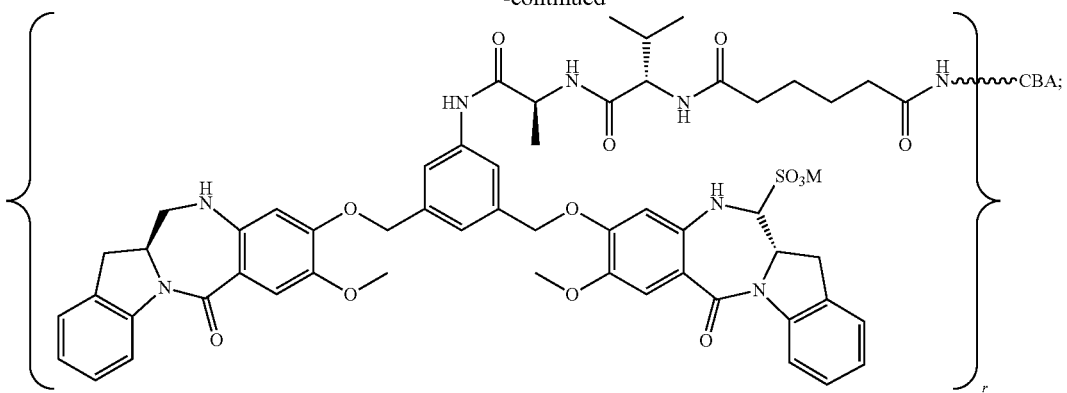
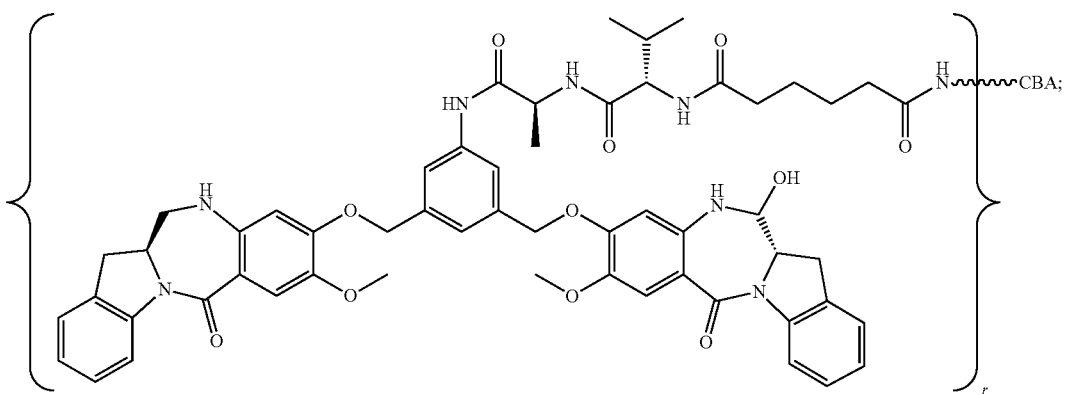
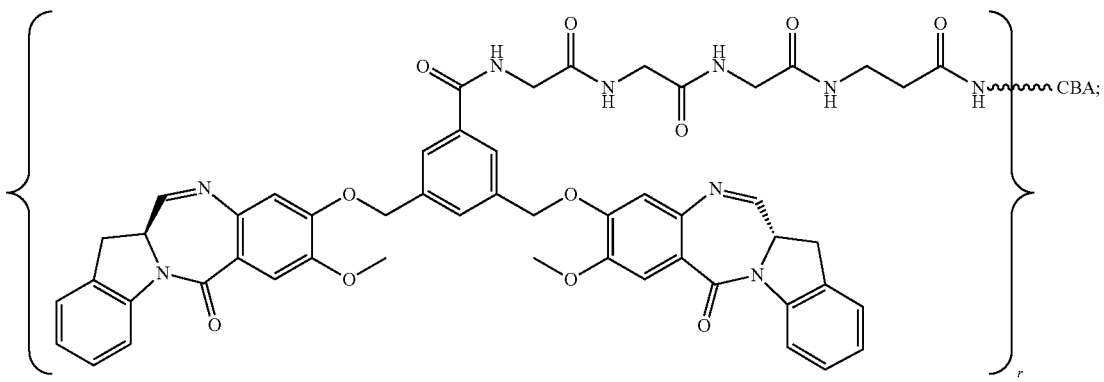
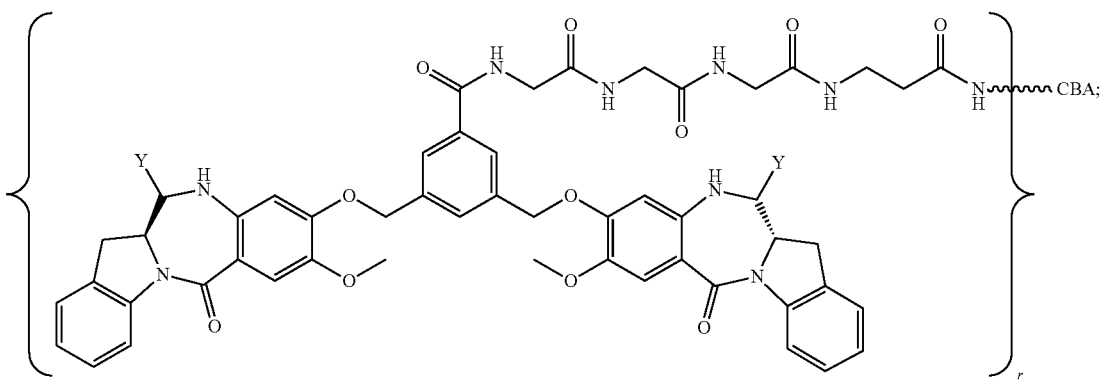

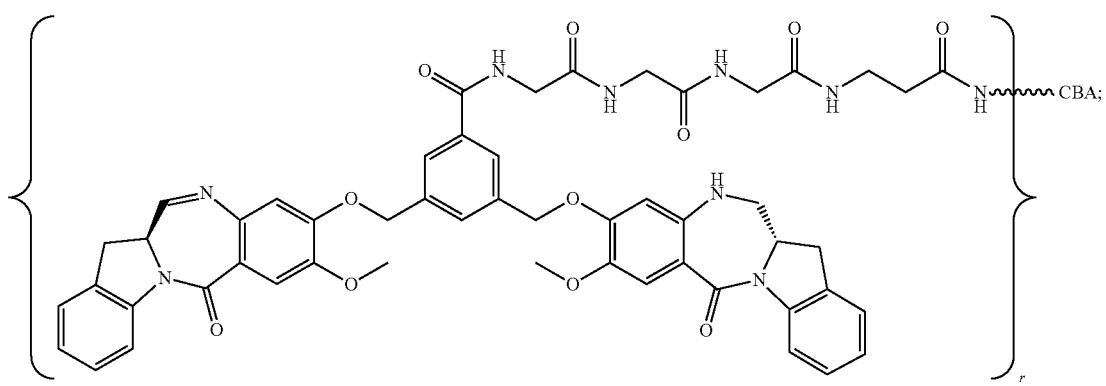
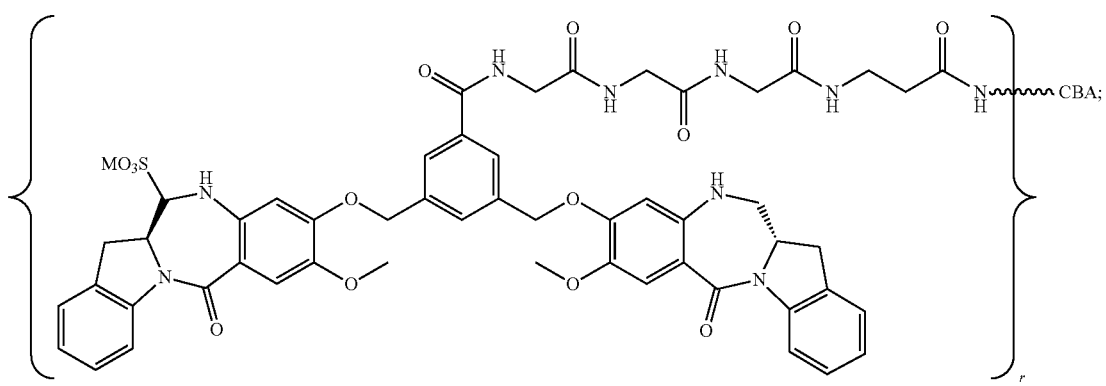
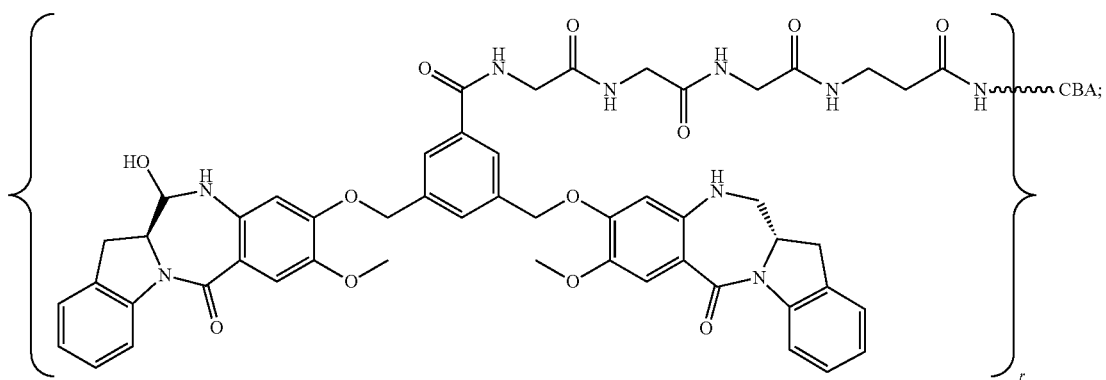
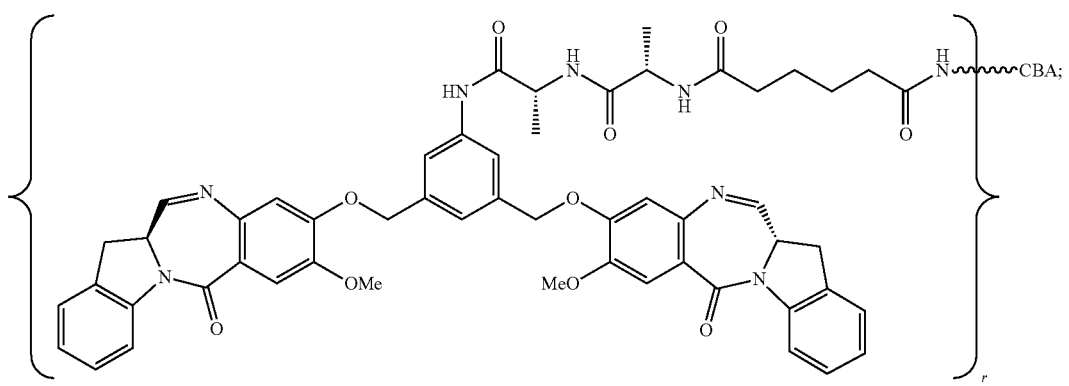

-continued
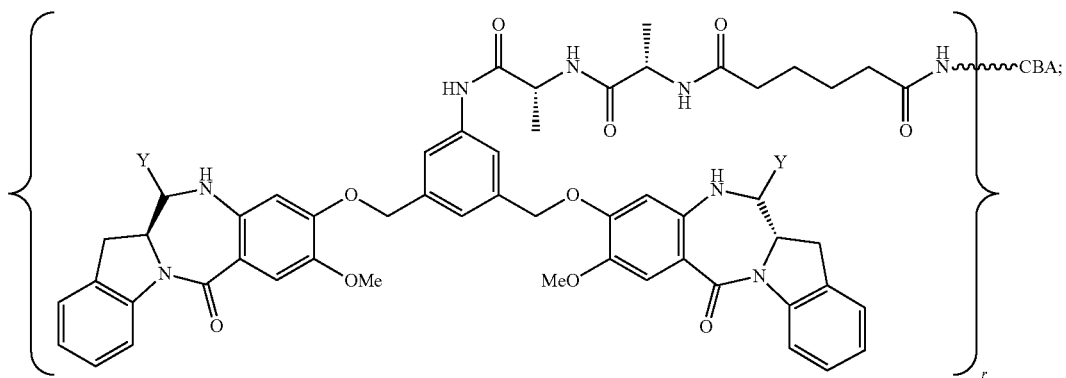
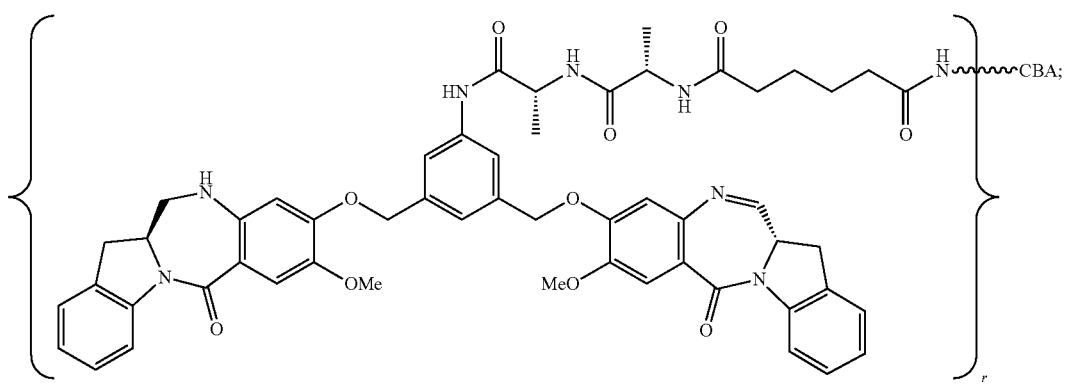
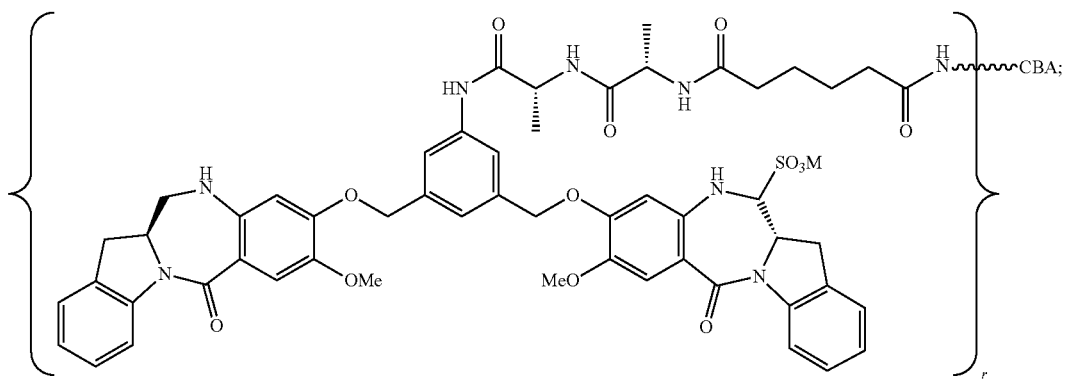
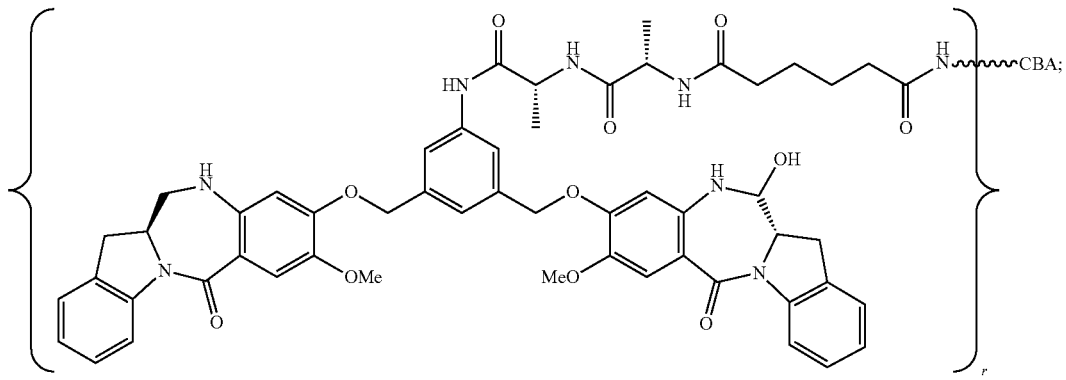

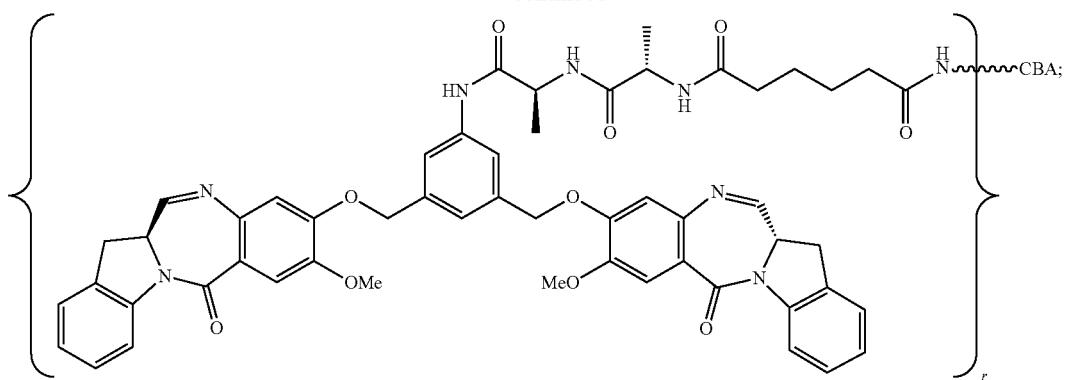
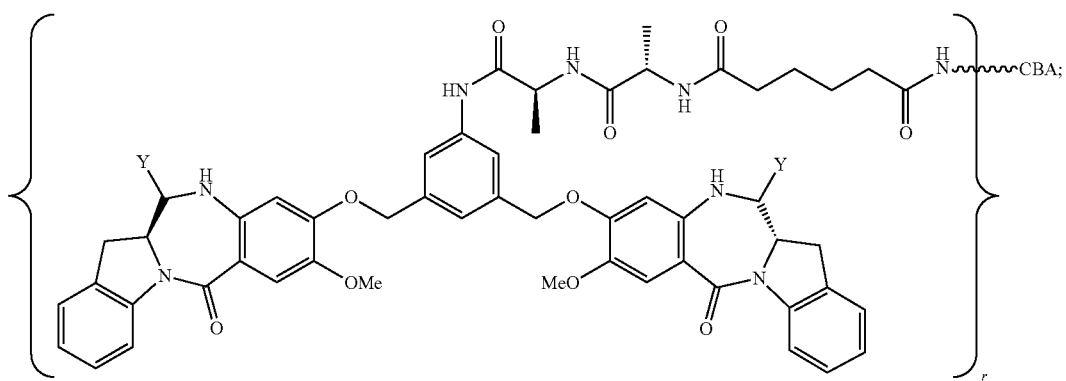
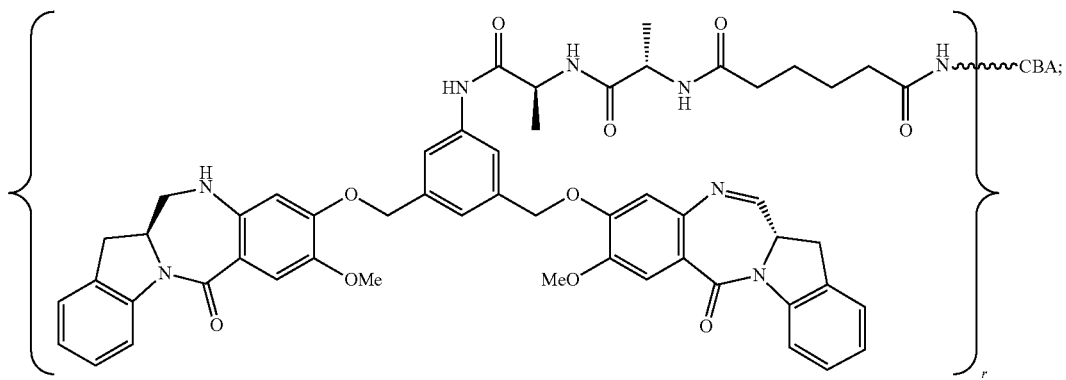
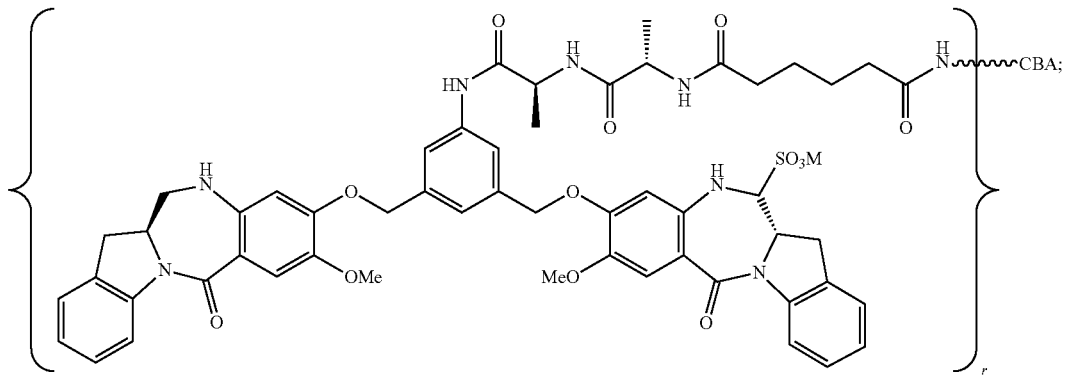

-continued
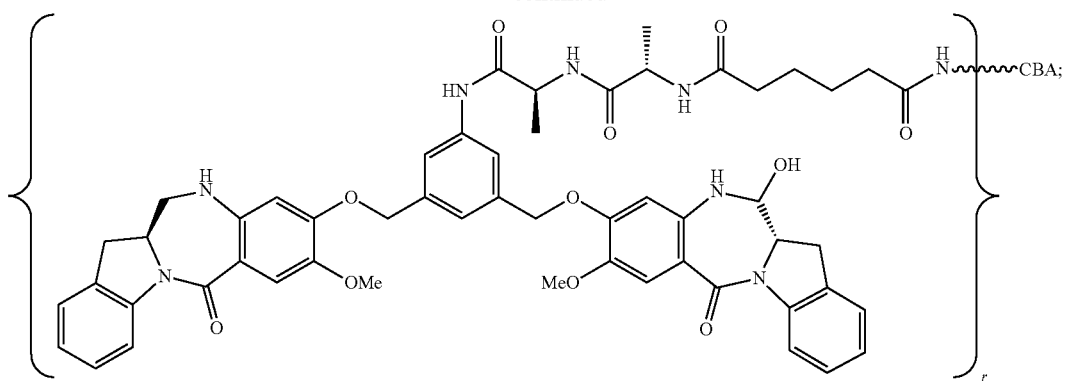
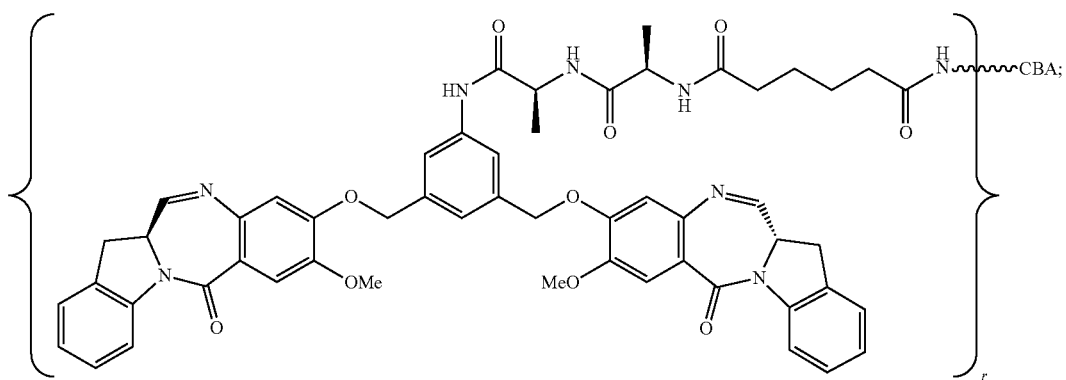
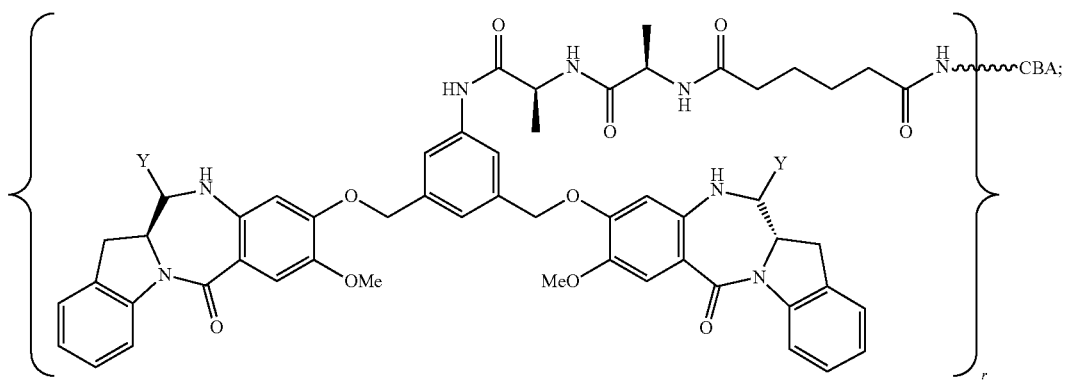
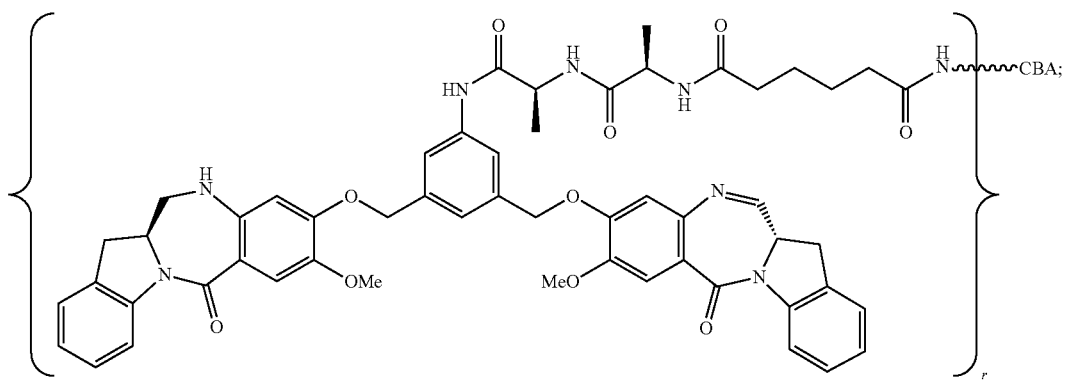

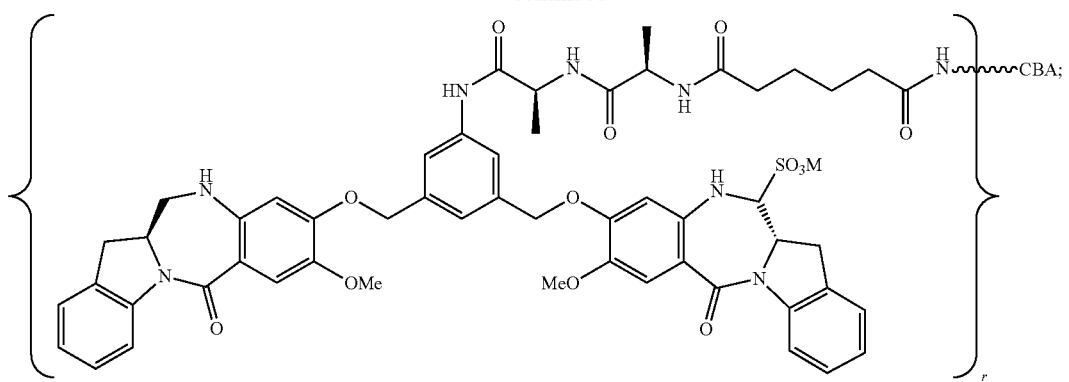
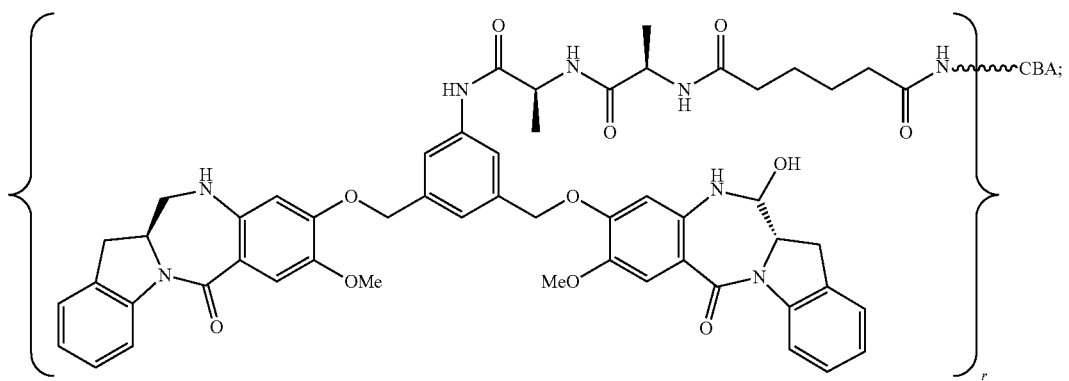
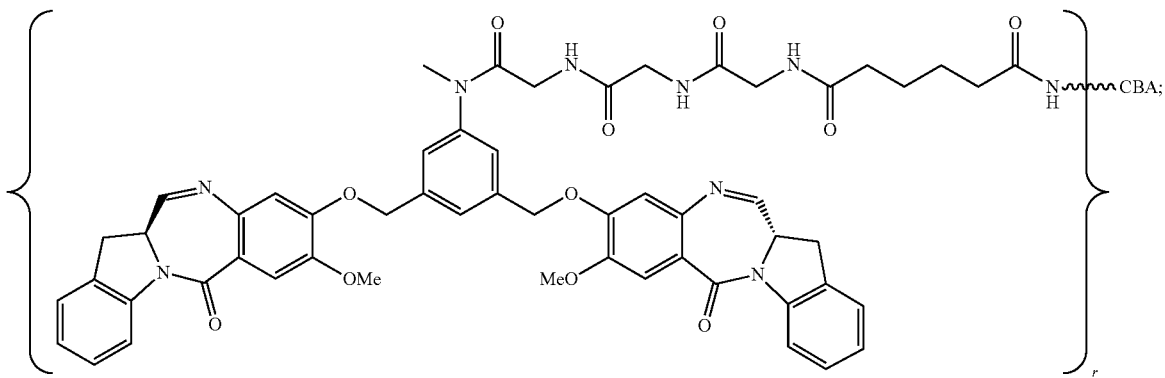
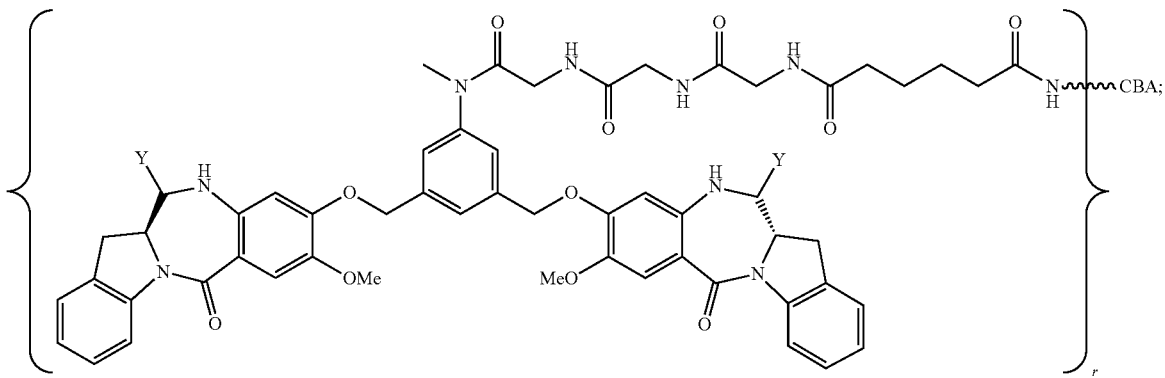

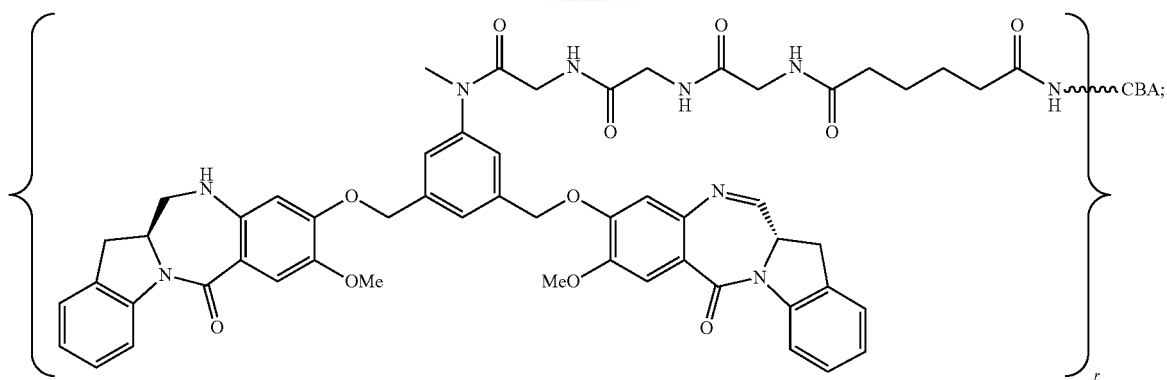
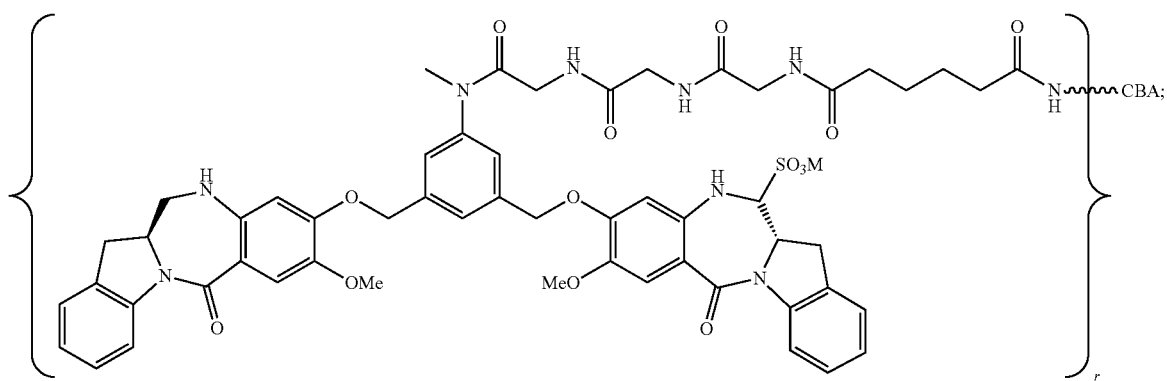
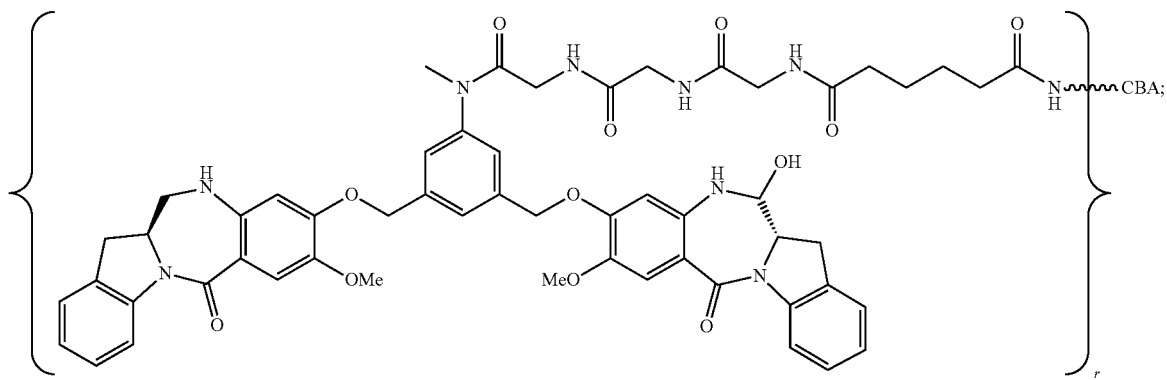
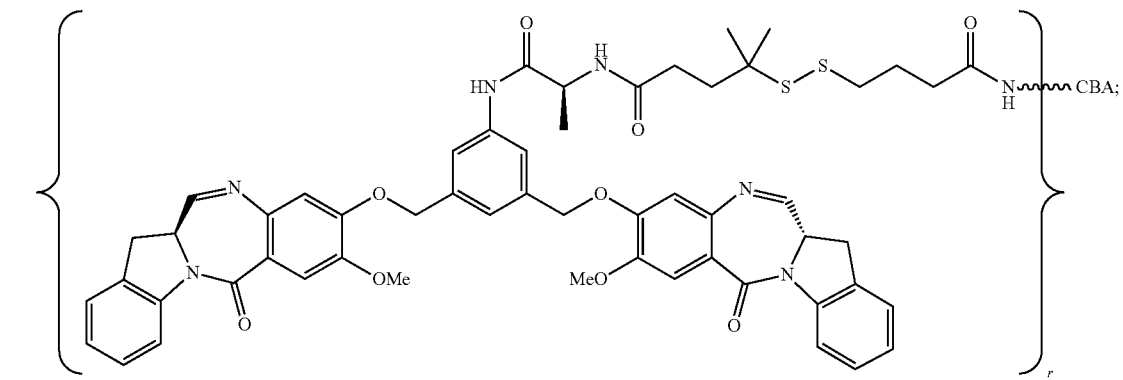

-continued
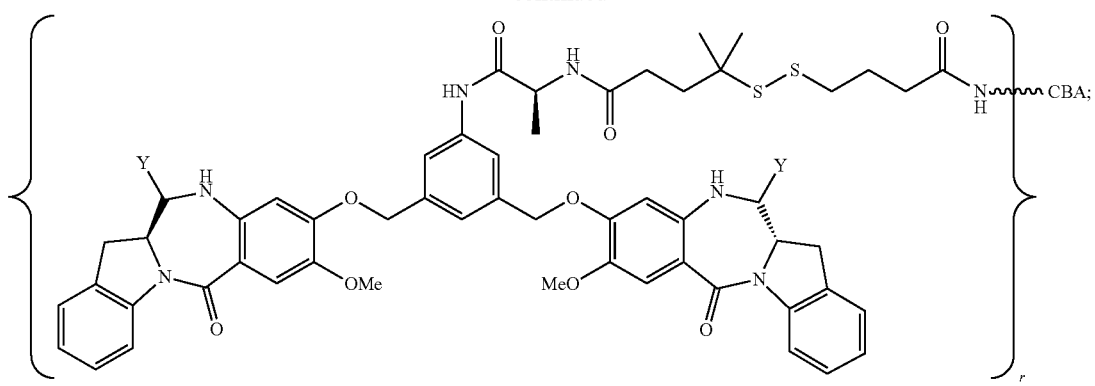
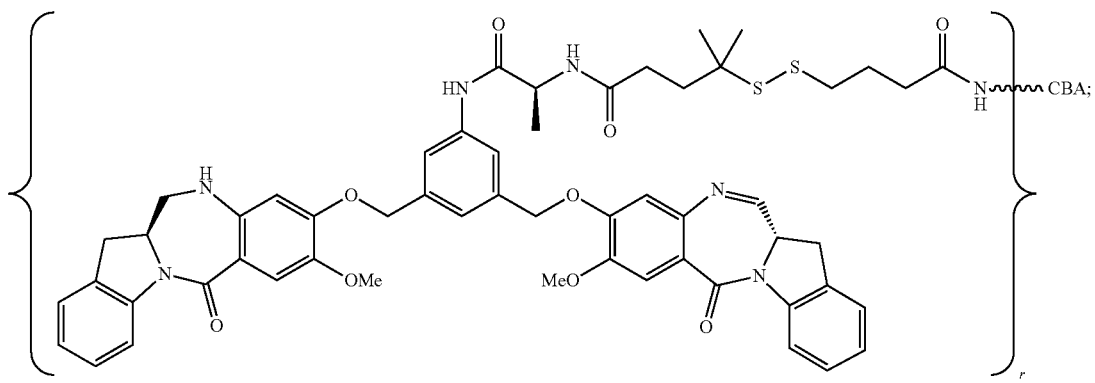
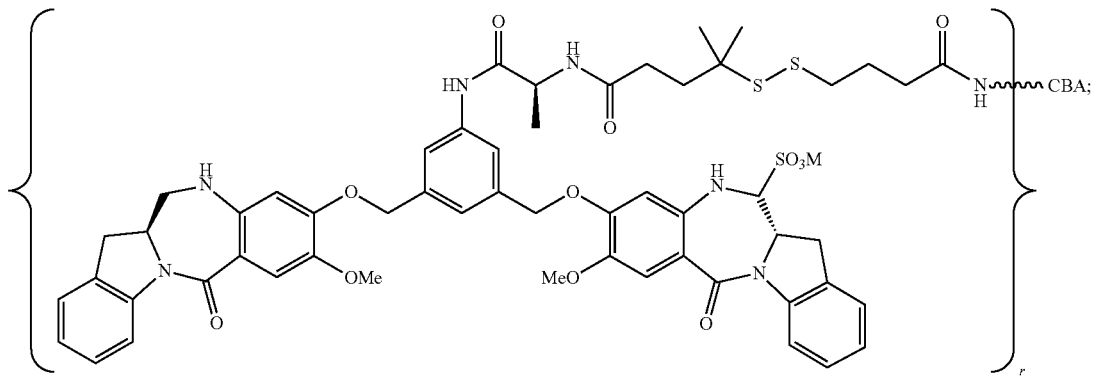
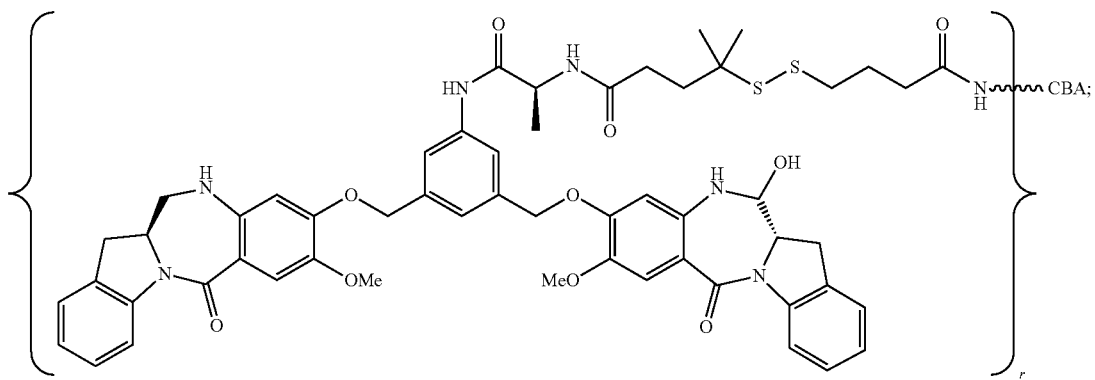

-continued
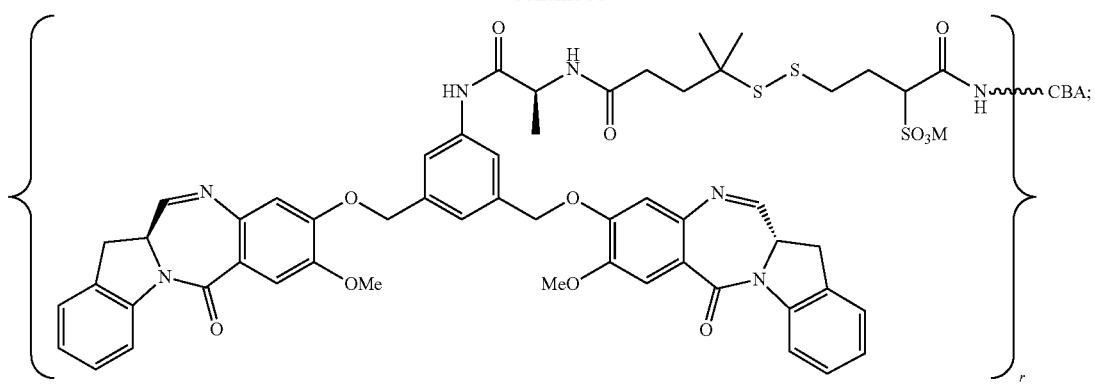
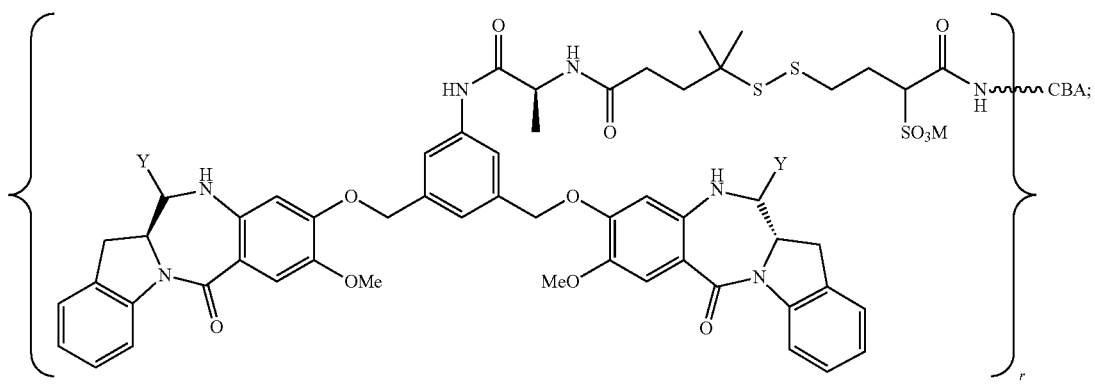
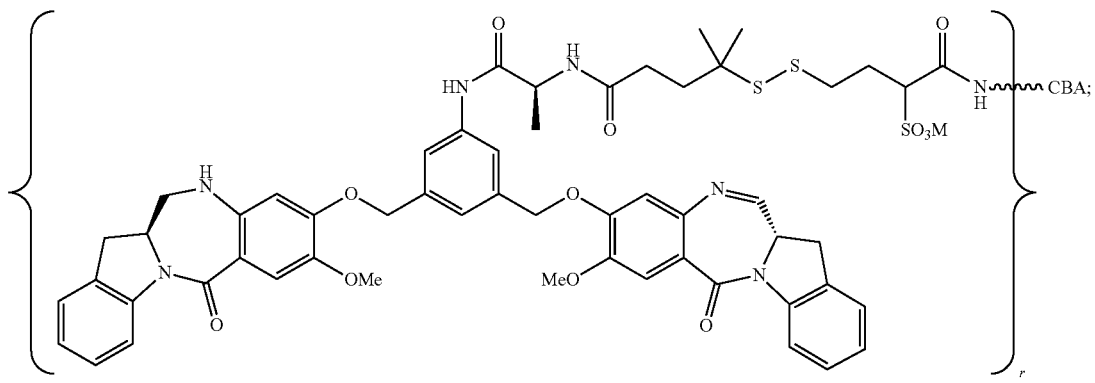
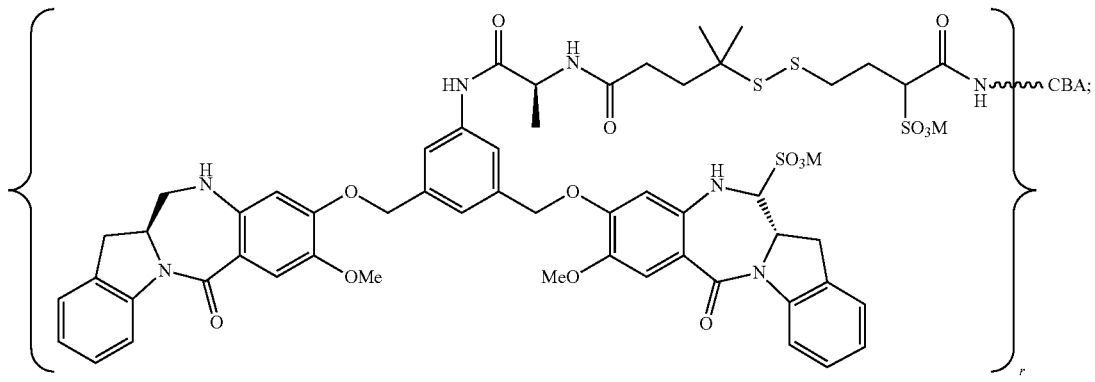

-continued
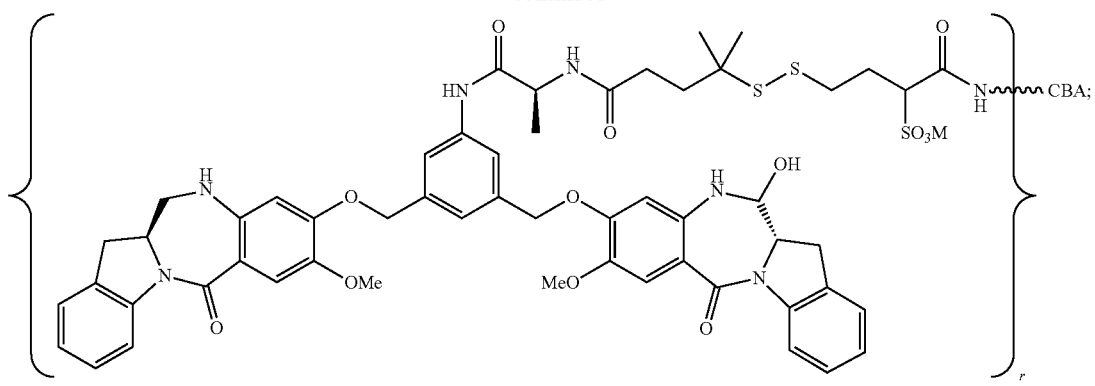
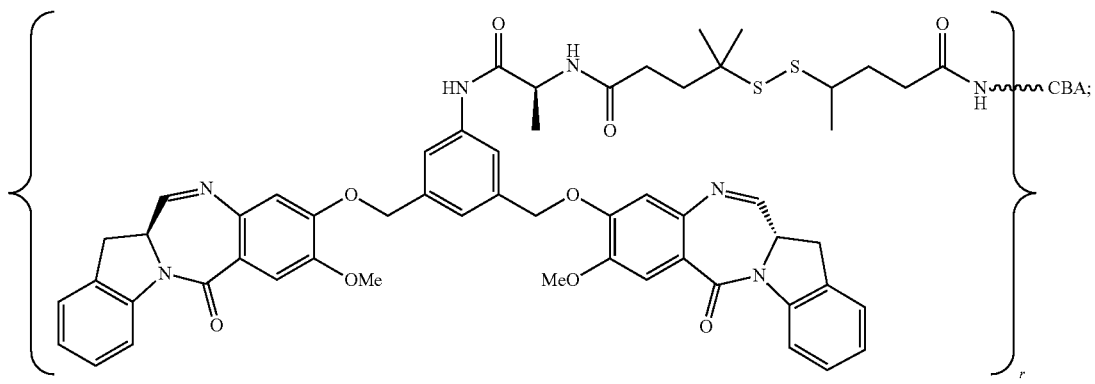
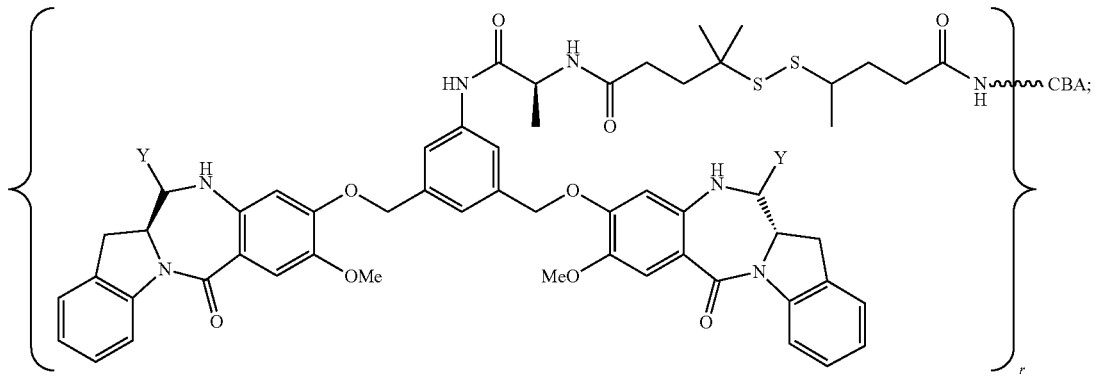
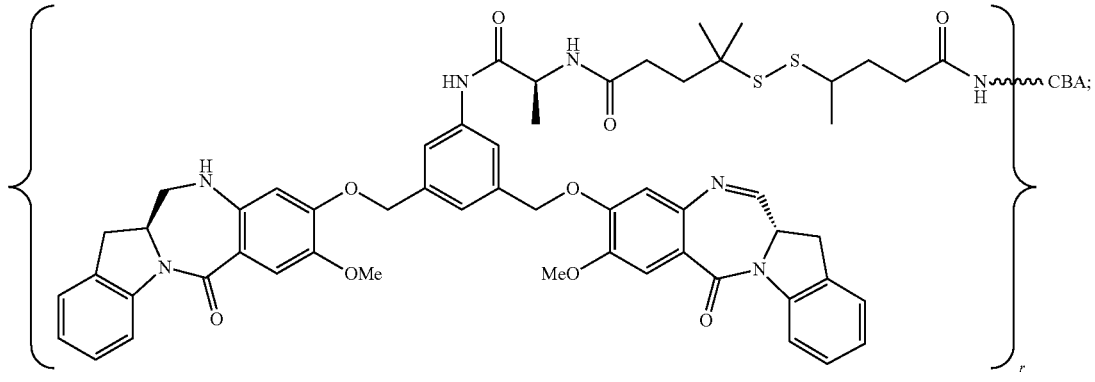

-continued
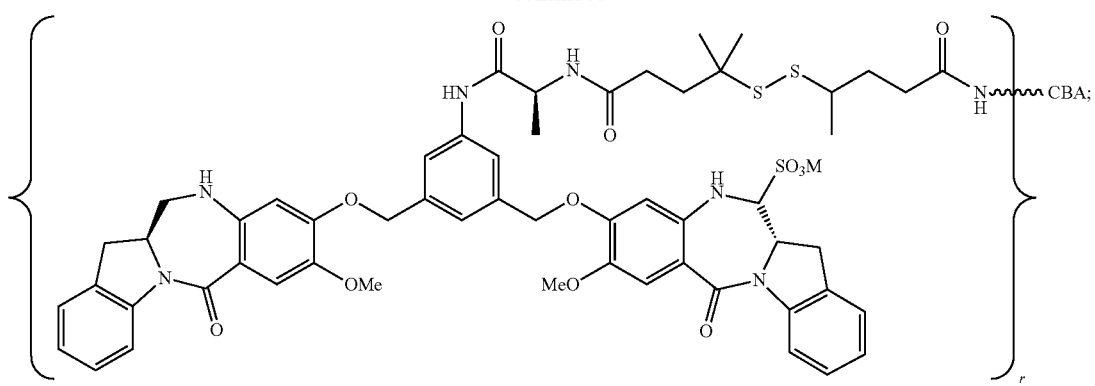
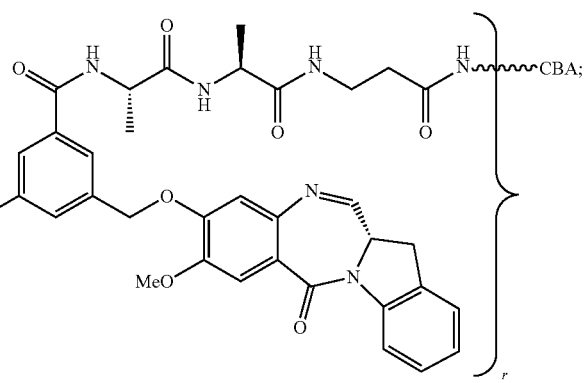
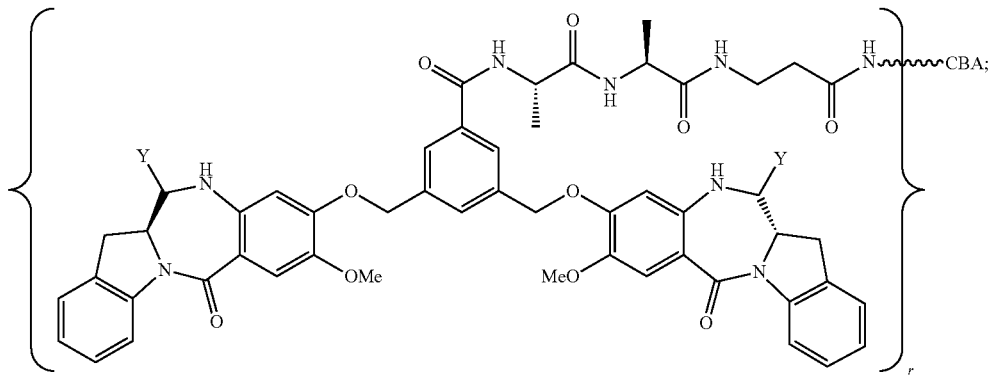
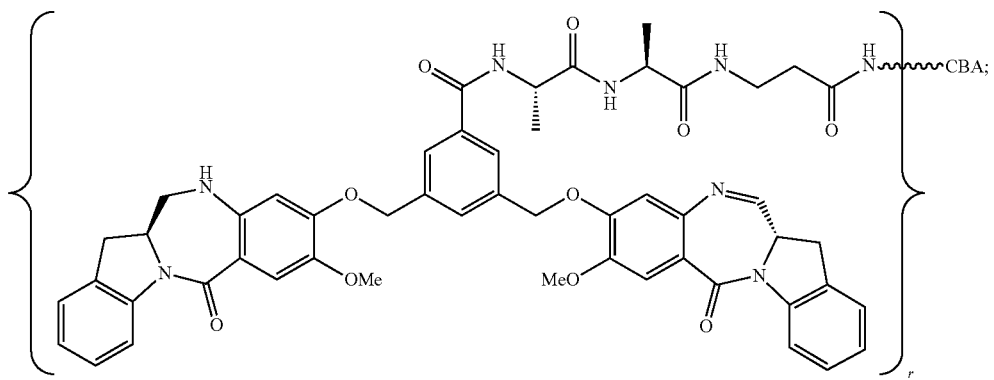

-continued
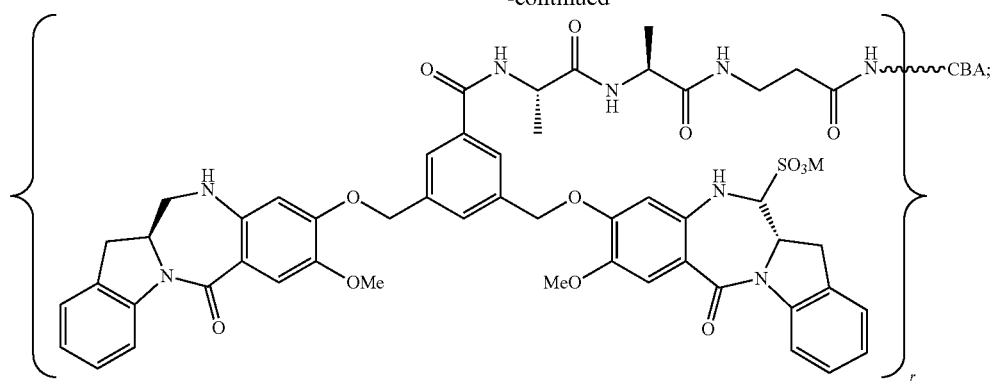
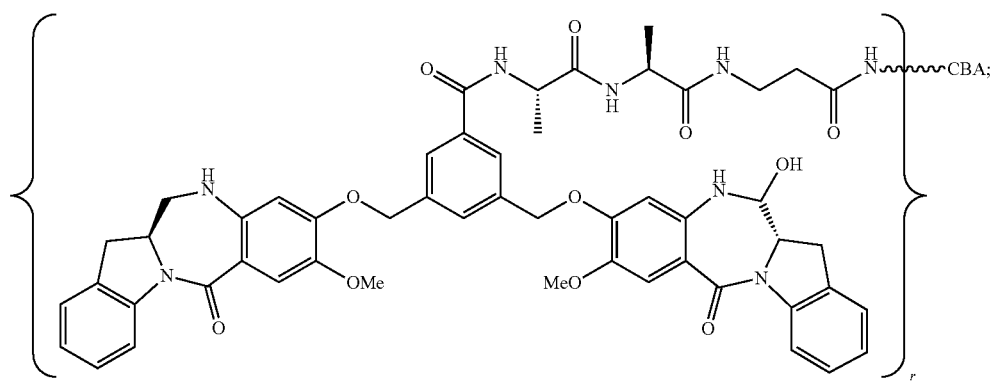
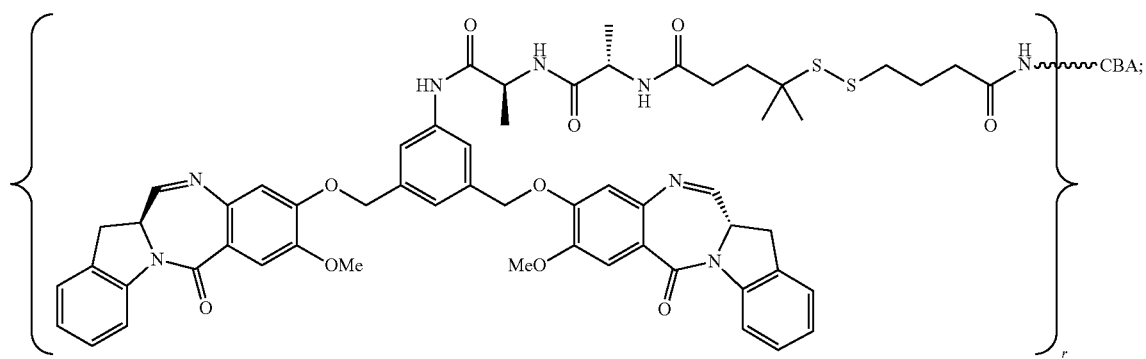
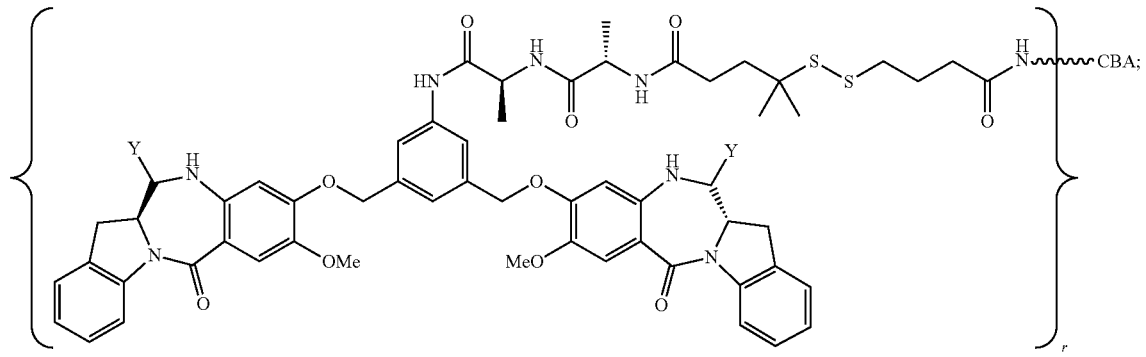

-continued
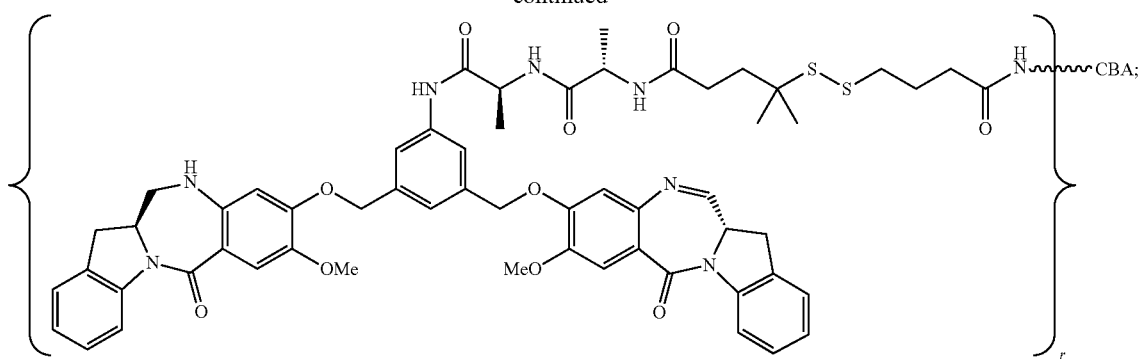
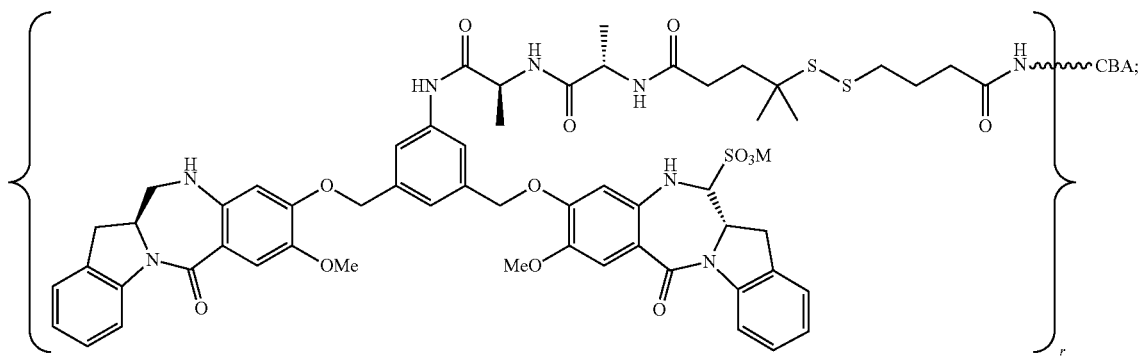
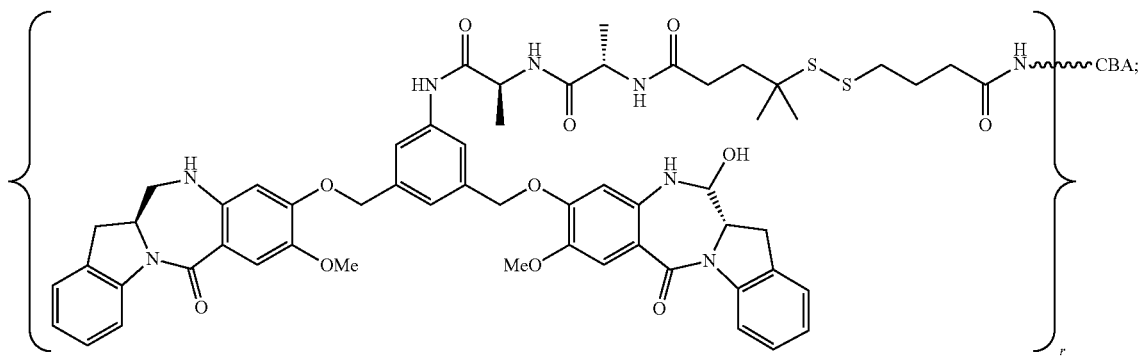
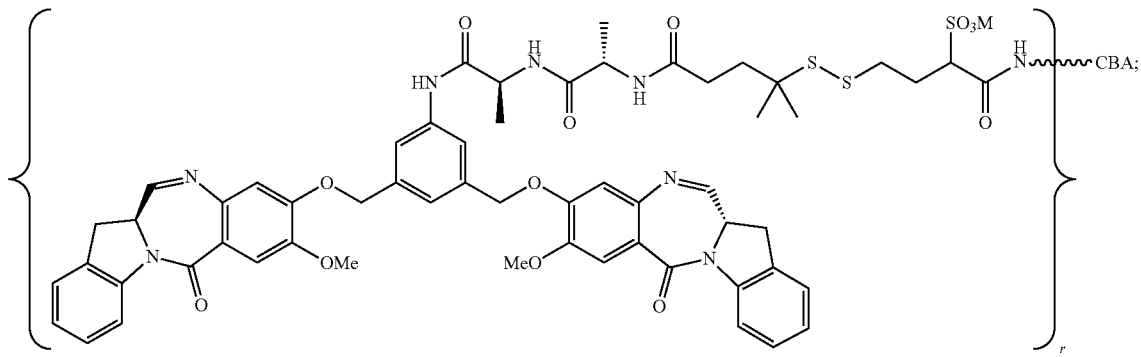

-continued
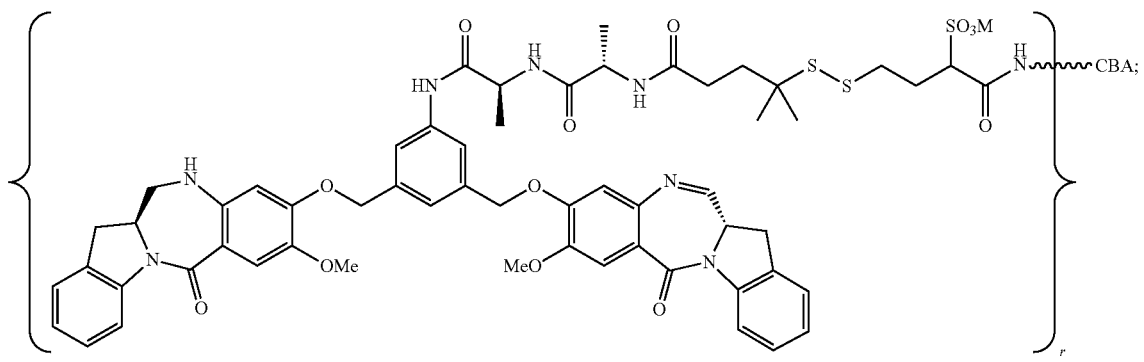
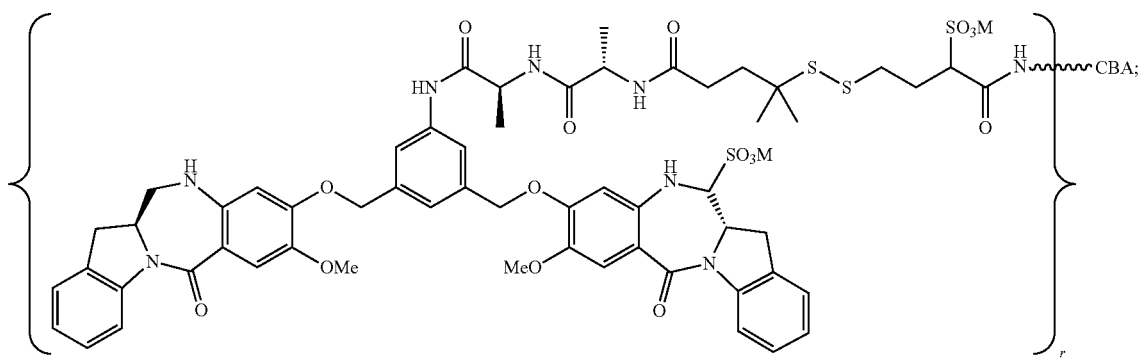
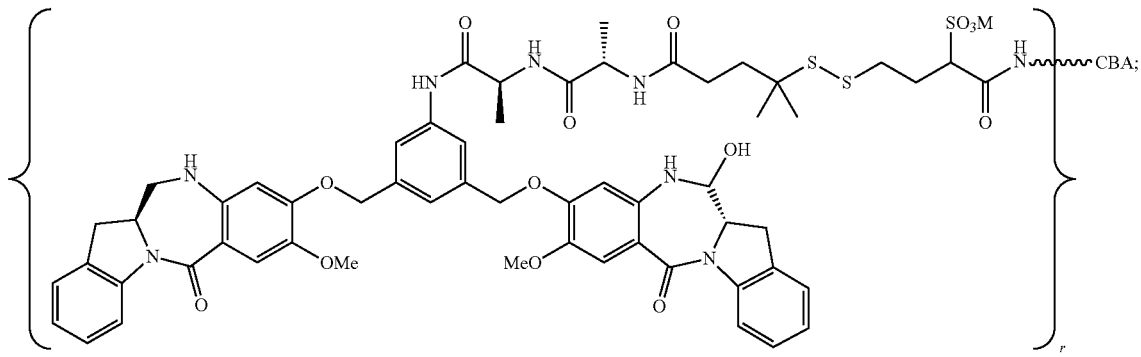

-continued
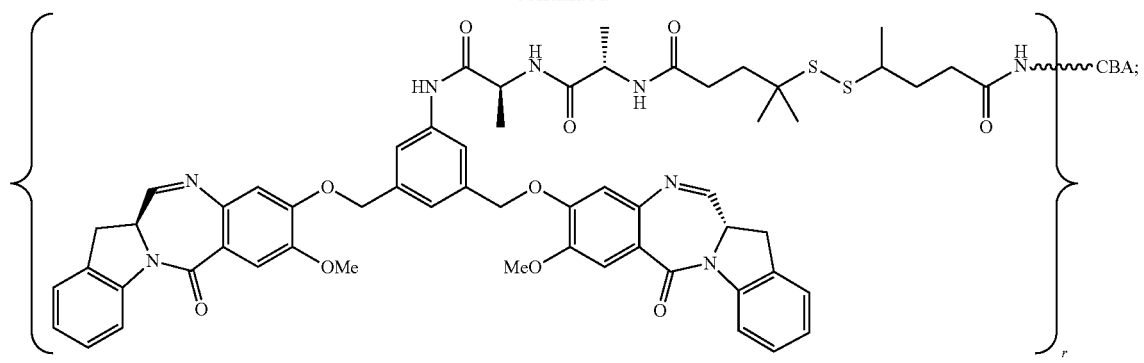
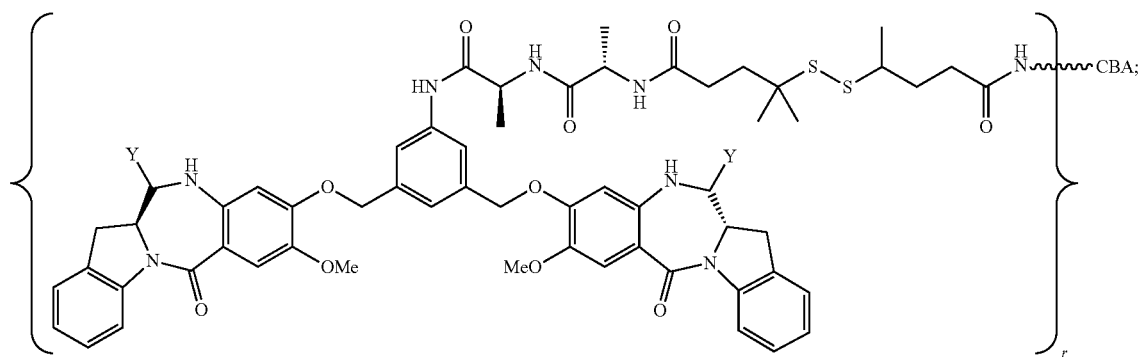
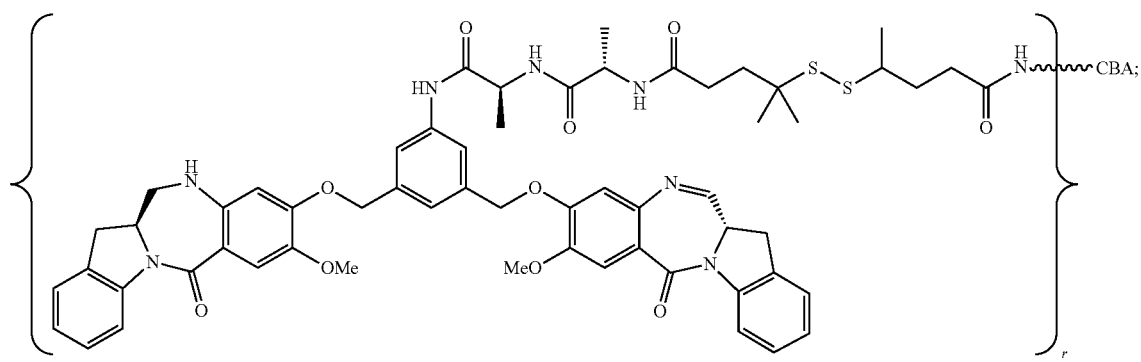
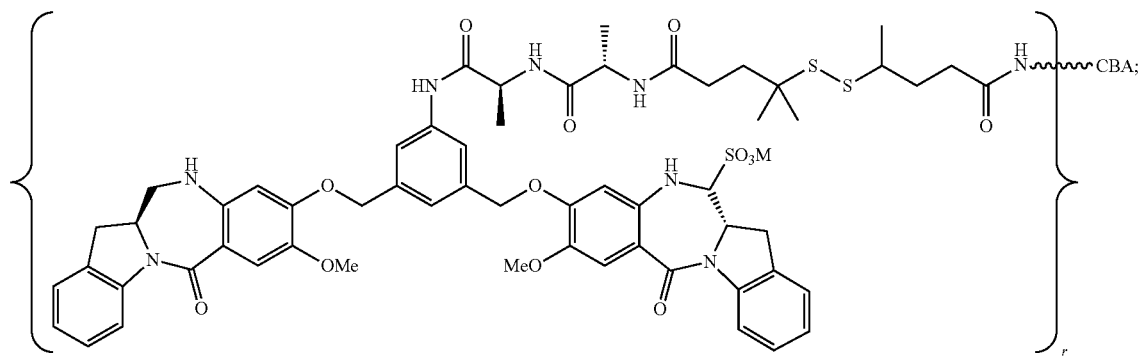

-continued
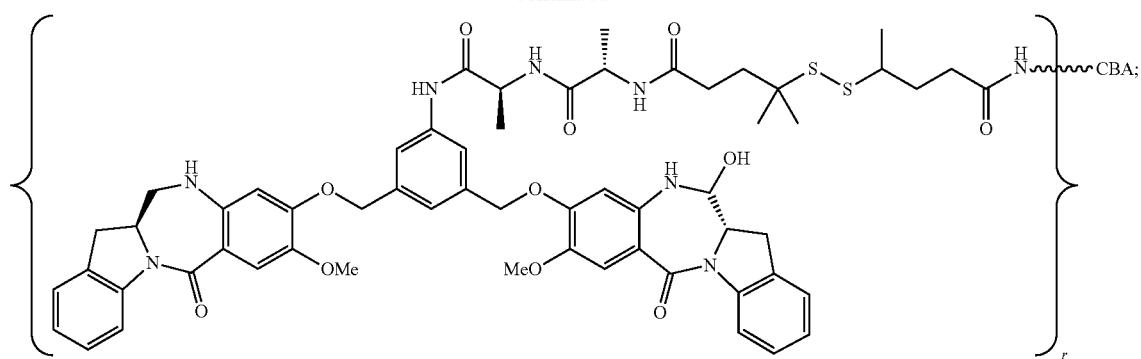
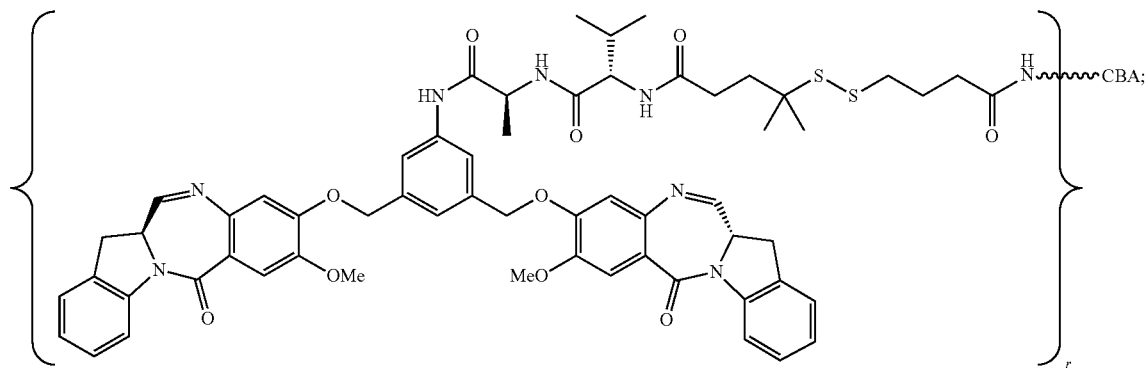
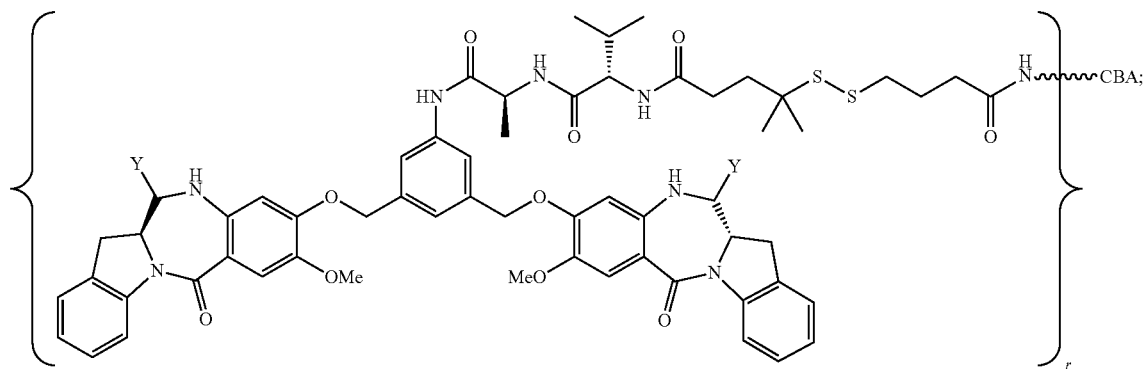
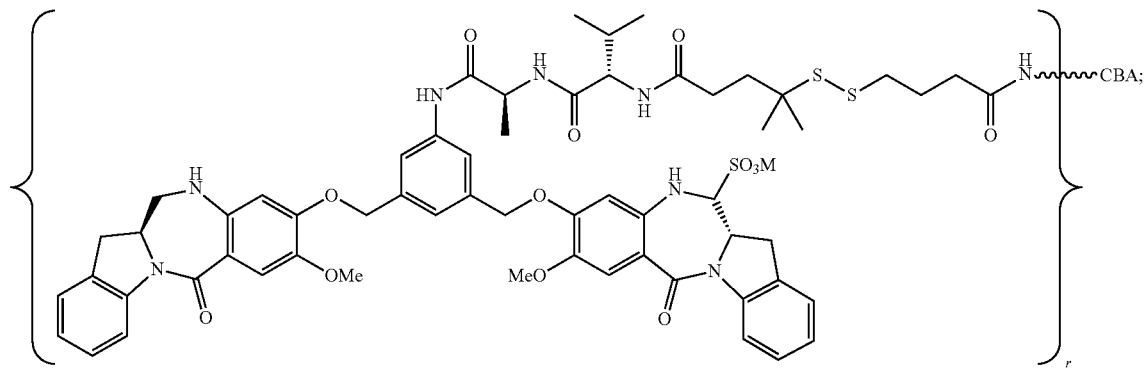

141                                   142
-continued
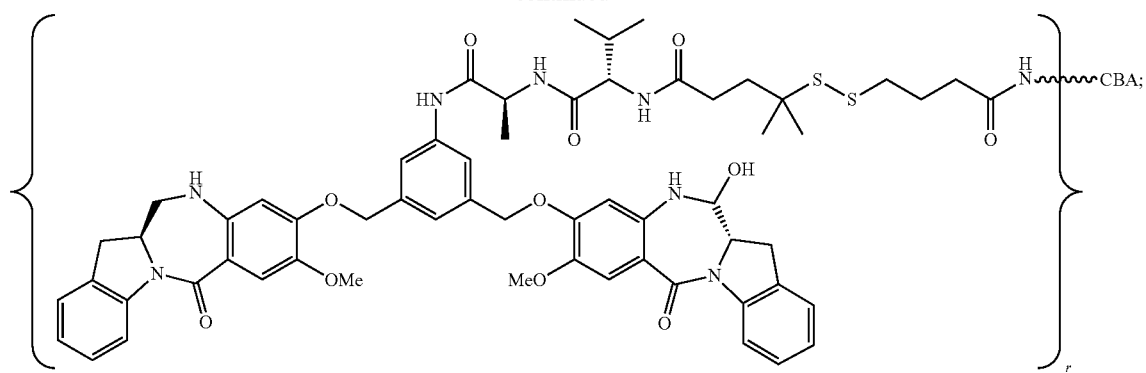
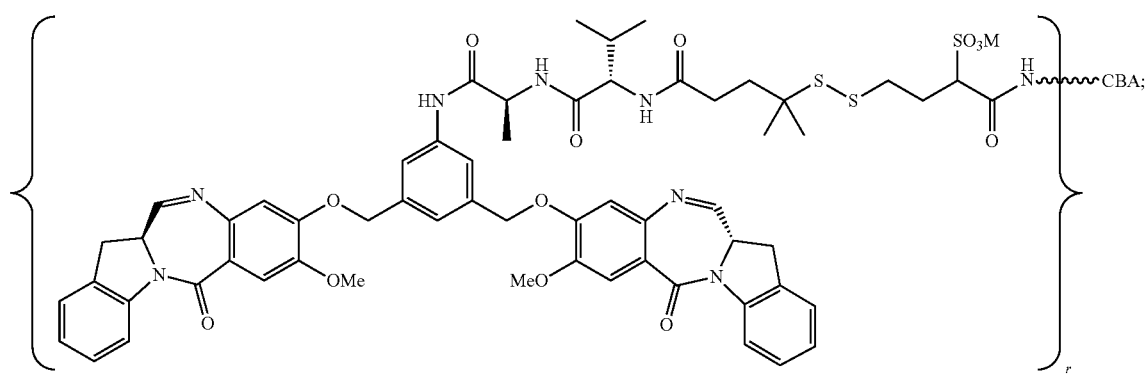
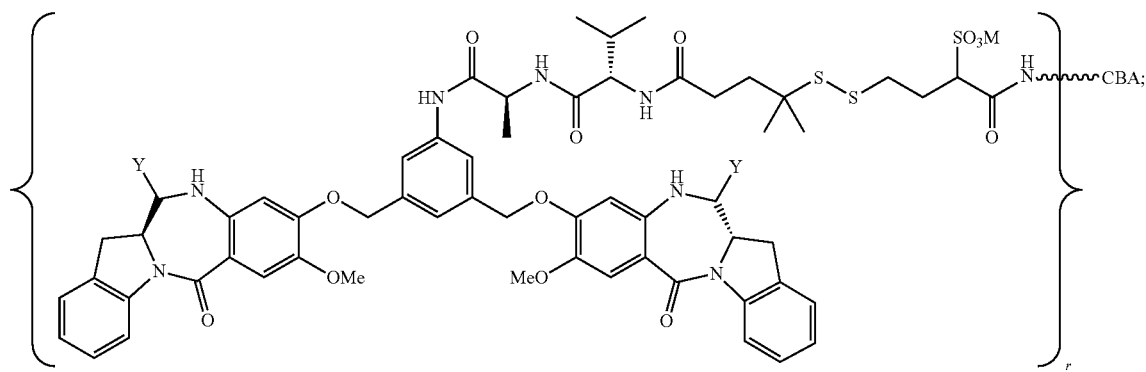
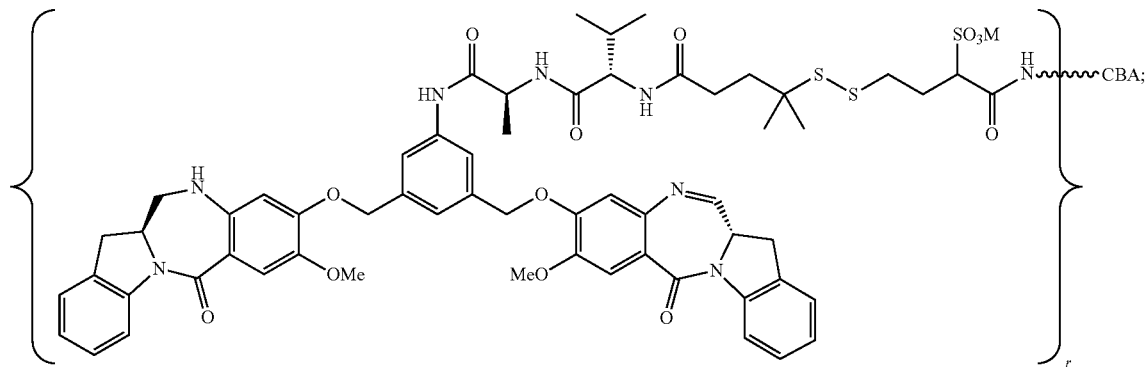

-continued
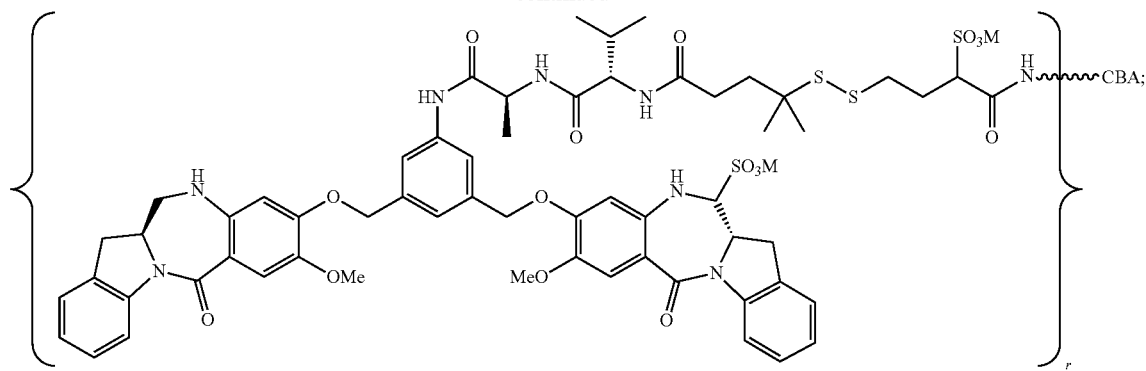
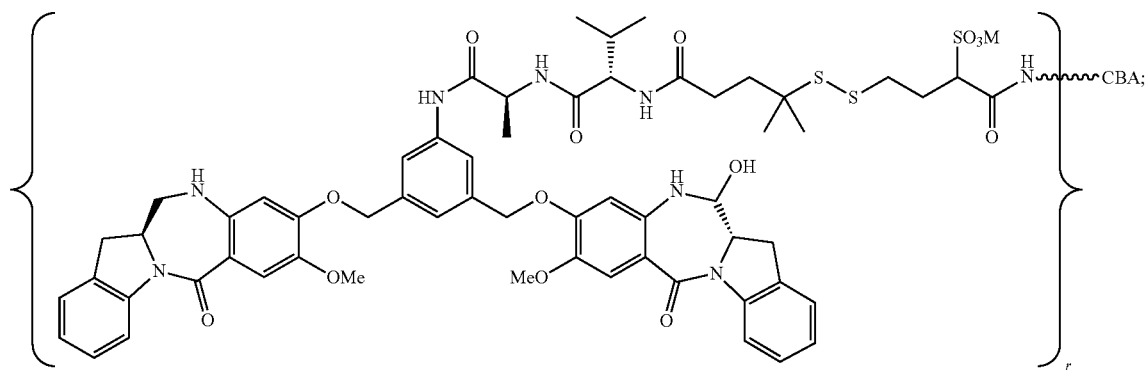
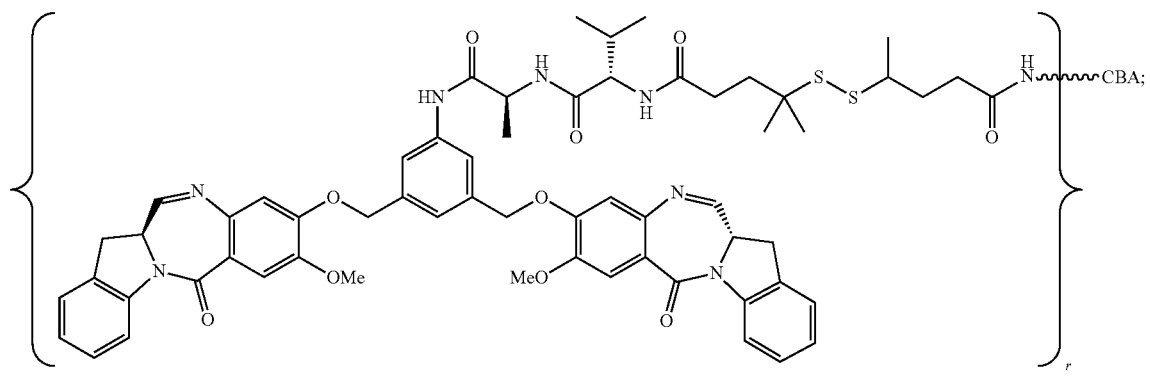
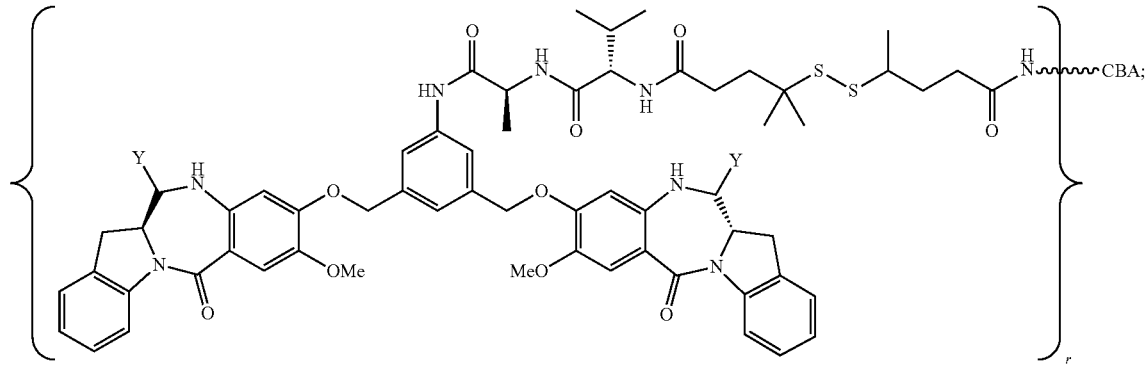

-continued
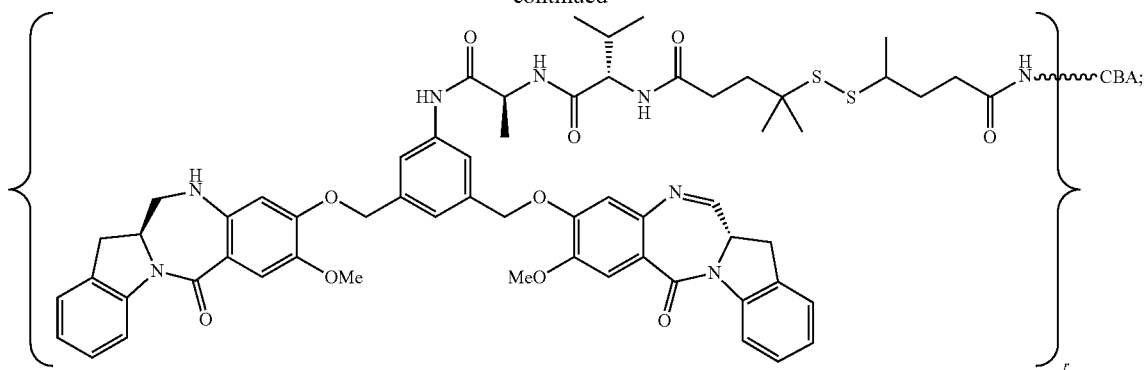
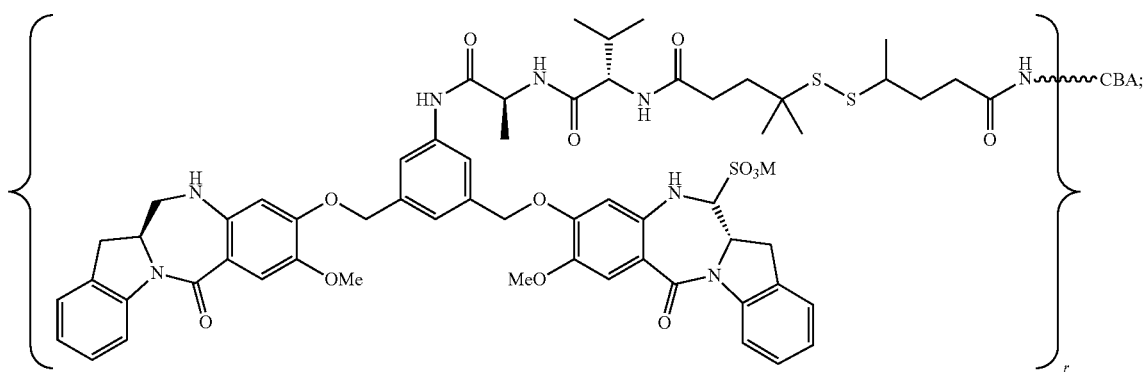
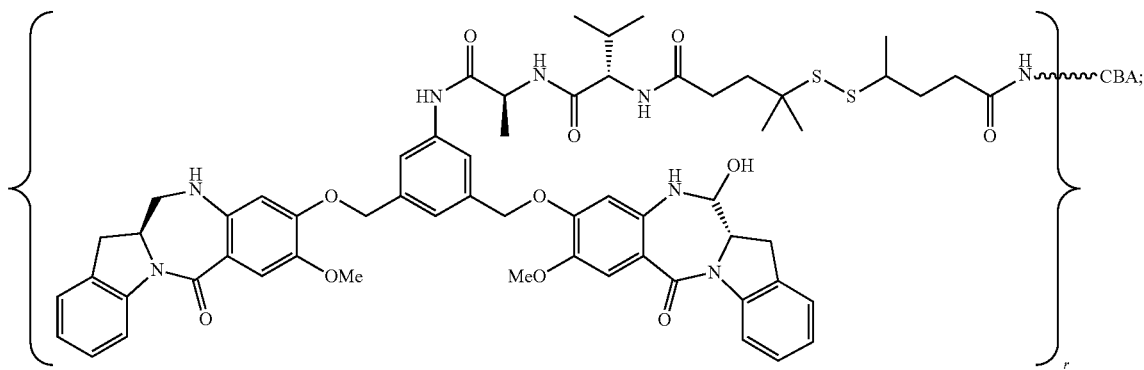
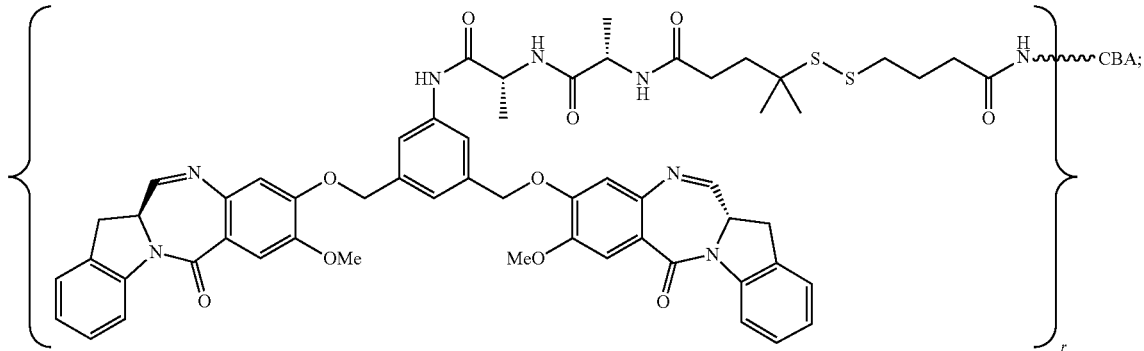

-continued
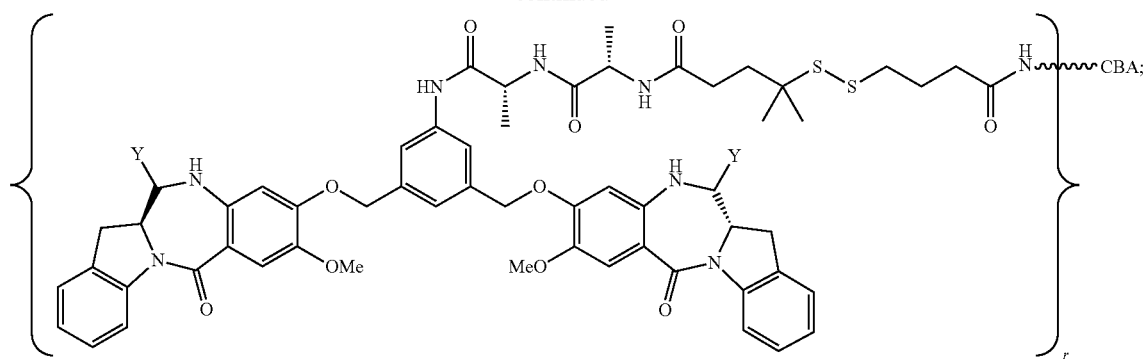
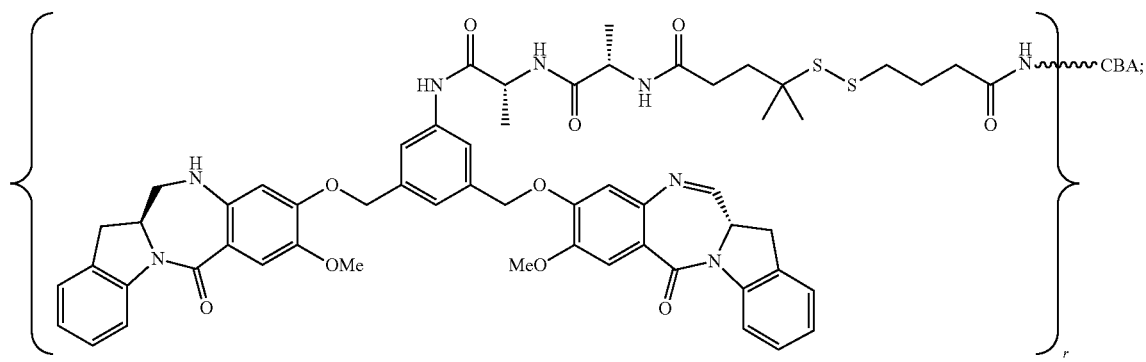
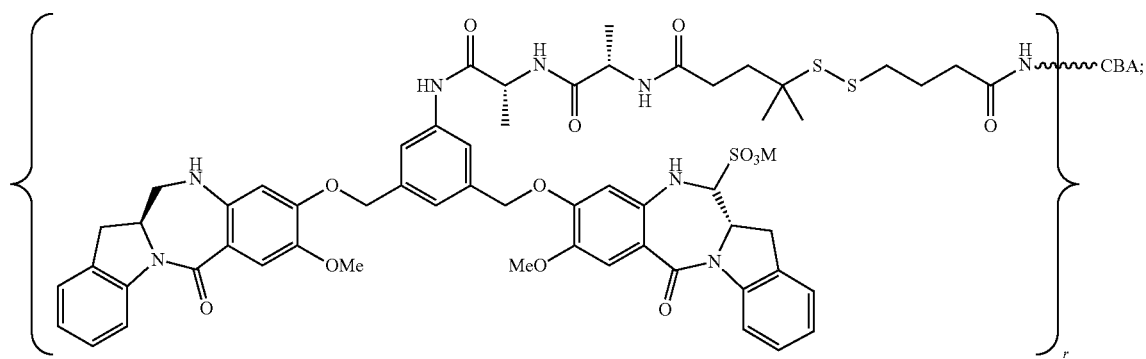
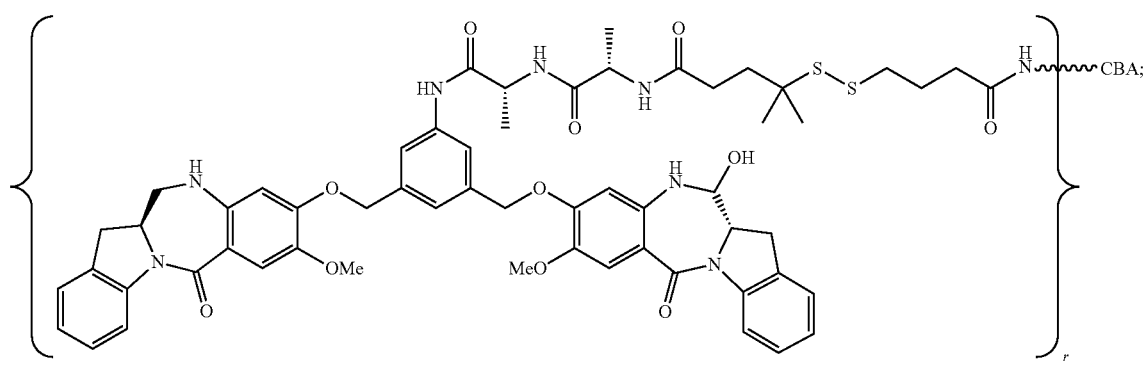

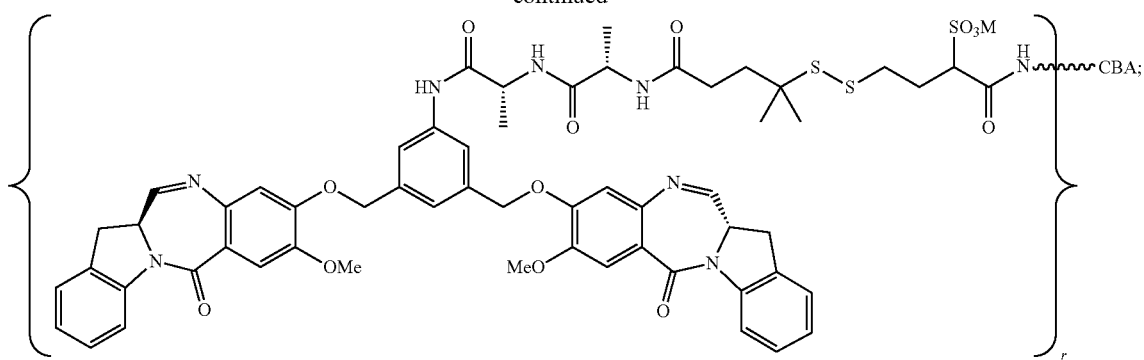
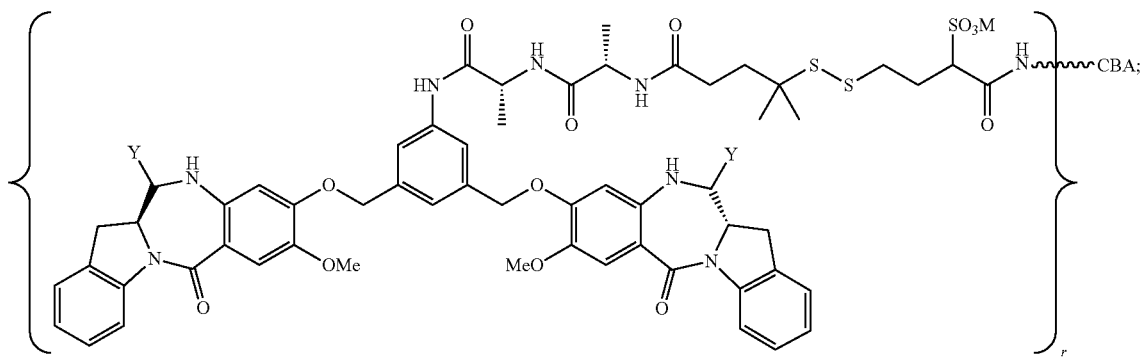
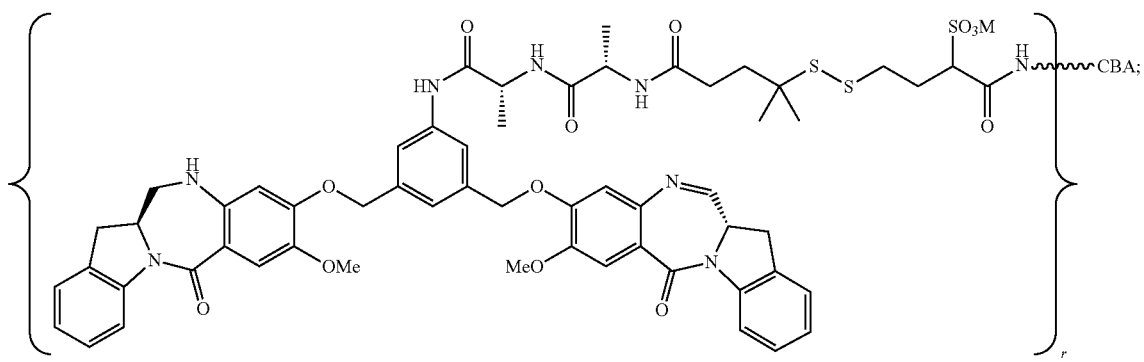
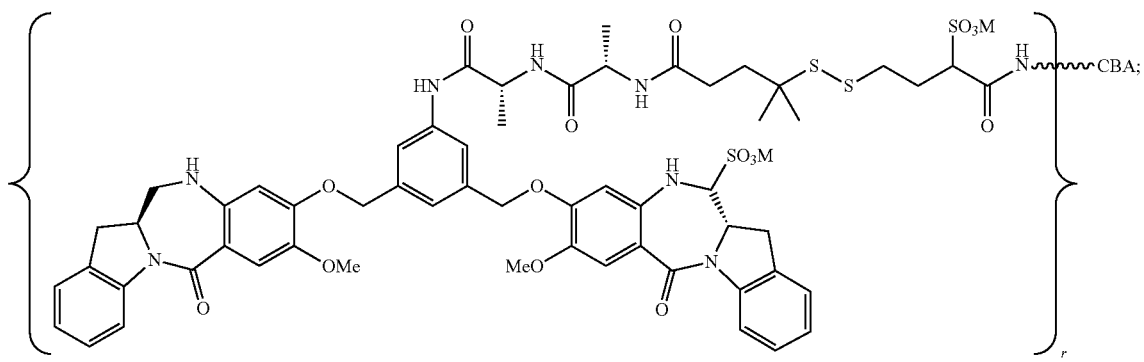

151    -continued    152
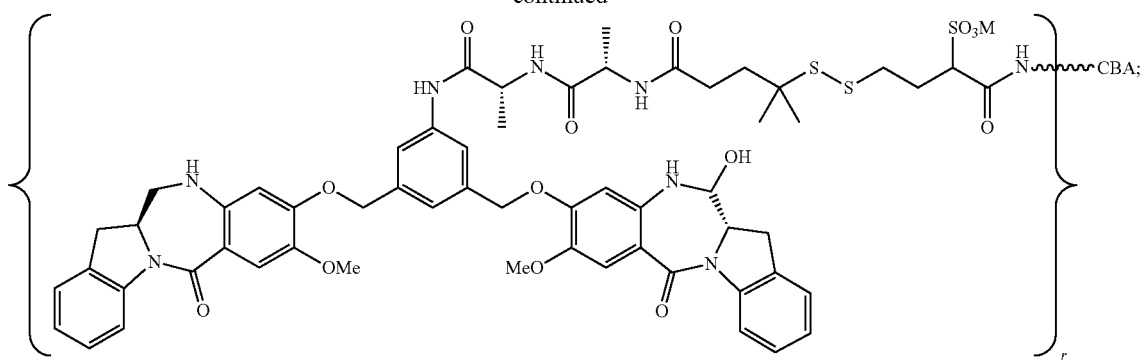
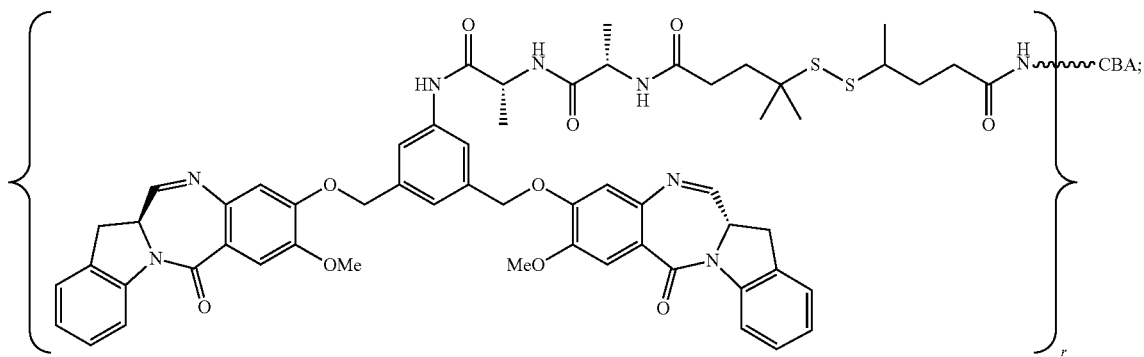
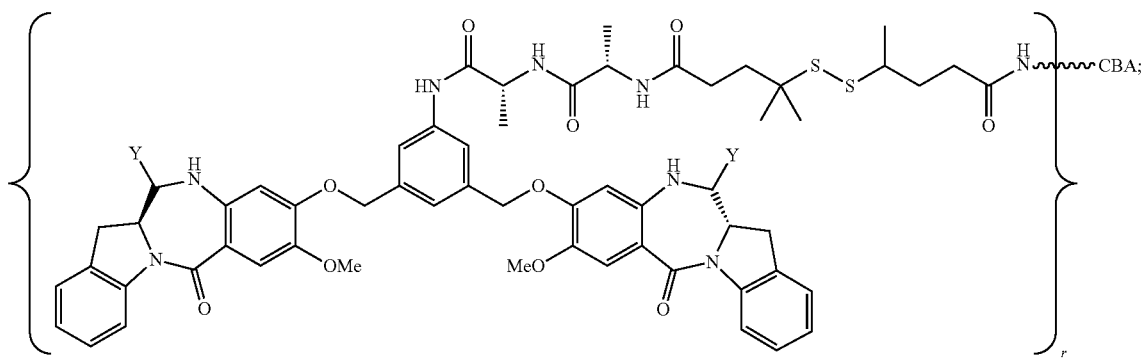
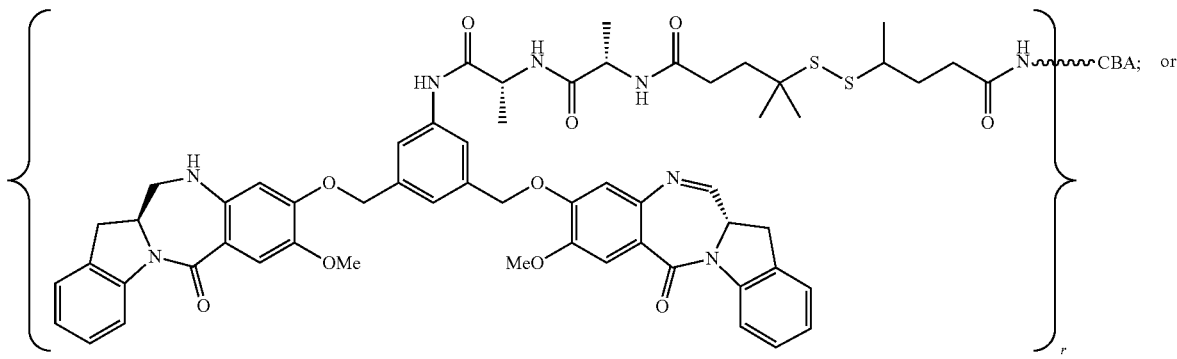

-continued

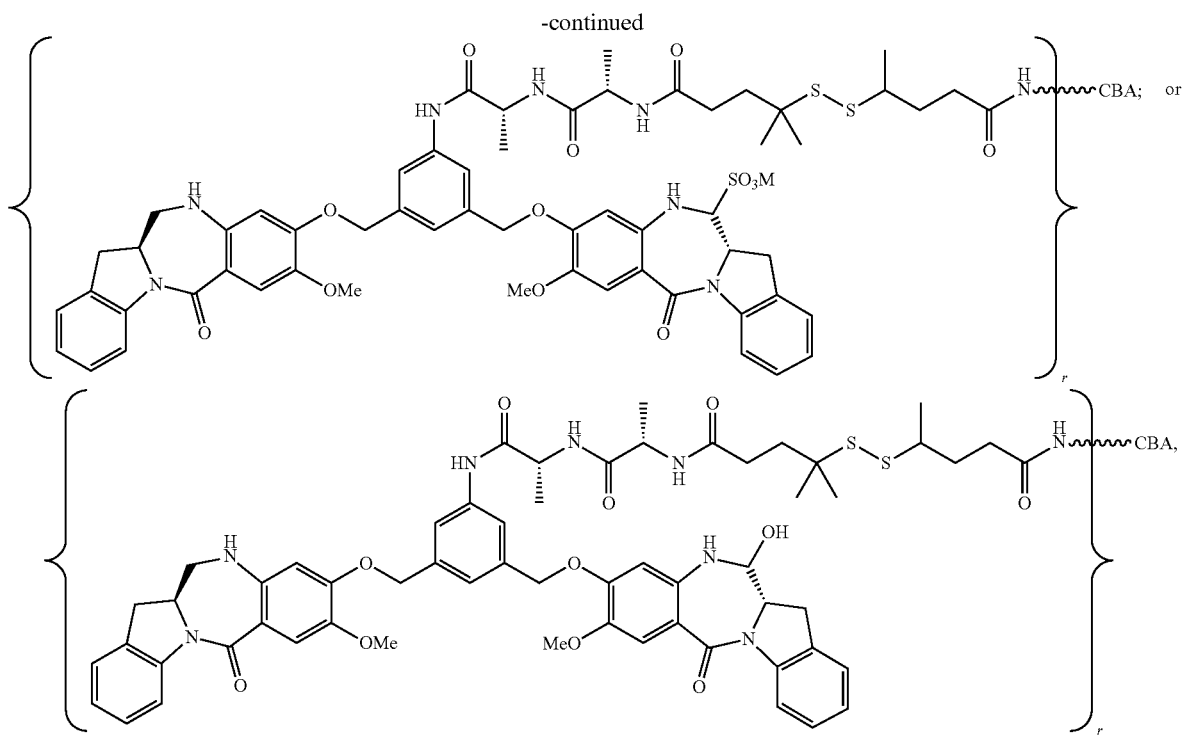

or a pharmaceutically acceptable salt thereof, wherein:
r is an integer from 1 to 10;
Y is —H, —OH or —SO$_3$M; and
M is a pharmaceutically acceptable cation (e.g., H$^+$, Na$^+$ or K$^+$).

More specifically, Y is —SO$_3$M. Alternatively, Y is —OH.

In certain embodiments, the conjugates described herein, such as those described in the second embodiment or the 1$^{st}$ to 15$^{th}$ specific embodiments, may comprise 1-10 cytotoxic compounds, 2-9 cytotoxic compounds, 3-8 cytotoxic compounds, 4-7 cytotoxic compounds, or 5-6 cytotoxic compounds, each cytotoxic compound comprising the linking group linking the cytotoxic compound to the CBA, and each cytotoxic compound on the conjugate is the same.

In any of the conjugates embodiments, such as the second embodiment or the 1$^{st}$ to 15$^{th}$ specific embodiments, the cell-binding agent may bind to target cells selected from tumor cells, virus infected cells, microorganism infected cells, parasite infected cells, autoimmune cells, activated cells, myeloid cells, activated T-cells, B cells, or melanocytes; cells expressing the CD4, CD6, CD19, CD20, CD22, CD30, CD33, CD37, CD38, CD40, CD44, CD56, EpCAM, CanAg, CALLA, or Her-2 antigens; Her-3 antigens; or cells expressing insulin growth factor receptor, epidermal growth factor receptor, and folate receptor.

In any of the conjugates embodiments, such as the second embodiment or the 1$^{st}$ to 15$^{th}$ specific embodiments, the cell-binding agent may be an antibody, a single chain antibody, an antibody fragment that specifically binds to the target cell, a monoclonal antibody, a single chain monoclonal antibody, or a monoclonal antibody fragment that specifically binds to a target cell, a chimeric antibody, a chimeric antibody fragment that specifically binds to the target cell, a domain antibody, a domain antibody fragment that specifically binds to the target cell, a lymphokine, a hormone, a vitamin, a growth factor, a colony stimulating factor, or a nutrient-transport molecule.

The antibody may be a resurfaced antibody, a resurfaced single chain antibody, or a resurfaced antibody fragment.

The antibody may be a monoclonal antibody, a single chain monoclonal antibody, or a monoclonal antibody fragment thereof.

The antibody may be a humanized antibody, a humanized single chain antibody, or a humanized antibody fragment.

In any of the conjugates embodiments above, such as the second embodiment or the 1$^{st}$ to 15$^{th}$ specific embodiments, the cell-binding agent may be an anti-folate receptor antibody or an antibody fragment thereof. More specifically, the anti-folate receptor antibody is huMOV19 antibody.

Alternatively, in any of the conjugates embodiments above, such as the second embodiment or the 1$^{st}$ to 15$^{th}$ specific embodiments, the cell-binding agent may be an anti-EGFR antibody or an antibody fragment thereof. In one embodiment, the anti-EGFR antibody is a non-antagonist antibody, including, for example, the antibodies described in WO2012058592, herein incorporated by reference. In another embodiment, the anti-EGFR antibody is a non-functional antibody, for example, humanized ML66. More specifically, the anti-EGFR antibody is huML66.

The invention further provides a pharmaceutical composition comprising any of the conjugates described herein, and a pharmaceutically acceptable carrier.

The invention additional provides a conjugate comprising any of the subject compounds linked to a cell-binding agent.

The invention further provides a method of inhibiting abnormal cell growth or treating a proliferative disorder, an autoimmune disorder, destructive bone disorder, infectious disease, viral disease, fibrotic disease, neurodegenerative disorder, pancreatitis or kidney disease in a mammal comprising administering to the mammal a therapeutically effective amount of any of the compounds (with or without any linker group) or conjugates of the invention, and, optionally, a second chemotherapeutic agent.

In certain embodiments, the second chemotherapeutic agent is administered to the mammal sequentially or consecutively.

In certain embodiments, the method is for treating a condition selected from cancer, rheumatoid arthritis, multiple sclerosis, graft versus host disease (GVHD), transplant rejection, lupus, myositis, infection, and immune deficiency.

In certain embodiments, the method or conjugate is for treating a cancer.

In certain embodiments, the cancer is a hematological cancer or a solid tumor. More specifically, the cancer is ovarian cancer, pancreatic cancer, cervical cancer, melanoma, lung cancer (e.g., non small-cell lung cancer (NSCLC)), breast cancer, squamous cell carcinoma of the head and neck, prostate cancer, endometrial cancer, lymphoma (e.g., non-Hodgkin lymphoma), myelodysplastic syndrome (MDS), peritoneal cancer, or leukemia (e.g., acute myeloid leukemia (AML), acute monocytic leukemia, promyelocytic leukemia, eosinophilic leukaemia, acute lymphoblastic leukemia (e.g., B-ALL), chronic lymphocytic leukemia (CLL) and chronic myeloid leukemia (CML)).

Production of Cell-Binding Agent-Drug Conjugates

In order to link the cytotoxic compounds or derivative thereof of the present invention to the cell-binding agent, the cytotoxic compound can comprise a linking moiety with a reactive group bonded thereto, such as compound 14 (Example 1), 23 (Example 2), 35 (Example 3), 49 (Example 4), 80 (Example 5), 90 (Example 6), 63 (Example 7), or 70 (Example 8). These compounds can be directly linked to the cell-binding agent. Representative processes for linking the cytotoxic compounds having a reactive group bonded thereof with the cell-binding agent to produce the cell-binding agent-cytotoxic agent conjugates are described in Examples 11, 13, 14-17, 19 and 20.

In one embodiment, a bifunctional crosslinking reagent can be first reacted with the cytotoxic compound to provide the compound bearing a linking moiety with one reactive group bonded thereto (i.e., drug-linker compound), which can then react with a cell binding agent. Alternatively, one end of the bifunctional crosslinking reagent can first react with the cell binding agent to provide the cell binding agent bearing a linking moiety with one reactive group bonded thereto, which can then react with a cytotoxic compound. The linking moiety can contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 2005/0169933, or charged linkers or hydrophilic linkers and are described in US 2009/0274713, US 2010/01293140 and WO 2009/134976, each of which is expressly incorporated herein by reference, each of which is expressly incorporated herein by reference.

In one embodiment, a solution of a cell-binding agent (e.g., an antibody) in aqueous buffer may be incubated with a molar excess of a bifunctional crosslinking agent, such as N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. The modified cell-binding agent (e.g., modified antibody) is then reacted with the thiol-containing cytotoxic compound described herein, such as compound 98 or 99 (Examples 9 and 10), to produce a disulfide-linked cell-binding agent-cytotoxic agent conjugate of the present invention.

In another embodiment, the thiol-containing cytotoxic compound described herein, such as compound 98 or 99 can react with a bifunctional crosslinking agent such as N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to form a cytotoxic agent-linker compound, which can then react with a cell-biding agent to produce a disulfide-linked cell-binding agent-cytotoxic agent conjugate of the present invention. The cytotoxic agent-linker compound can be prepared in situ without purification before reacting with the cell-binding agent. A representative process is described in Examples 12 and 18. Alternatively, the cytotoxic agent-linker compound can be purified prior to reacting with the cell-binding agent.

The cell binding agent-cytotoxic agent conjugate may be purified using any purification methods known in the art, such as those described in U.S. Pat. No. 7,811,572 and US Publication No. 2006/0182750, both of which are incorporated herein by reference. For example, the cell-binding agent-cytotoxic agent conjugate can be purified using tangential flow filtration, adsorptive chromatography, adsorptive filtration, selective precipitation, non-absorptive filtration or combination thereof. Preferably, tangential flow filtration (TFF, also known as cross flow filtration, ultrafiltration and diafiltration) and/or adsorptive chromatography resins are used for the purification of the conjugates.

Alternatively, the cell-binding agent (e.g., an antibody) may be incubated with a molar excess of an antibody modifying agent such as 2-iminothiolane, L-homocysteine thiolactone (or derivatives), or N-succinimidyl-S-acetylthioacetate (SATA) to introduce sulfhydryl groups. The modified antibody is then reacted with the appropriate disulfide-containing cytotoxic agent, to produce a disulfide-linked antibody-cytotoxic agent conjugate. The antibody-cytotoxic agent conjugate may then be purified by methods described above. The cell binding agent may also be engineered to introduce thiol moieties, such as cysteine-engineered antibodies disclosed in U.S. Pat. Nos. 7,772,485 and 7,855,275.

In another embodiment, a solution of a cell-binding agent (e.g., an antibody) in aqueous buffer may be incubated with a molar excess of an antibody-modifying agent such as N-succinimidyl-4-(N-maleimidomethyl)-cyclohexane-1-carboxylate to introduce maleimido groups, or with N-succinimidyl-4-(iodoacetyl)-aminobenzoate (SIAB) to introduce iodoacetyl groups. The modified cell-binding agent (e.g., modified antibody) is then reacted with the thiol-containing cytotoxic agent to produce a thioether-linked cell-binding agent-cytotoxic agent conjugate. The conjugate may then be purified by methods described above.

The number of cytotoxic molecules bound per antibody molecule can be determined spectrophotometrically by measuring the ratio of the absorbance at 280 nm and 330 nm. An average of 1-10 cytotoxic compounds/antibody molecule(s) can be linked by the methods described herein. The preferred average number of linked cytotoxic compounds per antibody molecule is 2-5, and the most preferred is 2.5-4.0.

Representative processes for preparing the cell-binding agent-drug conjugates of the present invention are described in U.S. Pat. No. 8,765,740 and U.S. Application Publication No. 2012/0238731. The entire teachings of these references are incorporated herein by reference.

Cytotoxicity of Compounds and Conjugates

The cytotoxic compounds and cell-binding agent-drug conjugates of the invention can be evaluated for their ability to suppress proliferation of various cancer cell lines in vitro. For example, cell lines such as human cervical carcinoma cell line KB, human acute monocytic leukemia cell line THP-1, human promyelocytic leukemia cell line HL60, human acute myeloid leukaemia cell line HNT-34, can be used for the assessment of cytotoxicity of these compounds and conjugates. Cells to be evaluated can be exposed to the compounds or conjugates for 1-5 days and the surviving fractions of cells measured in direct assays by known methods. $IC_{50}$ values can then be calculated from the results of the assays. Alternatively or in addition, an in vitro cell line sensitivity screen, such as the one described by the U.S. National Cancer Institute (see Voskoglou-Nomikos et al., 2003, Clinical Cancer Res. 9: 42227-4239, incorporated herein by reference) can be used as one of the guides to determine the types of cancers that may be sensitive to treatment with the compounds or conjugates of the invention.

Figure 2:
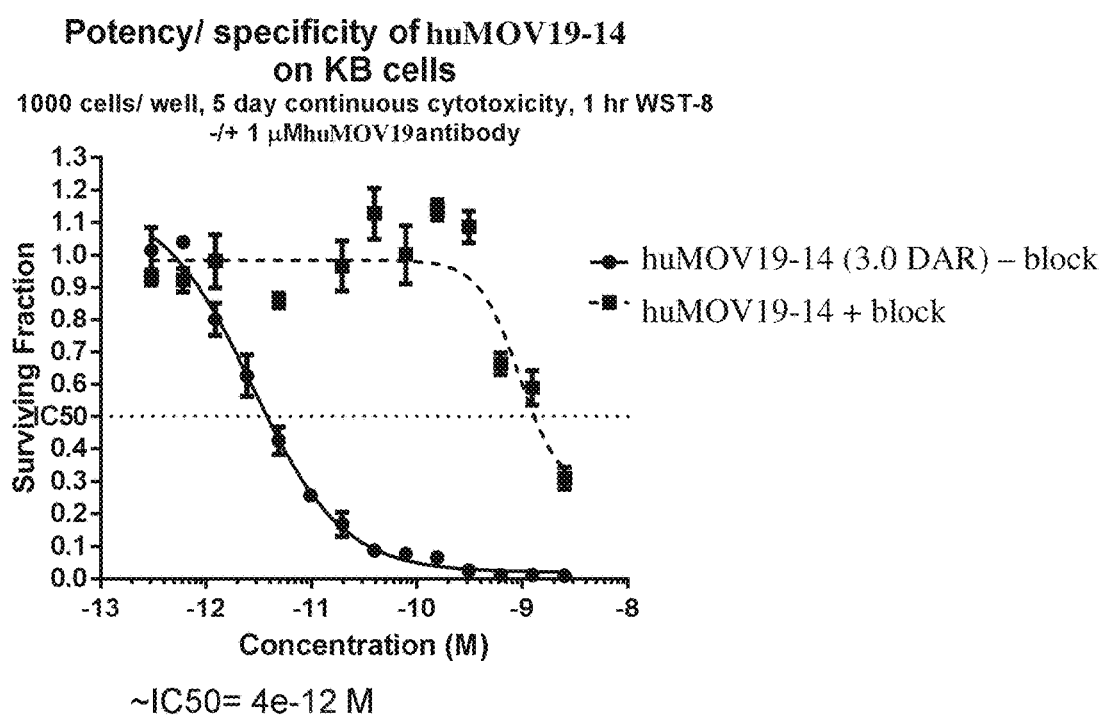
FIG. 2 shows in vitro cytotoxicity and specificity of huMOV19-14 conjugate.

Examples of in vitro potency and target specificity of antibody-cytotoxic agent conjugates of the present invention are shown in FIGS. 2 and 4. All of the conjugates are extremely cytotoxic on the antigen positive cancer cells with an $IC_{50}$ in the low picomolar range. Antigen negative cell lines remained viable when exposed to the same conjugates.

Figure 6:
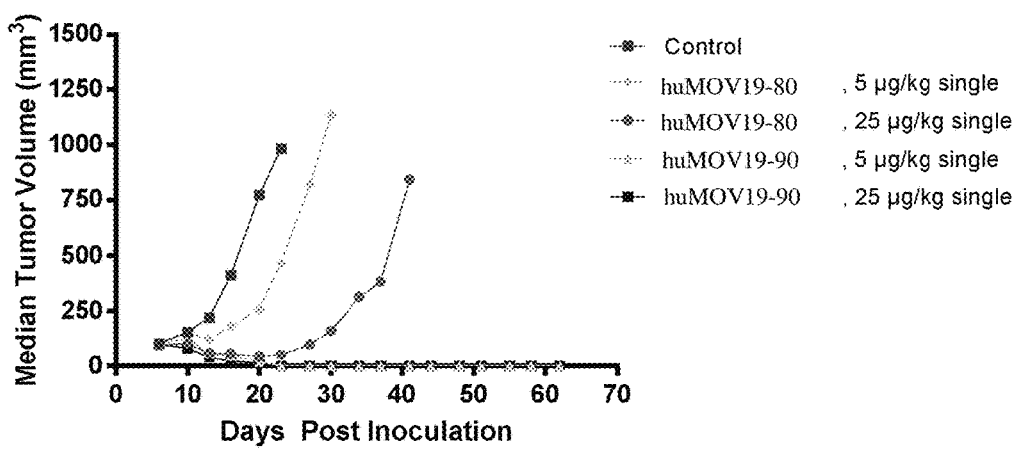
FIG. 6 shows in vivo efficacy of huMOV19-80 and huMOV19-90 conjugates in NCI-H2110 bearing SCID mice.

In one example, in vivo efficacy of a cell binding agent/cytotoxic agent conjugate was measured. SCID mice bearing NCI-H2110 tumor cells were treated with huMov19-80 and huMov19-90 conjugates and significant tumor regression was observed at multiple doses while untreated mice grew tumors rapidly (FIG. 6). Activity for huMov19-90 conjugate was observed at doses as low as 5 µg/kg.

Compositions and Methods of Use

The present invention includes a composition (e.g., a pharmaceutical composition) comprising novel benzodiazepine compounds described herein (e.g., indolinobenzodiazepine or oxazolidinobenzodiazepine), derivatives thereof, or conjugates thereof, (and/or solvates, hydrates and/or salts thereof) and a carrier (a pharmaceutically acceptable carrier). The present invention also includes a composition (e.g., a pharmaceutical composition) comprising novel benzodiazepine compounds described herein, derivatives thereof, or conjugates thereof, (and/or solvates, hydrates and/or salts thereof) and a carrier (a pharmaceutically acceptable carrier), further comprising a second therapeutic agent. The present compositions are useful for inhibiting abnormal cell growth or treating a proliferative disorder in a mammal (e.g., human). The present compositions are also useful for treating depression, anxiety, stress, phobias, panic, dysphoria, psychiatric disorders, pain, and inflammatory diseases in a mammal (e.g., human).

The present invention includes a method of inhibiting abnormal cell growth or treating a proliferative disorder in a mammal (e.g., human) comprising administering to said mammal a therapeutically effective amount of novel benzodiazepine compounds described herein (e.g., indolinobenzodiazepine or oxazolidinobenzodiazepine), derivatives thereof, or conjugates thereof, (and/or solvates and salts thereof) or a composition thereof, alone or in combination with a second therapeutic agent.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of a cytotoxic agent comprising any of the cytotoxic compound-cell-binding agents (e.g., indolinobenzodiazepine or oxazolidinobenzodiazepine dimer linked to a cell binding agent) of the present invention, a salt or solvate thereof. The target cells are cells to which the cell-binding agent can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 µM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 mL of normal saline to which 5 to 10 mL of human serum albumin can be added. Dosages will be 10 µg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer, autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include:

Comprehensive index
By Manufacturer
Products (by company's or trademarked drug name)
Category index
Generic/chemical index (non-trademark common drug names)
Color images of medications
Product information, consistent with FDA labeling
Chemical information
Function/action
Indications & Contraindications
Trial research, side effects, warnings
Analogues and Derivatives One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

EXAMPLES

The invention will now be illustrated by reference to non-limiting examples. Unless otherwise stated, all percents, ratios, parts, etc. are by weight. All reagents were purchased from the Aldrich Chemical Co., New Jersey, or other commercial sources. Nuclear Magnetic Resonance ($^1$H NMR) spectra were acquired on a Bruker 400 MHz instrument. Mass spectra were acquired on a Bruker Daltonics Esquire 3000 instrument and LCMS were acquired on an Agilent 1260 Infinity LC with an Agilent 6120 single quadropole MS using electrospray ionization.

The following solvents, reagents, protecting groups, moieties and other designations may be referred to by their abbreviations in parenthesis:

Me=methyl; Et=ethyl; Pr=propyl; i-Pr=isopropyl; Bu=butyl; t-Bu=tert-butyl; Ph=phenyl, and Ac=acetyl
AcOH or HOAc=acetic acid
ACN or $CH_3CN$=acetonitrile
Ala=alanine
aq=aqueous
$BH_3$.DMS=borane dimethylsulfide complex
Bn=benzyl
Boc or BOC=tert-butoxycarbonyl
$CBr_4$=carbontetrabromide
Cbz or Z=benzyloxycarbonyl
DCM or $CH_2Cl_2$=dichloromethane
DCE=1,2-dichloroethane
DMAP=4-dimethylaminopyridine
DI water=deionized water
DIBAL=diisobutylaluminum hydride
DIEA or DIPEA=N,N-diisopropylethylamine
DMA=N,N-dimethylacetamide
DMF=N,N-dimethylformamide
DMSO=dimethyl sulfoxide
DTT=dithiothreitol
EDC=1-ethyl-3-(3-dimethylaminopropyl)carbodiimide
EEDQ=N-Ethoxycarbonyl-2-ethoxy-1,2-dihydroquinoline
ESI or ES=electrospray ionization
EtOAc=ethylacetate
Gly=glycine
g=grams
h=hour
HATU=N,N,N'N'-tetramethyl-O-(7-azabenzotriazol-1-yl) uronium hexaphosphate
HPLC=high-performance liquid chromatography
HOBt or HOBT=1-hydroxybenzotriazole
LAH=lithium aluminum hydride
LC=liquid chromatography
LCMS=liquid chromatography mass spectrometry
min=minutes
mg=miligrams
mL=mililiters
mmol=milimoles
μg=micrograms
μL=microliters
μmol=micromoles
Me=methyl
MeOH=methanol
MeI=methyliodide
MS=mass spectrometry
MsCl=methanesulfonyl chloride (mesyl chloride)
$Ms_2O$=methanesulfonic anhydride
$NaBH(OAc)_3$=sodium triacetoxyborohydride
NHS=N-hydroxysuccinamide
NMR=nuclear magnetic resonance spectroscopy
$PPh_3$=triphenylphosphine
PTLC=preparative thin layer chromatography
rac=racemic mixture
$R_f$=retardation factor
RPHPLC or RP-HPLC=reverse phase high-performance liquid chromatography
RT or rt=room temperature (ambient, about 25° C.)
sat or sat'd=saturated
STAB=sodium triacetoxyborohydride ($NaBH(OAc)_3$)

TBSCl or TBDMSCl=tert-butyldimethylsilyl chloride
TBS=tert-butyldimethylsilyl
TCEP.HCl=tris(2-carboxyethyl)phosphine hydrochloride salt
TEA=triethylamine (Et₃N)
TFA=trifluoroacetic acid
THF=tetrahydrofuran
TLC=thin layer chromatography
Val=valine

Example 1

Synthesis of 2,5-dioxopyrrolidin-1-yl 6-((2-((2-((2-((3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)amino)-2-oxoethyl)amino)-2-oxoethyl)amino)-2-oxoethyl)amino)-6-oxohexanoate (Compound 14)

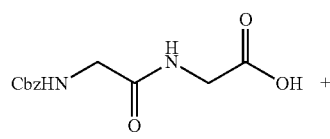

1

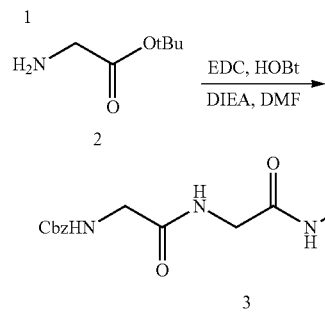

Step 1: Z-Gly-Gly-OH compound 1 (5.0 g, 18.78 mmol) and H-Gly-Ot-Bu.HCl compound 2 (3.46 g, 20.66 mmol) were dissolved in DMF (37.6 mL). EDC.HCl (3.96 g, 20.66 mmol) and HOBt (2.88 g, 18.78 mmol) were added to the reaction flask, followed by DIPEA (8.18 mL, 46.9 mmol). The reaction was stirred at rt under Ar overnight. The reaction mixture was diluted with CH₂Cl₂, washed with sat'd NH₄Cl, sat'd NaHCO₃, followed by water and brine. The organic layer was dried over Na₂SO₄, filtered and concentrated. The crude product was purified by silica gel flash chromatography (MeOH/DCM, gradient, 0% to 5%) to yield pure compound 3 as a white solid (6.35 g, 89% yield). ¹H NMR (400 MHz, DMSO-d6): δ 8.18-8.13 (m, 2H), 7.48 (t, 1H, J=6.0 Hz), 7.37-7.36 (m, 3H), 7.34-7.32 (m, 1H), 5.04 (s, 2H), 4.09 (q, 1H, J=5.2 Hz), 3.74 (t, 4H, J=6.1 Hz), 3.67 (d, 2H, J=6.0 Hz), 3.17 (d, 2H, J=5.2 Hz), 1.41 (s, 9H). LCMS=4.28 min (8 min method). Mass observed (ESI⁺): 324.15 (M-t-Bu+H).

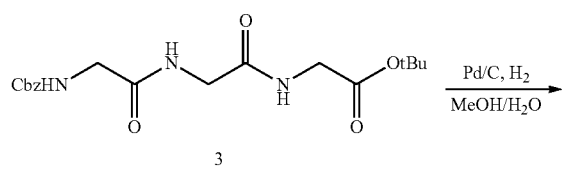

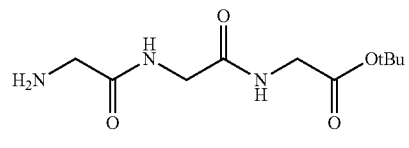

4

Step 2: Compound 3 (6.3 g, 16.60 mmol) was dissolved in MeOH (52.7 mL) and water (2.64 mL). The reaction mixture was purged with Ar and was degassed for 5 min. Pd/C (wet, 10%) (0.884 g, 0.830 mmol) was slowly added. Then bubbled in H₂ from a balloon for 1 min. The reaction was stirred under a balloon of H₂ at rt overnight. The reaction mixture was filtered through Celite and the filter cake was washed with MeOH (30 mL) and was concentrated. CH₃CN (20 mL) was added to the residue and was concentrated. This was repeated 2 more times to obtain a sticky solid. The residue was slurried in EtOAc/hexanes (2:1, 50 mL) and filtered and was rinsed with EtOAc/hexanes (1:1, 30 mL). The solid was dried under vacuum/N₂ for 1 h to obtain compound 4 as a white solid (3.66 g, 90% yield). ¹H NMR (400 MHz, DMSO-d6): δ 8.21-8.18 (m, 1H), 8.12 (bs, 1H), 3.76 (bs, 2H), 3.73 (d, 2H, J=6.0 Hz), 3.13 (s, 2H), 1.93 (bs, 2H), 1.41 (s, 9H).

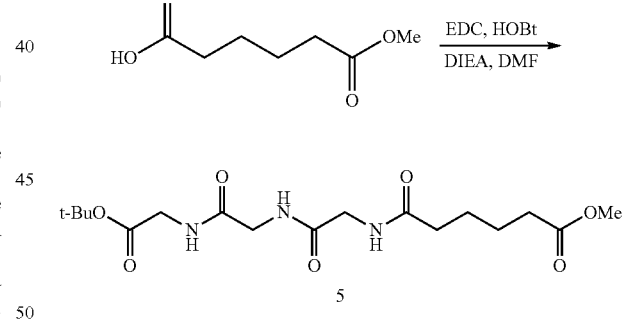

Step 3: Amine compound 4 (1.0 g, 4.08 mmol) and mono methyladipate (664 µL, 4.48 mmol) were dissolved in DMF (13.59 mL). EDC.HCl (860 mg, 4.48 mmol) and HOBt (624 mg, 4.08 mmol) were added to the reaction mixture, followed by DIEA (1.424 mL, 8.15 mmol). The reaction was stirred at rt overnight. The reaction mixture was diluted with DCM/MeOH (20 mL, 5:1) and was washed with sat'd NH₄Cl, sat'd NaHCO₃, water and brine. The organic layer was dried over Na₂SO₄, filtered and concentrated. The crude product was purified by silica gel flash chromatography (gradient, 0% to 20% MeOH/DCM) to obtain pure compound 5 as a white solid (1.5 g, 95% yield). ¹H NMR (400 MHz, DMSO-d6): δ 8.17-8.06 (m, 3H), 3.74-3.71 (m, 6H), 3.59 (s, 3H), 2.32 (bt, 2H, J=6.9 Hz), 2.14 (bt, 2H, J=6.7 Hz), 1.52-1.49 (m, 4H), 1.41 (s, 9H).

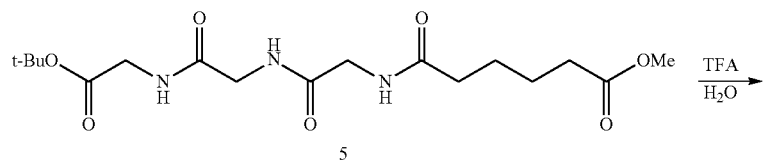

5

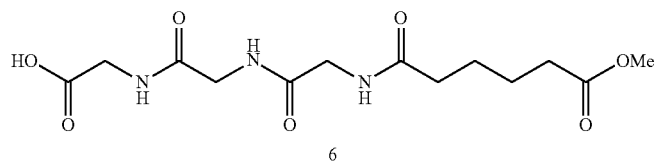

6

Step 4: Compound 5 (1.5 g, 3.87 mmol) was stirred in TFA (5.97 mL, 77.0 mmol) and deionized water (300 μL) at rt overnight. CH$_3$CN (10 mL) was added to the reaction mixture and was stirred for 5 min. The mixture became thick with lots of white precipitate. More CH$_3$CN (30 mL) was added and was further stirred for 5 min. The mixture was filtered and dried under vacuum/N$_2$ for 1 h to obtain pure compound 6 as a white solid (0.7 g, 55% yield). $^1$H NMR (400 MHz, DMSO-d6): δ 12.56 (s, 1H), 8.16-8.06 (m, 3H), 3.73 (dt, 6H, J=8.6, 6.1 Hz), 3.59 (s, 3H), 2.32-2.29 (m, 2H), 2.16-2.13 (m, 2H), 1.51 (bt, 4H, J=3.5 Hz).

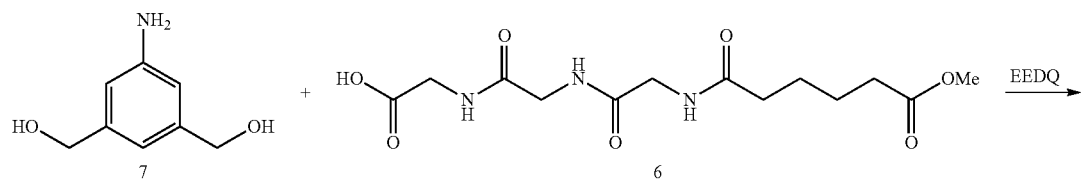

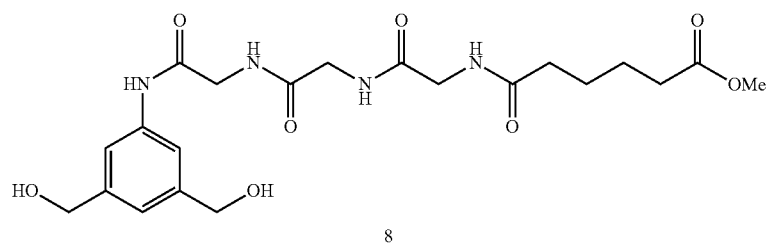

8

Step 5: Aniline compound 7 (100 mg, 0.653 mmol) and acid compound 6 (227 mg, 0.685 mmol) were suspended in CH$_2$Cl$_2$/MeOH (4.35 mL/2.2 mL) at rt. EEDQ (323 mg, 1.306 mmol) was added and the reaction was stirred at rt overnight. The solvent was concentrated and the residue was slurried in EtOAc (15 mL) and filtered. The solids were washed with EtOAc (2×15 mL) and was dried under vacuum/N$_2$ to obtain compound 8 as a white solid (260 mg, 85% yield). $^1$H NMR (400 MHz, DMSO-d6): δ 9.74 (s, 1H), 8.21-8.19 (m, 2H), 8.11-8.08 (m, 1H), 7.45 (s, 2H), 6.96 (s, 1H), 5.17 (t, 2H, J=5.7 Hz), 4.45 (d, 4H, J=5.6 Hz), 3.87 (d, 2H, J=5.8 Hz), 3.75 (dd, 4H, J=5.7, 13.4 Hz), 3.58 (s, 3H), 2.31-2.27 (m, 2H), 2.16-2.13 (m, 2H), 1.52-1.48 (m, 4H). LCMS=0.886 min (15 min method). Mass observed (ESI$^+$): 489.3 (M+Na).

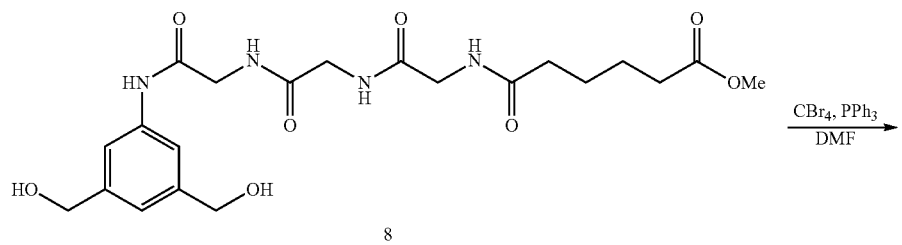

8

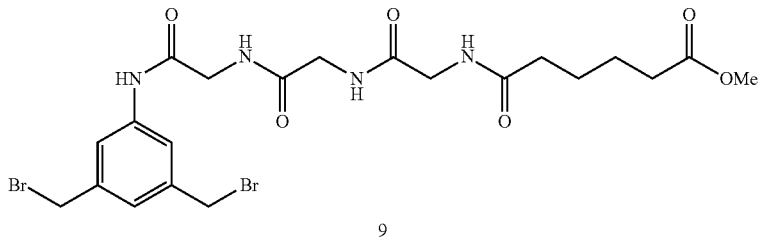

9

Step 6: Diol compound 8 (260 mg, 0.557 mmol) and carbontetrabromide (555 mg, 1.672 mmol) were dissolved in DMF (5.57 mL). Triphenylphosphine (439 mg, 1.672 mmol) was added and the brown mixture was stirred under Ar at rt for 4 h. The reaction mixture was diluted with DCM/MeOH (10:1, 30 mL) and was washed with water and brine. The organic layer was dried over Na$_2$SO$_4$, filtered and concentrated. The crude residue was purified by silica gel flash chromatography (MeOH/DCM, 0% to 10%, gradient) to obtain compound 9 as a yellow solid. The product was slurried in CH$_2$Cl$_2$/EtOAc (1:10, 30 mL) and then filtered. The solid was washed with EtOAc and was dried under vacuum/N$_2$ to obtained pure compound 9 as an off white solid (170 mg, 52% yield). $^1$H NMR (400 MHz, DMSO-d6): δ 9.95 (s, 1H), 8.25-8.20 (m, 2H), 8.12-8.10 (m, 1H), 7.65 (s, 2H), 7.22 (s, 1H), 4.68 (s, 3H), 3.89 (d, 2H, J=5.8 Hz), 3.77 (dd, 4H, J=5.7, 7.4 Hz), 3.58 (s, 3H), 2.31-2.27 (m, 2H), 2.16-2.13 (m, 2H), 1.51-1.49 (m, 4H). LCMS=3.335 min (15 min method). Mass observed (ESI$^+$): 593.2 (M+H).

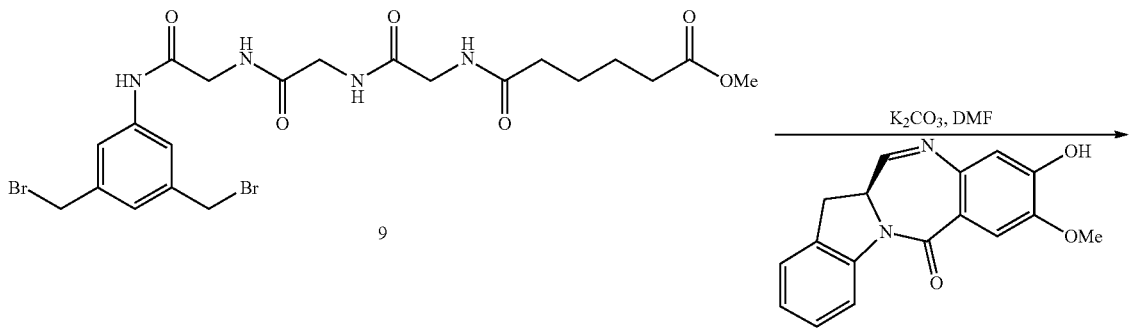

9

IGN monomer 10

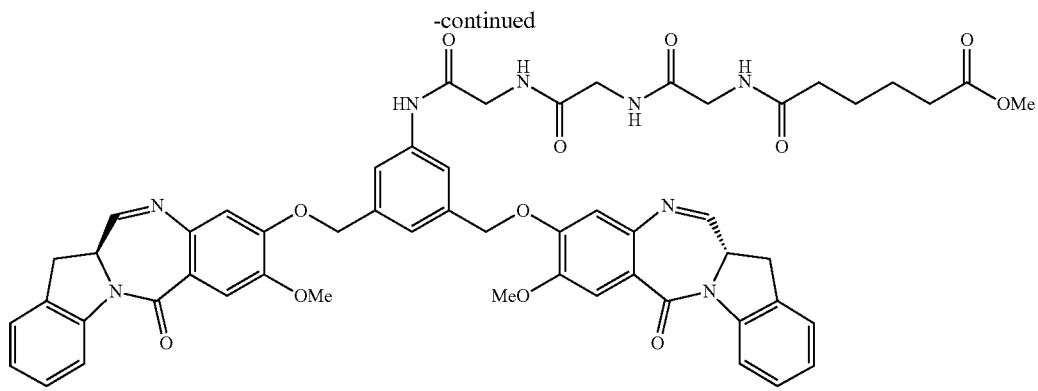

11

Step 7: Dibromide compound 9 (109 mg, 0.184 mmol) and IGN monomer compound 10 (119 mg, 0.405 mmol) were dissolved in DMF (1.84 mL). Potassium carbonate (63.6 mg, 0.460 mmol) was added and was stirred at rt overnight. Water (20 mL) was added to the reaction mixture to precipitate the product. The slurry was stirred at rt for 5 min and was then filtered and dried under vacuum/$N_2$ for 1 h. The crude product was purified by silica gel flash chromatography (MeOH/$CH_2Cl_2$, gradient, 0% to 5%) to obtain compound 11 as a yellow solid (160 mg, 60% yield, 70% purity). LCMS=5.240 min (15 min method). Mass observed (ESI$^+$): 1019.7 (M+H).

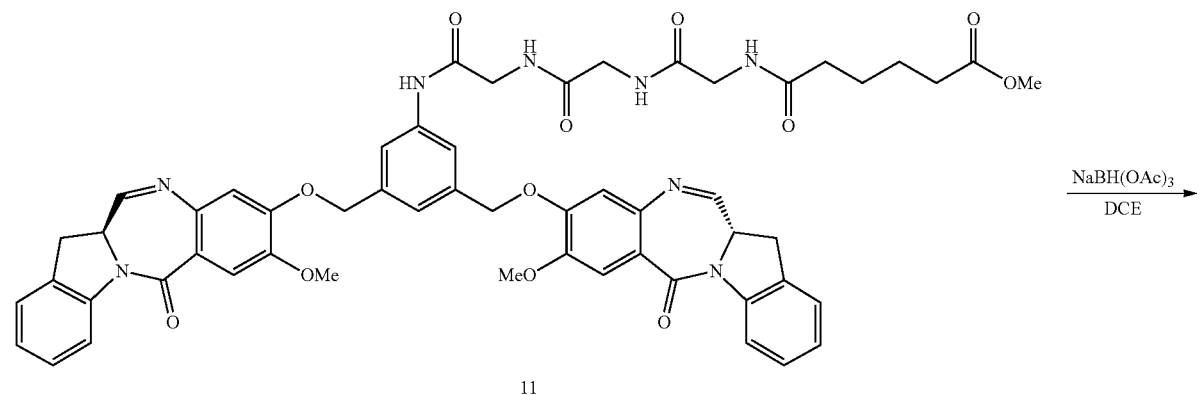

11

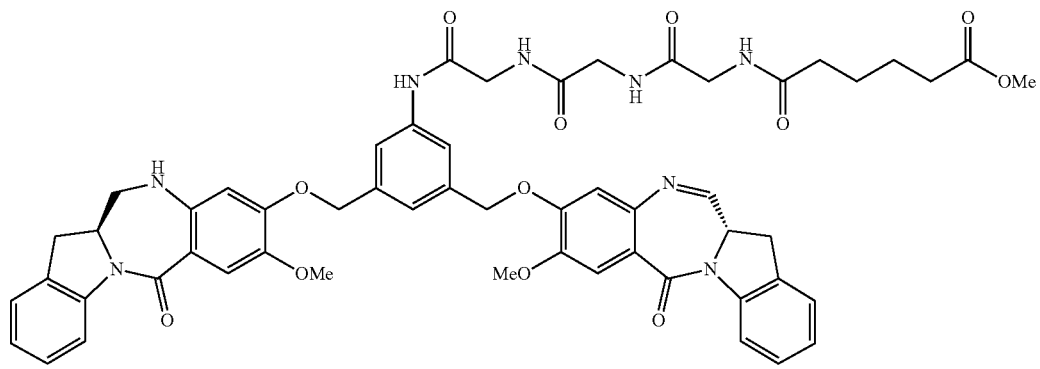

12

Step 8: Diimine compound 11 (140 mg, 0.11 mmol) was dissolved in 1,2-dichloroethane (1.1 mL). NaBH(OAc)₃ (23.29 mg, 0.11 mmol) was added to the reaction mixture and was stirred at rt for 1 h. The reaction was diluted with CH₂Cl₂ (30 mL) and was quenched with sat'd aq NH₄Cl solution (15 mL). The layers were separated and was washed with brine, dried over Na₂SO₄ and concentrated. The crude residue was purified by RPHPLC (C18 column, CH₃CN/H₂O, gradient, 35% to 55%) to yield mono imine compound 12 as a white fluffy solid (33 mg, 29% yield) and starting material compound 11 was also recovered (25 mg). LCMS=7.091 min (15 min method). Mass observed (ESI⁺): 1021.7 (M+H).

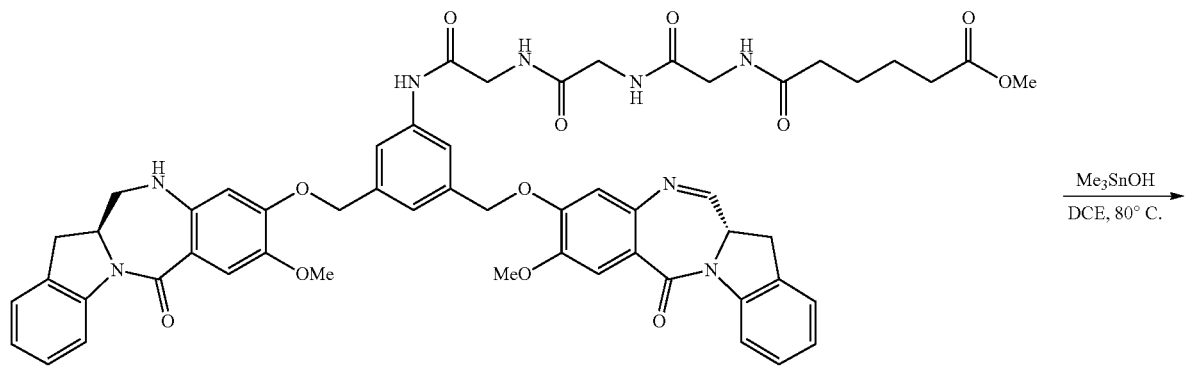

12

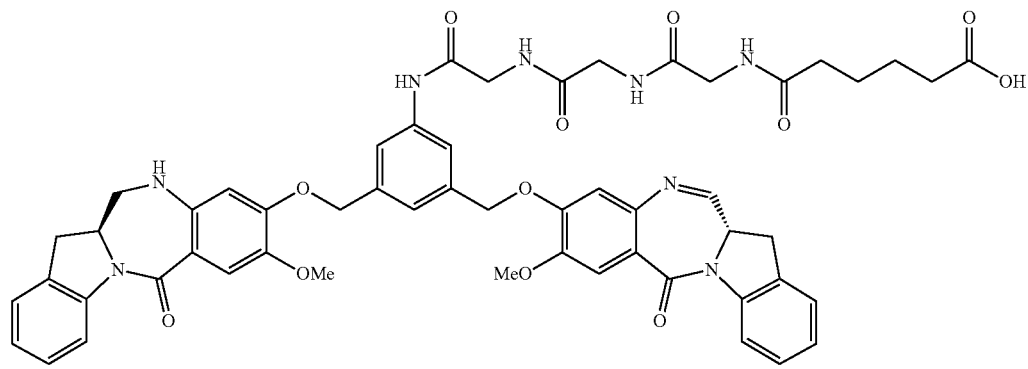

13

Step 9: Methylester compound 12 (33 mg, 0.029 mmol) was dissolved in THF (1.09 mL) and water (364 μL). LiOH (6.97 mg, 0.291 mmol) was added and the reaction was stirred at rt for 1.5 h. The reaction mixture was diluted with H₂O (5 mL) and acidified with 0.5 M aq HCl until pH~4. The aqueous layer was extracted with CH₂Cl₂/MeOH (3:1, 3×20 mL). The combined organic layers were dried over Na₂SO₄, filtered and concentrated to obtain crude compound 13 as a yellow solid (29 mg, 99% yield). LCMS=5.356 min (15 min method). Mass observed (ESI⁺): 1007.7 (M+H).

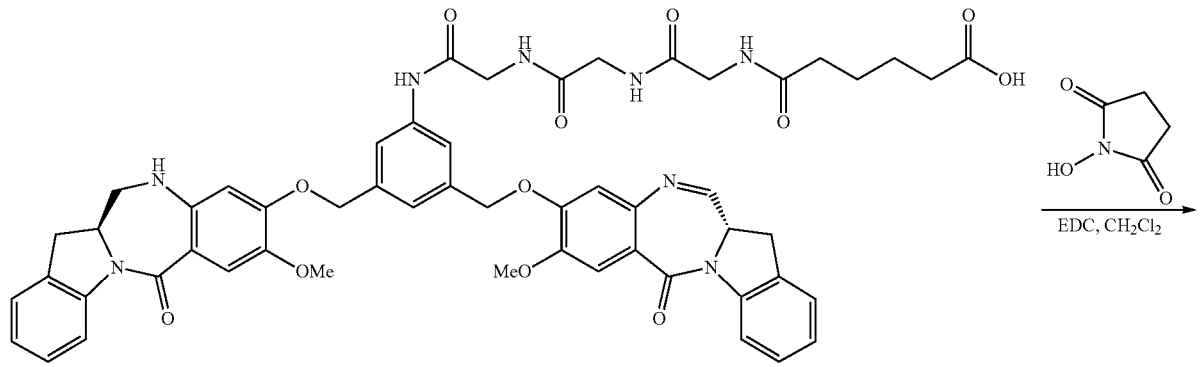

13

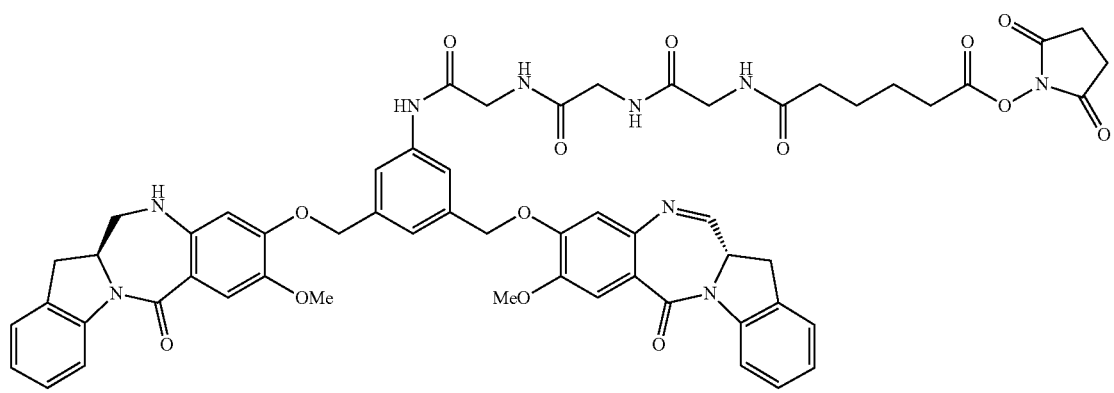

14

Step 10: EDC.HCl (22.08 mg, 0.115 mmol) was added to a stirred solution of acid compound 13 (29 mg, 0.023 mmol) and N-hydroxysuccinamide (21.21 mg, 0.184 mmol) in CH₂Cl₂ (2.3 mL) at rt. The reaction mixture was stirred for 2 h. The reaction mixture was diluted with CH₂Cl₂ and was washed with water (1×15 mL) and brine (1×15 mL). The organic layer was dried over Na₂SO₄, filtered and concentrated. The crude product was purified by RPHPLC (C18 column, CH₃CN/H₂O, gradient, 35% to 55%). Fractions containing product were combined and lyophilized to obtain 2,5-dioxopyrrolidin-1-yl 6-((2-((2-((2-((3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methylphenyl)amino)-2-oxoethyl)amino)-2-oxoethyl)amino)-2-oxoethyl)amino)-6-oxohexanoate, compound 14 as a white fluffy solid (8 mg, 31% yield). LCMS=5.867 min (15 min method). Mass observed (ESI⁺): 1104.7 (M+H).

Example 2

Synthesis of (1r,4r)-2,5-dioxopyrrolidin-1-yl 4-((2-((2-((2-((3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)amino)-2-oxoethyl)amino)-2-oxoethyl)amino)-2-oxoethyl)carbamoyl)cyclohexanecarboxylate, (Compound 23)

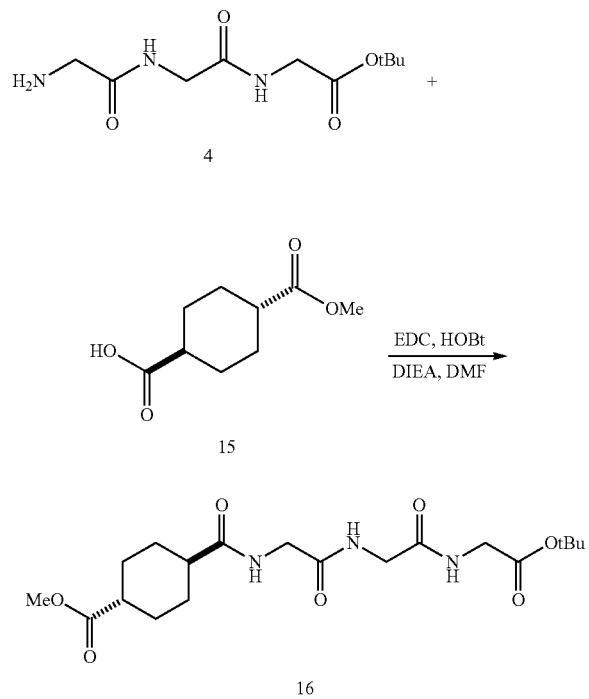

Step 1: Amine compound 4 (200 mg, 0.815 mmol) and 1,4-trans-cyclohexanedicarboxlic acid monomethylester compound 15 (182 mg, 0.978 mmol) were dissolved in DMF (2.72 mL). EDC.HCl (188 mg, 0.978 mmol) and HOBt (125 mg, 0.815 mmol) were added to the reaction mixture, followed by DIEA (285 µL, 1.631 mmol). The mixture was stirred at rt overnight. The reaction mixture was diluted with CH₂Cl₂ and washed with sat'd NH₄Cl, sat'd NaHCO₃, brine, and water. The organic layer was dried over Na₂SO₄ and concentrated to a sticky residue. CH₃CN (15 mL) was added to the residue and was concentrated. This was repeated 2 more times to obtain compound 16 as a dry white powder (300 mg, 85% yield). ¹H NMR (400 MHz, DMSO-d6): δ 8.16 (t, 1H, J=5.9 Hz), 8.04 (dt, 2H, J=5.6, 14.8 Hz), 3.74-3.69 (m, 6H), 3.59 (s, 3H), 2.31-2.25 (m, 1H), 2.20-2.13 (m, 1H), 1.94-1.91 (m, 2H), 1.82-1.79 (m, 2H), 1.41 (s, 9H), 1.34 (d, 3H, J=11.7 Hz).

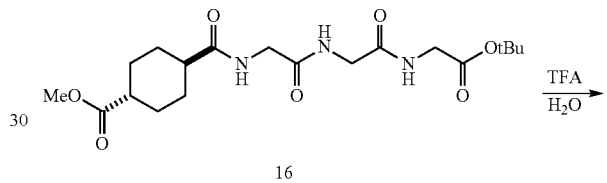

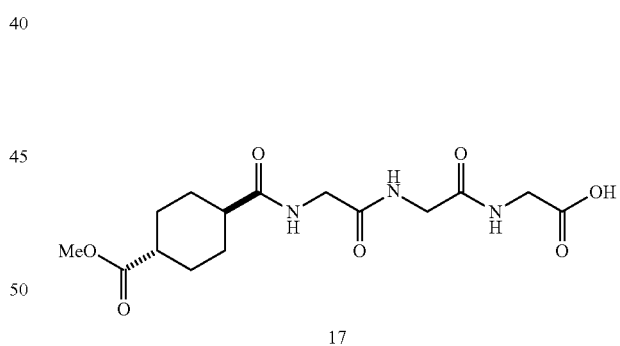

Step 2: TFA (1.40 mL, 18.14 mmol) and DI water (67.8 µL) were added to neat compound 16 (300 mg, 0.726 mmol) at rt and was stirred for 3 h. CH₃CN (20 mL) was added to the reaction mixture and was concentrated. This was repeated this two more times to obtain compound 17 as a white solid (230 mg, 89% yield). ¹H NMR (400 MHz, DMSO-d6): δ 8.16-8.13 (m, 1H), 8.07-8.01 (m, 2H), 3.76-3.73 (m, 4H), 3.70 (bd, 2H, J=5.1 Hz), 3.59 (s, 3H), 2.31-2.25 (m, 1H), 2.19-2.14 (m, 1H), 1.94-1.91 (m, 2H), 1.82-1.79 (m, 2H), 1.42-1.26 (m, 4H).

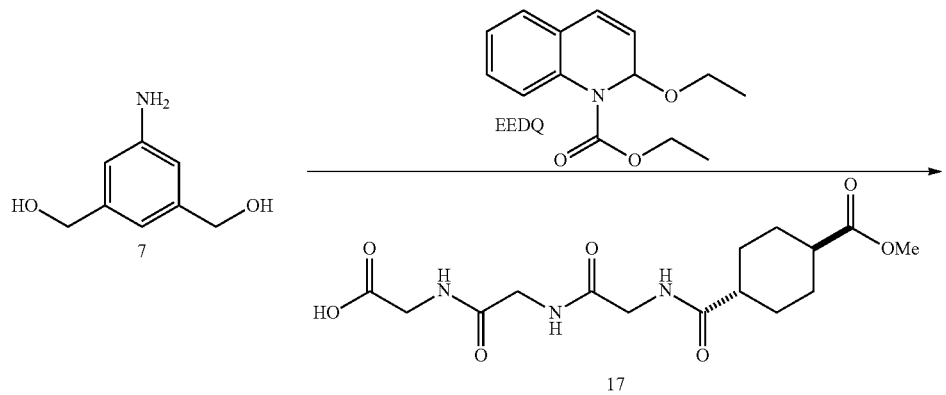

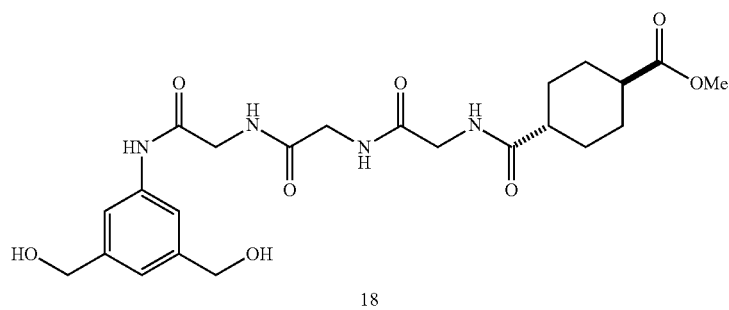

Step 3: Aniline compound 7 (135 mg, 0.881 mmol) and acid compound 17 (331 mg, 0.925 mmol) were suspended in CH$_2$Cl$_2$/MeOH (2.9 mL/1.5 mL) at rt. EEDQ (436 mg, 1.763 mmol) was added and the reaction was stirred at rt overnight. The solvent was concentrated and the residue was slurried in EtOAc (15 mL) and filtered. The solids were washed with EtOAc (2×15 mL) and was dried under vacuum/N$_2$ to obtain compound 18 as a white solid (330 mg, 61% yield). $^1$H NMR (400 MHz, DMSO-d6): δ 9.73 (s, 1H), 8.18 (dt, 2H, J=6.0, 19.2 Hz), 8.09-8.01 (m, 2H), 7.45 (s, 2H), 6.96 (s, 1H), 5.17 (t, 2H, J=5.7 Hz), 4.45 (d, 4H, J=5.6 Hz), 3.88-3.84 (m, 3H), 3.77-3.69 (m, 8H), 3.63 (s, 2H), 3.59 (s, 6H), 2.30-2.22 (m, 2H), 2.19-2.13 (m, 2H), 1.94-1.90 (m, 4H), 1.82-1.78 (m, 4H), 1.41-1.26 (m, 8H).

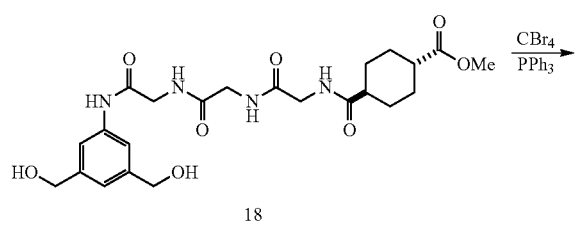

-continued

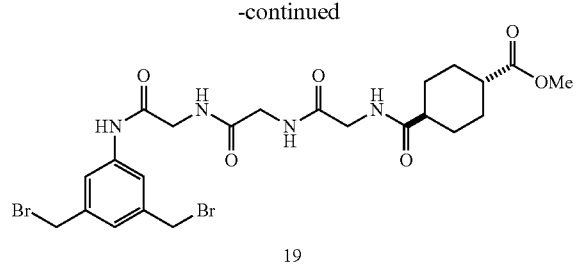

Step 4: Compound 18 (330 mg, 0.536 mmol) and CBr$_4$ (533 mg, 1.608 mmol) were dissolved in DMF (5.36 mL). PPh$_3$ (422 mg, 1.608 mmol) was added to the reaction mixture, at which point the reaction turned yellow with a slight exotherm. The reaction was stirred under Ar for 4 h. The reaction mixture was diluted with CH$_2$Cl$_2$ and was washed with water and brine. The organic layer was dried over Na$_2$SO$_4$ and concentrated. The crude residue was purified by silica gel flash chromatography (MeOH/CH$_2$Cl$_2$, gradient, 0% to 10%) to obtain compound 19 as a white solid (234 mg, 64% yield). LCMS=4.453 min (8 min method). Mass observed (ESI$^+$): 617.10 (M+H).

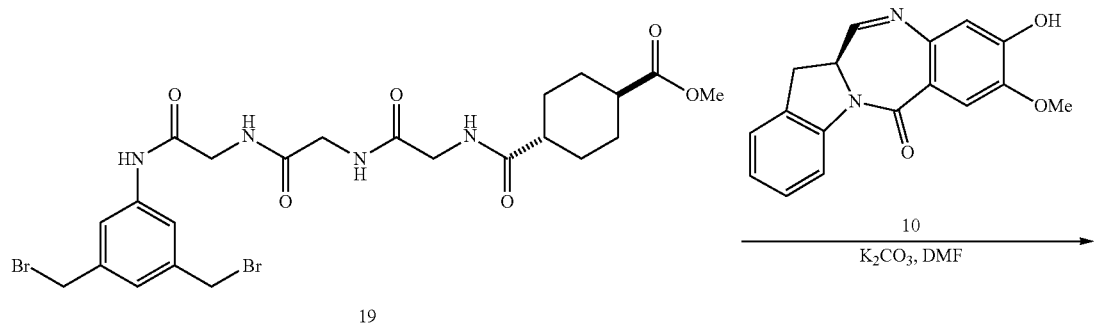
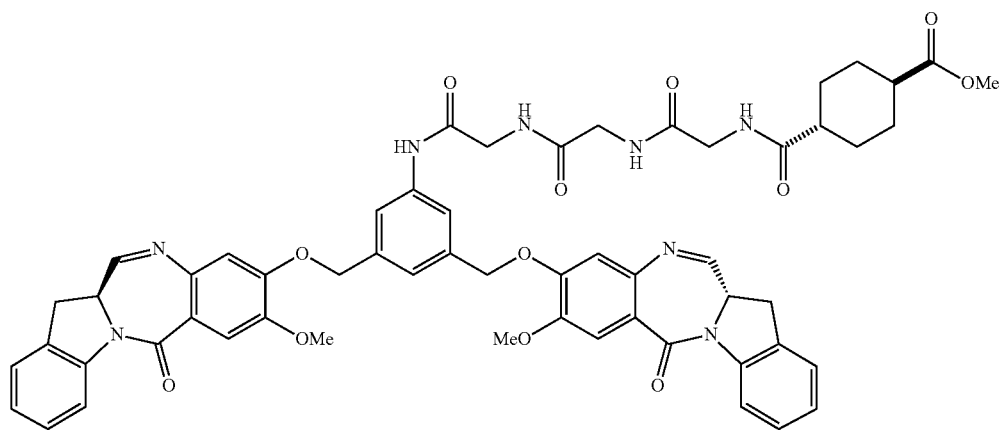
Step 5: Compound 20 was prepared similarly as compound 11 in Example 1. Compound 20 was obtained as a yellow solid after purification (264 mg, 60% yield). LCMS=4.831 min (8 min method). Mass observed (ESI+): 1045.20 (M+H).
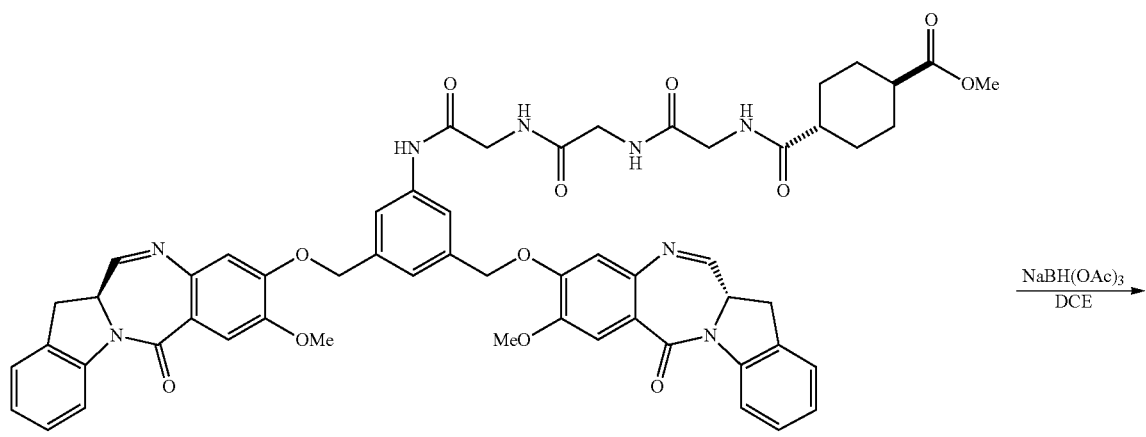

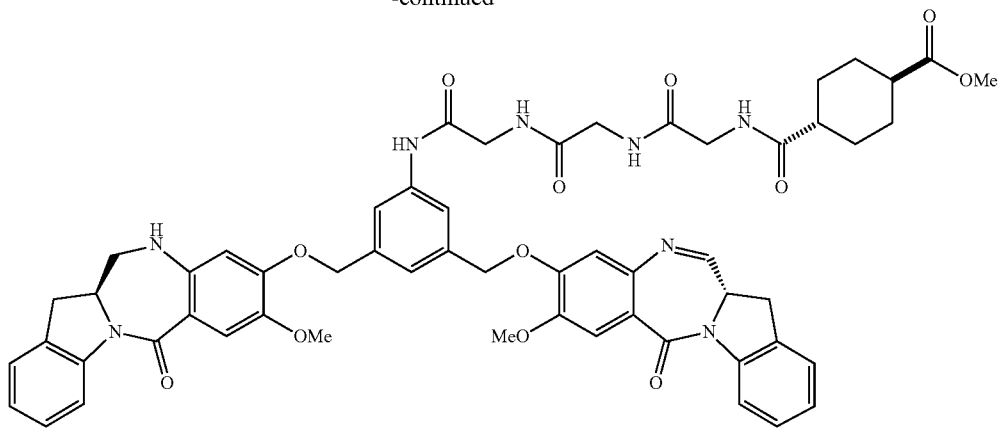
21
Step 6: Compound 21 was prepared similarly as compound 12 in Example 1. Compound 21 was obtained as a white solid after C18 purification (51 mg, 31% yield). LCMS=5.127 min (8 min method). Mass observed (ESI+): 1047.30 (M+H).
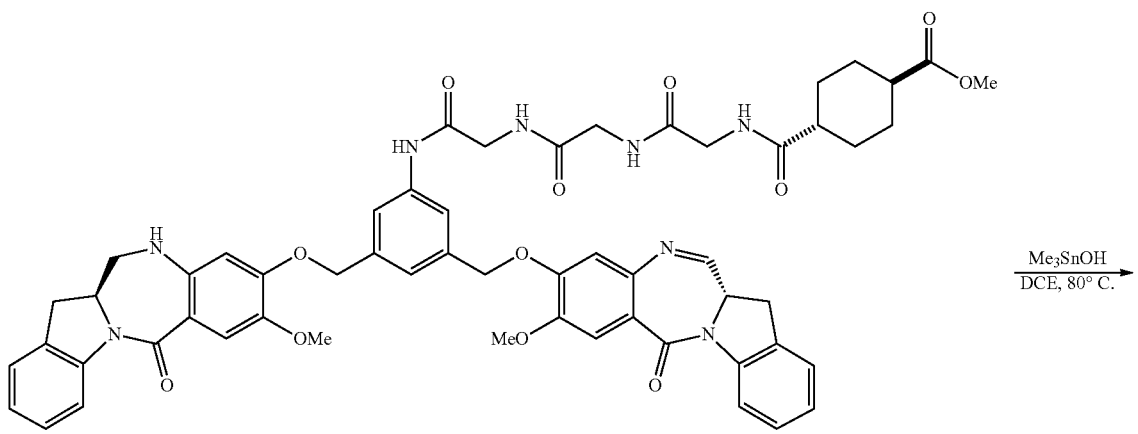
21
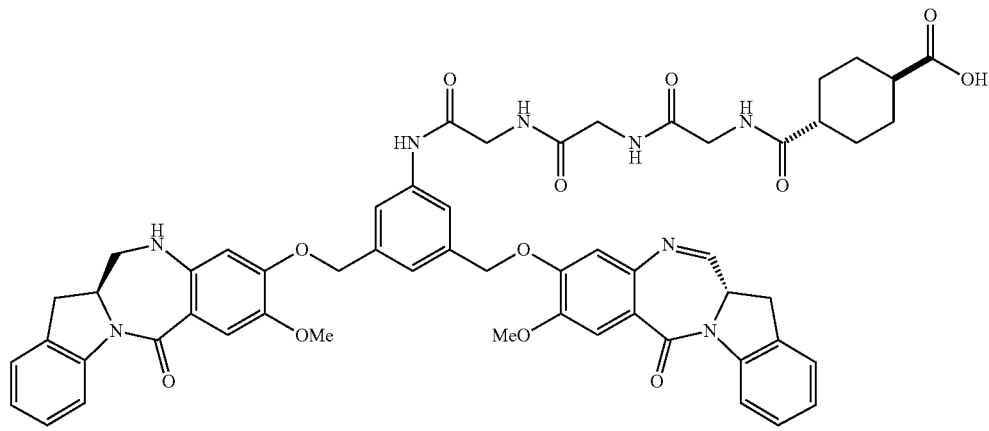
22

Step 7: Methylester compound 21 (48 mg, 0.046 mmol) was dissolved in 1,2-dichloroethane (3.06 mL). Trimethylstannanol (124 mg, 0.688 mmol) was added to the reaction mixture and was heated at 80° C. overnight. The reaction mixture was cooled to rt and was diluted with water (15 mL). The aqueous layer was acidified to pH~4 with 1 M HCl. The mixture was extracted with CH$_2$Cl$_2$/MeOH (10:1, 3×20 mL). The combined organic layers were washed with brine and was dried over Na$_2$SO$_4$ and concentrated. The crude residue was plugged through a short pad of silica gel and was flushed with CH$_2$Cl$_2$/MeOH (10:1, then 5:1, 2×30 mL) and was concentrated. Acid compound 22 was obtained as a yellow solid and was used in the next step without further purification (48 mg, 100% yield). LCMS=5.338 min (15 min method). Mass observed (ESI$^+$): 1033.7 (M+H).

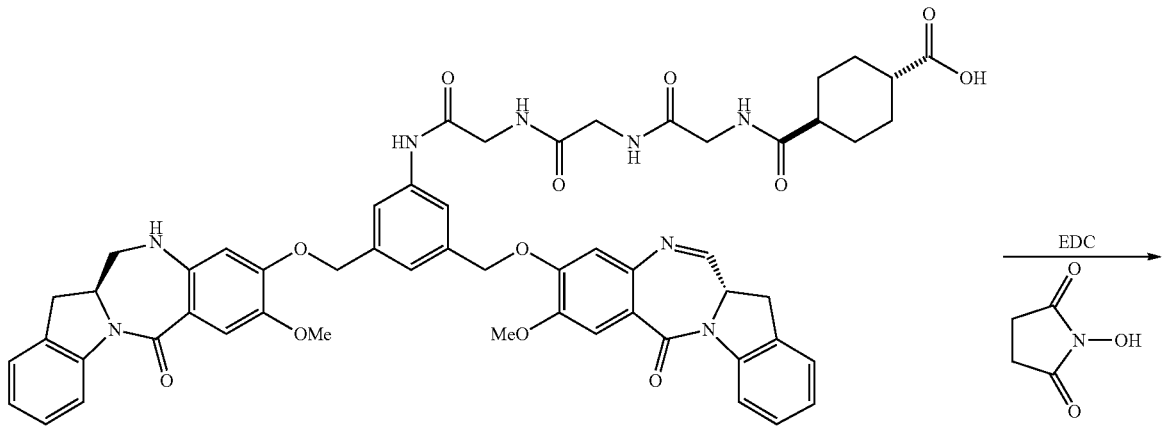

22

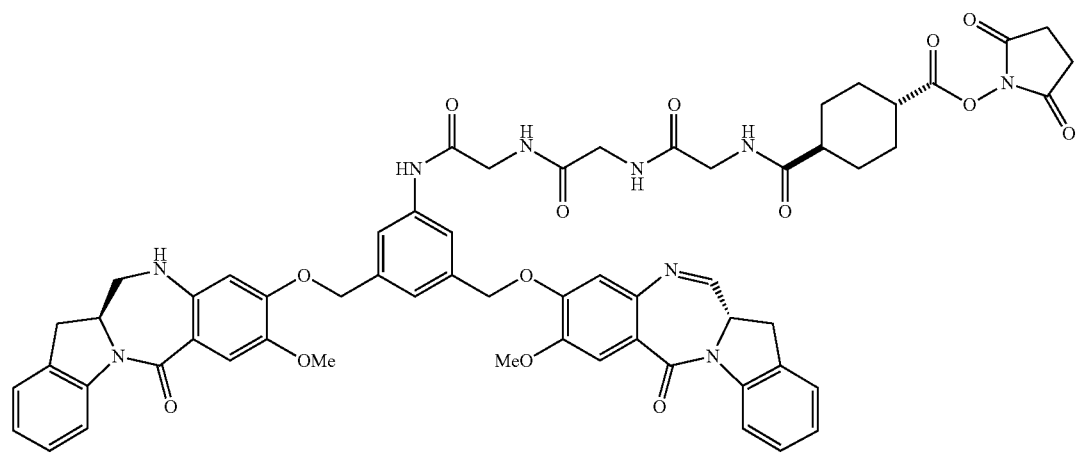

23

Step 8: Compound 23 was prepared similarly as compound 13 in Example 1. (1r,4r)-2,5-dioxopyrrolidin-1-yl 4-((2-((2-((2-((3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)amino)-2-oxoethyl)amino)-2-oxoethyl)amino)-2-oxoethyl)carbamoyl)cyclohexanecarboxylate, compound 23 was obtained as a white solid after C18 purification (8 mg, 19% yield). LCMS=6.007 min (15 min method). Mass observed (ESI+): 1130.8 (M+H).

Example 3

Synthesis of 2,5-dioxopyrrolidin-1-yl 6-(((S)-1-(((S)-1-((3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)amino)-1-oxopropan-2-yl)amino)-3-methyl-1-oxobutan-2-yl)amino)-6-oxohexanoate (Compound 35)

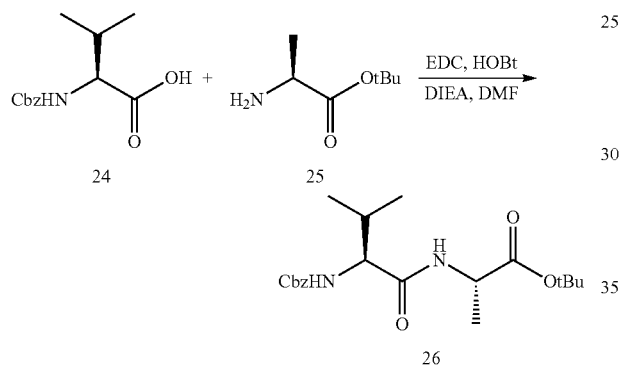

Step 1: Z-Val-OH compound 24 (3.0 g, 11.94 mmol) and L-Ala-OtBu compound 25 (1.907 g, 13.13 mmol) were dissolved in DMF (23.88 mL). EDC.HCl (2.52 g, 13.13 mmol) and HOBt (2.011 g, 13.13 mmol) were added to the reaction mixture, followed by DIEA (4.59 mL, 26.3 mmol). The reaction was stirred reaction at rt overnight under Ar. The reaction mixture was diluted with CH$_2$Cl$_2$ and was washed with sat'd NaHCO$_3$, sat'd NH$_4$Cl, water and brine. The organic layer was dried over Na$_2$SO$_4$, filtered and concentrated. The crude residue was purified by silica gel flash chromatography (EtOAc/hexanes, gradient, 0% to 50%) to obtain compound 26 as a white solid (3.68 g, 81% yield). $^1$H NMR (400 MHz, CDCl$_3$): δ 7.39-7.29 (m, 5H), 6.29 (bd, 1H, J=6.9 Hz), 5.34 (bd, 1H, J=8.4 Hz), 5.11 (s, 2H), 4.45 (p, 1H, J=7.2 Hz), 4.02-3.98 (m, 1H), 2.18-2.09 (m, 1H), 1.56 (s, 9H), 1.37 (d, 3H, J=7.0 Hz), 0.98 (d, 3H, J=6.8 Hz), 0.93 (d, 3H, J=6.8 Hz). LCMS=5.571 min (8 min method). Mass observed (ESI+): 323.25 (M-tBu+H).

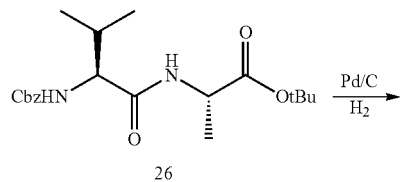

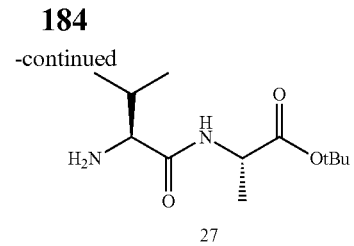

Step 2: Compound 26 (3.68 g, 9.72 mmol) was dissolved in MeOH (30.9 mL) and water (1.543 mL). The solution was purged with Ar and was degassed for 5 min. Pd/C (10%, wet, 0.517 g) was added slowly to the reaction mixture. H$_2$ was then bubbled in for a minute. Bubbling was discontinued and the reaction was then stirred under a H$_2$ balloon overnight. The reaction mixture was filtered through Celite and the filter cake was washed with MeOH (30 mL) and was concentrated to obtain compound 27 as a white solid (2.35 g, 99% yield). $^1$H NMR (400 MHz, CDCl$_3$): δ 7.79-7.77 (m, 1H), 4.50 (p, 1H, J=7.3 Hz), 3.27 (d, 1H, J=3.9 Hz), 2.34-2.26 (m, 1H), 1.49 (s, 9H), 1.40 (d, 3H, J=7.1 Hz), 1.01 (d, 3H, J=7.0 Hz), 0.86 (d, 3H, J=6.9 Hz).

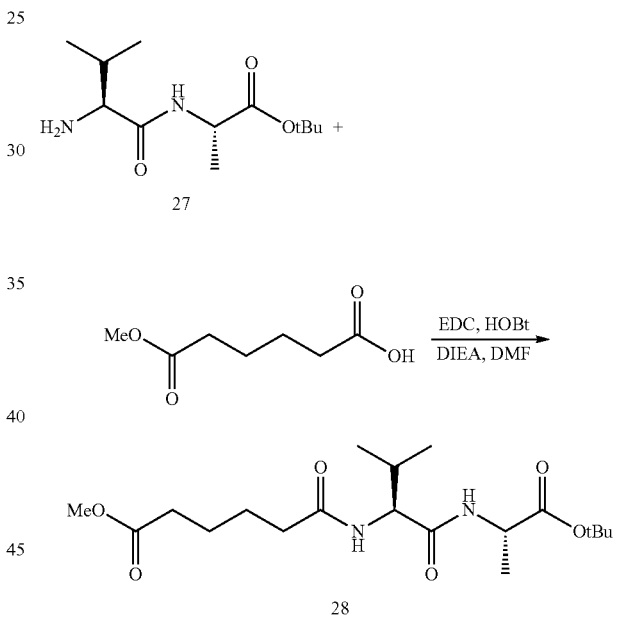

Step 3: Amine compound 27 (2.35 g, 9.62 mmol) and mono methyladipate (1.69 g, 10.58 mmol) were dissolved in DMF (32.1 mL). EDC.HCl (1.94 g, 10.10 mmol) and HOBt (1.47 g, 9.62 mmol) were added to the reaction mixture, followed by DIEA (3.36 mL, 19.24 mmol). The reaction was stirred at rt overnight. The reaction mixture was diluted with DCM/MeOH (20 mL, 5:1) and was washed with sat'd NH$_4$Cl, sat'd NaHCO$_3$, water and brine. The organic layer was dried over Na$_2$SO$_4$, filtered and concentrated. The crude product was purified by silica gel flash chromatography (EtOAc/hexanes, gradient, 0% to 50%) to obtain compound 28 as a white solid (2.77 g, 75% yield). $^1$H NMR (400 MHz, CDCl$_3$): δ 6.29 (d, 1H, J=7.2 Hz), 6.12 (d, 1H, J=8.6 Hz), 4.43 (p, 1H, J=7.2 Hz), 4.27 (dd, 1H, J=6.4, 8.6 Hz), 3.66 (s, 3H), 2.35-2.31 (m, 2H), 2.26-2.23 (m, 2H), 2.12-2.03 (m, 1H), 1.70-1.63 (m, 4H), 1.46 (s, 9H), 1.36 (d, 3H, J=7.1 Hz), 0.95 (apparent t, 6H, J=6.6 Hz).

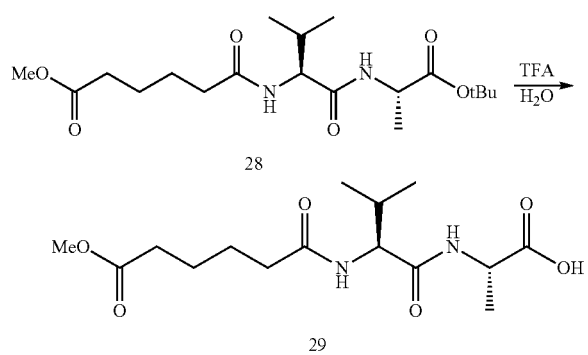

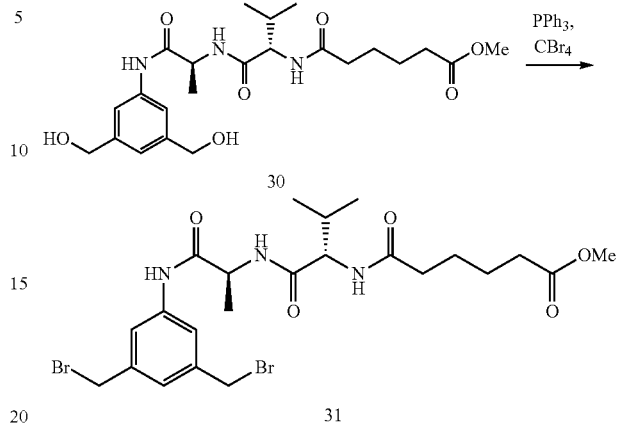

Step 4: TFA (8.28 mL, 108.0 mmol) and water (0.56 mL) were added to neat compound 28 (2.77 g, 7.17 mmol) at rt and was stirred for 2.5 h. CH$_3$CN (30 mL) was added to the reaction mixture and was concentrated. This was repeated 2 more times to obtain compound 29 as a pale yellow solid (2.0 g, 84% yield). $^1$H NMR (400 MHz, CDCl$_3$): δ 8.11 (bs, 1H), 7.29 (d, 1H, J=8.9 Hz), 7.14 (d, 1H, 6.8 Hz), 4.58 (p, 1H, J=7.1 Hz), 4.37 (t, 1H, J=8.7 Hz), 3.68 (s, 3H), 2.37-2.32 (m, 4H), 2.03-1.99 (m, 2H), 1.69-1.63 (m, 4H), 1.49 (d, 3H, J=7.2 Hz), 0.97 (d, 3H, J=4.8 Hz), 0.96 (d, 3H, J=4.8 Hz).

3H, J=4.8 Hz). LCMS=3.073 min (8 min method). Mass observed (ESI$^+$): 466.25 (M+H).

Step 6: Diol compound 30 (150 mg, 0.322 mmol) and CBr$_4$ (321 mg, 0.967 mmol) were dissolved in DMF (3222 µl). PPh$_3$ (254 mg, 0.967 mmol) was added to the reaction mixture, at which point the reaction turned red-pink with a slight exotherm. The reaction was stirred under Ar for 4 h.

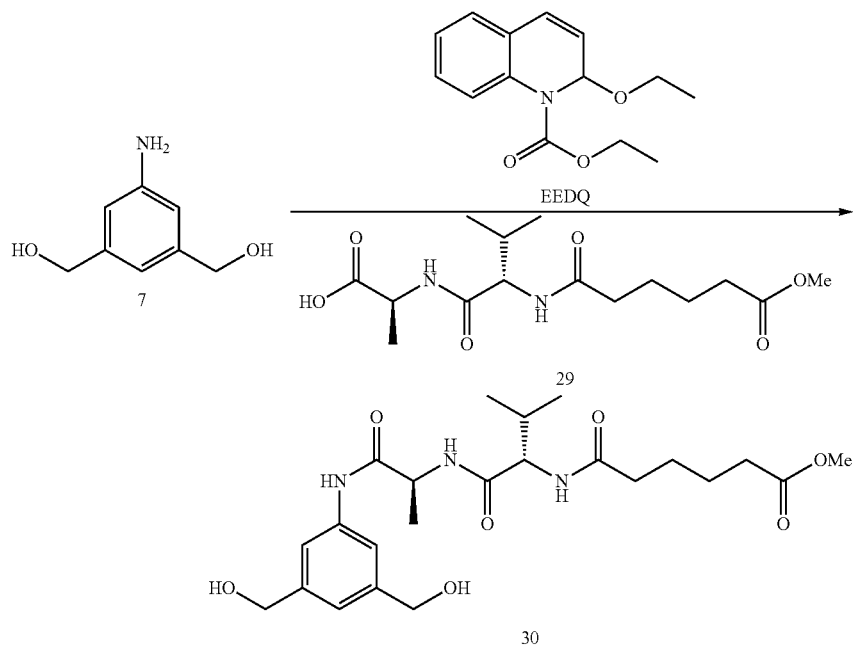

Step 5: Aniline compound 7 (150 mg, 0.98 mmol) and acid compound 29 (340 mg, 1.03 mmol) were suspended in CH$_2$Cl$_2$/MeOH (3.26 mL, 1.62 mL) at rt. EEDQ (484 mg, 1.96 mmol) was added and the reaction was stirred at rt overnight. The solvent was concentrated and the residue was slurried in EtOAc/Et$_2$O (15 mL, 15 mL) and filtered. The solids were washed with Et$_2$O (2×15 mL) and was dried under vacuum/N$_2$ to obtain compound 30 as a white solid (150 mg, 33% yield). $^1$H NMR (400 MHz, CDCl$_3$): δ 7.61 (s, 2H), 7.47 (d, 1H, J=7.1 Hz), 7.14 (s, 1H), 6.64 (d, 1H, J=8.0 Hz), 4.82-4.75 (m, 1H), 4.45-4.40 (m, 4H), 3.64 (s, 3H), 2.36-2.27 (m, 4H), 2.16-2.07 (m, 1H), 1.68-1.59 (m, 4H), 1.47 (d, 3H, J=7.0 Hz), 0.98 (d, 3H, J=3.6 Hz), 0.95 (d, The reaction mixture was diluted with CH$_2$Cl$_2$ and was washed with water and brine. The organic layer was dried over Na$_2$SO$_4$ and concentrated. The crude residue was purified by silica gel flash chromatography (EtOAc/hexanes, gradient, 0% to 100%) to obtain compound 31 as an off white solid (473 mg, 75% yield). $^1$H NMR (400 MHz, DMSO-d6): δ 8.19 (d, 1H, J=6.6 Hz), 7.85 (d, 1H, J=8.5 Hz), 7.64 (s, 2H), 7.21 (s, 1H), 4.68 (s, 3H), 4.37 (p, 1H, J=7.0 Hz), 4.18 (dd, 1H, J=7.2, 8.4 Hz), 3.58 (s, 3H), 2.32-2.29 (m, 2H), 2.33-2.12 (m, 2H), 2.01-1.91 (m, 1H), 1.53-1.49 (m, 4H), 1.31 (d, 3H, J=7.1 Hz), 0.89 (d, 3H, J=6.8 Hz), 0.85 (d, 3H, J=6.8 Hz). LCMS=5.259 min (8 min method). Mass observed (ESI$^+$): 592.05 (M+H).

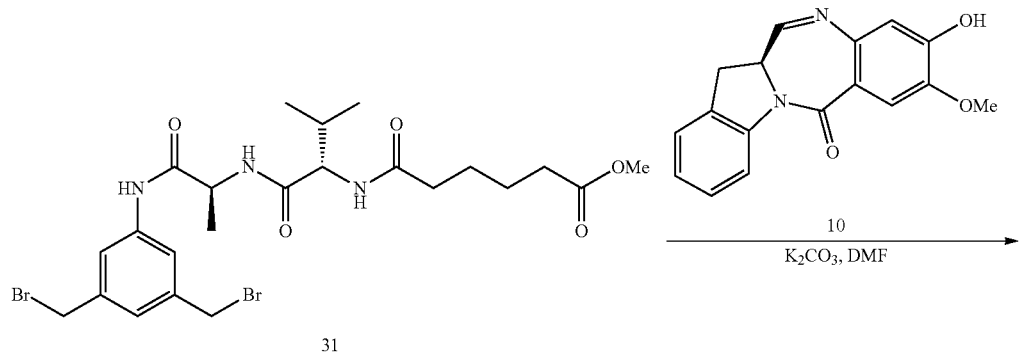
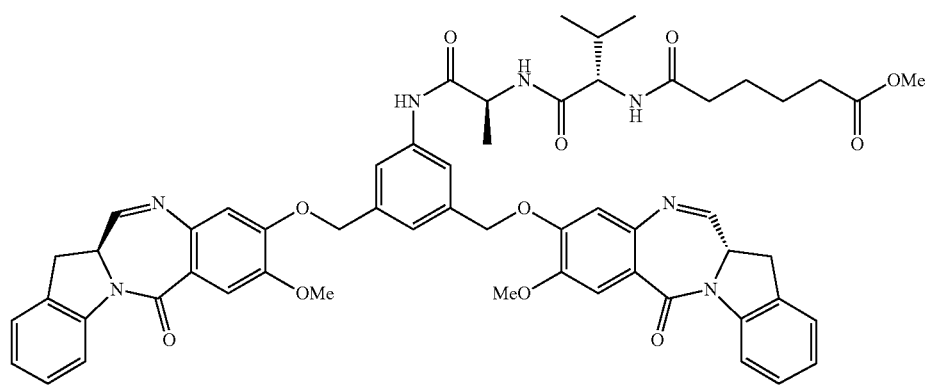
Step 7: Compound 32 was prepared similarly as compound 11 in Example 1. Compound 32 was obtained as a yellow solid after purification (162 mg, 57% yield, 70% purity). LCMS=6.461 min (15 min method). Mass observed (ESI+): 1018.7 (M+H).
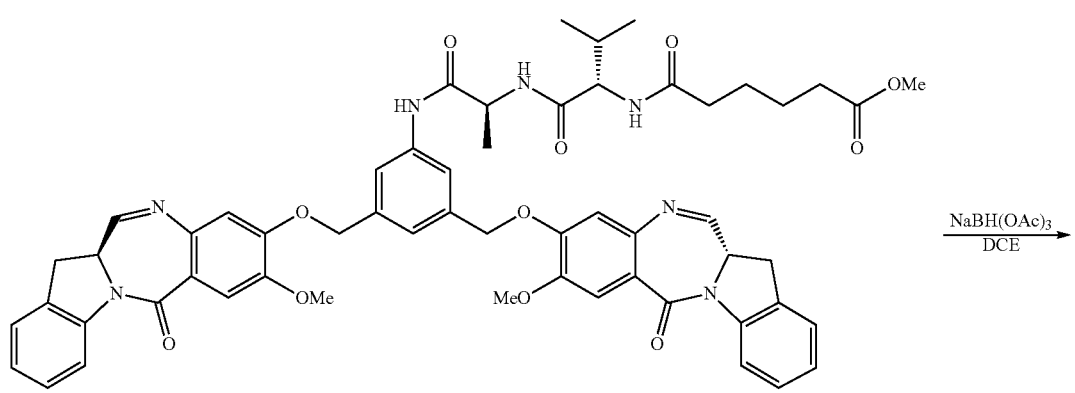

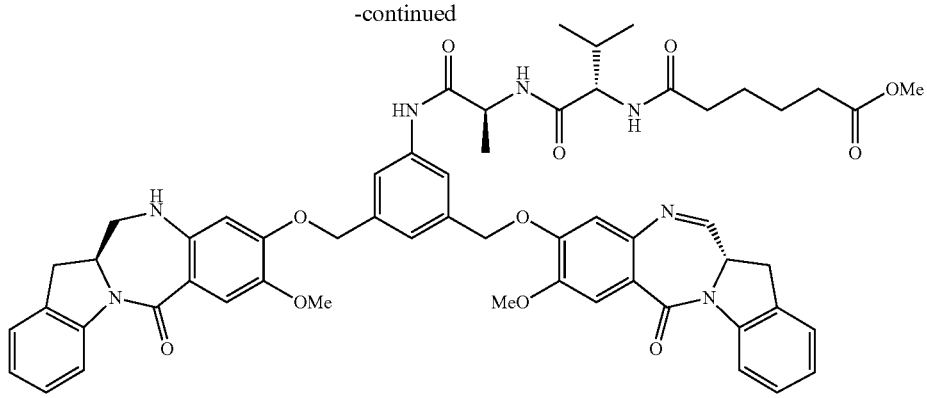
33
Step 8: Compound 33 was prepared similarly as compound 12 in Example 1. Compound 33 was obtained as a white solid after C18 purification (40 mg, 31% yield). LCMS=5.528 min (8 min method) Mass observed (ESI$^+$): 1020.30 (M+H).
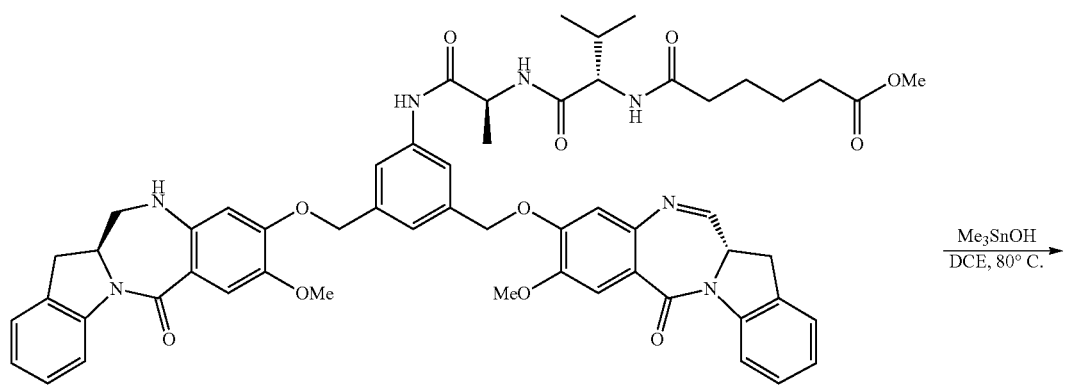
33
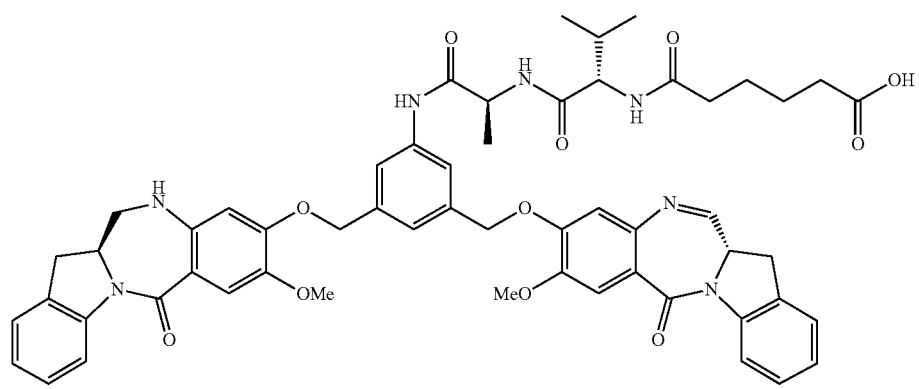
34

Step 9: Compound 34 was prepared similarly as compound 22 in Example 2. Compound 34 was obtained as a yellow solid after silica plug (38 mg, 100% yield). LCMS=5.211 min (8 min method). Mass observed (ESI$^+$): 1006.35 (M+H).

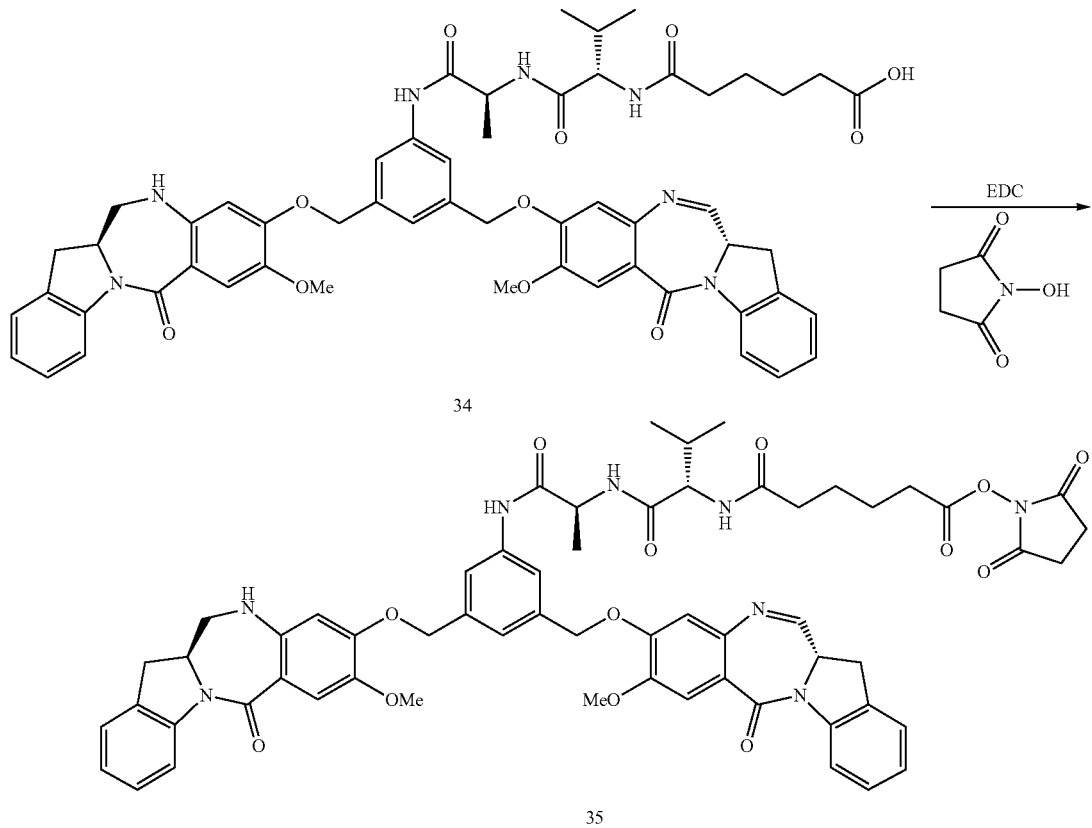

Step 10: Compound 35 was prepared similarly as compound 14 in Example 1. 2,5-dioxopyrrolidin-1-yl 6-(((S)-1-(((S)-1-((3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)amino)-1-oxopropan-2-yl)amino)-3-methyl-1-oxobutan-2-yl)amino)-6-oxohexanoate, compound 35 was obtained as a white solid after C18 purification (8 mg, 20% yield). LCMS=7.031 min (15 min method). Mass observed (ESI$^+$): 1103.7 (M+H).

Example 4

Synthesis of 2,5-dioxopyrrolidin-1-yl 2-(3-(((((S)-8-methoxy-6-oxo-11,12,12a,13-tetrahydro-6H-benzo[5,6][1,4]diazepino[1,2-a]indol-9-yl)oxy)methyl)-5-(((((S)-8-methoxy-6-oxo-12a,13-dihydro-6H-benzo[5,6][1,4]diazepino[1,2-a]indol-9-yl)oxy)methyl)phenyl)-3,6,9,12-tetraoxo-2,5,8,11-tetraazaheptadecan-17-oate (Compound 49)

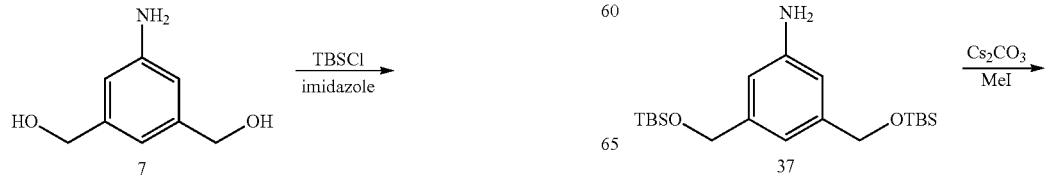

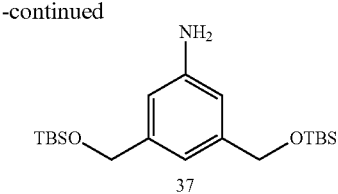

Step 1: (5-amino-1,3-phenylene)dimethanol compound 7 (5.0 g, 32.6 mmol) was dissolved in THF (65.3 mL). TBSCl (12.30 g, 82 mmol) and imidazole (6.67 g, 98 mmol) were added and was stirred at rt overnight under Ar. The reaction mixture was diluted with EtOAc and was washed with sat'd NH$_4$Cl and brine, dried over Na$_2$SO$_4$ and concentrated. The crude residue was purified by silica gel flash chromatography (EtOAc/hexanes, gradient, 0% to 30%) to obtain compound 37 as a yellow oil (13 g, 100% yield). $^1$H NMR (400 MHz, CDCl$_3$): δ 6.71 (s, 1H), 6.60 (s, 2H), 4.65 (s, 4H), 0.94 (s, 18 H), 0.10 (s, 12 H).

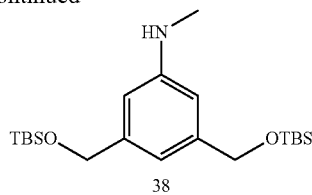

Step 2: Cs₂CO₃ (8.54 g, 26.2 mmol) was added to a stirred solution of aniline compound 37 (10 g, 26.2 mmol) in DMF (52.4 mL). Methyliodide (1.474 mL, 23.58 mmol) was added and the reaction was stirred at rt for 3 h. Water (10 mL) and EtOAc (30 mL) were added to the reaction mixture. The layers were separated and was extracted with EtOAc (2×). The organic layers were washed with water (4×), dried over Na₂SO₄, filtered and concentrated. The crude residue was purified by silica gel flash chromatography (EtOAc/hexanes, gradient, 0% to 10%) to obtain the desired monomethylated product compound 38 (3.8 g, 37% yield). ¹H NMR (400 MHz, CDCl₃): δ 6.63 (s, 1H), 6.52 (s, 2H), 4.67 (s, 4H), 2.84 (s, 3H), 0.94 (s, 18H), 0.10 (s, 12H).

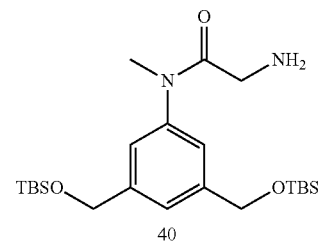

Step 4: Compound 39 (1.26 g, 2.147 mmol) was dissolved in MeOH (6.82 mL) and THF (6.8 mL) and the solution was purged with N₂. Pd/C (10%, 0.228 g, 0.215 mmol) was added and H₂ was bubbled in for a few minutes. The reaction was stirred under H₂ balloon overnight. The reaction mixture was filtered through Celite and was washed with MeOH and concentrated to give pure compound 40 (1 g, 100% yield). ¹H NMR (400 MHz, DMSO-d6): δ 7.41-7.30 (m, 2H), 7.27-7.21 (m, 1H), 7.06 (s, 2H), 4.65 (s, 4H), 3.23 (s, 3H), 3.12 (s, 2H), 0.82 (s, 18H), 0.00 (s, 12H).

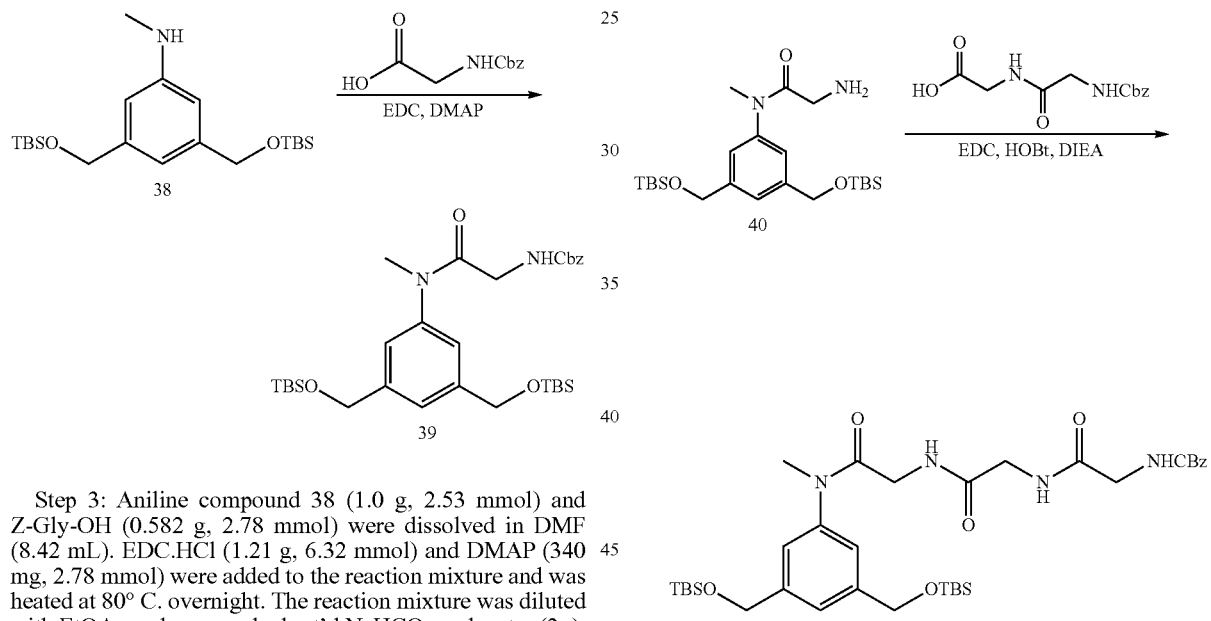

Step 3: Aniline compound 38 (1.0 g, 2.53 mmol) and Z-Gly-OH (0.582 g, 2.78 mmol) were dissolved in DMF (8.42 mL). EDC.HCl (1.21 g, 6.32 mmol) and DMAP (340 mg, 2.78 mmol) were added to the reaction mixture and was heated at 80° C. overnight. The reaction mixture was diluted with EtOAc and was washed sat'd NaHCO₃ and water (2×), dried over Na₂SO₄, filtered and concentrated. The crude residue was purified by silica gel chromotography (EtOAc/hexanes, gradient, 0% to 30% to 100%) to obtain compound 39 as a yellow sticky solid (780 mg, 53% yield). ¹H NMR (400 MHz, CDCl₃): δ 7.27 (m, 6H), 6.90 (s, 2H), 4.94 (s, 2H), 4.62 (s, 4H), 3.58 (s, 2H), 3.16 (s. 3H), 0.83 (s, 18H), 0.00 (s, 12 H).

Step 5: Amine compound 40 (1.0 g, 1.988 mmol) and Z-Gly-Gly-Gly-OH (662 mg, 2.385 mmol) were dissolved in DMF (6.63 mL). EDC.HCl (457 mg, 2.385 mmol) and HOBT (304 mg, 1.988 mmol) were added to the reaction mixture, followed by DIEA (694 µL, 3.98 mmol). The reaction was stirred at rt overnight. The reaction mixture was diluted with EtOAc and was washed with sat'd NaHCO₃, brine and water (2×). The organic layer was dried over Na₂SO₄, filtered and concentrated. The crude residue was purified by silica gel flash chromatography (MeOH/DCM, gradient, 0% to 10%) to obtain compound 41 as a white sticky foam (994 mg, 71% yield). ¹H NMR (400 MHz, CDCl₃): δ 7.38-7.32 (m, 7H), 7.31-7.27 (m, 2H), 7.01 (s, 2H), 5.13 (s, 2H), 4.74 (s, 4H), 3.97 (d, 2H, J=4.6 Hz), 3.92 (d, 2H, J=5.3 Hz), 3.74 (d, 2H, J=3.7 Hz), 3.27 (s, 3H), 0.94 (s, 18H), 0.11 (s, 12H).

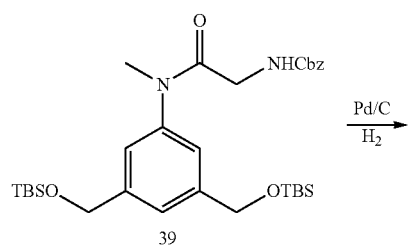

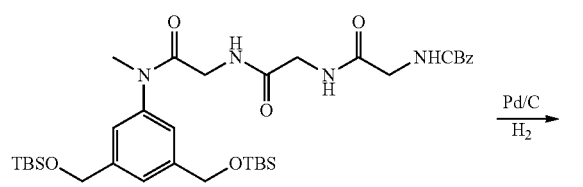

Step 6: Compound 41 (994 mg, 1.418 mmol) was suspended in MeOH (6.65 mL) and water (443 µL) and was purged with N₂. Pd/C (10% wet, 302 mg, 0.284 mmol) was added and H₂ was bubbled in for a few minutes. The reaction was stirred under H₂ balloon overnight. The solution was filtered through Celite and was washed with MeOH and concentrated to obtain pure compound 42 (725 mg, 90% yield). $^1$H NMR (400 MHz, DMSO-d6): δ 8.10-7.97 (m, 1H), 7.91-7.85 (m, 1H), 7.31-7.23 (m, 1H), 7.05 (s, 2H), 7.65 (s, 4H), 3.68-3.62 (m, 2H), 3.56-3.45 (m, 1H), 3.09 (s, 3H), 3.08-3.06 (m, 2H), 3.06-3.03 (m, 2H), 0.82 (s, 18H), 0.00 (s, 12H). LCMS=5.574 min (8 min method). Mass observed (ESI⁺): 567.30 (M+H).

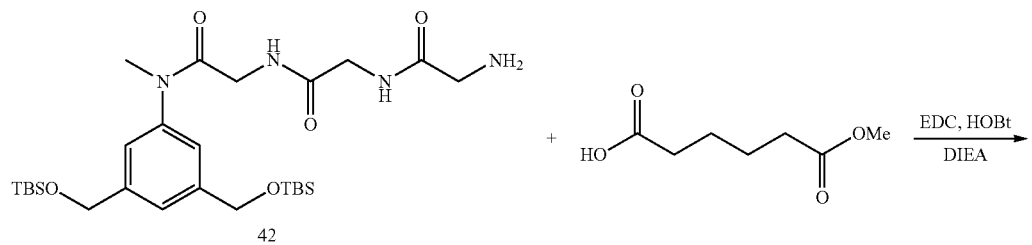

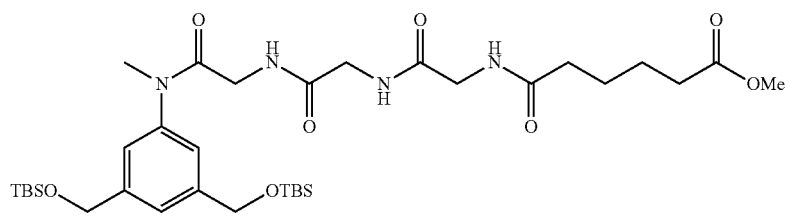

Step 7: Amine compound 42 (725 mg, 1.279 mmol) and mono methyladipate (246 mg, 1.535 mmol) were dissolved in DMF (6.5 mL). EDC.HCl (294 mg, 1.535 mmol) and HOBt (196 mg, 1.279 mmol) were added to the reaction mixture, followed by DIEA (447 μL, 2.56 mmol). The reaction was stirred at rt overnight. The reaction mixture was diluted with DCM (20 mL) and was washed with sat'd NH₄Cl, sat'd NaHCO₃, water and brine. The organic layer was dried over Na₂SO₄, filtered and concentrated. The crude product was purified by silica gel flash chromatography (MeOH/DCM, gradient, 0% to 10%) to obtain compound 43 (425 mg, 33% yield). ¹H NMR (400 MHz, CDCl₃): δ 7.30 (s, 1H), 7.01 (s, 2H), 6.89-6.85 (m, 1H), 6.75-6.72 (m, 1H), 6.41-6.40 (m, 1H), 4.73 (s, 4H), 3.98-3.96 (m, 4H), 3.74 (bd, 2H, J=3.5 Hz), 3.66 (s, 3H), 3.27 (s, 3H), 2.33 (t, 2H, J=6.8 Hz), 2.28 (t, 2H, J=6.5 Hz), 0.94 (s, 18H), 0.11 (s, 12H). LCMS=7.709 min (8 min method). Mass observed (ESI⁺): 709.35 (M+H).

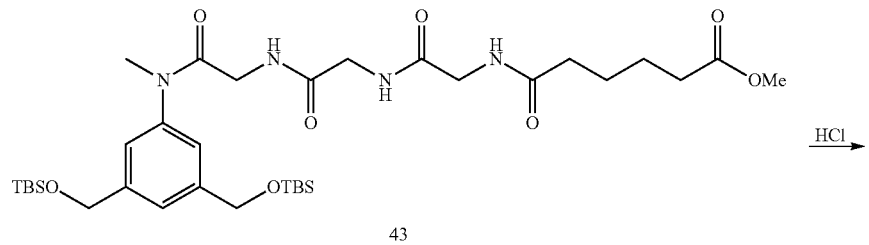

43

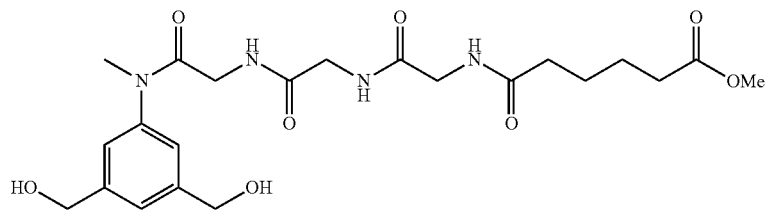

44

Step 8: Compound 43 (422 mg, 0.417 mmol) was dissolved in THF (1.89 mL) and water (189 μL). HCl (aqueous, 5 M) (833 μL, 4.17 mmol) was added and the reaction was stirred at rt for 2.5 h. The reaction mixture was concentrated. ACN (~15 mL) was added to the residue and was concentrated. This was repeated two more times to obtain compound 44 as a white foam (200 mg, 100% yield). LCMS=0.389 min (8 min method). $^1$H NMR (400 MHz, DMSO-d6): δ 8.09-8.04 (m, 2H), 7.93-7.90 (m, 1H), 7.30 (bs, 1H), 7.14 (s, 2H), 4.52 (s, 4H), 3.71-3.68 (m, 4H), 3.58 (s, 3H), 3.17 (bs, 3H), 2.22-2.18 (m, 2H), 2.15-2.12 (m, 2H), 1.53-1.47 (m, 4H).

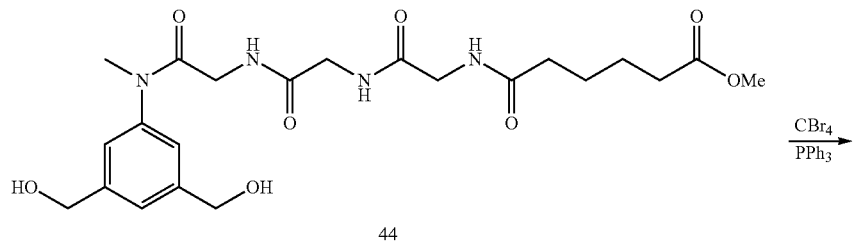

44

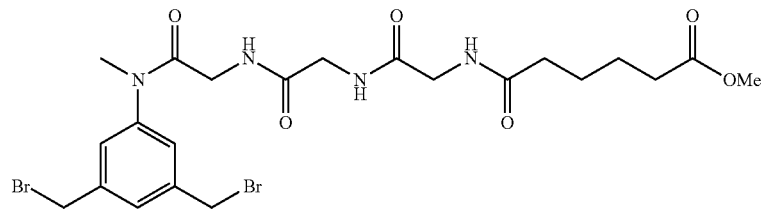

45

Step 9: Diol compound 44 (110 mg, 0.229 mmol) and CBr$_4$ (228 mg, 0.687 mmol) were dissolved in DMF (2.29 mL). PPh$_3$ (180 mg, 0.687 mmol) was added to the reaction mixture, at which point the reaction turned red-pink with a slight exotherm. The reaction was stirred under Ar for 6 h. The reaction mixture was diluted with CH$_2$Cl$_2$/MeOH (10:1) and was washed with water and brine. The organic layer was dried over Na$_2$SO$_4$ and concentrated. The crude residue was purified by silica gel flash chromatography (MeOH/CH$_2$Cl$_2$, gradient, 0% to 10%) to obtain compound 45 (30 mg, 22% yield). $^1$H NMR (400 MHz, CDCl$_3$): δ 7.46 (bs, 1H), 7.32-7.26 (m, 2H), 7.26-7.19 (m, 2H), 6.89-6.85 (m, 1H), 4.60 (d, 2H, J=3.6 Hz), 4.48 (d, 2H, J=3.9 Hz), 3.98 (d, 4H, J=5.1 Hz), 3.76 (bs, 1H), 3.67 (s, 3H), 3.30 (bs, 3H), 2.34 (bt, 2H, J=6.7 Hz), 2.30 (bt, 2H, J=6.6 Hz), 1.70-1.64 (m, 4H). LCMS=4.326 min (8 min method). Mass observed (ESI$^+$): 605.10 (M+H).

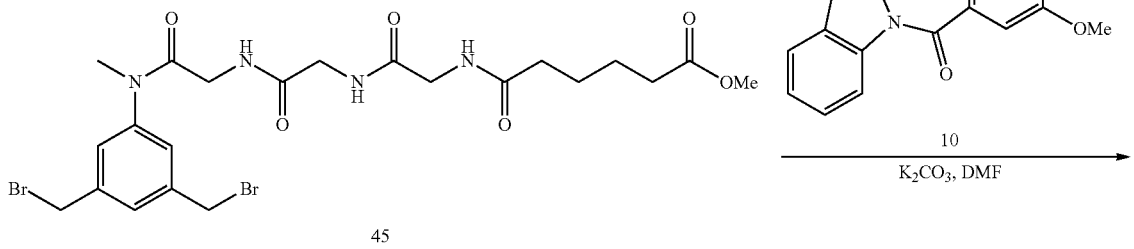

45

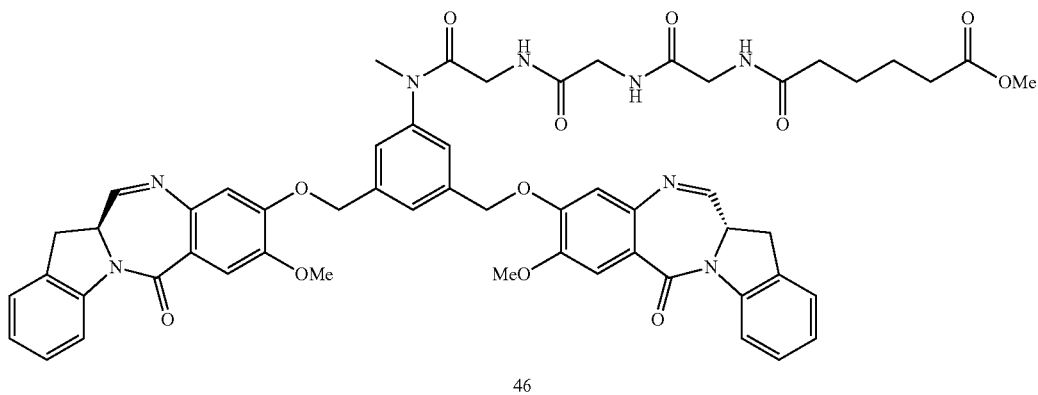

46

Step 10: Compound 46 was prepared similarly as compound 11 in Example 1. Compound 46 was obtained as a yellow solid after purification (40 mg, 59% yield). LCMS=4.751 min (8 min method). Mass observed (ESI$^+$): 1033.35 (M+H).

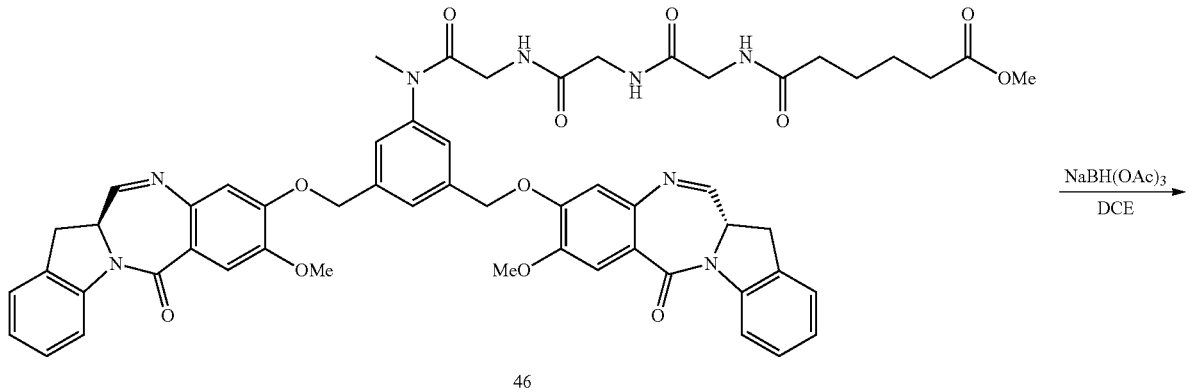

46

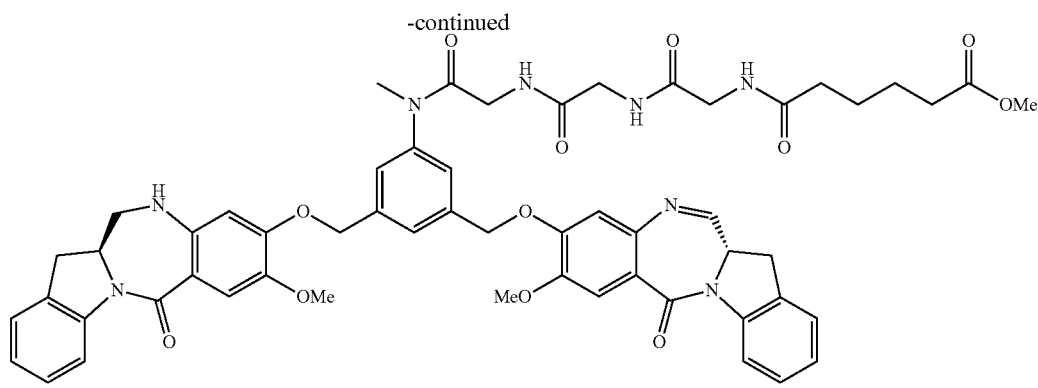
47
Step 11: Compound 47 was prepared similarly as compound 12 in Example 1. Compound 47 was obtained as a white solid after C18 purification (14 mg, 32% yield). LCMS=5.857 min (15 min method). Mass observed (ESI$^+$): 1035.7 (M+H).
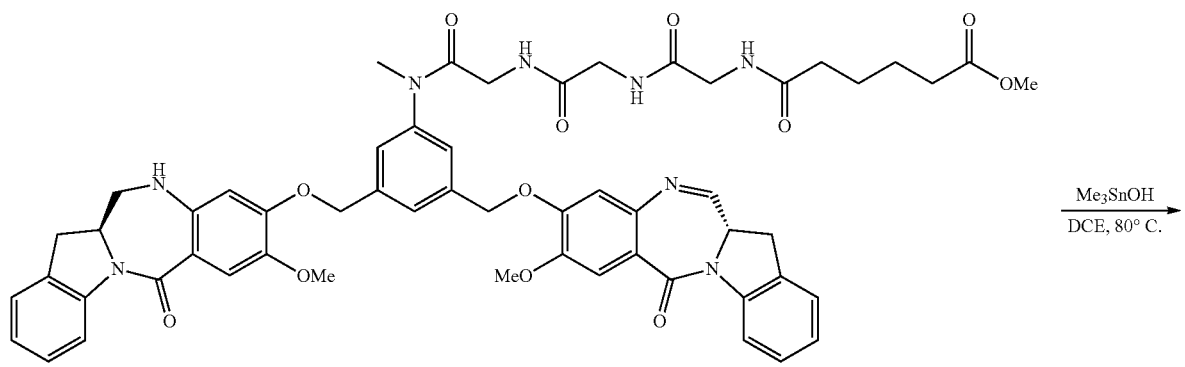
47
Me$_3$SnOH
DCE, 80° C.
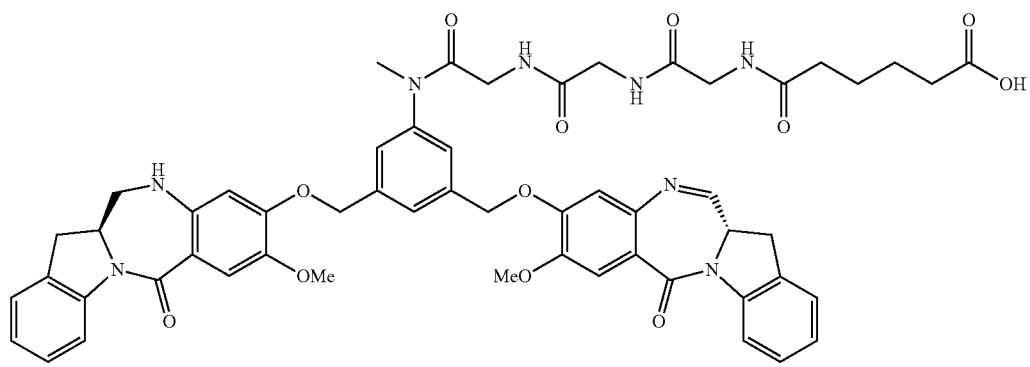
48

Step 12: Compound 48 was prepared similarly as 22 in Example 2. Compound 48 was obtained as a yellow solid after silica plug (7 mg, 100% yield). LCMS=4.817 min (8 min method). Mass observed (ESI+): 1021.35 (M+H).
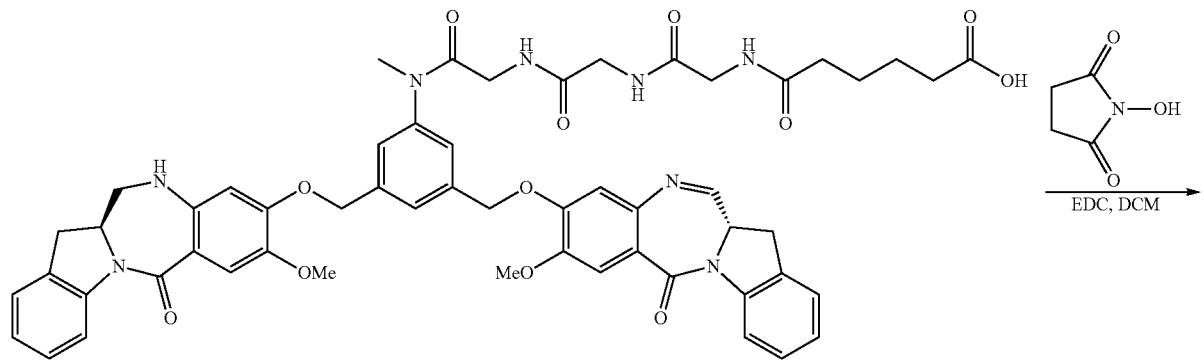
48
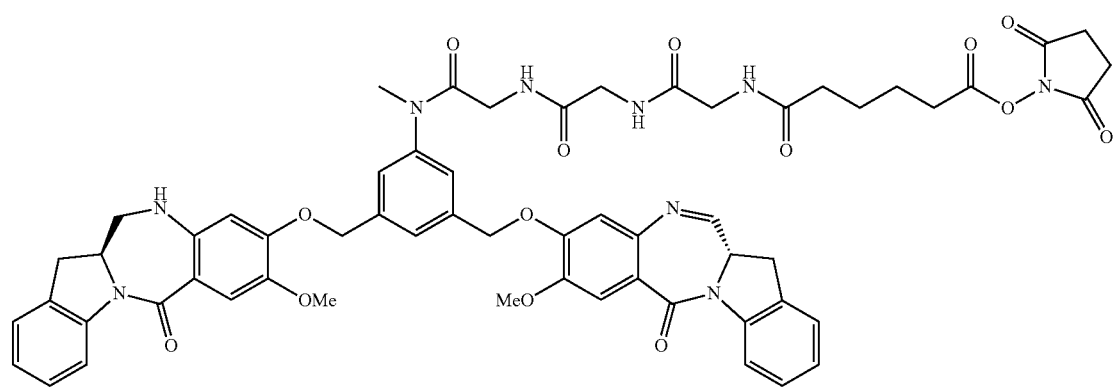
49

Step 13: Compound 49 was prepared similarly as compound 14 in Example 1. 2,5-dioxopyrrolidin-1-yl 2-(3-(((((S)-8-methoxy-6-oxo-11,12,12a,13-tetrahydro-6H-benzo[5,6][1,4]diazepino[1,2-a]indol-9-yl)oxy)methyl)-5-(((((S)-8-methoxy-6-oxo-12a,13-dihydro-6H-benzo[5,6][1,4]diazepino[1,2-a]indol-9-yl)oxy)methyl)phenyl)-3,6,9,12-tetraoxo-2,5,8,11-tetraazaheptadecan-17-oate, compound 49 was obtained as a white solid after C18 purification (6.5 mg, 74% yield). LCMS=5.805 min (15 min method). Mass observed (ESI+): 1118.7 (M+H).

Example 5

Synthesis of 2,5-dioxopyrrolidin-1-yl 6-(((S)-1-(((R)-1-((3-(((((S)-8-methoxy-6-oxo-11,12,12a,13-tetrahydro-6H-benzo[5,6][1,4]diazepino[1,2-a]indol-9-yl)oxy)methyl)-5-(((((R)-8-methoxy-6-oxo-12a,13-dihydro-6H-benzo[5,6][1,4]diazepino[1,2-a]indol-9-yl)oxy)methyl)phenyl)amino)-1-oxopropan-2-yl)amino)-1-oxopropan-2-yl)amino)-6-oxohexanoate (Compound 80)

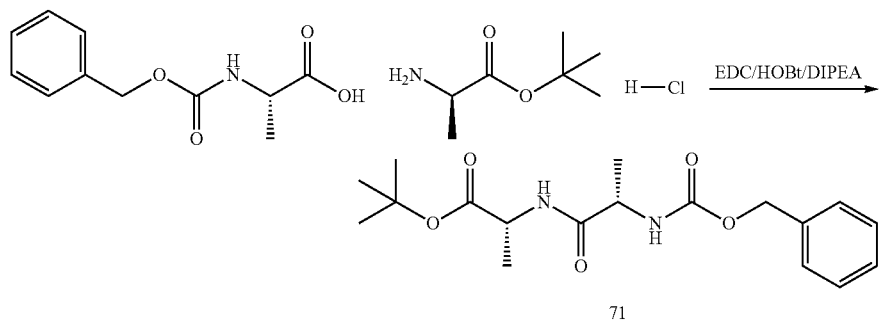

Step 1: (S)-2-(((benzyloxy)carbonyl)amino)propanoic acid (5 g, 22.40 mmol) and (R)-tert-butyl 2-aminopropanoate hydrochloride (4.48 g, 24.64 mmol) were dissolved in anhydrous DMF (44.8 ml). EDC.HCl (4.72 g, 24.64 mmol), HOBt (3.43 g, 22.40 mmol), and then DIPEA (9.75 ml, 56.0 mmol) were added. The reaction was stirred under argon at room temperature, overnight. The reaction mixture was diluted with dichloromethane and then washed with saturated ammonium chloride, saturated sodium bicarbonate, water, and brine. The organic layer was dried over sodium sulfate and concentrated. The crude oil was purified via silica gel chromatography (Hexanes/Ethyl Acetate) to yield compound 71 (5.6 g, 71% yield). $^1$H NMR (400 MHz, CDCl$_3$): δ 7.39-7.34 (m, 5H), 6.54 (s, 1H) 5.28 (s, 1H), 5.15 (s, 2H), 4.47-4.43 (m, 1H), 4.48 (s, 1H), 1.49 (s, 9H), 1.42-1.37 (m, 6H).

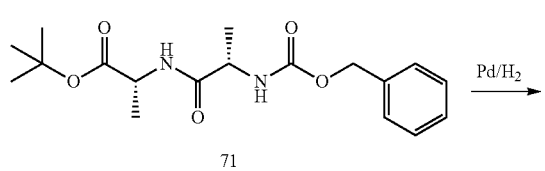

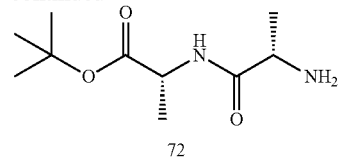

Step 2: Compound 71 (5.6 g, 15.98 mmol) was dissolved in methanol (50.7 mL) and water (2.54 mL). The solution was purged with argon for five minutes. Palladium on carbon (wet, 10%) (0.850 g, 0.799 mmol) was added slowly. The reaction was stirred overnight under an atmosphere of hydrogen. The solution was filtered through Celite, rinsed with methanol and concentrated. The residue was azeotroped with methanol and acetonitrile and the resulting oil was placed directly on the high vacuum to give compound 72 (3.57 g, 100% yield) which was used directly in the next step. $^1$H NMR (400 MHz, CDCl$_3$): δ 7.67 (s, 1H), 4.49-4.42 (m, 1H), 3.54-3.49 (m, 1H), 1.48 (s, 9H), 1.40 (d, 3H, J=7.2 Hz), 1.36 (d, 3H, J=6.8 Hz).

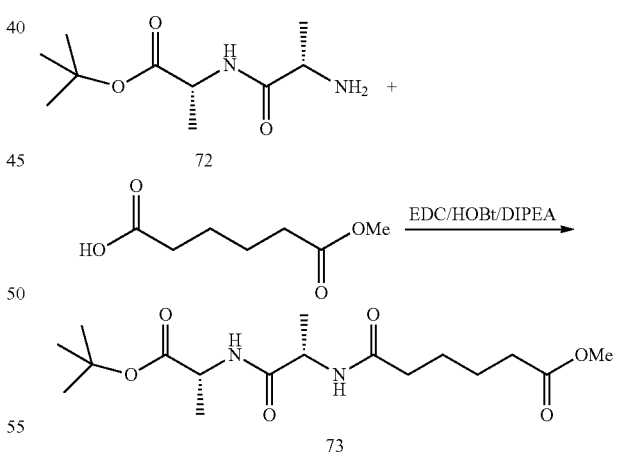

Step 3: Compound 72 (3.57 g, 16.51 mmol) and mono methyladipate (2.69 mL, 18.16 mmol) were dissolved in anhydrous DMF (55.0 mL). EDC.HCl (3.48 g, 18.16 mmol) and HOBt ((2.53 g, 16.51 mmol) were added, followed by DIPEA (5.77 mL, 33.0 mmol). The mixture was stirred overnight at room temperature. The reaction was diluted with dichloromethane/methanol (80 mL, 5:1) and washed with saturated ammonium chloride, saturated sodium bicarbonate, and brine. It was dried over sodium sulfate, filtered and stripped. The compound was azeotroped with acetonitrile (5×), then pumped on the high vacuum at 35° C. to give compound 73 (5.91 g, 100% yield). The crude material was taken onto next step without purification. ¹H NMR (400 MHz, CDCl₃): δ 6.67 (d, 1H, J=6.8 Hz), 6.22 (d, 1H, J=7.2 Hz), 4.56-4.49 (m, 1H), 4.46-4.38 (m, 1H), 3.68 (s, 3H), 2.37-2.33 (m, 2H), 2.27-2.24 (m, 2H), 1.70-1.68 (m, 4H), 1.47 (s, 9H), 1.40 (s, 3H), 1.38 (s, 3H).

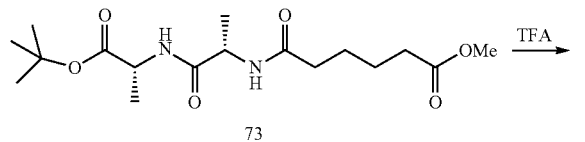

73

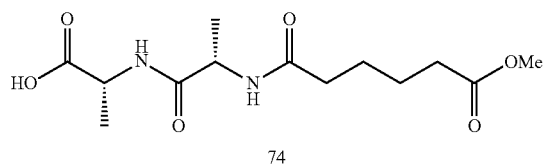

74

Step 4: Compound 73 (5.91 g, 16.5 mmol) was stirred in TFA (25.4 mL, 330 mmol) and deionized water (1.3 mL) at room temperature for three hours. The reaction mixture was concentrated with acetonitrile and placed on high vacuum to dryness to give crude compound 74 (4.99 g, 100% yield). ¹H NMR (400 MHz, CDCl₃): δ 7.44 (d, 1H, J=7.2 Hz), 6.97 (d, 1H, J=8.0 Hz), 4.81-4.73 (m, 1H), 4.59-4.51 (m, 1H), 3.69 (s, 3H), 2.39-2.32 (m, 2H), 2.31-2.23 (m, 2H), 1.70-1.61 (m, 4H), 1.48(d, 3H, J=7.2 Hz), 1.40 (d, 3H, J=7.2 Hz).

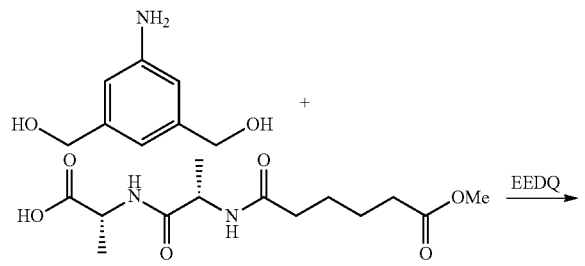

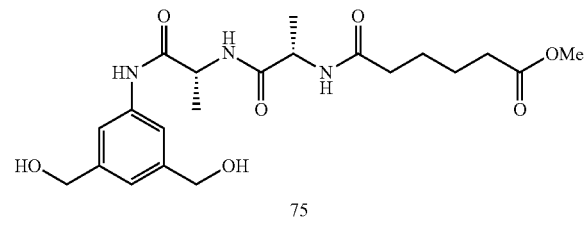

75

Step 5: Compound 74 (4.8 g, 15.88 mmol) was dissolved in anhydrous dichloromethane (101 mL) and anhydrous methanol (50.4 mL). (5-amino-1,3-phenylene)dimethanol (2.316 g, 15.12 mmol) and EEDQ (7.48 g, 30.2 mmol) were added and the reaction was stirred at room temperature, overnight. The solvent was stripped and the crude material purified by silica gel chromatography (dichloromethane/methanol) to give compound 75 (1.65 g, 25% yield). ¹H NMR (400 MHz, DMSO-d6): δ 9.68 (s, 1H), 8.29 (d, 1H, J=7.2 Hz), 8.11 (d, 1H, J=6.4 Hz), 7.52 (s, 2H), 6.97 (s, 1H), 5.15 (s, 2H), 4.45 (s, 4H), 4.39-4.32 (m, 1H), 4.28-4.21 (m, 1H), 3.57 (s, 3H), 2.30-2.27 (m, 2H), 2.17-2.13 (m, 2H), 1.54-1.45 (m, 4H) 1.30 (d, 3H, J=7.2 Hz), 1.20 (d, 3H, J=7.2 Hz). MS (m/z): 460.2 (M+Na)⁺.

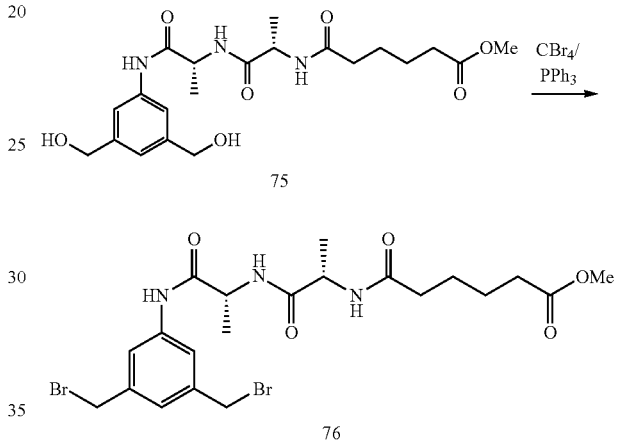

Step 6: Compound 75 (0.486 g, 1.111 mmol) and carbon tetrabromide (1.105 g, 3.33 mmol) were dissolved in anhydrous DMF (11.11 mL). Triphenylphosphine (0.874 g, 3.33 mmol) was added and the reaction stirred under argon for four hours. The reaction mixture was diluted with DCM/MeOH (10:1) and washed with water and brine. It was dried over sodium sulfate, filtered, and concentrated. The crude material was purified by silica gel chromatography (DCM/MeOH) to give compound 76 (250 mg, 40% yield). ¹H NMR (400 MHz, DMSO-d6): δ 9.82 (s, 1H), 8.38 (d, 1H, J=7.2 Hz), 8.17 (d, 1H, J=6.0 Hz), 7.76 (s, 2H), 7.22 (s, 1H), 4.66 (s, 4H), 4.38-4.31 (m, 1H), 4.25-4.19 (m, 1H), 3.56 (s, 3H), 2.30-2.27 (m, 2H), 2.18-2.15 (m, 2H), 1.53-1.51 (m, 4H), 1.32 (d, 3H, J=7.2 Hz), 1.21 (d, 3H, J=6.8 Hz).

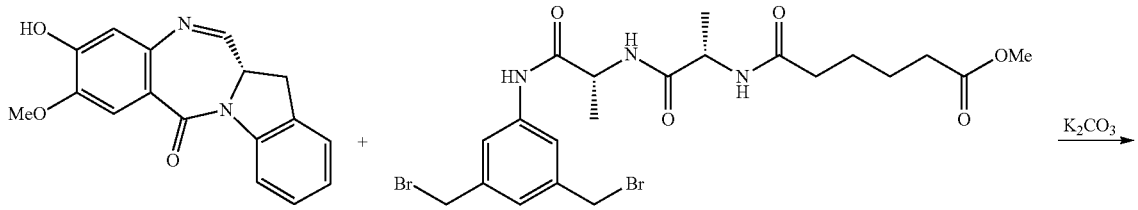

-continued
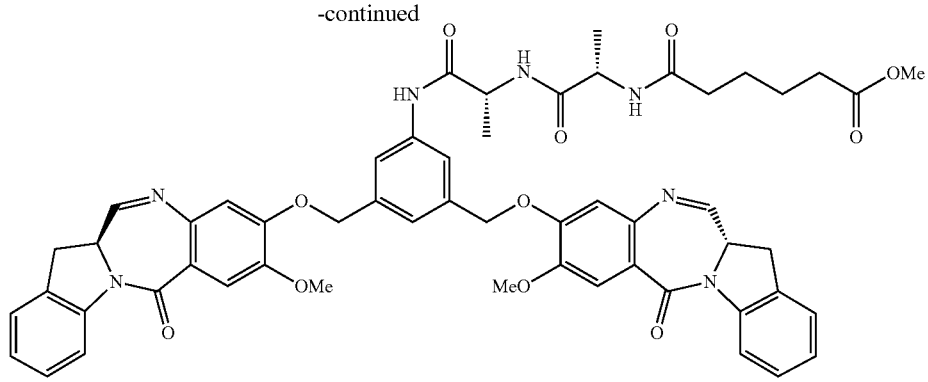
77
Step 7: Compound 77 was prepared similarly as 11 in Example 1. The crude material was purified by silica gel chromatography (dichloromethane/methanol) to give compound 77 (340 mg, 60% yield, 77% purity). LCMS=5.87 min (15 min method). MS (m/z): 990.6 (M+1)$^+$.
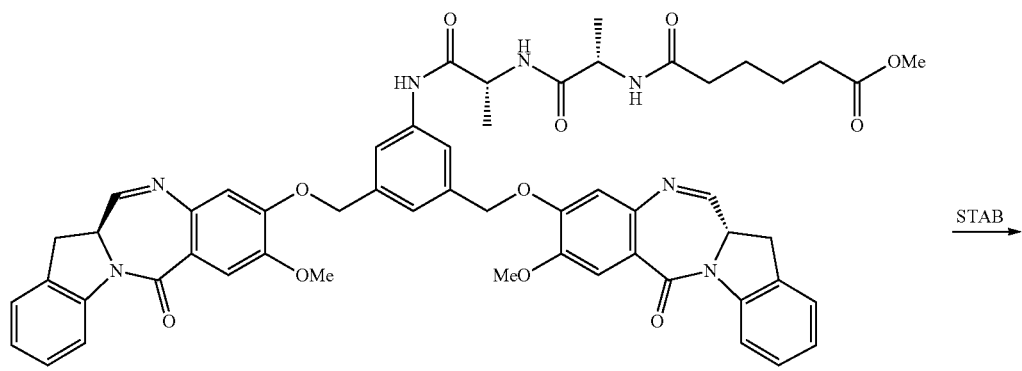
77
STAB →
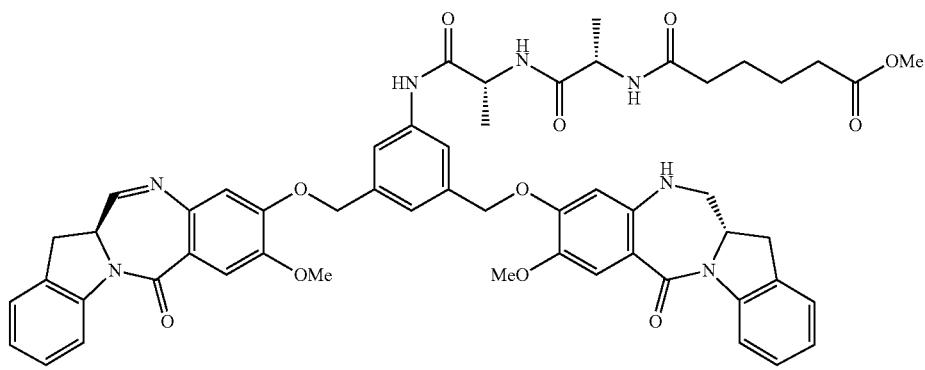
78

Step 8: Compound 78 was prepared similarly as compound 12 in Example 1 The crude material was purified via RPHPLC (C18 column, Acetonitrile/Water) to give compound 78 (103 mg, 30% yield). LCMS=6.65 min (15 min method). MS (m/z): 992.7 (M+1)+.
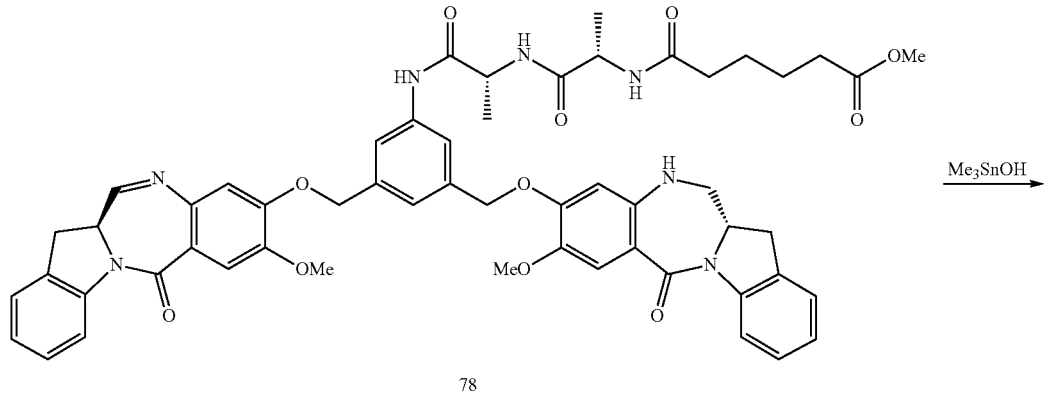
78
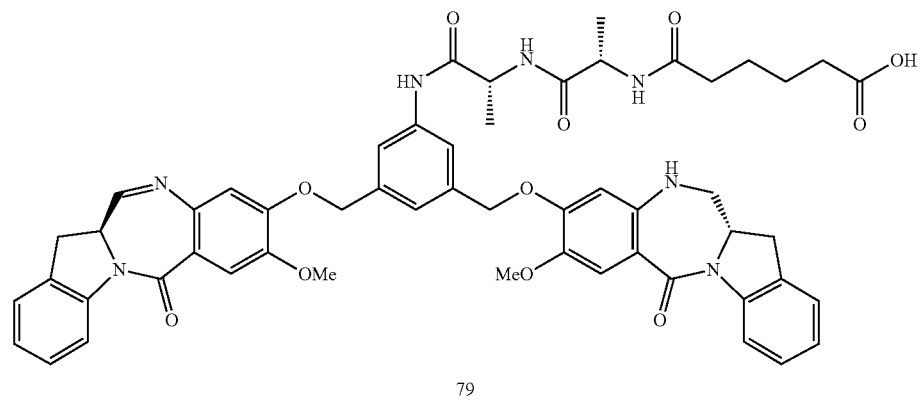
79
Step 9: Compound 78 was prepared similarly as 22 in Example 2. The crude material was passed through a silica plug to give compound 79 (38 mg, 55% yield, 75% purity). LCMS=5.83 min (15 min method). MS (m/z): 978.6 (M+1)+.
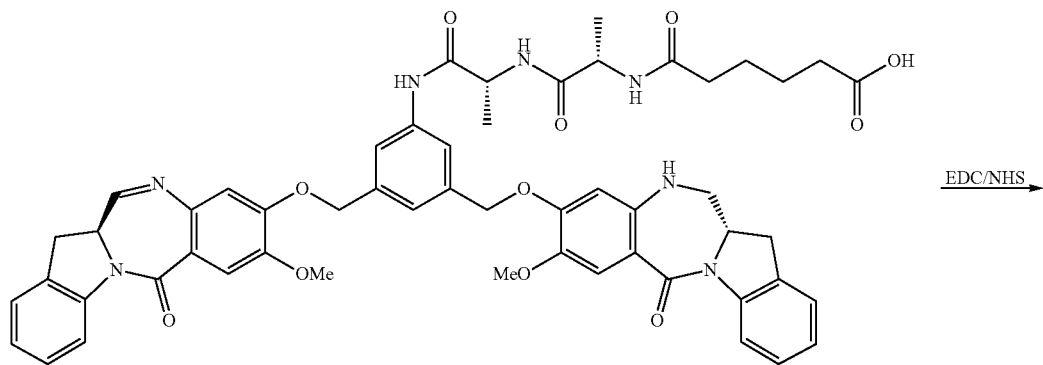
79

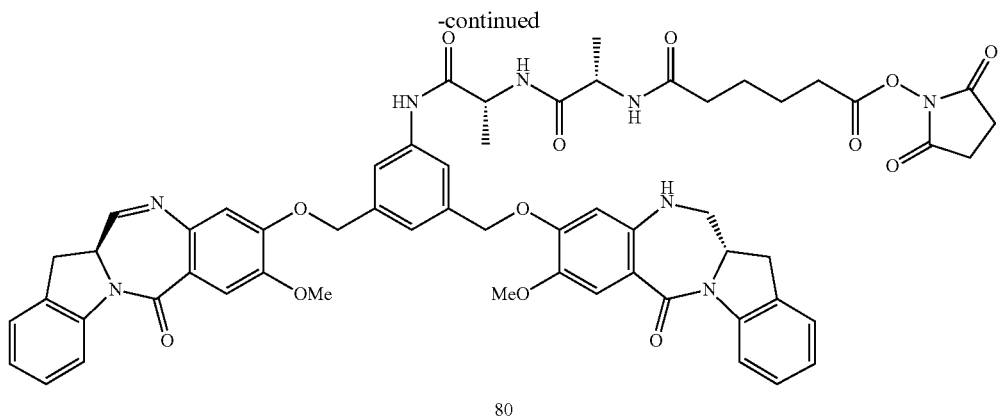

80

Step 10: Compound 80 was prepared similarly as compound 14 in Example 1. The crude material was purified via RPHPLC (C18 column, Acetonitrile/Water) to give 2,5-dioxopyrrolidin-1-yl 6-(((S)-1-(((R)-1-((3-((((S)-8-methoxy-6-oxo-11,12,12a,13-tetrahydro-6H-benzo[5,6][1,4]diazepino[1,2-a]indol-9-yl)oxy)methyl)-5-((((R)-8-methoxy-6-oxo-12a,13-dihydro-6H-benzo[5,6][1,4]diazepino[1,2-a]indol-9-yl)oxy)methyl)phenyl)amino)-1-oxopropan-2-yl)amino)-1-oxopropan-2-yl)amino)-6-oxohexanoate, compound 80 (6.5 mg, 30% yield). LCMS=6.53 min (15 min method). MS (m/z): 1075.7 (M+1)$^+$ and 1097.7(M+Na)$^+$.

Example 6

Synthesis of 2,5-dioxopyrrolidin-1-yl 6-(((S)-1-(((S)-1-((3-((((S)-8-methoxy-6-oxo-11,12,12a,13-tetrahydro-6H-benzo[5,6][1,4]diazepino[1,2-a]indol-9-yl)oxy)methyl)-5-((((R)-8-methoxy-6-oxo-12a,13-dihydro-6H-benzo[5,6][1,4]diazepino[1,2-a]indol-9-yl)oxy)methyl)phenyl)amino)-1-oxopropan-2-yl)amino)-1-oxopropan-2-yl)amino)-6-oxohexanoate, Compound 90

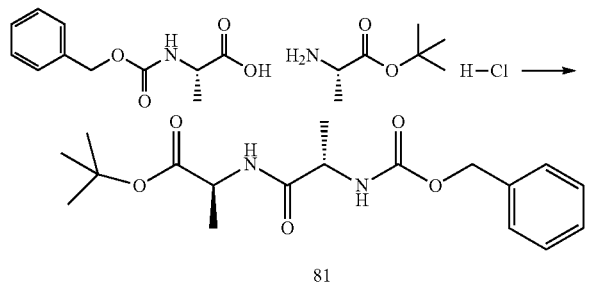

81

Step 1: (S)-2-(((benzyloxy)carbonyl)amino)propanoic acid (5 g, 22.40 mmol) and (S)-tert-butyl 2-aminopropanoate hydrochloride (4.48 g, 24.64 mmol) were dissolved in anhydrous DMF (44.8 mL). EDC.HCl (4.72 g, 24.64 mmol), HOBt (3.43 g, 22.40 mmol), and DIPEA (9.75 mL, 56.0 mmol) were added. The reaction stirred under argon, at room temperature, overnight. The reaction mixture was diluted with dichloromethane and then washed with saturated ammonium chloride, saturated sodium bicarbonate, water, and brine. The organic layer was dried over sodium sulfate and concentrated. The crude oil was purified via silica gel chromatography (Hexanes/Ethyl Acetate) to yield compound 81 (6.7 g, 85% yield). $^1$H NMR (400 MHz, CDCl$_3$): δ 7.38-7.31 (m, 5H), 6.53-6.42 (m, 1H), 5.42-5.33 (m, 1H), 5.14 (s, 2H), 4.48-4.41 (m, 1H), 4.32-4.20 (m, 1H), 1.49 (s, 9H), 1.42 (d, 3H, J=6.8 Hz), 1.38 (d, 3H, J=7.2 Hz).

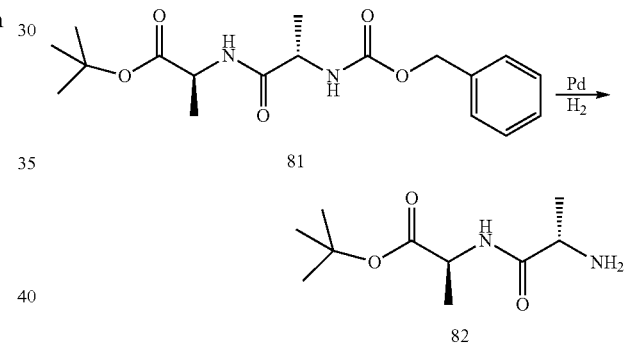

81

82

Step 2: Compound 81 (6.7 g, 19.12 mmol) was dissolved in methanol (60.7 mL) and water (3.03 mL). The solution was purged with argon for five minutes. Palladium on carbon (wet, 10%) (1.017 g, 0.956 mmol) was added slowly. The reaction was stirred overnight under an atmosphere of hydrogen. The solution was filtered through Celite, rinsed with methanol and concentrated. It was azeotroped with methanol and acetonitrile and the resulting oil was placed directly on the high vacuum to give compound 82 (4.02 g, 97% yield) which was used directly in the next step. $^1$H NMR (400 MHz, CDCl$_3$): δ 7.78-7.63 (m, 1H), 4.49-4.42 (m, 1H), 3.55-3.50 (m, 1H), 1.73 (s, 2H), 1.48 (s, 9H), 1.39 (d, 3H, J=7.2 Hz), 1.36 (d, 3H, J=6.8 Hz).

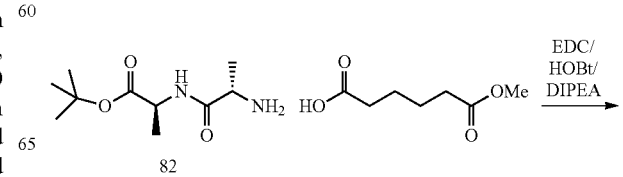

82

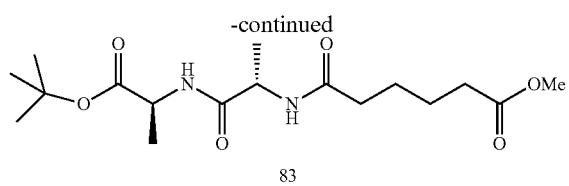

83

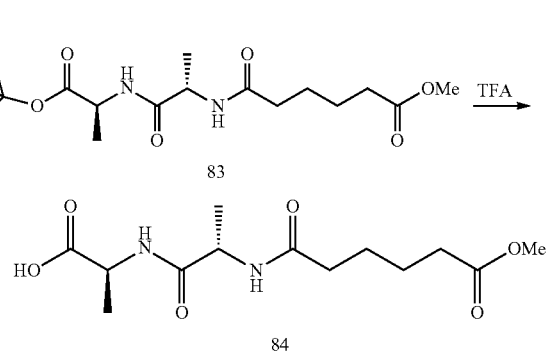

83

Step 3: Compound 82 (4.02 g, 18.59 mmol) and mono methyladipate (3.03 mL, 20.45 mmol) were dissolved in anhydrous DMF (62.0 mL). EDC.HCl (3.92 g, 20.45 mmol), HOBt (2.85 g, 18.59 mmol) and DIPEA (6.49 mL, 37.2 mmol) were added. The mixture was stirred overnight at room temperature. The reaction was diluted with dichloromethane/methanol (150 mL, 5:1) and washed with saturated ammonium chloride, saturated sodium bicarbonate, and brine. It was dried over sodium sulfate, filtered and stripped. The compound was azeotroped with acetonitrile (5×), then pumped on the high vacuum at 35° C. to give compound 83 (6.66 g, 100% yield). The crude material was taken onto next step without purification. $^1$H NMR (400 MHz, CDCl$_3$): δ 6.75 (d, 1H, J=6.8 Hz), 6.44 (d, 1H, J=6.8 Hz), 4.52-4.44 (m, 1H), 4.43-4.36 (m, 1H), 3.65 (s, 3H), 2.35-2.29 (m, 2H), 2.25-2.18 (m, 2H), 1.71-1.60 (m, 4H), 1.45 (s, 9H), 1.36 (t, 6H, J=6.0 Hz).

84

Step 4: Compound 83 (5.91 g, 16.5 mmol) was stirred in TFA (28.6 mL, 372 mmol) and deionized water (1.5 mL) at room temperature for three hours. The reaction mixture was concentrated with acetonitrile and placed on high vacuum to give crude compound 84 as a sticky solid (5.88 g, 100% yield). $^1$H NMR (400 MHz, CDCl$_3$): δ 7.21 (d, 1H, J=6.8 Hz), 6.81 (d, 1H, J=7.6 Hz), 4.69-4.60 (m, 1H), 4.59-4.51 (m, 1H), 3.69 (s, 3H), 2.40-2.33 (m, 2H), 2.31-2.24 (m, 2H), 1.72-1.63 (m, 4H), 1.51-1.45 (m, 3H), 1.42-1.37 (m, 3H).

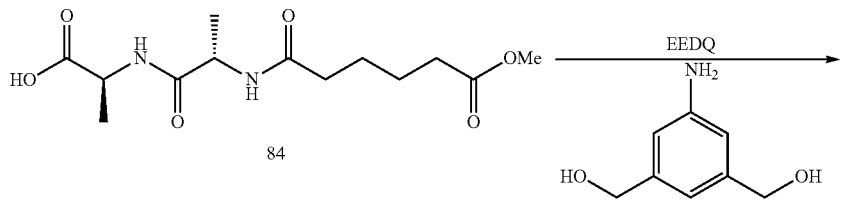

84

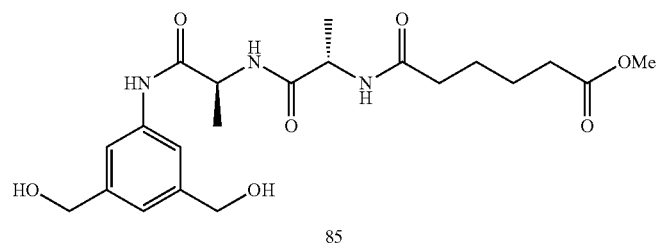

85

Step 5: Compound 84 (5.6 g, 18.52 mmol) was dissolved in anhydrous dichloromethane (118 mL) and anhydrous methanol (58.8 mL). (5-amino-1,3-phenylene)dimethanol (2.70 g, 17.64 mmol) and EEDQ (8.72 g, 35.3 mmol) were added and the reaction was stirred at room temperature, overnight. The solvent was stripped and ethyl acetate was added. The resulting slurry was filtered, washed with ethyl acetate and dried under vacuum/$N_2$ to give compound 85 (2.79 g, 36% yield). $^1$H NMR (400 MHz, DMSO-d6): δ 9.82 (s, 1H), 8.05, (d, 1H, J=9.2 Hz), 8.01 (d, 1H, J=7.2 Hz), 7.46 (s, 2H), 6.95 (3, 1H), 5.21-5.12 (m, 2H), 4.47-4.42 (m, 4H), 4.40-4.33 (m, 1H), 4.33-4.24 (m, 1H), 3.58 (s, 3H), 2.33-2.26 (m, 2H), 2.16-2.09 (m, 2H), 1.54-1.46 (m, 4H), 1.30 (d, 3H, J=7.2 Hz), 1.22 (d, 3H, J=4.4 Hz).

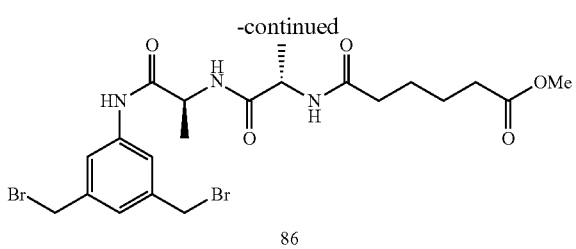

Step 6: Compound 85 (0.52 g, 1.189 mmol) and carbon tetrabromide (1.183 g, 3.57 mmol) were dissolved in anhydrous DMF (11.89 mL). Triphenylphosphine (0.935 g, 3.57 mmol) was added and the reaction stirred under argon for four hours. The reaction mixture was diluted with DCM/MeOH (10:1) and washed with water and brine, dried over sodium sulfate, filtered, and concentrated. The crude material was purified by silica gel chromatography (DCM/MeOH) to give compound 86 (262 mg, 39% yield). $^1$H NMR (400 MHz, DMSO-d6): δ 10.01 (s, 1H), 8.11 (d, 1H, J=6.8 Hz), 8.03 (d, 1H, J=6.8 Hz), 7.67 (s, 2H), 7.21 (s, 1H), 4.70-4.64 (m, 4H), 4.40-4.32 (m, 1H), 4.31-4.23 (m, 1H), 3.58 (s, 3H), 2.34-2.26 (m, 2H), 2.18-2.10 (m, 2H), 1.55-1.45 (m, 4H), 1.31 (d, 3H, J=7.2 Hz), 1.21 (d, 3H, J=7.2 Hz).

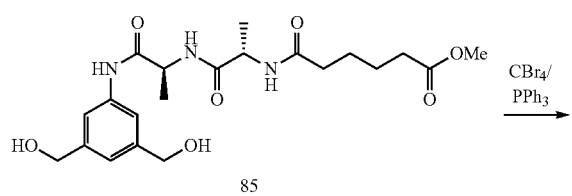

Step 7: Compound 87 was prepared similarly as compound 11 in Example 1. The crude material was purified by silica gel chromatography (dichloromethane/methanol) to give compound 87 (336 mg, 74% yield). LCMS=5.91 min (15 min method). MS (m/z): 990.6 (M+1)$^+$.

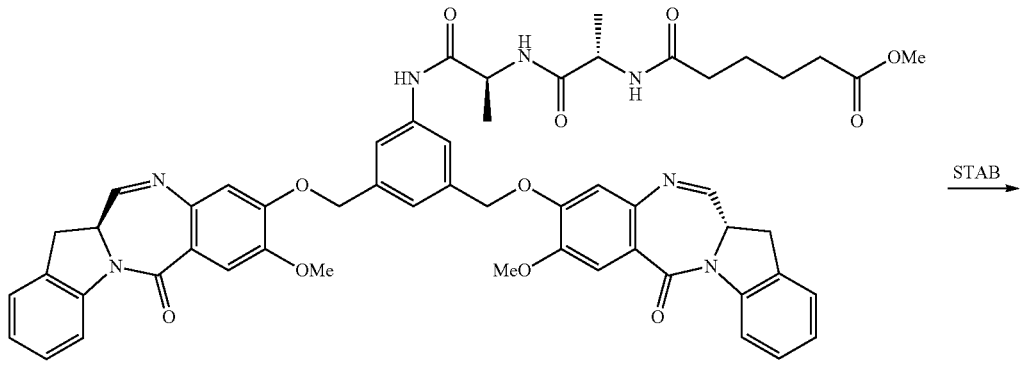

87

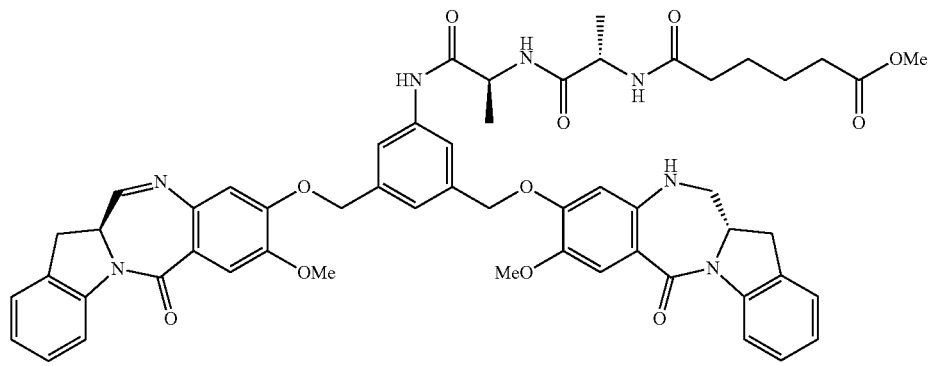

88

Step 8: Compound 88 was prepared similarly as compound 12 in Example 1. The crude material was purified via RPHPLC (C18 column, Acetonitrile/Water) to give compound 88 (85.5 mg, 25% yield). LCMS=6.64 min (15 min method). MS (m/z): 992.6 (M+1)$^+$.

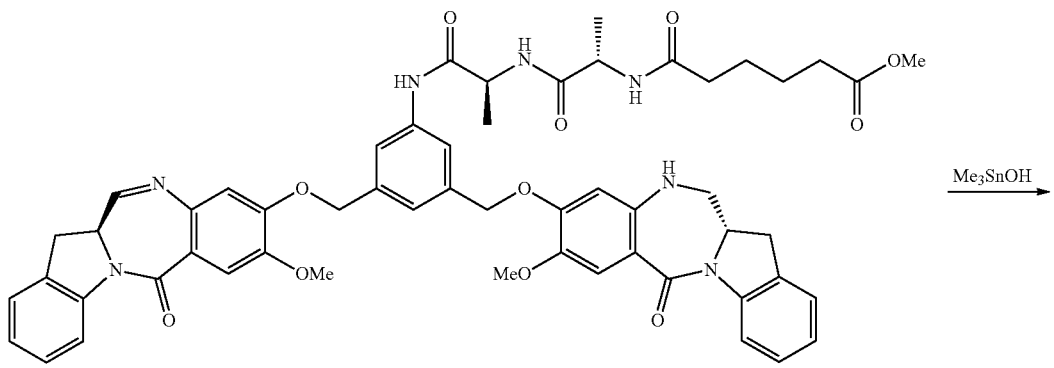

88

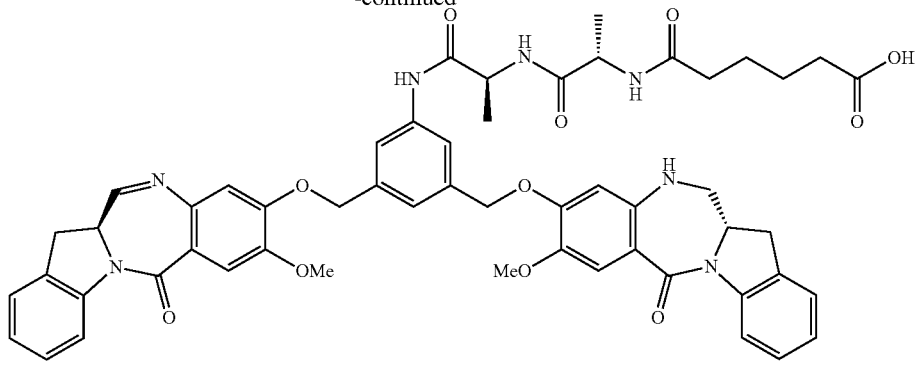
89
Step 9: Compound 88 was prepared similarly as 22 in Example 2. The crude material was passed through a silica plug to give compound 89 (48.8 mg, 80% yield). LCMS=5.89 min (15 min method). MS (m/z): 978.6 (M+1)$^+$.
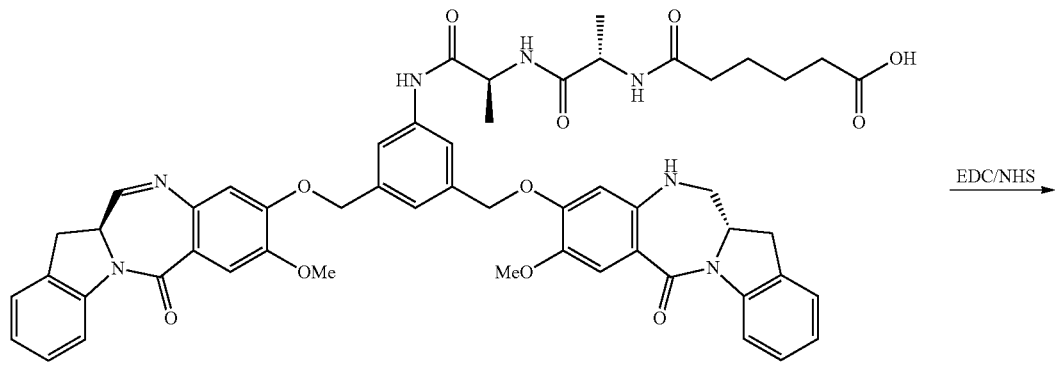
89
EDC/NHS
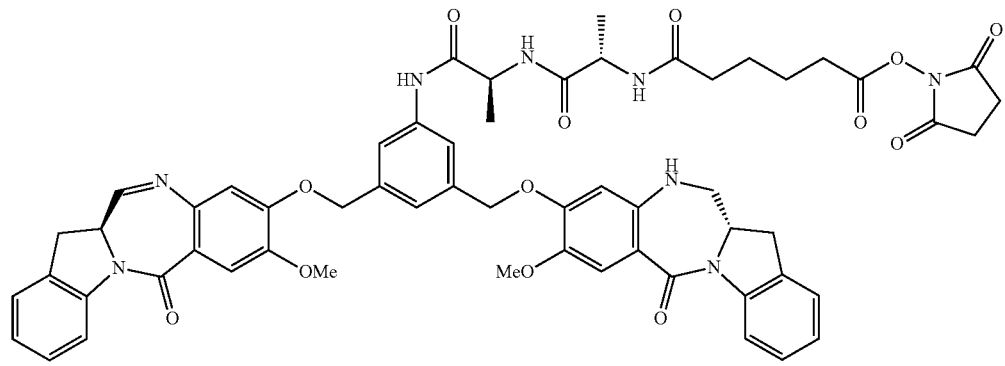
90

Step 10: Compound 90 was prepared similarly as 14 in Example 1. The crude material was purified via RPHPLC (C18 column, Acetonitrile/Water) to give 2,5-dioxopyrrolidin-1-yl 6-(((S)-1-(((S)-1-((3-((((S)-8-methoxy-6-oxo-11,12,12a,13-tetrahydro-6H-benzo[5,6][1,4]diazepino[1,2-a]indol-9-yl)oxy)methyl)-5-((((R)-8-methoxy-6-oxo-12a,13-dihydro-6H-benzo[5,6][1,4]diazepino[1,2-a]indol-9-yl)oxy)methyl)phenyl)amino)-1-oxopropan-2-yl)amino)-1-oxopropan-2-yl)amino)-6-oxohexanoate, compound 90 (8.2 mg, 30% yield). LCMS=6.64 min (15 min method). MS (m/z): 1075.4 (M+1)$^+$.

Example 7

Synthesis of 2,5-dioxopyrrolidin-1-yl 1-(3-(((((S)-8-methoxy-6-oxo-11,12,12a,13-tetrahydro-6H-benzo[5,6][1,4]diazepino[1,2-a]indol-9-yl)oxy)methyl)-5-(((((S)-8-methoxy-6-oxo-12a,13-dihydro-6H-benzo[5,6][1,4]diazepino[1,2-a]indol-9-yl)oxy)methyl)phenyl)-1,4,7,10-tetraoxo-2,5,8,11-tetraazatetradecan-14-oate (Compound 63)

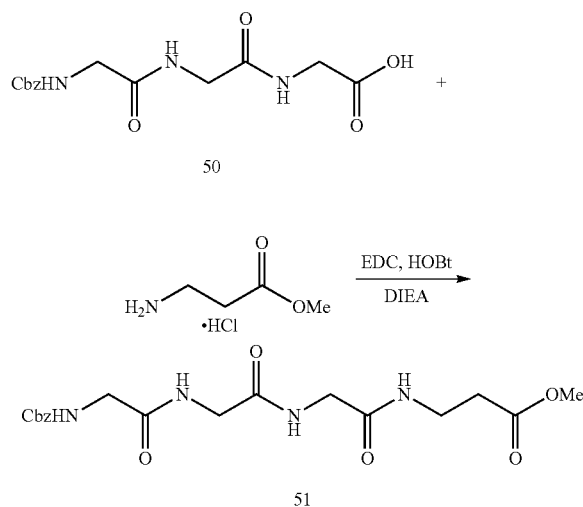

Step 1: Z-Gly-Gly-GlyOH compound 50 (1.0 g, 3.09 mmol) and β-alanine methylester.HCl (453 mg, 3.25 mmol) were dissolved in DMF (12.37 mL). EDC.HCl (623 mg, 3.25 mmol) and HOBt (497 mg, 3.25 mmol) were added to the reaction mixture, followed by DIEA (1.08 mL, 6.19 mmol). The reaction was stirred at rt overnight. The next day, a lot of white precipitate had formed. The reaction mixture was diluted with CH$_2$Cl$_2$/MeOH (5:1, 30 mL) and was washed with sat'd NaHCO$_3$, sat'd NH$_4$Cl and brine. The organic layer became clowdy. Added EtOAc (15 mL) to the organic layer to precipitate out the product. The mixture was filtered and the solid was washed water (10 mL) and CH$_3$CN (2×15 mL) to obtain pure compound 51 as a white powder (880 mg, 70% yield) without purification. $^1$H NMR (400 MHz, DMSO-d6): δ 8.16 (bt, 1H, J=5.4 Hz), 8.11 (bt, 1H, J=5.6 Hz), 7.88-7.85 (m, 1H), 7.49 (bt, 1H, J=5.5 Hz), 7.40-7.31 (m, 5H), 5.04 (s, 2H), 3.74 (d, 2H, J=5.5 Hz), 3.67 (t, 4H, J=6.2 Hz), 3.60 (s, 3H), 3.29 (q, 1H, J=6.4 Hz), 2.47 (t, 3H, J=6.9 Hz).

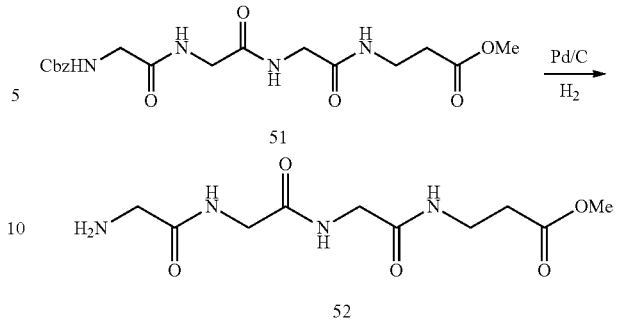

Step 2: Compound 51 (876 mg, 2.145 mmol) was dissolved in MeOH (20.4 mL) and water (1.02 mL) and was purged with Ar. The solution was degassed for 5 min. Pd/C (10%, wet with 50% water, 228 mg) was added slowly. H$_2$ was bubbled into the through a balloon for a minute. The reaction was stirred under a H$_2$ balloon overnight. H$_2$O (~3 mL) was added to reaction mixture to dissolve all white solids formed. The solution was then filtered through Celite and the filter cake was washed with MeOH (30 mL) and concentrated. The residue was dissolved in CH$_3$CN (20 mL) and was concentrated. This was repeated 2 more times. The resulting gummy solid was precipitated out with the addition of CH$_3$CN (~15 mL). The thick white slurry was stirred for 10 min, filtered and washed with CH$_3$CN. The solid was dried under vacuum/N$_2$ for 1.5 h to obtain compound 52 as a white solid (450 mg, 76% yield). $^1$H NMR (400 MHz, DMSO-d6): δ 8.18-8.12 (m, 2H), 7.88 (t, 1H, J=5.4 Hz), 3.75 (s, 2H), 3.65 (d, 2H, J=5.9 Hz), 3.6 (s, 3H), 3.33-3.27 (m, 4H), 2.47 (t, 2H, J=7.0 Hz), 1.94 (bs, 1H).

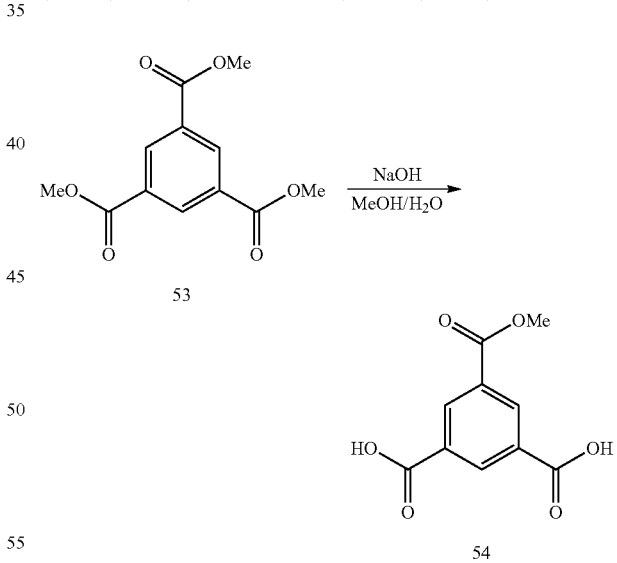

Step 3: NaOH (1.665 g, 41.6 mmol) was added to a stirred solution of trimethyl benzene-1,3,5-tricarboxylate compound 53 (5 g, 19.82 mmol) in MeOH (66.1 mL) and water (13.22 mL). The reaction mixture was refluxed under Ar for 3 h. Lots of white precipitate had formed. The solution was cooled to rt and was diluted with H$_2$O until all solids were dissolved. The mixture was acidified to pH~2-3 with aqueous 5 N HCl, extracted with EtOAc (3×), dried over Na$_2$SO$_4$, filtered and concentrated. The crude product was dissolved in hot EtOAc (50 mL) and was cooled to rt slowly.

The precipitate was filtered (precipitate was by-product and not product). The mother liquor was concentrated to obtain compound 54 as a white solid (3.45 g, 78% yield). $^1$H NMR (400 MHz, DMSO-d6): δ 13.62 (bs, 2H), 8.65 (s, 3H), 3.93 (s, 3H). LCMS=3.209 min (8 min method). Mass observed (ESI$^+$): 244.90 (M+H).

solution and brine, dried over $Na_2SO_4$, filtered and concentrated. The crude residue was purified by silica gel flash chromatography (EtOAc/hexanes, gradient, 20% to 100%) to obtain diol compound 55 as a white solid (385 mg, 44% yield). $^1$H NMR (400 MHz, DMSO-d6): δ 7.81 (s, 2H), 7.52 (s, 1H), 5.33 (bs, 2H), 4.56 (s, 4H), 3.86 (s, 3H).

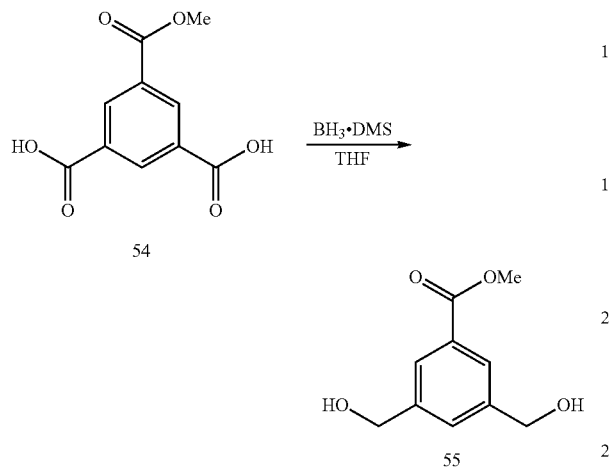

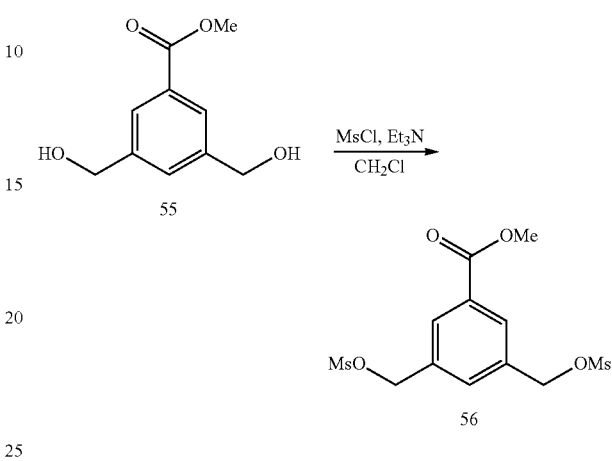

Step 4: Diacid compound 54 (1.0 g, 4.46 mmol) was dissolved in THF (17.84 mL). The solution was cooled to 0° C. and $BH_3$·DMS (2 M in THF) (8.92 mL, 17.84 mmol) was added slowly under Ar. The reaction was stirred at 0° C. for 5 min, then was warmed to rt and stirred overnight. The reaction was opened to air and was slowly quenched with MeOH, followed by slow addition of $H_2O$ until no gas evolution was observed. The mixture was extracted with EtOAc (2×) and the layers were separated. The organic layers were washed with aqueous ~3% $H_2O_2$, aq. citric acid Step 5: Diol compound 55 (320 mg, 1.631 mmol) was dissolved in DCM (10.9 mL) under Ar. The solution was cooled to −5° C. and TEA (0.568 mL, 4.08 mmol) was added, followed by a slow addition of MsCl (0.292 mL, 3.75 mmol), at which point the color immediately turned yellow upon addition, then dark red/brown. The reaction mixture was stirred at −5° C. under Ar for 1.5 h The reaction mixture was quenched with ice water and was extracted with EtOAc (2×). The organic layer was washed with water (2×), dried over $Na_2SO_4$, filtered and concentrated to obtain the crude dimesylate compound 56 (435 mg, 76% yield).

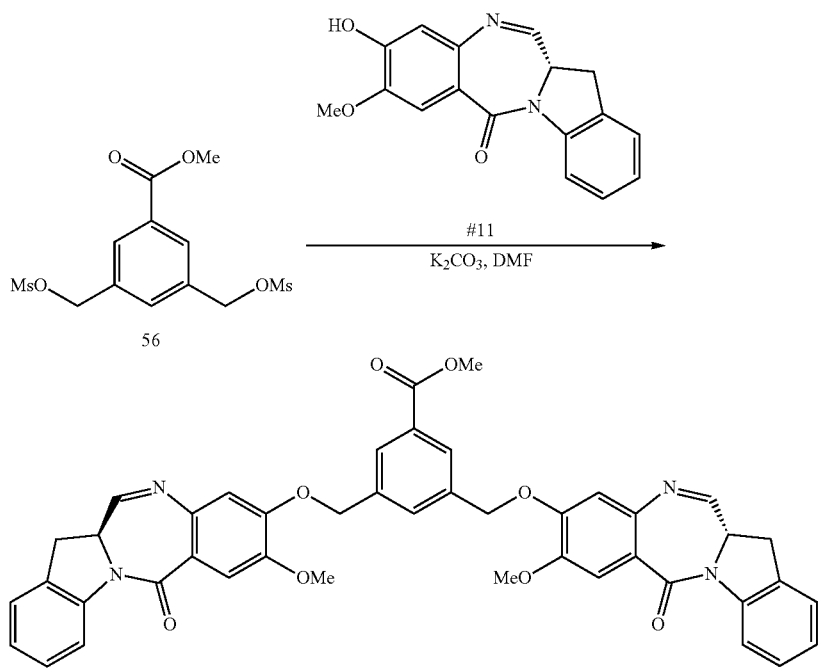

Step 6: Dimesylate compound 56 (435 mg, 1.11 mmol) was dissolved in DMF (5.55 mL). IGN monomer compound 10 (719 mg, 2.444 mmol) was added, followed by and K$_2$CO$_3$ (384 mg, 2.78 mmol) and was stirred at rt under Ar overnight. Water (20 mL) was added to precipitate out the product. The slurry was stirred for 5 min, filtered and dried under vacuum/N$_2$ for 1.5 h. The crude residue was purified by silica gel flash chromatography (EtOAc/hexanes, gradient, 50% to 100%; then 5% MeOH/DCM) to obtain compound 57 as a yellow solid (535 mg, 64% yield, 2 steps). LCMS=6.973 min (15 min method). Mass observed (ESI$^+$): 749.4 (M+H).

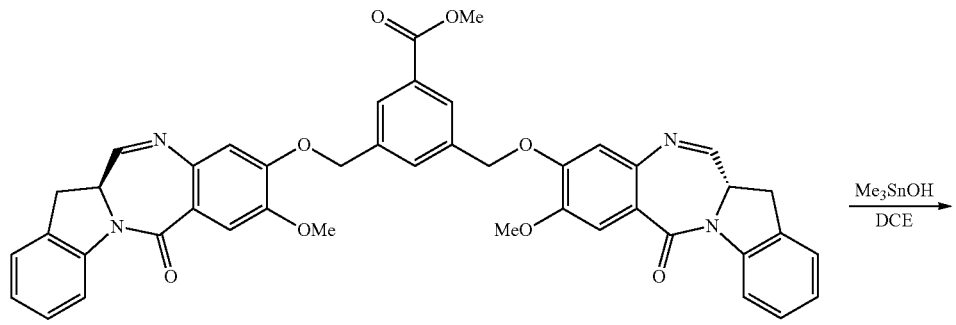

57

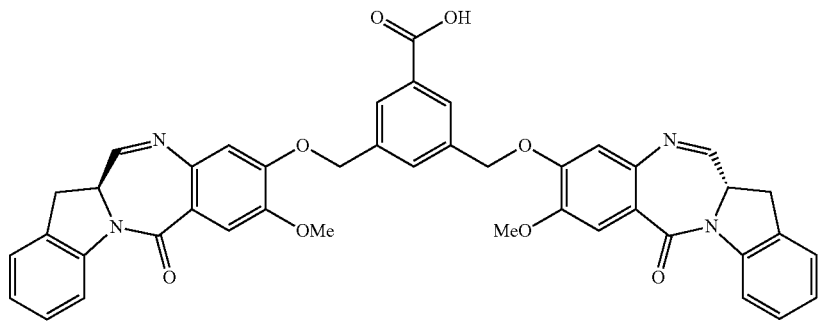

58

Step 7: compound 57 (100 mg, 0.134 mmol) was dissolved in DCE (1.34 mL). Trimethylstannanol (362 mg, 2.003 mmol) was added and was heated at 80° C. overnight. The reaction mixture was cooled to rt and was diluted with water. The aqueous layer was acidified to pH~4 with 1 M HCl and was extracted with DCM (3×), dried over Na₂SO₄, filtered and concentrated. Crude product was plugged through a short silica plug and was flushed with DCM/MeOH (10:1, 50 mL) and concentrated to obtain compound 58 as a pale yellow solid (100 mg, 100% yield). LCMS=5.872 min (15 min method). Mass observed (ESI⁺): 735.3 (M+H).

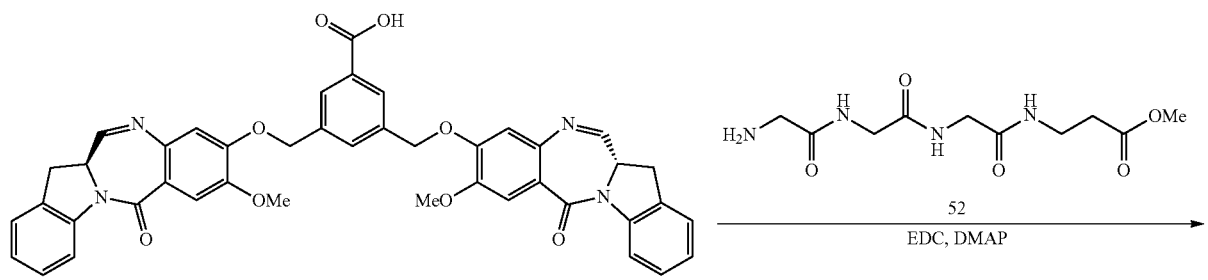

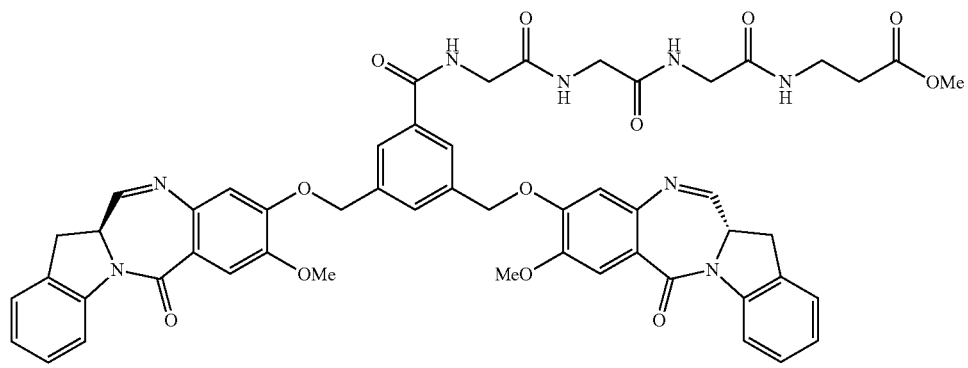

Step 8: Acid compound 58 (80 mg, 0.087 mmol) and amine compound 52 (36 mg, 0.131 mmol) were dissolved in DMF (871 μL). EDC.HCl (25 mg, 0.131 mmol) and DMAP (10.6 mg, 0.087 mmol) were added and was stirred at rt for 4 h. Water (4 mL) was added to precipitate out the product. The slurry was stirred for 5 min, filtered and was dried under vacuum/N₂. The crude residue was purified by silica gel flash chromatography (MeOH/DCM, gradient, 0% to 20%) to obtain compound 60 as a yellow solid (37 mg, 43% yield). LCMS=4.605 min (8 min method). Mass observed (ESI⁺): 991.35 (M+H).

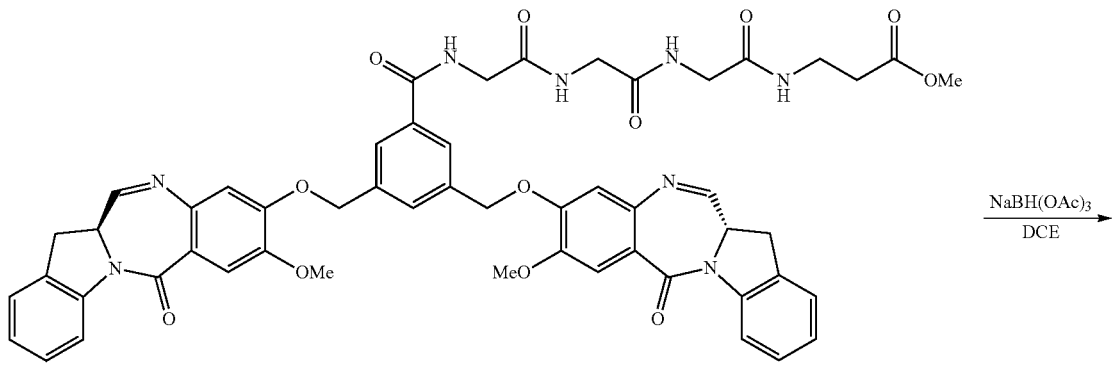

60

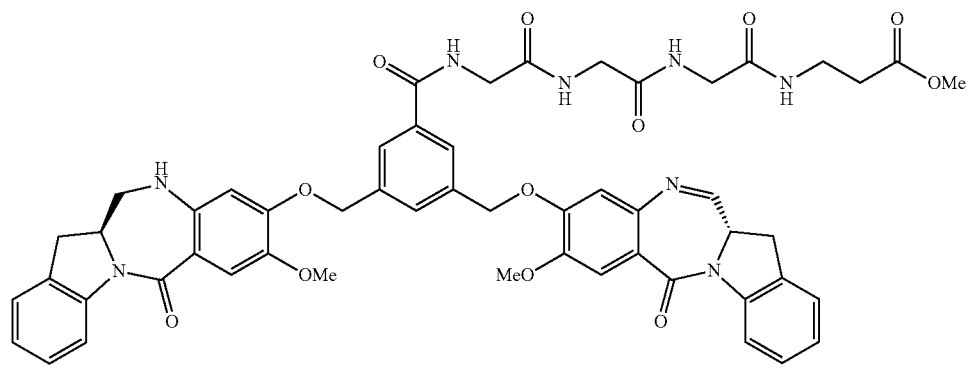

61

Step 9: Compound 61 was prepared similarly as compound 12 in Example 1. Compound 61 was obtained as a white solid after C18 purification (8 mg, 25% yield). LCMS=5.421 min (15 min method). Mass observed (ESI⁺): 993.7 (M+H).

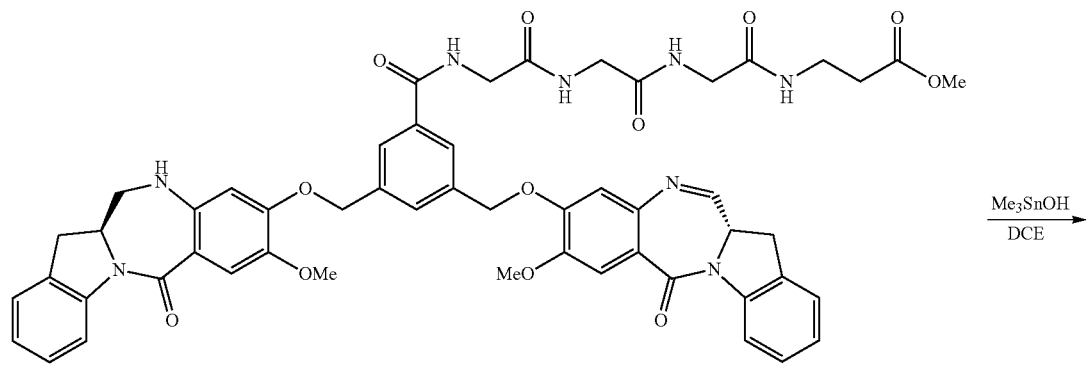

61

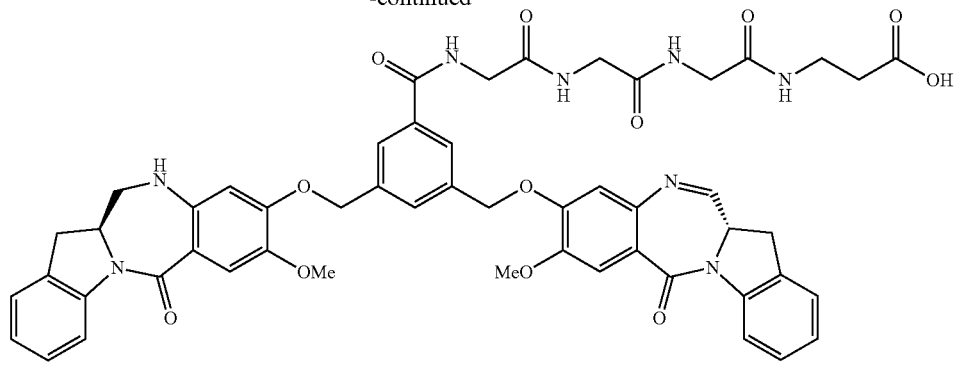
62
Step 10: Compound 62 was prepared similarly as compound 22 in Example 2. Crude compound 62 was obtained as a yellow solid after plugging through a short silica plug (13 g, 90% yield). LCMS=4.693 min (8 in method). Mass observed (ESI+): 979.35 (M+H).
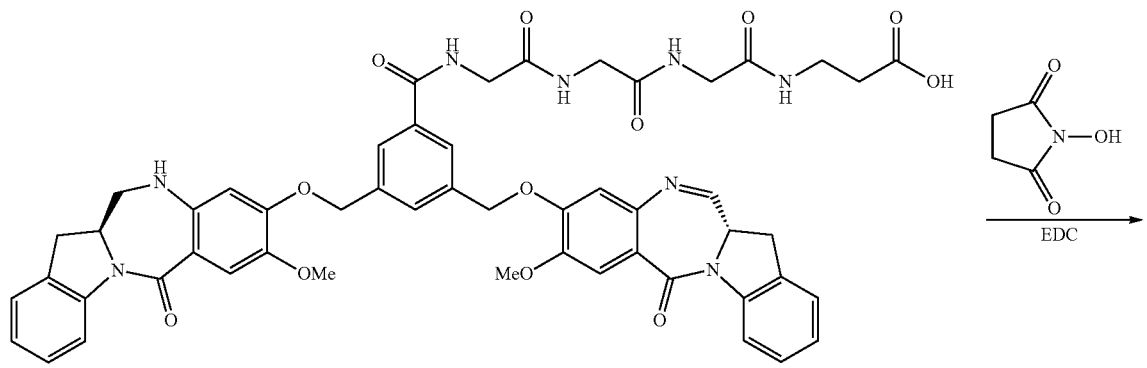
62
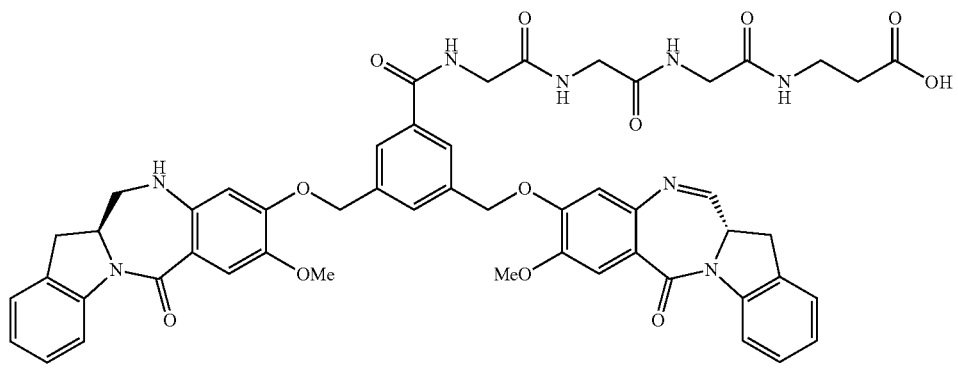
63

Step 11: Compound 63 was prepared similarly as compound 14 in Example 1. 2,5-dioxopyrrolidin-1-yl 1-(3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)phenyl)-1,4,7,10-tetraoxo-2,5,8,11-tetraazatetradecan-14-oate, compound 63 was obtained as a white solid after C18 purification (4 mg, 31% yield). LCMS=5.495 min (15 min method). Mass observed (ESI+): 1076.7 (M+H).

Example 8

Synthesis of 2,5-dioxopyrrolidin-1-yl 3-((S)-2-((S)-2-(3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)benzamido)propanamido)propanamido)propanoate (Compound 70)

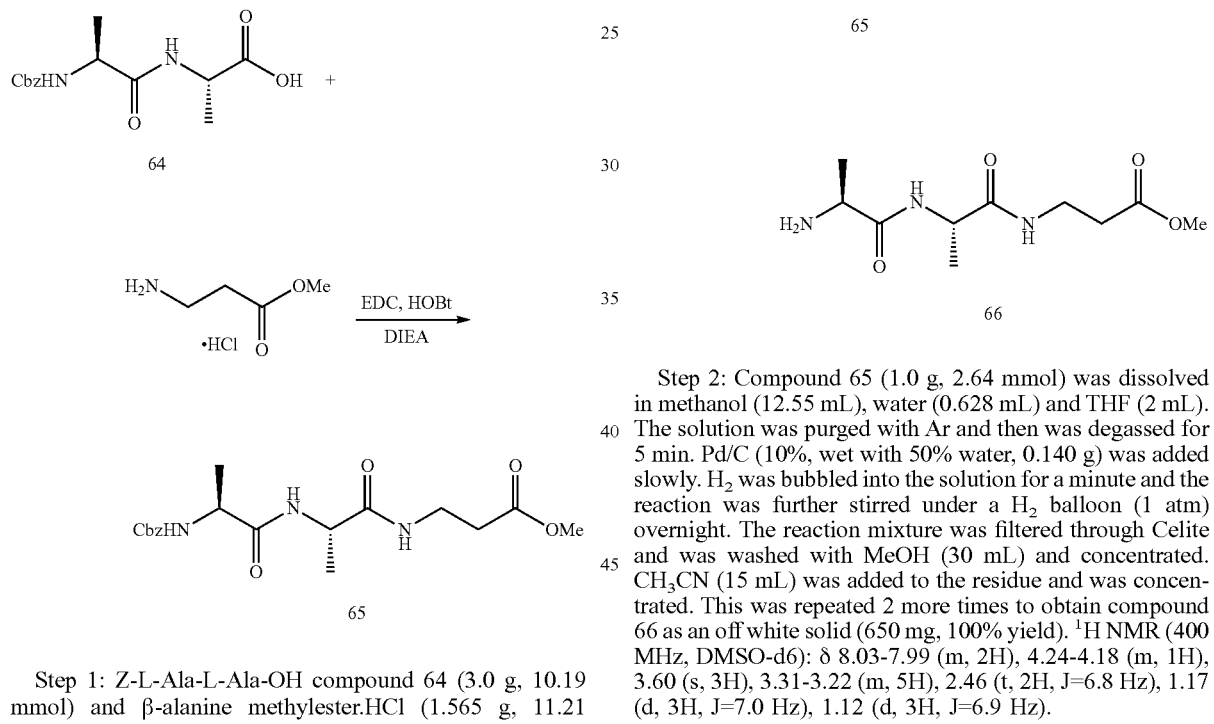

Step 1: Z-L-Ala-L-Ala-OH compound 64 (3.0 g, 10.19 mmol) and β-alanine methylester.HCl (1.565 g, 11.21 mmol) were dissolved in DMF (20.39 mL). EDC.HCl (2.150 g, 11.21 mmol) and HOBt (1.561 g, 10.19 mmol) were added, followed by DIPEA (4.44 mL, 25.5 mmol). The reaction was stirred rt under Ar overnight. The reaction mixture was diluted with EtOAc and was washed with sat'd NH₄Cl, sat'd NaHCO₃ and brine. Hexanes was added to the organic layer, at which point the solution became clowdy with precipitate. The slurry was stirred for a few minutes, filtered and washed solids with EtOAc/hexanes (3:1). The solid was dried under vacuum/N₂ to obtain pure compound 65 as a white solid (3.11 g, 80% yield). ¹H NMR (400 MHz, DMSO-d6): δ 7.91 (d, 2H, J=7.0 Hz), 7.46 (d, 1H, J=7.4 Hz), 6.39-7.30 (m, 5H), 5.02 (d, 2H, J=2.3 Hz), 4.20 (p, 1H, J=7.2 Hz), 4.04 (p, 1H, J=7.3 Hz), 3.59 (s, 3H), 3.30-3.22 (m, 1H), 2.45 (t, 2H, J=6.8 Hz), 1.18 (apparent t, 6H, J=7.2 Hz). LCMS=3.942 min (8 min method). Mass observed (ESI+): 380.10 (M+H).

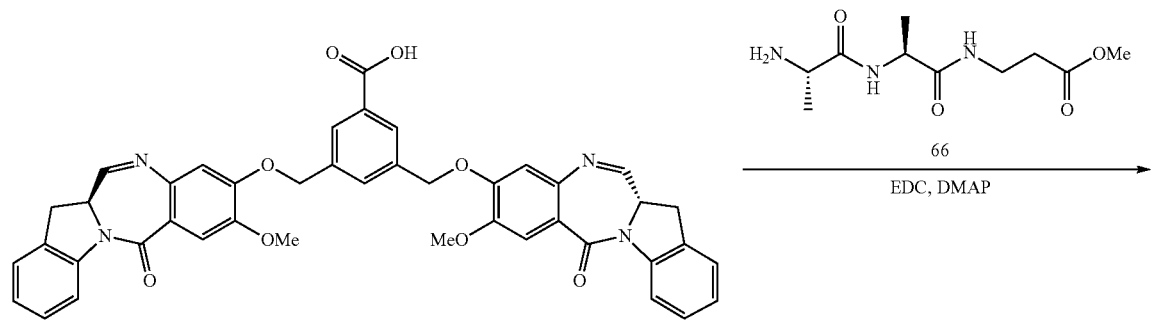

Step 2: Compound 65 (1.0 g, 2.64 mmol) was dissolved in methanol (12.55 mL), water (0.628 mL) and THF (2 mL). The solution was purged with Ar and then was degassed for 5 min. Pd/C (10%, wet with 50% water, 0.140 g) was added slowly. H₂ was bubbled into the solution for a minute and the reaction was further stirred under a H₂ balloon (1 atm) overnight. The reaction mixture was filtered through Celite and was washed with MeOH (30 mL) and concentrated. CH₃CN (15 mL) was added to the residue and was concentrated. This was repeated 2 more times to obtain compound 66 as an off white solid (650 mg, 100% yield). ¹H NMR (400 MHz, DMSO-d6): δ 8.03-7.99 (m, 2H), 4.24-4.18 (m, 1H), 3.60 (s, 3H), 3.31-3.22 (m, 5H), 2.46 (t, 2H, J=6.8 Hz), 1.17 (d, 3H, J=7.0 Hz), 1.12 (d, 3H, J=6.9 Hz).

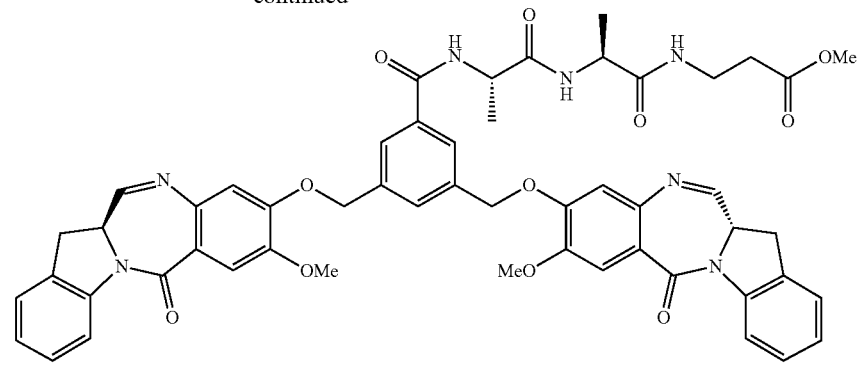
67
Step 3: Compound 67 was prepared similarly as 60 in Example 7. Compound 67 was obtained as a yellow solid after silica gel flash chromatography (69 mg, 53% yield). LCMS=4.843 min (8 min method). Mass observed (ESI+): 962.25 (M+H).
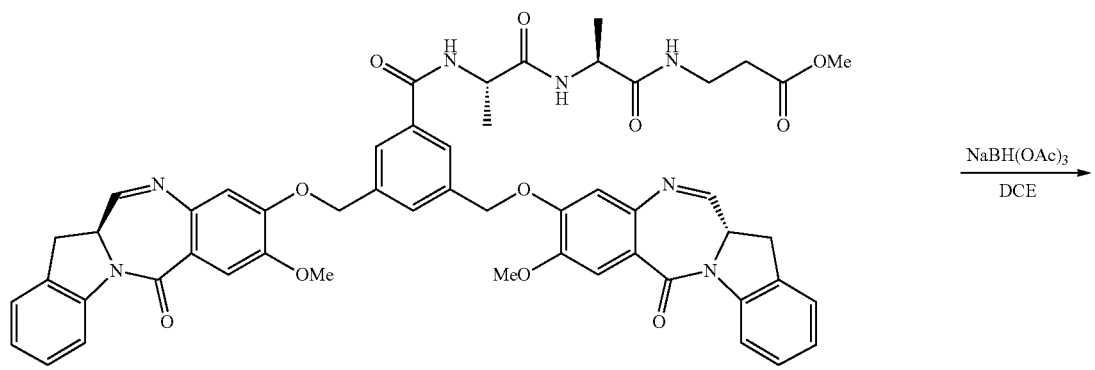
67
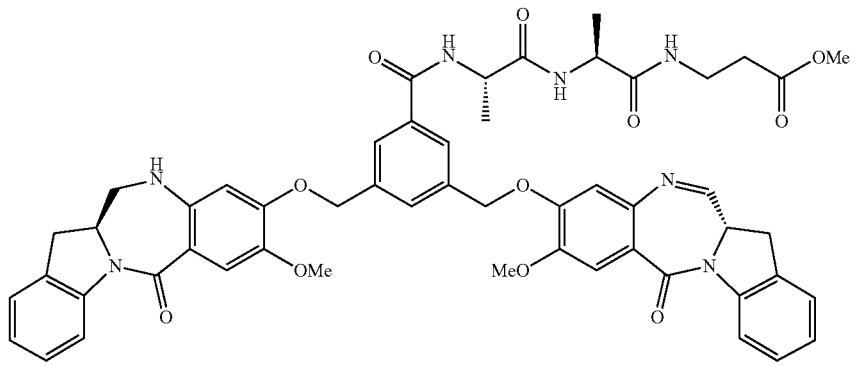
68

Step 4: Compound 68 was prepared similarly as compound 12 in Example 1. Compound 68 was obtained as a white solid after C18 purification (11.5 mg, 19% yield). LCMS=5.136 min (8 min method). Mass observed (ESI+): 964.35 (M+H).

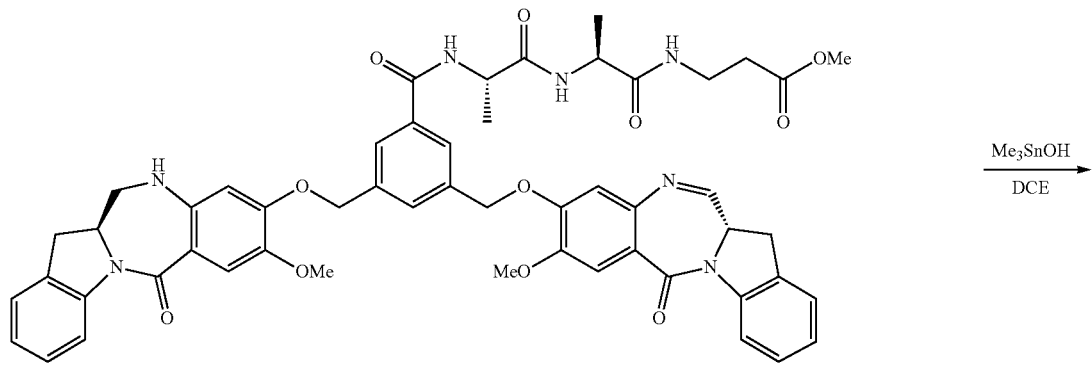

68

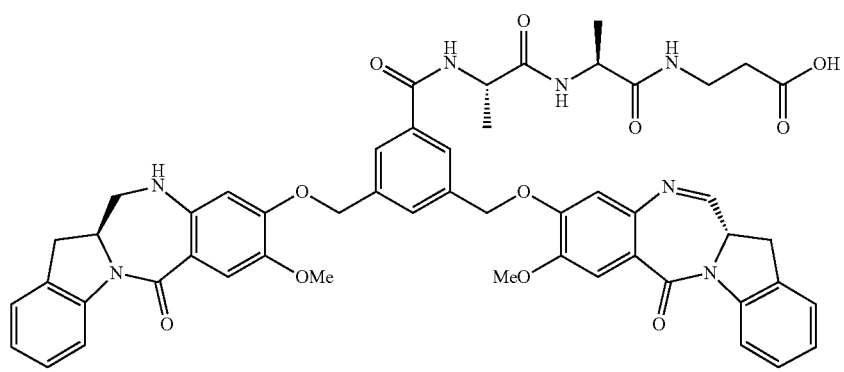

69

Step 5: Compound 69 was prepared similarly as compound 22 in Example 2. Crude compound 69 was obtained as a yellow solid after plugging through a short silica plug (13 mg, 100% yield). LCMS=5.640 min (15 min method). Mass observed (ESI+): 950.4 (M+H).

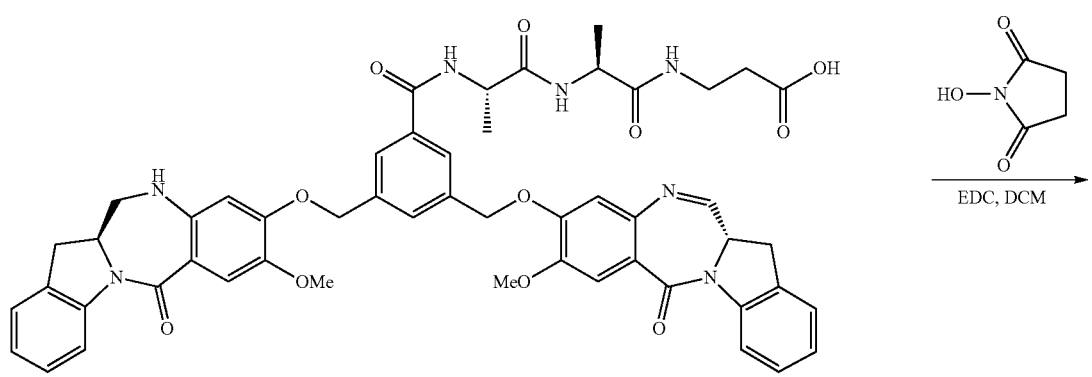

69

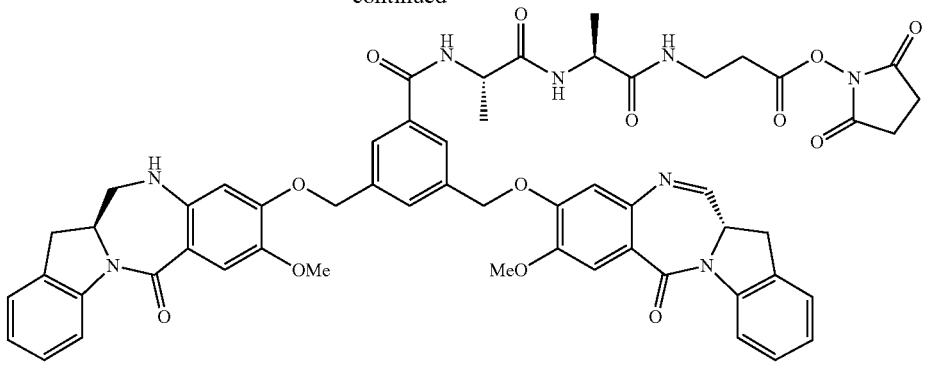

70

Step 6: Compound 70 was prepared similarly as compound 14 in Example 1. 2,5-dioxopyrrolidin-1-yl-3-((S)-2-((S)-2-(3-((((S)-8-methoxy-6-oxo-11,12,12a,13-tetrahydro-6H-benzo[5,6][1,4]diazepino[1,2-a]indol-9-yl)oxy)methyl)-5-((((S)-8-methoxy-6-oxo-12a,13-dihydro-6H-benzo[5,6][1,4]diazepino[1,2-a]indol-9-yl)oxy)methyl)benzamido)propanamido)propanamido) propanoate, compound 70 was obtained as a white solid after C18 purification (5 mg, 35% yield). LCMS=6.138 min (15 min method). Mass observed (ESI⁺): 1047.4 (M+H).

Example 9

Synthesis of (12S,12aS)-9-((3-(2-(2-(2-(4-mercapto-4-methylpentanamido)acetamido) acetamido)acetamido)-5-((((S)-8-methoxy-6-oxo-11,12,12a,13-tetrahydro-6H-benzo[5,6][1,4]diazepino[1,2-a]indol-9-yl)oxy)methyl)benzyl)oxy)-8-methoxy-6-oxo-11,12,12a,13-tetrahydro-6H-benzo[5,6][1,4]diazepino[1,2-a]indole-12-sulfonic acid (Compound 98)

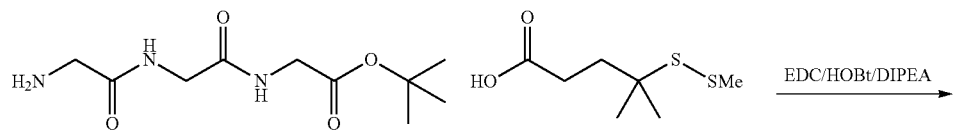

4

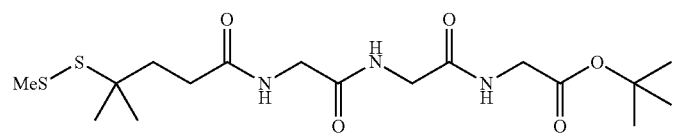

91

Step 1: Compound 4 (2.0 g, 8.15 mmol) and 4-methyl-4-(methyldisulfanyl)pentanoic acid (1.743 g, 8.97 mmol) were dissolved in anhydrous DMF (27.2 mL). EDC.HCl (1.719 g, 8.97 mmol) and HOBt (1.249 g, 8.15 mmol) were added, followed by DIPEA (2.85 mL, 16.31 mmol). The mixture was stirred at room temperature overnight. The reaction was diluted with dichloromethane/methanol (5:1) and washed with saturated ammonium chloride, saturated sodium bicarbonate, and brine. It was dried over sodium sulfate, filtered and stripped. The crude oil was azeotroped with acetonitrile (3×), then pumped on high vac at 35° C. for about 1.5 hours to give compound 91, which was taken on without further purification (3.44 g, 100% yield). $^1$H NMR (400 MHz, DMSO-d6): δ 8.18-8.09 (m, 3H), 3.76-3.68 (m, 6H), 2.41 (s, 3H), 2.28-2.21 (m, 2H), 1.84-1.77 (m, 2H), 1.41 (s, 9H), 1.25 (s, 6H).

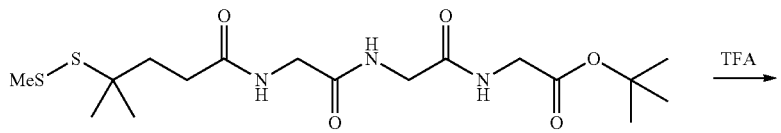

91

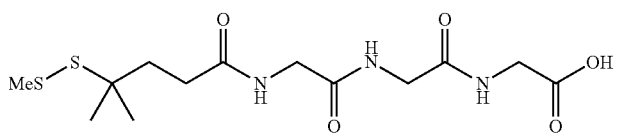

92

Step 2: Compound 91 (3.44 g, 8.15 mmol) was stirred in TFA (12.56 mL, 163 mmol) and deionized water (0.65 mL) at room temperature for 3.5 hours. The reaction was diluted with acetonitrile and evaporated to dryness. The crude solid was slurried with ethyl acetate, filtered and rinsed with ethyl acetate and then dichloromethane/methanol (1:1) to give compound 92 (2.98 g, 100% yield). ¹H NMR (400 MHz, DMSO-d6): δ 8.19-8.08 (m, 3H), 3.80-3.68 (m, 6H), 2.41 (s, 3H), 2.28-2.20 (m, 2H), 1.85-1.76 (m, 2H), 1.25 (s, 6H).
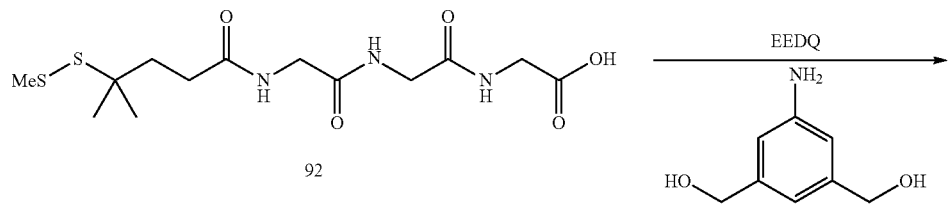
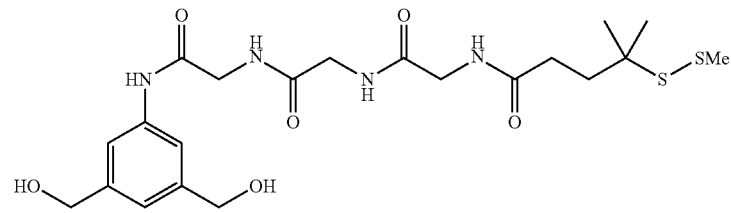

Step 3: Compound 92 (1.74 g, 4.76 mmol) was dissolved in dichloromethane (30.2 mL) and methanol (15.11 mL). N-Ethoxycarbonyl-2-ethoxy-1,2-dihydroquinoline (2.243 g, 9.07 mmol) and (5-amino-1,3-phenylene)dimethanol (0.695 g, 4.53 mmol) were added and the reaction was stirred at room temperature overnight. The solvent was removed and ethyl acetate was added. The solid was filtered through Celite and washed with ethyl acetate and then methanol. The filtrate was evaporated and purified by silica gel chromatography (Dichloromethan/Methanol) to give compound 93 (569 mg, 25% yield). $^1$H NMR (400 MHz, DMSO-d6): δ 9.74 (s, 1H), 8.24-8.15 (m, 3H), 7.45 (s, 2H), 6.96 (s, 1H), 5.17 (t, 2H, J=5.6 Hz), 4.45 (d, 4H, J=5.6 Hz), 3.87 (d, 2H, J=6.0 Hz), 3.77 (d, 2H, J=6.0 Hz), 3.73 (d, 2H, J=5.6 Hz), 2.40 (s, 3H), 2.28-2.21 (m, 2H), 1.83-1.76 (m, 2H), 1.24 (s, 6H).

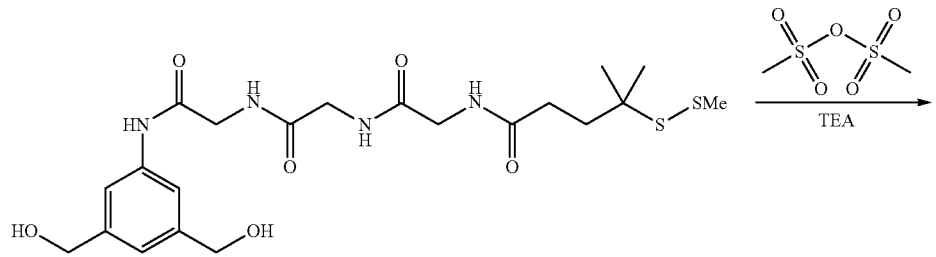

93

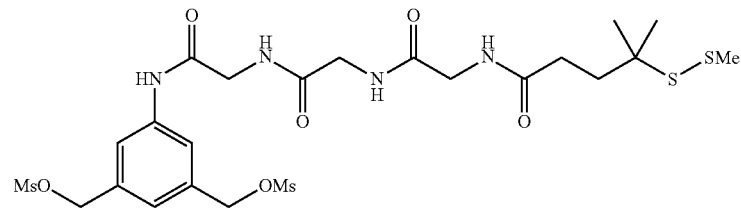

94

Step 4: Compound 93 (305 mg, 0.609 mmol) was suspended in anhydrous DCM (5.992 mL). Anhydrous DMF was added until the solution became homogeneous (~2.5 mL). The solution was cooled to −10° C. in an acetone/dry ice bath. Triethylamine (0.425 mL, 3.05 mmol) was added, followed by methanesulfonic anhydride (274 mg, 1.523 mmol). The mixture stirred at −10° C. for 1 hour. The reaction was quenched with ice water and extracted with cold ethyl acetate/methanol (20:1). The organic layer was washed with ice water and dried over anhydrous sodium sulfate, filtered and concentrated. The crude material was dried on high vacuum to give compound 94 (380 mg, 95% yield). LCMS=4.2 min (15 min method). MS (m/z): 655.0 (M−1)⁻.

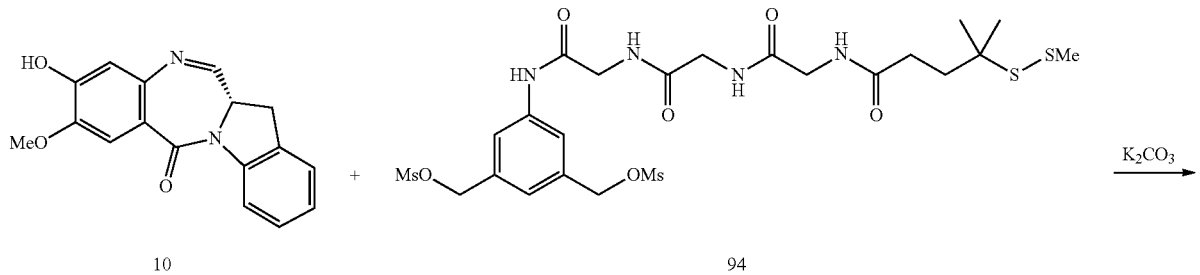

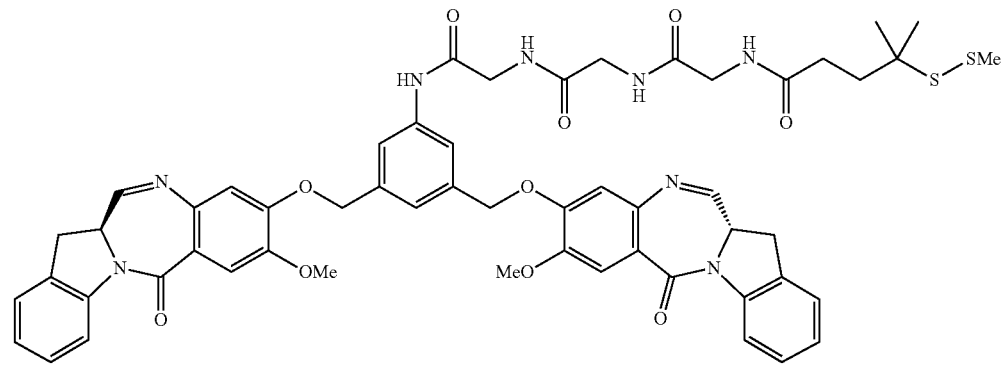

Step 5: Compound 95 was prepared similarly as compound 57 in Example 7. The crude solid was dissolved in Dichloromethane/Methanol (10:1) washed with water and the organic dried over anhydrous sodium sulfate. The solvent was removed in vacuo and purified by silica gel chromatography (dichloromethane/methanol) to give compound 95 (445 mg, 42% yield, 54% purity). LCMS=6.64 min (15 min method). MS (m/z): 1053.4 (M+1)$^+$ and 1051.3 (M−1)$^-$.

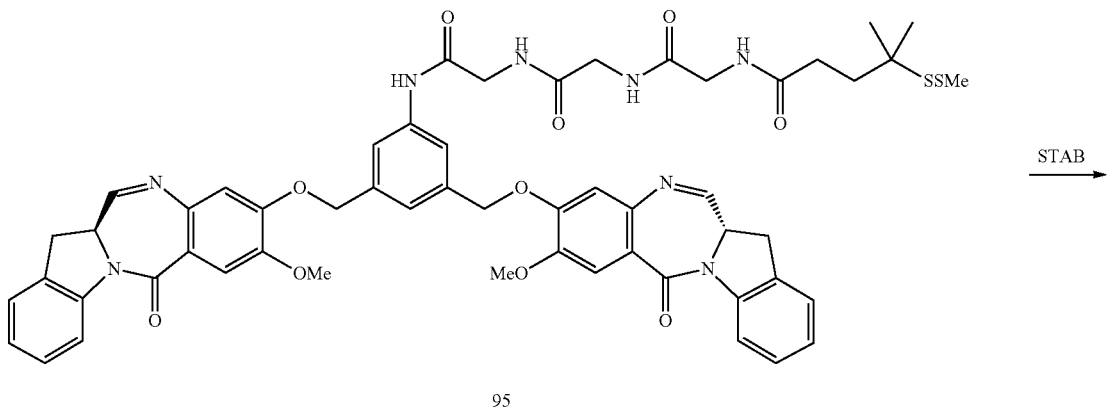

95

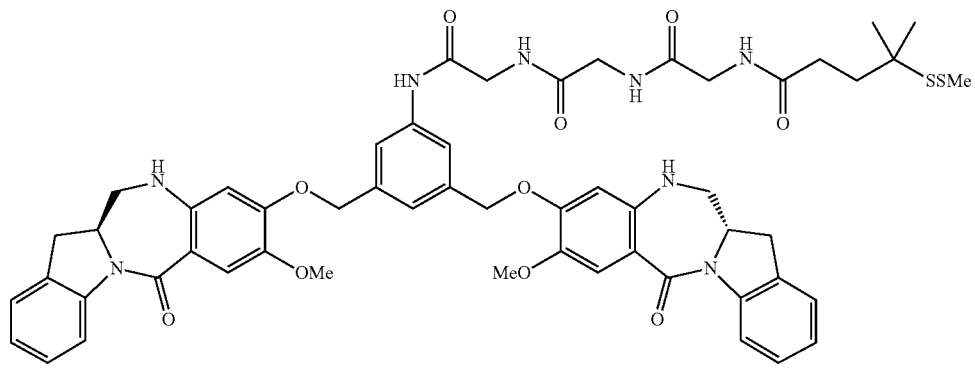

96a

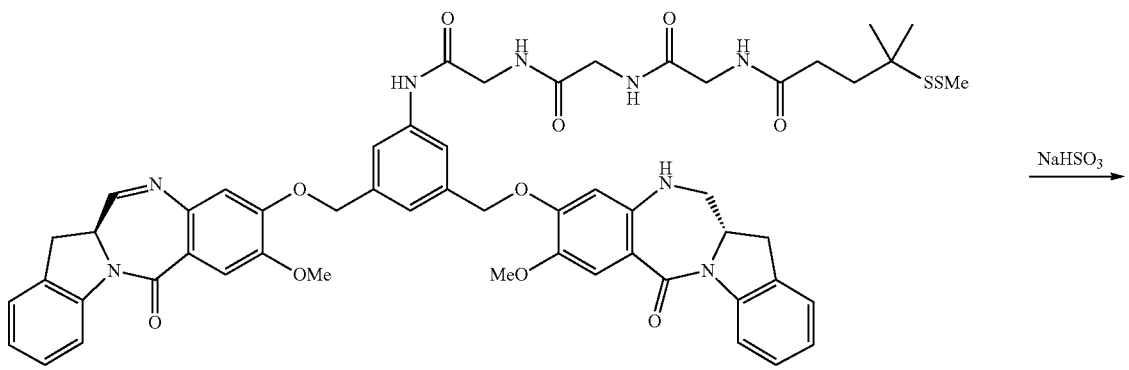

96

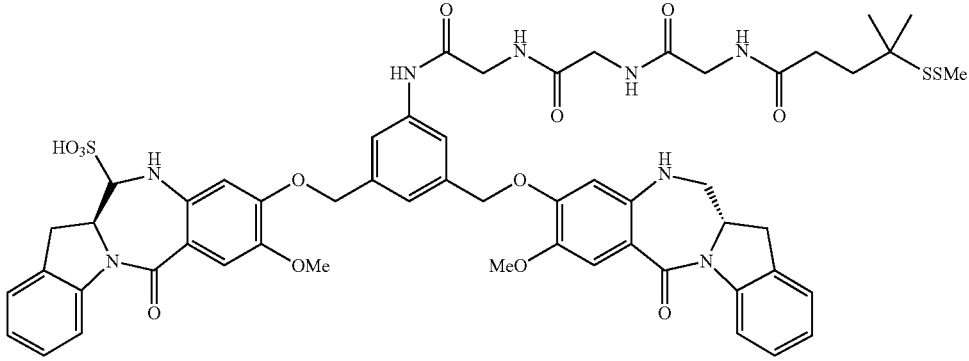

97

Step 6: Compound 95 (445 mg, 0.423 mmol) was dissolved in 1,2-dichloroethane (2.82 mL). Sodium triacytoxyborohydride (80 mg, 0.359 mmol) was added at room temperature and was stirred for 1 hour. The reaction was diluted with dichloromethane and washed with saturated ammonium chloride. The organic layer was washed with brine and dried to give of a mixture of compound 95, 96, and 96a (496 mg). This crude mixture was dissolved in 2-Propanol (39.17 mL) and water (19.59 mL). Sodium bisulfite (245 mg, 2.35 mmol) was added and was stirred at room temperature for 3.5 hours. The mixture was frozen and lyophilized to give a fluffy white solid that was purified by RPHPLC (C18, Acetonitrile/Water) to give compound 97 (54 mg, 10% yield) and compound 96a (24 mg, 5% yield). LCMS (compound 97)=4.83 min (15 min method) and LCMS (compound 96a)=8.05 min (15 min method).

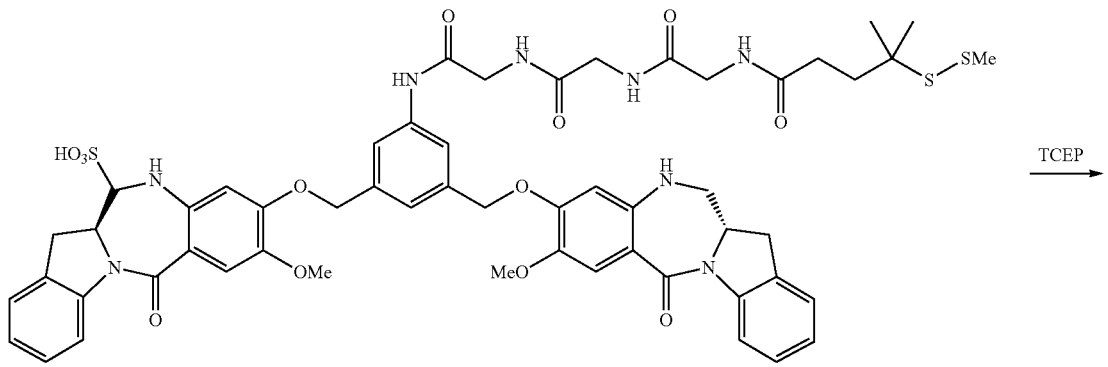

97

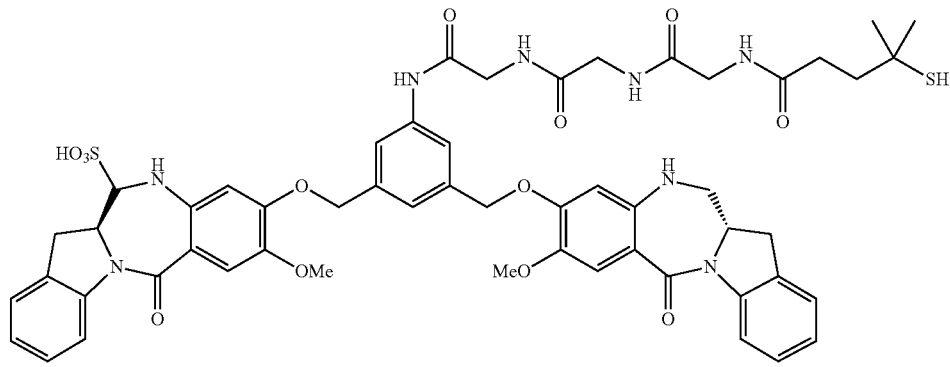

98

Step 7: To a stirred solution of compound 97 (54 mg, 0.047 mmol) in CH$_3$CN (3.85 mL) was added freshly prepared TCEP/pH 6.5 buffer solution (TCEP.HCl (46.7 mg) was dissolved in a few drops of deionized water, followed by saturated sodium bicarbonate dropwise until pH~6.5. The solution was diluted with 0.55 mL of pH=6.5, 1 M sodium phosphate buffer) and methanol (2.75 mL). The mixture was stirred at room temperature for 3 hours and then frozen and lyophilized. The solid was purified by RPHPLC (C18, Acetonitrile/water) to give (12S,12aS)-9-((3-(2-(2-(2-(4-mercapto-4-methylpentanamido)acetamido) acetamido)acetamido)-5-(((((S)-8-methoxy-6-oxo-11,12,12a,13-tetrahydro-6H-benzo[5,6][1,4]diazepino[1,2-a]indol-9-yl)oxy)methyl)benzyl)oxy)-8-methoxy-6-oxo-11,12,12a,13-tetrahydro-6H-benzo[5,6][1,4]diazepino[1,2-a]indole-12-sulfonic acid, compound 98 (2 mg, 4% yield). LCMS=4.32 min (15 min method). MS (m/z): 1089.3 (M−1)⁻.

Example 10

Synthesis of N-(2-((2-((2-((3,5-bis((((S)-8-methoxy-6-oxo-11,12,12a,13-tetrahydro-6H-benzo[5,6][1,4]diazepino[1,2-a]indol-9-yl)oxy)methyl)phenyl)amino)-2-oxoethyl)amino)-2-oxoethyl)amino)-2-oxoethyl)-4-mercapto-4-methylpentanamide (Compound 99)

after C18 purification (6.3 mg, 27% yield). LCMS=7.26 min (15 min method). MS (m/z): 1033.5 (M+Na)⁺.

Example 11

Preparation of huMOV19-14

A reaction containing 2.0 mg/mL huMOV19 antibody and 8 molar equivalents compound 14 (pretreated with 5-fold excess of sodium bisulfite in 90:10 DMA:water) in 50 mM HEPES (4-(2-hydroxyethyl)-1-piperazine ethanesulfonic acid) pH 8.5 buffer and 15% v/v DMA (N,N-Dimethylacetamide) cosolvent was allowed to conjugate for 6 hours at 25° C.

Post-reaction, the conjugate was purified and buffer exchanged into 250 mM Glycine, 10 mM Histidine, 1% sucrose, 0.01% Tween-20, 50 µM sodium bisulfite formulation buffer pH 6.2 using NAP desalting columns (Illustra Sephadex G-25 DNA Grade, GE Healthcare). Dialysis was performed in the same buffer for 20 hours at 4° C. utilizing Slide-a-Lyzer dialysis cassettes (ThermoScientific 20,000 MWCO).

The purified conjugate was found to have an average of 3.0 IGN91 molecules linked per antibody (by UV-Vis using

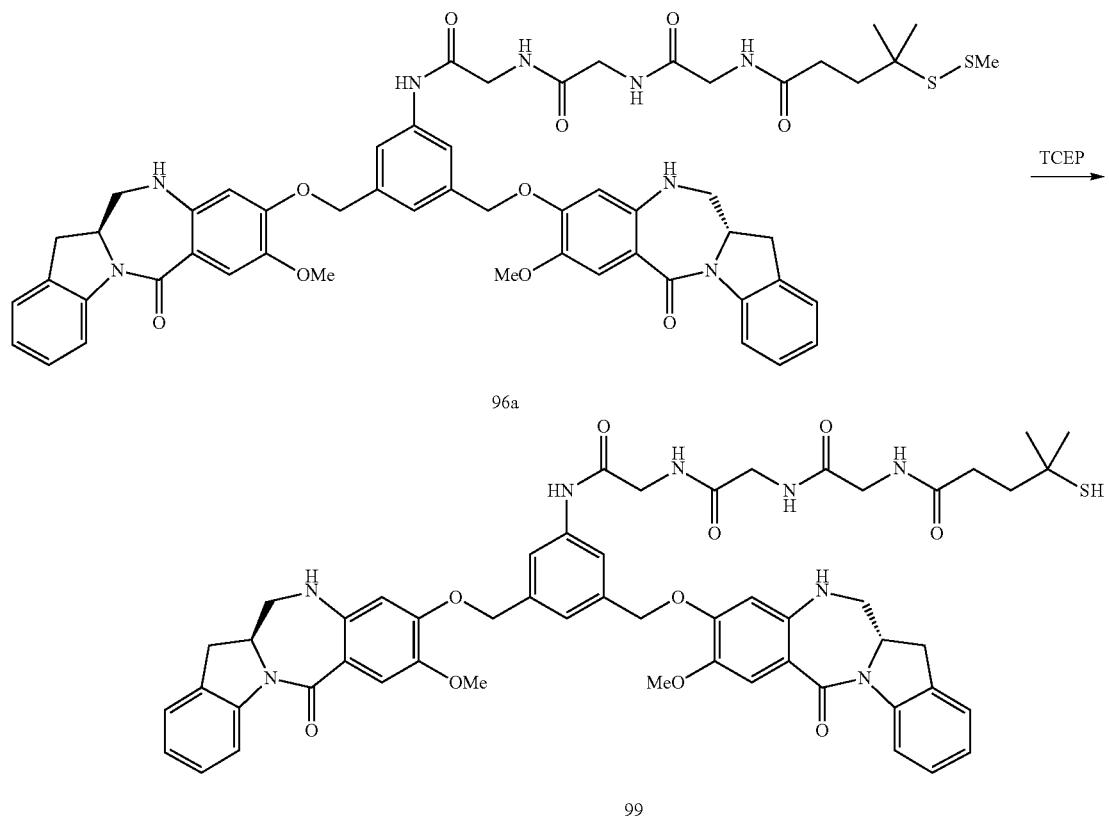

Compound 99 was prepared similarly as compound 98 in Example 9. N-(2-((2-((2-((3,5-bis((((S)-8-methoxy-6-oxo-11,12,12a,13-tetrahydro-6H-benzo[5,6][1,4]diazepino[1,2-a]indol-9-yl)oxy)methyl)phenyl)amino)-2-oxoethyl)amino)-2-oxoethyl)amino)-2-oxoethyl)-4-mercapto-4-methylpentanamide, compound 99 was obtained as a white solid molar extinction coefficients $\varepsilon_{330\ nm}$=15,280 cm⁻¹M⁻¹ and $\varepsilon_{280\ nm}$=30, 115 cm⁻¹M⁻¹ for compound 14, and $\varepsilon_{280\ nm}$=201,400 cm⁻¹M⁻¹ for huMOV19 antibody), 90% monomer (by size exclusion chromatography), <0.1% unconjugated compound 14 (by acetone precipitation, reverse-phase HPLC analysis) and a final protein concentration of 0.78 mg/ml. The conjugated antibody was found to be >87% intact by gel chip analysis. The MS spectrometry data is shown in FIG. 7A.

Example 12

Preparation of huMOV19-sulfo-SPDB-98

An in situ mix containing final concentrations of 3.9 mM compound 98 and 3 mM sulfo-SPDB linker in DMA containing 10 mM N,N-Diisopropylethyl amine (DIPEA) was incubated for 60 min before adding 20-fold excess of the resulting compound 98-sulfo-SPDB-NHS to a reaction containing 4 mg/ml huMOV19 antibody in 15 mM HEPES pH 8.5 (90:10 water: DMA). The solution was allowed to conjugate overnight at 25° C.

Post-reaction, the conjugate was purified and buffer exchanged into 100 mM Arginine, 20 mM Histidine, 2% sucrose, 0.01% Tween-20, 50 µM sodium bisulfite formulation buffer pH 6.2 using NAP desalting columns (Illustra Sephadex G-25 DNA Grade, GE Healthcare). Dialysis was performed in the same buffer over night at 4° C. utilizing Slide-a-Lyzer dialysis cassettes (ThermoScientific 10,000 MWCO).

The purified conjugate was found to have an average of 3.7 molecules of compound 98 linked per antibody (by SEC using molar extinction coefficients $\varepsilon_{330\ nm}=15,484\ cm^{-1}M^{-1}$ and $\varepsilon_{280\ nm}=30,115\ cm^{-1}M^{-1}$ for compound 98, and $\varepsilon_{280\ nm}=201,400\ cm^{-1}M^{-1}$ for huMOV19 antibody), 99% monomer (by size exclusion chromatography), and a final protein concentration of 0.18 mg/ml. The MS spectrometry data is shown in FIG. 7A.

Example 13

Preparation of huMOV19-35

A reaction containing 2.5 mg/mL huMOV19 antibody and 5 molar equivalents of compound 35, (pretreated with 5-fold excess of sodium bisulfite in 90:10 DMA:water) in 50 mM HEPES (4-(2-hydroxyethyl)-1-piperazine ethanesulfonic acid) pH 8.5 buffer and 15% v/v DMA (N,N-Dimethylacetamide) cosolvent was allowed to conjugate for 6 hours at 25° C.

Post-reaction, the conjugate was purified and buffer exchanged into 250 mM Glycine, 10 mM Histidine, 1% sucrose, 0.01% Tween-20, 50 µM sodium bisulfite formulation buffer pH 6.2 using NAP desalting columns (Illustra Sephadex G-25 DNA Grade, GE Healthcare). Dialysis was performed in the same buffer for 8 hours at room temperature utilizing Slide-a-Lyzer dialysis cassettes (ThermoScientific 10,000 MWCO).

The purified conjugate was found to have an average of 2.9 molecules of compound 35 linked per antibody (by UV-Vis using molar extinction coefficients $\varepsilon_{330\ nm}=15,484\ cm^{-1}M^{-1}$ and $\varepsilon_{280\ nm}=30,115\ cm^{-1}M^{-1}$ for IGN128, and $\varepsilon_{280\ nm}=201,400\ cm^{-1}M^{-1}$ for huMOV19 antibody), 97% monomer (by size exclusion chromatography), <1% unconjugated compound 35 (by acetone precipitation, reverse-phase HPLC analysis) and a final protein concentration of 1.4 mg/ml. The MS spectrometry data is shown in FIG. 7A.

Example 14

Preparation of huMOV19-63

A reaction containing 2.0 mg/mL huMOV19 antibody and 7 molar equivalents of compound 63 (pretreated with 5-fold excess of sodium bisulfite in 90:10 DMA:water) in 50 mM HEPES (4-(2-hydroxyethyl)-1-piperazine ethanesulfonic acid) pH 8.5 buffer and 15% v/v DMA (N,N-Dimethylacetamide) cosolvent was allowed to conjugate for 6 hours at 25° C.

Post-reaction, the conjugate was purified and buffer exchanged into 250 mM Glycine, 10 mM Histidine, 1% sucrose, 0.01% Tween-20, 50 µM sodium bisulfite formulation buffer pH 6.2 using NAP desalting columns (Illustra Sephadex G-25 DNA Grade, GE Healthcare). Dialysis was performed in the same buffer for 20 hours at 4° C. utilizing Slide-a-Lyzer dialysis cassettes (ThermoScientific 20,000 MWCO).

The purified conjugate was found to have an average of 2.7 molecules of compound 63 linked per antibody (by UV-Vis using molar extinction coefficients $\varepsilon_{330\ nm}=15,280\ cm^{-1}M^{-1}$ and $\varepsilon_{280\ nm}=30,115\ cm^{-1}M^{-1}$ for IGN131, and $\varepsilon_{280\ nm}=201,400\ cm^{-1}M^{-1}$ for huMOV19 antibody), 99% monomer (by size exclusion chromatography), <0.1% unconjugated compound 63 (by acetone precipitation, reverse-phase HPLC analysis) and a final protein concentration of 1.6 mg/ml. The conjugated antibody was found to be >90% intact by gel chip analysis. The MS spectrometry data is shown in FIG. 7B.

Example 15

Preparation of huMOV19-80

A reaction containing 2.0 mg/mL huMOV19 antibody and 7 molar equivalents of compound 80 (pretreated with 5-fold excess of sodium bisulfite in 90:10 DMA:water) in 50 mM HEPES (4-(2-hydroxyethyl)-1-piperazine ethanesulfonic acid) pH 8.5 buffer and 15% v/v DMA (N,N-Dimethylacetamide) cosolvent was allowed to conjugate for 6 hours at 25° C.

Post-reaction, the conjugate was purified and buffer exchanged into 250 mM Glycine, 10 mM Histidine, 1% sucrose, 0.01% Tween-20, 50 µM sodium bisulfite formulation buffer pH 6.2 using NAP desalting columns (Illustra Sephadex G-25 DNA Grade, GE Healthcare). Dialysis was performed in the same buffer for 20 hours at 4° C. utilizing Slide-a-Lyzer dialysis cassettes (ThermoScientific 20,000 MWCO).

The purified conjugate was found to have an average of 2.5 molecules of compound 80 linked per antibody (by UV-Vis using molar extinction coefficients $\varepsilon_{330\ nm}=15,280\ cm^{-1}M^{-1}$ and $\varepsilon_{280\ nm}=30,115\ cm^{-1}M^{-1}$ for compound 80, and $\varepsilon_{280\ nm}=201,400\ cm^{-1}M^{-1}$ for huMOV19 antibody), 99% monomer (by size exclusion chromatography), <0.1% unconjugated compound 80 (by acetone precipitation, reverse-phase HPLC analysis) and a final protein concentration of 2.4 mg/ml. The conjugated antibody was found to be >90% intact by gel chip analysis.

Example 16

Preparation of huMOV19-90

A reaction containing 2.0 mg/mL huMOV19 antibody and 3.9 molar equivalents of compound 90 (pretreated with 5-fold excess of sodium bisulfite in 95:5 DMA:50 mM succinate pH 5.5 for 4 hours at 25° C.) in 15 mM HEPES (4-(2-hydroxyethyl)-1-piperazine ethanesulfonic acid) pH 8.5 buffer and 15% v/v DMA (N,N-Dimethylacetamide) cosolvent was incubated for 4 hours at 25° C. Post-reaction, the conjugate was purified and buffer exchanged into 10 mM succinate, 50 mM sodium chloride, 8.5% w/v sucrose, 0.01% Tween-20, 50 µM sodium bisulfite pH 6.2 formulation buffer using NAP desalting columns (Illustra Sephadex G-25 DNA Grade, GE Healthcare). Dialysis was performed in the same buffer for 4 hours at room temperature and then overnight at 4° C. utilizing Slide-a-Lyzer dialysis cassettes (ThermoScientific 30,000 MWCO).

The purified conjugate was found to have a final protein concentration of 1.8 mg/ml and an average of 2.7 molecules of compound 90 linked per antibody (by UV-Vis using molar extinction coefficients $\varepsilon_{330\ nm}$=15,280 cm$^{-1}$M$^{-1}$ and $\varepsilon_{280\ nm}$=30,115 cm$^{-1}$M$^{-1}$ for IGN152, and $\varepsilon_{280\ nm}$=201,400 cm$^{-1}$M$^{-1}$ for huMOV19 antibody); 98.3% monomer (by size exclusion chromatography); and <1.1% unconjugated compound 90 (by acetone precipitation, reverse-phase HPLC analysis). The MS spectrometry data is shown in FIG. 7B.

Example 17

Preparation of huMOV19-49

A reaction containing 2.0 mg/mL huMOV19 antibody and 5 molar equivalents of compound 49 (pretreated with 5-fold excess of sodium bisulfite in 90:10 DMA:water) in 50 mM HEPES (4-(2-hydroxyethyl)-1-piperazine ethanesulfonic acid) pH 8.5 buffer and 10% v/v DMA (N,N-Dimethylacetamide) cosolvent was allowed to conjugate for 4 hours at 25° C.

Post-reaction, the conjugate was purified and buffer exchanged into 250 mM Glycine, 10 mM Histidine, 1% sucrose, 0.01% Tween-20, 50 µM sodium bisulfite formulation buffer pH 6.2 using NAP desalting columns (Illustra Sephadex G-25 DNA Grade, GE Healthcare). Dialysis was performed in the same buffer for 4 hours at room temperature utilizing Slide-a-Lyzer dialysis cassettes (ThermoScientific 20,000 MWCO).

The purified conjugate was found to have an average of 2.8 molecules of compound 49 linked per antibody (by UV-Vis using molar extinction coefficients $\varepsilon_{330\ nm}$=15,280 cm$^{-1}$M$^{-1}$ and $\varepsilon_{280\ nm}$=30,115 cm$^{-1}$M$^{-1}$ for compound 49, and $\varepsilon_{280\ nm}$=201,400 cm$^{-1}$M$^{-1}$ for huMOV19 antibody), 94% monomer (by size exclusion chromatography), <0.1% unconjugated compound 49 (by acetone precipitation, reverse-phase HPLC analysis) and a final protein concentration of 1.5 mg/ml. The conjugated antibody was found to be >95% intact by gel chip analysis. The MS spectrometry data is shown in FIG. 7C.

Example 18

Preparation of huMOV19-sulfo-SPDB-99

An in situ mix containing final concentrations of 1.95 mM compound 99 and 1.5 mM sulfo-SPDB Linker in DMA containing 10 mM N,N-Diisopropylethyl amine (DIPEA) was incubated for 20 min before capping with 4 mM maleimidopropionic acid MPA. A 6-fold excess of the resulting 99-sulfo-SPDB-NHS was added to a reaction containing 2.5 mg/ml huMOV19 antibody in 15 mM HEPES pH 8.5 (82:18 water:DMA). The solution was allowed to conjugate over night at 25° C.

Post-reaction, the conjugate was purified and buffer exchanged into 20 mM histidine, 50 mM sodium chloride, 8.5% sucrose, 0.01% Tween-20, 50 µM sodium bisulfite formulation buffer pH 6.2 using NAP desalting columns (Illustra Sephadex G-25 DNA Grade, GE Healthcare). Dialysis was performed in the same buffer over night at 4° C. utilizing Slide-a-Lyzer dialysis cassettes (ThermoScientific 10,000 MWCO).

The purified conjugate was found to have an average of 1.6 molecules of compound 99 linked per antibody (by UV/Vis using molar extinction coefficients $\varepsilon_{330\ nm}$=15,484 cm$^{-1}$M$^{-1}$ and $\varepsilon_{280\ nm}$=30, 115 cm$^{-1}$M$^{-1}$ for compound 99, and $\varepsilon_{280\ nm}$=201,400 cm$^{-1}$M$^{-1}$ for huMOV19 antibody), 99% monomer (by size exclusion chromatography), and a final protein concentration of 0.59 mg/ml. The MS spectrometry data is shown in FIG. 7C.

Example 19

Preparation of huMOV19-70

A reaction containing 2.0 mg/mL huMOV19 antibody and 5 molar equivalents of compound 70 (pretreated with 5-fold excess of sodium bisulfite in 90:10 DMA:water) in 50 mM HEPES (4-(2-hydroxyethyl)-1-piperazine ethanesulfonic acid) pH 8.5 buffer and 10% v/v DMA (N,N-Dimethylacetamide) cosolvent was allowed to conjugate for 4 hours at 25° C.

Post-reaction, the conjugate was purified and buffer exchanged into 20 mM Histidine, 100 mM Arginine, 2% sucrose, 0.01% Tween-20, 50 µM sodium bisulfite formulation buffer pH 6.2 using NAP desalting columns (Illustra Sephadex G-25 DNA Grade, GE Healthcare). After purification, dialysis was performed in the same buffer for 18 hours at 4° C. utilizing Slide-a-Lyzer dialysis cassettes (ThermoScientific 20,000 MWCO).

The purified conjugate was found to have an average of 3.0 molecules of compound 70 linked per antibody (by UV-Vis using molar extinction coefficients $\varepsilon_{330\ nm}$=15,484 cm$^{-1}$M$^{-1}$ and $\varepsilon_{280\ nm}$=30,115 cm$^{-1}$M$^{-1}$ for compound 70, and $\varepsilon_{280\ nm}$=201,400 cm$^{-1}$M$^{-1}$ for huMOV19 antibody), 94% monomer (by size exclusion chromatography), <0.1% unconjugated compound 70 (by acetone precipitation, reverse-phase HPLC analysis) and a final protein concentration of 1.3 mg/ml.

Example 20

Preparation of huMOV19-23

A reaction containing 2.5 mg/mL huMOV19 antibody and 4 molar equivalents of compound 23 (pretreated with 5-fold excess of sodium bisulfite in 90:10 DMA:water) in 50 mM HEPES (4-(2-hydroxyethyl)-1-piperazine ethanesulfonic acid) pH 8.5 buffer and 15% v/v DMA (N,N-Dimethylacetamide) cosolvent was allowed to conjugate for 6 hours at 25° C.

Post-reaction, the conjugate was purified and buffer exchanged into 250 mM Glycine, 10 mM Histidine, 1% sucrose, 0.01% Tween-20, 50 µM sodium bisulfite formulation buffer pH 6.2 using NAP desalting columns (Illustra Sephadex G-25 DNA Grade, GE Healthcare). Dialysis was performed in the same buffer for 8 hours at room temperature utilizing Slide-a-Lyzer dialysis cassettes (ThermoScientific 10,000 MWCO).

Figure 7D:
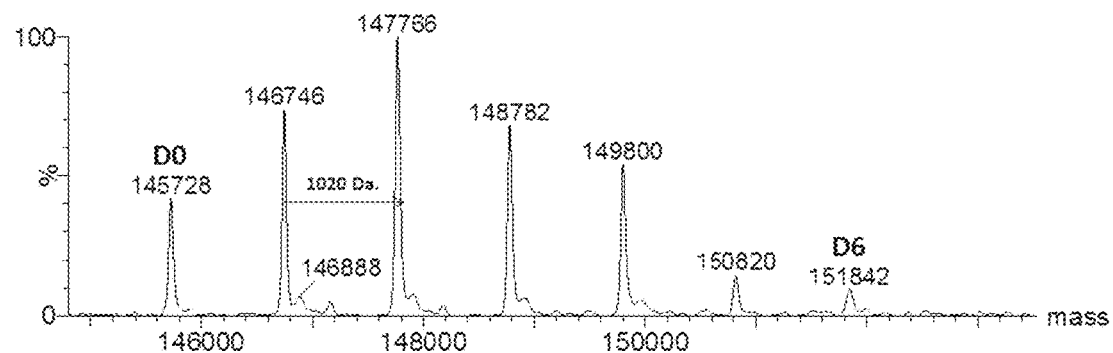

The purified conjugate was found to have an average of 2.8 molecules of compound 23 linked per antibody (by UV-Vis using molar extinction coefficients $\varepsilon_{330\ nm}$=15,484 cm$^{-1}$M$^{-1}$ and $\varepsilon_{280\ nm}$=30, 115 cm$^{-1}$M$^{-1}$ for compound 23, and $\varepsilon_{280\ nm}$=201,400 cm$^{-1}$M$^{-1}$ for huMOV19 antibody), 98% monomer (by size exclusion chromatography), <3% unconjugated compound 23 (by acetone precipitation, reverse-phase HPLC analysis) and a final protein concentration of 1.3 mg/ml. The MS spectrometry data is shown in FIG. 7D.

Example 21

Flow Cytometry Assay for Binding Affinity of huMOV19-14, huMOV19-90 and huMOV19-107 Conjugates 100 μl/well of the conjugate huMOV19-14, huMOV19-90 or huMOV19-107 or the antibody huMOV19 were diluted in FACS buffer (1% BSA, 1×PBS) in a 96-well plate (Falcon, round bottom) at a starting concentration of $3 \times 10^{-8}$ M in duplicate and serially diluted 3-fold in FACS buffer at 4° C. T47D cells (human breast tumor) grown in RPMI-1640 (Life Technologies) supplemented with heat-inactivated 10% FBS (Life Technologies), 0.1 mg/ml gentamycin (Life Technologies) and 0.2 IU bovine insulin/ml (Sigma) were washed once in PBS and removed with versene (Life Technogies). T47D cells were resuspended in growth media (see above) to neutralize versene and counted on a Coulter counter. Cells were then washed twice in cold FACS buffer, centrifuging in between washes at 1200 rpm for 5 min. 100 μl/ml of $2 \times 10^4$ cells/well were added to wells containing the conjugate, antibody or FACS buffer only and incubated at 4° C. for 2 hr. After incubation, cells were centrifuged as before and washed once in 200 μl/well cold FACS buffer. Cells were then stained with 200 μl/well FITC-conjugated Goat Anti-Human-IgG-Fcγ secondary antibody (controls included were unstained cells and those stained with secondary antibody only) for 40 min at 4° C., centrifuged and washed once in 200 μl/well cold PBS-D. Cells were fixed in 200 μl/well 1% formaldehyde/PBS-D and stored at 4° C. After storage, cellular surface staining of conjugate or antibody was detected using flow cytometry on a FACS Calibur (BD Biosciences). The geometric means were plotted against the log concentration of the conjugate or antibody using GraphPad Prism and the $EC_{50}$ was calculated via non-linear 4-parameter logistic regression analysis.

Figure 15A:
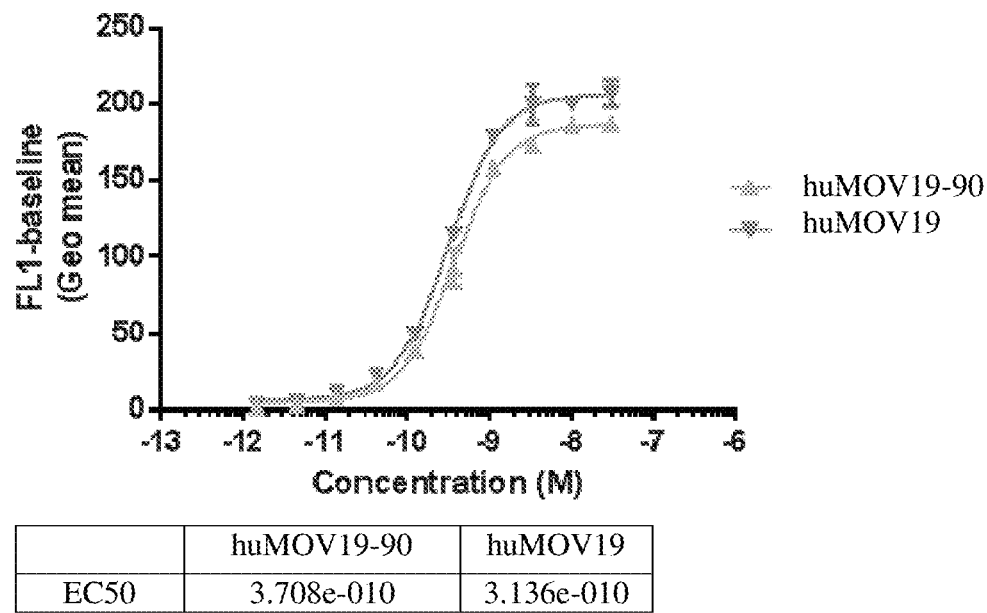
FIGS. 15A and 15B shows binding affinity of huMOV19-90 conjugate as compared to unconjugated antibody huMOV19 on T47D cells.
Figure 15B:
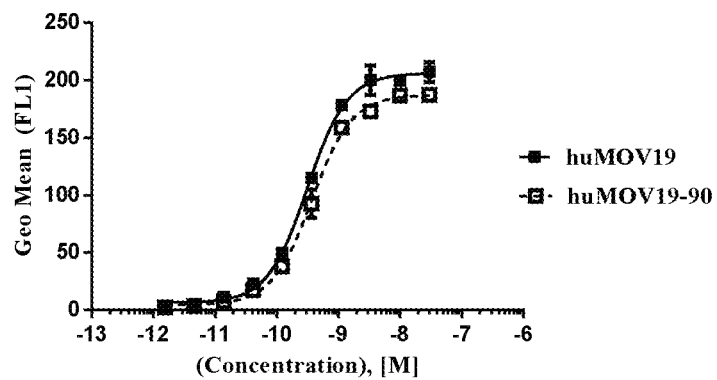

The binding assay was repeated for huMOV19-90 conjugate and the data is shown in FIG. 15B.

As shown in FIG. 1, FIG. 15A, FIG. 15B and FIG. 20, the conjugates binds similarly to the surface of T47D cells expressing the target antigen as the unconjugated antibody in flow cytometry, thereby demonstrating that binding is not affected by the conjugation process.

Example 22

Cytotoxicity Assay for huMOV19-14 Conjugate

100 μl/well of huMOV19-14 conjugate was diluted in RPMI-1640 (Life Technologies) supplemented with heat-inactivated 10% FBS (Life Technologies) and 0.1 mg/ml gentamycin (Life Technologies) in a 96-well plate (Corning, flat bottom) at starting concentrations of $3.5 \times 10^{-9}$ M to $3.5 \times 10^{-8}$ M in triplicate and serially diluted 3-fold in media above at ambient temperature. KB cells (buccal epithelial tumor) grown in EMEM (ATCC) supplemented with heat-inactivated 10% FBS (Life Technologies) and 0.1 mg/ml gentamycin (Life Technologies) were washed once in PBS and removed with 0.05% trypsin-EDTA (Life Technogies). KB cells were resuspended in growth media (see above) to neutralize trypsin and counted on a Coulter counter. 100 μl/ml of $1 \times 10^3$ cells/well were added to wells containing the conjugate or media only and incubated in a 37° C. incubator with 5% $CO_2$ for 5 days with and without 1 μM blocking anti-FOLR1 antibody (huMOV19). Total volume is 200 μl/well. After incubation, cell viability was analyzed by addition of 20 μl/well WST-8 (Dojindo) and allowed to develop for 2 hr. Absorbance was read on a plate reader at 450 and 620 nm. Absorbances at 620 nm were subtracted from absorbances at 450 nm. Background in wells containing media only was further subtracted from corrected absorbances and surviving fraction (SF) of untreated cells was calculated in Excel. An XY graph of ADC concentration (M) vs. SF was created using Graph Pad Prism.

As shown in FIG. 2, the conjugate is highly potent against the KB cells with an $IC_{50}$ of $4 \times 10^{-12}$ M. Addition of an excess of unconjugated antibody significantly reduce the cytotoxic effect, demonstrating antigen-specificity.

Example 23

Bystander Cytotoxicity Assay for huMOV19-14 and huMOV19-90 Conjugates

100 μl/well of huMOV19-14 or huMOV19-90 was diluted in RPMI-1640 (Life Technologies) supplemented with heat-inactivated 10% FBS (Life Technologies), 0.1 mg/ml gentamycin (Life Technologies) and βME (Life Technologies) in a 96-well plate (Falcon, round bottom) at concentrations between 1 e-10 M to 4 e-10 M in sextuplicate. Both 300.19 cells (mouse) expressing recombinant FOLR1 (FR1#14) or no expression vector (parental) were counted on a Coulter counter. 50 μl/ml of 1000 FR1#14 cells/well were added to wells containing the conjugate or media only, 50 μl/ml of 2000 parental cells/well were added to wells containing the conjugate or media only and both FR1#14 and parental cells were added together to wells containing the conjugate or media only. All plates were incubated in a 37° C. incubator with 5% $CO_2$ for 4 days. Total volume was 150 μl/well. After incubation, cell viability was analyzed by addition of 75 μl/well Cell Titer Glo (Promega) and allowed to develop for 45 min. Luminescence was read on a luminometer and background in wells containing media only was subtracted from all values. A bar graph of the average of each cell treatment was graphed using Graph Pad Prism.

Figure 3:
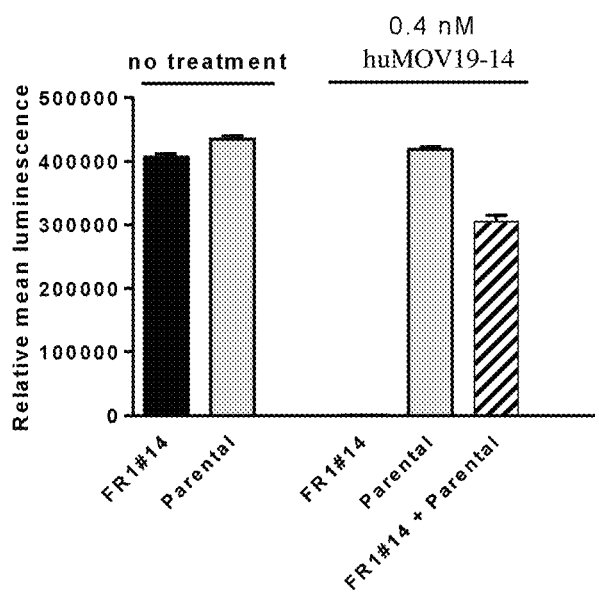
FIG. 3 shows that the huMOV19-14 conjugate exhibits weak bystander cytotoxic effect on the neighboring antigen-negative cells.

As shown in FIG. 3, the conjugate huMOV19-14 exhibits weak bystander cytotoxic effect on the neighboring antigen-negative cells.

Figure 13:
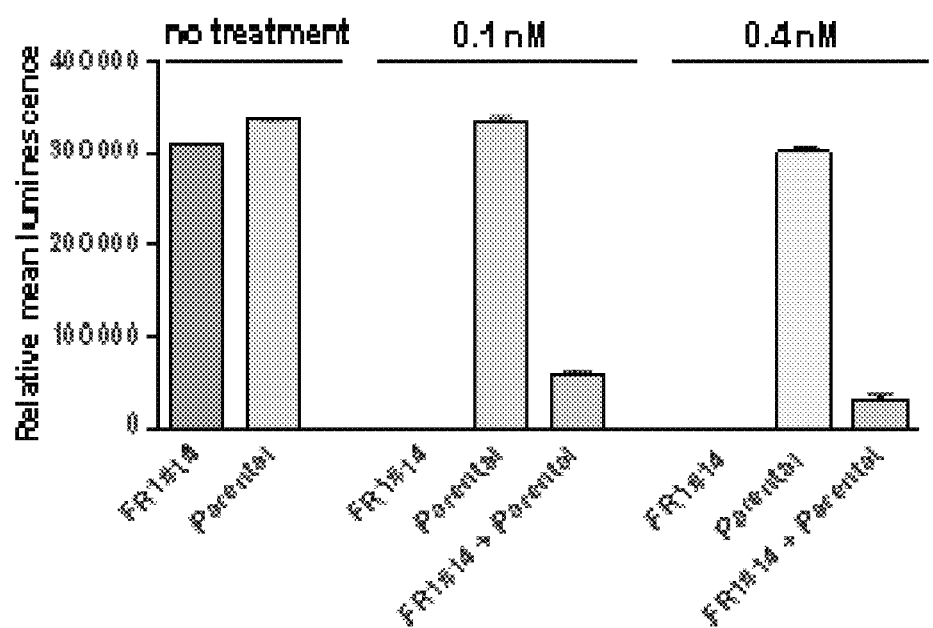
FIG. 13 shows that the huMOV19-90 conjugate exhibits strong bystander cytotoxic effect on the neighboring antigen-negative cells.

As shown in FIG. 13, the conjugate huMov19-90 exhibits strong bystander killing activity.

Example 24

In Vitro Cytotoxicity Assay for huMy9-6-14 Conjugate

Dilutions of conjugates were added to wells of 96-well plates containing $2 \times 10^3$ to $1 \times 10^4$ cells per well in appropriate growth media. Control wells containing cells and the medium but lacking test compounds, as well as wells contained medium only, were included in each assay plate. The plates were incubated for four to six days at 37° C. in a humidified atmosphere containing 6% $CO_2$. WST-8 reagent, 10% v/v, (Dojindo Molecular Technologies, Gaithersburg, Md.), was then added to the wells, and the plates were incubated at 37° C. for 2 to 6 h. Then the absorbance was measured on a plate-reader spectrophotometer in the dual wavelength mode 450 nm/650 nm, and the absorbance at the 650 nm (non-specific light scattering by cells) was subtracted. The apparent surviving fraction of cells in each well was calculated by first correcting for the medium background absorbance, and then dividing each value by the average of the values in the control wells (non-treated cells).

As shown in FIG. 3, the conjugate is highly potent against various antigen positive cancer cells; while antigen negative L-540 cells remain viable when exposed to the same conjugate.

Example 25

Bystander Cytotoxicity Assay for huMy9-6-14 Conjugate

Preliminary tests were done to determine the concentration of huMy9-6-14 that was not cytotoxic to the antigen-negative RADA-1 cells, but killed all of the antigen-positive KARA cells. RADA-1 (500 cells per well) and KARA (500, 1000, 2000, 4000 cells per well) were plated in 96-well round bottomed plates. Dilutions of huMy9-6-14 were prepared in the cell culture medium (RPMI1640 medium supplemented with 10% heat inactivated fetal bovine serum and 50 mg/L gentamicin) and added to the cells. Plates were incubated for 4 days at 37° C., and viability of the cells in each well was determined using WST-8 reagent (Dojindo Molecular Technologies, Inc.). To test the bystander potency of the conjugates, RADA-1 and KARA cells were mixed together at different ratios (500 RADA-1 cells plus no KARA cells; 500 RADA-1 cells plus 500 KARA cells; 500 RADA-1 cells plus 1000 KARA cells; 500 RADA-1 cells plus 2000 KARA cells; 500 RADA-1 cells plus 4000 KARA cells), and plated in 96-well round bottomed plates. Then 1.0e-9M or 5.0e-10M of huMy9-6-14—the concentrations that were not cytotoxic to RADA-1 cells but killed all KARA cells—were added to the cell mixtures. Plates were incubated for 4 days at 37° C., and viability of RADA-1 cells in each well was determined using WST-8 reagent (Dojindo Molecular Technologies, Inc.). The absorbance was measured on a plate-reader spectrophotometer in the dual wavelength mode 450 nm/650 nm, and the absorbance at the 650 nm (non-specific light scattering by cells) was subtracted.

Figure 5A:
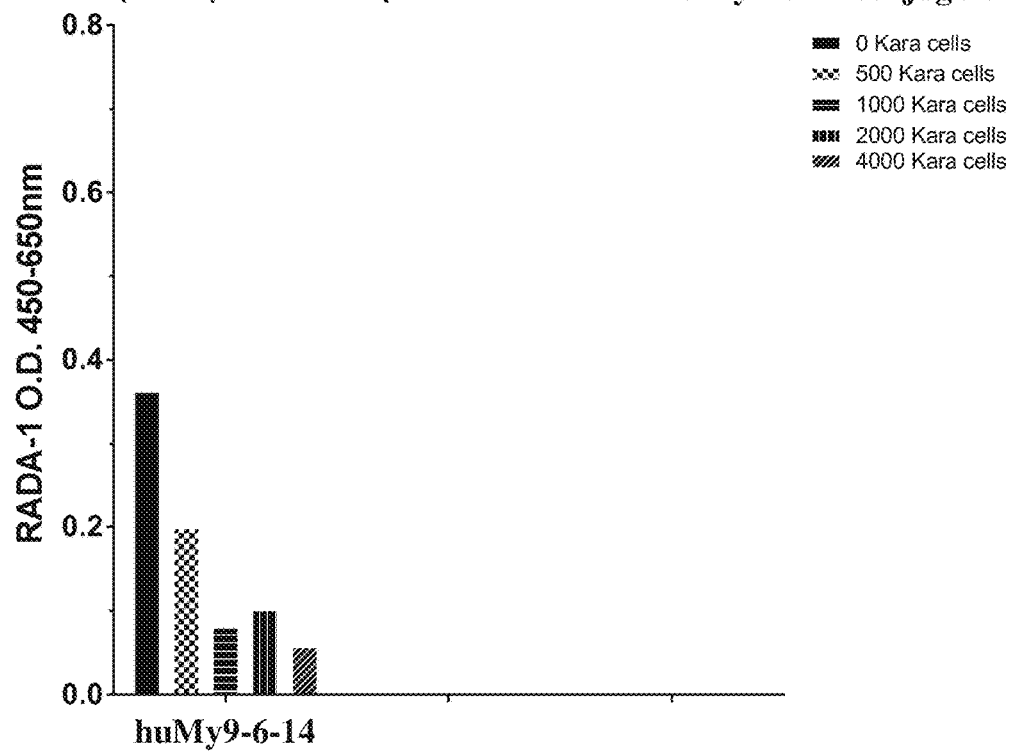
FIGS. 5A and 5B show that the huMy9-6-14 conjugate exhibits bystander cytotoxic effect on the neighboring antigen-negative cells.
Figure 5B:
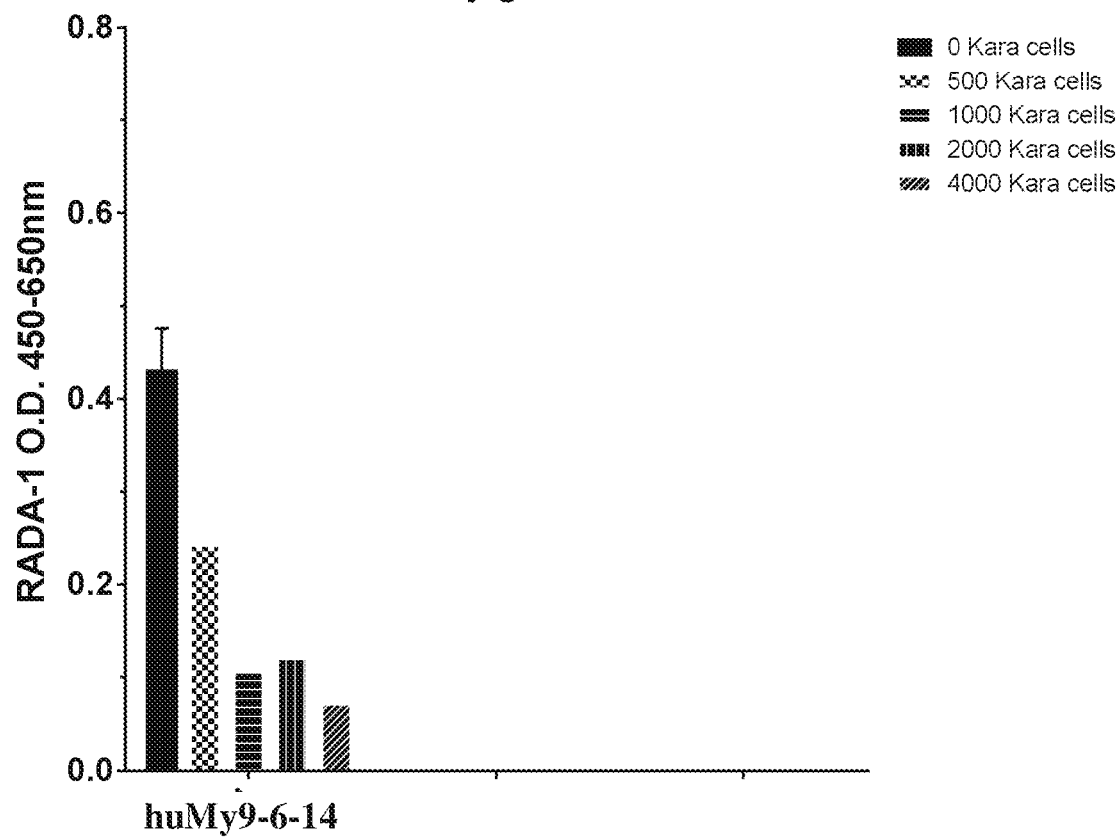

As shown in FIG. 5, the conjugate exhibits bystander killing effect on the neighboring antigen-negative cells.

Example 26

Antitumor Activity of Single-dose huMOV19-80 and huMOV19-90 Against NCI-H2110 NSCLC Xenografts in Female SCID Mice Female CB.17 SCID mice, 6 weeks old, were received from Charles River Laboratories. Mice were inoculated with $1\times10^7$ NCI-H2110 tumor cells suspended in 0.1 ml 50% matrigel/serum free medium by subcutaneous injection in the right flank. When tumor volumes reached approximately 100 mm$^3$ (day 7 post inoculation), animals were randomized based on tumor volume into 5 groups of 6 mice each. Mice received a single IV administration of vehicle control (0.2 ml/mouse), huMOV19-80 or huMOV19-90 at 5 and 25 µg/kg based on huMOV19-80 or huMOV19-90 concentration on day 1 (day 8 post inoculation). huMOV19 is a humanized monoclonal antibody that selectively binds to folate receptor 1 (FOLR1).

Tumor size was measured twice to three times weekly in three dimensions using a caliper. The tumor volume was expressed in mm$^3$ using the formula V=Length×Width×Height×½. A mouse was considered to have a partial regression (PR) when tumor volume was reduced by 50% or greater, complete tumor regression (CR) when no palpable tumor could be detected. Tumor volume was determined by StudyLog software. Tumor growth inhibition (T/C Value) was determined using the following formula:

T/C (%)=Median tumor volume of the treated/Median tumor volume of the control×100.

Tumor volume was determined simultaneously for treated (T) and the vehicle control (C) groups when tumor volume of the vehicle control reached predetermined size of 1000 mm$^3$. The daily median tumor volume of each treated group was determined, including tumor-free mice (0 mm$^3$). According to NCI standards, a T/C≤42% is the minimum level of anti-tumor activity. A T/C<10% is considered a high anti-tumor activity level.

As shown in FIG. 6, the huMOV19-90 conjugate is highly active at both 5 and 25 µg/kg dose; while huMOV19-80 conjugate is highly active at 25 µg/kg dose.

Example 27

Preparation of huML66-90

A reaction containing 2.0 mg/mL huML66 antibody, an anti-EGFR antibody (see WO 2012/058592, incorporated herein by reference in its entirety), and 3.5 molar equivalents compound 90 (pretreated with 5-fold excess of sodium bisulfite in 90:10 DMA:50 mM succinate pH 5.5 for 4 hours at 25° C.) in 15 mM HEPES (4-(2-hydroxyethyl)-1-piperazine ethanesulfonic acid) pH 8.5 buffer and 10% v/v DMA (N,N-Dimethylacetamide) cosolvent was incubated for 4 hours at 25° C. Post-reaction, the conjugate was purified and buffer exchanged into 20 mM histidine, 50 mM sodium chloride, 8.5% w/v sucrose, 0.01% Tween-20, 50 µM sodium bisulfite pH 6.2 formulation buffer using NAP desalting columns (Illustra Sephadex G-25 DNA Grade, GE Healthcare). Dialysis was performed in the same buffer for 4 hours at room temperature and then overnight at 4° C. utilizing Slide-a-Lyzer dialysis cassettes (ThermoScientific 30,000 MWCO).

Figure 8:
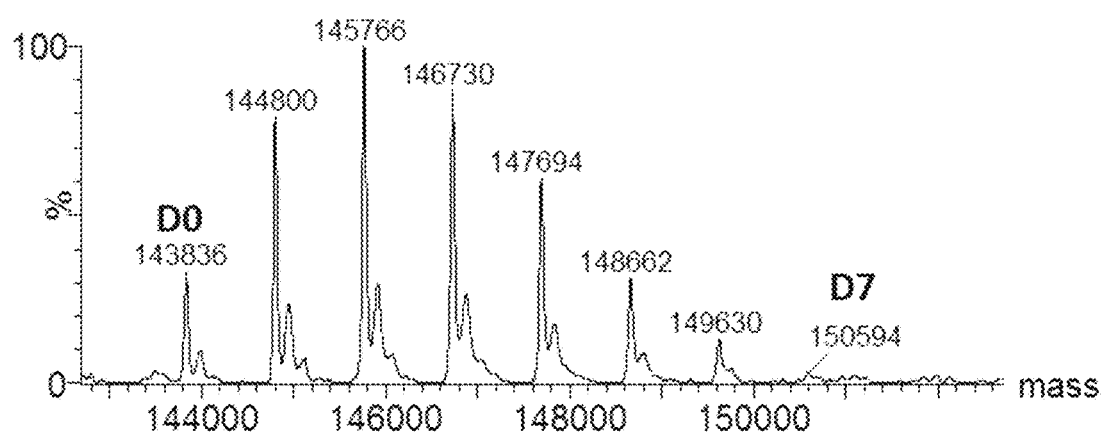
FIG. 8 shows mass spectrometry profile of huML66-90 conjugate.

The purified conjugate was found to have a final protein concentration of 0.9 mg/ml and an average of 2.7 molecules of compound 90 linked per antibody (by UV-Vis using molar extinction coefficients $\varepsilon_{330\ nm}$=15,280 cm-1M-1 and $\varepsilon_{280\ nm}$=30, 115 cm-1M-1 for compound 90, and $\varepsilon_{280\ nm}$=205,520 cm-1M-1 for huML66 antibody); 99.1% monomer (by size exclusion chromatography); and <1% unconjugated IGN149 (dual column, reverse-phase HPLC analysis). The MS spectrometry data is shown in FIG. 8.

Example 28

In Vitro Cytotoxic Assays for huML66-90 Conjugate

The ability of huML66-90 conjugate to inhibit cell growth was measured using in vitro cytotoxicity assays. Target cells were plated at 1-2,000 cells per well in 100 µL in complete RPMI media (RPMI-1640, 10% fetal bovine serum, 2 mM glutamine, 1% penicillin-streptomycin, all reagents from Invitrogen). Antibodies were diluted into complete RPMI media using 3-fold dilution series and 100 µL were added per well. The final concentration typically ranged from $3\times10$-8 M to $4.6\times10$-12 M. Cells were incubated at 37° C. in a humidified 5% CO2 incubator for 5-6 days. Viability of remaining cells was determined by colorimetric WST-8 assay (Dojindo Molecular Technologies, Inc., Rockville, Md., US). WST-8 is reduced by dehydrogenases in living cells to an orange formazan product that is soluble in tissue culture medium. The amount of formazan produced is directly proportional to the number of living cells. WST-8 was added to 10% of the final volume and plates were incubated at 37° C. in a humidified 5% CO2 incubator for an additional 2-4 hours. Plates were analyzed by measuring the absorbance at 450 nm (A450) in a multiwell plate reader. Background A450 absorbance of wells with media and WST-8 only was subtracted from all values. The percent viability was calculated by dividing each treated sample value by the average value of wells with untreated cells. Percent viability=100*(A450 treated sample−A450 background)/(A450 untreated sample−A450 background). The percent viability value was plotted against the antibody concentration in a semi-log plot for each treatment. Dose-response curves were generated by non-linear regression and the $EC_{50}$ value of each curve was calculated using GraphPad Prism (GraphPad software, San Diego, Calif.).

In Vitro Cytotoxic Activity

Figure 9:
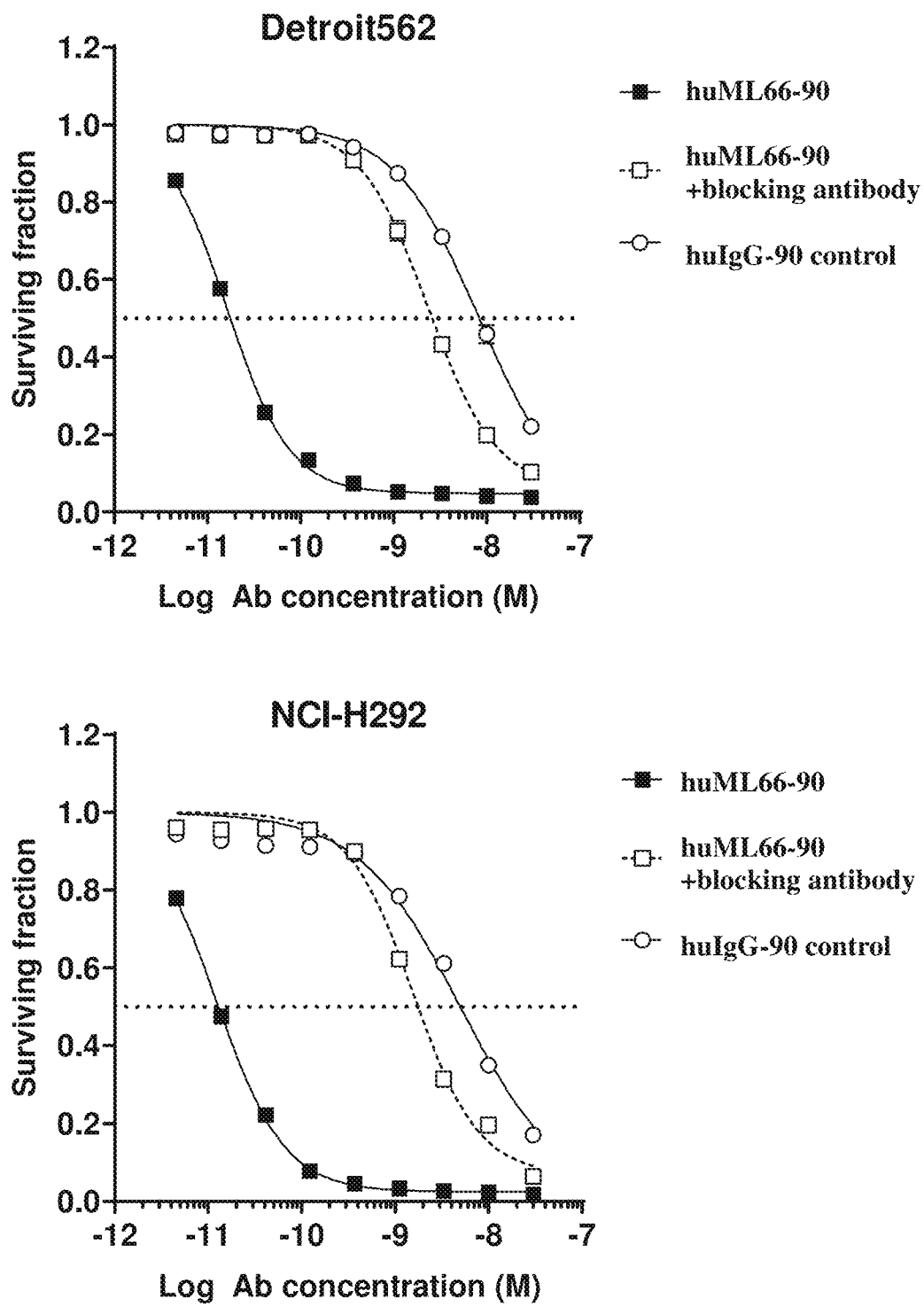
FIG. 9 shows in vitro cytotoxicity and specificity of huML66-90 conjugate.

The in vitro cytotoxicity of huML66-90 conjugate was evaluated in the presence and absence of excess unconjugated antibody and compared to the activity of a non-specific huIgG-90 conjugate in EGFR-expressing cells and the results from a typical cytotoxicity assay are shown in FIG. 9. The huML66-90 conjugate resulted in specific cell killing of Detroit-562 SCC-HN cells with an $EC_{50}$ value of 16 μM. The presence of excess unconjugated antibody significantly reduced activity and resulting in an $EC_{50}$ value of approximately 2 nM. Similarly, huIgG-90 conjugate with a non-binding huIgG control antibody resulted in cell killing with an $EC_{50}$ value of approximately 8 nM.

Likewise, the huML66-90 conjugate resulted in specific cell killing of NCI-H292 NSCLC cells with an $EC_{50}$ value of 12 pM. The presence of excess unconjugated antibody significantly reduced activity and resulting in an $EC_{50}$ value of approximately 2 nM. Similarly, huIgG-90 conjugate with a non-binding huIgG control antibody resulted in cell killing with an $EC_{50}$ value of approximately 8 nM.

Similarly, specific cell killing of NCI-H1703 cells were also observed.

TABLE 1

| Conjugate | Detroit $EC_{50}$ in pM | NCI-H292 $EC_{50}$ in pM | NCI-H1703 $EC_{50}$ in pM |
| --- | --- | --- | --- |
| huML66-90 | 16 | 12 | 20 |
| huML66-90 + block | 2,350 | 1,570 | 2,140 |
| huIgG-90 ctrl | 8,350 | 8,350 | N/A |

Example 29

In Vitro Cytotoxic Activity for huMOV19-90

100 μl/well of huMOV19-90 conjugate was each diluted in RPMI-1640 (Life Technologies) supplemented with heat-inactivated 10% FBS (Life Technologies) and 0.1 mg/ml gentamycin (Life Technologies) in a 96-well plate (Corning, flat bottom) at starting concentrations of 3.5e-9 M and to 3.5 e-8 M in triplicate and serially diluted 3-fold in media above at ambient temperature. KB cells (buccal epithelial tumor), grown in EMEM (ATCC) supplemented with heat-inactivated 10% FBS (Life Technologies) and 0.1 mg/ml gentamycin (Life Technologies), were washed once in PBS and removed with 0.05% trypsin-EDTA (Life Technogies). Other cells tested were NCI-H2110 (NSCLC) and T47D (breat epthelial) grown in RPMI-1640 (LifeTechnologies) supplemented with heat-inactivated 10% FBS (Life Technologies) and 0.1 mg/ml gentamycin (Life Technologies). T47D media also was supplemented with 0.2 IU/ml bovine insulin. All cells were resuspended in growth media (see above) to neutralize trypsin and counted using a hemacytometer. 100 μl/ml of 1000 KB cells/well or 2000 T47D and NCI-H2110 cells/well were added to wells containing the conjugate or media only and incubated in a 37° C. incubator with 5% $CO_2$ for 5 days with and without 1 μM blocking anti-FOLR1 antibody (huMOV19). Total volume is 200 μl/well. The starting concentration of each conjugate on KB cells was 3.5e-9 M and for T47D and NCI-H2110 cells, the starting concentration of each conjugate was 3.5e-8 M. After incubation, cell viability was analyzed by addition of 20 μl/well WST-8 (Dojindo) and allowed to develop for 2 hr. Absorbance was read on a plate reader at 450 and 620 nm. Absorbances at 620 nm were subtracted from absorbances at 450 nm. Background in wells containing media only was further subtracted from corrected absorbances and surviving fraction (SF) of untreated cells was calculated in Excel. An XY graph of ADC concentration (M) vs. SF was created using Graph Pad Prism.

Figure 10:
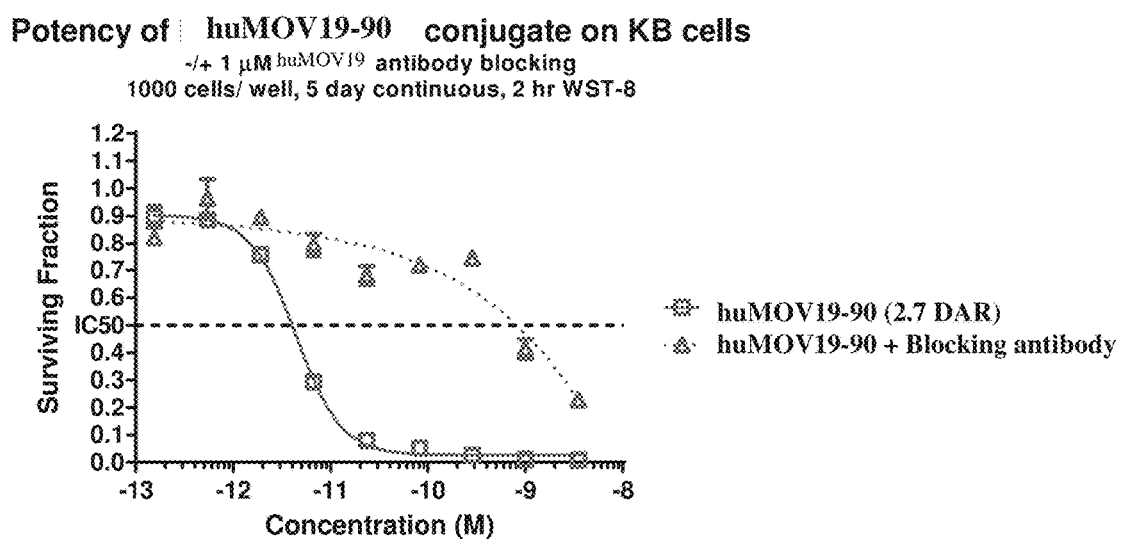
FIGS. 10, 11 and 12 show in vitro cytotoxicity and specificity of huMOV19-90 conjugate.
Figure 11:
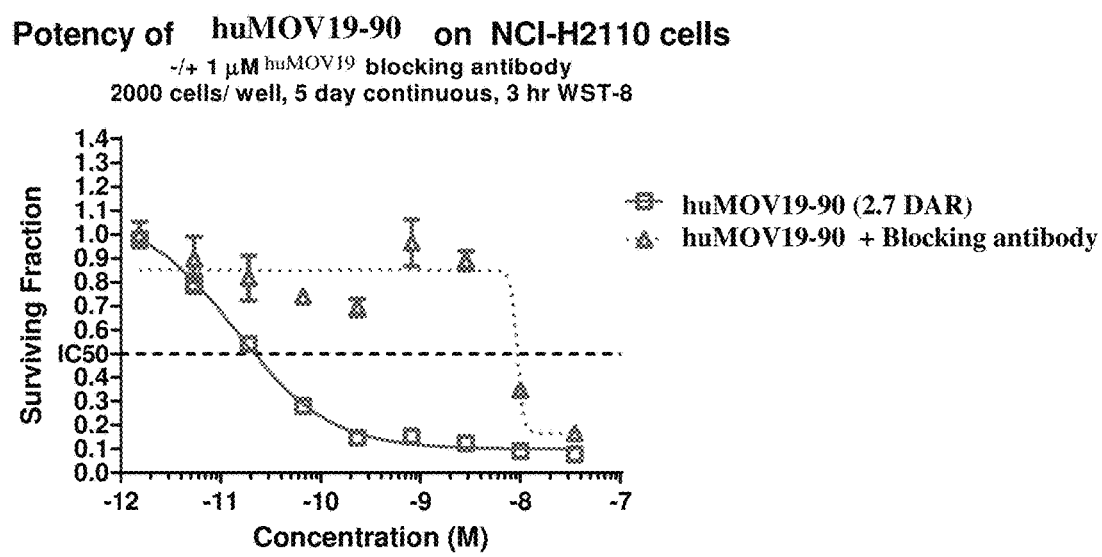
Figure 12:
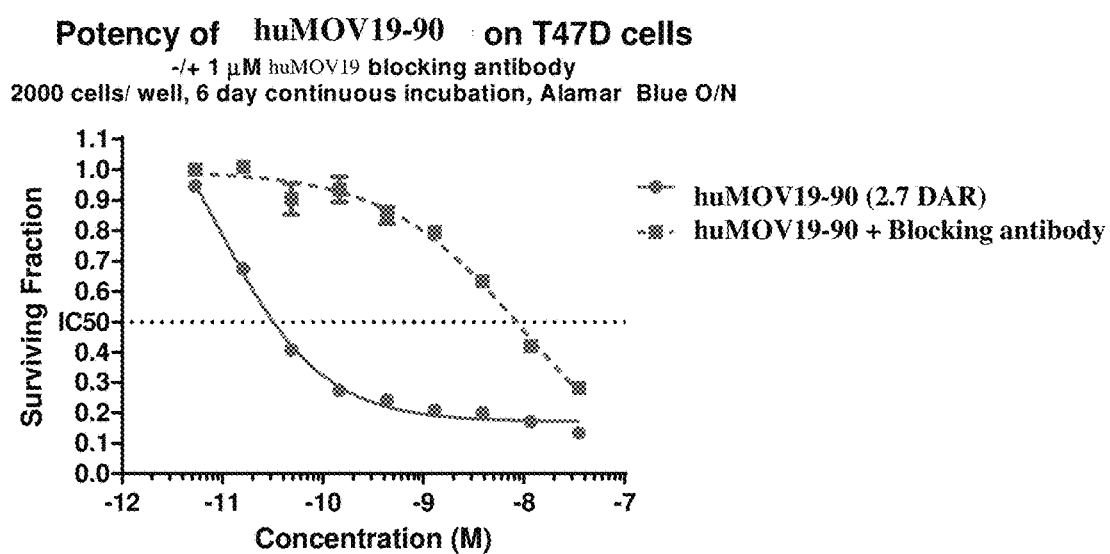

As shown in FIGS. 10-12 and Table 2, the huMOV19-90 conjugate is highly potent against the KB cells, T47 D cells and NCI-H2110 cells. Addition of an excess of unconjugated antibody significantly reduce the cytotoxic effect, demonstrating antigen-specificity.

TABLE 2

| | KB | | NCI-H2110 | | T47D | |
| --- | --- | --- | --- | --- | --- | --- |
| | −Block | +Block | −Block | +Block | −Block | +Block |
| $IC_{50}$ | 4e-12M | 8e-10M | 2e-11M | 1e-8M | 3e-11M | 8e-9M |

In another experiment, the ability of the conjugates to inhibit cell growth was measured using a WST-8-based in vitro cytotoxicity assay. Cells in 96-well plates (typically, 1×10³ per well) were treated with the conjugate at various concentrations in an appropriate cell culture medium with a total volume of 0.2 ml. Control wells containing cells and the medium but lacking test compounds, and wells containing medium only, were included in each assay plate. The plates were incubated for 4 to 6 days at 37° C. in a humidified atmosphere containing 6% $CO_2$. WST-8 reagent (10%, volume/volume; Dojindo Molecular Technologies) was then added to the wells, and the plates were incubated at 37° C. for 2 to 6 hours depending on a cell line. Then, the absorbance was measured on a plate reader spectrophotometer in the dual-wavelength mode 450 nm/620 nm, and the absorbance at the 620 nm (nonspecific light scattering by cells) was subtracted. The resulting $OD_{450}$ values were utilized to calculate apparent surviving fractions of cells using GraphPad Prism v4 (GraphPad software, San Diego, Calif.). The apparent surviving fraction of the cells in each well was calculated by first correcting for the medium background absorbance and then dividing each value by the average of the values in the control wells (non-treated cells). Dose response curves were generated by non-linear regression using a sigmoidal curve fit with variable slope in Graph Pad Prism. $IC_{50}$ (inhibitory concentration 50%) was generated by the software.

The conjugates were active against the tested cell lines Ishikawa (endometrial cancer), KB (cervical cancer) and NCI-H2110 (non-small cell lung carcinoma) as shown in FIG. 21 and Table 3. The cell-killing activity was FOLR1-dependent, since an excess of unmodified huMOV19 antibody (1 μM) markedly decreased potency of the conjugate (from 20 to 200-fold).

TABLE 3

| Cell line | IC50, nM | | | |
|---|---|---|---|---|
| | huMOV19-90 | | huMOV19-107 | |
| | Conjugate | Conjugate + unmodified antibody | Conjugate | Conjugate + unmodified antibody |
| Ishikawa | 0.05 | 1.0 | 0.05 | 2.0 |
| KB | 0.005 | 1.0 | 0.005 | 0.8 |
| NCI-H2110 | 0.1 | 4.0 | 0.1 | 7.0 |

Example 30

Antitumor Activity of Single-dose huMOV19-90 Conjugate Against NCI-H2110 NSCLC Xenografts in Female SCID Mice Female CB.17 SCID mice, 6 weeks old, were received from Charles River Laboratories. Mice were inoculated with 1×107 NCI-H2110 tumor cells suspended in 0.1 ml 50% matrigel/serum free medium by subcutaneous injection in the right flank. When tumor volumes reached approximately 100 mm³ (day 7 post inoculation), animals were randomized based on tumor volume into 4 groups of 6 mice each. Mice received a single IV administration of vehicle control (0.2 ml/mouse) or huMOV19-90 at 1, 3 or 5 μg/kg based on concentration of compound 90 on day 1 (day 8 post inoculation).

Tumor size was measured twice to three times weekly in three dimensions using a caliper. The tumor volume was expressed in mm³ using the formula V=Length×Width×Height×½. A mouse was considered to have a partial regression (PR) when tumor volume was reduced by 50% or greater, complete tumor regression (CR) when no palpable tumor could be detected. Tumor volume was determined by StudyLog software.

Tumor growth inhibition (T/C Value) was determined using the following formula:

T/C (%)=Median tumor volume of the treated/Median tumor volume of the control×100.

Tumor volume was determined simultaneously for treated (T) and the vehicle control (C) groups when tumor volume of the vehicle control reached predetermined size of 1000 mm3. The daily median tumor volume of each treated group was determined, including tumor-free mice (0 mm3). According to NCI standards, a T/C≤42% is the minimum level of anti-tumor activity. A T/C<10% is considered a high anti-tumor activity level.

Figure 14:
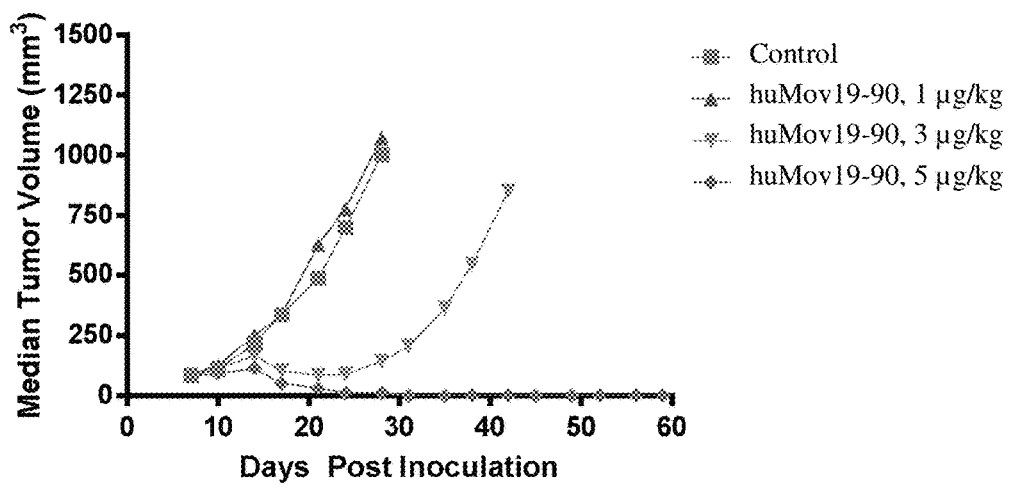
FIG. 14 shows in vivo efficacy of huMOV19-90 conjugate in NCI-H2110 bearing SCID mice.

As shown in FIG. 14, the huMOV19-90 conjugate is active at 3 μg/kg dose and is highly active at 5 μg/kg dose.

Example 31

Synthesis of Compound 107

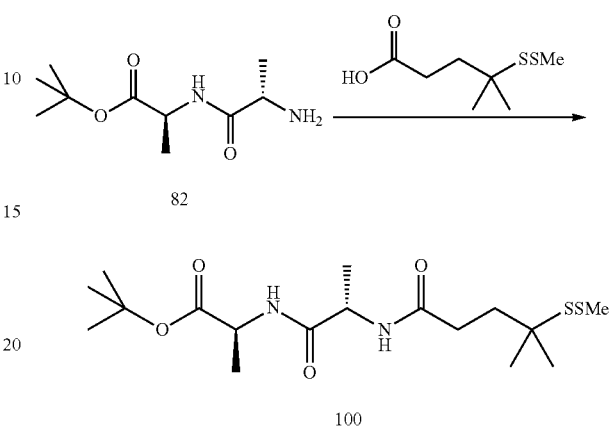

Step 1: Compound 82 (500 mg, 2.31 mmol), 4-methyl-4-(methyldisulfanyl)pentanoic acid (449 mg, 2.31 mmol), EDC.HCl (465 mg, 2.43 mmol), HOBt (354 mg, 2.31 mmol), and DIPEA (0.81 mL, 4.62 mmol) were dissolved in DMF (7.7 mL) and stirred overnight until the reaction was complete. The reaction was diluted with ethyl acetate and washed with saturated sodium bicarbonate, saturated ammonium chloride, and twice with water. The organic was dried and concentrated in vacuo to give compound 100 (875 mg, 96% yield) which was used directly in the next step. $^1$H NMR (400 MHz, DMSO): δ 8.15 (d, 1H, J=6.8 Hz), 8.02 (d, 1H, J=6.8 Hz), 4.26-4.33 (m, 1H), 4.03-4.12 (m, 1H), 2.41 (s, 3H), 2.18-2.22 (m, 2H), 1.76-1.80 (m, 2H), 1.39 (s, 9H), 1.24 (s, 6H), 1.24 (d, 3H, J=7.2 Hz), 1.19 (d, 3H, J=7.2 Hz).

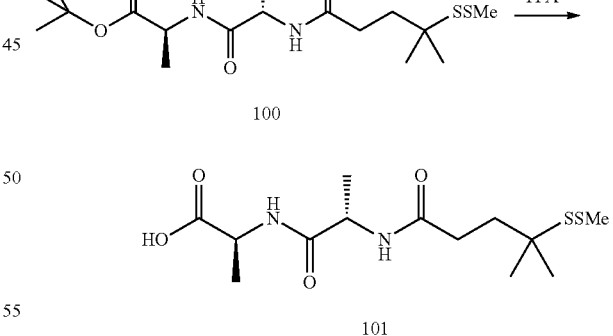

Step 2: TFA (2.6 ml) and water (0.17 ml) were added to neat Compound 100 (875 mg, 2.23 mmol) and were stirred at room temperature until the reaction was complete. The reaction was diluted and azeotroped with acetonitrile to obtain a sticky oil. It was then diluted with acetonitrile and water, frozen and lyophilized to give compound 101 (1 g, 100% yield) as an off white solid that was used without further purification. LCMS=3.99 min (8 min method). MS (m/z): 337.0 (M+1)$^+$.

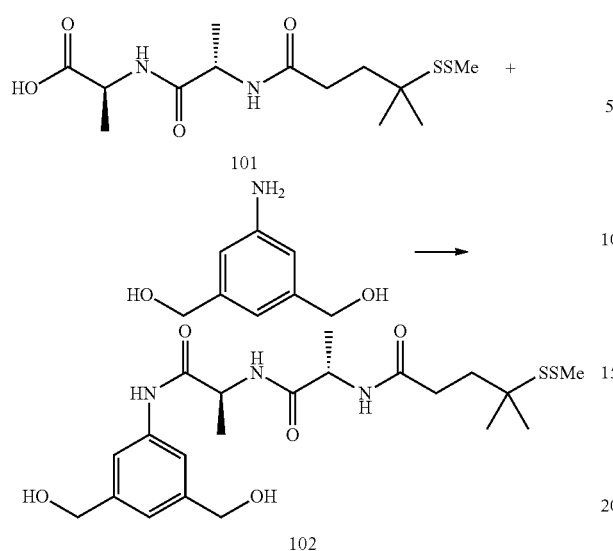

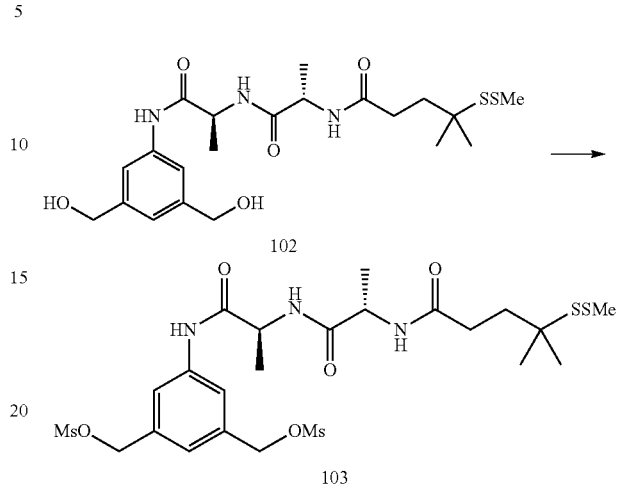

(s, 1H), 4.58 (s, 4H), 4.44-4.48 (m, 1H), 4.29-4.32 (m, 1H), 3.34 (s, 2H), 2.38 (s, 3H), 2.34-2.40 (m, 2H), 1.90-1.95 (m, 2H), 1.43 (d, 3H, J=7.2 Hz), 1.36 (d, 3H, J=7.2 Hz), 1.30 (s, 6H).

Step 3: Compound 101 (923 mg, 1.65 mmol) and (5-amino-1,3-phenylene)dimethanol (240 mg, 1.57 mmol) were dissolved in DMF (5.2 ml). EDC.HCl (601 mg, 3.13 mmol), and DMAP (96 mg, 0.78 mmol) were added at room temperature and the reaction was stirred overnight at room temperature. The reaction was diluted with ethyl acetate and washed with water three times. The organic layer was dried, concentrated in vacuo and purified by silica gel chromatography (DCM/MeOH) to give Compound 102 (150 mg, 20% yield). LCMS=3.91 min (8 min method). MS (m/z): 472.2 (M+1)⁺. ¹H NMR (400 MHz, MeOD): δ 9.69 (s, 1H), 8.21 (d, 1H, J=6.8 Hz), 8.18 (d, 1H, J=6.8 Hz), 7.52 (s, 2H), 7.12

Step 4: Compound 102 was prepared similarly as compound 94 in Example 9. The crude material was dried under high vacuumed to give Compound 103 (174 mgs, 101% yield) that was used directly in the next step without further purification. LCMS=4.95 min (8 min method).

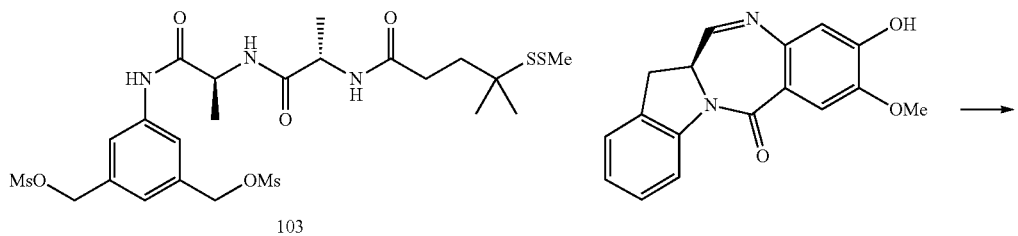

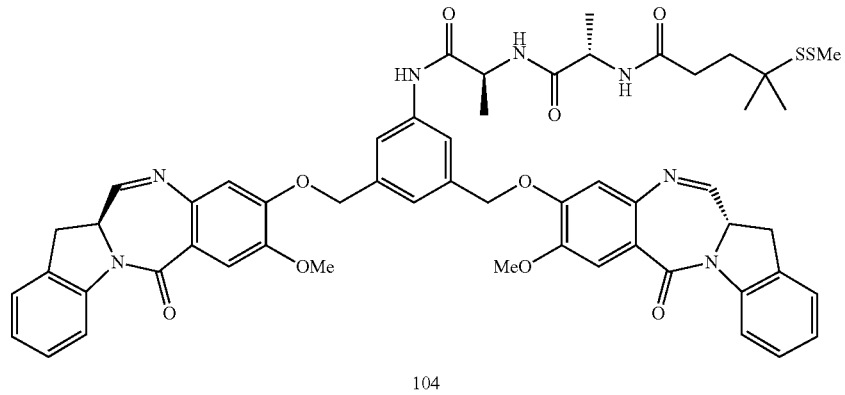

Step 5: Compound 103 was prepared similarly as compound 57 in Example 7. The crude solid contained compound 104 (203 mg, 44% yield, 60% purity) which was used without further purification. LCMS=5.68 min (8 min method). MS (m/z): 1024.3 (M+1)⁺.

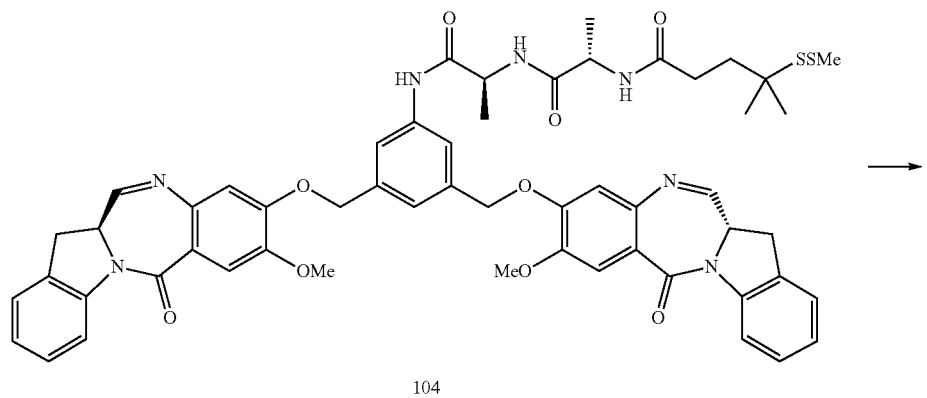
104
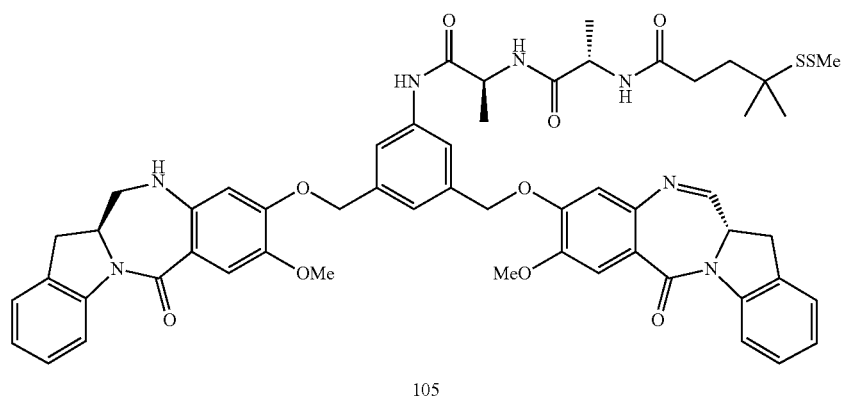
105
Step 6: Compound 104 was prepared similarly as compound 12 in Example 1. The crude residue was purified by RPHPLC (C18 column, CH₃CN/H₂O, gradient, 50% to 65%) to yield mono imine compound 105 as a solid (22 mg, 16% yield, 90% pure). LCMS=6.00 min (8 min method). MS (m/z): 1027.3 (M+1)⁺.
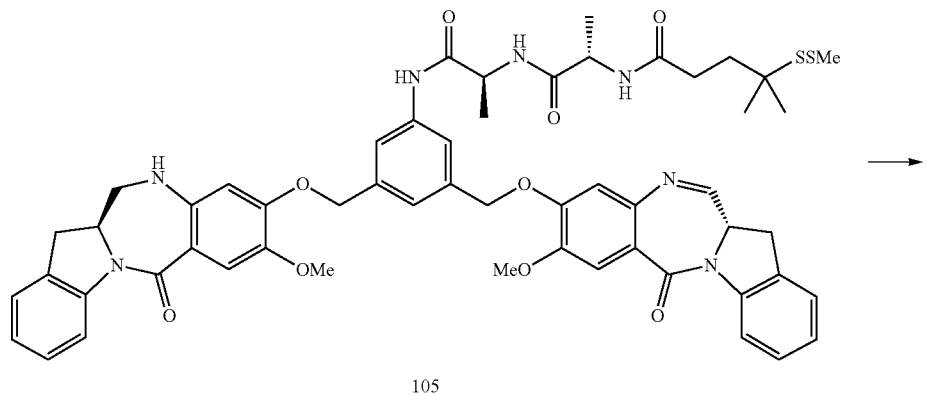
105

-continued

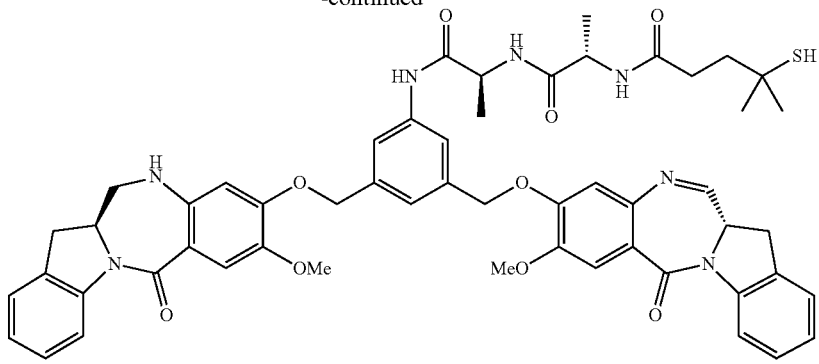

106

Step 7: Compound 106 was dissolved in THF (0.5 mL) and ACN (0.23 mL) at room temperature. It was then prepared similarly to compound 98 in Example 9. The mixture was stirred until completion and then diluted with DCM and DI water. The organic layer was washed with brine, dried and filtered. The filtrate was concentrated to give the crude thiol, compound 106 (21 mg, 100% yield) which was used directly in the next reaction. LCMS=5.67 min (8 min method). MS (m/z): 980.4 (M+1)$^+$.

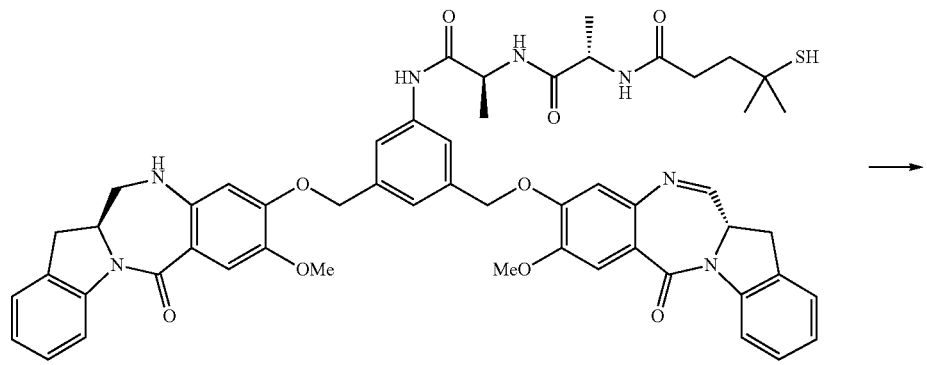

106

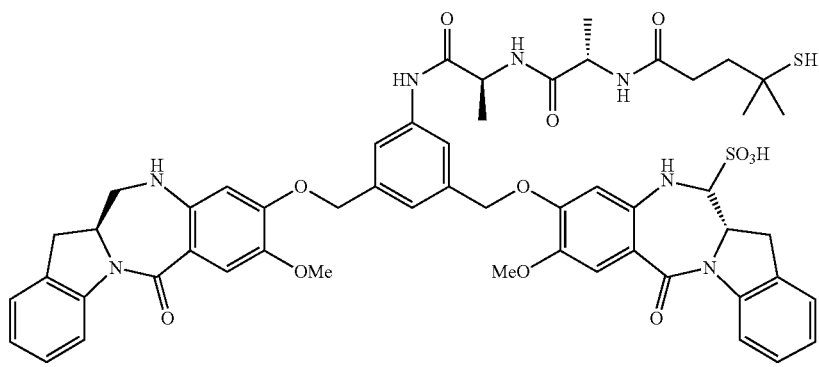

107

Step 8: Compound 106 (21 mg, 0.021 mmol) was suspended in 2-propanol (1428 μl) and water (714 μl). Sodium metabisulfite (22.30 mg, 0.214 mmol) was added and the reaction stirred at room temperature until completion. The reaction mixture was diluted with acetonitrile/water, frozen and lyophilized. The resulting white powder was purified by RPHPLC (C18 column, $CH_3CN/H_2O$, gradient, 20% to 40%) and the desired fractions were collected and lyophilized to give compound 107 (5.3 mg, 23% yield). LCMS=5.67 min (8 min method). MS (m/z): 1060.2 (M−1)⁻.

Example 32

Preparation of huMOV19-sulfo-SPDB-107 (or huMOV19-107) Conjugate

An in situ mix containing final concentrations of 1.95 mM Compound 107 and 1.5 mM sulfo-SPDB Linker in succinate buffer (pH 5):DMA (30:70) was incubated for 6 h before adding a 7-fold excess of 107-sulfo-SPDB-NHS to a reaction containing 4 mg/ml huMOV19 antibody in 15 mM HEPES pH 8.5 (87:13, water:DMA). The solution was allowed to conjugate over night at 25° C.

Post-reaction, the conjugate was purified and buffer exchanged into 10 mM Tris, 80 mM NaCl, 50 uM Bisulfite, 3.5% Sucrose, 0.01% Tween-20 formulation buffer pH 7.6 using NAP desalting columns (Illustra Sephadex G-25 DNA Grade, GE Healthcare). Dialysis was performed in the same buffer over night at 4° C. utilizing Slide-a-Lyzer dialysis cassettes (ThermoScientific 10,000 MWCO).

Figure 16:
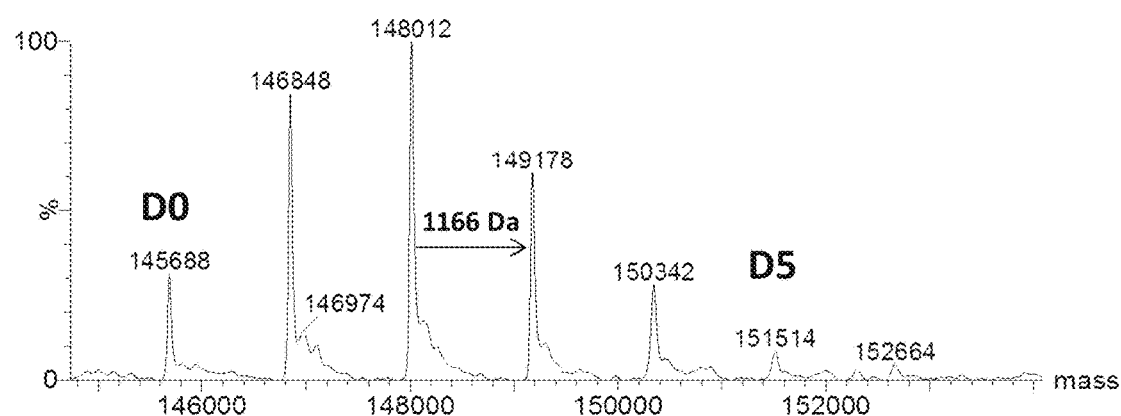
FIG. 16 shows mass spectrometry profiles of a representative conjugates of the present invention.

The purified conjugate was found to have an average of 2.7 molecules of compound 107 linked per antibody (by UV/Vis and SEC using molar extinction coefficients $\varepsilon_{330\ nm}=15,484\ cm^{-1}M^{-1}$ and $\varepsilon_{280\ nm}=30,115\ cm^{-1}M^{-1}$ for compound 107, and $\varepsilon_{280\ nm}=201,400\ cm^{-1}M^{-1}$ for huMOV19 antibody), 95% monomer (by size exclusion chromatography), and a final protein concentration of 1.1 mg/ml. The MS spectrometry data is shown in FIG. 16.

Example 33

Antitumor Activity of Single-dose huML66-90 Conjugate Against NCI-H1703 NSCLC Xenografts in Female SCID Mice Female CB.17 SCID mice, 6 weeks old, were received from Charles River Laboratories. Mice were inoculated with 5×10⁶ NCI-H1703 tumor cells suspended in 0.2 ml 50% matrigel/serum free medium by subcutaneous injection in the right flank. When tumor volumes reached approximately 100 mm³ (day 16 post inoculation), animals were randomized based on tumor volume into 4 groups of 6 mice each. Mice received a single IV administration of vehicle control (0.1 ml/mouse) or huML66-90 conjugate at 5, 20 or 50 μg/kg based on compound 90 concentration on day 1 (day 17 post inoculation).

Tumor size was measured twice to three times weekly in three dimensions using a caliper. The tumor volume was expressed in mm³ using the formula V=Length×Width× Height×½. A mouse was considered to have a partial regression (PR) when tumor volume was reduced by 50% or greater, complete tumor regression (CR) when no palpable tumor could be detected. Tumor volume was determined by StudyLog software.

Tumor growth inhibition (T/C Value) was determined using the following formula:

T/C (%)=Median tumor volume of the treated/Median tumor volume of the control×100.

Tumor volume was determined simultaneously for treated (T) and the vehicle control (C) groups when tumor volume of the vehicle control reached predetermined size of 1000 mm³. The daily median tumor volume of each treated group was determined, including tumor-free mice (0 mm³). According to NCI standards, a T/C≤42% is the minimum level of anti-tumor activity. A T/C<10% is considered a high anti-tumor activity level.

Figure 17:
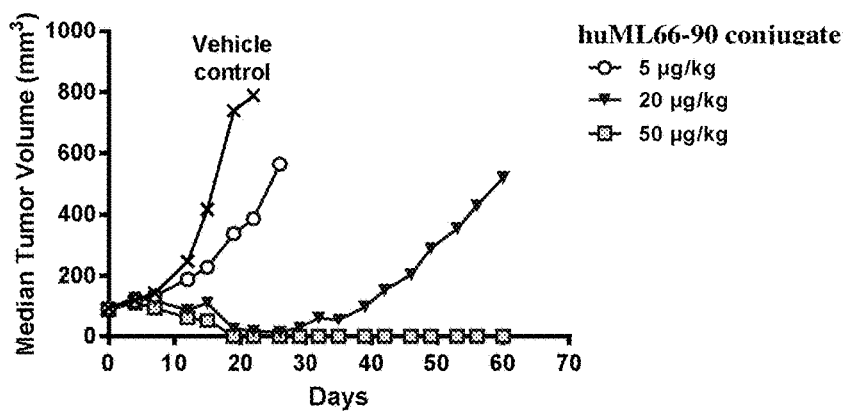
FIG. 17 shows in vivo efficacy of huML66-90 conjugate in NCI-H1703 NSCLC bearing SCID mice.

As shown in FIG. 17, the huML66-90 conjugate is highly active at 20 μg/kg and 50 μg/kg, with 20 μg/kg as minimal effective dose (MED).

Example 34

Pharmacokinetics of Single-dose huMov19-90 Conjugate in Female CD-1 Mice

Female CD-1 mice, 7 weeks old, were received from Charles River Laboratories. Mice received a single IV administration of huMov19-90 conjugate as a single intravenous bolus injection via a lateral tail vein. Each mouse received a dose of 2.5 mg/kg based on Ab. The dose and injected volume were individualized on the basis of the body weight of each mouse. Injections were carried out using a 1.0 mL syringe fitted with a 27 gauge, ½ inch needle. At 2 and 30 min, and at 2, 4 and 8 hours, and at 1, 2, 3, 5, 7, 10, 14, 21 and 28 days after administration of the huMov19-90 conjugate, mice were anesthetized by isoflurane inhalation, and approximately 150 μL of blood was collected from mice via the right retro-orbital blood sinus into a heparinized capillary tube. At each time point (from 0 to 21 days), blood was collected from all three mice in one group. Groups were bled in turn; so that the mice in the set were not bled more than two times in a 24-hour period. At the final time point, 28 days post-administration, all mice were included for sample collection. Blood samples were centrifuged to separate the plasma. 30 μl plasma was transferred to individual labeled microcentrifuge tubes for each sample and time point, and then stored frozen at −80° C. to allow subsequent analysis by ELISA to determine concentrations of total Ab (both unconjugated Ab and intact conjugate) and intact conjugate using an anti-indolinobenzodiazepine antibody.

Figure 18:
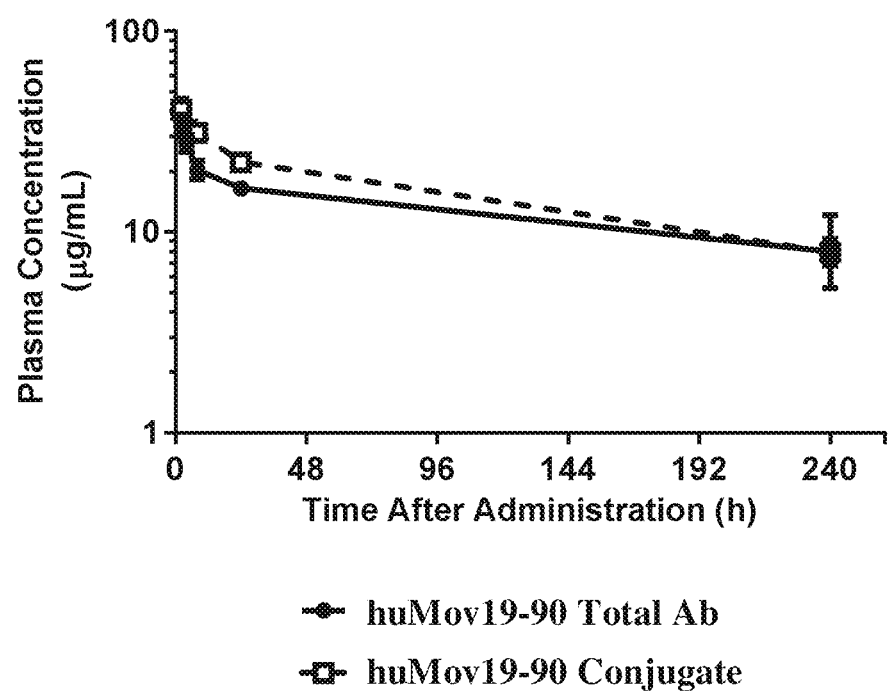
FIG. 18 shows pharmacokinetics of huMOV19-90 in CD-1 mice.

As shown in FIG. 18, the huMov19-90 conjugate has similar clearance to that of the antibody.

Example 35

Catabolite Enrichment by Affinity Capture with Protein A Resin

KB cells expressing folate receptor α (FRα) were cultured in 5×T150 tissue culture plates. Saturating amount of FRα-targeting huMov19-90 conjugate was incubated with KB cells for 24 hours at 37° C. in a humidified incubator buffered with 5% $CO_2$. After 24 hours, the media containing cell-effluxed catabolites were harvested and pooled for the following assay.

Saturating amount of anti-indolinobenzodiazepine antibody was bound to a slurry of protein A resins by overnight incubation at 4° C. 1 mL of pre-bound protein A/anti-indolinobenzodiazepine antibody complex was incubated with 25 mL of media on an end-to-end rotator for several hours. The resins were centrifuged gently at 1000 rpm, and the supernatant was decanted. The protein-A/anti-indolinobenzodiazepine antibody resins bound to the catabolites were washed with PBS. The catabolites were released into organic phase by acetone extraction. The catabolites were vacuum-dried overnight until the organic solution was completely evaporated. The catabolites were reconstituted with 20% acetonitrile in water, and analyzed by LC/MS.

MS Analysis

Figure 19A:
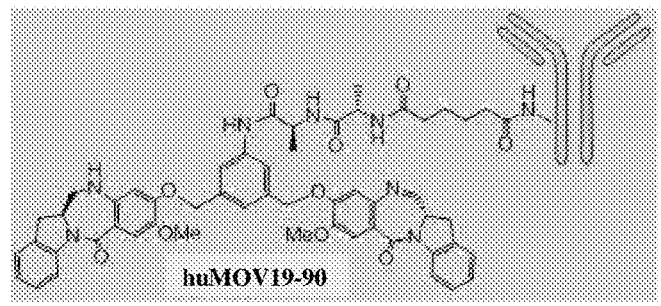
FIGS. 19A and 19B show the structure of huMOV19-90 conjugate (FIG. 19A), and a scheme for incubation, purification, and isolation of catabolites from huMOV19-90 conjugate formed in KB cervical cancer cells in vitro (FIG. 19B). The three catabolites identified by LC-MS are shown along with the calculated mass.
Figure 19B:
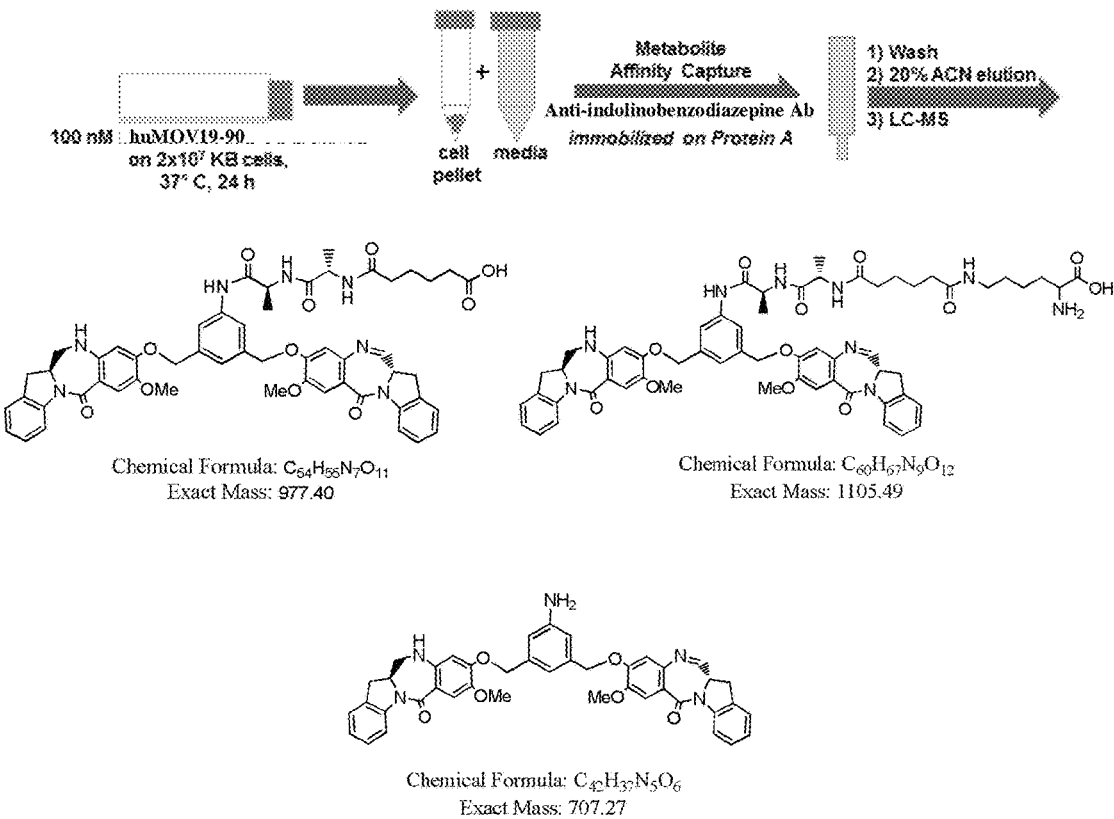
Figure 20:
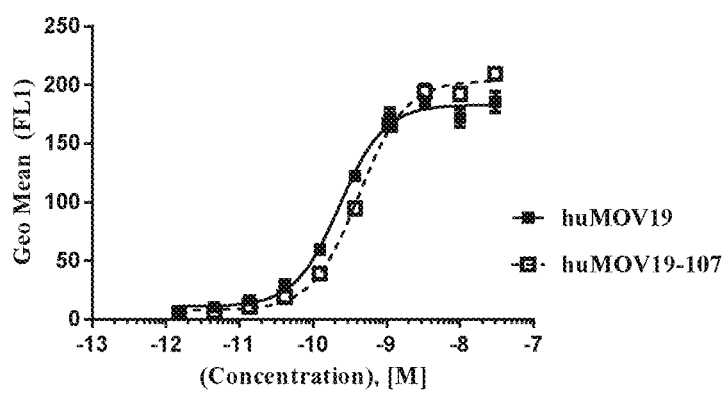
FIG. 20 shows binding affinity of huMOV19-107 conjugate as compared to unconjugated antibody huMOV19 on T47D cells.

Cell catabolites were identified by UHPLC/MS/MS using Q-Exactive high resolution mass spec (Thermo). Extracted ion-chromatograms (XIC) were used to identify and characterize the target cell catabolites. All catabolite species containing the characteristic indolinobenzodiazepine (286 m/z) mass signatures were identified (see FIGS. 19A and 19B).

Example 36

Antitumor Activity of Single-dose huMov19-90 Against NCI-H2110 NSCLC Xenografts, Hec-1b Endometrial Xenografts and Ishikawa Endometrial Xenografts in Female CB.17 SCID Mice Female CB.17 SCID mice, 6 weeks old, were received from Charles River Laboratories. One cohort of mice were inoculated with $1\times10^7$ NCI-H2110 tumor cells suspended in 0.1 ml 50% matrigel/serum free medium by subcutaneous injection in the right flank. The second cohort of mice were inoculated with $1\times10^7$ Hec-1b tumor cells suspended in 0.1 ml serum free medium by subcutaneous injection in the right flank. The third cohort of mice were inoculated with $1\times10^7$ Ishikawa tumor cells suspended in 0.1 ml 50% matrigel/serum free medium by subcutaneous injection in the right flank.

When tumor volumes reached approximately 100 mm³ (NCI-H2110 on day 7, Hec-1b on day 7, and Ishikawa on day 17 post inoculation), animals were randomized based on tumor volume into groups of 6 mice each.

Mice in the NCI-H2110 xenograft experiment received a single IV administration of vehicle control (0.2 ml/mouse) or huMov19-90 at 1, 3, or 5 µg/kg based on drug concentration on day 1 (day 8 post inoculation).

Mice in the Hec-1b xenograft experiment received a single IV administration of vehicle control (0.2 ml/mouse) or huMov19-90 at 10 or 30 µg/kg or the non-targeting control conjugate chKTI-90 at 30 µg/kg based on drug concentration on day 1 (day 8 post inoculation).

Mice in the Ishikawa xenograft experiment received a single IV administration of vehicle control (0.2 ml/mouse) or huMov19-90 at 10 or 30 µg/kg or the non-targeting control conjugate chKTI-90 at 30 µg/kg based on drug concentration on day 1 (day 18 post inoculation).

For all experiments, tumor size was measured twice to three times weekly in three dimensions using a caliper. The tumor volume was expressed in mm³ using the formula V=Length×Width×Height×½. A mouse was considered to have a partial regression (PR) when tumor volume was reduced by 50% or greater, complete tumor regression (CR) when no palpable tumor could be detected. Tumor volume was determined by StudyLog software.

Tumor growth inhibition (T/C Value) was determined using the following formula:

T/C (%)=Median tumor volume of the treated/Median tumor volume of the control×100.

Tumor volume was determined simultaneously for treated (T) and the vehicle control (C) groups when tumor volume of the vehicle control reached predetermined size of 1000 mm³. The daily median tumor volume of each treated group was determined, including tumor-free mice (0 mm³). According to NCI standards, a T/C≤42% is the minimum level of anti-tumor activity. A T/C<10% is considered a high anti-tumor activity level.

Figure 22:
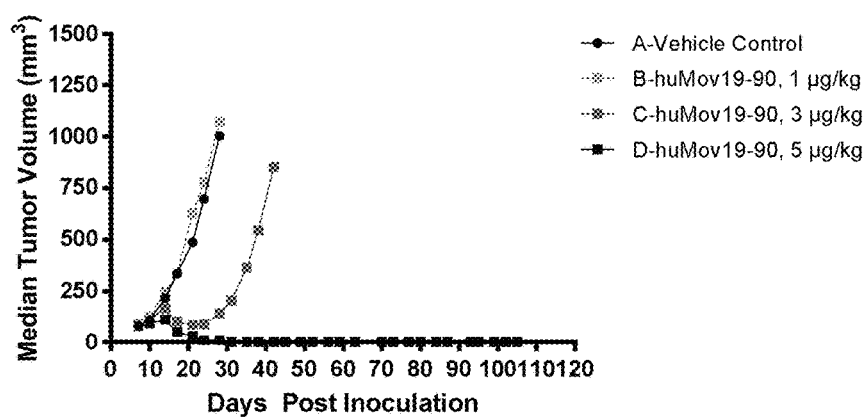
FIG. 22 shows in vivo efficacy of huMOV19-90 conjugate in bearing SCID mice bearing NCI-H2110 NSCLC xenografts.

As shown in FIG. 22, the huMov19-90 conjugate was inactive in the NCI-H2110 xenograft model at a dose of 1 µg/kg, active at a dose of 3 µg/kg with a T/C of 13% and 1/6 PRs and highly active at a dose of 5 µg/kg with a T/C of 2%, 6/6 PRs and 4/6 CRs.

Figure 23:
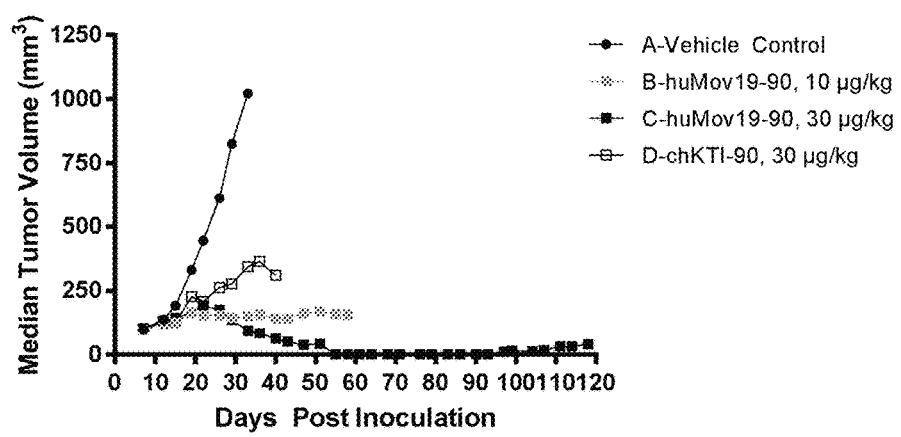
FIG. 23 shows in vivo efficacy of huMOV19-90 conjugate in SCID mice bearing Hec-1b endometrial xenografts.

As shown in FIG. 23, the huMov19-90 conjugate was active in the Hec-1b xenograft model at a dose of 10 µg/kg with a T/C of 15% and 1/6 PRs and highly active at a dose of 30 µg/kg with a T/C of 9%, 6/6 PRs and 6/6 CRs. The non-targeting control conjugate chKTI-90 was active at a dose of 30 µg/kg with a T/C of 34%.

Figure 24:
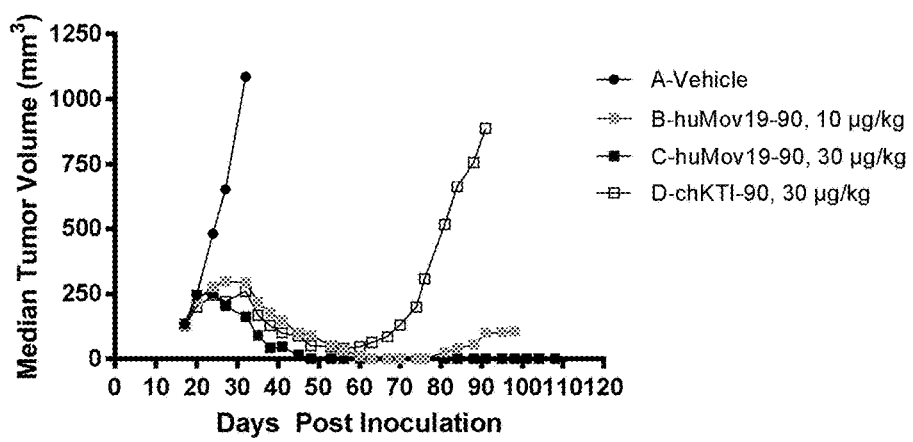
FIG. 24 shows in vivo efficacy of huMOV19-90 conjugate in SCID mice bearing Ishikawa endometrial xenografts.

As shown in FIG. 24, the huMov19-90 conjugate was active in the Ishikawa xenograft model at a dose of 10 µg/kg with a T/C of 27%, 6/6 PRs and 6/6 CRs and active at a dose of 30 µg/kg with a T/C of 15%, 6/6 PRs and 6/6 CRs. The non-targeting control conjugate chKTI-90 was active at a dose of 30 µg/kg with a T/C of 24% and 4/6 PRs.

Example 37

Figure 25:
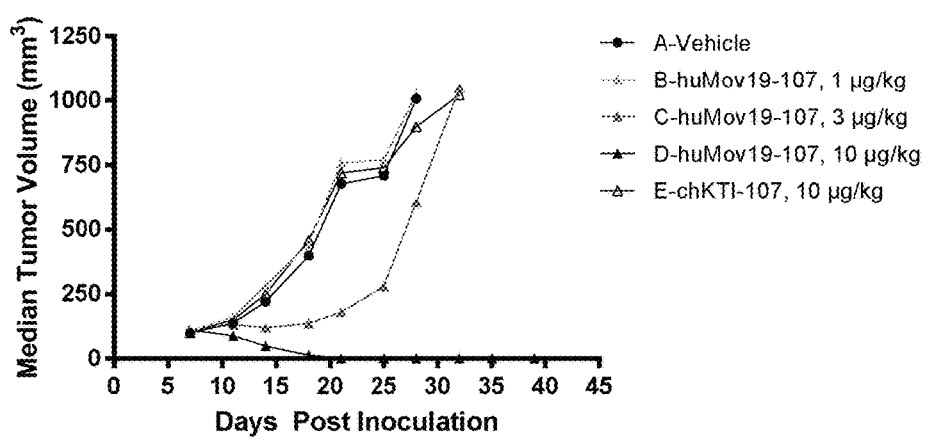
FIG. 25 shows in vivo efficacy of huMOV19-107 conjugate in bearing SCID mice bearing NCI-H2110 NSCLC xenografts.

Antitumor Activity of Single-dose huMov19-107 Against NCI-H2110 NSCLC Xenografts, in Female CB.17 SCID Mice In vivo antitumor activity of huMOV19-107 in SCID mice was conducted according to protocols described in Example 30 above. As shown in FIG. 25, the huMov19-107 conjugate was highly active at 10 µg/kg dose and 6/6 CRs.

Example 38

Binding Affinity of CD123-90 Conjugate

Binding affinity of the ADC conjugate of an exemplary humanized anti-CD123 antibody, huCD123-6Gv4.7S3 antibody, was assayed and compared to the corresponding unconjugated antibody by flow cytometry using HNT-34 cells. HNT-34 cells ($5\times10^4$ cells per sample) were incubated with varying concentrations of the ADC and the unconjugated huCD123-6Gv4.7S3 antibody in 200 µL FACS buffer (DMEM medium supplemented with 2% normal goat serum). The cells were then pelleted, washed twice, and incubated for 1 hr with 100 µL of phycoerythrin (PE)-conjugated goat anti-human IgG-antibody (Jackson Laboratory). The cells were pelleted again, washed with FACS buffer and resuspended in 200 µL of PBS containing 1% formaldehyde. Samples were acquired using a FACSCalibur flow cytometer with the HTS multiwell sampler, or a FACS array flow cytometer, and analyzed using CellQuest Pro (all from BD Biosciences, San Diego, US). For each sample the geomean fluorescence intensity for FL2 was calculated and plotted against the antibody concentration in a semi-log plot. A dose-response curve was generated by non-linear regression and the EC50 value of each curve, which corresponds to the apparent dissociation constant (Kd) of each antibody, was calculated using GraphPad Prism v4 (GraphPad software, San Diego, Calif.).

Figure 26:
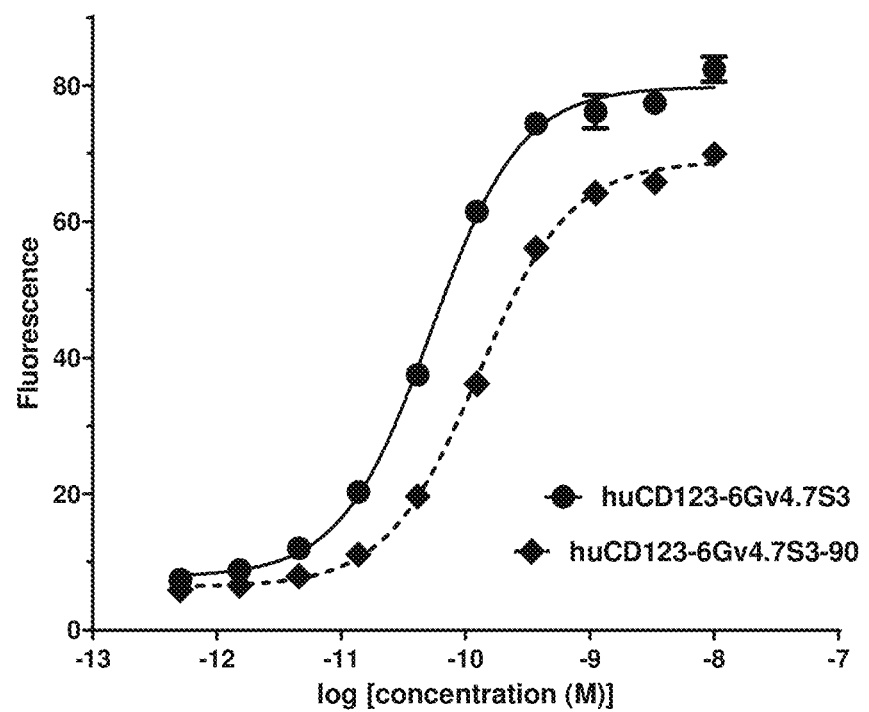
FIG. 26 shows binding affinity of huCD123-6Gv4.7S3-90 conjugate as compared to the unconjugated antibody on HNT-34 cells.

As shown in FIG. 26, conjugation only moderately affected the binding affinity of the exemplary anti-CD123 antibody.

Example 39

In Vitro Cytotoxic Activity for huCD123-90

The ability of antibody-drug conjugates (ADC) of huCD123-6, an anti-CD123 antibody, to kill cells that express CD123 on their cell surface was measured using in vitro cytotoxicity assays. The cell lines were cultured in culture medium as recommended by the cell supplier (ATCC or DSMZ). The cells, 2,000 to 10,000 in 100 µL of the culture medium, were added to each well of flat bottom 96-well plates. To block Fc receptors on the cell surface, the culture medium was supplemented with 100 nM chKTI antibody (an antibody of the same isotype). Conjugates were diluted into the culture medium using 3-fold dilution series and 100 µL were added per well. To determine the contribution of CD123-independent cytotoxicity, CD123 block (e.g., 100 nM of chCD123-6 antibody) was added to some wells prior to the conjugates. Control wells containing cells and the medium but lacking the conjugates, as well as wells contained medium only, were included in each assay plate. Assays were performed in triplicate for each data point. The plates were incubated at 37° C. in a humidified 6% $CO_2$ incubator for 4 to 7 days. Then the relative number of viable cells in each well was determined using the WST-8 based Cell Counting Kit-8 (Dojindo Molecular Technologies, Inc., Rockville, Md.). The apparent surviving fraction of cells in each well was calculated by first correcting for the medium background absorbance, and then dividing each value by the average of the values in the control wells (non-treated cells). The surviving fraction of cells was plotted against conjugate concentration in semi-log plots.

Fifteen CD123-positive cell lines of different origin (AML, B-ALL, CML and NHL) were used in the study (Table 4). The majority of the cell lines were derived from patients carrying a malignancy with at least one negative prognostic factor (e.g., overexpression of P-glycoprotein, overexpression of EVI1, p53 alterations, DNMT3A mutation, FLT3 internal tandem duplication). The conjugates demonstrated high potency on these cell lines with IC50 values ranging from sub-pM to low nM (Table 4).

TABLE 4

In vitro cytotoxicity of huCD123-6-90 conjugate against CD123-positive cell lines of different origin

| Cell Line | Origin | Negative Prognostic Factor | $IC_{50}$ (M) |
|---|---|---|---|
| THP1 | AML | p53 deletion | 6.7E−12 |
| SHI-1 | AML | p53 gene alterations | 1.3E−11 |
| KO52 | AML | p53 mutant, Pgp overexpression | 1.4E−11 |
| KASUMI-3 | AML | EVI1 and Pgp overexpression | 9.8E−12 |
| KG-1 | AML | p53 mutant, Pgp overexpression | 2.2E−10 |
| OCI-AML2 | AML | DNMT3A mutation | 8.8E−11 |
| HNT-34 | AML | MECOM (EVI1) overexpression | 2.0E−12 |
| MV4-11 | AML | FLT3 internal tadem duplication | 5.6E−13 |
| MOLM-13 | AML | FLT3 internal tadem duplication | 4.9E−13 |
| EOL-1 | AML |  | 2.5E−12 |
| MOLM-1 | CML | EVI1 and Pgp overexpression | 2.9E−11 |
| KOPN8 | B-ALL |  | 1.1E−11 |
| JM-1 | B-ALL |  | 2.4E−11 |
| KCL-22 | CML |  | 3.0E−11 |
| Granta519 | NHL |  | 1.2E−12 |

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

The invention claimed is:

1. A compound represented by any one of the following formulas:

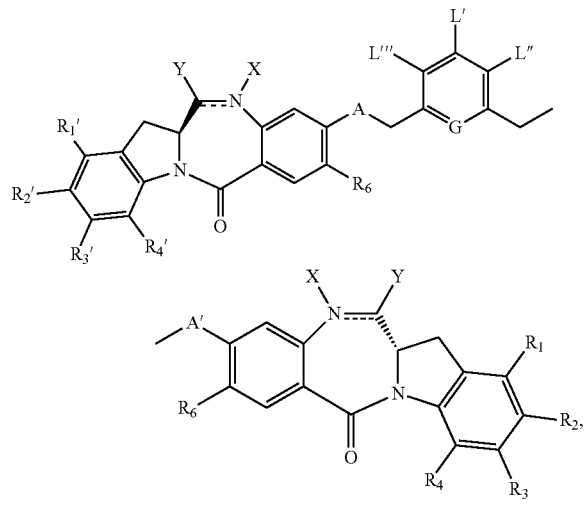

(V)

or a pharmaceutically acceptable salt thereof, wherein:
one of L', L", and L''' is represented by the following formula:

$-Z_1-P-Z_2-R_x-J$  (A)

and the other two are the same or different, and are independently selected from —H, an optionally substituted linear, branched or cyclic alkyl, alkenyl or alkynyl having from 1 to 10 carbon atoms, —$(CH_2CH_2O)_n$—$R^c$, halogen, NH(C=NH)NH$_2$, —OR, —NR'R", —NO$_2$, —NR'COR", —SR, —SOR', —SO$_2$R', —SO$_3$H, —OSO$_3$H, —SO$_2$NR'R", cyano, an azido, —COR', —OCOR', and —OCONR'R";

one of the $Z_1$ and $Z_2$ is —C(=O)—, and the other is —NR$_5$—;

P is an amino acid residue or a peptide containing between 2 to 20 amino acid residues;

$R_x$ is an optionally substituted linear, branched or cyclic alkyl, alkenyl or alkynyl having from 1 to 10 carbon atoms;

J is a moiety comprising —COOH or —COE, wherein —COE represents a reactive ester selected from N-hydroxysuccinimde ester, N-hydroxy sulfosuccinimide ester, nitrophenyl ester, dinitrophenyl ester, sulfo-tetraflurophenylester, and pentafluorophenyl ester;

the double line ═ between N and C represents a single bond or a double bond, provided that when it is a double bond X is absent and Y is —H, or a linear or branched alkyl having 1 to 4 carbon atoms, and when it is a single bond, X is —H or an amine protecting moiety;

Y is a leaving group selected from —OR, —OCOR', —OCOOR', —OCONR'R", —NR'R", —NR'COR", —NR'NR'R", an optionally substituted 5- or 6-membered nitrogen-containing monocyclic heterocycle —NR'(C═NH)NR'R", an amino acid, or a peptide represented by —NRCOP', —SR, —SOR', halogen, cyano, azido, —OSO$_3$H, —SO$_3$H, H$_2$S$_2$O$_5$, PO$_3$SH$_3$, PO$_2$S$_2$H$_2$, POS$_3$H$_2$, PS$_4$H$_2$, (R$^i$O)$_2$PS (OR$^i$), R$^i$S—, R$^i$SO, R$^i$SO$_2$, R$^i$SO$_3$, HS$_2$O$_3$, HS$_2$O$_4$, P(═S)(OR$^{k'}$)(S)(OH), R$^{k'}$C(═O)NOH, and HOCH$_2$SO$_2^-$, or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^j$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

P' is an amino acid residue or a polypeptide containing between 2 to 20 amino acid residues, R, for each occurrence, is independently selected from the group consisting of —H, an optionally substituted linear, branched or cyclic alkyl, alkenyl or alkynyl having from 1 to 10 carbon atoms, —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or an optionally substituted linear or branched alkyl having 1 to 4 carbon atoms;

n is an integer from 1 to 24;

R$_1$, R$_2$, R$_3$, R$_4$, R$_1$', R$_2$', R$_3$' and R$_4$' are each independently selected from the group consisting of —H, an optionally substituted linear, branched or cyclic alkyl, alkenyl or alkynyl having from 1 to 10 carbon atoms, —(CH$_2$CH$_2$O)$_n$—R$^c$, halogen, —NH(C═NH)NH$_2$, —OR, —NR'R", —NO$_2$, —NCO, —NR'COR", —SR, —SOR', —SO$_2$R', —SO$_3^-$H, —OSO$_3$H, —SO$_2$NR'R", cyano, an azido, —COR', —OCOR', and —OCONR'R";

R$_6$ is —H, —R, —OR, —SR, —NR'R", —NO$_2$, or halogen;

G is —CH— or —N—;

A and A' are the same or different, and are independently selected from —O—, —C(═O)—, —CRR'O—, —CRR'—, —S—, —CRR'S—, —NR$_5$ and —CRR'N(R$_5$)—; and R$_5$ for each occurrence is independently —H or an optionally substituted linear or branched alkyl having 1 to 10 carbon atoms;

wherein the optional substituent described above is a linear, branched or cyclic alkyl, alkenyl or alkynyl having from 1 to 10 carbon atoms, aryl, heteroaryl, heterocyclyl, halogen, —NH(C═NH)NH$_2$, —OR$^{100}$, NR$^{101}$R$^{102}$, —NO$_2$, —NR$^{101}$COR$^{102}$, —SR$^{100}$, —SOR$^{101}$, —SO$_2$R$^{101}$, —SO$_3$M, —OSO$_3$M, —SO$_2$NR$^{101}$R$^{102}$, cyano, an azido, —COR$^{101}$, —OCOR$^{101}$, —OCONR$^{101}$R$^{102}$ or (—CH$_2$CH$_2$O)$_n$R$^{101}$, wherein M is H or a cation; R$^{100}$, R$^{101}$, and R$^{102}$ are each independently selected from H, linear, branched or cyclic alkyl, alkenyl or alkynyl having from 1 to 10 carbon atoms, (—CH$_2$CH$_2$O)$_n$—R$^{104}$, an aryl having from 6 to 10 carbon atoms, a heterocyclic ring having from 3 to 10 carbon atoms and a heteroaryl having 5 to 10 carbon atoms, wherein n is an integer from 1 to 24; and R$^{104}$ is H or a linear or branched alkyl having 1 to 4 carbon atoms, wherein the alkyl, alkenyl, alkynyl, aryl, heteroaryl and heterocyclyl in the groups represented by R$^{100}$, R$^{101}$, R$^{102}$, and R$^{104}$ are optionally substituted with one or more substituents independently selected from halogen, —OH, —CN, —NO$_2$ and unsubstituted linear or branched alkyl having 1 to 4 carbon atoms.

2. The compound of claim 1, wherein L' is represented by the following formula:

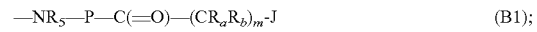  (B1);

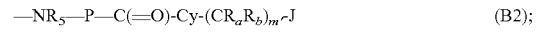  (B2);

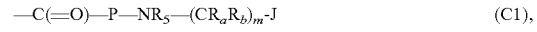  (C1), or

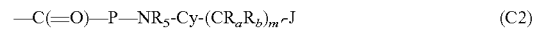  (C2)

wherein:

J is —COE;

R$_a$ and R$_b$, for each occurrence, are each independently —H, (C$_1$-C$_3$)alkyl or a charged substituent or an ionizable group Q, wherein Q is —SO$_3$H, or a pharmaceutically acceptable salt thereof;

m is an integer from 1 to 6;

m' is 0 or an integer from 1 to 6; and

Cy is a cyclic alkyl having 5 or 6 ring carbon atoms optionally substituted with halogen, —OH, (C$_1$-C$_3$) alkyl, (C$_1$-C$_3$)alkoxy, or halo(C$_1$-C$_3$)alkyl.

3. The compound of claim 1, wherein L' is represented by the following formula:

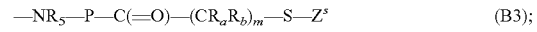  (B3);

or

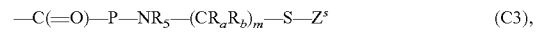  (C3), wherein:

R$_a$ and R$_b$, for each occurrence, are each independently —H, (C$_1$-C$_3$)alkyl or a charged substituent or an ionizable group Q, wherein Q is —SO$_3$H, or a pharmaceutically acceptable salt thereof;

m is an integer from 1 to 6;

Z$^s$ is —H, —SR$^d$, —C(═O)R$^{d1}$ or is selected from any one of the following formulas:

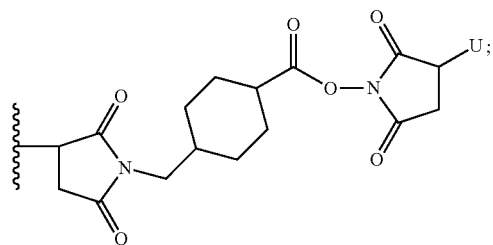
(a1)
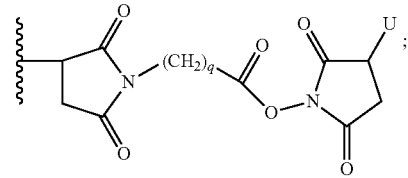
(a2)
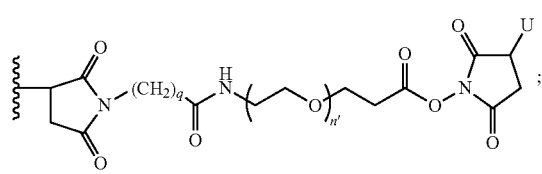
(a3)
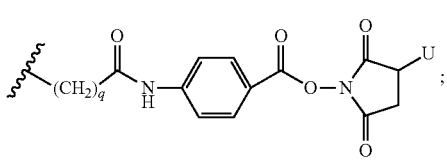
(a4)
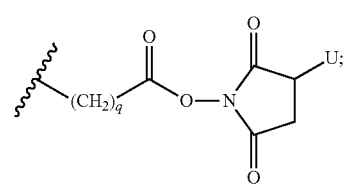
(a5)
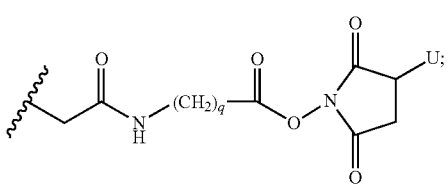
(a6)
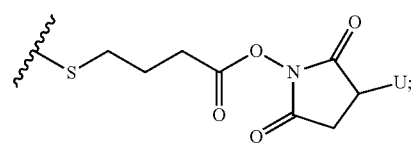
(a7)
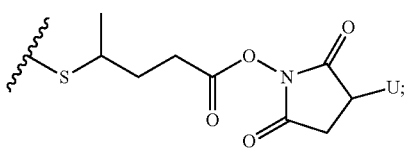
(a8)
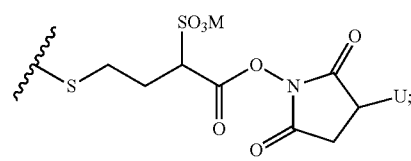
(a9)
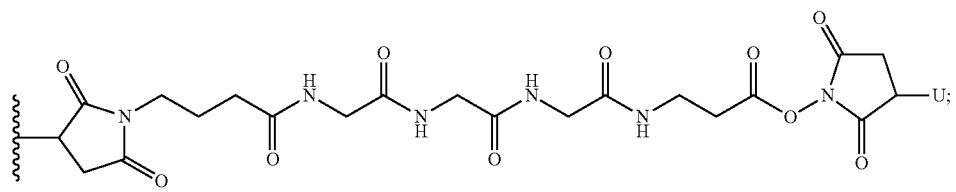
(a10)
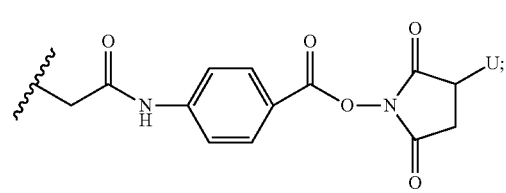
(a11)
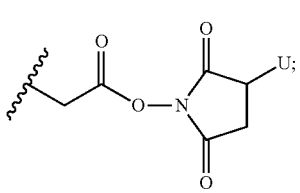
(a12)
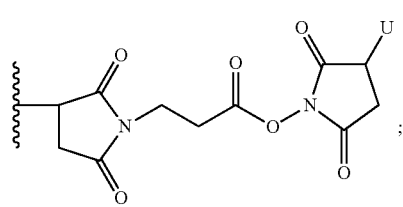
(a13)
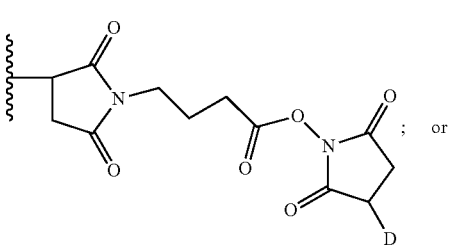
(a14) ; or

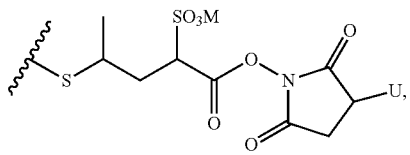

(a15)

wherein:
q is an integer from 1 to 5;
n' is an integer from 2 to 6;
U is —H or SO$_3$M;
M is H$^+$, Na$^+$ or K$^+$;
R$^d$ is a linear or branched alkyl having 1 to 6 carbon atoms or is selected from phenyl, nitrophenyl, dinitrophenyl, carboxynitrophenyl, pyridyl, or nitropyridyl; and
R$^{d1}$ is a linear or branched alkyl having 1 to 6 carbon atoms.

4. The compound of claim 2, wherein P is a peptide containing 2 to 5 amino acid residues.

5. The compound of claim 4, wherein P is selected from Gly-Gly-Gly, Ala-Val, Val-Ala, Val-Cit, Val-Lys, Phe-Lys, Lys-Lys, Ala-Lys, Phe-Cit, Leu-Cit, Lle-Cit, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu, β-Ala-Leu-Ala-Leu and Gly-Phe-Leu-Gly, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala.

6. The compound of claim 5, wherein:
the double line ═ between N and C represents a single bond or double bond, provided that when it is a double bond X is absent and Y is —H, and when it is a single bond, X is —H, Y is —OH or —SO$_3$M;
R$_1$, R$_2$, R$_3$, R$_4$, R$_1$', R$_2$', R$_3$' and R$_4$' are all —H;
R$_6$ is —OMe;
A and A' are —O—; and
M is H, Na$^+$ or K$^+$.

7. The compound of claim 1, wherein the compound is selected from any one of the following formulas:

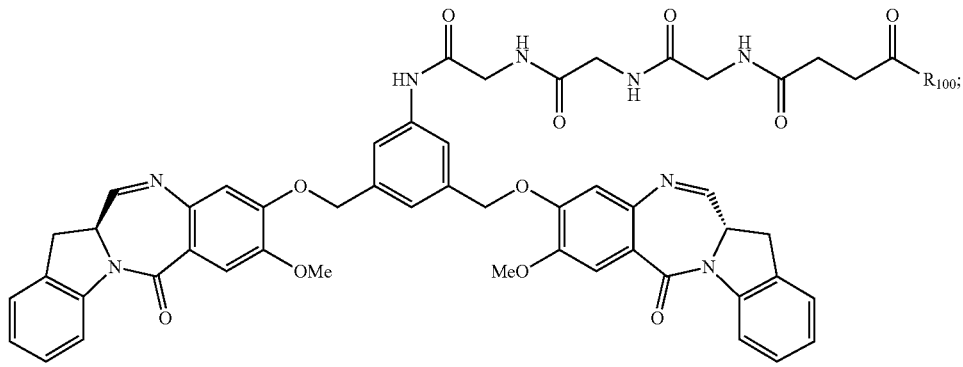

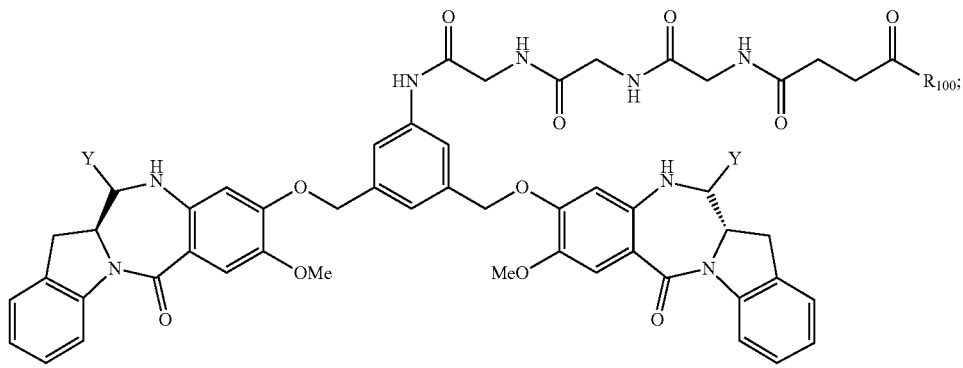

-continued
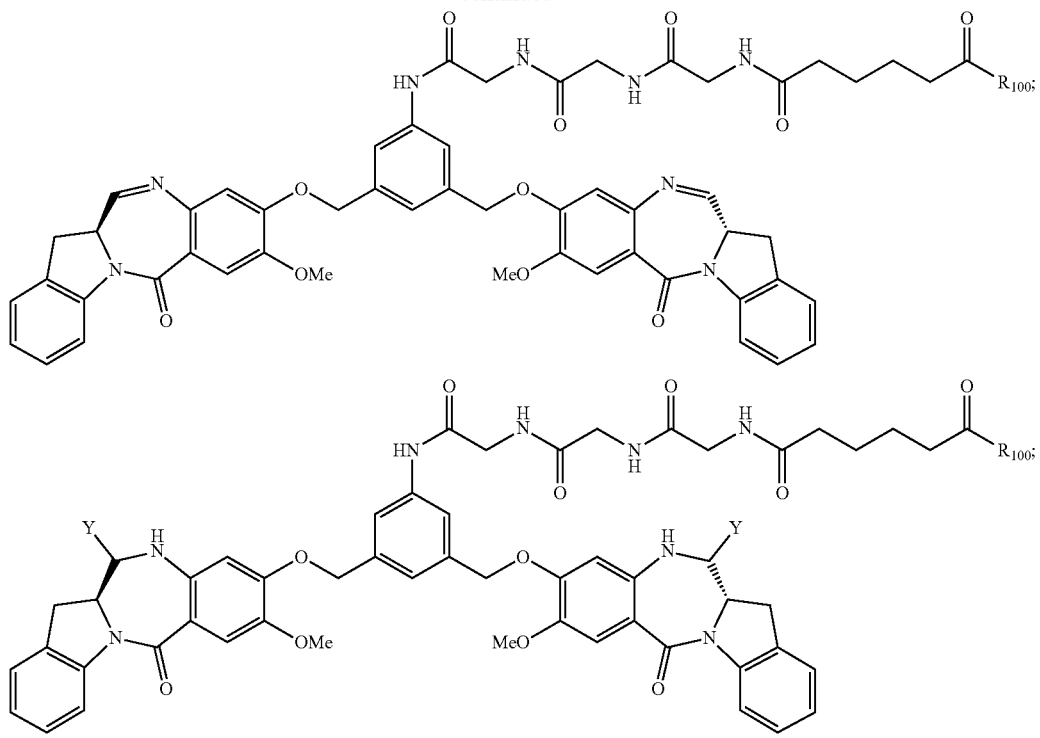
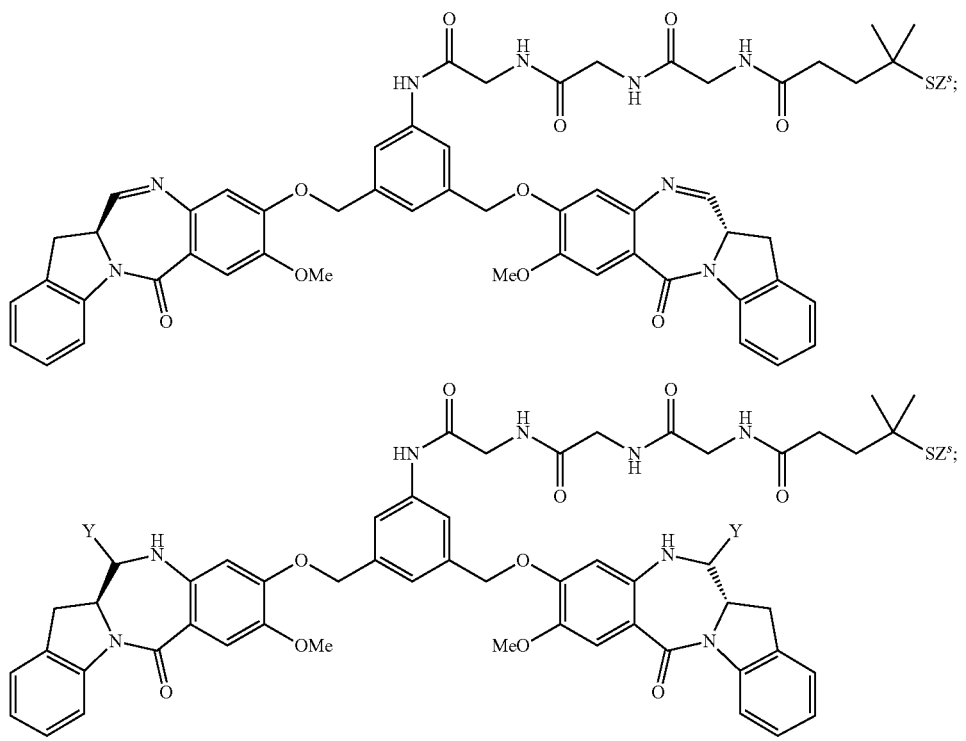

-continued
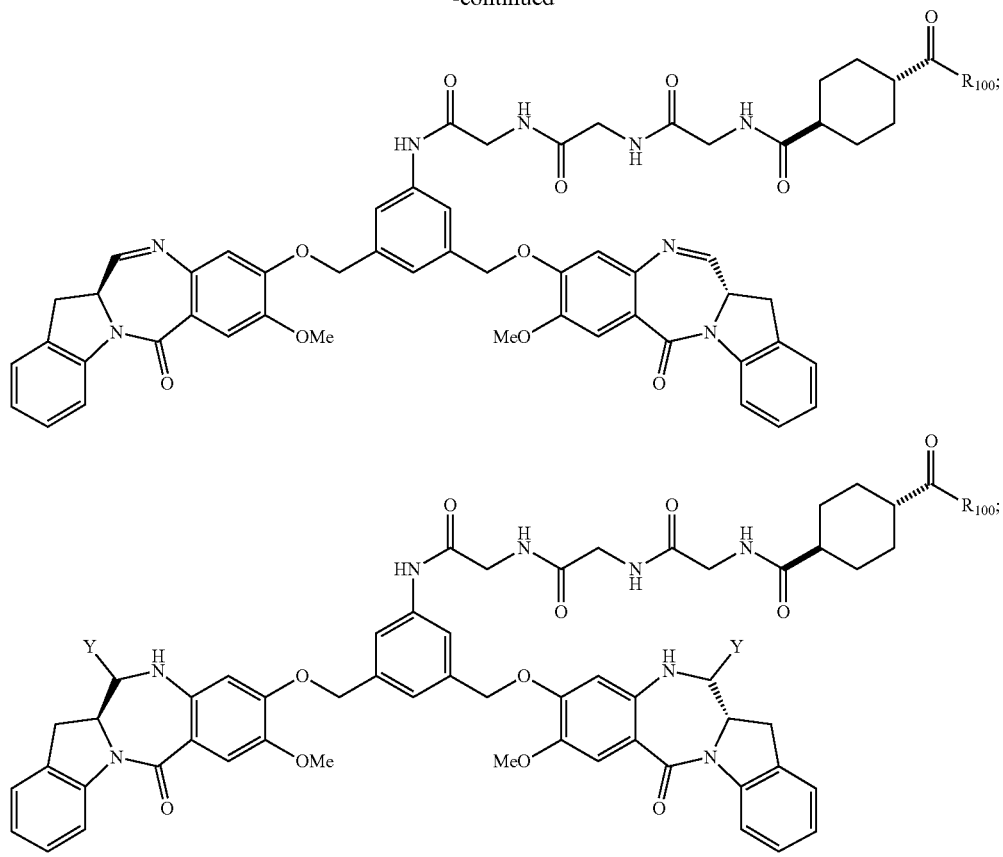
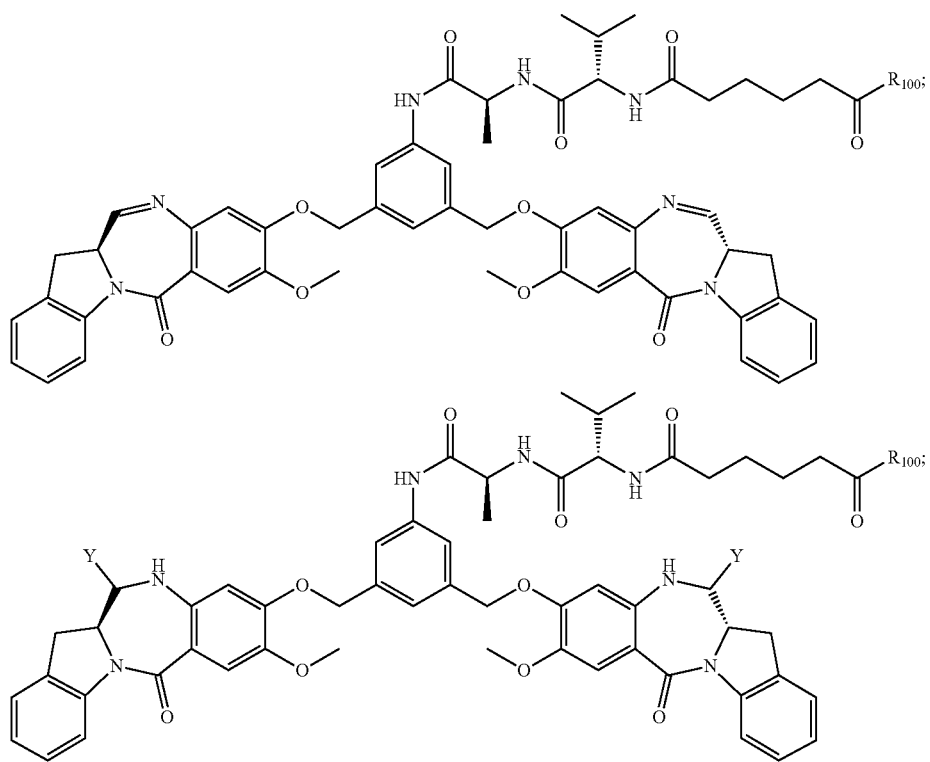

-continued
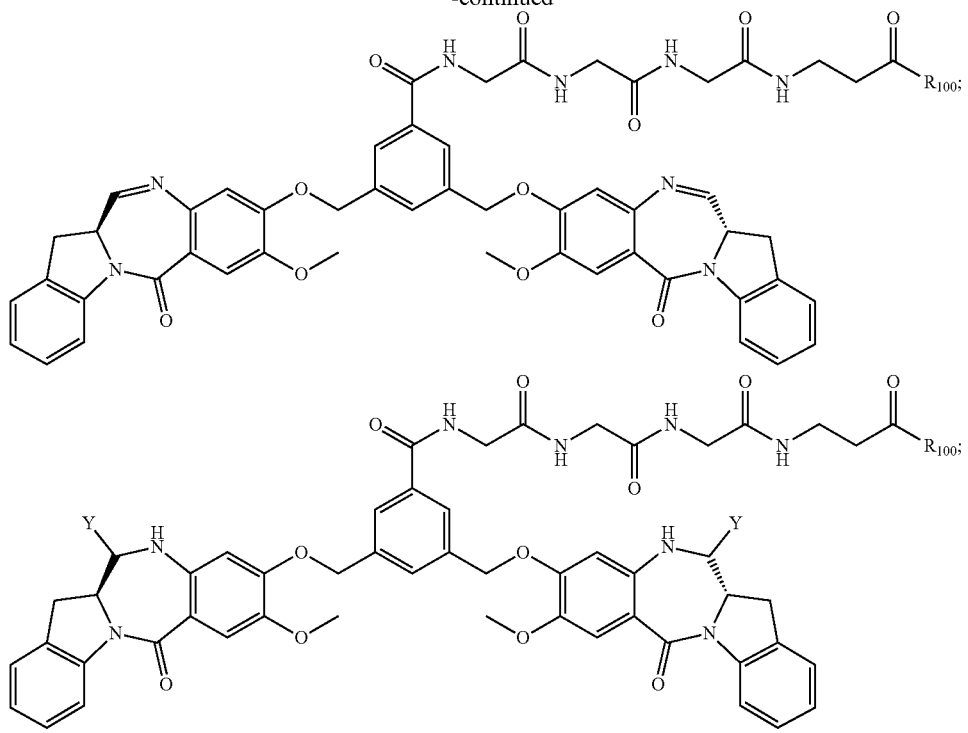
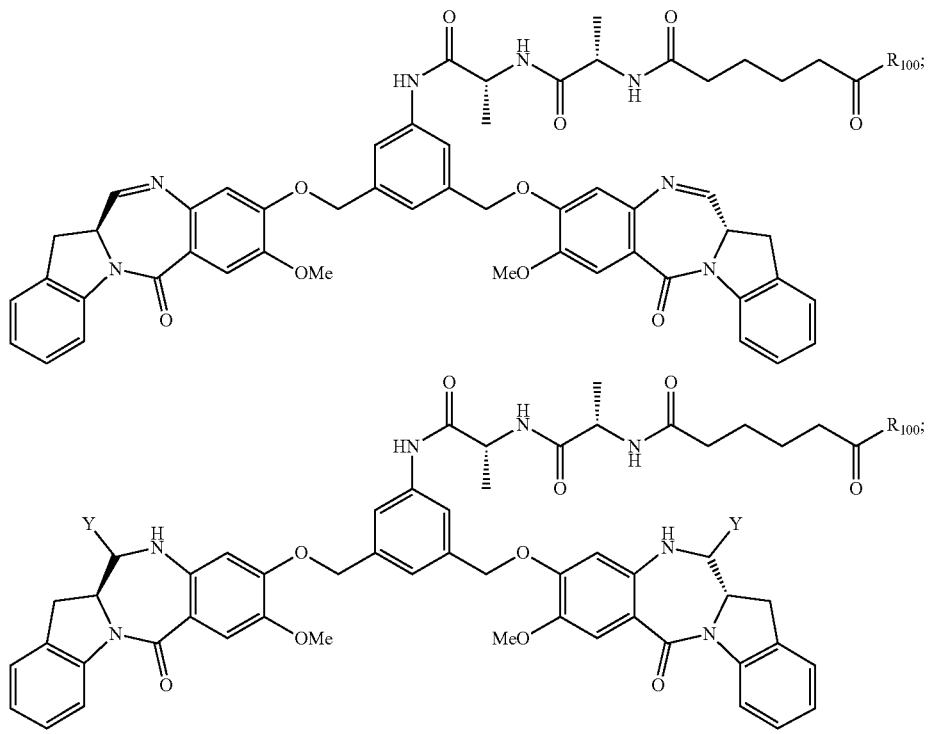

-continued
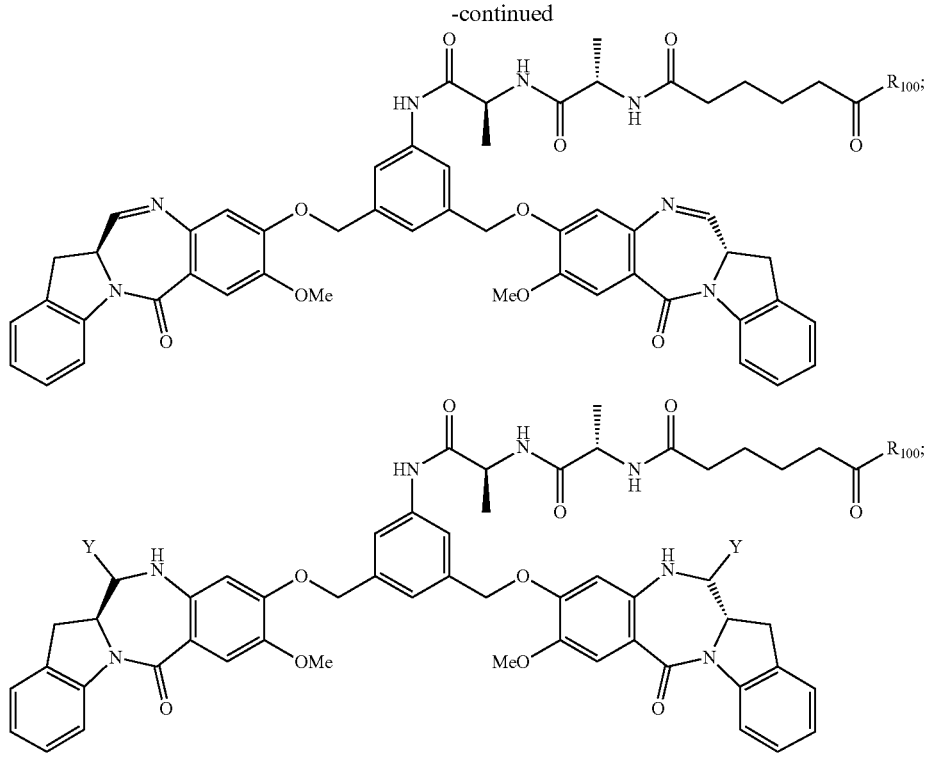
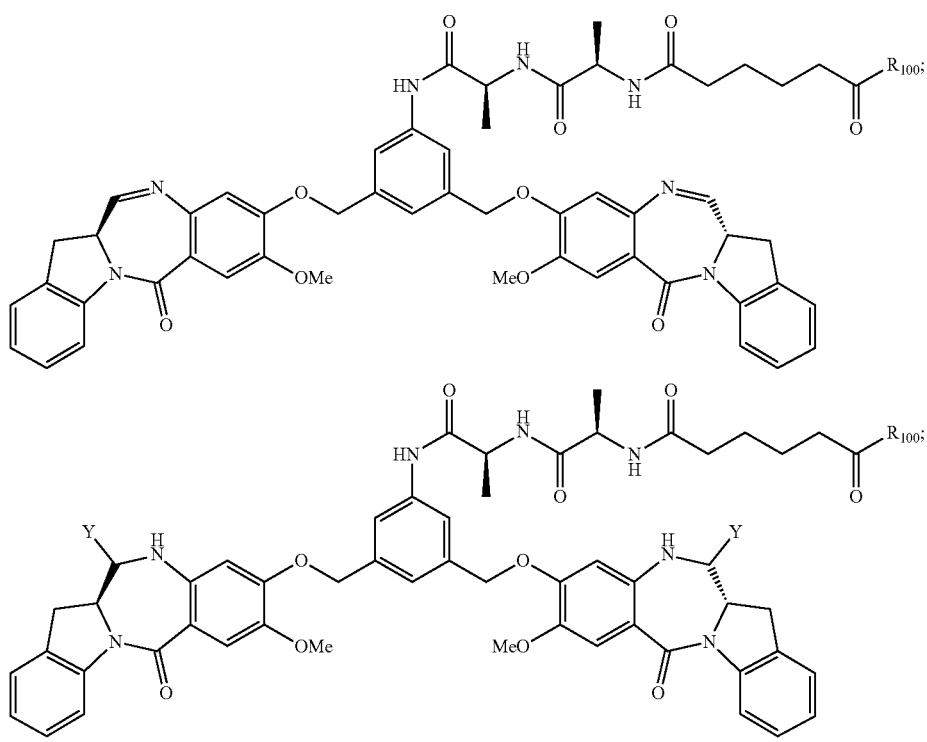

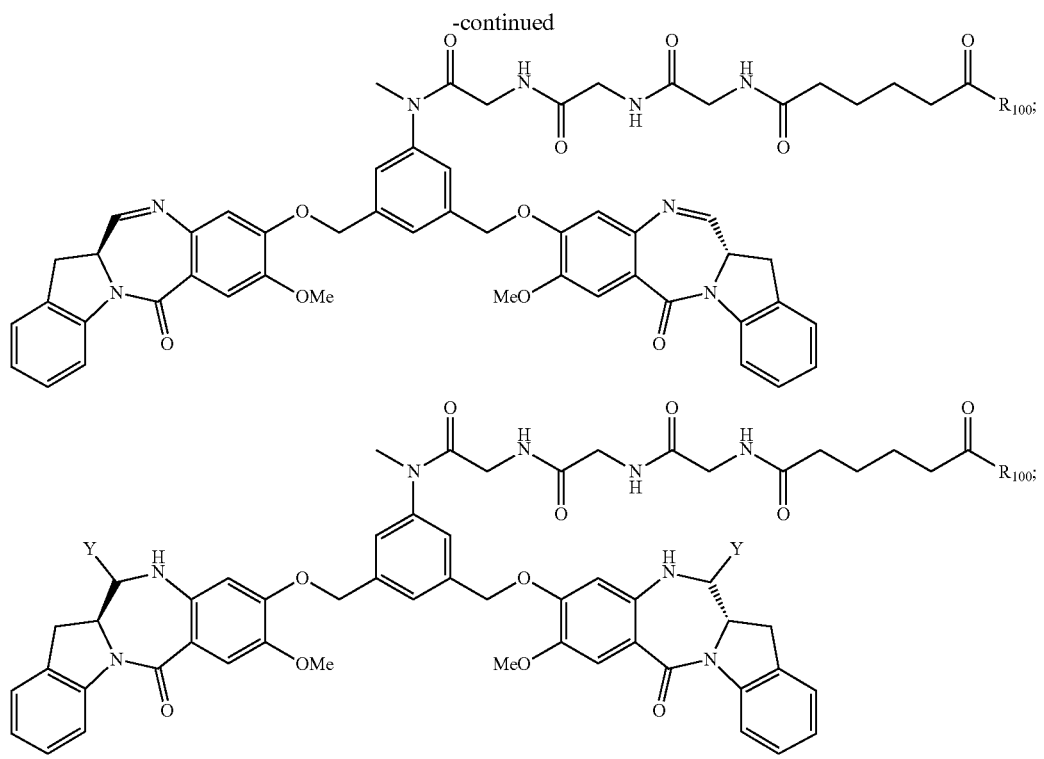
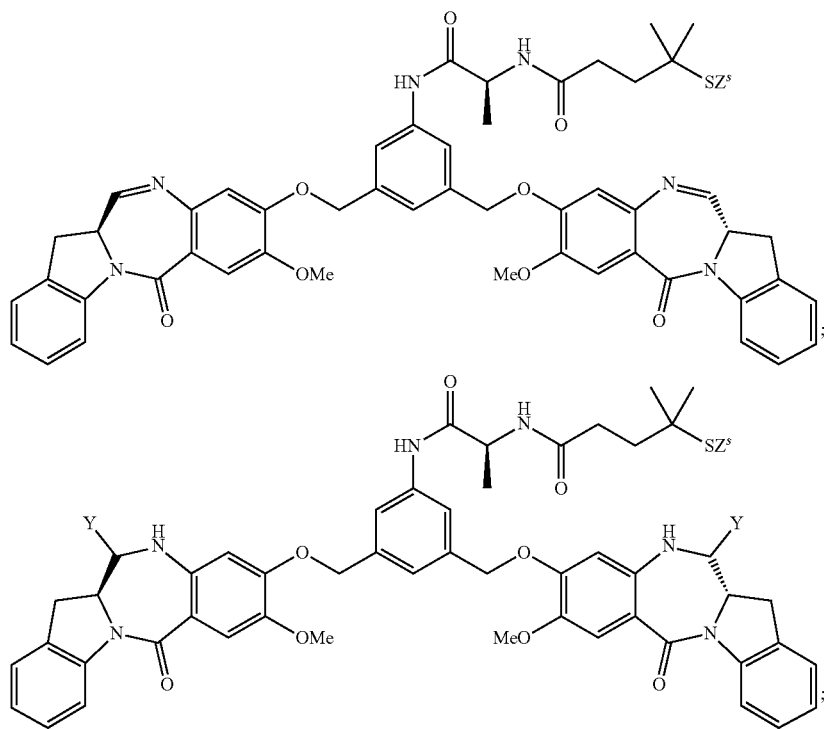

-continued
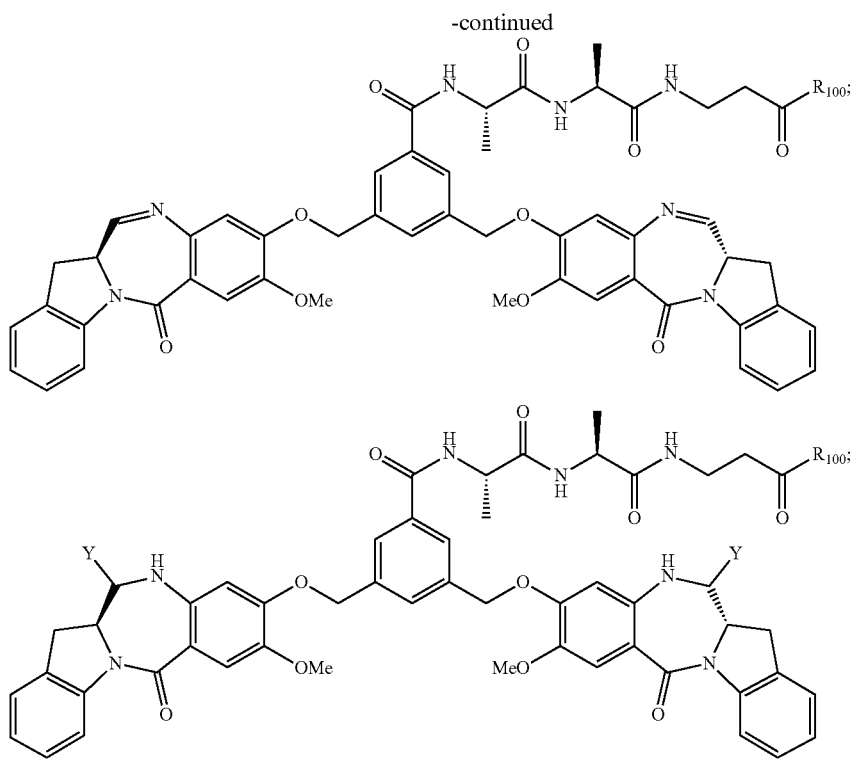
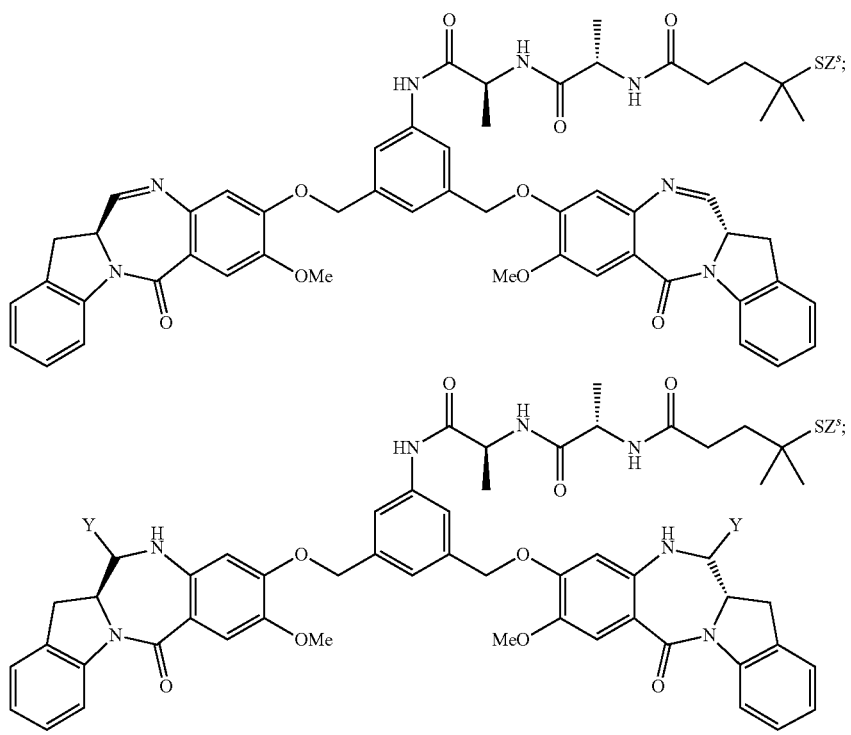

-continued
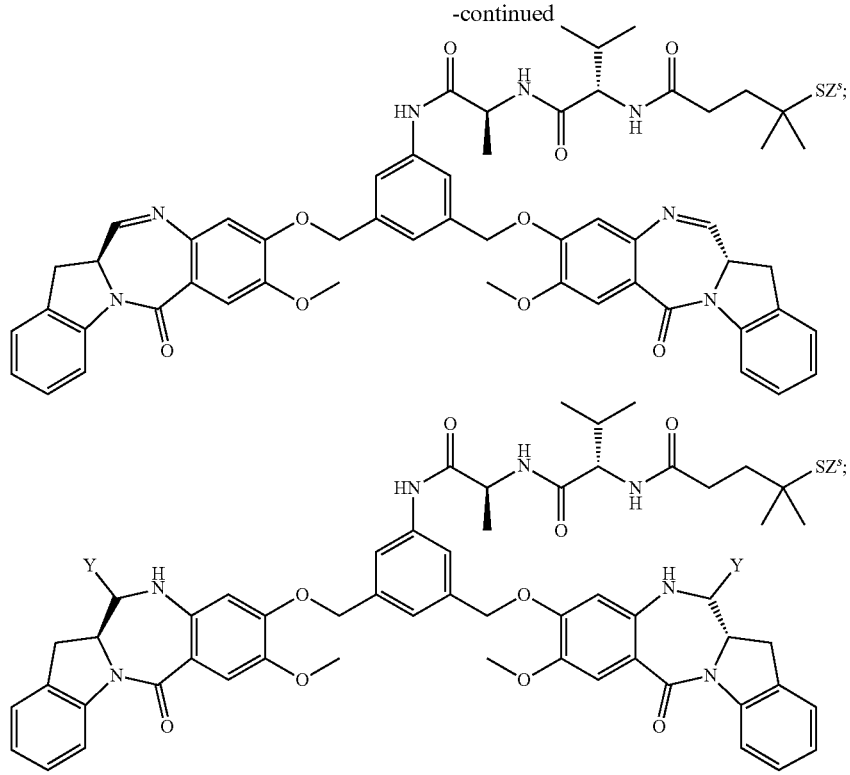
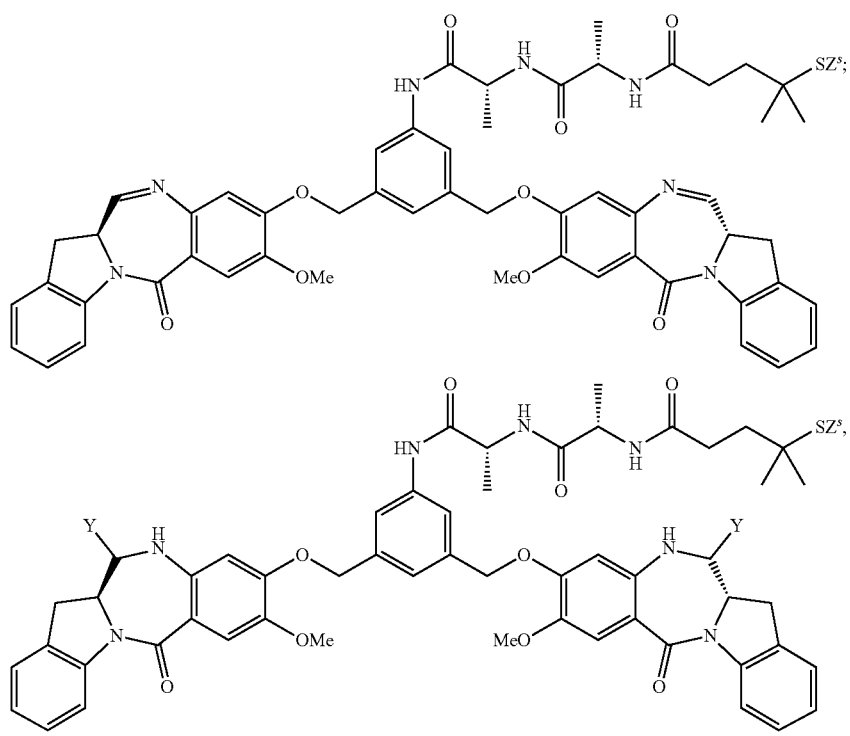

or a pharmaceutically acceptable salt thereof, wherein:
R$_{100}$ is —OH, —OMe or
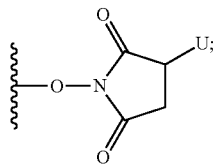
(5)
(10)
Y is —H, —OH or —SO$_3$M;
M is H$^+$, Na$^+$ or K$^+$;
Z$^s$ is —H, —SR$^d$, —C(=O)R$^{d1}$ or is selected from any one of the following formulas:
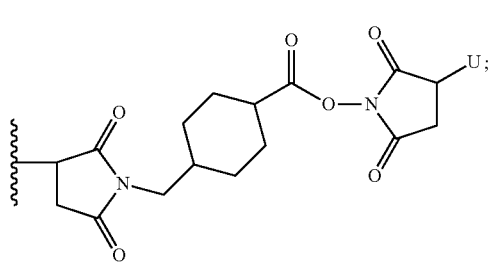
(a1)
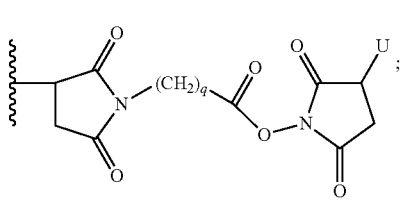
(a2)
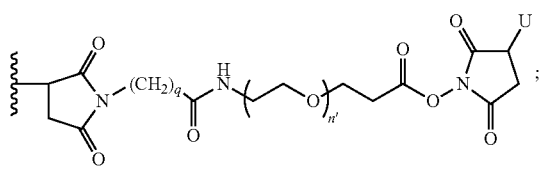
(a3)
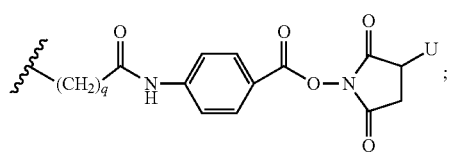
(a4)
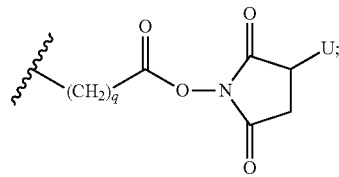
(a5)
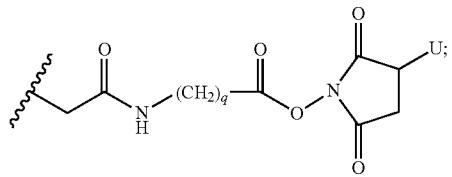
(a6)
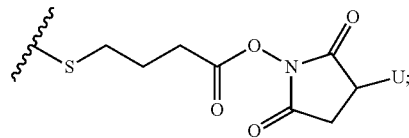
(a7)
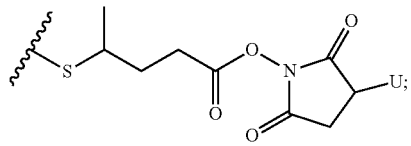
(a8)
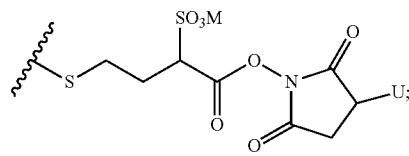
(a9)
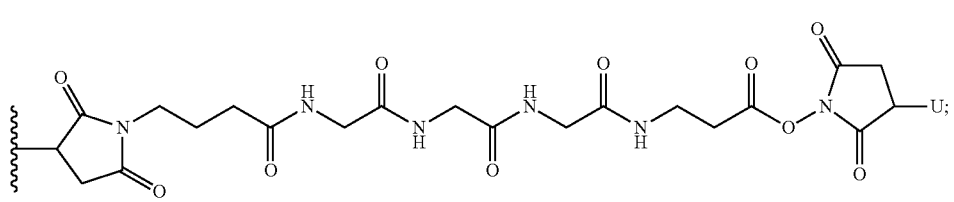
(a10)

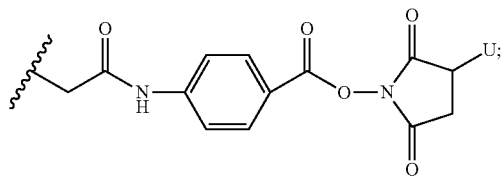 (a11)

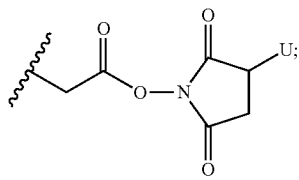 (a12)

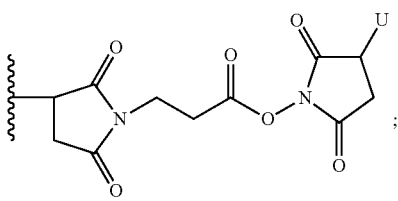 (a13)

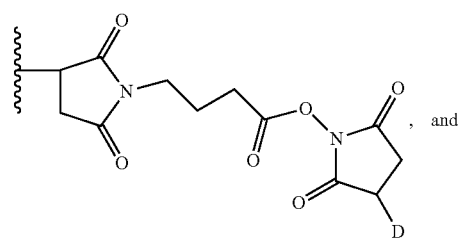 (a14)

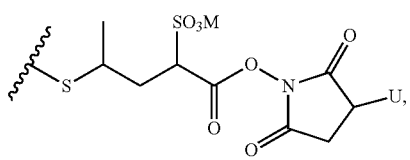 (a15)

wherein:
q is an integer from 1 to 5;
n' is an integer from 2 to 6;
U is —H or $SO_3M$; and
$R^d$ is a linear or branched alkyl having 1 to 6 carbon atoms or is selected from phenyl, nitrophenyl, dinitrophenyl, carboxynitrophenyl, pyridyl, and nitropyridyl; and
$R^{d1}$ is a linear or branched alkyl having 1 to 6 carbon atoms.

8. A conjugate comprising a cytotoxic compound and a cell-binding agent (CBA), wherein the cytotoxic compound is covalently linked to the CBA, and wherein said cytotoxic compound is represented by any one of the following formulas:

—$(CH_2CH_2O)_n$—$R^c$, halogen, —NH(C=NH)NH$_2$, —OR, —NR'R", —NO$_2$, —NR'COR", —SR, a sulfoxide represented by —SOR', a sulfone represented by —SO$_2$R', a sulfonate —SO$_3$M, a sulfate —OSO$_3$M, a sulfonamide represented by —SO$_2$NR'R", cyano, an azido, —COR', —OCOR', and —OCONR'R";
one of the $Z_1$ and $Z_2$ is —C(=O)—, and the other is —NR$_5$—;
P is an amino acid residue or a peptide containing between 2 to 20 amino acid residues;
$R_x$ is an optionally substituted linear, branched or cyclic alkyl, alkenyl or alkynyl having from 1 to 10 carbon atoms;

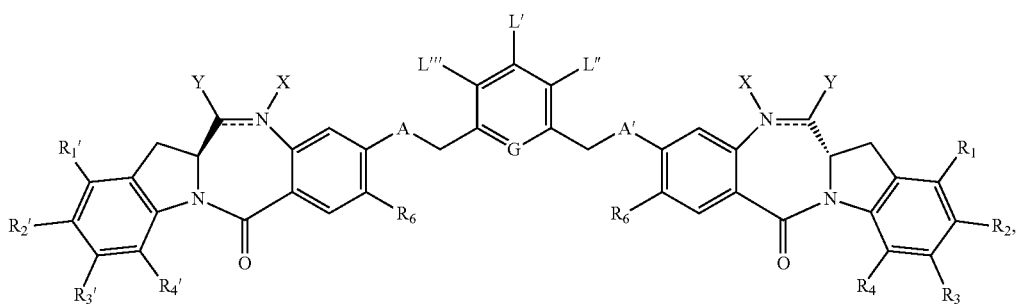 (V')

or a pharmaceutically acceptable salt thereof, wherein:
CBA is an antibody;
one of L', L", and L'" is represented by the following formula:

—$Z_1$—P—$Z_2$—$R_x$-J'  (A')

and the other two are the same or different, and are independently selected from —H, an optionally substituted linear, branched or cyclic alkyl, alkenyl or alkynyl having from 1 to 10 carbon atoms, J' is a moiety comprising —C(=O)—;
the double line = between N and C represents a single bond or a double bond, provided that when it is a double bond X is absent and Y is —H, or a linear or branched alkyl having 1 to 4 carbon atoms, and when it is a single bond, X is —H or an amine protecting moiety;
Y is a leaving group selected from —OR, —OCOR', —OCOOR', —OCONR'R", —NR'R", —NR'COR", —NR'NR'R", an optionally substituted 5- or 6-membered nitrogen-containing monocyclic heterocycle, —NR'(C=NH)NR'R", an amino acid residue, or a peptide represented by —NRCOP', —SR, —SOR', halogen, cyano, azido, —OSO$_3$H, —SO$_3$H, H$_2$S$_2$O$_5$, PO$_3$SH$_3$, PO$_2$S$_2$H$_2$, POS$_3$H$_2$, PS$_4$H$_2$, (R$^i$O)$_2$PS(OR$^i$), R$^i$S—, R$^i$SO, R$^i$SO$_2$, R$^i$SO$_3$, HS$_2$O$_3$, HS$_2$O$_4$, P(=S)(OR$^{k'}$)(S)(OH), R$^k$C(=O)NOH and HOCH$_2$SO$_2^-$, or a mixture thereof, wherein R$^i$ is a linear or branched alkyl having 1 to 10 carbon atoms and is substituted with at least one substituent selected from —N(R$^j$)$_2$, —CO$_2$H, —SO$_3$H, and —PO$_3$H; R$^i$ can be further optionally substituted with a substituent for an alkyl described herein; R$^j$ is a linear or branched alkyl having 1 to 6 carbon atoms; R$^{k'}$ is a linear, branched or cyclic alkyl, alkenyl or alkynyl having 1 to 10 carbon atoms, aryl, heterocyclyl or heteroaryl;

P' is an amino acid residue or a polypeptide containing 2 to 20 amino acid residues;

R, for each occurrence, is independently selected from the group consisting of —H, an optionally substituted linear, branched or cyclic alkyl, alkenyl or alkynyl having from 1 to 10 carbon atoms, —(CH$_2$CH$_2$O)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR$_2$, —COR, an optionally substituted linear, branched or cyclic alkyl, alkenyl or alkynyl having from 1 to 10 carbon atoms, —(CH$_2$CH$_2$O)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms;

n is an integer from 1 to 24;

R$_1$, R$_2$, R$_3$, R$_4$, R$_1'$, R$_2'$, R$_3'$ and R$_4'$ are each independently selected from the group consisting of —H, an optionally substituted linear, branched or cyclic alkyl, alkenyl or alkynyl having from 1 to 10 carbon atoms, —(CH$_2$CH$_2$O)$_n$—R$^c$, halogen, NH(C=NH)NH$_2$, —OR, —NR'R", —NO$_2$, —NCO, —NR'COR", —SR, —SOR', —SO$_2$R', —SO$_3$H, —OSO$_3$H, —SO$_2$NR'R", cyano, an azido, —COR', —OCOR', and —OCONR'R";

R$_6$ is —H, —R, —OR, —SR, —NR'R", —NO$_2$, or halogen;

G is —CH— or —N—;

A and A' are the same or different, and are independently selected from —O—, —C(=O)—, —CRR'O—, —CRR'—, —S—, —CRR'S—, —NR$_5$ and —CRR'N(R$_5$)—;

R$_5$ for each occurrence is independently —H or an optionally substituted linear or branched alkyl having 1 to 10 carbon atoms;

wherein the optional substituent described above is a linear, branched or cyclic alkyl, alkenyl or alkynyl having from 1 to 10 carbon atoms, aryl, heteroaryl, heterocyclyl, halogen, —NH(C=NH)NH$_2$, —OR$^{100}$, NR$^{101}$R$^{102}$, —NO$_2$, —NR$^{101}$COR$^{102}$, —SR$^{100}$, —SOR$^{101}$, —SO$_2$R$^{101}$, —SO$_3$M, —OSO$_3$M, —SO$_2$NR$^{101}$R$^{102}$, cyano, an azido, —COR$^{101}$, —OCOR$^{101}$, —OCONR$^{101}$R$^{102}$ or a polyethylene glycol unit (—CH$_2$CH$_2$O)R$^{101}$, wherein M is H or a cation; R$^{100}$, R$^{101}$, and R$^{102}$ are each independently selected from H, linear, branched or cyclic alkyl, alkenyl or alkynyl having from 1 to 10 carbon atoms, a polyethylene glycol unit (—CH$_2$CH$_2$O)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclyl in the groups represented by R$^{100}$, R$^{101}$, R$^{102}$ and R$^{104}$ are optionally substituted with one or more substituents independently selected from halogen, —OH, —CN, —NO$_2$ and unsubstituted linear or branched alkyl having 1 to 4 carbon atoms.

9. The conjugate of claim 8, wherein L' is represented by the following formula:

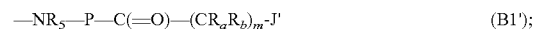  (B1');

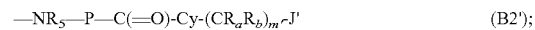  (B2');

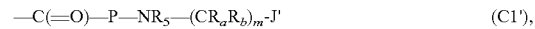  (C1'), or

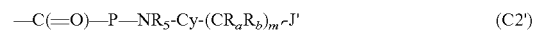  (C2')

wherein:

J' is —C(=O)—;

R$_a$ and R$_b$, for each occurrence, are each independently —H, (C$_1$-C$_3$)alkyl or a charged substituent or an ionizable group Q, wherein Q is —SO$_3$H, or a pharmaceutically acceptable salt thereof;

m is an integer from 1 to 6;

m' is 0 or an integer from 1 to 6; and

Cy is a cyclic alkyl having 5 or 6 ring carbon atoms optionally substituted with halogen, —OH, (C$_1$-C$_3$) alkyl, (C$_1$-C$_3$)alkoxy, or halo(C$_1$-C$_3$)alkyl.

10. The conjugate of claim 8, wherein L' is represented by the following formula:

  (B3');

or

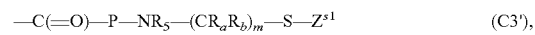  (C3'), wherein:

R$_a$ and R$_b$, for each occurrence, are each independently —H, (C$_1$-C$_3$)alkyl, or a charged substituent or an ionizable group Q, wherein Q is —SO$_3$H, or a pharmaceutically acceptable salt thereof;

m is an integer from 1 to 6;

$Z^{s1}$ is selected from any one of the following formulas:
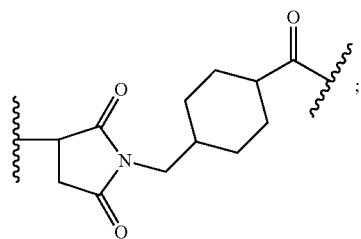 (b1)
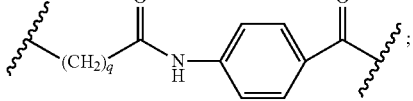 (b2)
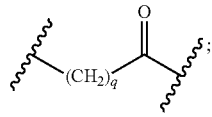 (b3)
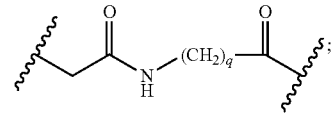 (b4)
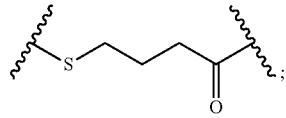 (b5)
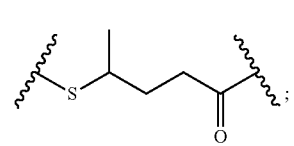 (b6)
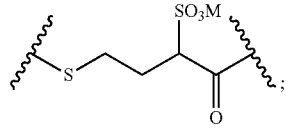 (b7)
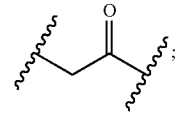 (b8)
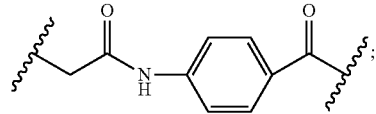 (b9)
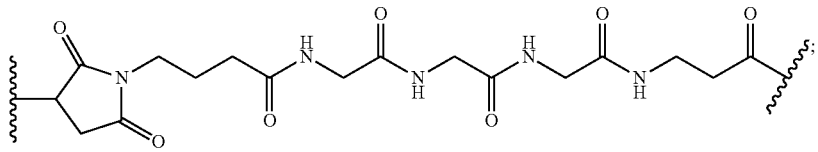 (b10)
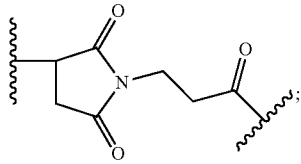 (b11)
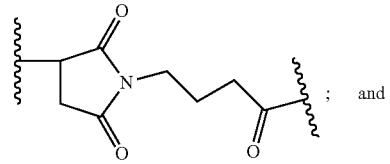 (b12)
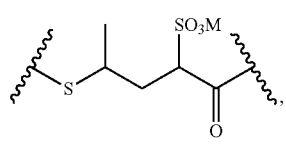 (b13)
 (b14) ; and
(b15)

wherein:
q is an integer from 1 to 5;
n' is an integer from 2 to 6;
U is —H or SO$_3$M; and
M is H$^+$, Na$^+$ or K$^+$.

11. The conjugate of claim 9, wherein P is a peptide containing 2 to 5 amino acid residues.

12. The conjugate of claim 9, wherein P is selected from Gly-Gly-Gly, Ala-Val, Val-Ala, Val-Cit, Val-Lys, Phe-Lys, Lys-Lys, Ala-Lys, Phe-Cit, Leu-Cit, Lle-Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu, β-Ala-Leu-Ala-Leu, Gly-Phe-Leu-Gly, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala.

13. The conjugate of claim 12, wherein:
the double line == between N and C represents a single bond or double bond, provided that when it is a double bond X is absent and Y is —H, and when it is a single bond, X is —H, Y is —OH or —SO$_3$M;
R$_1$, R$_2$, R$_3$, R$_4$, R$_1$', R$_2$', R$_3$' and R$_4$' are all —H;
R$_6$ is —OMe;
A and A' are —O—; and
M is H, Na$^+$ or K$^+$.

14. The conjugate of claim 8, wherein the compound is selected from any one of the following formulas:

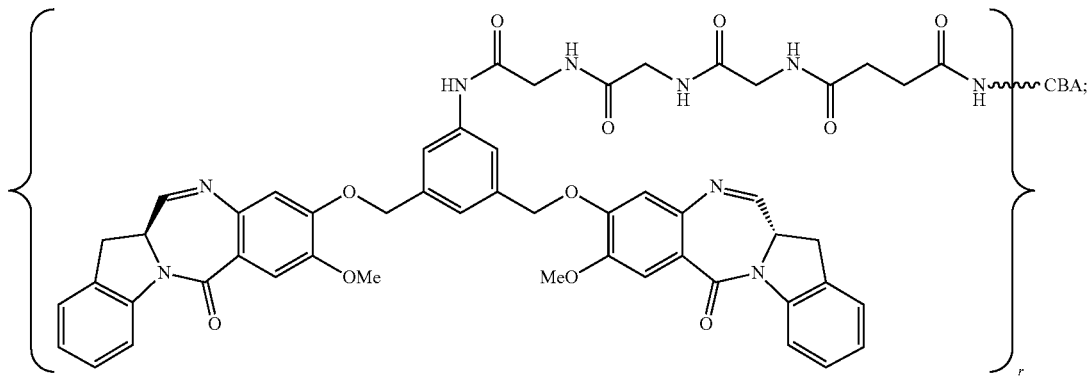

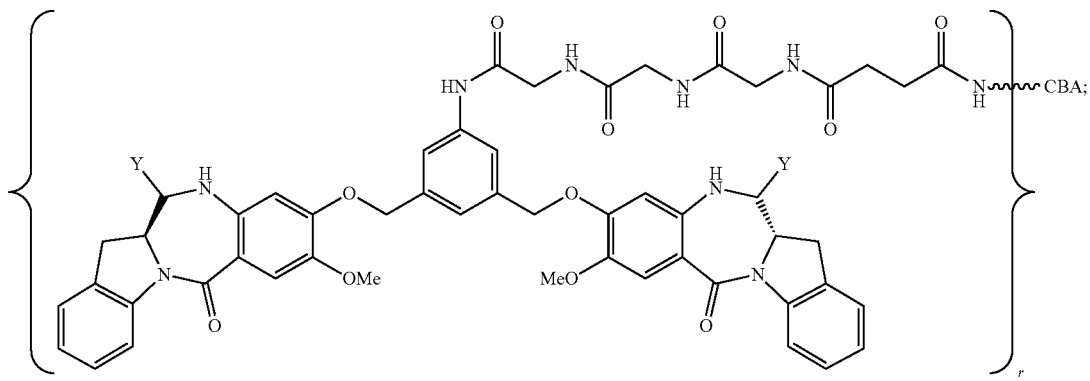

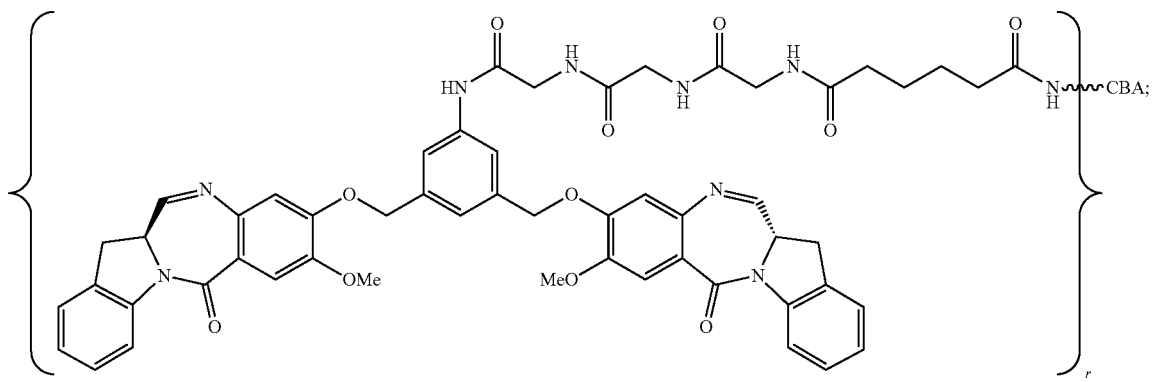

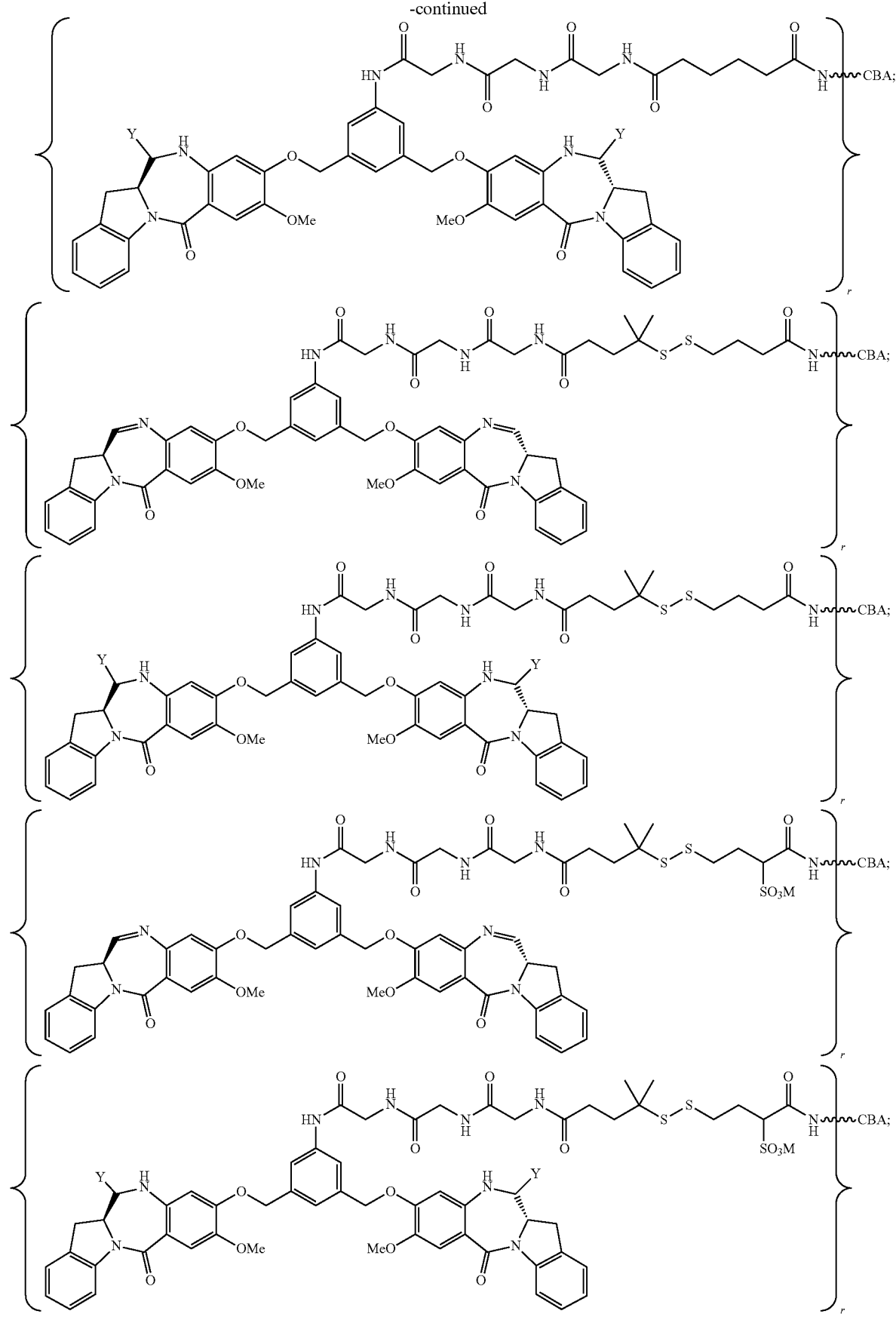

355
-continued
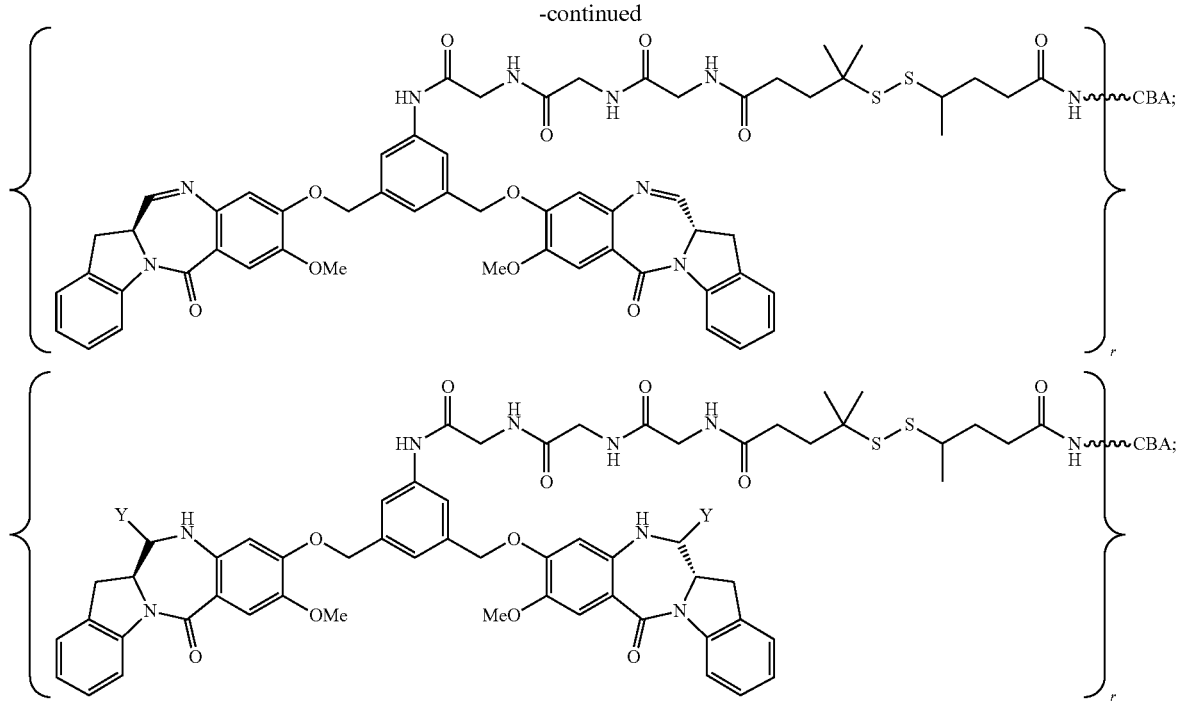
356
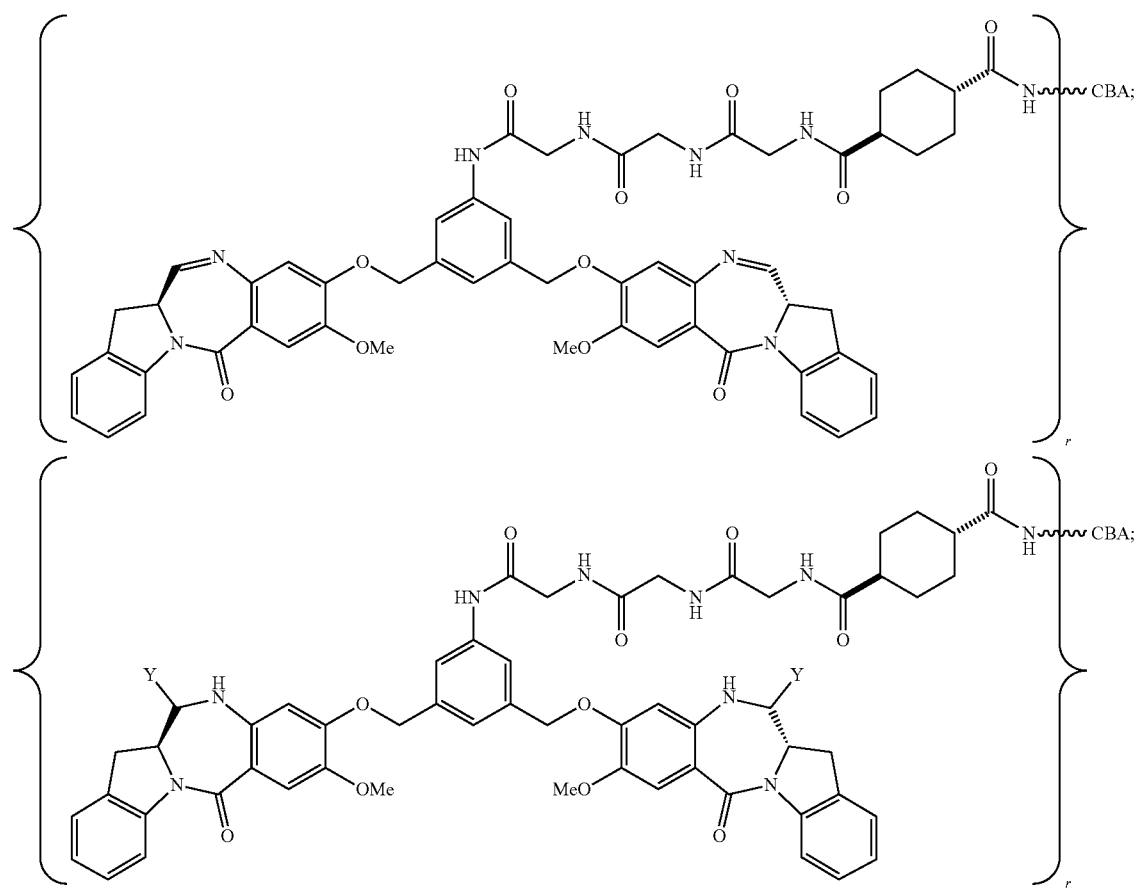

-continued
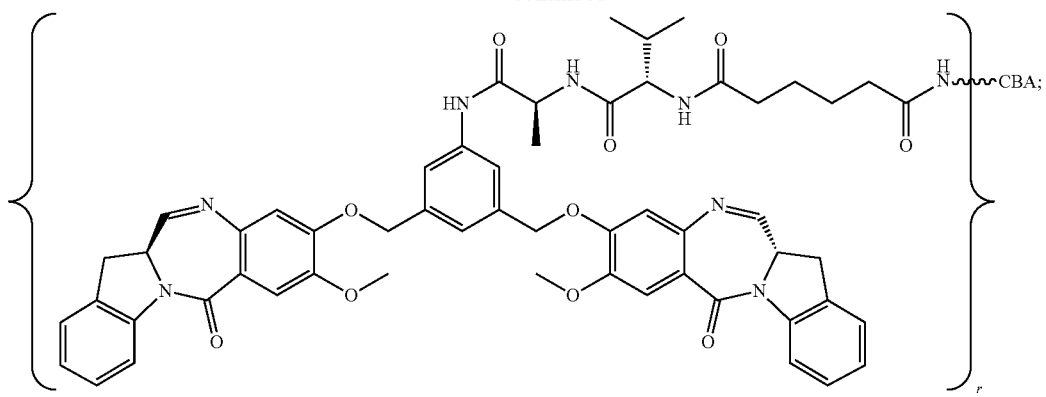
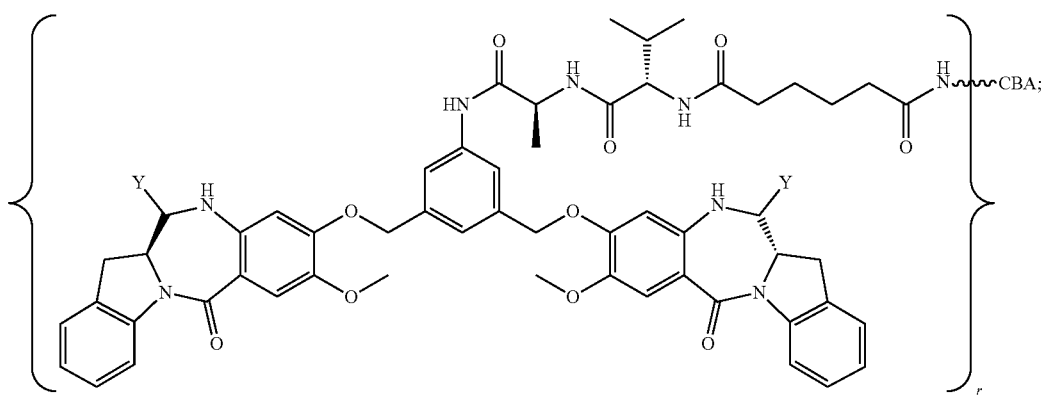
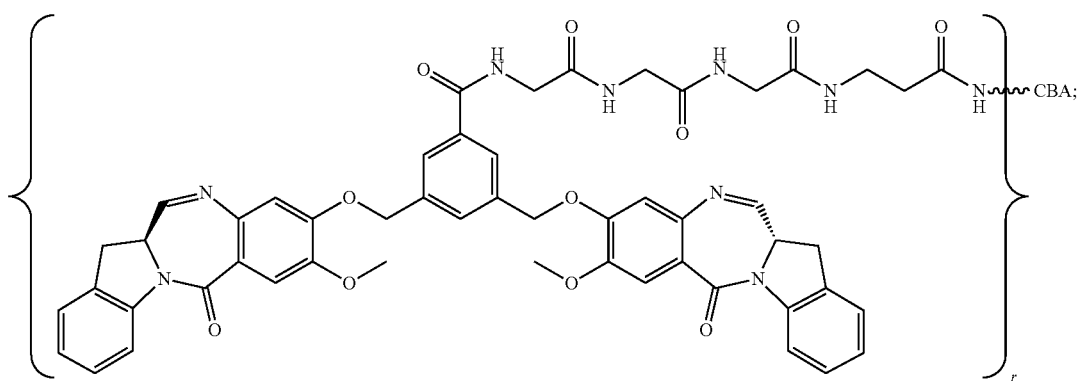
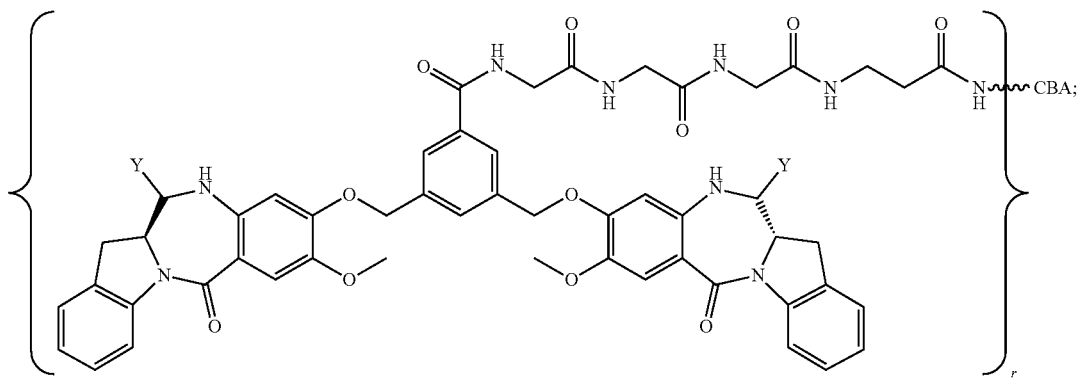

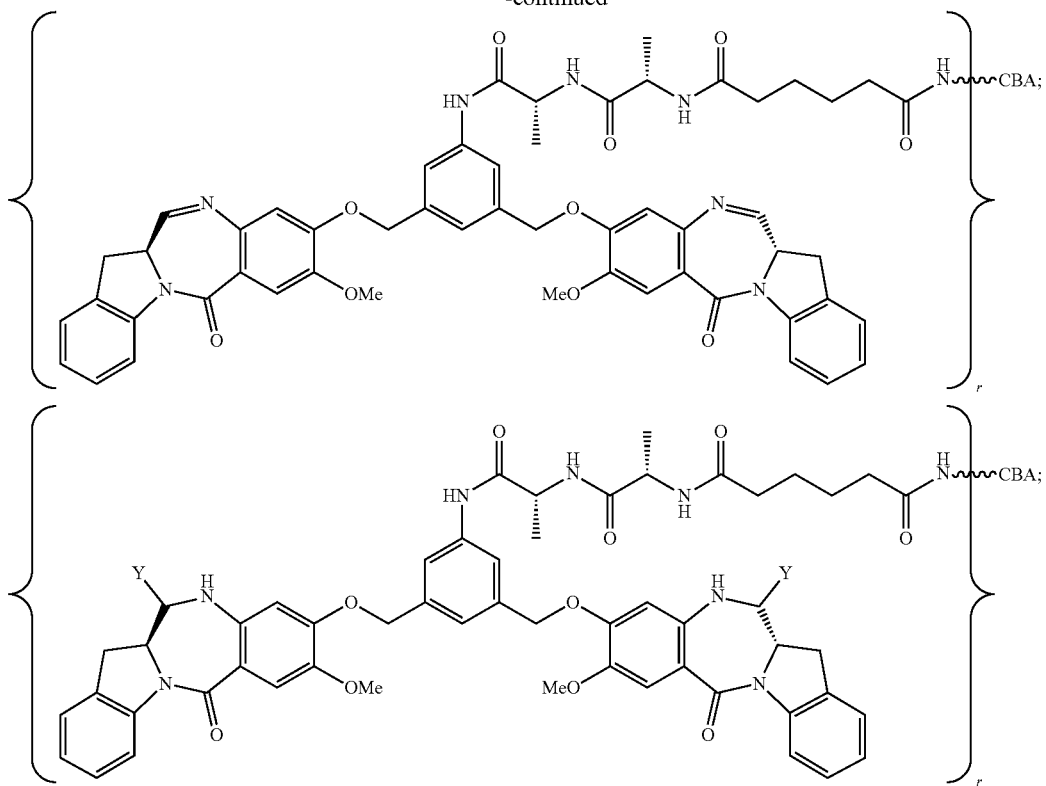
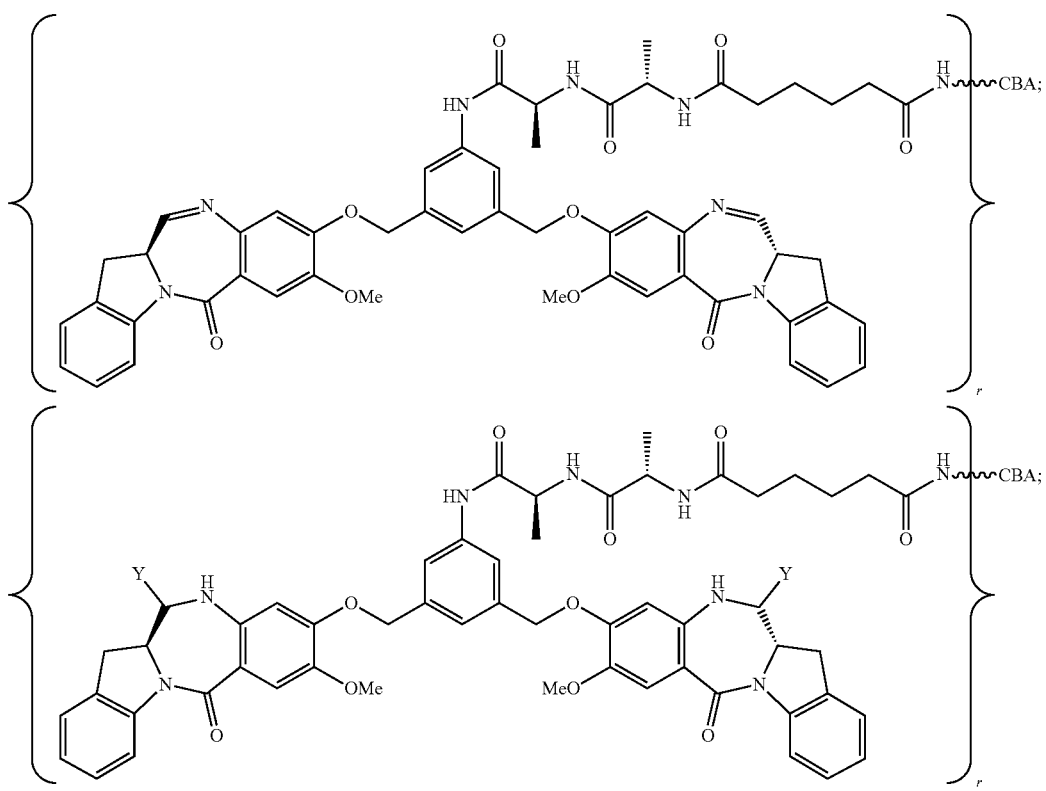

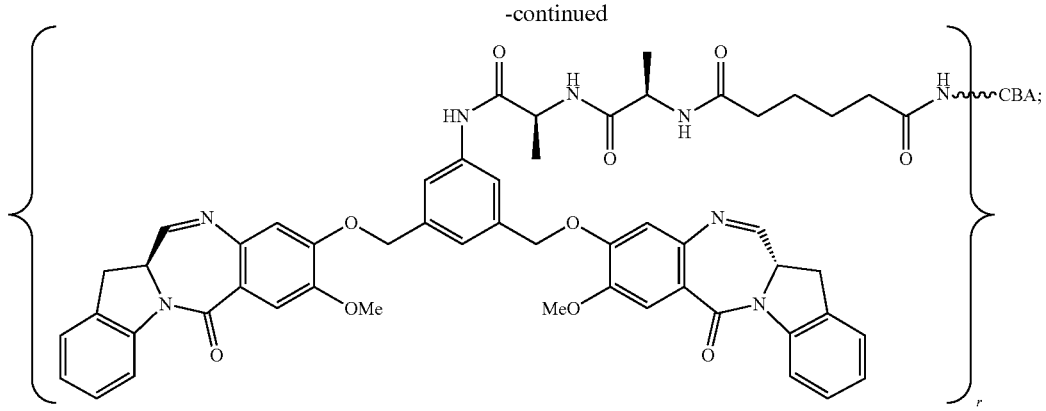
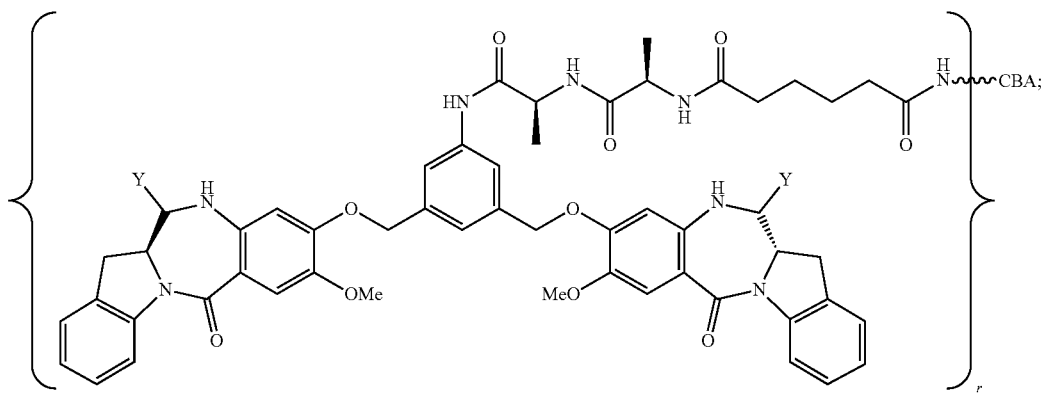
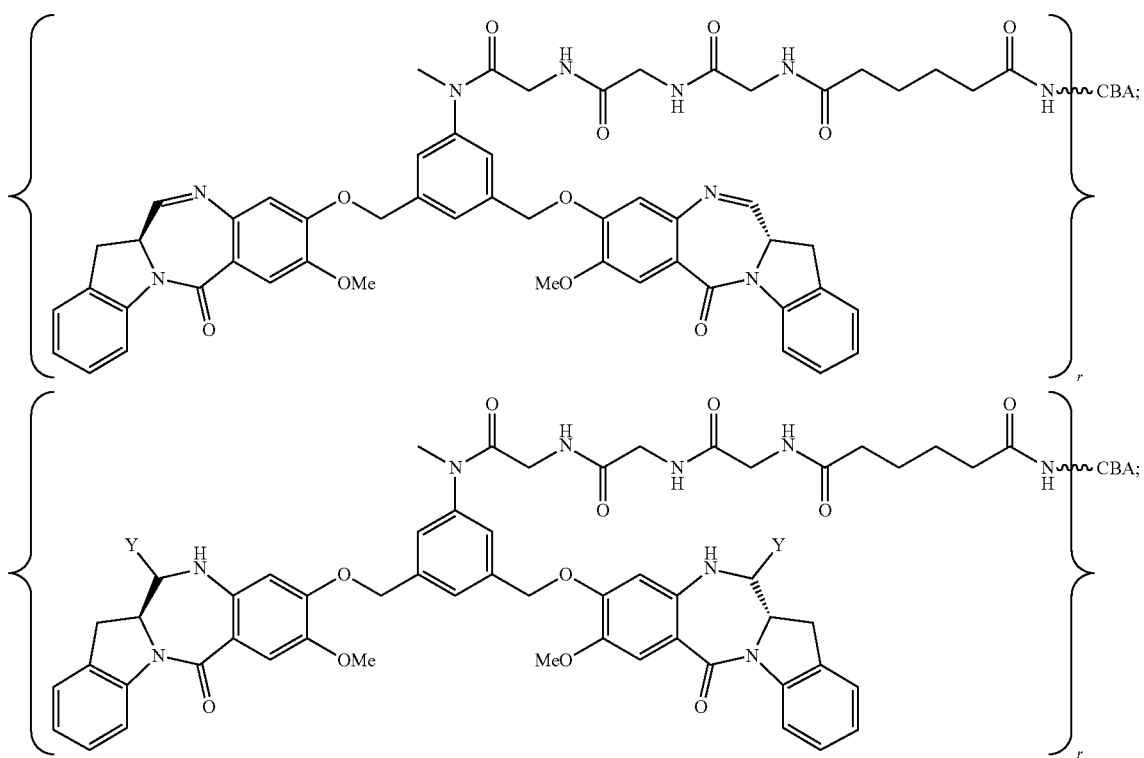

-continued
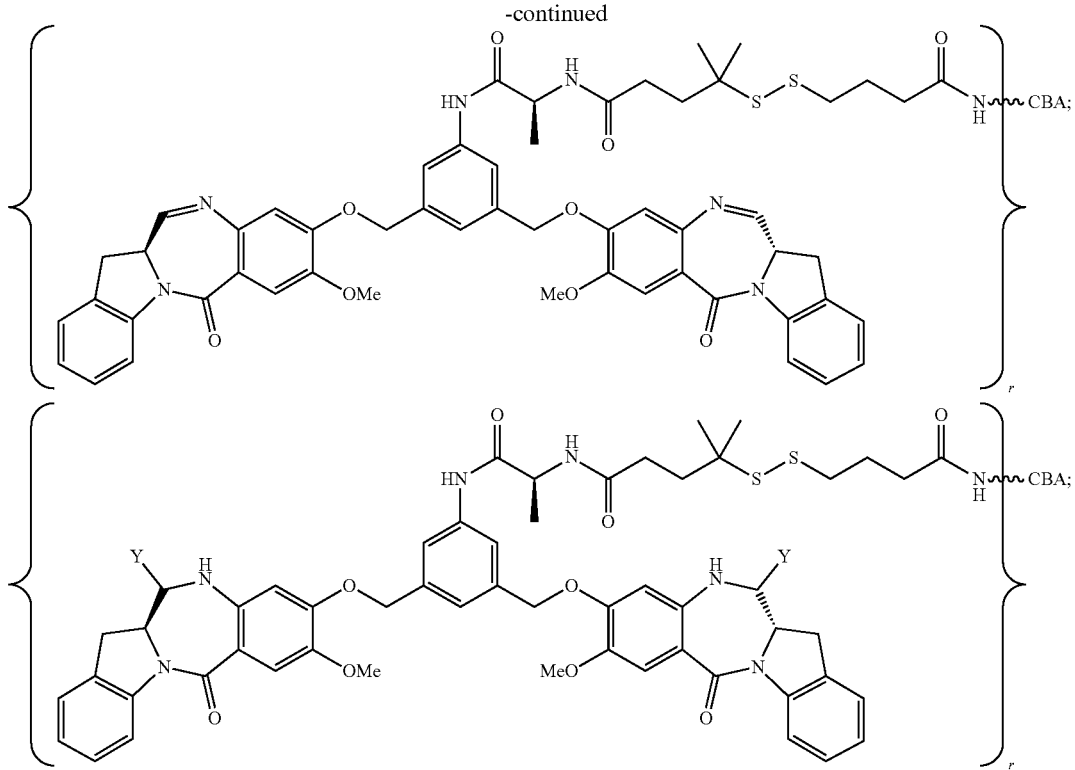
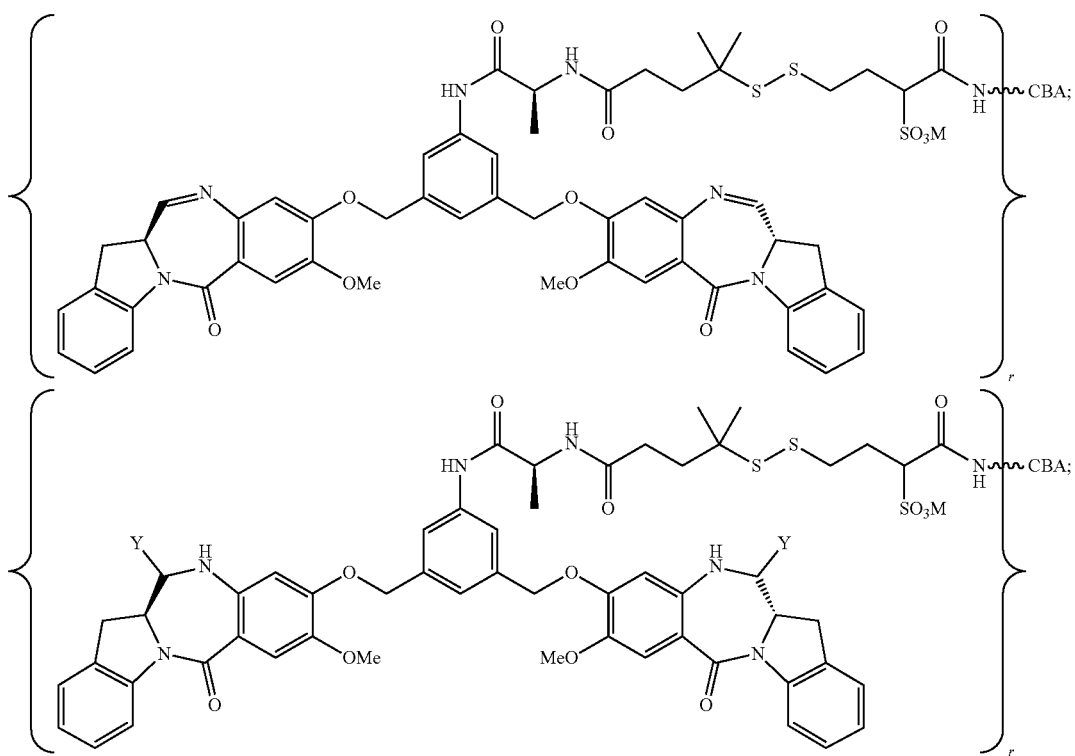

-continued
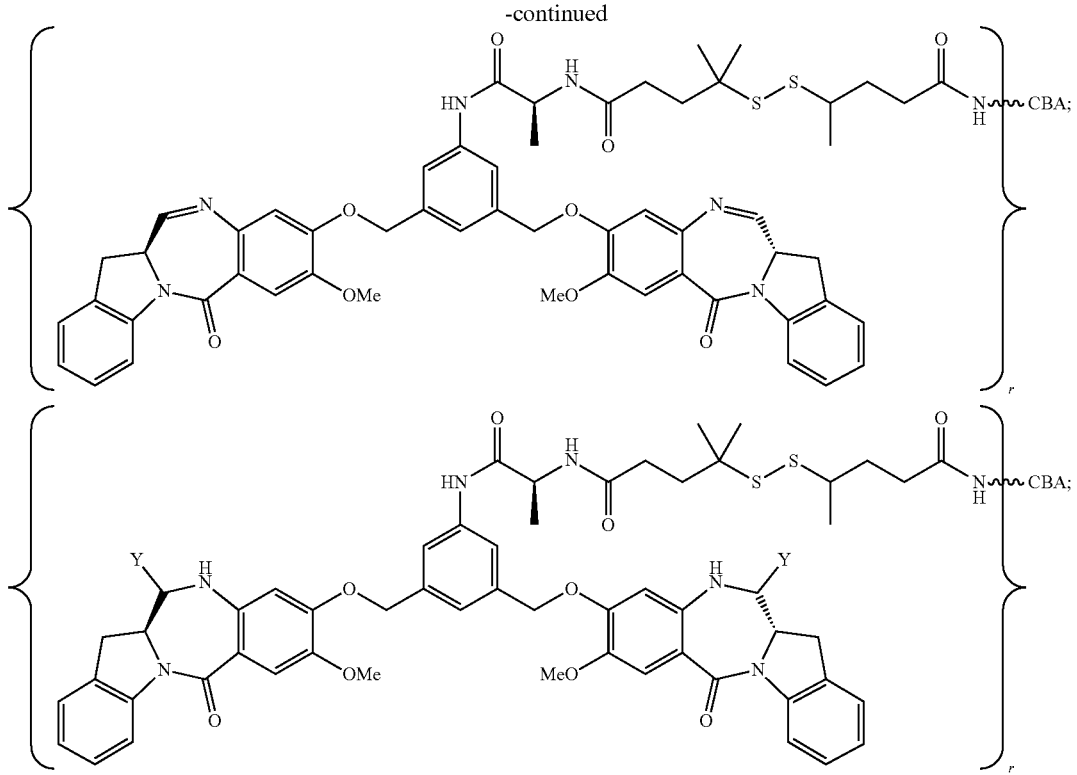
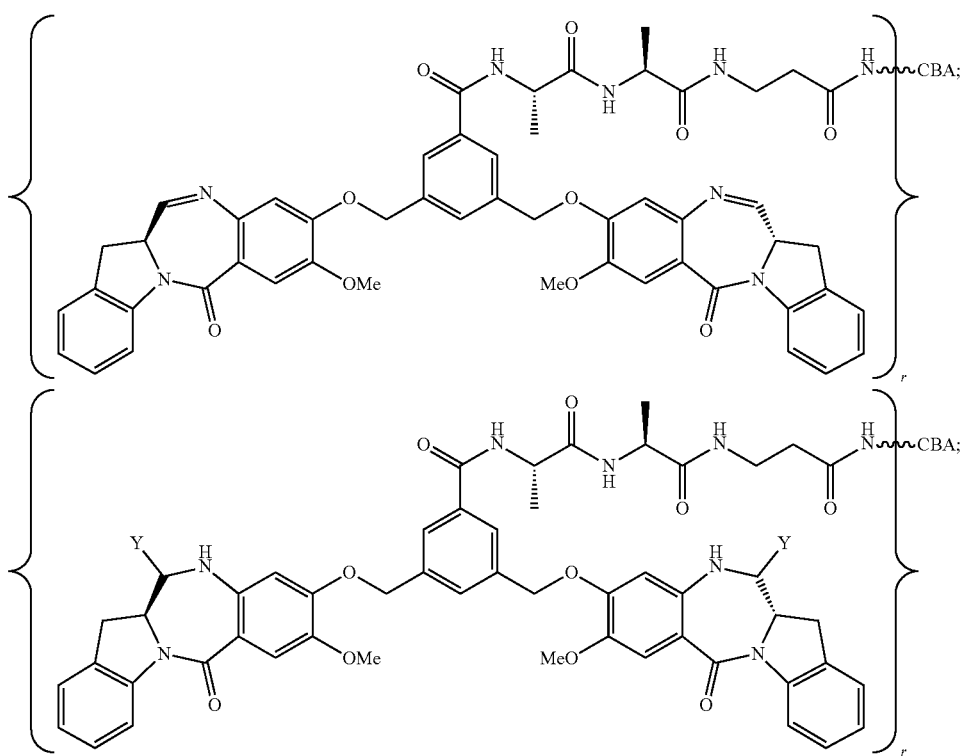

-continued
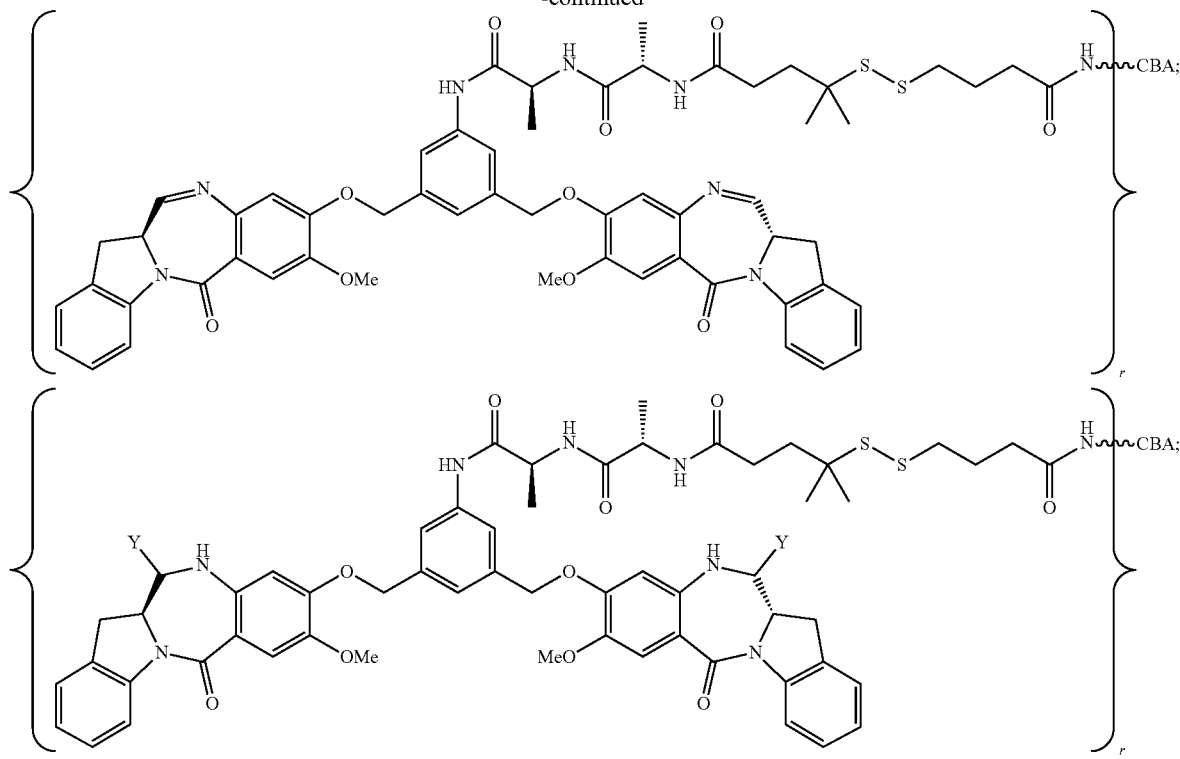
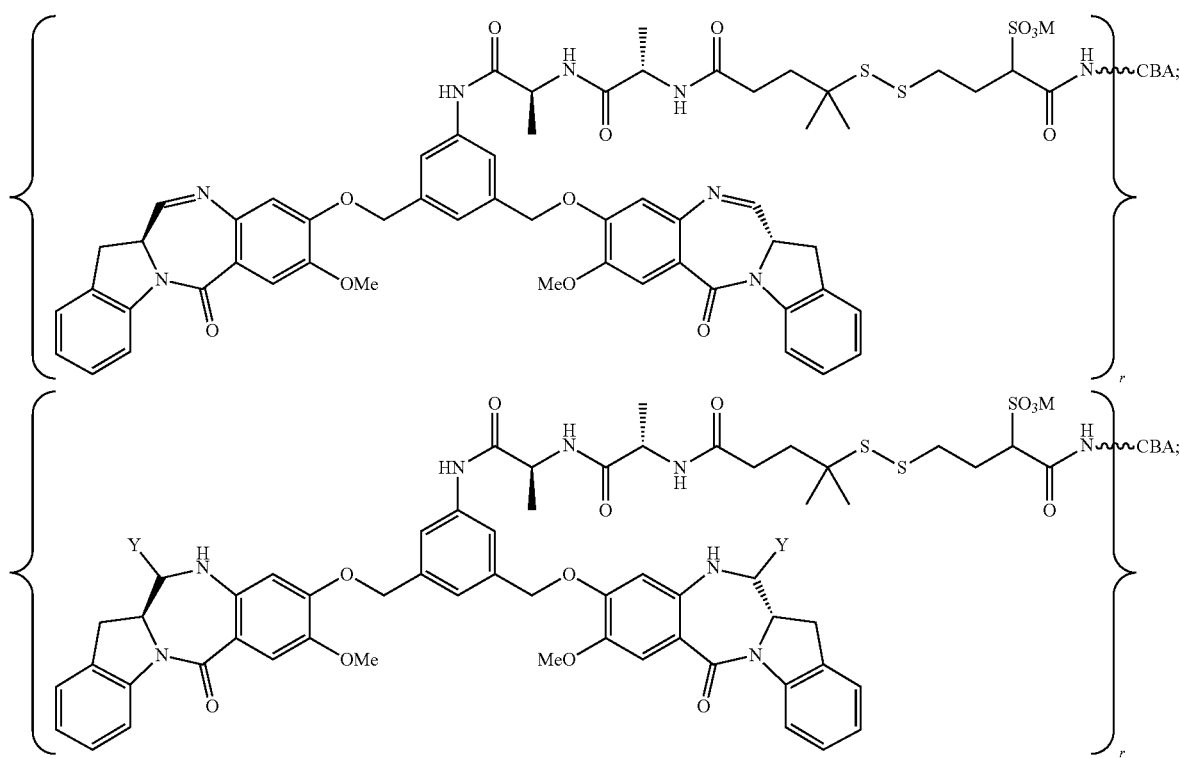

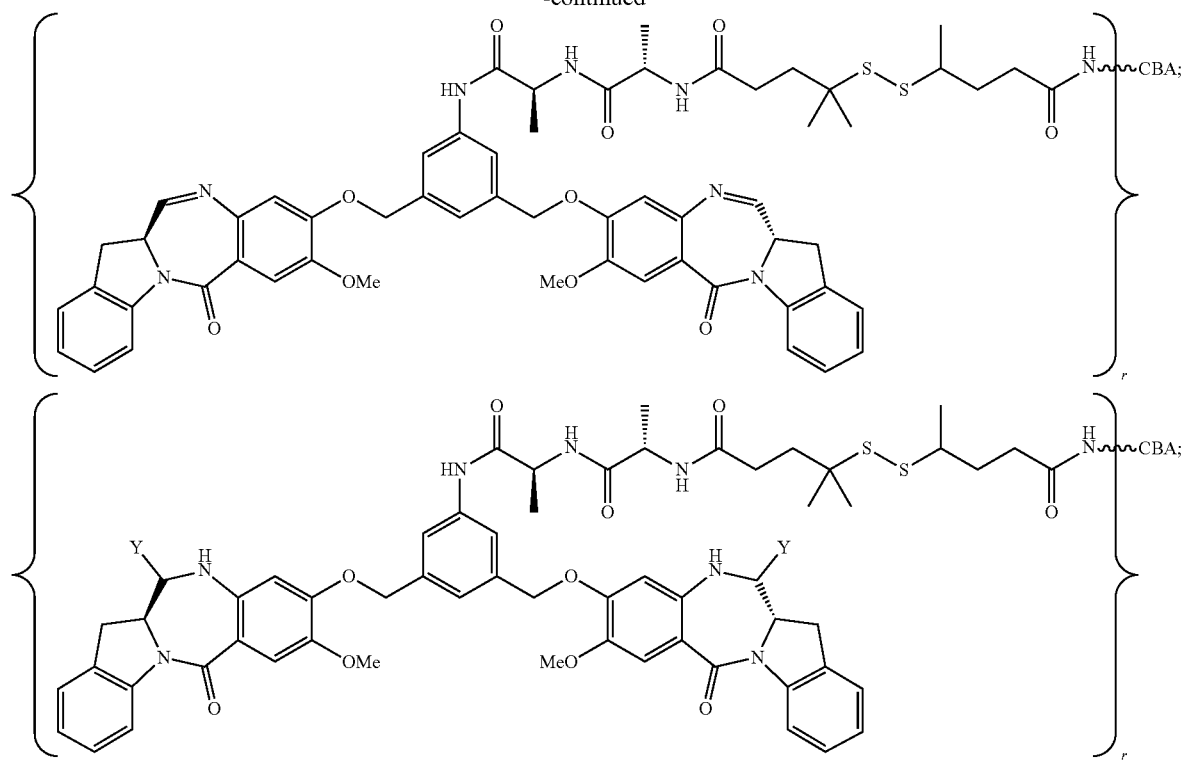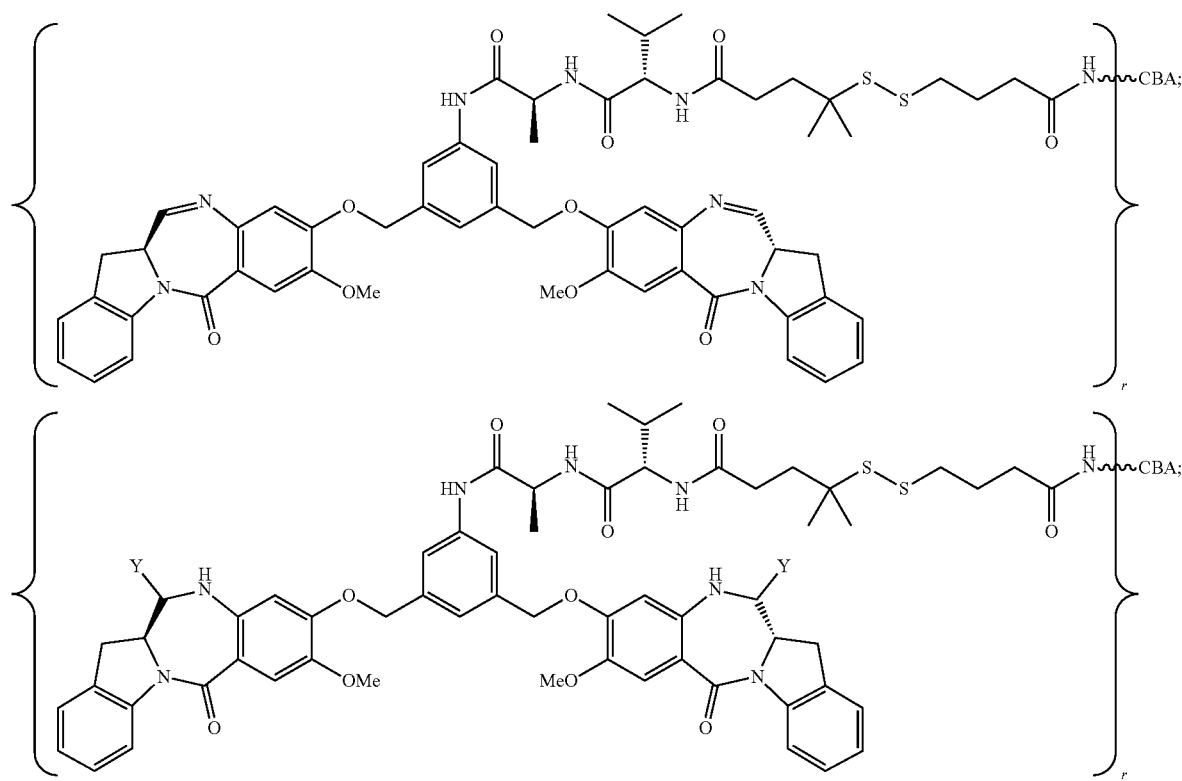

-continued
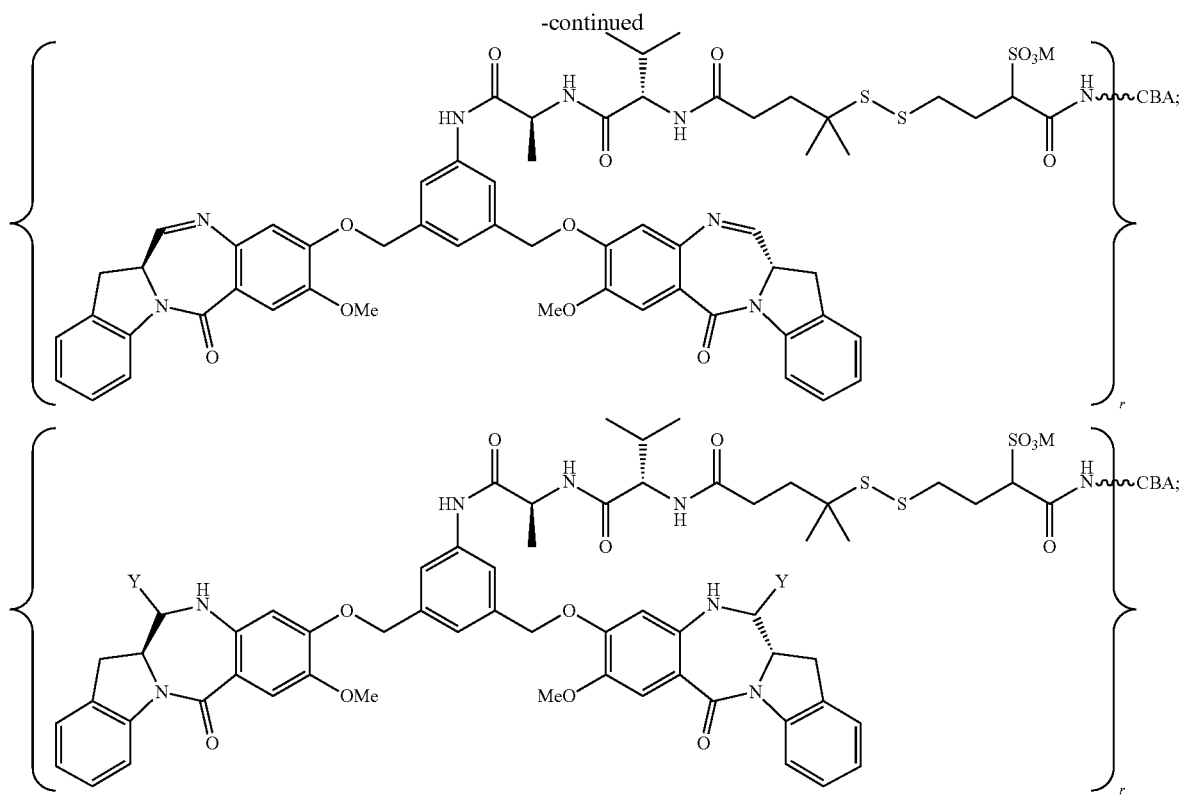
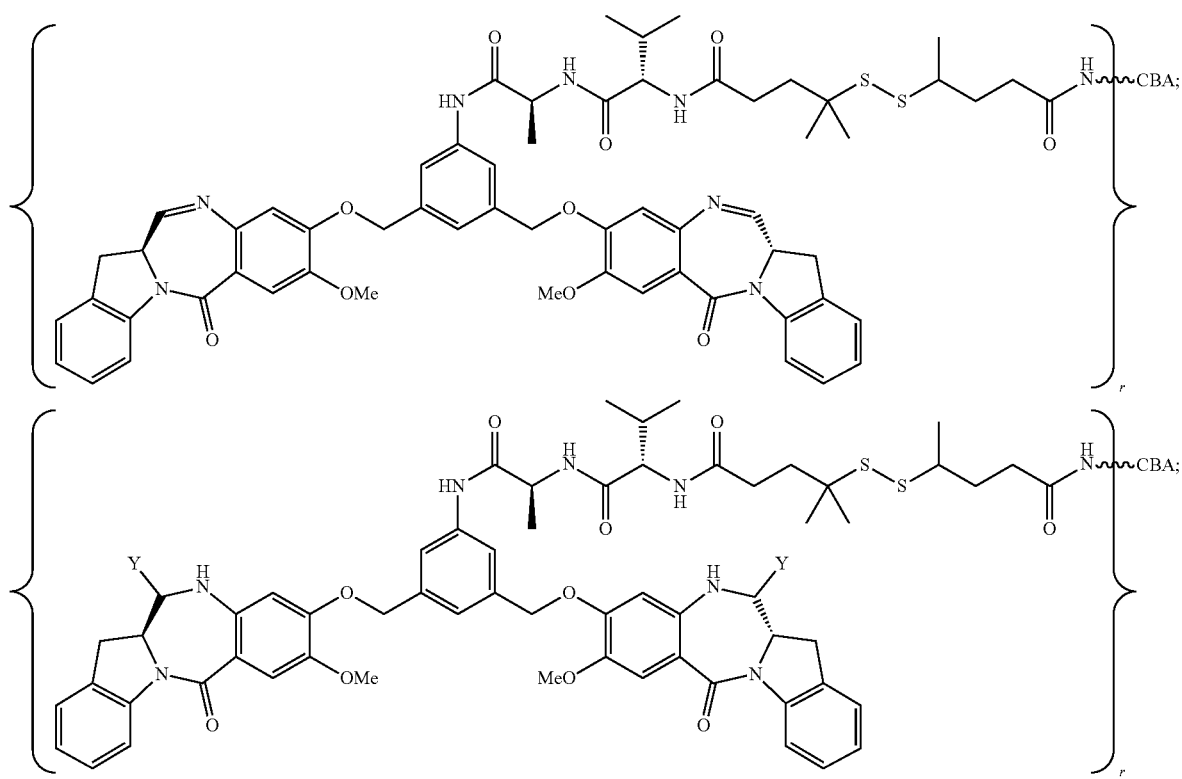

373
-continued
374
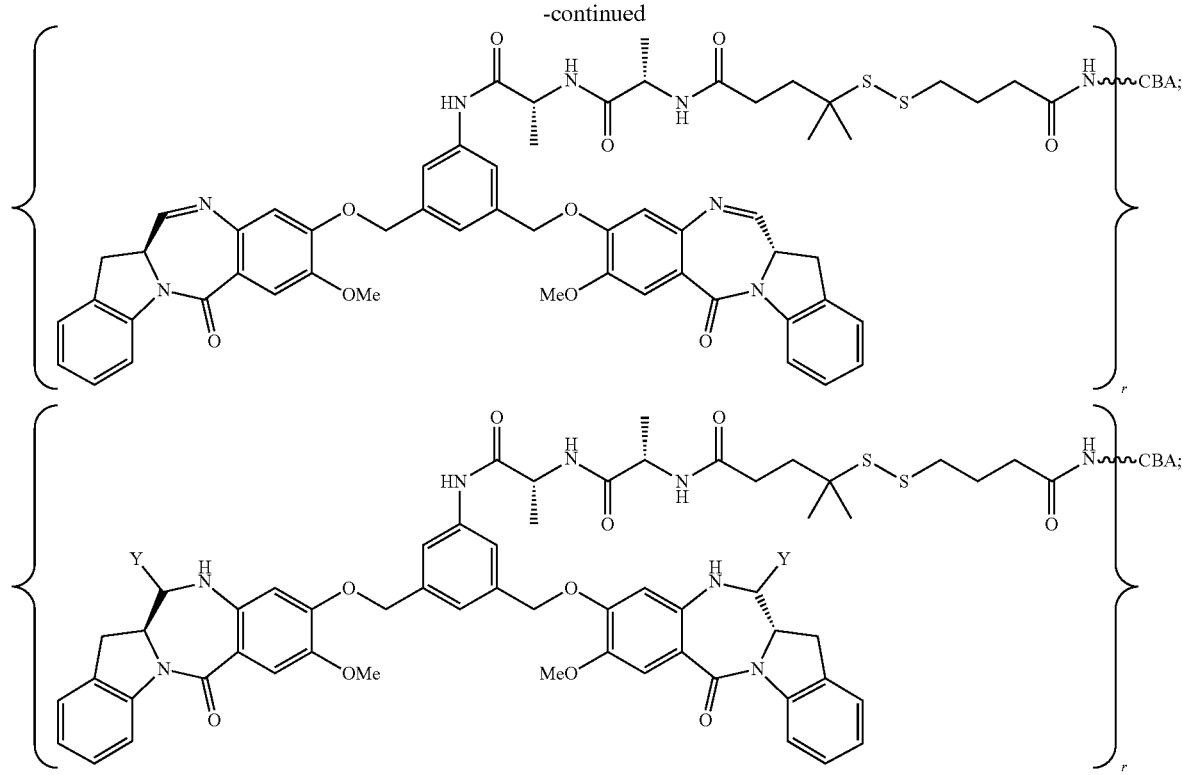
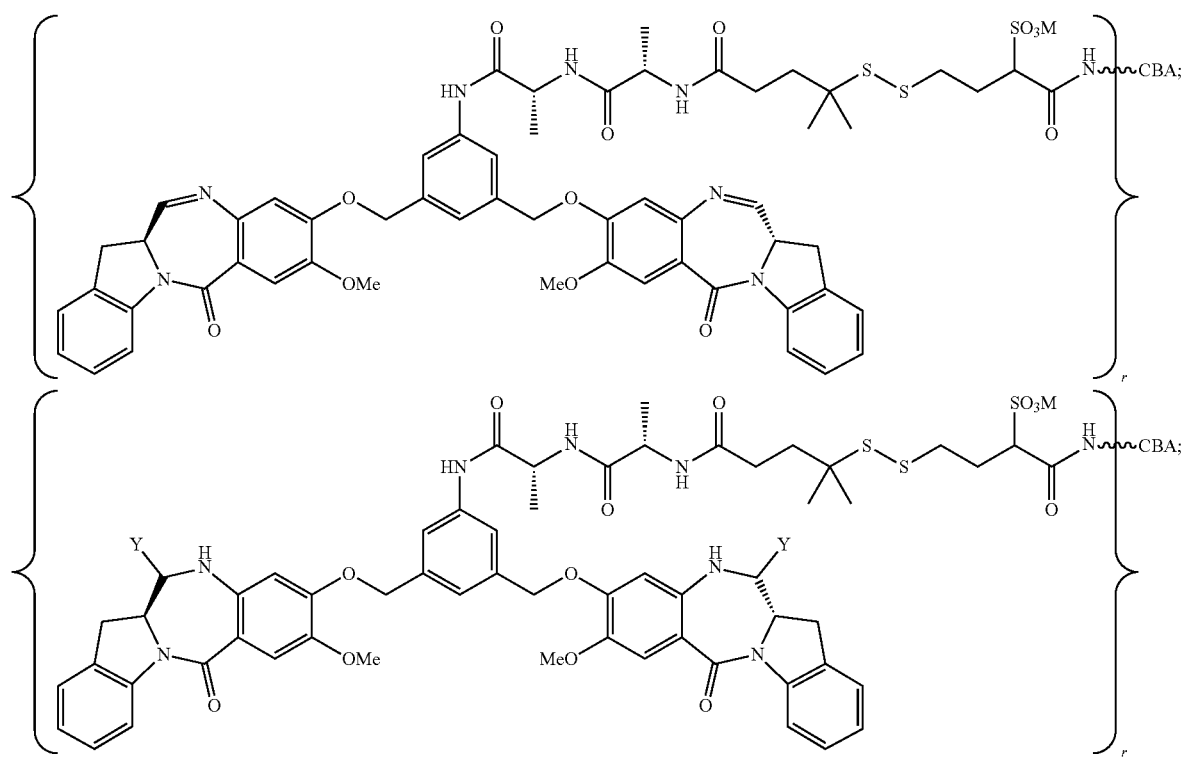

-continued

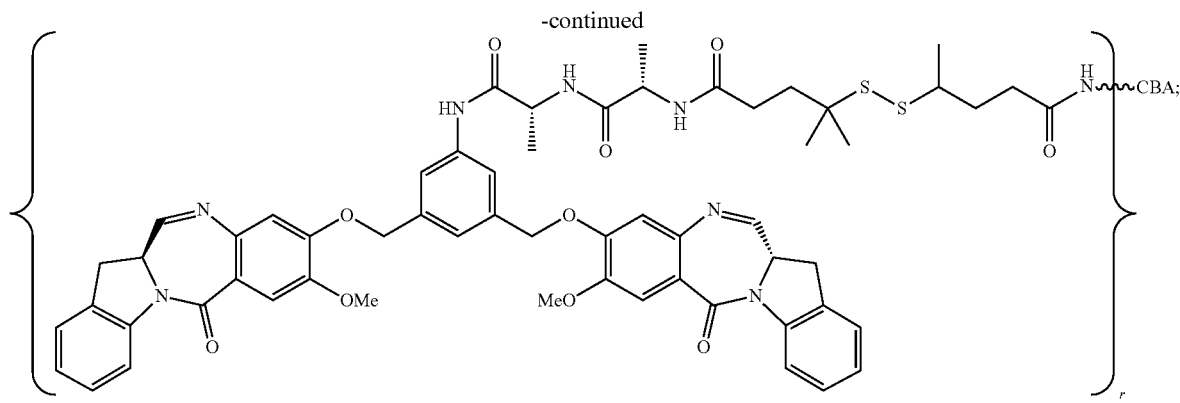

or a pharmaceutically acceptable salt thereof, wherein:
  r is an integer from 1 to 10;
  Y is —H, —OH or —SO$_3$M; and
  M is H$^+$, Na$^+$ or K$^+$.

15. The conjugate of claim 8, wherein the cell-binding agent is a monoclonal antibody, a chimeric antibody, or a domain antibody.

16. A pharmaceutical composition comprising the conjugate of claim 8 and a pharmaceutically acceptable carrier.

17. A method of treating acute myeloid leukemia (AML), cervical cancer, ovarian cancer, breast cancer, non-small cell lung cancer, endometrial cancer, or colon cancer in a mammal, comprising administering to said mammal a therapeutically effective amount of a conjugate of claim 8, and optionally, a chemotherapeutic agent.

18. The compound of claim 7, wherein the compound is represented by the following formula:

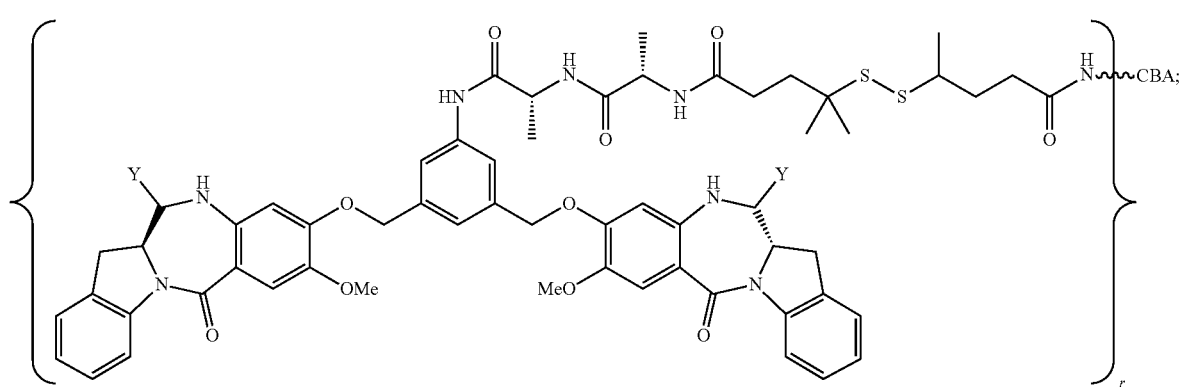

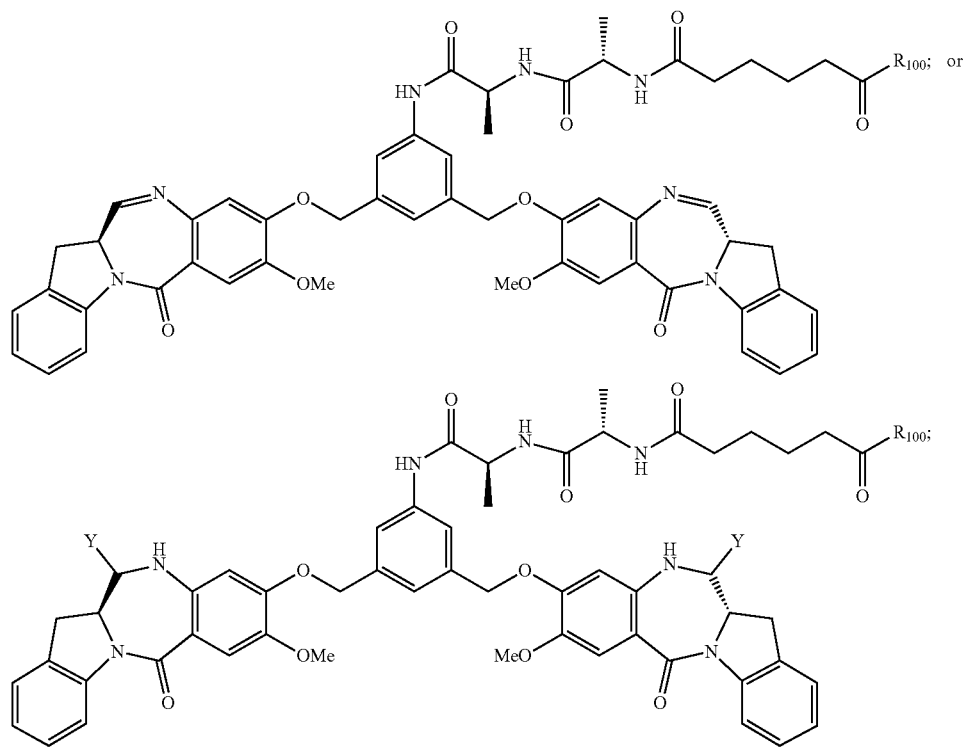
or a pharmaceutically acceptable salt thereof.
19. The conjugate of claim 14, wherein the conjugate is represented by the following formula:
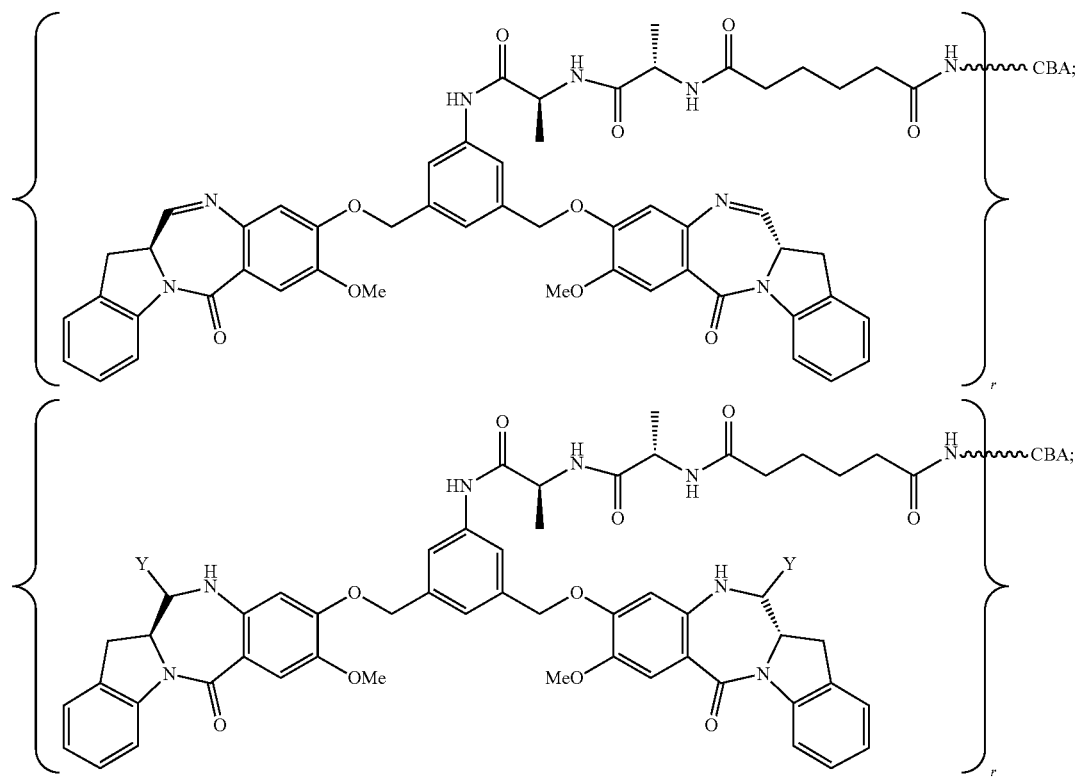

or a pharmaceutically acceptable salt thereof, wherein the CBA is an antibody.

20. The method of claim 17, wherein the method is for treating acute myeloid leukemia (AML).

\* \* \* \* \*

UNITED STATES PATENT AND TRADEMARK OFFICE
CERTIFICATE OF CORRECTION

PATENT NO. : 10,238,751 B2
APPLICATION NO. : 15/581749
DATED : March 26, 2019
INVENTOR(S) : Ravi V. J. Chari et al.

It is certified that error appears in the above-identified patent and that said Letters Patent is hereby corrected as shown below:

In the Claims

In Claim 1, at Column 321, please replace the preamble of the claim below:
*A compound represented by any one of the following formulas:*

With the following preamble:
A compound represented by the following formula:.

In Claim 1, at Column 321, please replace the following structural formula:

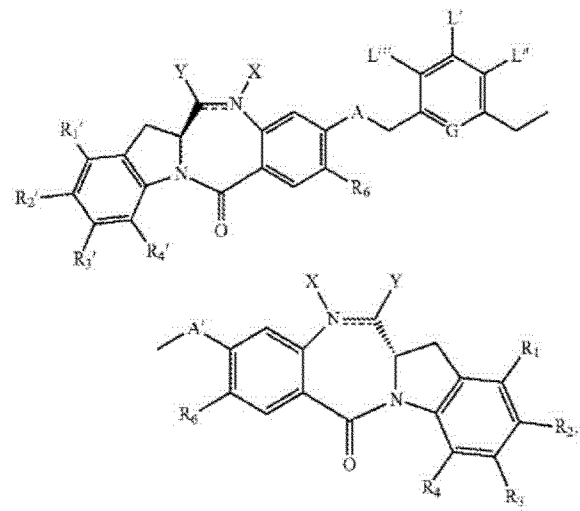

Signed and Sealed this
Thirteenth Day of August, 2019

Andrei Iancu
*Director of the United States Patent and Trademark Office*

With the following structural formula:

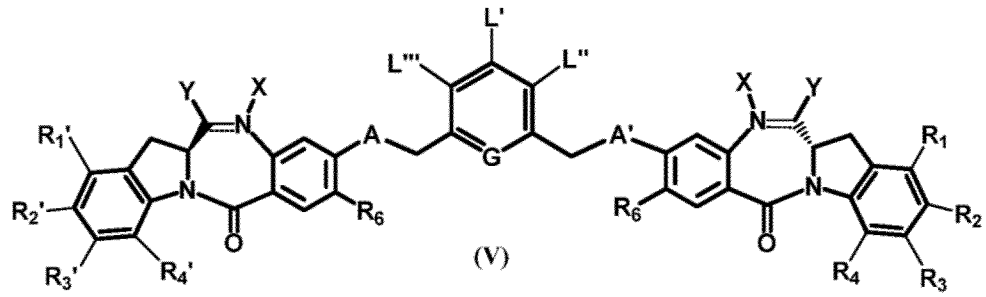

In Claim 8, at Column 345, please replace the preamble of the claim below:
*A conjugate comprising a cytotoxic compound and a cell-binding agent (CBA), wherein the cytotoxic compound is covalently linked to the CBA, and wherein said cytotoxic compound is represented by any one of the following formulas:*

With the following preamble:
A conjugate comprising a cytotoxic compound and a cell-binding agent (CBA), wherein the cytotoxic compound is covalently linked to the CBA, and wherein said cytotoxic compound is represented the following formula:.

SEQUENCE LISTING

```
<160> NUMBER OF SEQ ID NOS: 29

<210> SEQ ID NO 1
<211> LENGTH: 5
<212> TYPE: PRT
<213> ORGANISM: Artificial
<220> FEATURE:
<223> OTHER INFORMATION: FOLR1 antibody heavy chain CDR1

<400> SEQUENCE: 1

Gly Tyr Phe Met Asn
1               5

<210> SEQ ID NO 2
<211> LENGTH: 17
<212> TYPE: PRT
<213> ORGANISM: Artificial
<220> FEATURE:
<223> OTHER INFORMATION: FOLR1 antibody heavy chain CDR2
<220> FEATURE:
<221> NAME/KEY: X
<222> LOCATION: (14)..(14)
<223> OTHER INFORMATION: Lys, Gln, His, or Arg
<220> FEATURE:
<221> NAME/KEY: X
<222> LOCATION: (16)..(16)
<223> OTHER INFORMATION: Gln, His, Asn, or Arg
<220> FEATURE:
<221> NAME/KEY: X
<222> LOCATION: (17)..(17)
<223> OTHER INFORMATION: Gly, GLu, Thr, Ser, Ala, or Val
```

```
<220> FEATURE:
<221> NAME/KEY: X
<222> LOCATION: (17)..(17)
<223> OTHER INFORMATION: Gly, Glu, Thr, Ser, Ala, or Val

<400> SEQUENCE: 2

Arg Ile His Pro Tyr Asp Gly Asp Thr Phe Tyr Asn Gln Xaa Phe Xaa
1               5                   10                  15

Xaa

<210> SEQ ID NO 3
<211> LENGTH: 9
<212> TYPE: PRT
<213> ORGANISM: Artificial
<220> FEATURE:
<223> OTHER INFORMATION: FOLR1 antibody heavy chain CDR3

<400> SEQUENCE: 3

Tyr Asp Gly Ser Arg Ala Met Asp Tyr
1               5

<210> SEQ ID NO 4
<211> LENGTH: 15
<212> TYPE: PRT
<213> ORGANISM: Artificial
<220> FEATURE:
<223> OTHER INFORMATION: FOLR1 antibody light chain CDR1

<400> SEQUENCE: 4

Lys Ala Ser Gln Ser Val Ser Phe Ala Gly Thr Ser Leu Met His
1               5                   10                  15

<210> SEQ ID NO 5
<211> LENGTH: 7
<212> TYPE: PRT
<213> ORGANISM: Artificial
<220> FEATURE:
<223> OTHER INFORMATION: FOLR1 antibody light chain CDR2

<400> SEQUENCE: 5

Arg Ala Ser Asn Leu Glu Ala
1               5

<210> SEQ ID NO 6
<211> LENGTH: 9
<212> TYPE: PRT
<213> ORGANISM: Artificial
<220> FEATURE:
<223> OTHER INFORMATION: FOLR1 antibody light chain CDR3

<400> SEQUENCE: 6

Gln Gln Ser Arg Glu Tyr Pro Tyr Thr
1               5

<210> SEQ ID NO 7
<211> LENGTH: 17
<212> TYPE: PRT
<213> ORGANISM: Artificial
<220> FEATURE:
<223> OTHER INFORMATION: FOLR1 antibody heavy chain CDR2

<400> SEQUENCE: 7

Arg Ile His Pro Tyr Asp Gly Asp Thr Phe Tyr Asn Gln Lys Phe Gln
1               5                   10                  15

Gly
```

```
<210> SEQ ID NO 8
<211> LENGTH: 448
<212> TYPE: PRT
<213> ORGANISM: Artificial
<220> FEATURE:
<223> OTHER INFORMATION: FOLR1 antibody heavy chain

<400> SEQUENCE: 8
```

| Gln | Val | Gln | Leu | Val | Gln | Ser | Gly | Ala | Glu | Val | Val | Lys | Pro | Gly | Ala |
|---|---|---|---|---|---|---|---|---|---|---|---|---|---|---|---|
| 1 | | | | 5 | | | | | 10 | | | | | 15 | |
| Ser | Val | Lys | Ile | Ser | Cys | Lys | Ala | Ser | Gly | Tyr | Thr | Phe | Thr | Gly | Tyr |
| | | | 20 | | | | | 25 | | | | | 30 | | |
| Phe | Met | Asn | Trp | Val | Lys | Gln | Ser | Pro | Gly | Gln | Ser | Leu | Glu | Trp | Ile |
| | | 35 | | | | | 40 | | | | | 45 | | | |
| Gly | Arg | Ile | His | Pro | Tyr | Asp | Gly | Asp | Thr | Phe | Tyr | Asn | Gln | Lys | Phe |
| | 50 | | | | | 55 | | | | | 60 | | | | |
| Gln | Gly | Lys | Ala | Thr | Leu | Thr | Val | Asp | Lys | Ser | Ser | Asn | Thr | Ala | His |
| 65 | | | | | 70 | | | | | 75 | | | | | 80 |
| Met | Glu | Leu | Leu | Ser | Leu | Thr | Ser | Glu | Asp | Phe | Ala | Val | Tyr | Tyr | Cys |
| | | | | 85 | | | | | 90 | | | | | 95 | |
| Thr | Arg | Tyr | Asp | Gly | Ser | Arg | Ala | Met | Asp | Tyr | Trp | Gly | Gln | Gly | Thr |
| | | | 100 | | | | | 105 | | | | | 110 | | |
| Thr | Val | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Ser | Ser | Lys | Ser | Thr | Ser | Gly | Gly | Thr | Ala | Ala | Leu | Gly |
| | 130 | | | | | 135 | | | | | 140 | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | 195 | | | | | 200 | | | | | 205 | | | |
| Asn | Thr | Lys | Val | Asp | Lys | Lys | Val | Glu | Pro | Lys | Ser | Cys | Asp | Lys | Thr |
| | 210 | | | | | 215 | | | | | 220 | | | | |
| His | Thr | Cys | Pro | Pro | Cys | Pro | Ala | Pro | Glu | Leu | Leu | Gly | Gly | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | 260 | | | | | 265 | | | | | 270 | | |
| Glu | Val | Lys | Phe | Asn | Trp | Tyr | Val | Asp | Gly | Val | Glu | Val | His | Asn | Ala |
| | | 275 | | | | | 280 | | | | | 285 | | | |
| Lys | Thr | Lys | Pro | Arg | Glu | Glu | Gln | Tyr | Asn | Ser | Thr | Tyr | Arg | Val | Val |
| | 290 | | | | | 295 | | | | | 300 | | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Arg | Asp | Glu | Leu | Thr | Lys | Asn | Gln | Val | Ser | Leu | Thr | Cys |
| | | 355 | | | | | 360 | | | | | 365 | | | |

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 9
<211> LENGTH: 218
<212> TYPE: PRT
<213> ORGANISM: Artificial
<220> FEATURE:
<223> OTHER INFORMATION: FOLR1 antibody light chain

<400> SEQUENCE: 9

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 10
<211> LENGTH: 218
<212> TYPE: PRT
<213> ORGANISM: Artificial
<220> FEATURE:
<223> OTHER INFORMATION: FOLR1 antibody light chain

<400> SEQUENCE: 10

Asp Ile Val Leu Thr Gln Ser Pro Leu Ser Leu Ala Val Ser Leu Gly
1               5                   10                  15

-continued

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
 50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 11
<211> LENGTH: 118
<212> TYPE: PRT
<213> ORGANISM: Artificial
<220> FEATURE:
<223> OTHER INFORMATION: FOLR1 antibody heavy chain variable domain

<400> SEQUENCE: 11

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
 50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 12
<211> LENGTH: 112
<212> TYPE: PRT
<213> ORGANISM: Artificial

```
<220> FEATURE:
<223> OTHER INFORMATION: FOLR1 antibody light chain variable domain

<400> SEQUENCE: 12

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 13
<211> LENGTH: 112
<212> TYPE: PRT
<213> ORGANISM: Artificial
<220> FEATURE:
<223> OTHER INFORMATION: FOLR1 antibody light chain variable domain

<400> SEQUENCE: 13

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 14
<211> LENGTH: 445
<212> TYPE: PRT
<213> ORGANISM: Artificial
<220> FEATURE:
<223> OTHER INFORMATION: huML66HC Full-Length Heavy Chain

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Leu Ser Leu Ala Ser Asn
            20                  25                  30

Ser Val Ser Trp Ile Arg Gln Pro Pro Gly Lys Gly Leu Glu Trp Met
        35                  40                  45

Gly Val Ile Trp Asn His Gly Gly Thr Asp Tyr Asn Pro Ser Ile Lys
    50                  55                  60
```

```
Ser Arg Leu Ser Ile Ser Arg Asp Thr Ser Lys Ser Gln Val Phe Leu
 65                  70                  75                  80

Lys Met Asn Ser Leu Thr Ala Ala Asp Thr Ala Met Tyr Phe Cys Val
                 85                  90                  95

Arg Lys Gly Gly Ile Tyr Phe Asp Tyr Trp Gly Gln Gly Val Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 15
<211> LENGTH: 213
<212> TYPE: PRT
<213> ORGANISM: Artificial
<220> FEATURE:
<223> OTHER INFORMATION: huML66LC Full-Length Light Chain
```

<400> SEQUENCE: 15

Asp Thr Val Leu Thr Gln Ser Pro Ser Leu Ala Val Ser Pro Gly Glu
1               5                   10                  15

Arg Ala Thr Ile Ser Cys Arg Ala Ser Glu Ser Val Ser Thr Leu Met
            20                  25                  30

His Trp Tyr Gln Gln Lys Pro Gly Gln Gln Pro Lys Leu Leu Ile Tyr
        35                  40                  45

Leu Ala Ser His Arg Glu Ser Gly Val Pro Ala Arg Phe Ser Gly Ser
    50                  55                  60

Gly Ser Gly Thr Asp Phe Thr Leu Thr Ile Asp Pro Met Glu Ala Glu
65                  70                  75                  80

Asp Thr Ala Thr Tyr Tyr Cys Gln Gln Ser Arg Asn Asp Pro Trp Thr
                85                  90                  95

Phe Gly Gln Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 16
<211> LENGTH: 448
<212> TYPE: PRT
<213> ORGANISM: Artificial
<220> FEATURE:
<223> OTHER INFORMATION: anti-EGFR antibody immunoglobulin heavy chain

<400> SEQUENCE: 16

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Tyr Thr Gln Lys Phe
    50                  55                  60

Gln Gly Lys Ala Thr Leu Thr Ala Asp Lys Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 17
<211> LENGTH: 214
<212> TYPE: PRT
<213> ORGANISM: Artificial
<220> FEATURE:
<223> OTHER INFORMATION: anti-EGFR antibody immunoglobulin light chain

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Tyr Gln His Lys Pro Gly Lys Gly Pro Lys Leu Leu Ile
        35                  40                  45

```
His Tyr Thr Ser Thr Leu His Pro Gly Ile Pro Ser Arg Phe Ser Gly
 50                  55                  60

Ser Gly Ser Gly Arg Asp Tyr Ser Phe Ser Ile Ser Ser Leu Glu Pro
 65                  70                  75                  80

Glu Asp Ile Ala Thr Tyr Tyr Cys Leu Gln Tyr Asp Asn Leu Leu Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 18
<211> LENGTH: 214
<212> TYPE: PRT
<213> ORGANISM: Artificial
<220> FEATURE:
<223> OTHER INFORMATION: anti-EGFR antibody immunoglobulin light chain

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Asn Tyr
                 20                  25                  30

Leu Ala Trp Tyr Gln His Lys Pro Gly Lys Gly Pro Lys Leu Leu Ile
             35                  40                  45

His Tyr Thr Ser Thr Leu His Pro Gly Ile Pro Ser Arg Phe Ser Gly
 50                  55                  60

Ser Gly Ser Gly Arg Asp Tyr Ser Phe Ser Ile Ser Ser Leu Glu Pro
 65                  70                  75                  80

Glu Asp Ile Ala Thr Tyr Tyr Cys Leu Gln Tyr Asp Asn Leu Leu Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

Ala Cys Glu Val Thr His Gln Gly Leu Ser Ser Pro Val Thr Lys Ser
            195                 200                 205

Phe Asn Arg Gly Glu Cys
    210

<210> SEQ ID NO 19
<211> LENGTH: 450
<212> TYPE: PRT
<213> ORGANISM: Artificial
<220> FEATURE:
<223> OTHER INFORMATION: anti-CD19 antibody heavy chain

<400> SEQUENCE: 19

Gln Val Gln Leu Val Gln Pro Gly Ala Glu Val Val Lys Pro Gly Ala
1               5                  10                  15

Ser Val Lys Leu Ser Cys Lys Thr Ser Gly Tyr Thr Phe Thr Ser Asn
            20                  25                  30

Trp Met His Trp Val Lys Gln Ala Pro Gly Gln Gly Leu Glu Trp Ile
            35                  40                  45

Gly Glu Ile Asp Pro Ser Asp Ser Tyr Thr Asn Tyr Asn Gln Asn Phe
    50                  55                  60

Gln Gly Lys Ala Lys Leu Thr Val Asp Lys Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Arg Gly Ser Asn Pro Tyr Tyr Ala Met Asp Tyr Trp Gly Gln
            100                 105                 110

Gly Thr Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 20
<211> LENGTH: 211
<212> TYPE: PRT
<213> ORGANISM: Artificial
<220> FEATURE:
<223> OTHER INFORMATION: anti-CD19 antibody light chain

<400> SEQUENCE: 20

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Ser Leu Thr Ile Ser Ser Met Glu Pro Glu
65                  70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 21
<211> LENGTH: 447
```

-continued

```
<212> TYPE: PRT
<213> ORGANISM: Artificial
<220> FEATURE:
<223> OTHER INFORMATION: anti-Muc1 antibody heavy chain

<400> SEQUENCE: 21
```

| | | | | | | | | | | | | | | | |
|---|---|---|---|---|---|---|---|---|---|---|---|---|---|---|---|
| Gln | Ala | Gln | Leu | Val | Gln | Ser | Gly | Ala | Glu | Val | Val | Lys | Pro | Gly | Ala |
| 1 | | | | 5 | | | | | 10 | | | | | 15 | |
| Ser | Val | Lys | Met | Ser | Cys | Lys | Ala | Ser | Gly | Tyr | Thr | Phe | Thr | Ser | Tyr |
| | | | 20 | | | | | 25 | | | | | 30 | | |
| Asn | Met | His | Trp | Val | Lys | Gln | Thr | Pro | Gly | Gln | Gly | Leu | Glu | Trp | Ile |
| | | 35 | | | | | 40 | | | | | 45 | | | |
| Gly | Tyr | Ile | Tyr | Pro | Gly | Asn | Gly | Ala | Thr | Asn | Tyr | Asn | Gln | Lys | Phe |
| 50 | | | | | 55 | | | | | 60 | | | | | |
| Gln | Gly | Lys | Ala | Thr | Leu | Thr | Ala | Asp | Thr | Ser | Ser | Thr | Ala | Tyr |
| 65 | | | | 70 | | | | | 75 | | | | | 80 |
| Met | Gln | Ile | Ser | Ser | Leu | Thr | Ser | Glu | Asp | Ser | Ala | Val | Tyr | Phe | Cys |
| | | | | 85 | | | | | 90 | | | | | 95 | |
| Ala | Arg | Gly | Asp | Ser | Val | Pro | Phe | Ala | Tyr | Trp | Gly | Gln | Gly | Thr | Leu |
| | | | 100 | | | | | 105 | | | | | 110 | | |
| Val | Thr | Val | Ser | Ala | Ala | Ser | Thr | Lys | Gly | Pro | Ser | Val | Phe | Pro | Leu |
| | | 115 | | | | | 120 | | | | | 125 | | | |
| Ala | Pro | Ser | Ser | Lys | Ser | Thr | Ser | Gly | Gly | Thr | Ala | Ala | Leu | Gly | Cys |
| 130 | | | | | 135 | | | | | 140 | | | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | 195 | | | | | 200 | | | | | 205 | | | |
| Thr | Lys | Val | Asp | Lys | Lys | Val | Glu | Pro | Lys | Ser | Cys | Asp | Lys | Thr | His |
| 210 | | | | | 215 | | | | | 220 | | | | | |
| Thr | Cys | Pro | Pro | Cys | Pro | Ala | Pro | Glu | Leu | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Tyr | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Pro | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Arg | Asp | Glu | Leu | Thr | Lys | Asn | Gln | Val | Ser | Leu | Thr | Cys | Leu |
| | | 355 | | | | | 360 | | | | | 365 | | | |
| Val | Lys | Gly | Phe | Tyr | Pro | Ser | Asp | Ile | Ala | Val | Glu | Trp | Glu | Ser | Asn |
| 370 | | | | | 375 | | | | | 380 | | | | | |

```
Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 22
<211> LENGTH: 213
<212> TYPE: PRT
<213> ORGANISM: Artificial
<220> FEATURE:
<223> OTHER INFORMATION: anti-Muc1 antibody light chain

<400> SEQUENCE: 22

```
Glu Ile Val Leu Thr Gln Ser Pro Ala Thr Met Ser Ala Ser Pro Gly
1               5                   10                  15

Glu Arg Val Thr Ile Thr Cys Ser Ala His Ser Ser Val Ser Phe Met
            20                  25                  30

His Trp Phe Gln Gln Lys Pro Gly Thr Ser Pro Lys Leu Trp Ile Tyr
        35                  40                  45

Ser Thr Ser Ser Leu Ala Ser Gly Val Pro Ala Arg Phe Gly Ser
50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Arg Ser Ser Phe Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 23
<211> LENGTH: 447
<212> TYPE: PRT
<213> ORGANISM: Artificial
<220> FEATURE:
<223> OTHER INFORMATION: anti-CD33 antibody immunoglobulin heavy chain

<400> SEQUENCE: 23

```
Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30
```

```
Tyr Ile His Trp Ile Lys Gln Thr Pro Gly Gln Gly Leu Glu Trp Val
        35                  40                  45

Gly Val Ile Tyr Pro Gly Asn Asp Ile Ser Tyr Asn Gln Lys Phe
50                  55                  60

Gln Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Gln Gly Thr
                100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445
```

```
<210> SEQ ID NO 24
<211> LENGTH: 219
<212> TYPE: PRT
<213> ORGANISM: Artificial
<220> FEATURE:
<223> OTHER INFORMATION: anti-CD33 antibody immunoglobulin light chain

<400> SEQUENCE: 24

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 25
<211> LENGTH: 214
<212> TYPE: PRT
<213> ORGANISM: Artificial
<220> FEATURE:
<223> OTHER INFORMATION: anti-CD37 antibody immunoglobulin light chain

<400> SEQUENCE: 25

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95
```

```
Thr Phe Gly Gln Gly Thr Lys Leu Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 26
<211> LENGTH: 444
<212> TYPE: PRT
<213> ORGANISM: artificial
<220> FEATURE:
<223> OTHER INFORMATION: anti-CD37 antibody immunoglobulin heavy chain

<400> SEQUENCE: 26

Gln Val Gln Val Gln Glu Ser Gly Pro Gly Leu Val Ala Pro Ser Gln
1               5                   10                  15
Thr Leu Ser Ile Thr Cys Thr Val Ser Gly Phe Ser Leu Thr Thr Ser
            20                  25                  30
Gly Val Ser Trp Val Arg Gln Pro Pro Gly Lys Gly Leu Glu Trp Leu
        35                  40                  45
Gly Val Ile Trp Gly Asp Gly Ser Thr Asn Tyr His Pro Ser Leu Lys
    50                  55                  60
Ser Arg Leu Ser Ile Lys Lys Asp His Ser Lys Ser Gln Val Phe Leu
65                  70                  75                  80
Lys Leu Asn Ser Leu Thr Ala Ala Asp Thr Ala Thr Tyr Tyr Cys Ala
                85                  90                  95
Lys Gly Gly Tyr Ser Leu Ala His Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 27
<211> LENGTH: 444
<212> TYPE: PRT
<213> ORGANISM: artificial
<220> FEATURE:
<223> OTHER INFORMATION: anti-CD37 antibody immunoglobulin heavy chain

<400> SEQUENCE: 27

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 28
<211> LENGTH: 213
<212> TYPE: PRT
<213> ORGANISM: artificial
<220> FEATURE:
<223> OTHER INFORMATION: anti-CD37 antibody immunoglobulin light chain

<400> SEQUENCE: 28

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
            35                  40                  45

Asp Thr Ser Asn Leu Pro Tyr Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

```
Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 29
<211> LENGTH: 449
<212> TYPE: PRT
<213> ORGANISM: artificial
<220> FEATURE:
<223> OTHER INFORMATION: anti-CD37 antibody immunoglobulin heavy chain

<400> SEQUENCE: 29

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln His Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
        210                 215                 220
```

```
Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Met Ile
            245             250                     255

Ser Arg Thr Pro Glu Val Thr Cys Val Val Val Asp Val Ser His Glu
        260             265                 270

Asp Pro Glu Val Lys Phe Asn Trp Tyr Val Asp Gly Val Glu Val His
        275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Asp Glu Leu Thr Lys Asn Gln Val Ser Leu
        355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly
```